(12) United States Patent
Laurent et al.

(10) Patent No.: US 7,795,298 B2
(45) Date of Patent: *Sep. 14, 2010

(54) IAP BIR DOMAIN BINDING COMPOUNDS

(75) Inventors: Alain Laurent, Montreal (CA); Kim Hewitt, Montreal (CA); Stephen Morris, Beaconsfield (CA); Patrick Bureau, Kirkland (CA); Alain Boudreault, Dorval (CA); Scott Jarvis, Longueuil (CA); James Jaquith, Pincourt (CA)

(73) Assignee: Aegera Therapeutics, Inc., Verdun, Quebec ( * ) Notice: Subject to any disclaimer, the term of this patent is extended or adjusted under 35 U.S.C. 154(b) by 64 days.

This patent is subject to a terminal disclaimer.

(21) Appl. No.: 11/607,998

(22) Filed: Dec. 4, 2006

(65) Prior Publication Data

US 2007/0093429 A1    Apr. 26, 2007

Related U.S. Application Data

(63) Continuation of application No. 11/583,816, filed on Oct. 20, 2006.

(60) Provisional application No. 60/830,662, filed on Jul. 14, 2006, provisional application No. 60/729,727, filed on Oct. 25, 2005.

(51) Int. Cl.
*A61K 31/40* (2006.01)
*C07D 207/06* (2006.01)

(52) U.S. Cl. .......................... 514/422; 548/518; 514/423

(58) Field of Classification Search ................. 548/518; 514/422, 423
See application file for complete search history.

(56) References Cited

U.S. PATENT DOCUMENTS

| | | | |
|---|---|---|---|
| 6,110,691 | A | 8/2000 | Wang et al. |
| 6,608,026 | B1 | 8/2003 | Wang et al. |
| 6,992,063 | B2 | 1/2006 | Shi |
| 7,041,784 | B2 | 5/2006 | Wang et al. |
| 7,094,758 | B2 | 8/2006 | Wang et al. |
| 7,229,617 | B2 | 6/2007 | Nasoff et al. |
| 7,244,851 | B2 | 7/2007 | Cohen et al. |
| 7,309,792 | B2 | 12/2007 | Harran et al. |
| 7,456,209 | B2 | 11/2008 | Condon et al. |
| 7,517,906 | B2 | 4/2009 | Condon et al. |
| 2004/0180828 | A1 | 9/2004 | Shi |
| 2005/0197403 | A1 | 9/2005 | Harran et al. |
| 2006/0014700 | A1 | 1/2006 | Cohen et al. |
| 2006/0025347 | A1 | 2/2006 | Condon et al. |
| 2006/0194741 | A1 | 8/2006 | Condon et al. |
| 2006/0211627 | A1 | 9/2006 | Reed et al. |
| 2006/0258581 | A1 | 11/2006 | Reed et al. |
| 2007/0032437 | A1 | 2/2007 | Shi et al. |
| 2007/0042428 | A1 | 2/2007 | Springs et al. |
| 2007/0093428 | A1 | 4/2007 | Laurent |
| 2007/0093429 | A1 | 4/2007 | Laurent et al. |
| 2007/0219140 | A1 | 9/2007 | Laurent et al. |
| 2008/0069812 | A1 | 3/2008 | Boudreault et al. |
| 2008/0089896 | A1 | 4/2008 | Wang et al. |
| 2008/0207525 | A1 | 8/2008 | Boudreault et al. |

FOREIGN PATENT DOCUMENTS

| | | |
|---|---|---|
| CA | 2 582 734 A1 | 9/2005 |
| CA | 2 560 162 A1 | 10/2005 |
| CA | 2 574 040 A1 | 2/2006 |
| JP | 61183297 A | 8/1986 |
| JP | 04208299 A | 7/1992 |
| WO | WO 02/30959 | 4/2002 |
| WO | WO 2004/005248 | 1/2004 |
| WO | WO 2005/069888 | 8/2005 |
| WO | WO-2005/069888 A2 * | 8/2005 |
| WO | WO 2005/084317 A2 | 9/2005 |
| WO | WO 2005/094818 | 10/2005 |
| WO | WO 2005/097791 A1 | 10/2005 |
| WO | WO 2006/010118 A2 | 1/2006 |
| WO | WO 2006/017295 | 2/2006 |
| WO | WO 2006/069063 A1 | 6/2006 |
| WO | WO 2006/113376 A1 | 10/2006 |
| WO | WO 2006/122408 | 11/2006 |
| WO | WO 2006/128455 A2 | 12/2006 |
| WO | WO 2006/133147 A2 | 12/2006 |
| WO | WO 2007/048224 A1 | 5/2007 |
| WO | WO 2007/075525 A2 | 7/2007 |

(Continued)

OTHER PUBLICATIONS

Voskoglou-Nomikos et al, "Clinical Predictive Value of the in vitro Cell Line, Human Xenograft, and Mouse Allograft Preclinical Cancer Models," 2003. Clinical Cancer Research, vol. 9, pp. 4227-4239.*

(Continued)

*Primary Examiner*—Rei-Tsang Shiao
*Assistant Examiner*—Janet L Coppins
(74) *Attorney, Agent, or Firm*—Leydig, Voit & Mayer, Ltd.

(57) ABSTRACT

Disclosed is an isomer, enantiomer, diastereoisomer or tautomer of a compound represented by Formula I:

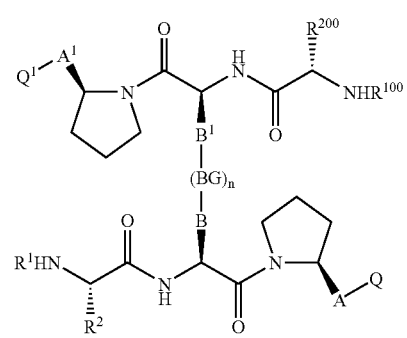

or a salt thereof, in which $R^1$, $R^2$, $R^{100}$, $R^{200}$, A, $A^1$, B, $B^1$, BG, n, Q and $Q^1$ are substituents described. Also disclosed is the use of compounds of Formula 1 to treat proliferative disorders.

33 Claims, 1 Drawing Sheet

FOREIGN PATENT DOCUMENTS

| | | |
|---|---|---|
| WO | WO 2007/101347 A1 | 9/2007 |
| WO | WO 2007/104162 A1 | 9/2007 |
| WO | WO 2007/106192 A2 | 9/2007 |
| WO | WO 2007/131366 A1 | 11/2007 |
| WO | WO 2007/136921 A2 | 11/2007 |
| WO | WO 2008/014229 A2 | 1/2008 |
| WO | WO 2008/014236 A1 | 1/2008 |
| WO | WO 2008/014238 A2 | 1/2008 |
| WO | WO 2008/014240 A2 | 1/2008 |
| WO | WO 2008/014252 A2 | 1/2008 |
| WO | WO 2008/014263 A2 | 1/2008 |
| WO | WO 2008/016893 A1 | 2/2008 |
| WO | WO 2008/045905 A1 | 4/2008 |
| WO | WO 2008/057172 A2 | 5/2008 |
| WO | WO 2008/067280 A2 | 6/2008 |
| WO | WO 2008/073306 A1 | 6/2008 |
| WO | WO 2008/079735 A1 | 7/2008 |
| WO | WO 2008/085610 A1 | 7/2008 |
| WO | WO 2008/128121 A1 | 10/2008 |
| WO | WO 2008/134679 A1 | 11/2008 |
| WO | WO 2008/144925 A1 | 12/2008 |

OTHER PUBLICATIONS

U.S. Appl. No. 11/583,816, commonly owned, filed Oct. 20, 2006.*
Structure-Based Design, Synthesis and Evaluation of Conformationally constrained mimetics of the second mitochondria-derived activator of caspase (Smac) that target the X-linked inhibitor of apoptosis protein/caspase-9 Interaction site; Sun et al.; J. Med. Chem. 2004, 47, 4147-4150.
Structure-Based Design, Synthesis and Evaluation of Conformationally constrained mimetics of the second mitochondria-derived activator of caspase (Smac) that target the X-linked inhibitor of apoptosis protein/caspase-9 Interaction site; Sun et al.; JM0499108, Supporting Information.
Discovery of potent antagonists of the antiapoptotic protein XIAP for the treatment of cancer; Oost et al; Journal of Medicinal Chemistry; pp. A-J; Feb. 13, 2004.
Discovery of potent antagonists of the anti-apoptotic protein XIAP for the treatment of cancer; Oost et al; 2004 American Chemical Society, J. Med. Chem.; Supporting Information.
A small molecule smac mimic potentiates TRAIL—and TNFα-Mediated Cell death; Li et al.; Science vol. 305; Sep. 3, 2004; 1471-1474.
A small molecule smac mimic potentiates TRAIL—and TNFα-Mediated Cell death; Li et al.; Supporting information.
Non-peptidic small molecule inhibitors of XIAP; Park et al.; Bioorganic & Medicinal Chemistry Letters 15 (2005) 771-775.
Discovery of embelin as a Cell-Permeable, Small-Molecular Weight Inhibitor of XIAP through Structure-Based Computational Screening of a Traditional Herbal Medicine Three-Dimensional structure Database; Nikolovska-Coleska et al.; J. Med. Chem. 2004, 47, 2430-2440.
Structure-based design, synthesis and biochemical testing of novel and potent Smac peptide-mimetics; Sun et al.; Bioorganic & Medicinal Chemistry Letters 15 (2005) 793-797.
Design and synthesis of a potent biotinylated Smac mimetic; Sun et al.; Tetrahedron Letters 46 (2005) 7015-7018.
Development and Characterization of Nonpeptidic Small Molecule Inhibitors of the XIAP/Caspase-3 Interaction; Wu et al.; Chemistry & Biology, vol. 10, 759-767, Aug. 2003.
Design, Synthesis, and Biological Activity of a potent Smac Mimetic that sensitizes cancer cells to apoptosis by antagonizing IAPs; Zobel et al.; ACS Chemical Biology; vol. 1 No. 8, 2006; 525-533.
Design, synthesis, and characterization of new embelin derivatives as potent inhibitors of X-linked inhibitor of apoptosis protein; Chen et al.; Bioorganic & Medicinal Chemistry Letters (2006); doi:10.1016.
Arnt et al., J. Biol. Chem., "Synthetic Smac/DIABLO peptides enhance the effects of chemotherapeutic agents by binding XIAP and cIAP1 in Situ," 277(46): 44236-44243 (2002).
Bertrand et al., Mol. Cell, "cIAP1 and cIAP2 facilitate cancer cell survival by functioning as E3 ligases that promote RIP1 ubiquitination," 30: 689-700 (2008).
Bucher et al., Helv. Chim. Acta., 78(4):935-46 (1995).
Chai et al., Nature, "Structural and biochemical basis of apoptotic activation by Smac/DIABLO," 406: 855-62 (2000).
Chauhan et al., Blood, "Targeting mitochondrial factor Smac/DIABLO as therapy for multiple myeloma (MM)," 109(3): 1220-7 (2007).
Eckelman et al., Cell Death Differ., "The mechanism of peptide-binding specificity of IAP BIR domains," 15(5): 920-8 (2008).
Elmore et al., Annual Rep. Med. Chem., "Inhibitors of Anti-apoptotic Proteins for Cancer Therapy," 40: 245-62 (2006).
Franklin et al., Biochemistry, "Structure and function analysis of peptide antagonists of melanoma inhibitor of apoptosis (ML-IAP)," 42: 8223-31 (2003).
Fulda et al., Nature Medicine, "Smac agonists sensitize for Apo2L/TRAIL- or anticancer drug-induced apoptosis and induce regression of malignant glioma in vivo," 8: 808-15 (2002).
Gao et al., J. Biol. Chem., "A dimeric Smac/Diablo peptide directly relieves caspase-3 inhibition by XIAP. Dynamic and cooperative regulation of XIAP by Smac/Diablo," 282(42): 30718-27 (2007).
Haining et al., Proc. Natl. Acad. Sci. USA, "The proapoptotic function of Drosophila HID is conserved in mammalian cells," 96(9): 4936-41 (1999).
Kipp et al., Biochemistry, "Molecular targeting of inhibitor of apoptosis proteins based on small molecule mimics of natural binding partners," 41: 7344-9 (2002).
Liu et al., Nature, "Structural basis for binding of Smac/DIABLO to the XIAP BIR3 domain," 408: 1004-8 (2000).
Marik et al., J. Peptide. Res., "Synthesis and effect of shortened oostatic decapeptide (TMOF) analogs with isosteric structures on reproduction of Neobellieria bullata," 57(5): 401-8 (2001).
McCarthy et al., J. Biol. Chem., "Apoptosis induced by Drosophila reaper and grim in a human system. Attenuation by inhibitor of apoptosis proteins (cIAPs)," 273(37): 24009-15 (1998).
Nikolovska-Coleska et al., Anal. Biochem., "Development and optimization of a binding assay for the XIAP BIR3 domain using fluorescence polarization," 332: 261-273 (2004).
Nikolovska-Coleska et al., Anal. Biochem., "Design and characterization of bivalent Smac-based peptides as antagonists of XIAP and development and validation of a fluorescence polarization assay for XIAP containing both BIR2 and BIR3 domains," 374(1): 87-98 (2008).
Petersen et al., Cancer Cell, "Autocrine TNFalpha signaling renders human cancer cells susceptible to Smac-mimetic-induced apoptosis," 12(5): 445-56 (2007).
Srinivasula et al., J. Biol. Chem., "Molecular determinants of the caspase-promoting activity of Smac/DIABLO and its role in the death receptor pathway," 275(46): 36152-7 (2000).
Sun et al., J. Am. Chem. Soc., "Structure-Based Design of Potent, Conformationally Constrained Smac Mimetics," 126(51): 16686-87 (2004).
Sun et al., J. Med. Chem., "Design, synthesis, and evaluation of a potent, cell-permeable, conformationally constrained second mitochondria derived activator of caspase (Smac) mimetic," 49(26): 7916-20 (2006).
Sun et al., J. Am. Chem. Soc., "Design, synthesis, and characterization of a potent, nonpeptide, cell-permeable, bivalent Smac mimetic that concurrently targets both the BIR2 and BIR3 domains in XIAP," 129(49): 15279-94 (2007).
Sweeney et al., Biochemistry, "Determination of the sequence specificity of XIAP BIR domains by screening a combinatorial peptide library," 45(49): 14740-8 (2006).
Terui et al., Cancer Res., "NH2-terminal pentapeptide of endothelial interleukin 8 is responsible for the induction of apoptosis in leukemic cells and has an antitumor effect in vivo," Cancer Res 59(22): 5651-5 (1999).
Varfolomeev et al., Cell, "IAP antagonists induce autoubiquitination of c-IAPs, NF-kappaB activation, and TNFalpha-dependent apoptosis," 131(4): 669-81 (2007).

Vince et al., *Cell*, "IAP antagonists target cIAP1 to induce TNFalpha-dependent apoptosis," 131(4): 682-93 (2007).

Vucic et al., *Mol. Cell. Biol.*, "Inhibitor of apoptosis proteins physically interact with and block apoptosis induced by Drosophila proteins HID and GRIM," 18(6): 3300-9 (1998).

Wist et al., *Bioorg. Med. Chem.*, "Structure-activity based study of the Smac-binding pocket within the BIR3 domain of XIAP," 15(8): 2935-43 (2007).

Wu et al., *Nature*, "Structural basis of IAP recognition by Smac/DIABLO," 408: 1008-12 (2000).

* cited by examiner

IAP BIR DOMAIN BINDING COMPOUNDS

CROSS REFERENCE TO RELATED APPLICATIONS

This application is a continuation of U.S. patent application Ser. No. 11/583,816, filed Oct. 20, 2006, which claims priority from previously filed U.S. Provisional Patent Application Ser. No. 60/729,727, filed Oct. 25, 2005 and U.S. Provisional Patent Application Ser. No. 60/830,662, filed Jul. 14, 2006, the entire contents of which are hereby incorporated by reference.

FIELD OF THE INVENTION

The present invention concerns compounds that bind to IAP BIR domains, and more particularly the BIR2 and BIR3 domains, and are useful to treat proliferative disorders.

BACKGROUND OF THE INVENTION

Apoptosis, or programmed cell death, typically occurs in the development and maintenance of healthy tissues in multicellular organisms. Apoptotic pathways are known to play a critical role in embryonic development, viral pathogenesis, cancer, autoimmune disorders, and neurodegenerative diseases, as well as other events. Alterations in an apoptotic response has been implicated in the development of cancer, autoimmune diseases, such as systemic lupus erythematosis and multiple sclerosis, and in viral infections, including those associated with herpes virus, poxvirus, and adenovirus.

Caspases, a class of cysteine proteases, are known to initiate apoptosis after they have been activated. Inhibitors of apoptosis proteins (IAPs) are a family of proteins, which contain one to three baculovirus IAP repeat (BIR) domains, namely BIR1, BIR2, and BIR3, and may also contain a RING zinc finger domain at the C-terminus. Examples of human IAPs include, XIAP, HIAP1 (also referred to as cIAP2), and HIAP2 (cIAP1) each have three BIR domains, and a carboxy terminal RING zinc finger. NAIP has three BIR domains (BIR1, BIR2 and BIR3), but no RING domain, whereas Livin and ILP2 have a single BIR domain and a RING domain. The prototype X chromosome linked inhibitor of apoptosis (XIAP) can not only inhibits the activated caspases by direct binding to the caspases, but XIAP can also remove caspases and the second mitochondrial activator of caspases (Smac) through the ubiquitylation-mediated proteasome pathway via the E3 ligase activity of a RING zinc finger domain. The BIR3 domain of XIAP binds and inhibits caspase-9, which can activate caspase-3. The linker-BIR2 domain of XIAP inhibits the activity of effector caspases-3 and -7. The BIR domains have also been associated with the interactions of IAPs with tumor necrosis factor-associated factor (TRAFs)-1 and -2, and to TAB1.

Overall the IAPs function as a 'constraint' to apoptosis.and may directly contribute to the tumor progression and resistance to pharmaceutical intervention. Interestingly, results demonstrate that resistance to apoptosis can be decrease by siRNA and antisense directed against specific IAP's in the cells. Hence, suggesting that interfering with the activity of the IAP's might prove advantageous in sensitizing disease cells to apoptosis.

A series of endogenous ligands are capable of interfering with IAP-caspase interactions. The X-ray crystallographic structure of XIAP BIR2 and BIR3 reveal a critical binding pocket and groove on the surface of each BIR domain. Two mammalian mitochondrial proteins, namely second mitochondria-derived activator of caspases (Smac) and Omi/Htra2, and four *Drosophila* proteins (Reaper, HID, Grim, and Sickle), which interfere with IAP function by binding to these sites on their respective BIR domain, have been identified. Each of these IAP inhibitors possesses a short amino-terminal tetrapeptide, AXPY or AVPI-like, sequence that fits into this binding pocket and disrupts protein/protein interactions such as IAP-caspase interactions. Although the overall folding of individual BIR domains is generally conserved, there are alterations in the amino acid sequences that form the binding pocket and groove. As such, binding affinities vary between each of the BIR domains.

A number of compounds have been described, which reportedly bind XIAP including Wu et al., Chemistry and Biology, Vol. 10, 759-767 (2003); United States published patent application number US2006/0025347A1; United States published patent application number US2005/0197403A1; United States published patent application number US2006/0194741A1. Some of the aforesaid compounds, while they appear to target the BIR3 domain of XIAP, may have limited bioavailability and therefore limited therapeutic application. Moreover, the compounds may not be selective against other IAPs and indeed other BIR domains, such as BIR2; this lack of specificity may lead to unexpected side effects.

Thus, IAP BIR domains represent an attractive target for the discovery and development of novel therapeutic agents, especially for the treatment of proliferative disorders such as cancer.

SUMMARY OF THE INVENTION

We have discovered a novel series of compounds that bind the IAPs and enhance cellular apoptosis through IAP modulation, and which have pharmaceutically acceptable stability and bioavailability. The compounds cause a reduction and/or loss of IAP proteins in cells before mitochondrial depolarization occurs and prevent the interaction of caspase 3, caspase 7, and caspase 9. Hence the results suggest that a small molecule is capable of down-regulating IAP proteins before cell death, thus indicating that clinically the use of the compounds may offer advantages when administered in combination with other inducers of apoptosis.

Specifically, we have demonstrated that the compounds bind to the BIR2 and BIR3 domain of mammalian XIAP and promote apoptosis of cancer cells as a single agent or in combination with a chemotherapeutic agent or a death receptor agonist, such as TRAIL or agonist TRAIL receptor antibodies. Moreover, the compounds were shown to cause reduction of cellular IAPs from cells which can be blocked by a proteasome inhibitor. Advantageously, the compounds described herein have pro-apoptotic activity in various cancer cell lines such as bladder, breast, pancreatic, colon, leukemic, lung, lymphoma, multiple myloma and ovarian, and may also find application in other cancer cell lines and in diseases where cells are resistant to apoptosis. The compounds were found to kill cancer cells in a synergistic manner with TRAIL or with agonist TRAIL receptor antibodies. These results suggest that compounds of the instant invention will demonstrate anti-cancer activity against solid tumours and tumours originating from the hematological malignancies. Moreover, the compounds of the present invention may also find application in preventing cancer cell metastasis, invasion, inflammation, and in other diseases characterized by cells that are resistant to apoptosis. The compounds may also be useful in the treatment of autoimmune diseases.

According to one aspect embodiment of the present invention, there is provided an isomer, enantiomer, diastereoisomer or tautomer of a compound represented by Formula I:

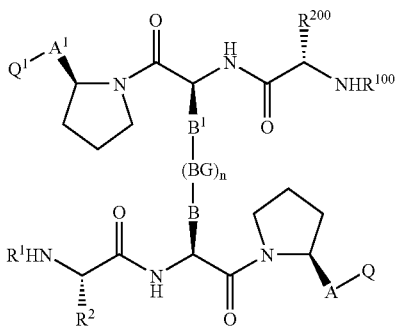

or a salt thereof, wherein:
n is 0 or 1;
m is 0, 1 or 2;
p is 1 or 2;
Y is NH, O or S;
A and $A^1$ are independently selected from
1) —$CH_2$—,
2) —$CH_2CH_2$—,
3) —$C(CH_3)_2$—,
4) —CH($C_1$-$C_6$ alkyl)-,
5) —CH($C_3$-$C_7$ cycloalkyl)-,
6) —$C_3$-$C_7$ cycloalkyl-,
7) —CH($C_1$-$C_6$ alkyl-$C_3$-$C_7$ cycloalkyl)-, or
8) —C(O)—;
B and $B^1$ are independently $C_1$-$C_6$ alkyl;
BG is
1) —X-L-$X^1$—; or
BG is

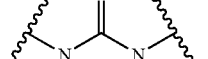

X and $X^1$ are independently selected from

1)
O, $NR^{13}$, S,

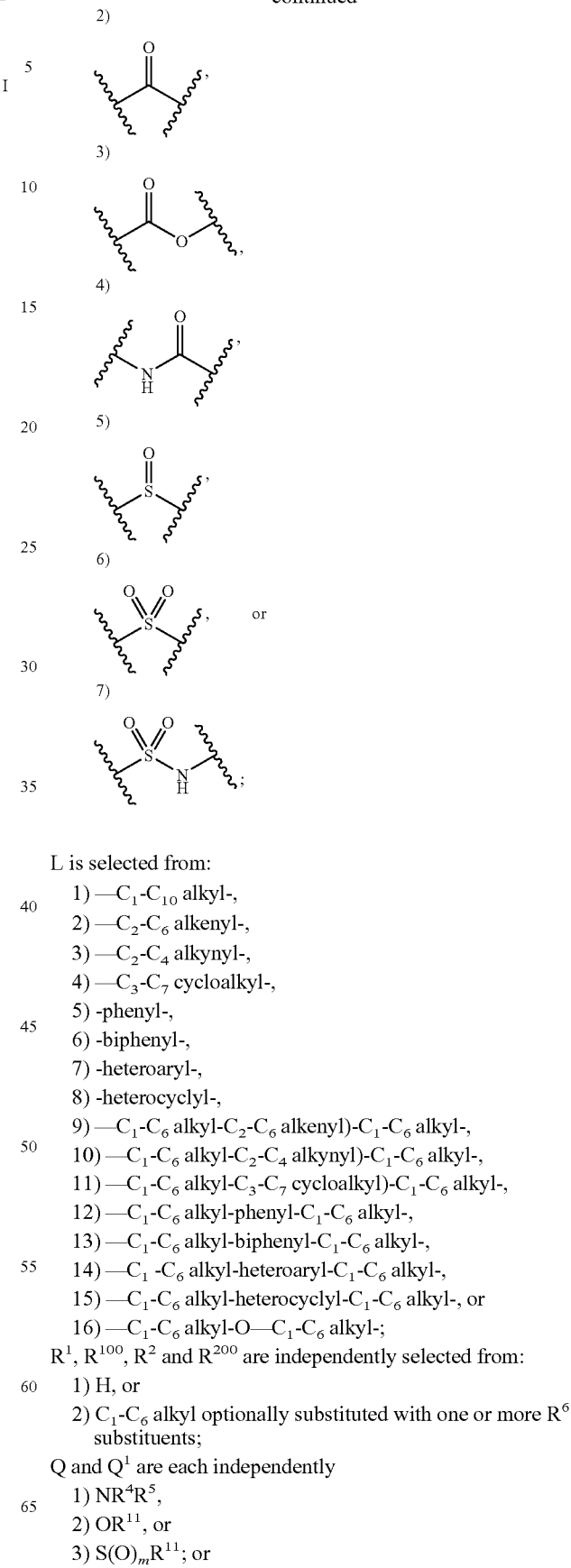

L is selected from:
1) —$C_1$-$C_{10}$ alkyl-,
2) —$C_2$-$C_6$ alkenyl-,
3) —$C_2$-$C_4$ alkynyl-,
4) —$C_3$-$C_7$ cycloalkyl-,
5) -phenyl-,
6) -biphenyl-,
7) -heteroaryl-,
8) -heterocyclyl-,
9) —$C_1$-$C_6$ alkyl-$C_2$-$C_6$ alkenyl)-$C_1$-$C_6$ alkyl-,
10) —$C_1$-$C_6$ alkyl-$C_2$-$C_4$ alkynyl)-$C_1$-$C_6$ alkyl-,
11) —$C_1$-$C_6$ alkyl-$C_3$-$C_7$ cycloalkyl)-$C_1$-$C_6$ alkyl-,
12) —$C_1$-$C_6$ alkyl-phenyl-$C_1$-$C_6$ alkyl-,
13) —$C_1$-$C_6$ alkyl-biphenyl-$C_1$-$C_6$ alkyl-,
14) —$C_1$-$C_6$ alkyl-heteroaryl-$C_1$-$C_6$ alkyl-,
15) —$C_1$-$C_6$ alkyl-heterocyclyl-$C_1$-$C_6$ alkyl-, or
16) —$C_1$-$C_6$ alkyl-O—$C_1$-$C_6$ alkyl-;
$R^1$, $R^{100}$, $R^2$ and $R^{200}$ are independently selected from:
1) H, or
2) $C_1$-$C_6$ alkyl optionally substituted with one or more $R^6$ substituents;
Q and $Q^1$ are each independently
1) $NR^4R^5$,
2) $OR^{11}$, or
3) $S(O)_mR^{11}$; or Q and $Q^1$ are each independently

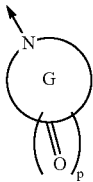

wherein G is a 5, 6 or 7 membered ring which optionally incorporates one or more heteroatoms chosen from S, N or O, the ring being optionally substituted with one or more $R^{12}$ substituents;

$R^4$ and $R^5$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) C(O)—$R^{11}$,
13) C(O)O—$R^{11}$,
14) C(=Y)$NR^8R^9$, or
15) $(O)_2$—$R^{11}$, wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

$R^6$ is
1) halogen,
2) $NO_2$,
3) CN,
4) haloalkyl,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) aryl,
11) heteroaryl,
12) heterocyclyl,
13) heterobicyclyl,
14) $OR^7$,
15) $S(O)_mR^7$,
16) $NR^8R^9$,
17) $NR^8S(O)_2R^{11}$,
18) $COR^7$,
19) $C(O)OR^7$,
20) $CONR^8R^9$,
21) $S(O)_2NR^8R^9$,
22) $OC(O)R^7$,
23) OC(O)Y—$R^{11}$,
24) $SC(O)R^7$, or
25) $NC(Y)NR^8R^9$, wherein the aryl, heteroaryl, heterocyclyl, and heterobicyclyl is optionally substituted with one or more $R^{10}$ substituents;

$R^7$ is
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $R^8R^9NC(=Y)$, or
13) $C_1$-$C_6$ alkyl-$C_2$-$C_4$ alkenyl, or
14) $C_1$-$C_6$ alkyl-$C_2$-$C_4$ alkynyl, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R_{10}$ substituents;

$R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)R^{11}$,
13) C(O)Y—$R^{11}$, or
14) $S(O)_2$—$R^{11}$, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

or $R^8$ and $R^9$ together with the nitrogen atom to which they are bonded form a five, six or seven membered heterocyclic ring optionally substituted with one or more $R^6$ substituents;

$R^{10}$ is
1) halogen,
2) $NO_2$,
3) CN,
4) $B(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^8R^9$,
13) $SR^7$,
14) $COR^7$,
15) $C(O)OR^7$,
16) $S(O)_mR^7$,
17) $CONR^8R^9$,
18) $S(O)_2NR^8R^9$,
19) aryl,
20) heteroaryl,
21) heterocyclyl, or
22) heterobicyclyl, wherein the alkyl, alkenyl, alkynyl, cycloalkyl, and cycloalkenyl is optionally substituted with one or more $R^6$ substituents;
$R^{11}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl, wherein the alkyl, alkenyl, alkynyl, cycloalkyl, cycloalkenyl, is optionally substituted with one or more $R^6$ substituents; and wherein the aryl, heteroaryl, heterocyclyl, and heterobicyclyl is optionally substituted with one or more $R^{10}$ substituents;
$R^{12}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl,
10) heterobicyclyl,
11) $C(O)$—$R^{11}$,
12) $C(O)O$—$R^{11}$,
13) $C(O)NR^8R^9$,
14) $S(O)_m$—$R^{11}$, or
15) $C(=Y)NR^8R^9$, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;
$R^{13}$ and $R^{14}$ are each independently
1) H, or
2) $C_1$-$C_6$ alkyl; or
$R^{13}$ and $R^{14}$ are combined to form a heterocyclic ring or a heterobicyclyl ring;
or a prodrug; or the compound of Formula I is labeled with a detectable label or an affinity tag.

According to one alternative aspect of the present invention, there is provided a compound, according to Formula 2:

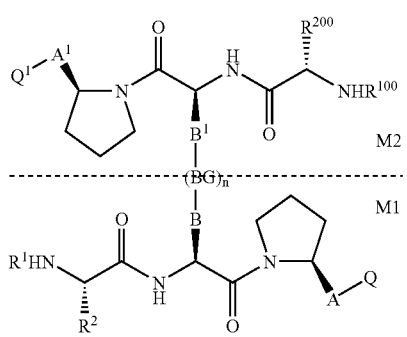

wherein n, $R^1$, $R^2$, $R^{100}$, $R^{200}$, A, $A^1$, Q, $Q^1$, B, $B^1$, and BG as defined above;

wherein the dotted line represents a hypothetical dividing line for comparing the substituents associated with M1 and M2.

In another aspect of the present invention, M1 is the same as M2.

In another aspect of the present invention, M1 is different from M2.

In one aspect of the present invention, there is provided an intermediate compound represented by Formula 2(iii):

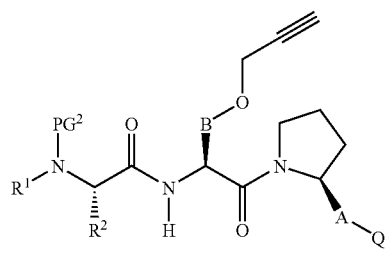

wherein $PG^2$ is a protecting group, and $R^1$, $R^2$, B, A, and Q are as defined herein.

In another aspect of the present invention, there is provided an intermediate compound represented by Formula 3(iii):

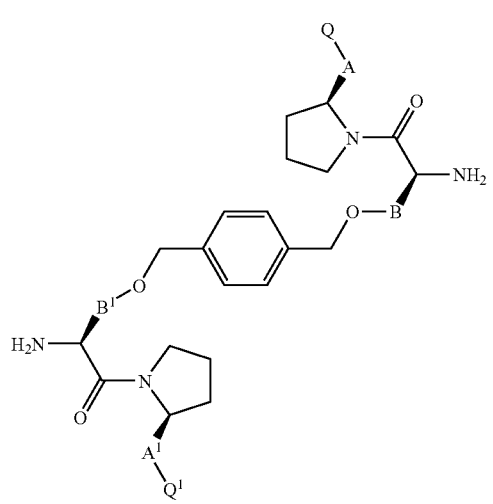

wherein B, $B^1$, A, $A^1$, Q and $Q^1$ are as defined herein.

In another aspect of the present invention, there is provided an intermediate compound represented by Formula 4(iii):

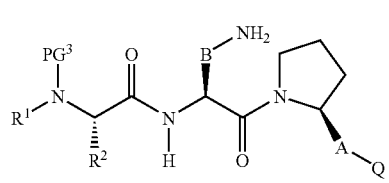

wherein $PG^3$ is a protecting group, and B, $R^1$, $R^2$, A, and Q are as defined herein.

In another aspect of the present invention, there is provided an intermediate compound represented by Formula 5(i):

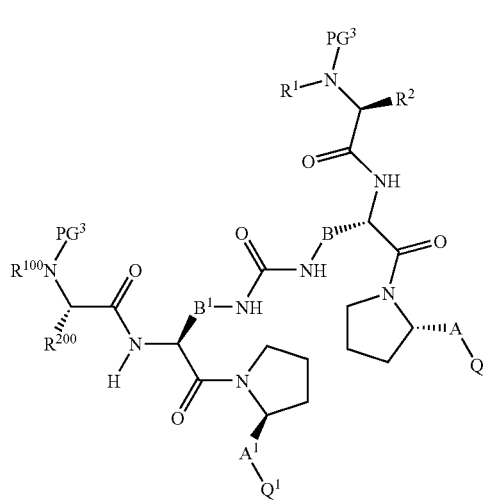

5 (i)

wherein $PG^3$ are protecting groups, and B, $B^1$, $R^1$, $R^{100}$, $R^2$, $R^{200}$, A, $A^1$, Q and $Q^1$ are as defined herein.

In another aspect of the present invention, there is provided an intermediate compound represented by Formula 6(iii):

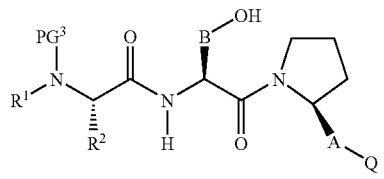

6 (iii)

wherein $PG^3$ is a protecting group, and $R^1$, $R^2$, B, A, and Q are as defined herein.

In another aspect of the present invention, there is provided an intermediate compound represented by Formula 7(iii):

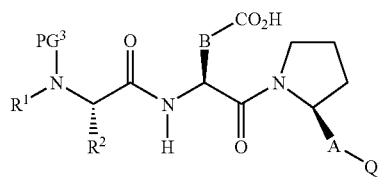

7 (iii)

wherein $PG^3$ is a protecting group, and $R^1$, $R^2$, B, A, and Q are as defined herein.

In another aspect of the present invention, there is provided an intermediate compound represented by Formula 8(iii):

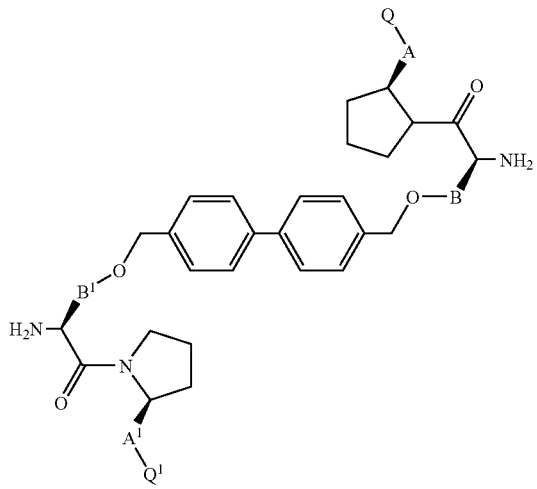

8(iii)

wherein B, $B^1$, A, $A^1$, Q and $Q^1$ are as defined herein.

In another aspect of the present invention, there is provided a process for producing compounds represented by Formula I, described hereinabove, the process comprising:

a) coupling two intermediates represented by Formula 2(iii):

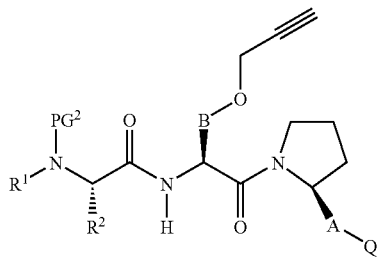

2 (iii)

in a solvent; and b) removing the protecting groups so as to form compounds of Formula I.

In another aspect of the present invention, there is provided a process for producing compounds represented by Formula I, described hereinabove, the process comprising:

a) coupling an intermediate represented by Formula 3(iii):

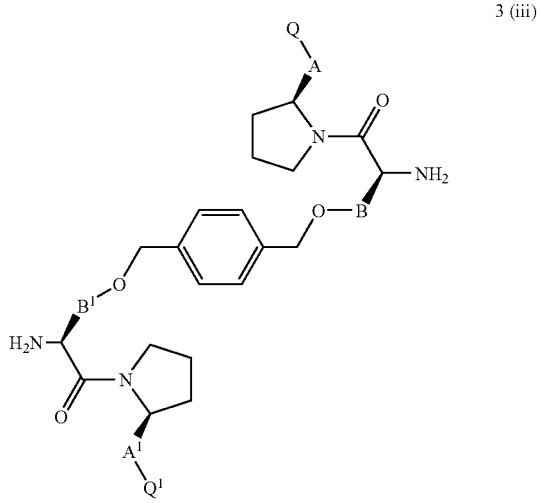

3 (iii)

and

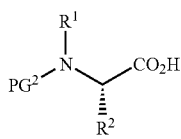

in a solvent; and b) removing the protecting groups so as to form compounds of Formula I.

In another aspect of the present invention, there is provided a process for producing compounds represented by Formula I, described herein, the process comprising:

a) coupling an intermediate represented by Formula 4(iii):

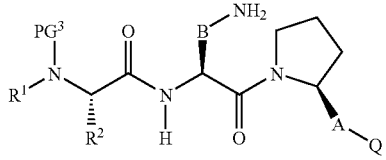

4 (iii)

and an activated diacid, such as a diacid chloride or a diacid activated using 2 equiv of peptide coupling agents, in a solvent; and b) removing the protecting groups so as to form compounds of Formula I.

In another aspect of the present invention, there is provided a process for producing compounds represented by Formula I, described herein, the process comprising:

a) coupling two intermediates represented by Formula 4(iii):

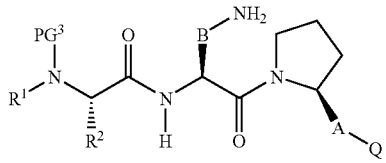

4 (iii)

with triphosgene, or a triphosgene equivalent, in a solvent; and b) removing the protecting groups so as to form compounds of Formula I.

In another aspect of the present invention, there is provided a process for producing compounds represented by Formula I, described herein, the process comprising:

a) coupling two intermediates represented by Formula 4(iii):

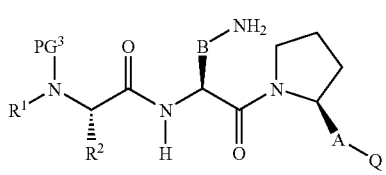

4 (iii)

with oxalyl chloride in a solvent; and b) removing the protecting groups so as to form compounds of Formula I.

In another aspect of the present invention, there is provided a process for producing compounds represented by Formula I, described herein, the process comprising:

a) coupling an intermediate represented by Formula 6(iii):

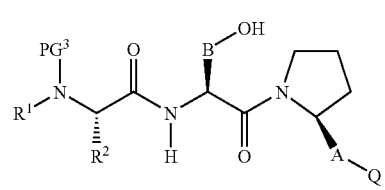

6 (iii)

and either a bis-acid chloride or a bis-acid, using a coupling agent, in a solvent; and b) removing the protecting groups so as to form compounds of Formula I.

In another aspect of the present invention, there is provided a process for producing compounds represented by Formula I, described herein, the process comprising:

a) coupling an intermediate represented by Formula 7(iii):

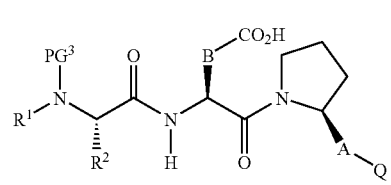

7 (iii)

and a diamine using a coupling agent in a solvent; and b) removing the protecting groups so as to form compounds of Formula I.

In another aspect of the present invention, there is provided a process for producing compounds represented by Formula I, described hereinabove, the process comprising:

a) coupling an intermediate represented by Formula 8(iii):

8(iii)

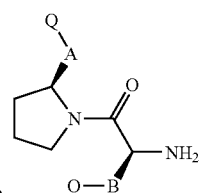
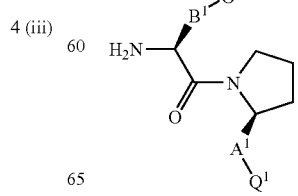

and

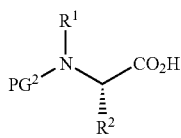

in a solvent; and b) removing the protecting groups so as to form compounds of Formula I.

In another aspect of the present invention, there is provided a process for producing compounds represented by Formula I, described hereinabove, the process comprising:

a) hydrogenation of a compound represented by 1g

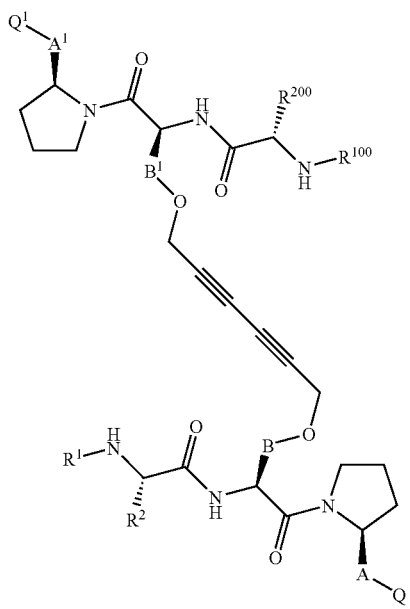

1g in a solvent, b) filtration and concentration of the solvent to provide a compound of formula 1q.

In another aspect of the present invention, there is provided a pharmaceutical composition comprising a compound, as described above, mixed with a pharmaceutically acceptable carrier, diluent or excipient.

In another aspect of the present invention, there is provided a pharmaceutical composition adapted for administration as an agent for treating a proliferative disorder in a subject, comprising a therapeutically effective amount of a compound, as described above.

In another aspect of the present invention, there is provided a pharmaceutical composition comprising a compound of Formula I in combination with one or more death receptor agonists, for example, an agonist of TRAIL receptor.

In another aspect of the present invention, there is provided a pharmaceutical composition comprising a compound of formula I in combination with any therapeutic agent that increases the response of one or more death receptor agonists, for example cytotoxic cytokines such as interferons.

In another aspect of the present invention, there is provided a method of preparing a pharmaceutical composition, the method comprising: mixing a compound, as described above, with a pharmaceutically acceptable carrier, diluent or excipient.

In another aspect of the present invention, there is provided a method of treating a disease state characterized by insufficient apoptosis, the method comprising: administering to a subject in need thereof, a therapeutically effective amount of a pharmaceutical composition, as described above, so as to treat the disease state.

In another aspect of the present invention, there is provided a method of modulating IAP function, the method comprising: contacting a cell with a compound of the present invention so as to prevent binding of a BIR binding protein to an IAP BIR domain thereby modulating the IAP function.

In another aspect of the present invention, there is provided a method of treating a proliferative disease, the method comprising: administering to a subject in need thereof, a therapeutically effective amount of the pharmaceutical composition, as described above, so as to treat the proliferative disease.

In another aspect of the present invention, there is provided a method of treating cancer, the method comprising: administering to a subject in need thereof, a therapeutically effective amount of the pharmaceutical composition, as described above, so as to treat the cancer.

In another aspect of the present invention, there is provided a method of treating cancer, the method comprising: administering to the subject in need thereof, a therapeutically effective amount of a pharmaceutical composition, as described above, in combination or sequentially with an agent selected from:

a) an estrogen receptor modulator,
b) an androgen receptor modulator,
c) retinoid receptor modulator,
d) a cytotoxic agent,
e) an antiproliferative agent,
f) a prenyl-protein transferase inhibitor,
g) an HMG-CoA reductase inhibitor,
h) an HIV protease inhibitor,
i) a reverse transcriptase inhibitor,
k) an angiogenesis inhibitor,
l) a PPAR-γ agonist,
m) a PPAR-δ agonist,
n) an inhibitor of inherent multidrug resistance,
o) an anti-emetic agent,
p) an agent useful in the treatment of anemia,
q) agents useful in the treatment of neutropenia,
r) an immunologic-enhancing drug.
s) a proteasome inhibitor;
t) an HDAC inhibitor;
u) an inhibitor of the chymotrypsin-like activity in the proteasome;
v) E3 ligase inhibitors;
w) a modulator of the immune system such as, but not limited to, interferon-alpha, Bacillus Calmette-Guerin (BCG), and ionizing radition (UVB) that can induce the release of cytokines, such as the interleukins, TNF, or induce release of death receptor ligands such as TRAIL;
x) a modulator of death receptors TRAIL and TRAIL receptor agonists such as the humanized antibodies HGS-ETR1 and HGS-ETR2;

or in combination or sequentially with radiation therapy, so as to treat the cancer.

In another aspect of the present invention, there is provided a method for the treatment or prevention of a proliferative disorder in a subject, the method comprising: administering to the subject a therapeutically effective amount of the composition, described above.

In another aspect of the present invention, the method further comprises administering to the subject a therapeutically effective amount of a chemotherapeutic agent prior to, simultaneously with or after administration of the composition.

In yet another aspect, the method further comprises administering to the subject a therapeutically effective amount of a death receptor agonist prior to, simultaneously with or after administration of the composition. The death receptor agonist is TRAIL or the death receptor agonist is a TRAIL receptor antibody. The death receptor agonist is typically administered in an amount that produces a synergistic effect.

In another aspect of the present invention, there is provided a probe, the probe being a compound of Formula I above, the compound being labeled with a detectable label or an affinity tag.

In another aspect of the present invention, there is provided a method of identifying compounds that bind to an IAP BIR domain, the assay comprising:
 a) contacting an IAP BIR domain with a probe to form a probe:BIR domain complex, the probe being displaceable by a test compound;
 b) measuring a signal from the probe so as to establish a reference level;
 c) incubating the probe:BIR domain complex with the test compound;
 d) measuring the signal from the probe;
 e) comparing the signal from step d) with the reference level, a modulation of the signal being an indication that the test compound binds to the BIR domain, wherein the probe is a compound of Formula I labeled with a detectable label or an affinity label.

BRIEF DESCRIPTION OF THE DRAWINGS

Further aspects and advantages of the present invention will become better understood with reference to the description in association with the following Figure, wherein.

DETAILED DESCRIPTION OF THE INVENTION

Figure 1:
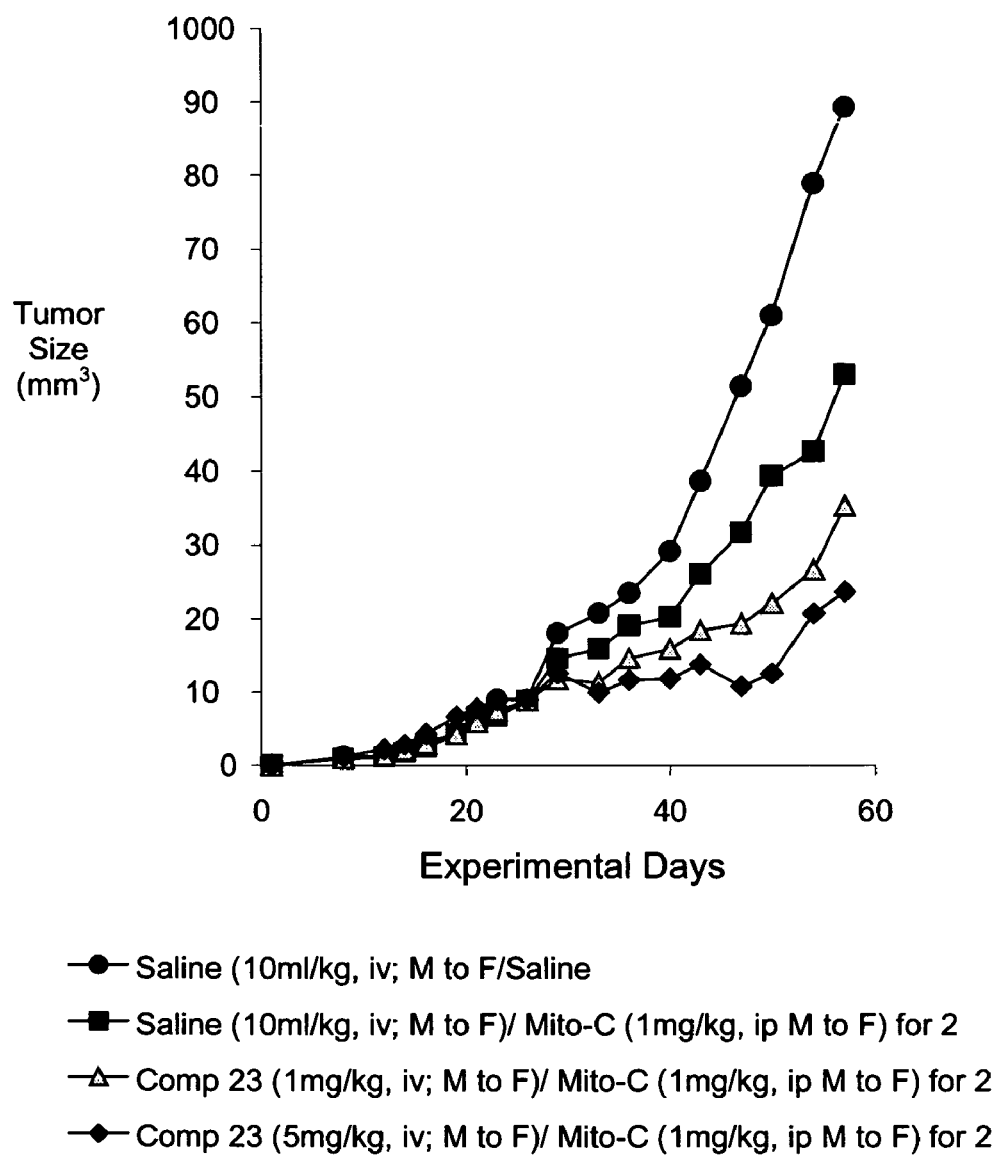
FIG. 1 is a graph illustrating a combination anti-cancer therapy in vivo in which compound 23 showed an increasing anti-tumor effect in combination with mitomycin-C with increasing dose, with 5 mg/kg showing superior anti-tumor effects compared to the 1 mg/kg dose.

In many cancer and other diseases, an up-regulation of IAP induced by gene defects or by chemotherapeutic agents has been correlated to an increased resistance to apoptosis. Interestingly our results show that cells decreased in IAPs level are more sensitive to TRAIL induced apoptosis. It is believed that a small molecule, which will induce IAP loss from disease cells, will be useful as a therapeutic agent. We report herein compounds that can directly bind to IAPs, cause a down regulation of the IAP proteins in cell before cell death, induce apoptosis in cancer cells, and have a synergistic effect in combination with inducers of apoptosis. This may provide clinical advantages in terms of the selectivity of therapy based on the phenotype of the cancer cells. Also advantageous would be the use of the compounds of the present invention in combination therapy with other agents in terms of the doses of administration and the time of scheduling the doses.

The compounds of the present invention are useful as BIR domain binding compounds in mammalian IAPs and are represented by Formula I. The following are embodiments, groups and substituents of the compounds according to Formula I, which are described hereinafter in detail.

n:

In one subset of compounds of Formula I, n is 1.

Any and each individual definition of n as set out herein may be combined with any and each individual definition of Core, $R^1$, $R^2$, $R^{100}$, $R^{200}$, A, $A^1$, Q, $Q^1$, B, $B^1$, and BG as set out herein.

A and $A^1$:

In one subset of compounds of Formula I, A and $A^1$ are both $CH_2$.

In an alternative subset of compounds of Formula I, A and $A^1$ are both C=O.

In another alternative subset of compounds of Formula I, A is $CH_2$ and $A^1$ is C=O.

Any and each individual definition of A and $A^1$ as set out herein may be combined with any and each individual definition of Core, n, $R^1$, $R^2$, $R^{100}$, $R^{200}$, Q, $Q^1$, B, $B^1$, and BG as set out herein.

Core:

Therefore, the present invention comprises compounds of Formula 1a through 1c:

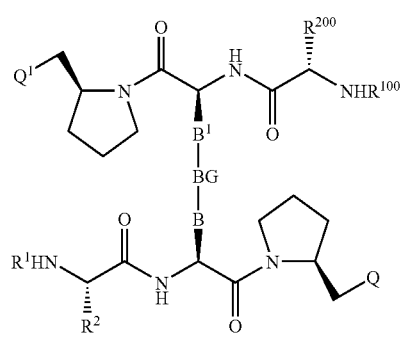

1a

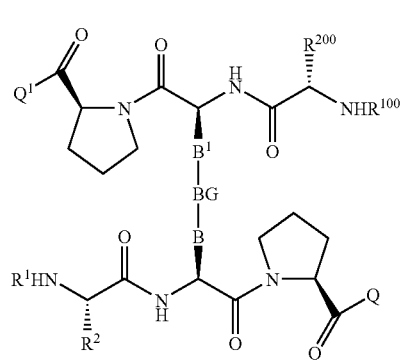

1b

-continued

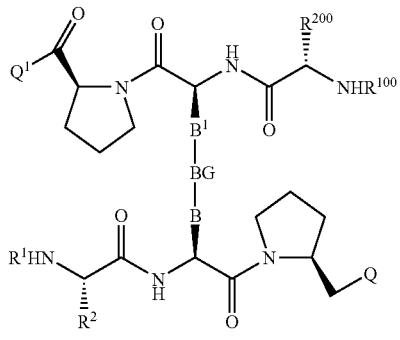

1c wherein BG, B, B¹, Q, Q¹, R¹, R¹⁰⁰, R² and R²⁰⁰ are as defined hereinabove and hereinafter.

In one example, the present invention comprises compounds of Formula 1a.

In an alternative example, the present invention comprises compounds of Formula 1b.

Any and each individual definition of Core as set out herein may be combined with any and each individual definition of A, A¹, n, R¹, R², R¹⁰⁰, R²⁰⁰, Q, Q¹, B, B¹, and BG as set out herein.

B and B¹:

In one subset of the aforesaid compounds, B and B¹ are both $C_1$-$C_4$ alkyl.

Any and each individual definition of B and B¹ as set out herein may be combined with any and each individual definition of Core, A, A¹, n, R¹, R², R¹⁰⁰, R²⁰⁰, Q, Q¹, and BG as set out herein.

BG:

In one subset of the aforesaid compounds, BG is —X-L-X¹—.

Therefore the invention comprises compounds of Formula 1d and 1e:

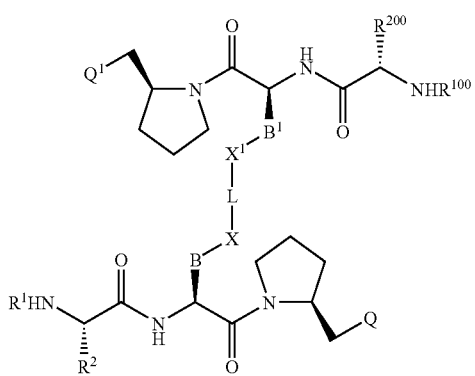

1d

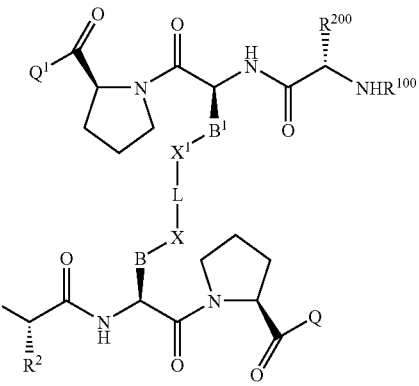

1e wherein L, B, B¹, X, X¹, Q, Q¹, R¹, R¹⁰⁰, R² and R²⁰⁰ are as defined herein.

In an alternative subset of the aforesaid compounds, BG is

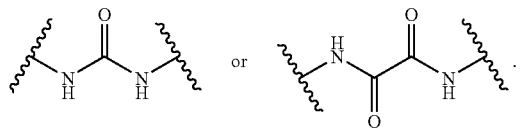

Therefore, the invention alternatively comprises compounds of Formula 1f or 1g:

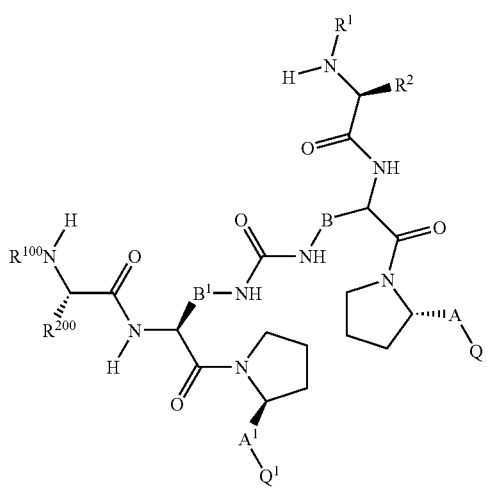

1f

-continued

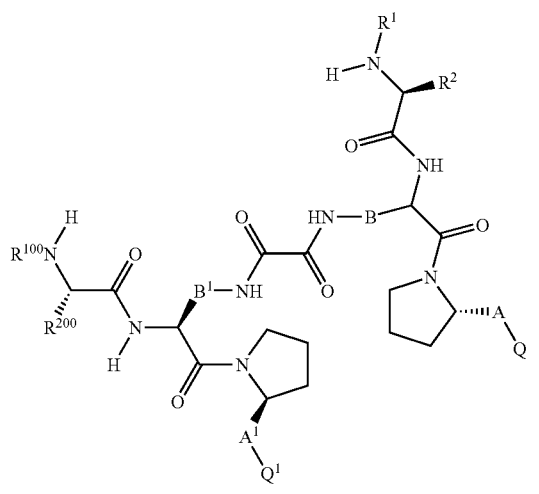

1g wherein A, A$^1$, B, B$^1$, Q, Q$^1$, R$^{100}$, R$^2$ and R$^{200}$ are as defined herein.

Any and each individual definition of BG as set out herein may be combined with any and each individual definition of Core, A, A$^1$, n, R$^1$, R$^2$, R$^{100}$, R$^{200}$, Q, Q$^1$, B, and B$^1$ as set out herein.

X and X$^1$:

In one subset of the aforesaid compounds, X and X$^1$ are independently selected from

1) O, NH,

2) 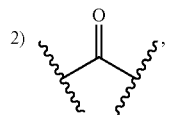,

3) 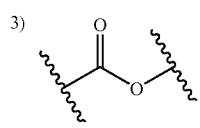,

4) 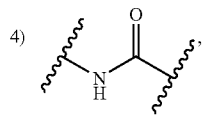,

5) 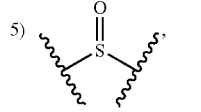,

6) 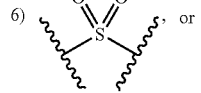, or

7) 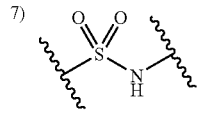;

In another subset of the aforesaid compounds, X and X$^1$ are independently selected from:

1) O,

2) 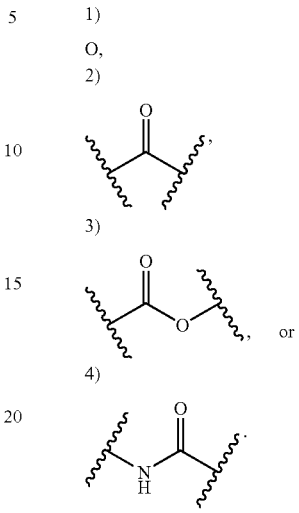,

3) [ester structure], or

4) [amide structure]

Typical examples of X and X$^1$ include both X and X$^1$ as being

O, 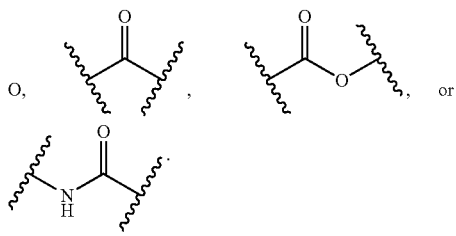, or

[amide structure].

Any and each individual definition of X and X$^1$ as set out herein may be combined with any and each individual definition of Core, A, A$^1$, n, R$^1$, R$^2$, R$^{100}$, R$^{200}$Q, Q$^1$, B, B$^1$, and BG as set out herein.

L:

In one subset of the aforesaid compounds, L is selected from:

1) —C$_1$-C$_{10}$ alkyl-,
2) —C$_2$-C$_4$ alkynyl-,
3) -phenyl-,
4) -biphenyl-,
5) —C$_1$-C$_6$ alkyl-C$_2$-C$_4$ alkynyl)-C$_1$-C$_6$ alkyl,
6) —C$_1$-C$_6$ alkyl-phenyl-C$_1$-C$_6$ alkyl,
7) —C$_1$-C$_6$ alkyl-biphenyl-C$_1$-C$_6$ alkyl, or
8) —C$_1$-C$_6$ alkyl-O—C$_1$-C$_6$ alkyl.

In another subset of the aforesaid compounds, L is selected from

1) —C$_1$-C$_{10}$ alkyl-,
2) -phenyl-,
3) -biphenyl-,
4) —CH$_2$—C$_1$-C$_4$ alkynyl)CH$_2$—,
5) —CH$_2$-phenyl-CH$_2$—,
6) —CH$_2$-biphenyl-CH$_2$—, or
7) —C$_1$-C$_6$ alkyl-O—C$_1$-C$_6$ alkyl.

Typical examples of L include

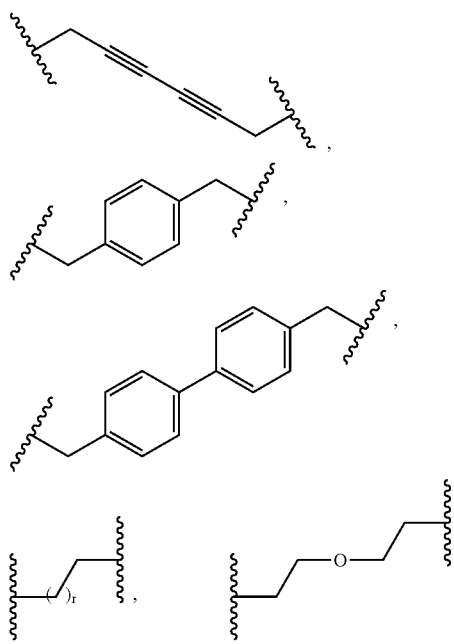

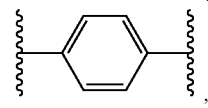

Any and each individual definition of L as set out herein may be combined with any and each individual definition of Core, A, $A^1$, n, $R^1$, $R^2$, $R^{100}$, $R^{200}$, Q, $Q_1$, B, and $B_1$ as set out herein.

r:

In the aforesaid aspect, r is an integer of 1, 2, 3, 4, 5, 6, 7, or 8.

Any and each individual definition of r as set out herein may be combined with any and each individual definition of Core, A, $A^1$, n, $R^1$, $R^2$, $R^{100}$, $R^{200}$, Q, $Q^1$, B, and $B^1$ as set out herein.

More explicitly, the invention comprises compounds of Formulae 1h, 1i, 1j, 1k, 1l, and 1m:

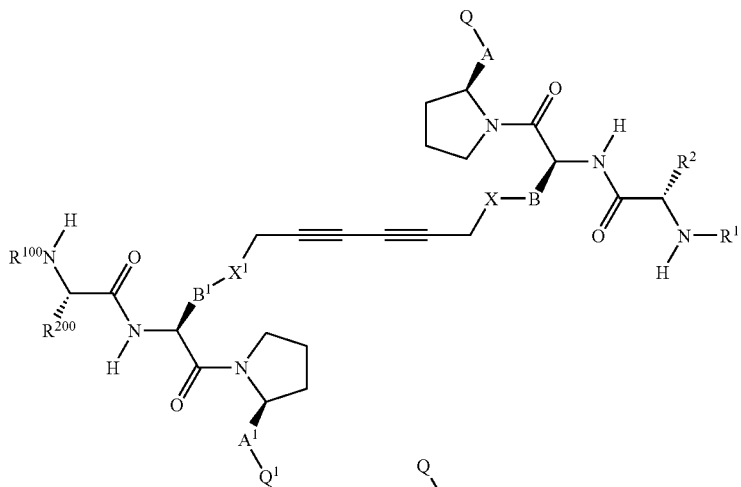

1h

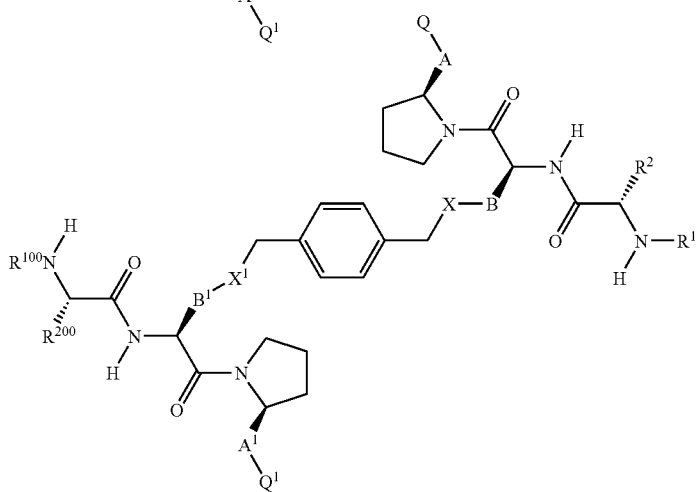

1i

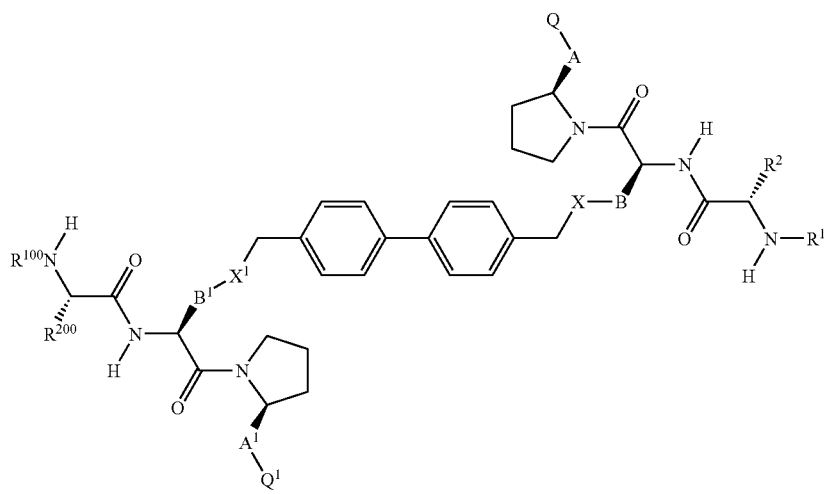
1j
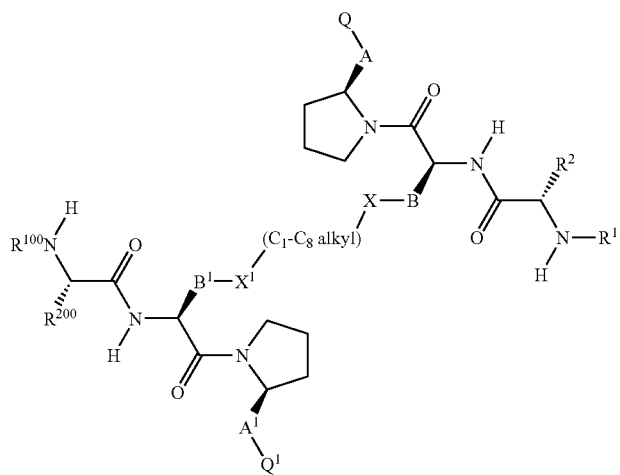
1k
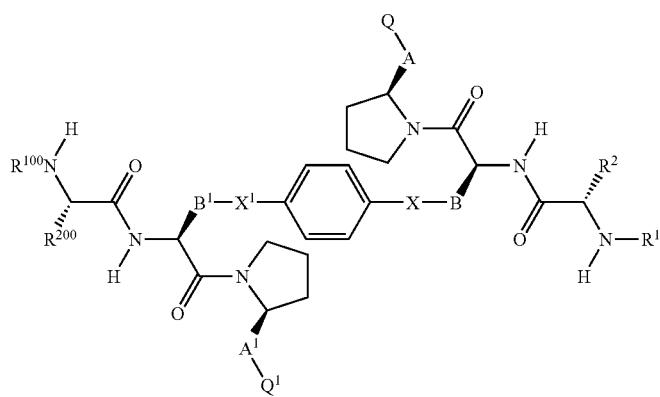
1l

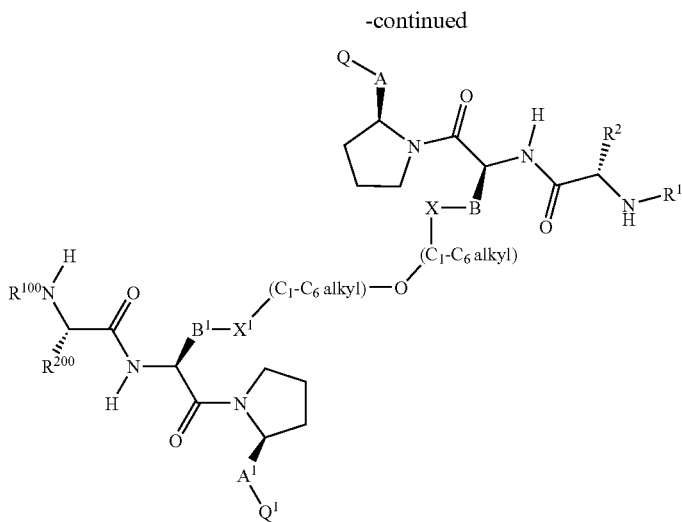

wherein B, B¹, X, X¹, Q, Q¹, R¹, R¹⁰⁰, R² and R²⁰⁰ are as defined herein.

R¹ and R¹⁰⁰:

In one subset of the aforesaid compounds R¹ and R¹⁰⁰ are both $C_1$-$C_6$ alkyl.

In one example, R¹ and R¹⁰⁰ are both $CH_3$.

Any and each individual definition of R¹ and R¹⁰⁰ as set out herein may be combined with any and each individual definition of Core, A, A¹, n, R², R²⁰⁰, Q, Q₁, B, B¹ and BG as set out herein.

R² and R²⁰⁰:

In one subset of the aforesaid compounds R² and R²⁰⁰ are both $C_1$-$C_6$ alkyl. In one example, R² and R²⁰⁰ are both $CH_3$.

Any and each individual definition of R² and R²⁰⁰ as set out herein may be combined with any and each individual definition of Core, A, A¹, n, R¹, R¹⁰⁰, Q, Q¹, B, B¹, and BG as set out herein.

Q and Q¹:

In one subset of the aforesaid compounds, Q and Q¹ are both $NR^4R^5$, wherein R⁴ and R⁵ are as defined herein.

Any and each individual definition of Q and Q¹ as set out herein may be combined with any and each individual definition of Core, A, A¹, n, R¹, R¹⁰⁰, R², R²⁰⁰, B, B¹, and BG as set out herein.

R⁴ and R⁵:

In one subset of the aforesaid compounds in which A and A¹ are both C=O, R⁴ is H and R⁵ is selected from
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl, wherein the alkyl, alkenyl, alkynyl, and cycloalkyl, cycloalkenyl are optionallly substituted with one or more R⁶ substituents; and wherein the aryl, heteroaryl, heterocyclyl, and heterobicyclyl are optionally substituted with one or more R¹⁰ substituents;

wherein R⁶ and R¹⁰ are as defined herein.

In another subset of the above compounds, R⁴ is H and R⁵ is selected from:
1) $C_3$-$C_7$ cycloalkyl,
2) $C_3$-$C_7$ cycloalkenyl,
3) aryl,
4) heteroaryl,
5) heterocyclyl, or
6) heterobicyclyl.

In still another subset of the above compounds, R⁴ is H and R⁵ is aryl.

In one example, R⁴ is H and R⁵ is

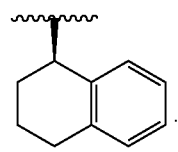

Therefore, when A and A¹ are both C=O, then Q and Q¹ are both

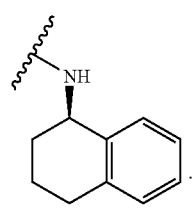

In an alternative subset of the aforesaid compounds in which A and A¹ are both $CH_2$, then R⁴ and R⁵ are each independently
1) H,
2) haloalkyl,
3) $C_1$-$C_6$ alkyl,
4) $C_2$-$C_6$ alkenyl,
5) $C_2$-$C_4$ alkynyl, 6) $C_3$-$C_7$ cycloalkyl,
7) $C_3$-$C_7$ cycloalkenyl,
8) aryl,
9) heteroaryl,
10) heterocyclyl,
11) heterobicyclyl,
12) C(O)—$R^{11}$,
13) C(O)O—$R^{11}$,
13) C(=Y)N$R^8R^9$, or
14) S(O)$_2$—$R^{11}$, wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

wherein Y, $R^6$, $R^8$, $R^9$, $R^{10}$ and $R^{11}$ are as defined herein.

In another subset of the above compounds, $R^4$ and $R^5$ are independently selected from
1) H,
2) $C_1$-$C_6$ alkyl,
3) C(O)—$R^{11}$,
4) C(O)O—$R^{11}$, or
5) S(O)$_2$—$R^{11}$, wherein the alkyl is substituted with an $R^6$ substituent;

wherein $R^6$, and $R^{11}$ are as defined herein.

In one subset of the aforesaid compounds,
$R^4$ is
1) H,
2) C(O)—$R^{11}$,
3) C(O)O—$R^{11}$, or
4) S(O)$_2$—$R^{11}$; and
$R^5$ is $C_1$-$C_6$ alkyl substituted with a phenyl;

wherein $R^{11}$ is as defined herein.

In another subset of the aforesaid compounds,
$R^4$ is
1) H,
2) C(O)—$R^{11}$,
3) C(O)O—$R^{11}$, or
4) S(O)$_2$—$R^{11}$; and
$R^5$ is

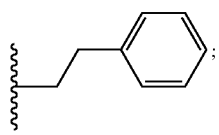

wherein $R^{11}$ is as defined herein.

Any and each individual definition of $R^4$ and $R^5$ as set out herein may be combined with any and each individual definition of Core, A, $A^1$, n, $R^1$, $R^{100}$, $R^2$, $R^{200}$, B, $B^1$, and BG as set out herein.

$R^{11}$:

In one subset of the aforesaid compounds,
$R^{11}$ is
1) haloalkyl,
2) $C_1$-$C_6$ alkyl,
3) $C_2$-$C_6$ alkenyl,
4) $C_2$-$C_4$ alkynyl,
5) aryl,
6) heteroaryl,
7) heterocyclyl, or
8) heterobicyclyl, wherein the alkyl, alkenyl, alkynyl is optionally substituted with one or more $R^6$ substituents; and wherein the aryl, heteroaryl, heterocyclyl, and heterobicyclyl is optionally substituted with one or more $R^{10}$ substituents;

wherein $R^6$ and $R^{10}$ are as defined herein.

In another subset of the aforesaid compounds, $R^{11}$ is
1) haloalkyl,
2) $C_1$-$C_6$ alkyl,
3) aryl,
4) heteroaryl, or
5) heterocyclyl, wherein the alkyl is optionally substituted with one or two $R^6$ substituents; and wherein the aryl, heteroaryl and heterocyclyl is substituted with one $R^{10}$ substituent;

wherein $R^6$ and $R^{10}$ are as defined herein.

In one subset of the aforesaid compounds, $R^{11}$ is
1) haloalkyl,
2) $C_1$-$C_6$ alkyl optionally substituted with one or two $R^6$ substituents, or
3) phenyl optionally substituted with one $R^{10}$ substituent;

wherein the $R^6$ and the $R^{10}$ substituents are as defined herein.

Any and each individual definition of $R^{11}$ as set out herein may be combined with any and each individual definition of Core, A, $A^1$, n, $R^1$, $R^{100}$, $R^2$, $R^{200}$, R, $R^5$, B, $B^1$, and BG as set out herein.

$R^6$:

In one subset of the aforesaid compounds, $R^6$ is
1) halogen,
2) $NO_2$,
3) CN,
4) aryl,
5) heteroaryl,
6) heterocyclyl,
7) heterobicyclyl,
8) $OR^7$,
9) $SR^7$, or
10) $NR^8R^9$, wherein the aryl, heteroaryl, heterocyclyl, and heterobicyclyl is optionally substituted with one or more $R^{10}$ substituents;

wherein $R^7$, $R^8$, $R^9$ and $R^{10}$ are as defined herein.

In another subset of the aforesaid compounds, $R^6$ is
1) halogen,
2) aryl, or
3) $NR^8R^9$, wherein the aryl is optionally substituted with one $R^{10}$ substituent;

wherein $R^8$, $R^9$ and $R^{10}$ are as defined herein.

In one subset of the aforesaid compounds, $R^6$ is
1) halogen,
2) phenyl, or
3) $NR^8R^9$, wherein the phenyl is optionally substituted with one $R^{10}$ substituent;

wherein $R^8$ and $R^9$ are as defined herein.

Any and each individual definition of $R^6$ as set out herein may be combined with any and each individual definition of Core, A, A¹, n, R¹, R¹⁰⁰, R², R²⁰⁰, R⁴, R⁵, B, B¹, and BG as set out herein.

$R^8$ and $R^9$:

In one subset of the aforesaid compounds, $R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl, or
7) $C_3$-$C_7$ cycloalkenyl, wherein the alkyl, alkenyl, alkynyl, cycloalkyl, cycloalkenyl is optionally substituted with one or more $R^6$ substituents;

wherein the $R^6$ substituents are defined herein.

In another subset of the aforesaid compounds, $R^8$ and $R^9$ are each independently
1) H, or
2) $C_1$-$C_6$ alkyl, wherein the alkyl is optionally substituted with an aryl.

Any and each individual definition of $R^8$ and $R^9$ as set out herein may be combined with any and each individual definition of Core, A, A¹, n, R¹, R¹⁰⁰, R², R²⁰⁰, R⁴, R⁵, B, B¹, and BG as set out herein.

$R^{10}$:

In one aspect of the aforesaid compounds, $R^{10}$ is
1) halogen,
2) $NO_2$,
3) CN,
4) haloalkyl,
5) $OR^7$,
6) $NR^8R^9$, or
7) $SR^7$;

wherein $R^7$, $R^8$, and $R^9$ are as defined herein.

In another aspect of the aforesaid compounds, $R^{10}$ is
1) halogen, or
2) $OC_1$-$C_6$ alkyl.

Any and each individual definition of $R^{10}$ as set out herein may be combined with any and each individual definition of Core, A, A¹, n, R¹, R¹⁰⁰, R², R²⁰⁰, R⁴, R⁵, B, B¹, and BG as set out herein.

Thus, when A and A¹ are both $CH_2$, then Q and $Q^1$ are independently selected from:

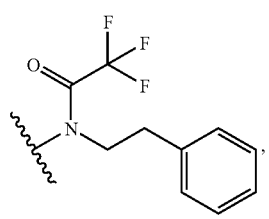

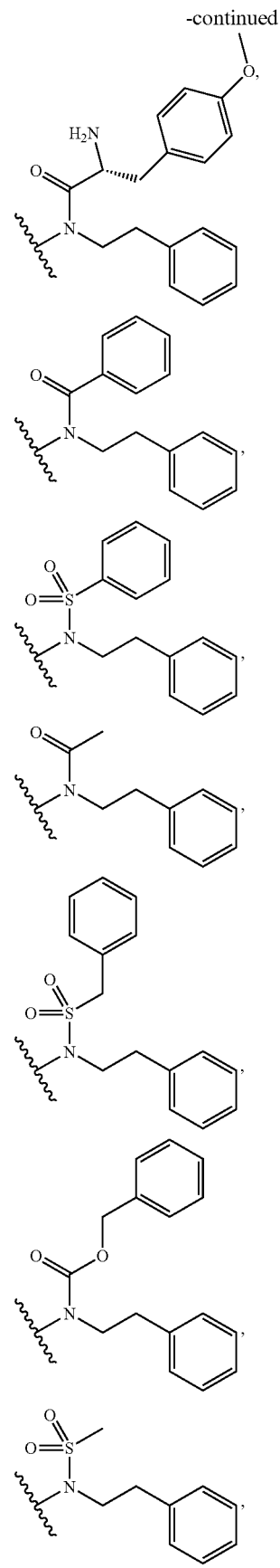

-continued
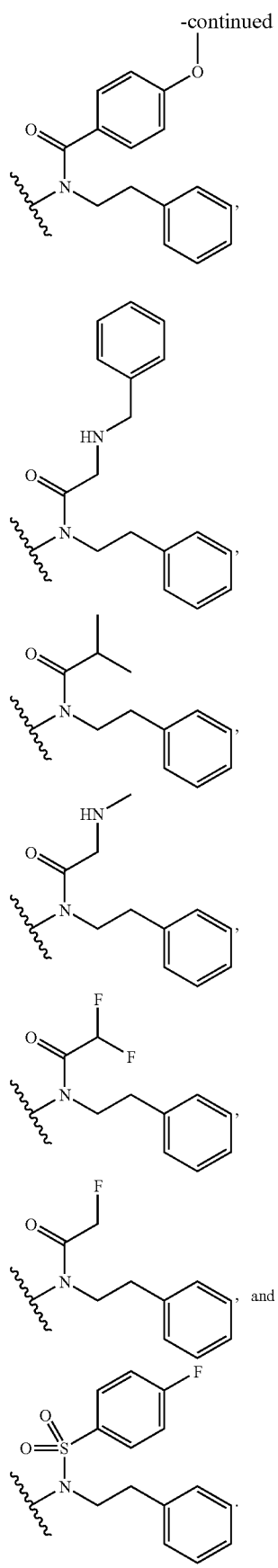
, and
The present invention also encompasses an isomer, enantiomer, diastereoisomer or tautomer of a compound represented by Formula I:
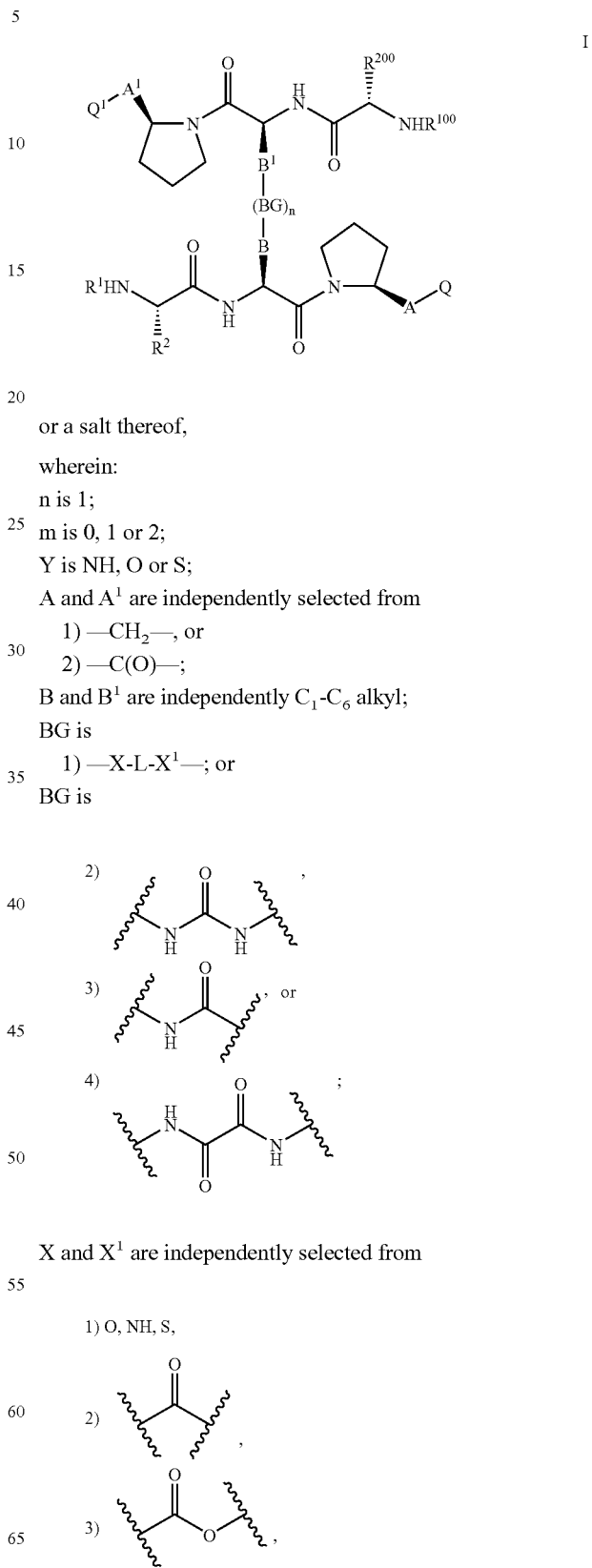
or a salt thereof,
wherein:
n is 1;
m is 0, 1 or 2;
Y is NH, O or S;
A and $A^1$ are independently selected from
1) —$CH_2$—, or
2) —C(O)—;
B and $B^1$ are independently $C_1$-$C_6$ alkyl;
BG is
1) —X-L-$X^1$—; or
BG is
2)
3) , or
4) ;
X and $X^1$ are independently selected from
1) O, NH, S,
2) ,
3) ,

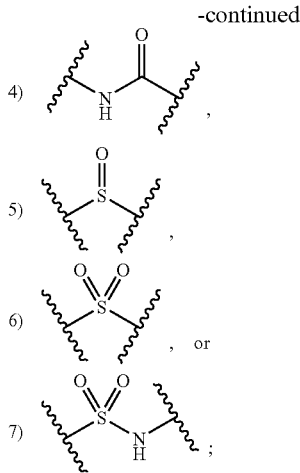

L is selected from:
1) —C$_1$-C$_{10}$ alkyl-,
2) —C$_2$-C$_6$ alkenyl-,
3) —C$_2$-C$_4$ alkynyl-,
4) —C$_3$-C$_7$ cycloalkyl-,
5) -phenyl-,
6) -biphenyl-,
7) -heteroaryl-,
8) -heterocyclyl-,
9) —C$_1$-C$_6$ alkyl-C$_2$-C$_6$ alkenyl)-C$_1$-C$_6$ alkyl-,
10) —C$_1$-C$_6$ alkyl-C$_2$-C$_4$ alkynyl)-C$_1$-C$_6$ alkyl-,
11) —C$_1$-C$_6$ alkyl-C$_3$-C$_7$ cycloalkyl)-C$_1$-C$_6$ alkyl-,
12) —C$_1$-C$_6$ alkyl-phenyl-C$_1$-C$_6$ alkyl-,
13) —C$_1$-C$_6$ alkyl-biphenyl-C$_1$C$_6$ alkyl-,
14) —C$_1$-C$_6$ alkyl-heteroarly-C$_1$-C$_6$ alkyl-,
15) —C$_1$-C$_6$ alkyl heterocyclyl-C$_1$-C$_6$ alkyl-, or
16) —C$_1$-C$_6$ alkyl-O—C$_1$-C$_6$ alkyl-;

R$^1$, R$_{100}$, R$^2$ and R$^{200}$ are independently selected from:
1) H, or
2) C$_1$-C$_6$ alkyl optionally substituted with one or more R$^6$ substituents;

Q and Q$^1$ are each independently NR$^4$R$^5$;
R$^4$ and R$^5$ are each independently
1) H,
2) haloalkyl,
3) C$_1$-C$_6$ alkyl,
4) C$_2$-C$_6$ alkenyl,
5) C$_2$-C$_4$ alkynyl,
6) C$_3$-C$_7$ cycloalkyl,
7) C$_3$-C$_7$ cycloalkenyl,
8) aryl,
9) heteroaryl,
10) heterocyclyl,
11) heterobicyclyl,
12) C(O)—R$^{11}$,
13) C(O)O—R$^{11}$,
14) C(=Y)NR$^8$R$^9$, or
15) S(O)$_2$—R$^{11}$, wherein the alkyl, alkenyl, alkynyl, cycloalkyl, and cycloalkenyl are optionally substituted with one or more R$^6$ substituents; and wherein the aryl, heteroaryl, heterocyclyl, and heterobicyclyl are optionally substituted with one or more R$^{10}$ substituents;

R$^6$ is
1) halogen,
2) NO$_2$,
3) CN,
4) haloalkyl,
5) C$_1$-C$_6$ alkyl,
6) C$_2$-C$_6$ alkenyl,
7) C$_2$-C$_4$ alkynyl,
8) C$_3$-C$_7$ cycloalkyl,
9) C$_3$-C$_7$ cycloalkenyl,
10) aryl,
11) heteroaryl,
12) heterocyclyl,
13) heterobicyclyl,
14) OR$^7$,
15) S(O)$_m$R$^7$,
16) NR$^8$R$^9$,
17) NR$^8$S(O)$_2$R$^{11}$,
18) COR$^7$,
19) C(O)OR$^7$,
20) CONR$^8$R$^9$,
21) S(O)$_2$NR$^8$R$^9$
22) OC(O)R$^7$,
23) OC(O)Y—R$^{11}$,
24) SC(O)R$^7$, or
25) NC(Y)NR$^8$R$^9$, wherein the aryl, heteroaryl, heterocyclyl, and heterobicyclyl is optionally substituted with one or more R$^{10}$ substituents;

R$^7$ is
1) H,
2) haloalkyl
3) C$_1$-C$_6$ alkyl,
4) C$_2$-C$_6$ alkenyl,
5) C$_2$-C$_4$ alkynyl,
6) C$_3$-C$_7$ cycloalkyl,
7) C$_3$-C$_7$ cycloalkenyl,
8) aryl,
9) heteroaryl,
10) heterocyclyl,
11) heterobicyclyl,
12) R$^8$R$^9$NC(=Y), or
13) C$_1$-C$_6$ alkly-C$_2$-C$_4$ alkenyl, or
14) C$_1$-C$_6$ alkly-C$_2$-C$_4$ alkynyl, wherein the alkyl, alkenyl, alkynyl, cycloalkyl, cycloalkenyl is optionally substituted with one or more R$^6$ substituents; and wherein the aryl, heteroaryl, heterocyclyl, and heterobicyclyl is optionally substituted with one or more R$^{10}$ substituents;

R$^8$ and R$^9$ are each independently
1) H,
2) haloalkyl,
3) C$_1$-C$_6$ alkyl,
4) C$_2$-C$_6$ alkenyl,
5) C$_2$-C$_4$ alkynyl,
6) C$_3$-C$_7$ cycloalkyl,
7) C$_3$-C$_7$ cycloalkenyl,
8) aryl,
9) heteroaryl,
10) heterocyclyl,
11) heterobicyclyl,
12) C(O)R$^{11}$,
13) C(O)Y—R$^{11}$, or
14) S(O)$_2$—R$^{11}$, wherein the alkyl, alkenyl, alkynyl, cycloalkyl, cycloalkenyl is optionally substituted with one or more R$^6$ substituents; and wherein the aryl, heteroaryl, heterocyclyl, and heterobicyclyl is optionally substituted with one or more $R^{10}$ substituents;

or $R^8$ and $R^9$ together with the nitrogen atom to which they are bonded form a five, six or seven membered heterocyclic ring optionally substituted with one or more $R^6$ substituents;
$R^{10}$ is
1) halogen,
2) $NO_2$,
3) CN,
4) $B(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^8R^9$,
13) $SR^7$,
14) $COR^7$,
15) $C(O)OR^7$,
16) $S(O)_mR^7$,
17) $CONR^8R^9$,
18) $S(O)_2NR^8R^9$,
19) aryl,
20) heteroaryl,
21) heterocyclyl, or
22) heterobicyclyl, wherein the alkyl, alkenyl, alkynyl, cycloalkyl, and cycloalkenyl is optionally substituted with one or more $R^6$ substituents; and
$R^{11}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl, wherein the alkyl, alkenyl, alkynyl, cycloalkyl, cycloalkenyl is optionally substituted with one or more $R^6$ substituents; and wherein the aryl, heteroaryl, heterocyclyl, and heterobicyclyl is optionally substituted with one or more $R^{10}$ substituents;

or a prodrug; or the compound of Formula I is labeled with a detectable label or an affinity tag.

In one subset of the compounds of Formula I, specifically compounds of Formula 1b, wherein n=1;
A and $A^1$ are both C=O;
B and $B^1$ are independently $C_1$-$C_4$ alkyl;
BG is —X-L-$X^1$; or
BG is

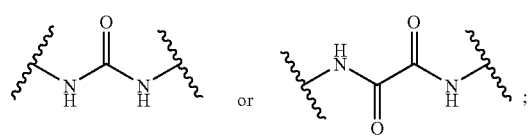

X and $X^1$ are independently selected from

1) O,

2) 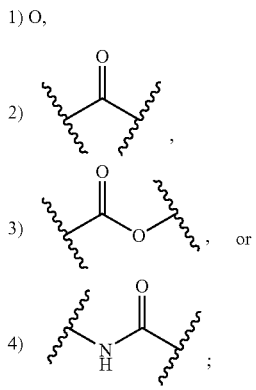, 3) (ester group), or 4) (amide group);

L is selected from
1) —$C_1$-$C_{10}$ alkyl-,
2) -phenyl-,
3) -biphenyl-,
4) —$CH_2$—($C_2$-$C_4$ alkynyl)-$CH_2$—,
5) —$CH_2$-phenyl-$CH_2$—,
6) —$CH_2$-biphenyl-$CH_2$—, or
7) —$C_1$-$C_6$ alkyl-O—$C_1$-$C_6$ alkyl-;
$R^1$, $R^{100}$, $R^2$ and $R^{200}$ are each independently $CH_3$;
Q and $Q_1$ are both $NR^4R^5$;
$R^4$ is H; and
$R^5$ is selected from:
1) ←$C_3$-$C_7$ cycloalkyl,
2) ←$C_3$-$C_7$ cycloalkenyl,
3) ←aryl,
4) ←heteroaryl,
5) ←heterocyclyl, or
6) ←heterobicyclyl.

In another subset of the compounds described above,
A and $A^1$ are both C=O,
B and $B^1$ are independently $C_1$-$C_4$ alkyl;
BG is —X-L-$X^1$; or
BG is

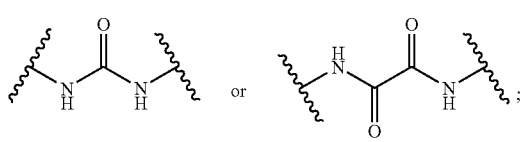

X and $X^1$ are both

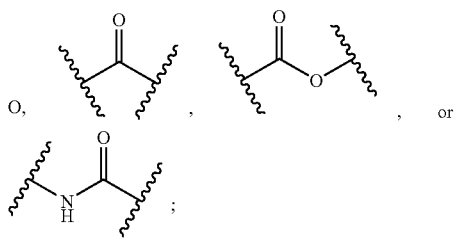

L is

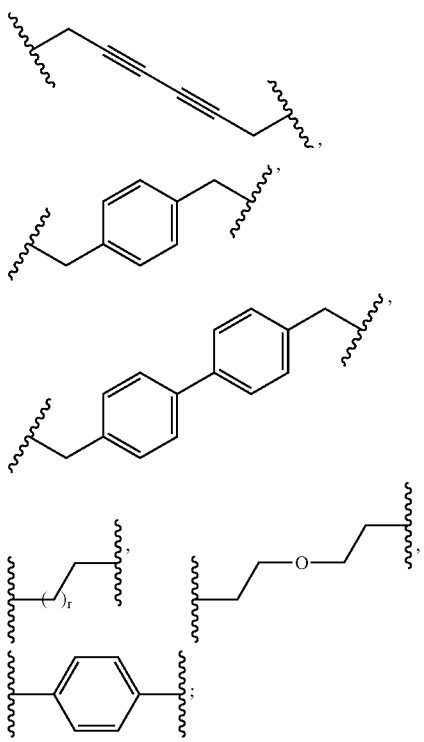

$R^1$, $R^{100}$, $R^2$ and $R^{200}$ are each independently $CH_3$;
Q and $Q^1$ are both $NR^4R^5$;
$R^4$ is H; and
$R^5$ is

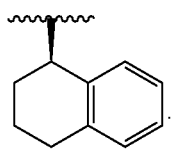

In an alternative subset of the compounds of Formula 1, specifically compounds of Formula 1a, wherein
n=1;
A and $A^1$ are both $CH_2$;
B and $B^1$ are independently $C_1$-$C_4$ alkyl;
BG is —X-L-$X^1$; or
BG is

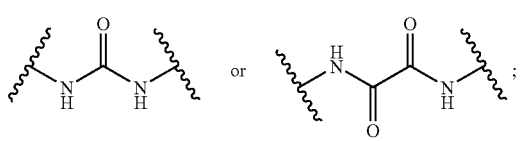

X and $X^1$ are independently selected from

1) O,

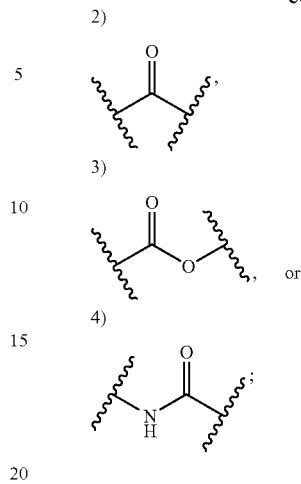

L is selected from
1) —$C_1$-$C_{10}$ alkyl-,
2) -phenyl-,
3) -biphenyl-.
4) —$CH_2$—($C_2$-$C_4$ alkynyl)$CH_2$—,
5) —$CH_2$-phenyl-$CH_2$—,
6) —$CH_2$-biphenyl-$CH_2$—, or
7) —$C_1$-$C_6$ alkyl-O—$C_1$-$C_6$ alkyl-;
$R^1$, $R^{100}$, $R^2$ and $R^{200}$ are each independently $CH_3$;
Q and $Q^1$ are both $NR^4R^5$;
$R^4$ is
1) H,
2) ←C(O)—$R^{11}$,
3) ←C(O)O—$R^{11}$, or
4) ←S(O)$_2$—$R^{11}$; and
$R^5$ is $C_1$-$C_6$ alkyl substituted with a phenyl;

wherein $R^{11}$ is as defined herein;
$R^{11}$ is
1) haloalkyl,
2) $C_1$-$C_6$ alkyl,
3) aryl,
4) heteroaryl, or
5) heterocyclyl, wherein the alkyl is optionally substituted with one or two $R^6$ substituents; and wherein the aryl, heteroaryl and heterocyclyl is substituted with one $R^{10}$ substituent;
wherein $R^6$ and $R^{10}$ are as defined herein;
$R^6$ is
1) halogen,
2) aryl, or
3) $NR^8R^9$, wherein the aryl is optionally substituted with one $R^{10}$ substituent:

wherein $R^8$, $R^9$ and $R^{10}$ are as defined herein;
$R^8$ and $R^9$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl, or
7) $C_3$-$C_7$ cycloalkenyl, wherein the alkyl, alkenyl, alkynyl, cycloalkyl, cycloalkenyl is optionally substituted with one or more $R^6$ substituents;

wherein the $R^6$ substituents are as defined herein; and
$R^{10}$ is
1) halogen,
2) $NO_2$,
3) CN,
4) haloalkyl,
5) $OR^7$,
6) $NR^8R^9$, or
7) $SR^7$;

wherein $R^7$, $R^8$, and $R^9$ are as defined herein.

In another subset of the aforesaid compounds,
n=1;
A and $A^1$ are both $CH_2$;
B and $B^1$ are independently $C_1$-$C_4$ alkyl;
BG is —X-L-$X^1$; or
BG is

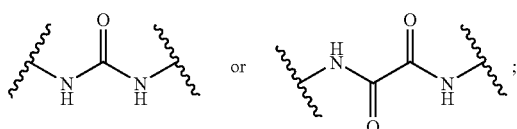

X and $X^1$ are independently selected from

1)
O,
2)

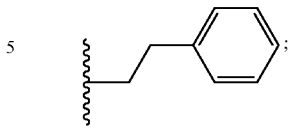

3)

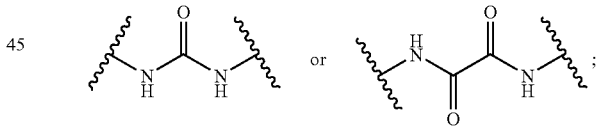

4)

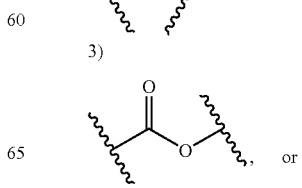

L is selected from
1) —$C_1$-$C_{10}$ alkyl-,
2) -phenyl-,
3) -biphenyl-,
4) —$CH_2$-phenyl-$C_2$-$C_4$ alkynyl)-$CH_2$—,
5) —$CH_2$-phenyl-$CH_2$—,
6) —$CH_2$biphenyl-$CH_2$—, or
7) —$C_1$-$C_6$ alkyl-O—$C_1$-$C_6$ alkyl-;
$R^1$, $R^{100}$, $R^2$ and $R^{200}$ are each independently $CH_3$;
Q and $Q^1$ are both $NR^4R^5$;
$R^4$ is
1) H,
2) C(O)—$R^{11}$,
3) C(O)O—$R^{11}$, or
4) $S(O)_2$—$R^{11}$; and $R^5$ is

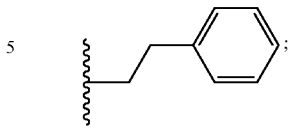

wherein $R^{11}$ is as defined herein;
$R^{11}$ is
1) haloalkyl,
2) $C_1$-$C_6$ alkyl optionally substituted with one or two $R^6$ substituents, or
3) phenyl optionally substituted with one $R^{10}$ substituent;

wherein the $R^6$ and the $R^{10}$ substituents are as defined herein;
$R^6$ is
1) halogen,
2) phenyl, or
3) $NR^8R^9$, wherein the phenyl is optionally substituted with one $R^{10}$ substituent;

wherein $R^8$ and $R^9$ are as defined herein;
$R^8$ and $R^9$ are each independently
1) H, or
2) $C_1$-$C_6$ alkyl, wherein the alkyl is optionally substituted with an aryl; and
$R^{10}$ is
1) halogen, or
2) $OC_1$-$C_6$ alkyl.

In still another subset of the aforesaid compounds,
n=1;
A and $A^1$ are both $CH_2$;
B and $B^1$ are independently $C_1$-$C_4$ alkyl;
BG is —X-L-$X^1$; or
BG is

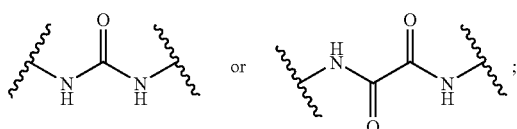

X and $X^1$ are independently selected from

1)
O,
2)

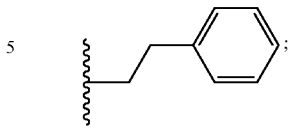

3)

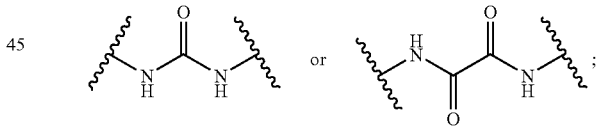, or

-continued
4) 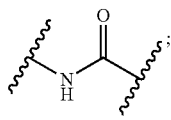
L is selected from
1) —C$_1$-C$_{10}$ alkyl-,
2) -phenyl-,
3) -biphenyl-,
4) —CH$_2$—(C$_2$-C$_4$ alkynyl)CH$_2$—,
5) —CH$_2$-phenyl-CH$_2$—,
6) —CH$_2$-biphenyl-CH$_2$—, or
7) —C$_1$-C$_6$ alkyl-O—C$_1$-C$_6$ alkyl-;
R$^1$, R$^{100}$, R$^2$ and R$^{200}$ are each independently CH$_3$; and
Q and Q$^1$ are both independently selected from:
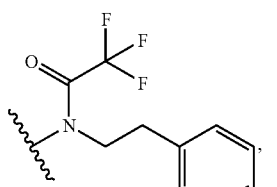
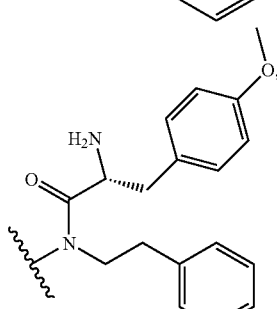
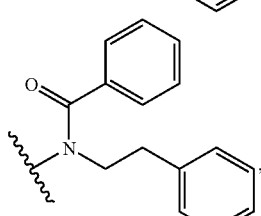
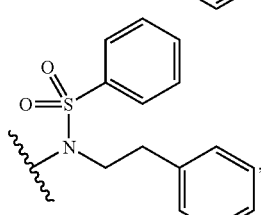
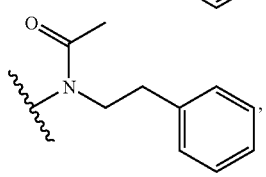
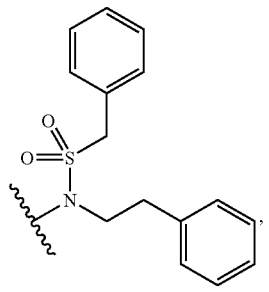
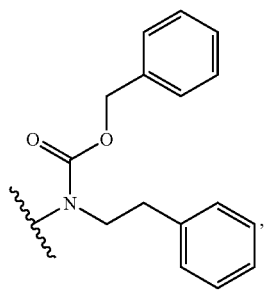
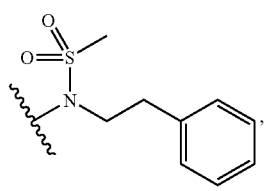
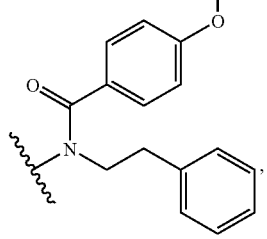
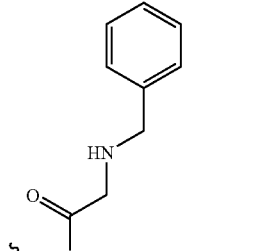
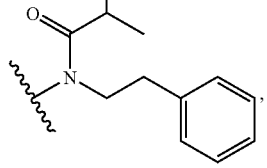

-continued

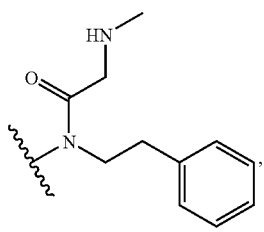

,

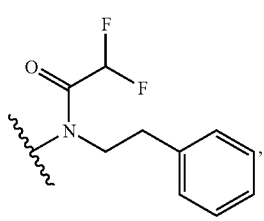

,

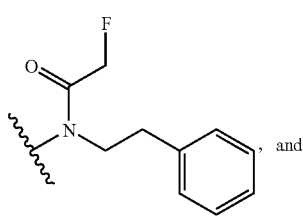

, and

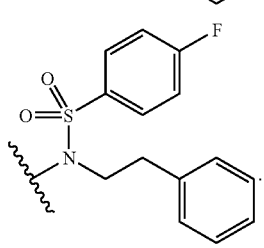

.

In one aspect of the present invention, the compounds of the present invention may also be represented by Formula 2 in which M1 and M2 represent independent BIR binding domains.

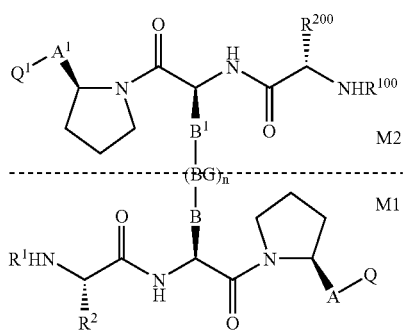

2 wherein n, $R^1$, $R^2$, $R^{100}$, $R^{200}$, A, $A^1$, Q, $Q^1$, B, $B^1$, and BG as defined herein, and the dotted line represents a hypothetical dividing line for comparing the substituents associated with M1 and M2.

In one subset of compounds of Formula 2, M1 is the same as M2.

In an alternative subset of compounds of Formula 2, M1 is different from M2.

In still another subset, B is the same as $B^1$.

In still another subset B is different from $B^1$.

One skilled in the art will recognize that when M1 and M2 are the same, the $R^1$, $R^2$, $R^4$, $R^5$, $R^6$, $R^7$, $R^8$, $R^9$, $R^{10}$, $R^{11}$, $R^{13}$, $R^{14}$, m, p, Y, A, Q, and B substituents in M1 have the same meaning as the $R^{100}$, $R^{200}$, $R^4$, $R^5$, $R^6$, $R^7$, $R^8$, $R^9$, $R^{10}$, $R^{11}$, $R^{13}$, $R^{14}$, m, p, Y, $A^1$, $Q^1$, and $B^1$ substituents repesctively in M2. When M1 and M2 are different, at least one $R^1$, $R^2$, $R^{100}$, $R^{200}$, $R^4$, $R^5$, $R^6$, $R^7$, $R^8$, $R^9$, $R^{10}$, $R^{11}$, $R^{13}$, $R^{14}$, m, p, Y, A, $A^1$, Q, $Q^1$, B, and $B^1$ substituent is different in either of M1 or M2.

Alternatively the substituents in M1 can be defined as $R^1$, $R^2$, $R^4$, $R^5$, $R^6$, $R^7$, $R^8$, $R^9$, $R^{10}$, $R^{11}$, $R^{13}$, $R^{14}$, m, p, Y, A, Q, and B, and those in M2 can be defined as $R^{100}$, $R^{200}$, $R^{400}$, $R^{500}$, $R^{600}$, $R^{700}$, $R^{800}$, $R^{900}$, $R^{1000}$, $R^{1100}$, $R^{1300}$, $R^{1400}$, $m^1$, $p^1$, $Y^1$, $A^1$, $Q^1$ and $B^1$ respectively. In the case where M1 and M2 are the same, the $R^1$, $R^2$, $R^4$, $R^5$, $R^6$, $R^7$, $R^8$, $R^9$, $R^{10}$, $R^{11}$, $R^{13}$, $R^{14}$, m, p, Y, A, Q, and B substituents in M1 have the same meanings as $R^{100}$, $R^{200}$, $R^{400}$, $R^{500}$, $R^{600}$, $R^{700}$, $R^{800}$, $R^{900}$, $R^{1000}$, $R^{1100}$, $R^{1300}$, $R^{1400}$ $m^1$ $p^1$, $y^1$, $A^1$, $Q^1$ and $B^1$ respectively in M2. In the case where M1 and M2 are different, at least one of the aforesaid substituents is different.

If any variable, such as $R^6$, $R^{600}$, $R^{10}$, $R^{1000}$ and the like, occurs more than one time in any constituent structure, the definition of the variable at each occurrence is independent at every other occurrence. If a substituent is itself substituted with one or more substituents, it is to be understood that that the one or more substituents may be attached to the same carbon atom or different carbon atoms. Combinations of substituents and variables defined herein are allowed only if they produce chemically stable compounds.

One skilled in the art will understand that substitution patterns and substituents on compounds of the present invention may be selected to provide compounds that are chemically stable and can be readily synthesized using the chemistry set forth in the examples and chemistry techniques well known in the art using readily available starting materials.

It is to be understood that many substituents or groups described herein have functional group equivalents, which means that the group or substituent may be replaced by another group or substituent that has similar electronic, hybridization or bonding properties.

Definitions

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, $C_1$-$C_{10}$ as in $C_1$-$C_{10}$ alkyl is defined as including groups having 1, 2, 3, 4, 5, 6, 7, 8, 9 or 10 carbons in a linear or branched arrangement, and $C_1$-$C_6$ as in $C_1$-$C_6$-alkyl is defined as including groups having 1, 2, 3, 4, 5 or 6 carbons in a linear or branched arrangement, and $C_1$-$C_4$ as in $C_1$-$C_4$ alkyl is defined as including groups having 1, 2, 3, or 4 carbons in a linear or branched arrangement. Examples of $C_1$-$C_6$-alkyl and $C_1$-$C_4$ alkyl as defined above include, but are not limited to, methyl, ethyl, n-propyl, i-propyl, n-butyl, t-butyl, i-butyl, pentyl and hexyl.

As used herein, the term, "alkenyl" is intended to mean unsaturated straight or branched chain hydrocarbon groups having the specified number of carbon atoms therein, and in which at least two of the carbon atoms are bonded to each other by a double bond, and having either E or Z regeochemistry and combinations thereof. For example, $C_2$-$C_6$ as in $C_2$-$C_6$ alkenyl is defined as including groups having 1, 2, 3, 4, 5, or 6 carbons in a linear or branched arrangement, at least two of the carbon atoms being bonded together by a double bond. Examples of $C_2$-$C_6$ alkenyl include ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example $C_2$-$C_4$ as in $C_2$-$C_4$ alkynyl is defined as including groups having 2, 3, or 4 carbon atoms in a chain, at least two of the carbon atoms being bonded together by a triple bond. Examples of such alynyls include ethynyl, 1-propynyl, 2-propynyl and the like.

As used herein, the term "cycloalkyl" is intended to mean a monocyclic saturated aliphatic hydrocarbon group having the specified number of carbon atoms therein, for example, $C_3$-$C_7$ as in $C_3$-$C_7$ cycloalkyl is defined as including groups having 3, 4, 5, 6, or 7 carbons in a monocyclic arrangement. Examples of $C_3$-$C_7$ cycloalkyl as defined above include, but are not limited to, cyclopropyl, cyclobutyl, cyclopentyl, cyclohexyl and cycloheptyl.

As used herein, the term "cycloalkenyl" is intended to mean a monocyclic saturated aliphatic hydrocarbon group having the specified number of carbon atoms therein, for example, $C_3$-$C_7$ as in $C_3$-$C_7$ cycloalkenyl is defined as including groups having 3, 4, 5, 6, or 7 carbons in a monocyclic arrangement. Examples of $C_3$-$C_7$ cycloalkenyl as defined above include, but are not limited to, cyclopentenyl, and cyclohexenyl.

As used herein, the term "halo" or "halogen" is intended to mean fluorine, chlorine, bromine and iodine.

As used herein, the term "haloalkyl" is intended to mean an alkyl as defined above, in which each hydrogen atom may be successively replaced by a halogen atom. Examples of haloalkyls include, but are not limited to, $CH_2F$, $CHF_2$ and $CF_3$.

As used herein, the term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The fused aryls may be connected to another group either at a suitable position on the cycloalkyl ring or the aromatic ring. For example:

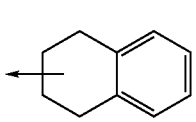 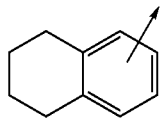

-continued

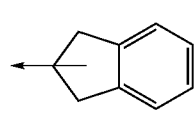 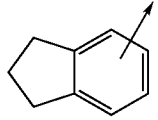

Arrowed lines drawn from the ring system indicate that the bond may be attached to any of the suitable ring atoms.

As used herein, the term "biphenyl" is intended to mean two phenyl groups bonded together at any one of the available sites on the phenyl ring. The biphenyl may be covalently bonded to other groups from any available position on the phenyl rings. For example:

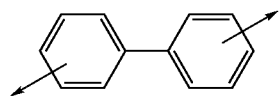

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, and fluoroscene derivatives such as:

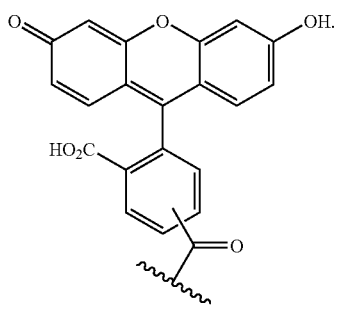

As used herein, the term "heterocycle", "heterocyclic" or "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, pyrazolinyl, and

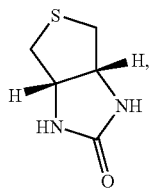

As used herein, the term "heterobicycle" either alone or in combination with another radical, is intended to mean a heterocycle as defined above fused to another cycle, be it a heterocycle, an aryl or any other cycle defined herein. Examples of such heterobicycles include, but are not limited to, coumarin, benzo[d][1,3]dioxole, 2,3-dihydrobenzo[b][1,4]dioxine and 3,4-dihydro-2H-benzo[b][1,4]dioepine.

Examples of

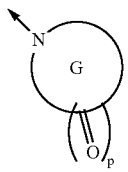

wherein G is a 5, 6 or 7 membered ring which optionally incorporates one or more heteroatoms selected from S, N or O and p is 1 or 2, and is optionally substituted with one or more $R^{12}$ substituents, include, but are not limited to:

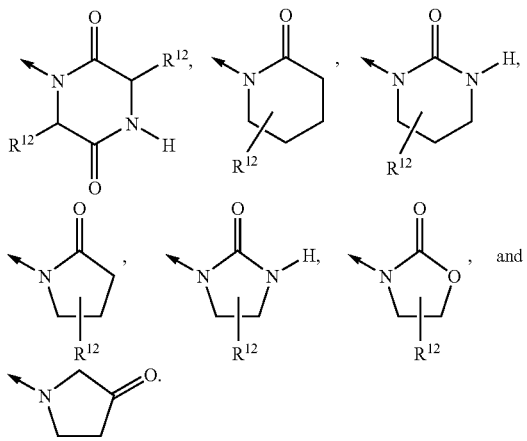

As used herein, the term "heteroatom" is intended to mean O, S or N.

As used herein, the term "detectable label" is intended to mean a group that may be linked to a compound of the present invention to produce a probe or to an IAP BIR domain, such that when the probe is associated with the BIR domain, the label allows either direct or indirect recognition of the probe so that it may be detected, measured and quantified.

As used herein, the term "affinity tag" is intended to mean a ligand or group, which is linked to either a compound of the present invention or to an IAP BIR domain to allow another compound to be extracted from a solution to which the ligand or group is attached.

As used herein, the term "probe" is intended to mean a compound of Formula I which is labeled with either a detectable label or an affinity tag, and which is capable of binding, either covalently or non-covalently, to an IAP BIR domain. When, for example, the probe is non-covalently bound, it may be displaced by a test compound. When, for example, the probe is bound covalently, it may be used to form cross-linked adducts, which may be quantified and inhibited by a test compound.

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

If the substituents themselves are incompatible with the synthetic methods of the present invention, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Examples of protecting groups used throughout include, but are not limited to Fmoc, Bn, Boc, CBz and $COCF_3$. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

Abbreviations for α-amino acids used throughout are as follows:

| Amino acid | Abbreviation |
| --- | --- |
| α-Amino butyric acid | Abu |
| Alanine | Ala |
| Arginine | Arg |
| Aspartic acid | Asp |
| Asparagine | Asn |
| Cysteine | Cys |
| Glutamic acid | Glu |
| Glutamine | Gln |
| Glycine | Gly |
| Isoleucine | Ile |
| Histidine | His |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

As used herein, the term "residue" when referring to α-amino acids is intended to mean a radical derived from the corresponding α-amino acid by eliminating the hydroxyl of the carboxy group and one hydrogen of the α-amino group. For example, the terms Gln, Ala, Gly, Ile, Arg, Asp, Phe, Ser, Leu, Cys, Asn, and Tyr represent the residues of L-glutamine, L-alanine, glycine, L-isoleucine, L-arginine, L-aspartic acid, L-phenylalanine, L-serine, L-leucine, L-cysteine, L-asparagine, and L-tyrosine, respectively.

As used herein, the term "subject" is intended to mean humans and non-human mammals such as primates, cats, dogs, swine, cattle, sheep, goats, horses, rabbits, rats, mice and the like.

As used herein, the term "prodrug" is intended to mean a compound that may be converted under physiological conditions or by solvolysis to a biologically active compound of the present invention. Thus. the term "prodrug" refers to a precursor of a compound of the invention that is pharmaceutically acceptable. A prodrug may be inactive or display limited activity when administered to a subject in need thereof, but is converted in vivo to an active compound of the present invention. Typically, prodrugs are transformed in vivo to yield the compound of the invention, for example, by hydrolysis in blood or other organs by enzymatic processing. The prodrug compound often offers advantages of solubility, tissue compatibility or delayed release in the subject (see, Bundgard, H., Design of Prodrugs (1985), pp. 7-9, 21-24 (Elsevier, Amsterdam). The definition of prodrug includes any covalently bonded carriers which release the active compound of the invention in vivo when such prodrug is administered to a subject. Prodrugs of a compound of the present invention may be prepared by modifying functional groups present in the compound of the invention in such a way that the modifications are cleaved, either in routine manipulation or in vivo, to a parent compound of the invention.

As used herein, the term "pharmaceutically acceptable carrier, diluent or excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethyleneglycol matrix, which is acceptable for use in the subject, preferably humans.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

As used herein, the term "BIR domain binding" is intended to mean the action of a compound of the present invention upon an IAP BIR domain, which blocks or diminishes the binding of IAPs to BIR binding proteins or is involved in displacing BIR binding proteins from an IAP. Examples of BIR binding proteins include, but are not limited to, caspases and mitochondrially derived BIR binding proteins such as Smac, Omi/WTR2A and the like.

As used herein, the term "insufficient apoptosis" is intended to mean a state wherein a disease is caused or continues because cells deleterious to the subject have not apoptosed. This includes, but is not limited to, cancer cells that survive in a subject without treatment, cancer cells that survive in a subject during or following anti-cancer treatment, or immune cells whose action is deleterious to the subject, and includes, neutrophils, monocytes and auto-reactive T-cells.

As used herein, the term "therapeutically effective amount" is intended to mean an amount of a compound of Formula I which, when administered to a subject is sufficient to effect treatment for a disease-state associated with insufficient apoptosis. The amount of the compound of Formula I will vary depending on the compound, the condition and its severity, and the age of the subject to be treated, but can be determined routinely by one of ordinary skill in the art having regard to his own knowledge and to this disclosure.

As used herein, the term "treating" or "treatment" is intended to mean treatment of a disease-state associated with insufficient apoptosis, as disclosed herein, in a subject, and includes: (i) preventing a disease or condition associated with insufficient apoptosis from occurring in a subject, in particular, when such mammal is predisposed to the disease or condition but has not yet been diagnosed as having it; (ii) inhibiting a disease or condition associated with insufficient apoptosis, i.e., arresting its development; or (iii) relieving a disease or condition associated with insufficient apoptosis, i.e., causing regression of the condition.

As used herein, the term "treating cancer" is intended to mean the administration of a pharmaceutical composition of the present invention to a subject, preferably a human, which is afflicted with cancer to cause an alleviation of the cancer by killing, inhibiting the growth, or inhibiting the metastasis of the cancer cells.

As used herein, the term "preventing disease" is intended to mean, in the case of cancer, the post-surgical, post-chemotherapy or post-radiotherapy administration of a pharmaceutical composition of the present invention to a subject, preferably a human, which was afflicted with cancer to prevent the regrowth of the cancer by killing, inhibiting the growth, or inhibiting the metastasis of any remaining cancer cells. Also included in this definition is the prevention of prosurvival conditions that lead to diseases such as asthma, MS and the like.

As used herein, the term "synergistic effect" is intended to mean that the effect achieved with the combination of the compounds of the present invention and either the chemotherapeutic agents or death receptor agonists of the invention is greater than the effect which is obtained with only one of the compounds, agents or agonists, or advantageously the effect which is obtained with the combination of the above compounds, agents or agonists is greater than the addition of the effects obtained with each of the compounds, agents or agonists used separately. Such synergy enables smaller doses to be given.

As used herein. the term "apoptosis" or "programmed cell death" is intended to mean the regulated process of cell death wherein a dying cell displays a set of well-characterized biochemical hallmarks that include cell membrane blebbing, cell soma shrinkage, chromatin condensation, and DNA laddering, as well as any caspase-mediated cell death.

As used herein, the term "BIR domain" or "BIR" are used interchangeably throughout and are intended to mean a domain which is characterized by a number of invariant amino acid residue including conserved cysteines and one conserved hisitidine residue within the sequence Cys-$(Xaa1)_2$ Cys-$(Xaa1)_{16}$His-$(Xaa1)_{6-8}$Cys. Typically, the amino acid sequence of the consensus sequence is: Xaa1-Xaa1-Xaa1-Arg-Leu-Xaa1-Thr-Phe-Xaa1-Xaa1-Trp-Pro-Xaa2-Xaa1-Xaa1-Xaa2-Xaa2-Xaa1-Xaa1-Xaa1-Xaa1-Leu-Ala-Xaa1-Ala-Gly-Phe-Tyr-Tyr-Xaa1-Gly-Xaa1-Xaa1-Asp-Xaa1-Val-Xaa1-Cys-Phe-Xaa1-Cys-Xaa1-Xaa1-Xaa1-Xaa1-Xaa1-Xaa1-Trp-Xaa1-Xaa1-Xaa1-Asp-Xaa1-Xaa1-Xaa1-Xaa1-Xaa1-His-Xaa-1-Xaa1-Xaa1-Xaa1-Pro-Xaa1-Cys-Xaa1-Phe-Val, wherein Xaa1 is any amino acid and Xaa2 is any amino acid or is absent. Preferably the sequence is substantially identical to one of the BIR domain sequences provided for XIAP, HIAP1, or HIAP2 herein.

The BIR domain residues are listed below (see Genome Biology (2001) 1-10):

|  | XIAP | HIAP-1 | HIAP-2 |
| --- | --- | --- | --- |
| BIR1 | 21-93 | 41-113 | 24-96 |
| BIR2 | 159-230 | 179-250 | 164-235 |
| BIR3 | 258-330 | 264-336 | 250-322 |
| Seq. # | P98170 | XP-006266 | XP-006267 |

As used herein, the term "ring zinc finger" or "RZF" is intended to mean a domain having the amino acid sequence of the consensus sequence: Glu-Xaa1-Xaa1-Xaa1-Xaa1-Xaa1-Xaa-1-Xaa2-Xaa1-Xaa1-Xaa1-Cys-Lys-Xaa3-Cys-Met-Xaa1-Xaa1-Xaa1-Xaa1-Xaa1-Xaa3-X-aa1-Phe-Xaa1-Pro-Cys-Gly-His-Xaa1-Xaa1-Cys-Xaa1-Xaa1-Cys-Ala-Xaa1-Xaa-1-Xaa1-Xaa1-Xaa1-Cys-Pro-Xaa1-Cys, wherein Xaa1 is any amino acid, Xaa2 is Glu or Asp, and Xaa3 is Val or Ile.

As used herein, the term "IAP" is intended to mean a polypeptide or protein, or fragment thereof, encoded by an IAP gene. Examples of IAPs include, but are not limited to, human or mouse NAIP (Birc 1), HIAP-1 (cIAP2, Birc 3), HIAP-2 (cIAP1, Birc 2), XIAP (Birc 4), surviving (Birc 5), livin (ML-IAP, Birc 7), ILP-2 (Birc 8) and Apollon/BRUCE (Birc 6) (see for example U.S. Pat. Nos. 6,107,041; 6,133, 437; 6,156,535; 6,541,457; 6,656,704; 6,689,562; Deveraux and Reed, Genes Dev. 13, 239-252, 1999; Kasof and Gomes, J. Biol. Chem., 276, 3238-3246, 2001; Vucic et al., Curr. Biol. 10, 1359-1366, 2000; Ashab et al. FEBS Left., 495, 56-60, 2001, the contents of which are hereby incorporated by reference).

As used herein, the term "IAP gene" is intended to mean a gene encoding a polypeptide having at least one BIR domain and which is capable of modulating (inhibiting or enhancing) apoptosis in a cell or tissue. The IAP gene is a gene having about 50% or greater nucleotide sequence identity to at least one of human or mouse NAIP (Birc 1), HIAP-1 (cIAP2, Birc 3), HIAP-2 (cIAP1, Birc 2), XIAP (Birc 4), surviving (Birc 5), livin (ML-IAP, Birc 7), ILP-2 (Birc 8) and Apollon/ BRUCE (Birc 6). The region of sequence over which identity is measured is a region encoding at least one BIR domain and a ring zinc finger domain. Mammalian IAP genes include nucleotide sequences isolated from any mammalian source.

As used herein, the term "$IC_{50}$" is intended to mean an amount, concentration or dosage of a particular compound of the present invention that achieves a 50% inhibition of a maximal response, such as displacement of maximal fluorescent probe binding in an assay that measures such response.

As used herein, the term "$EC_{50}$" is intended to mean an amount, concentration or dosage of a particular compound of the present invention that achieves a 50% inhibition of cell survival.

As used herein, the term "modulate" or "modulating" is intended to mean the treatment, prevention, suppression, enhancement or induction of a function or condition using the compounds of the present invention. For example, the compounds of the present invention can modulate IAP function in a subject, thereby enhancing apoptosis by significantly reducing, or essentially eliminating the interaction of activated apoptotic proteins, such as caspase-3, 7 and 9, with the BIR domains of mammalian IAPs or by inducing the loss of IAP protein in a cell.

As used herein, the term "enhancing apoptosis" is intended to mean increasing the number of cells that apoptose in a given cell population either in vitro or in vivo. Examples of cell populations include, but are not limited to, ovarian cancer cells, colon cancer cells, breast cancer cells, lung cancer cells, pancreatic cancer cells, or T cells and the like. It will be appreciated that the degree of apoptosis enhancement provided by an apoptosis-enhancing compound of the present invention in a given assay will vary, but that one skilled in the art can determine the statistically significant change in the level of apoptosis that identifies a compound that enhances apoptosis otherwise limited by an IAP. Preferably "enhancing apoptosis" means that the increase in the number of cells undergoing apoptosis is at least 25%, more preferably the increase is 50%, and most preferably the increase is at least one-fold. Preferably the sample monitored is a sample of cells that normally undergo insufficient apoptosis (i.e., cancer cells). Methods for detecting the changes in the level of apoptosis (i.e., enhancement or reduction) are described in the Examples and include methods that quantitate the fragmentation of DNA, methods that quantitate the translocation phosphatoylserine from the cytoplasmic to the extracellular side of the membrane, determination of activation of the caspases and methods quantitate the release of cytochrome C and the apoptosis inhibitory factor into the cytoplasm by mitochondria.

As used herein, the term "proliferative disease" or "proliferative disorder" is intended to mean a disease that is caused by or results in inappropriately high levels of cell division, inappropriately low levels of apoptosis, or both. For example, cancers such as lymphoma, leukemia, melanoma, ovarian cancer, breast cancer, pancreatic cancer, and lung cancer, and autoimmune disorders are all examples of proliferative diseases.

As used herein, the term "death receptor agonist" is intended to mean an agent capable of stimulating by direct or indirect contact the pro apoptotic response mediated by the death-receptors. For example, an agonist TRAIL receptor Antibody would bind to TRAIL receptor (S) and trigger an apoptotic response. On the other hand, other agent such as interferon-a could trigger the release of endogeneous TRAIL and/or up regulate the TRAIL receptors in such a way that the cell pro-apoptotic response is amplified.

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present invention is intended to include all such possible isomers, as well as, their racemic and optically pure forms. Optically active (+) and (−), (R)- and (S)-, or (D)- and (L)- isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist in Zwitterionic form and the present invention includes Zwitterionic forms of these compounds and mixtures thereof.

Utilities

The compounds of the present invention are useful as IAP BIR domain binding compounds and as such the compounds, compositions and method of the present invention include application to the cells or subjects afflicted with or having a predisposition towards developing a particular disease state, which is characterized by insufficient apoptosis. Thus, the compounds, compositions and methods of the present invention are used to treat cellular proliferative diseases/disorders, which include, but are not limited to, i) cancer, ii) autoimmune disease, iii) inflammatory disorders, iv) proliferation induced post medical procedures, including, but not limited to, surgery, angioplasty, and the like.

The compounds of the present invention may also be useful in the treatment of diseases in which there is a defect in the programmed cell-death or the apoptotic machinery (TRAIL, FAS, apoptosome), such as multiple sclerosis, asthma, artherosclerosis, inflammation, autoimmunity and the like.

The treatment involves administration to a subject in need thereof a compound of the present invention or a pharmaceutically acceptable salt thereof, or a pharmaceutical composition comprising a pharmaceutical carrier and a therapeutically effective amount of a compound of the present invention, or a pharmaceutically acceptable salt thereof.

In particular, the compounds, compositions and methods of the present invention are useful for the treatment of cancer including solid tumors such as skin, breast, brain, lung, testicular carcinomas, and the like. Cancers that may be treated by the compounds, compositions and methods of the invention include, but are not limited to the following:

| Tissue | Example |
| --- | --- |
| Adrenal gland | neuroblastoma |
| Bone | osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors |
| Cardiac | sarcoma (angiosarcoma, fibrosarcoma, rhabdomyosarcoma, liposarcoma), myxoma, rhabdomyoma, fibroma, lipoma and teratoma |
| Gastrointestinal | esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) |
| Genitourinary tract | kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) |
| Gynecological | uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma) |
| Hematologic | blood (myeloid leukemia [acute and chronic], acute lymphoblastic leukemia, chronic lymphocytic leukemia, myeloproliferative diseases, multiple myeloma, myelodysplastic |

-continued

| Tissue | Example |
|---|---|
| | syndrome), Hodgkin's disease, non-Hodgkin's lymphoma [malignant lymphoma] |
| Liver | hepatoma (hepatocellular carcinoma), cholangiocarcinoma, hepatoblastoma, angiosarcoma, hepatocellular adenoma, hemangloma |
| Lung | bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma |
| Nervous system | skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma) |
| Skin | malignant melanoma, basal cell carcinoma, squamous cell carcinoma, Karposi's sarcoma, moles dysplastic nevi, lipoma, angioma, dermatofibroma, keloids |

The compounds of the present invention, or their pharmaceutically acceptable salts or their prodrugs, may be administered in pure form or in an appropriate pharmaceutical composition, and can be carried out via any of the accepted modes of Galenic pharmaceutical practice.

The pharmaceutical compositions of the present invention can be prepared by admixing a compound of the present invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral (subcutaneous injections, intravenous, intramuscular, intrasternal injection or infusion techniques), sublingual, ocular, rectal, vaginal, and intranasal. Pharmaceutical compositions of the present invention are formulated so as to allow the active ingredients contained therein to be bioavailable upon administration of the composition to a subject. Compositions that will be administered to a subject or patient take the form of one or more dosage units, where for example, a tablet may be a single dosage unit, and a container of a compound of the present invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the present invention, or a pharmaceutically acceptable salt thereof, for treatment of a disease-state as described above.

A pharmaceutical composition of the present invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example inhalatory administration.

For oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil such as soybean or vegetable oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the present invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

A liquid pharmaceutical composition of the present invention used for either parenteral or oral administration should contain an amount of a compound of the present invention such that a suitable dosage will be obtained. Typically, this amount is at least 0.01% of a compound of the present invention in the composition. When intended for oral administration, this amount may be varied to be between 0.1 and about 70% of the weight of the composition. For parenteral usage, compositions and preparations according to the present invention are prepared so that a parenteral dosage unit contains between 0.01 to 1% by weight of the compound of the present invention.

The pharmaceutical composition of the present invention may be used for topical administration, in which case the carrier may suitably comprise a solution, emulsion, ointment or gel base. The base, for example, may comprise one or more of the following: petroleum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the present invention from about 0.1 to about 10% w/v (weight per unit volume).

The pharmaceutical composition of the present invention may be used for rectal administration to treat for example, colon cancer, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the present invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present invention in solid or liquid form may include an agent that binds to the compound of the present invention and thereby assists in the delivery of the compound. Suitable agents that may act in this capacity include, but are not limited to, a monoclonal or polyclonal antibody, a protein or a liposome.

The pharmaceutical composition of the present invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the present invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the present invention may be prepared by methodology well known in the pharmaceutical art. For example, a pharmaceutical composition intended to be administered by injection can be prepared by admixing a compound of the present invention with sterile, distilled water so as to form a solution. A surfactant may be added to facilitate the formation of a homogeneous solution or suspension. Surfactants are compounds that non-covalently interact with the compound of the present invention so as to facilitate dissolution or homogeneous suspension of the compound in the aqueous delivery system.

The compounds of the present invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose may be from about 0.1 mg to about 40 mg/kg of body weight per day or twice per day of a compound of the present invention, or a pharmaceutically acceptable salt thereof.

Combination Therapy

The compounds of the present invention, or pharmaceutically acceptable salts thereof, may also be administered simultaneously with, prior to, or after administration of one or more of the therapeutic agents described below. Such combination therapy may include administration of a single pharmaceutical dosage formulation which contains a compound of the present invention and one or more additional agents given below, as well as administration of the compound of the present invention and each additional agent in its own separate pharmaceutical dosage formulation. For example, a compound of the present invention and a chemotherapeutic agent, such as taxol (paclitaxel), taxotere, etoposide, cisplatin, vincristine, vinblastine, and the like, can be administered to the patient either together in a single dosage composition, or each agent administered in separate oral dosage formulations or via intravenous injection. Where separate dosage formulations are used, the compounds of the present invention and one or more additional agents can be administered at essentially the same time, i.e., concurrently, or at separately staggered times, i.e., sequentially; combination therapy is understood to include all these regimens. In addition, these compounds may synergize with molecules that may stimulate the death receptor apoptotic pathway through a direct or indirect manner, as for example, the compounds of the present invention may be used in combination with soluble TRAIL or any agent that can cause an increase in circulating level of TRAIL, such as interferon-alpha, BCG, or though radiation.

Thus, the present invention also encompasses the use of the compounds of the present invention in combination with radiation therapy or one or more additional agents such as those described in WO 03/099211 (PCT/US03/15861), which is hereby incorporated by reference.

Examples of such additional agents include, but are not limited to the following:

a) an estrogen receptor modulator,
b) an androgen receptor modulator,
c) retinoid receptor modulator,
d) a cytotoxic agent,
e) an antiproliferative agent,
f) a prenyl-protein transferase inhibitor,
g) an HMG-CoA reductase inhibitor,
h) an HIV protease inhibitor,
i) a reverse transcriptase inhibitor,
k) an angiogenesis inhibitor, l) a PPAR-γ agonist,
m) a PPAR-δ agonist,
n) an inhibitor of inherent multidrug resistance,
o) an anti-emetic agent,
p) an agent useful in the treatment of anemia,
q) agents useful in the treatment of neutropenia,
r) an immunologic-enhancing drug.
s) a proteasome inhibitor such as Velcade and MG132 (7-Leu-Leu-aldehyde) (see He at al. in Oncogene (2004) 23, 2554-2558);
t) an HDAC inhibitor, such as sodium butyrate, phenyl butyrate, hydroamic acids, cyclin tetrapeptide and the like (see Rosato et al,. Molecular Cancer Therapeutics 2003, 1273-1284);
u) an inhibitor of the chymotrypsin-like activity in the proteasome;
v) E3 ligase inhibitors;
w) a modulator of the immune system such as, but not limited to, interferon-alpha or BCG that can induce the release of cytokines, such as the interleukins, TNF, or induce release of death receptor ligands such as TRAIL;
x) a modulator of death receptors TRAIL and TRAIL receptor agonists such as the humanized antibodies HGS-ETR1 and HGS-ETR2; and
or in combination or sequentially with radiation therapy, so as to treat the cancer.

Additional combinations may also include agents which reduce the toxicity of the aforesaid agents, such as hepatic toxicity, neuronal toxicity, nephrotoxicity and the like.

In one example, co-administration of one of the compounds of Formula I of the present invention with a death receptor agonist such as TRAIL, such as a small molecule or an antibody that mimics TRAIL may cause an advantageous synergistic effect. Moreover, the compounds of the present invention may be used in combination with any compounds that cause an increase in circulating levels of TRAIL.

Vinca Alkaloids and Related Compounds

Vinca alkaloids that can be used in combination with the nucleobase oligomers of the invention to treat cancer and other neoplasms include vincristine, vinblastine, vindesine, vinflunine, vinorelbine, and anhydrovinblastine.

Dolastatins are oligopeptides that primarily interfere with tubulin at the vinca alkaloid binding domain. These compounds can also be used in combination with the compounds of the invention to treat cancer and other neoplasms. Dolastatins include dolastatin-10 (NCS 376128), dolastatin-15, ILX651, TZT-1027, symplostatin 1, symplostatin 3, and LU103793 (cemadotin).

Cryptophycins (e.g., cryptophycin 1 and cryptophycin 52 (LY355703)) bind tubulin within the vinca alkaloid-binding domain and induce G2/M arrest and apoptosis. Any of these compounds can be used in combination with the compounds of the invention to treat cancer and other neoplasms.

Other microtubule disrupting compounds that can be used in conjunction with the compounds of the invention to treat cancer and other neoplasms are described in U.S. Pat. Nos. 6,458,765; 6,433,187; 6,323,315; 6,258,841; 6,143,721; 6,127,377; 6,103,698; 6,023,626; 5,985,837; 5,965,537; 5,955,423; 5,952,298; 5,939,527; 5,886,025; 5,831,002; 5,741,892; 5,665,860; 5,654,399; 5,635,483; 5,599,902; 5,530,097; 5,521,284; 5,504,191; 4,879,278; and 4,816,444, and U.S. patent application Publication Nos. 2003/0153505 A1; 2003/0083263 A1; and 2003/0055002 A1, each of which is hereby incorporated by reference.

Taxanes and Other Micortubule Stabilizing Compounds

Taxanes such as paclitaxel, doxetaxel, RPR 109881A, SB-T-1213, SB-T-1250, SB-T-101187, BMS-275183, BRT 216, DJ-927, MAC-321, IDN5109, and IDN5390 can be used in combination with the compounds of the invention to treat cancer and other neoplasms. Taxane analogs (e.g., BMS-184476, BMS-188797) and functionally related non-taxanes (e.g., epothilones (e.g., epothilone A, epothilone B (EP0906), deoxyepothilone B, and epothilone B lactam (BMS-247550)), eleutherobin, discodermolide, 2-epi-discodermolide, 2-des-methyldiscodermolide, 5-hydroxymethyldiscoder-molide, 19-des-aminocarbonyidiscodermolide, 9(13)-cyclodiscodermolide, and laulimalide) can also be used in the methods and compositions of the invention.

Other microtubule stabilizing compounds that can be used in combination with the compounds of the invention to treat cancer and other neoplasms are described in U.S. Pat. Nos. 6,624,317; 6,610,736; 6,605,599; 6,589,968; 6,583,290; 6,576,658; 6,515,017; 6,531,497; 6,500,858; 6,498,257; 6,495,594; 6,489,314; 6,458,976; 6,441,186; 6,441,025; 6,414,015; 6,387,927; 6,380,395; 6,380,394; 6,362,217; 6,359,140; 6,306,893; 6,302,838; 6,300,355; 6,291,690; 6,291,684; 6,268,381; 6,262,107; 6,262,094; 6,147,234; 6,136,808; 6,127,406; 6,100,411; 6,096,909; 6,025,385; 6,011,056; 5,965,718; 5,955,489; 5,919,815; 5,912,263; 5,840,750; 5,821,263; 5,767,297; 5,728,725; 5,721,268; 5,719,177; 5,714,513; 5,587,489; 5,473,057; 5,407,674; 5,250,722; 5,010,099; and 4,939,168; and U.S. patent application Publication Nos. 2003/0186965 A1; 2003/0176710 A1; 2003/0176473 A1; 2003/0144523 A1; 2003/0134883 A1; 2003/0087888 A1; 2003/0060623 A1; 2003/0045711 A1; 2003/0023082 A1; 2002/0198256 A1; 2002/0193361 A1; 2002/0188014 A1; 2002/0165257 A1; 2002/0156110 A1; 2002/0128471 A1; 2002/0045609 A1; 2002/0022651 A1; 2002/0016356 A1; 2002/0002292 A1, each of which is hereby incorporated by reference.

Other chemotherapeutic agents that may be administered with a compound of the present invention are listed in the following Table:

| | | |
|---|---|---|
| Alkylating agents | cyclophosphamide | mechlorethamine |
| | lomustine | thiotepa |
| | busulfan | streptozocin |
| | procarbazine | chlorambucil |
| | ifosfamide | temozolomide |
| | altretamine | dacarbazine |
| | melphalan | semustine |
| | estramustine phosphate | carmustine |
| | hexamethylmelamine | |
| Platinum agents | cisplatin | tetraplatin |
| | carboplatinum | BBR-3464 (Hoffmann-La Roche) |
| | oxaliplatin | Ormiplatin |

|  |  |  |
|---|---|---|
|  | ZD-0473 (AnorMED) | SM-11355 (Sumitomo) |
|  | spiroplatinum | iproplatin |
|  | lobaplatin (Aeterna) | AP-5280 (Access) |
|  | carboxyphthalatoplatinum |  |
|  | satraplatin (Johnson Matthey) |  |
| Antimetabolites | azacytidine | 6-mercaptopurine |
|  | tomudex | hydroxyurea |
|  | gemcitabine | 6-thioguanine |
|  | trimetrexate | decitabine (SuperGen) |
|  | capecitabine | cytarabin |
|  | deoxycoformycin | clofarabine (Bioenvision) |
|  | 5-fluorouracil | 2-fluorodeoxy |
|  | fludarabine | cytidine |
|  | floxuridine | irofulven (MGI Pharma) methotrexate |
|  | pentostatin | DMDC (Hoffmann-La Roche) |
|  | 2-chlorodeoxyadenosine | idatrexate |
|  | raltitrexed | ethynylcytidine (Taiho) |
| Topoisomerase | amsacrine | TAS-103 (Taiho) |
| inhibitors | rubitecan (SuperGen) | Topotecan |
|  | epirubicin | elsamitrucin (Spectrum) dexrazoxanet |
|  | exatecan mesylate (Daiichi) | (TopoTarget) |
|  | etoposide | J-107088 (Merck & Co) |
|  | quinamed (ChemGenex) | pixantrone (Novuspharma) |
|  | teniposide or mitoxantrone | BNP-1350 (BioNumerik) |
|  | gimatecan (Sigma-Tau) | rebeccamycin analogue (Exelixis) |
|  | irinotecan (CPT-11) | CKD-602 (Chong Kun Dang) |
|  | diflomotecan (Beaufour-Ipsen) | BBR-3576 (Novuspharma) |
|  | 7-ethyl-10-hydroxy-camptothecin | KW-2170 (Kyowa Hakko) |
| Antitumor | dactinomycin (actinomycin D) | bleomycinic acid |
| antibiotics | amonafide | idarubicin |
|  | doxorubicin (adriamycin) | bleomycin A |
|  | azonafide | rubidazone |
|  | deoxyrubicin | bleomycin B |
|  | anthrapyrazole | plicamycinp |
|  | valrubicin | mitomycin C |
|  | oxantrazole | porfiromycin |
|  | daunorubicin (daunomycin) | MEN-10755 (Menarini) |
|  | losoxantrone | cyanomorpholinodoxorubicin |
|  | epirubicin | GPX-100 (Gem Pharmaceuticals) |
|  | bleomycin sulfate (blenoxane) | mitoxantrone (novantrone) |
|  | therarubicin |  |
| Antimitotic | paclitaxel | RPR 109881A (Aventis) |
| agents | SB 408075 (GlaxoSmithKline) | ZD 6126 (AstraZeneca) |
|  | docetaxel | TXD 258 (Aventis) |
|  | E7010 (Abbott) | PEG-paclitaxel (Enzon) |
|  | Colchicines | epothilone B (Novartis) |
|  | PG-TXL (Cell Therapeutics) | AZ10992 (Asahi) |
|  | vinblastine | T 900607 (Tularik) |
|  | IDN 5109 (Bayer) | IDN-5109 (Indena) |
|  | Vincristine | T 138067 (Tularik) |
|  | A 105972 (Abbott) | AVLB (Prescient NeuroPharma) |
|  | Vinorelbine | cryptophycin 52 (Eli Lilly) |
|  | A 204197 (Abbott) | azaepothilone B (BMS) |
|  | Vindesine | vinflunine (Fabre) |
|  | LU 223651 (BASF) | BNP-7787 (BioNumerik) |
|  | dolastatin 10 (NCI) | auristatin PE (Teikoku Hormone) |
|  | D 24851 (ASTAMedica) | CA-4 prodrug (OXiGENE) |
|  | rhizoxin (Fujisawa) | BMS 247550 (BMS) |
|  | ER-86526 (Eisai) | dolastatin-10 (NIH) |
|  | mivobulin (Warner-Lambert) | BMS 184476(BMS) |
|  | combretastatin A4 (BMS) | CA-4 (OXiGENE) |
|  | cemadotin (BASF) | BMS 188797 (BMS) |
|  | isohomohalichondrin-B (PharmaMar) | taxoprexin (Protarga) |
| Aromatase | Aminoglutethimide | anastrazole |
| inhibitors | Exemestane | YM-511 (Yamanouchi) |
|  | Letrozole | formestane |
|  | atamestane (BioMedicines) |  |
| Thymidylate | pemetrexed (Eli Lilly) | ZD-9331 (BTG) |
| synthase | nolatrexed (Eximias) | CoFactor ™ (BioKeys) |
| inhibitors |  |  |
| DNA | trabectedin (PharmaMar) | albumin + 32P (Isotope Solutions) |
| antagonists | mafosfamide (Baxter International) | O6 benzyl guanine (Paligent) |
|  | glufosfamide (Baxter International) | thymectacin (NewBiotics) edotreotide |
|  | apaziquone (Spectrum | (Novartis) |
|  | Pharmaceuticals) |  |
| Farnesyltransferase | arglabin (NuOncology Labs) | perillyl alcohol (DOR BioPharma) |
| inhibitors | tipifarnib (Johnson & Johnson) | BAY-43-9006 (Bayer) |
|  | lonafarnib (Schering-Plough) |  |

-continued

| | | |
|---|---|---|
| Pump inhibitors | CBT-1 (CBA Pharma) | tariquidar (Xenova) |
| | zosuquidar trihydrochloride (Eli Lilly) | biricodar dicitrate (Vertex) |
| | | MS-209 (Schering AG) |
| Histone acetyltransferase inhibitors | tacedinaline (Pfizer) | depsipeptide (Fujisawa) |
| | pivaloyloxymethyl butyrate (Titan) | MS-275 (Schering AG) |
| | SAHA (Aton Pharma) | |
| Metalloproteinase inhibitors | Neovastat (Aeterna Laboratories) | marimastat (British Biotech) BMS-275291 (Celltech) |
| | CMT-3 (CollaGenex) | |
| Ribonucleoside reductase inhibitors | gallium maltolate (Titan) | triapine (Vion) |
| | tezacitabine (Aventis) | didox (Molecules for Health) |
| TNF alpha agonists/antagonists | virulizin (Lorus Therapeutics) | CDC-394 (Celgene) |
| | revimid (Celgene) | |
| Endothelin A receptor antagonist | atrasentan (Abbott) | ZD-4054 (AstraZeneca) |
| | YM-598 (Yamanouchi) | |
| Retinoic acid receptor agonists | fenretinide (Johnson & Johnson) | LGD-1550 (Ligand) |
| | alitretinoin (Ligand) | |
| Immuno-modulators | Interferon | norelin (Biostar) |
| | dexosome therapy (Anosys) | IRX-2 (Immuno-Rx) |
| | oncophage (Antigenics) | BLP-25 (Biomira) |
| | pentrix (Australian Cancer Technology) | PEP-005 (Peplin Biotech) |
| | | MGV (Progenics) |
| | GMK (Progenics) | synchrovax vaccines (CTL Immuno) |
| | ISF-154 (Tragen) | beta.-alethine (Dovetail) |
| | adenocarcinoma vaccine (Biomira) | melanoma vaccine (CTL Immuno) |
| | cancer vaccine (Intercell) | CLL therapy (Vasogen) |
| | CTP-37 (AVI BioPharma) | p21 RAS vaccine (GemVax) |
| Hormonal and antihormonal agents | estrogens | bicalutamide |
| | Prednisone | testosterone propionate; |
| | conjugated estrogens | fluoxymesterone |
| | methylprednisolone | flutamide |
| | ethinyl estradiol | methyltestosterone |
| | prednisolone | octreotide |
| | chlortrianisen | diethylstilbestrol |
| | aminoglutethimide | nilutamide |
| | idenestrol | megestrol |
| | leuprolide | mitotane tamoxifen |
| | hydroxyprogesterone caproate | P-04 (Novogen) |
| | goserelin | Toremofine |
| | medroxyprogesterone | 2-methoxyestradiol (EntreMed) |
| | leuporelin | dexamethasone |
| | testosterone | arzoxifene (Eli Lilly) |
| Photodynamic agents | talaporfin (Light Sciences) | motexafin |
| | Pd-bacteriopheophorbide (Yeda) | gadolinium (Pharmacyclics) |
| | Theralux (Theratechnologies) | hypericin |
| | lutetium texaphyrin (Pharmacyclics) | |
| Tyrosine Kinase Inhibitors | imatinib (Novartis) | C225 (ImClone) |
| | kahalide F (PharmaMar) | ZD4190 (AstraZeneca) |
| | leflunomide (Sugen/Pharmacia) | rhu-Mab (Genentech) |
| | CEP-701 (Cephalon) | ZD6474 (AstraZeneca) |
| | ZD1839 (AstraZeneca) | MDX-H210 (Medarex) |
| | CEP-751 (Cephalon) | vatalanib (Novartis) |
| | erlotinib (Oncogene Science) | 2C4 (Genentech) |
| | MLN518 (Millenium) | PKI166 (Novartis) |
| | canertinib (Pfizer) | MDX-447 (Medarex) |
| | PKC412 (Novartis) | GW2016 (GlaxoSmithKline) |
| | squalamine (Genaera) | ABX-EGF (Abgenix) |
| | phenoxodiol ( ) | EKB-509 (Wyeth) |
| | SU5416 (Pharmacia) | IMG-1C11 (ImClone) |
| | trastuzumab (Genentech) | EKB-569 (Wyeth) |
| | SU6668 (Pharmacia) | |

| Miscellaneous agents | |
|---|---|
| SR-27897 (CCK A inhibitor, Sanofi-Synthelabo) | gemtuzumab (CD33 antibody, Wyeth Ayerst) |
| BCX-1777 (PNP inhibitor, BioCryst) | CCI-779 (mTOR kinase inhibitor, Wyeth) |
| tocladesine (cyclic AMP agonist, Ribapharm) | PG2 (hematopoiesis enhancer, Pharmagenesis) |
| ranpirnase (ribonuclease stimulant, Alfacell) | exisulind (PDE V inhibitor, Cell Pathways) |
| alvocidib (CDK inhibitor, Aventis) | Immunol ™ (triclosan oral rinse, Endo) |
| galarubicin (RNA synthesis inhibitor, Dong-A) | CP-461 (PDE V inhibitor, Cell Pathways) |
| CV-247 (COX-2 inhibitor, Ivy Medical) | triacetyluridine (uridine prodrug, Wellstat) |
| tirapazamine (reducing agent, SRI International) | AG-2037 (GART inhibitor, Pfizer) |
| P54 (COX-2 inhibitor, Phytopharm) | SN-4071 (sarcoma agent, Signature BioScience) |
| N-acetylcysteine (reducing agent, Zambon) | WX-UK1 (plasminogen activator inhibitor, Wilex) |
| CapCell ™ (CYP450 stimulant, Bavarian Nordic) | TransMID-107 .TM. (immunotoxin, KS Biomedix) |

| | |
|---|---|
| R-flurbiprofen (NF-kappaB inhibitor, Encore) | PBI-1402 (PMN stimulant, ProMetic |
| GCS-100 (gal3 antagonist, GlycoGenesys) | LifeSciences) |
| 3CPA (NF-kappaB inhibitor, Active Biotech) | PCK-3145 (apoptosis promotor, Procyon) |
| G17DT immunogen (gastrin inhibitor, Aphton) | bortezomib (proteasome inhibitor, Millennium) |
| seocalcitol (vitamin D receptor agonist, Leo) | doranidazole (apoptosis promotor, Pola) |
| efaproxiral (oxygenator, Allos Therapeutics) | SRL-172 (T cell stimulant, SR Pharma) CHS- |
| 131-I-TM-601 (DNA antagonist, TransMolecular) | 828 (cytotoxic agent, Leo) |
| | TLK-286 (glutathione S transferase inhibitor, |
| PI-88 (heparanase inhibitor, Progen) | Telik) |
| eflornithine (ODC inhibitor, ILEX Oncology) | trans-retinoic acid (differentiator, NIH) |
| tesmilifene (histamine antagonist, YM BioSciences) | PT-100 (growth factor agonist, Point Therapeutics) |
| minodronic acid (osteoclast inhibitor, Yamanouchi) | MX6 (apoptosis promotor, MAXIA) midostaurin (PKC inhibitor, Novartis) |
| histamine (histamine H2 receptor agonist, Maxim) | apomine (apoptosis promotor, ILEX Oncology) bryostatin-1 (PKC stimulant, GPC Biotech) |
| indisulam (p53 stimulant, Eisai) | urocidin (apoptosis promotor, Bioniche) |
| tiazofurin (IMPDH inhibitor, Ribapharm) | CDA-II (apoptosis promotor, Everlife) |
| aplidine (PPT inhibitor, PharmaMar) | Ro-31-7453 (apoptosis promotor, La Roche) |
| cilengitide (integrin antagonist, Merck KGaA) | SDX-101 (apoptosis promotor, Salmedix) |
| rituximab (CD20 antibody, Genentech) | brostallicin (apoptosis promotor, Pharmacia) |
| SR-31747 (IL-1 antagonist, Sanofi-Synthelabo) | ceflatonin (apoptosis promotor, ChemGenex) |

Additional combinations may also include agents which reduce the toxicity of the aforesaid agents, such as hepatic toxicity, neuronal toxicity, nephprotoxicity and the like.

Screening Assays

The compounds of the present invention may also be used in a method to screen for other compounds that bind to an IAP BIR domain. Generally speaking, to use the compounds of the invention in a method of identifying compounds that bind to an IAP BIR domain, the IAP is bound to a support, and a compound of the invention is added to the assay. Alternatively, the compound of the invention may be bound to the support and the IAP is added.

There are a number of ways in which to determine the binding of a compound of the present invention to the BIR domain. In one way, the compound of the invention, for example, may be fluorescently or radioactively labeled and binding determined directly. For example, this may be done by attaching the IAP to a solid support, adding a detectably labeled compound of the invention, washing off excess reagent, and determining whether the amount of the detectable label is that present on the solid support. Numerous blocking and washing steps may be used, which are known to those skilled in the art.

In some cases, only one of the components is labeled. For example, specific residues in the BIR domain may be labeled. Alternatively, more than one component may be labeled with different labels; for example, using $I^{125}$ for the BIR domain, and a fluorescent label for the probe.

The compounds of the invention may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity. The compounds may be capable of directly or indirectly altering the IAP biological activity.

Drug candidates can include various chemical classes, although typically they are small organic molecules having a molecular weight of more than 100 and less than about 2,500 Daltons. Candidate agents typically include functional groups necessary for structural interaction with proteins, for example, hydrogen bonding and lipophilic binding, and typically include at least an amine, carbonyl, hydroxyl, ether, or carboxyl group. The drug candidates often include cyclical carbon or heterocyclic structures and/or aromatic or polyaromatic structures substituted with one or more functional groups.

Drug candidates can be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Competitive screening assays may be done by combining an IAP BIR domain and a probe to form a probe:BIR domain complex in a first sample followed by adding a test compound from a second sample. The binding of the test is determined, and a change, or difference in binding between the two samples indicates the presence of a test compound capable of binding to the BIR domain and potentially modulating the IAP's activity.

In one case, the binding of the test compound is determined through the use of competitive binding assays. In this embodiment, the probe is labeled with an an affinity label such as biotin. Under certain circumstances, there may be competitive binding between the test compound and the probe, with the probe displacing the candidate agent.

In one case, the test compound may be labeled. Either the test compound, or a compound of the present invention, or both, is added first to the IAP BIR domain for a time sufficient to allow binding to form a complex.

Formation of the probe:BIR domain complex typically require Incubations of between 4° C. and 40° C. for between 10 minutes to about 1 hour to allow for high-throughput screening. Any excess of reagents are generally removed or washed away. The test compound is then added, and the presence or absence of the labeled component is followed, to indicate binding to the BIR domain.

In one case, the probe is added first, followed by the test compound. Displacement of the probe is an indication the test compound is binding to the BIR domain and thus is capable of binding to, and potentially modulating, the activity of IAP.

Either component can be labeled. For example, the presence of probe in the wash solution indicates displacement by the test compound. Alternatively, if the test compound is labeled, the presence of the probe on the support indicates displacement.

In one case, the test compound may be added first with incubation and washing, followed by the probe. The absence of binding by the probe may indicate the test compound is bound to the BIR domain with a higher affinity. Thus, if the probe is detected on the support, coupled with a lack of test compound binding, may indicate the test compound is capable of binding to the BIR domain.

Modulation is tested by screening for a test compound's ability to modulate the activity of IAP and includes combining a test compound with an IAP BIR domain, as described above, and determining an alteration in the biological activity of the IAP. Therefore in this case, the test compound should both bind to the BIR domain (although this may not be necessary), and alter its biological activity as defined herein.

Positive controls and negative controls may be used in the assays. All control and test samples are performed multiple times to obtain statistically significant results. Following incubation, all samples are washed free of non-specifically bound material and the amount of bound probe determined. For example, where a radiolabel is employed, the samples may be counted in a scintillation counter to determine the amount of bound compound.

Typically, the signals that are detected in the assay may include fluorescence, resonance energy transfer, time resolved fluorescence, radioactivity, fluorescence polarization, plasma resonance, or chemiluminescence and the like, depending on the nature of the label. Detectable labels useful in performing screening assays in this invention include a fluorescent label such as Fluorescein, Oregon green, dansyl, rhodamine, tetramethyl rhodamine, texas red, $Eu^{3+}$; a chemiluminescent label such as luciferase; calorimetric labels; enzymatic markers; or radioisotopes such as tritium, $I^{125}$ and the like Affinity tags, which may be useful in performing the screening assays of the present invention include be biotin, polyhistidine and the like.

Synthesis and Methodology

General methods for the synthesis of the compounds of the present invention are shown below and are disclosed merely for the purpose of illustration and are not meant to be interpreted as limiting the processes to make the compounds by any other methods. Those skilled in the art will readily appreciate that a number of methods are available for the preparation of the compounds of the present invention. A number of intermediate compounds disclosed herein may be synthesized using synthetic methods disclosed in previously filed U.S. patent application Ser. No. 11/434,166, filed May 17, 2006, the entire contents of which is hereby incorporated by reference.

Scheme 1 illustrates the synthesis of a typical synthetic intermediate represented by 1(i). Examples of 1(i) represent proline derivatives such as 1(ii) and 2-(aminomethyl)pyrrolidine derivatives represented by intermediates 1(iii-viii). Proline derivatives of 1(i) may be prepared by the treatment of Boc-Pro-OH with typical peptide coupling agents and an amine, to provide intermediate 1(ii). The 2-(aminomethyl) pyrrolidine intermediate 1(iii) is prepared by the condensation of an amine with N-Boc-prolinal. The resulting amine may be acylated with an acid chloride, anhydride or suitably activated carboxylic acid, such as succinamidyl esters, HOBt esters and the like, to provide intermediates such as 1(iv-vi).

The intermediates 1(iv) and 1(v) feature protecting groups, which may be further removed and functionalized later in the synthesis. Sulfonylation with a sulfonyl chloride provides 1(vii). Appropriately activated, side chain protected amino acids may be coupled to intermediate 1(iii) using standard peptide coupling agents to provide intermediate 1(viii), the PG can be removed later in the synthesis.

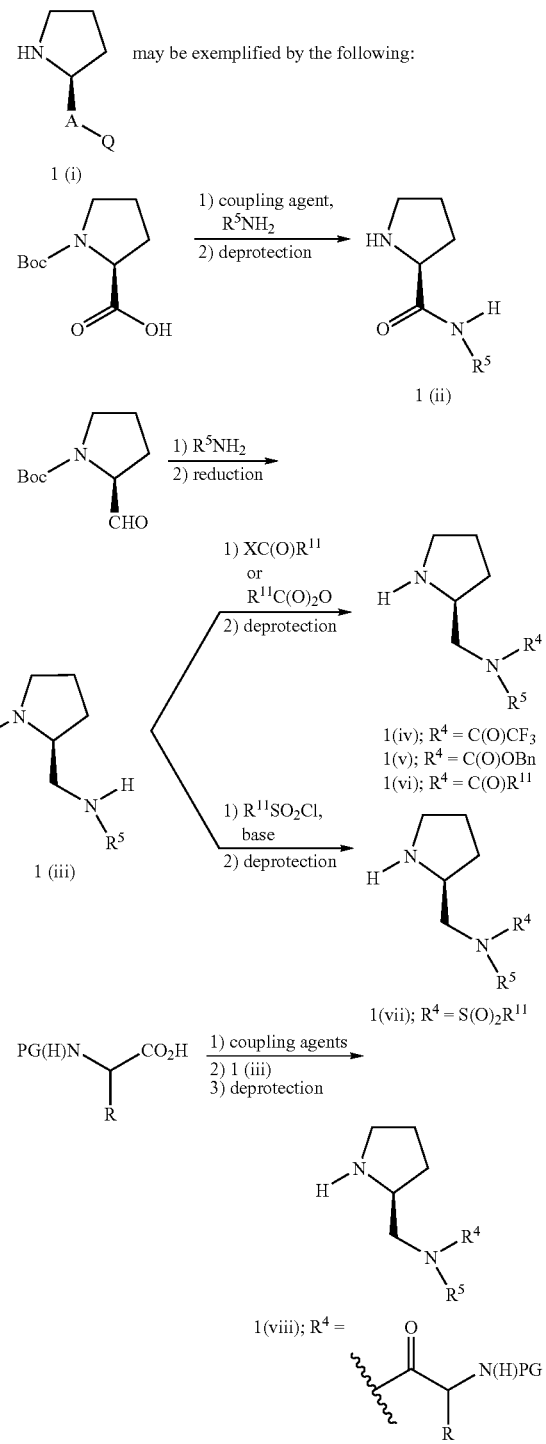

General Procedure for the Preparation of Bis-Alkynyl Derivatives of Formula Ig.

Scheme 2 illustrates a general procedure for preparing bis-alkynyl bridged compounds of formula Ig. $PG^1$-Thr-OH is deprotonated with NaH and treated with propargyl bromide to provide the Thr intermediate 2(i). Activation of the carboxylic acid of 2(i) with standard peptide coupling agents and treatment with intermediate 1(i) provides the amide intermediate 2(ii). Peptide coupling of $PG^2(R^1)N(R^2)(H)CCO_2H$ with 2(ii) is effected by activation of the carboxylic acid of $PG^2(R^1)N(R^2)(H)CCO_2H$ with standard peptide coupling agents, followed by the addition of 2(ii) to provide the fully protected amide 2(iii). The bis-alkynyl bridging moiety is prepared by homo-coupling if the alkyne moieties of 2(iii) using an appropriate Cu catalyst, and subsequent deprotection of $PG^2$, to provide compounds of formula Ig.

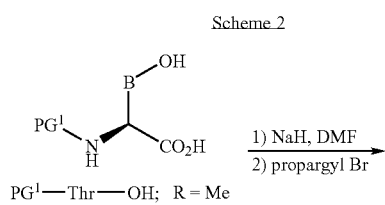

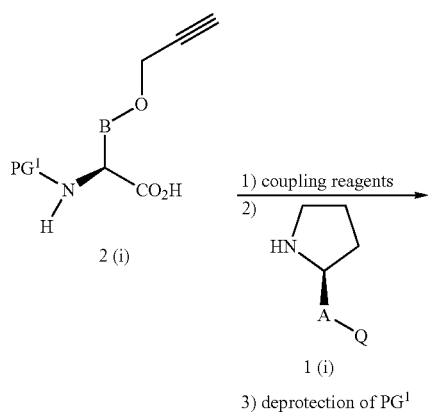

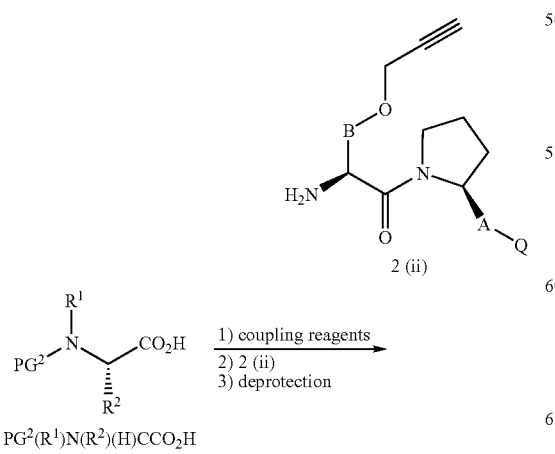

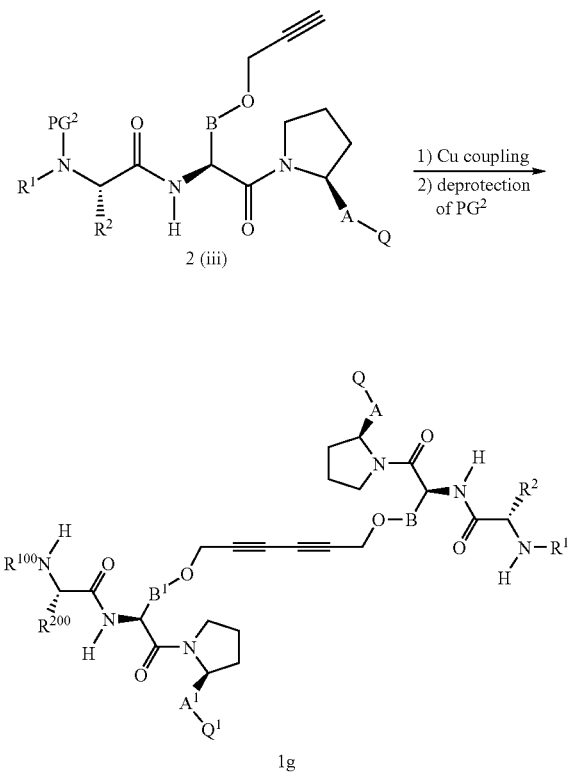

General Procedure for the Preparation of Compounds of Formula Ih.

Scheme 3 illustrates a general procedure for the preparation of di(bromomethyl)benzene derived compounds of Formula I. $PG^1$-Ser-OH is deprotonated with NaH and treated with 1,4-di(bromomethyl)benzene to provide the Ser intermediate 3(i). Activation of the carboxylic acid of 3(i) with standard peptide coupling agents and treatment with intermediate 1(i) provides intermediate 3(ii), which is deprotected at $PG^1$ to provide the amide intermediate 3(iii). Peptide coupling of $PG^2(R^1)N(R^2)(H)CCO_2H$ with 3(iii) is effected by activation of the carboxylic acid of $PG^2(R^1)N(R^2)(H)CCO_2H$ with standard peptide coupling agents, followed by the addition of 3(iii) to provide the fully protected amide, which may be further deprotected at $PG^2$ to provide compounds of formula Ih.

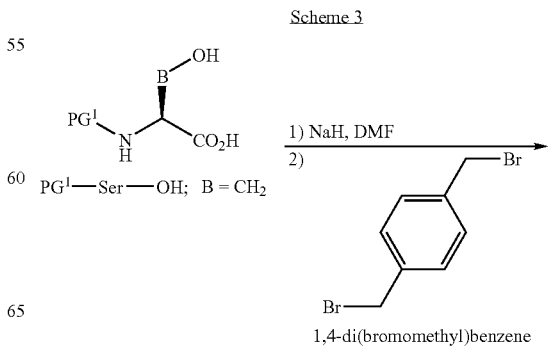

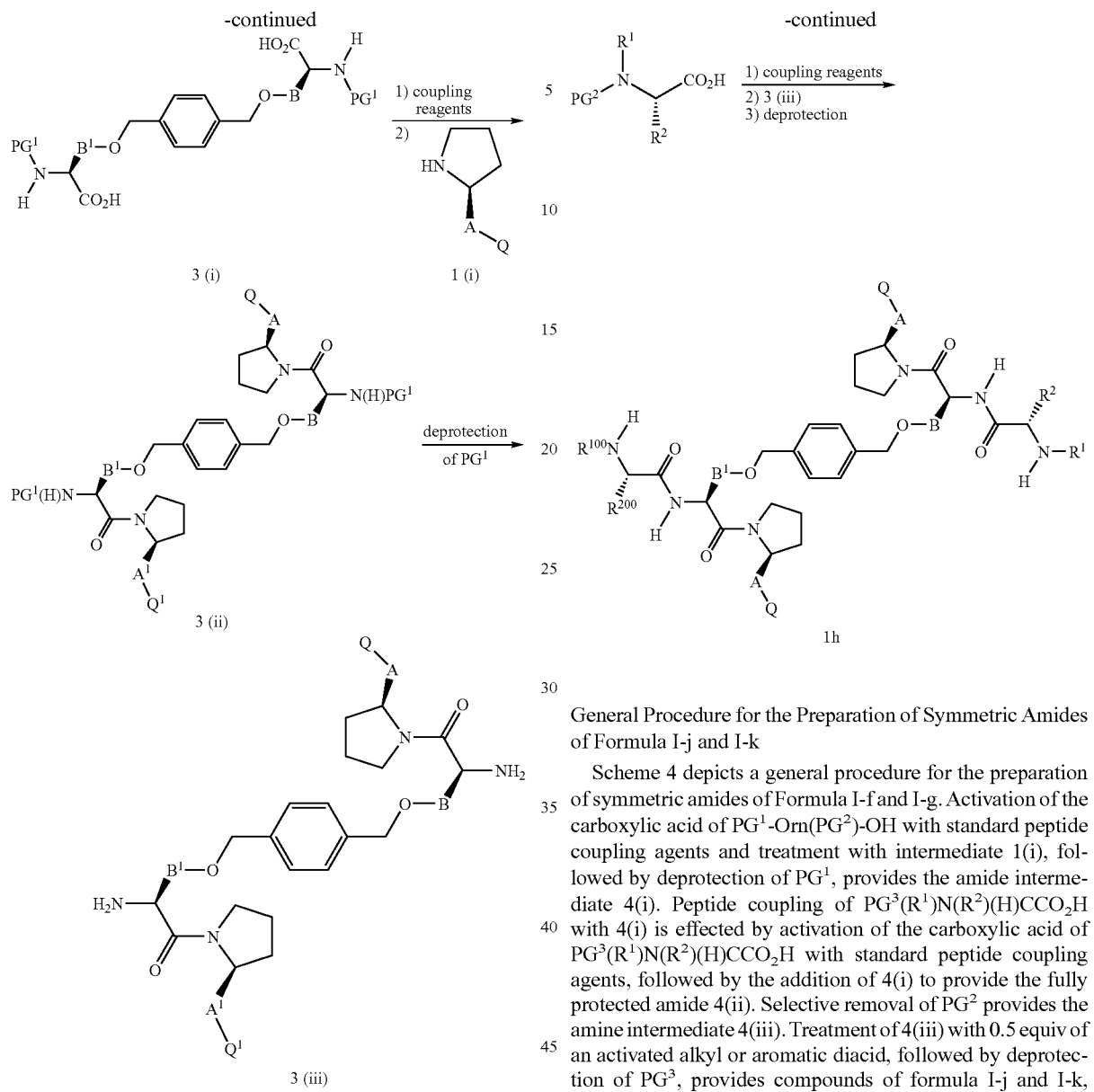

General Procedure for the Preparation of Symmetric Amides of Formula I-j and I-k Scheme 4 depicts a general procedure for the preparation of symmetric amides of Formula I-f and I-g. Activation of the carboxylic acid of $PG^1$-Orn($PG^2$)-OH with standard peptide coupling agents and treatment with intermediate 1(i), followed by deprotection of $PG^1$, provides the amide intermediate 4(i). Peptide coupling of $PG^3(R^1)N(R^2)(H)CCO_2H$ with 4(i) is effected by activation of the carboxylic acid of $PG^3(R^1)N(R^2)(H)CCO_2H$ with standard peptide coupling agents, followed by the addition of 4(i) to provide the fully protected amide 4(ii). Selective removal of $PG^2$ provides the amine intermediate 4(iii). Treatment of 4(iii) with 0.5 equiv of an activated alkyl or aromatic diacid, followed by deprotection of $PG^3$, provides compounds of formula I-j and I-k, respectively.

Scheme 4

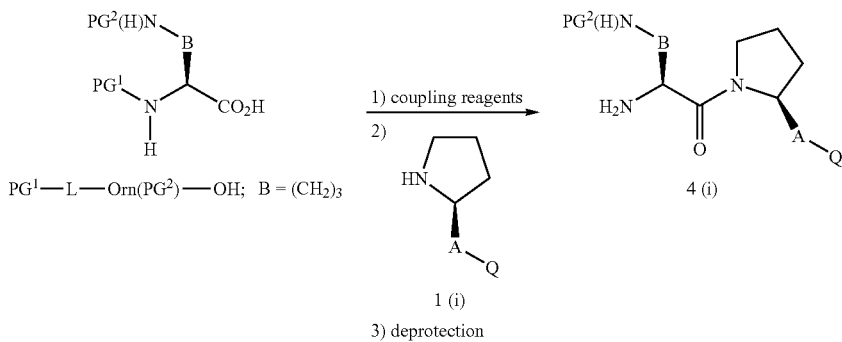

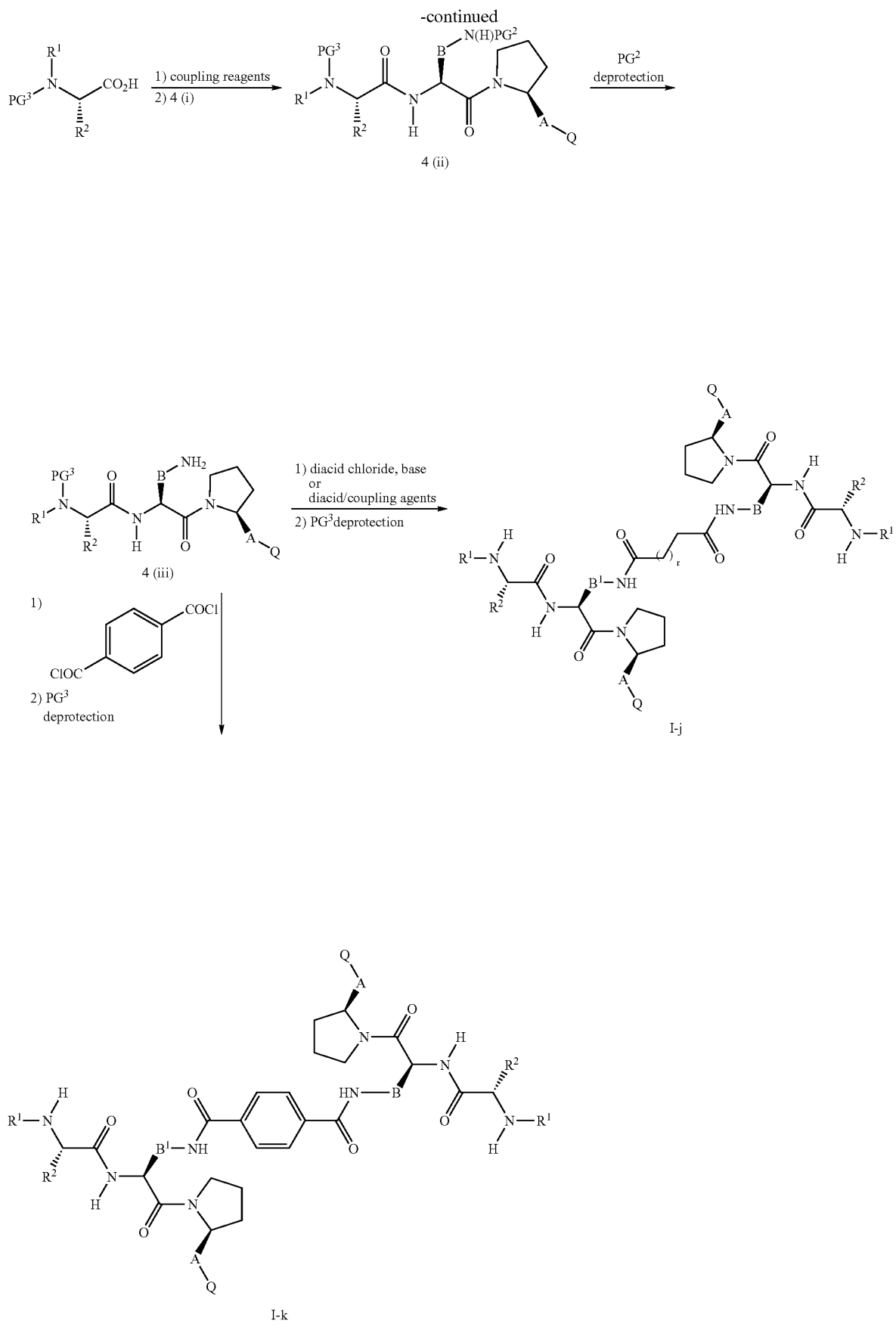

General Procedure for the Preparation of Compounds of Formula I-l

Scheme 5 illustrates a general procedure for the preparation of symmetrical ureas of general formula I-l. Intermediate 4(iii) is treated with 0.5 equiv of triphosgene, or a triphosgene equivalent, to provide a protected urea intermediate 5(i). Removal of $PG^3$ provides compounds of general Formula I-l.

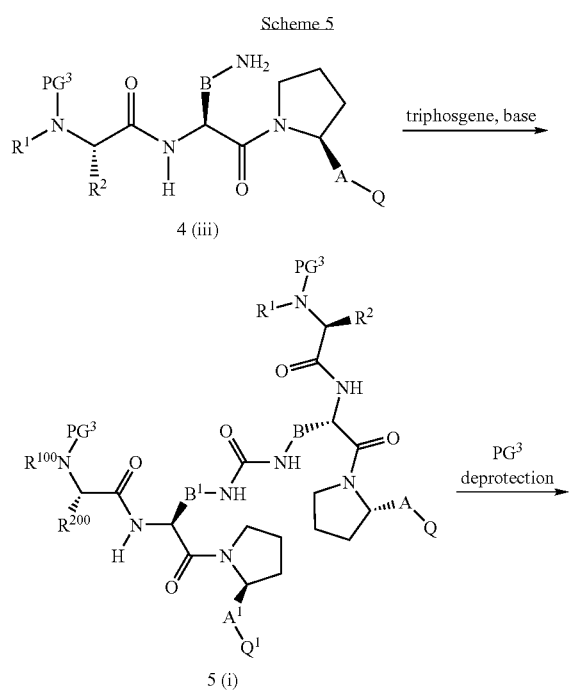

Scheme 5

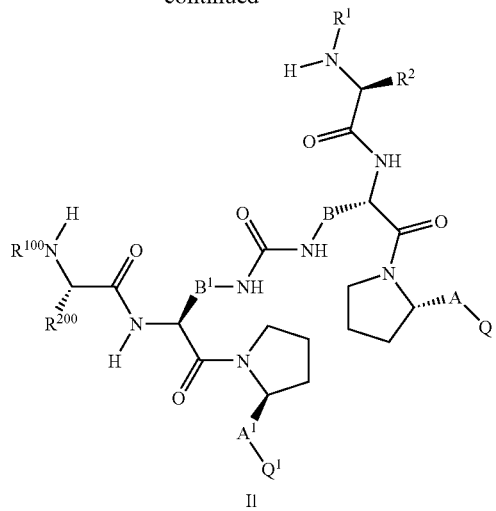

II

General Procedure for the Preparation of Symmetrical Esters

Scheme 6 illustrates the preparation of symmetrical esters of general formula 1-m and I-n. An amino acid derivative displaying a hydroxy moiety on its side chain such as $PG^1$-Ser($PG^2$)-OH is activated with standard peptide coupling reagents and treated with 1(i), and the resulting amide is deprotected at $PG^1$ to provide the amine intermediate 6(i). Activation of the carboxylic acid of $PG^3(R^3)N(H)(R^2)CCO_2H$ using standard peptide coupling agents and treatment of the resulting activated amino acid with 6(i) provides 6(ii). Selective deprotection of $PG^2$ provides the intermediate alcohol 6(iii). Treatment of 6(iii) with 0.5 equiv of an activated dicarboxylic acid, and deprotection of $PG^3$, provides compounds of general formula I-m and I-n.

Scheme 6

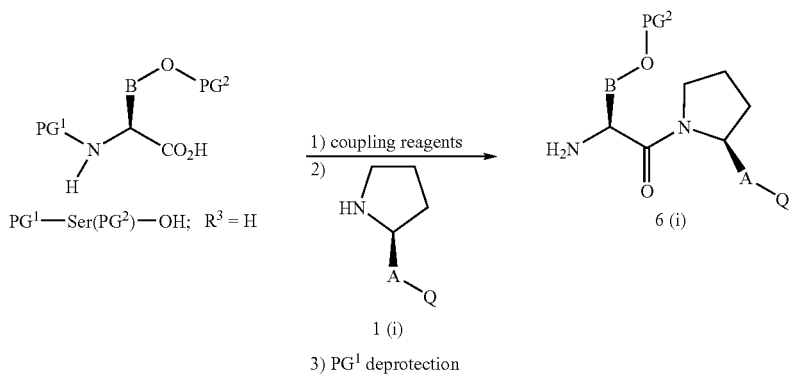

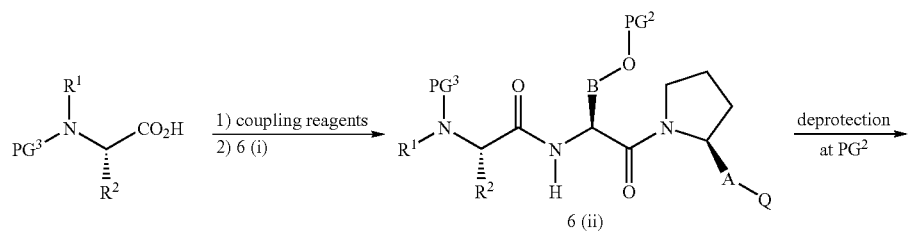

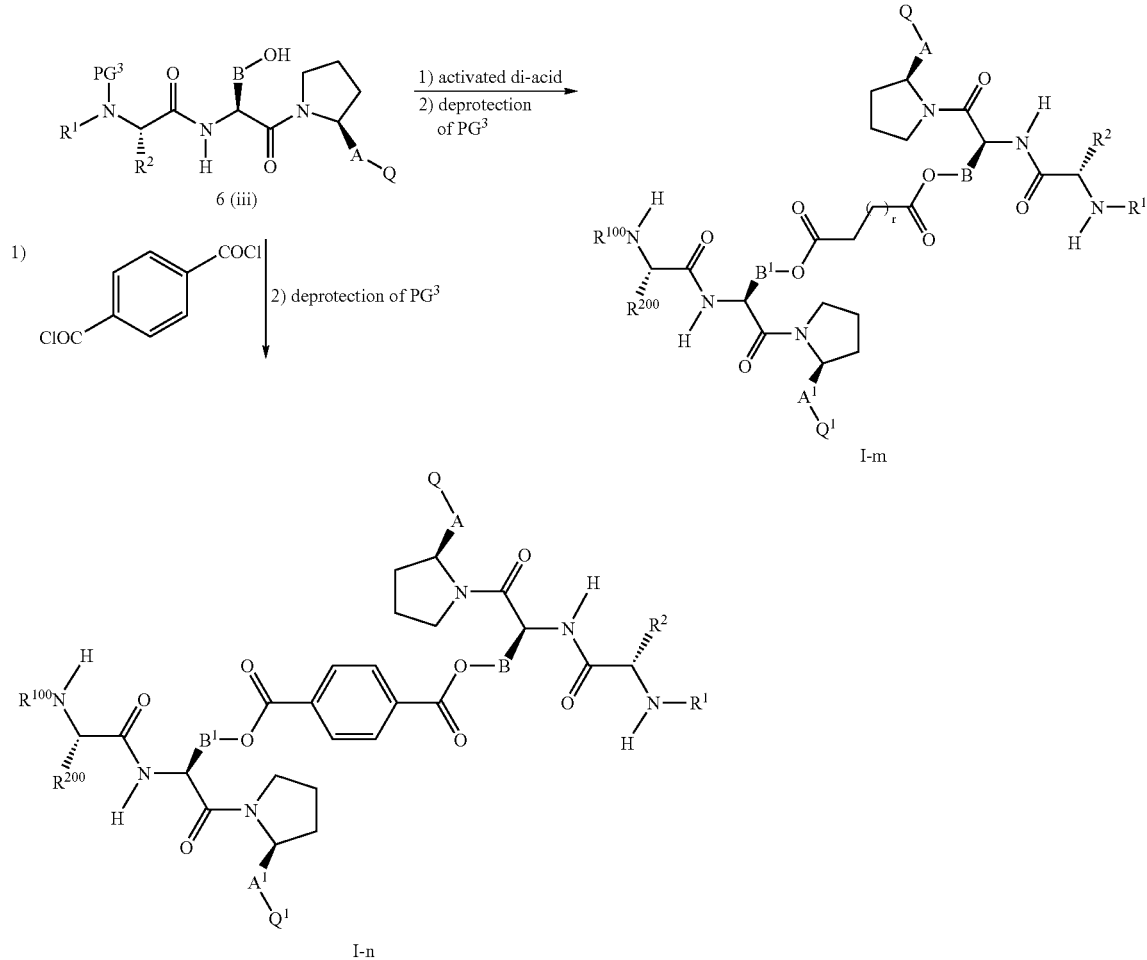

General Procedure for the Preparation of Symmetrical Amides of Formula I-o

Scheme 7 illustrates the preparation of symmetrical amides of general formula 1-o. An amino acid derivative displaying a carboxylic acid on its side chain such as $PG^1$-Glu($PG^2$)-OH is activated with standard peptide coupling reagents and treated with 1(i) and the resulting amide is deprotected at $PG^1$ to provide the amine intermediate 7(ii). Activation of the carboxylic acid of $PG^3(R^3)N(R^2)(H)CCO_2H$ using standard peptide coupling agents, followed by treatment with 7(i) provides 7(ii). Selective deprotection of $PG^2$ provides the intermediate carboxylic acid 7(iii). Activation of the carboxylic acid with standard peptide coupling agents and treatment with 0.5 equiv of a diamine provides intermediate 7(iv). Deprotection of $PG^3$ provides compounds of general formula I-o.

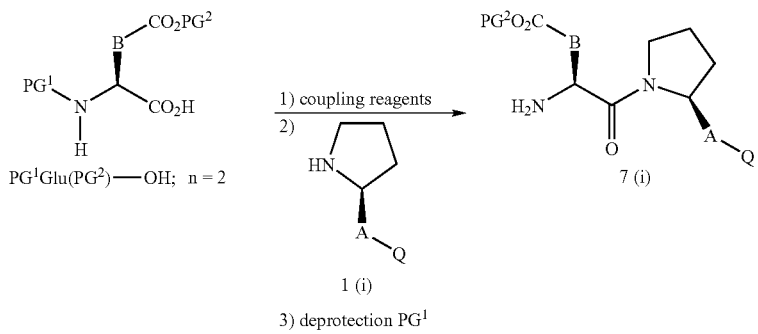

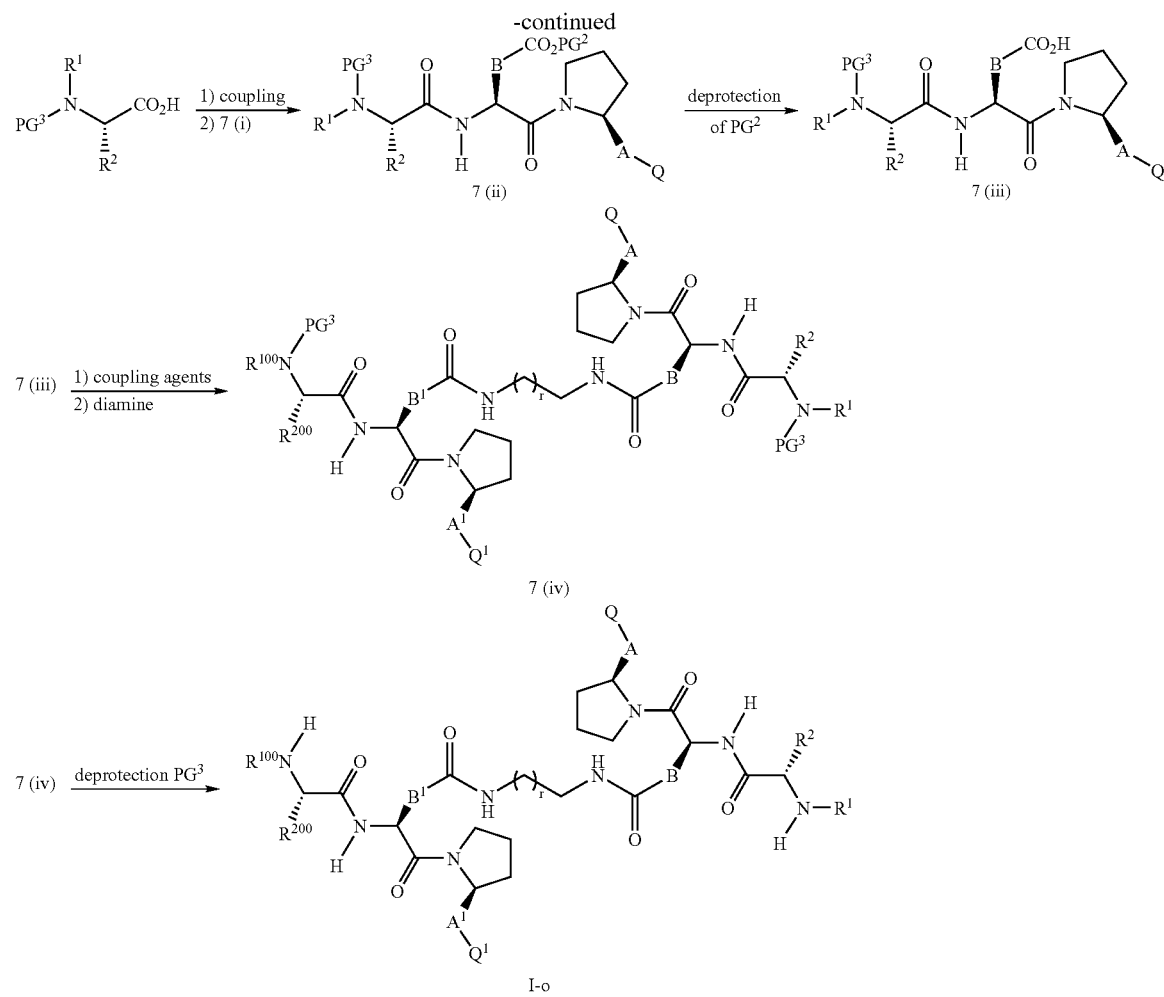

General Procedure for the Preparation of Compounds of Formula Ii.

Scheme 8 illustrates a general procedure for the preparation of compounds of Formula Ii. $PG^1$-Ser-OH is deprotonated with NaH and treated with 2,2'-bis(bromomethyl)-1,1'-biphenyl to provide the Ser intermediate 8 (i). Activation of the carboxylic acid of 8(i) with standard peptide coupling agents and treatment with intermediate 1(i) provides intermediate 8 (ii), which is deprotected at $PG^1$ to provide the amide intermediate 8(iii). Peptide coupling of $PG^2(R^1)N(R^2)(H)$ $CCO_2H$ with 3(iii) is effected by activation of the carboxylic acid of $PG^2(R^1)N(R^2)CHCO_2H$ with standard peptide coupling agents, followed by the addition of 3(ii) to provide the fully protected amide, which may be further deprotected at $PG^2$ to provide compounds of formula Ii.

Scheme 8

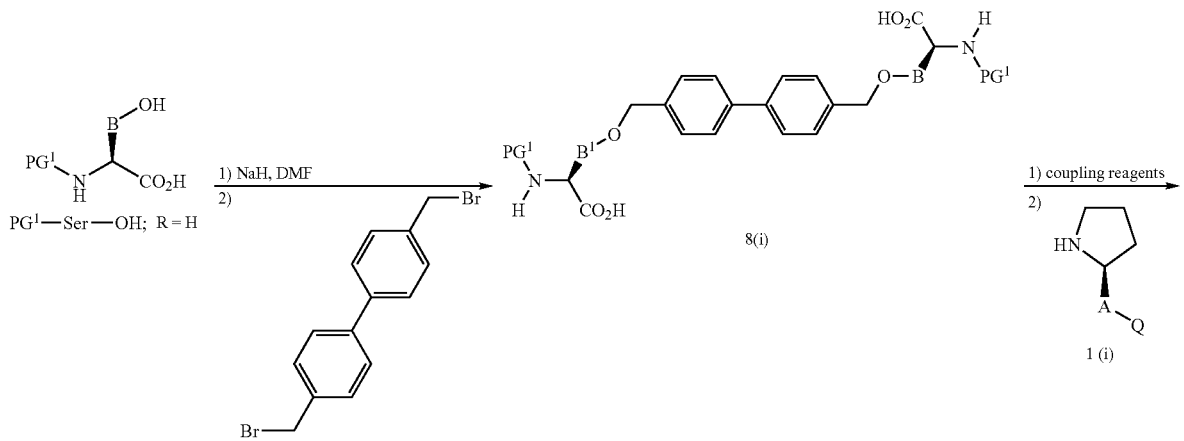

-continued
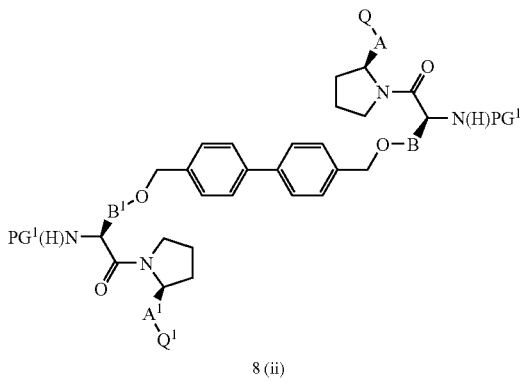
8(ii)
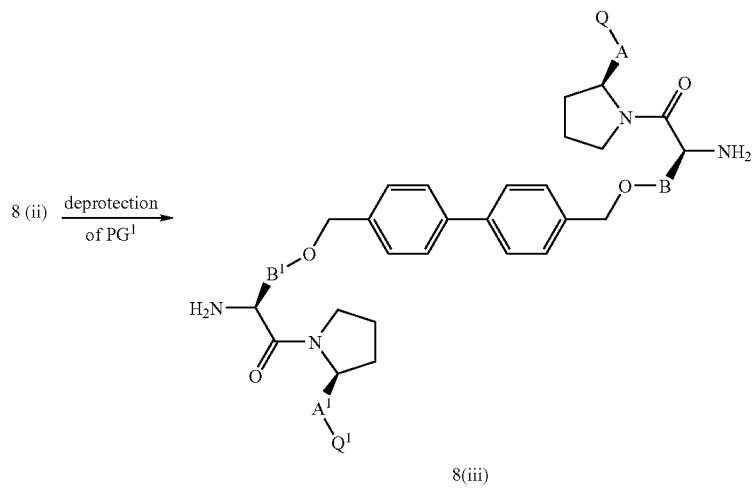
8(iii)
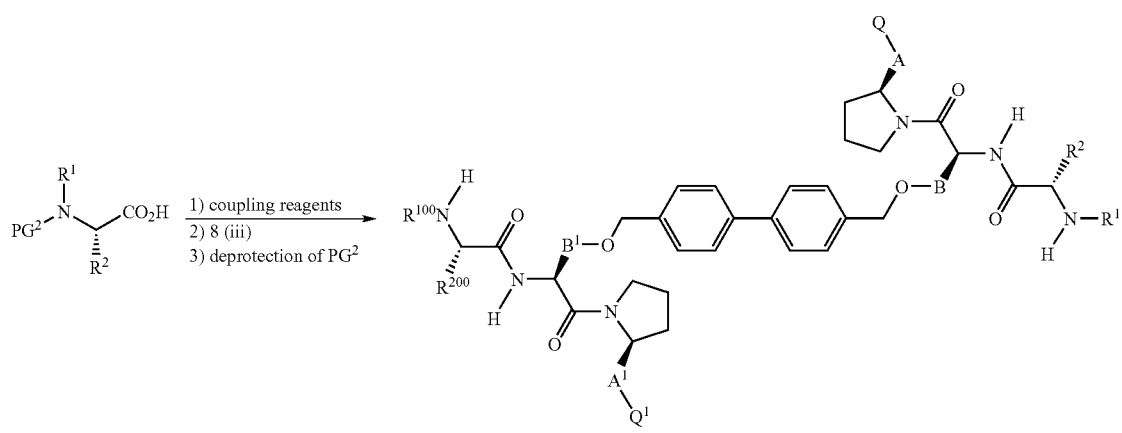
Ii

General Procedure for the Preparation of Compounds of Formula Ip

Scheme 9 illustrates a general procedure for the preparation of glyoxalamides of general formula Ip. Intermediate 4(iii) is treated with 0.5 equiv of oxalyl chloride, or an oxalyl chloride equivalent, to provide a protected urea intermediate 9(i). Removal of $PG^3$ provides compounds of general formula Ip.

Scheme 9

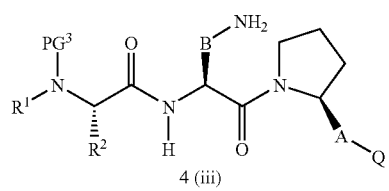

4 (iii)

(COCl)$_2$

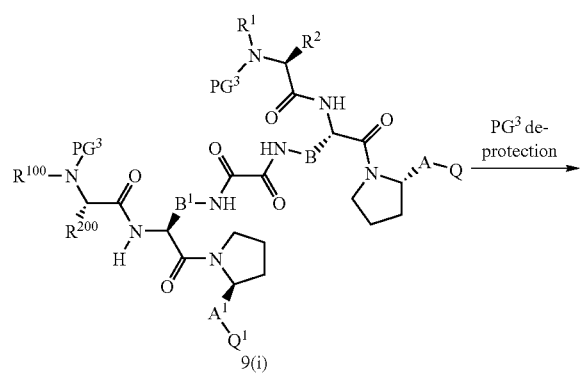

9(i)

PG$^3$ deprotection

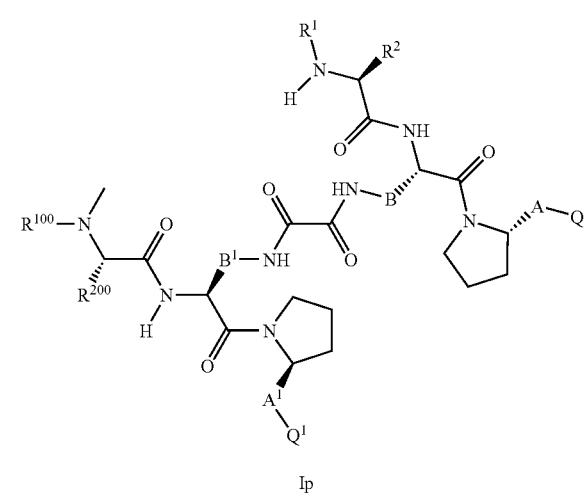

Ip

General Procedure for the Preparation of Compounds of Formula Iq

Reduction of the triple bonds of Compounds of general formula 1g provide compounds of the general formula 1q. For example, hydrogenation of compounds of general formula 1g with H$_2$ gas in the presence of a catalyst system such as Pd/C provides compounds of general formula 1p.

1g

H$_2$, Pd/C
MeOH

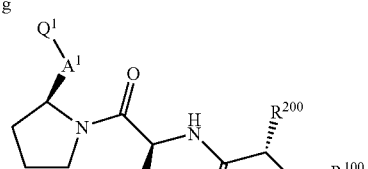

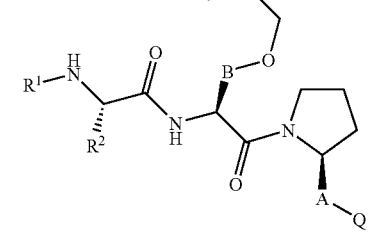

1p

The above Schemes are applicable to both symmetrical compounds and unsymmetrical compounds of the present invention. The substituents B, $B^1$, $A^1$, A, Q, $Q^1$, $R^1$, $R^{100}$, $R^2$, $R^{200}$, $R^4$, $R^5$, $R^{11}$, r and the like are as defined herein.

EXAMPLES

The following abbreviations are used throughout:
Boc: t-butoxycarbonyl;
CBz: benzyloxycarbonyl;
DCM: dichloromethane;
DIPEA: diisopropylethylamine;
DMAP: 4-(dimethylamino)pyridine;
DMF: N,N-dimethylformamide;
DTT: dithiothreitol;
EDC: 3-dimethylaminopropyl)-3-ethylcarbodiimide hydrochloride;

EDTA: ethylenediaminetetracetic acid;
Fmoc: N-(9-fluorenylmethoxycarbonyl);
HBTU: O-(benzotriazol-1-yl)-N,N,N',N'-tetramethyluronium hexafluorophosphate;
HCl: hydrochloric acid;
HOAc: acetic acid;
HOBt: 1-hydroxybenzotriazole;
HPLC: high performance liquid chromatography;
LCMS: liquid chromatography-mass spectrometer;
MeOH: methanol;
MgSO₄: magnesium sulfate;
MS: mass spectrum;
NaHCO₃: sodium hydrogen carbonate;
Pd/C: palladium on carbon;
TEA: triethylamine; and
THF: tetrahydrofuran.

1. Synthesis of Intermediate 1-4b

Step One:

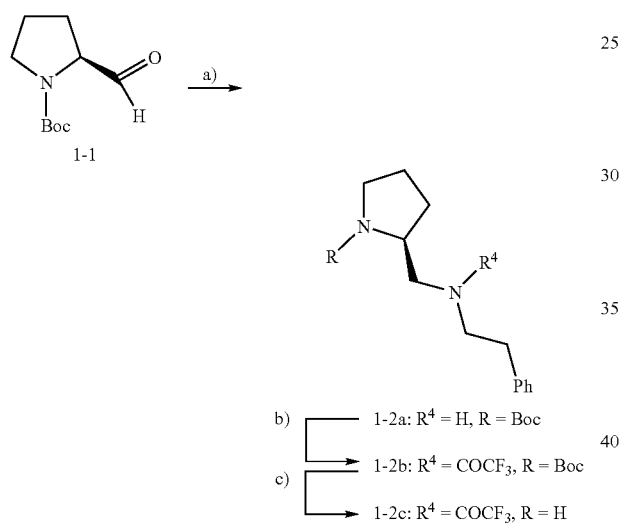

Step a)

To a solution of N-(tert-butoxycarbonyl)-L-prolinal 1-1 (6.0 g, 30.1 mmol) in methylene chloride was added phenethylamine (3.8 mL, 30.1 mmol). After stirring for 1 h at RT sodium cyanoborohydride (12.8 g, 60.2 mmol) was added and the reaction mixture was stirred at room temperature overnight. Aqueous NaHCO₃ and ethyl acetate were added, the organic layer was separated, washed with brine, dried over MgSO₄ and concentrated in vacuo. Purification by flash chromatography provides 1-2a as colorless oil. MS (m/z) M+1=305.

Step b)

To a solution of 1-2a (6.0 g, 19.7 mmol) in methylene chloride were sequentially added triethylamine (5.5 mL, 39.5 mmol), 4-dimethylamino pyridine (catalytic) and trifluoroacetic anhydride (4.2 mL, 29.6 mmol) and the reaction mixture was stirred for 3 h at room temperature. Aqueous NaHCO₃ and ethyl acetate were added, the organic layer was separated, washed with brine, dried over MgSO₄ and concentrated in vacuo. Purification by flash chromatography provides 1-2b as colorless oil.

Step c)

A 4 N solution of HCl in 1,4-dioxane (20 mL) was added to 1-2b (7.4 g, 18.5 mmol) at room temperature and the solution was stirred for 2 h and then concentrated in vacuum. Crystallization from ether provides 1-2c as a white solid. MS (m/z) M+1=301.

Step Two

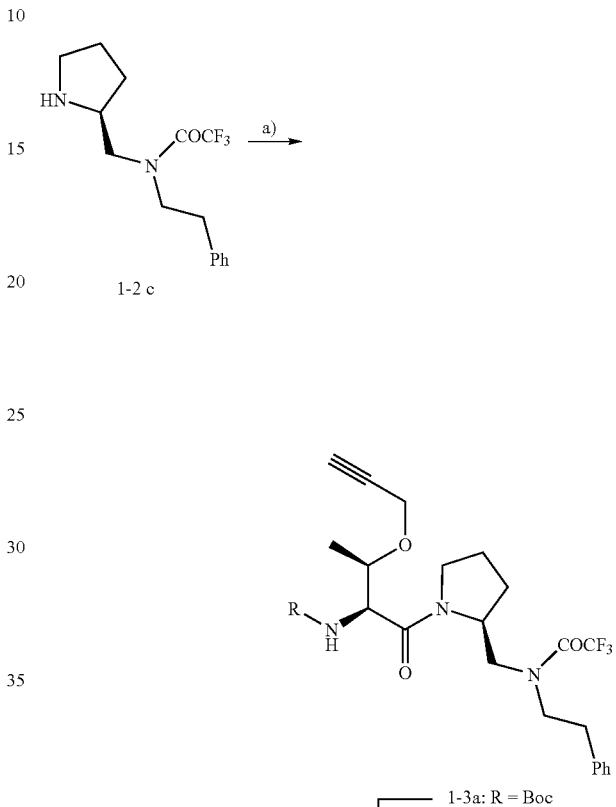

Step a)

To a solution of 1-2d (7.2 g, 21.3 mmol) in DMF were sequentially added DIPEA (19.0 mL, 106 mmol), HOBt (4.24 g, 27.7 mmol) and HBTU (10.5 g, 27.7 mmol). After stirring for 5 min 1-2c (7.1 g, 27.7 mmol) was added and the reaction mixture was stirred overnight at room temperature. Water and ethyl acetate were added, the organic layer was separated, washed with 10% citric acid, aqueous NaHCO₃ and brine, dried over MgSO₄ and concentrated in vacuo. Purification by flash chromatography provides 1-3a compound as a white solid.

Step b)

A 4 N solution of HCl in 1,4-dioxane (15 mL) was added to 1.3a (10.7 g, 18.0 mmol) at room temperature and the solution was stirred for 2 h and then concentrated in vacu. Crystallization from ether provides 1-3b as a white solid. MS (m/z) M+1=440.

Step Three

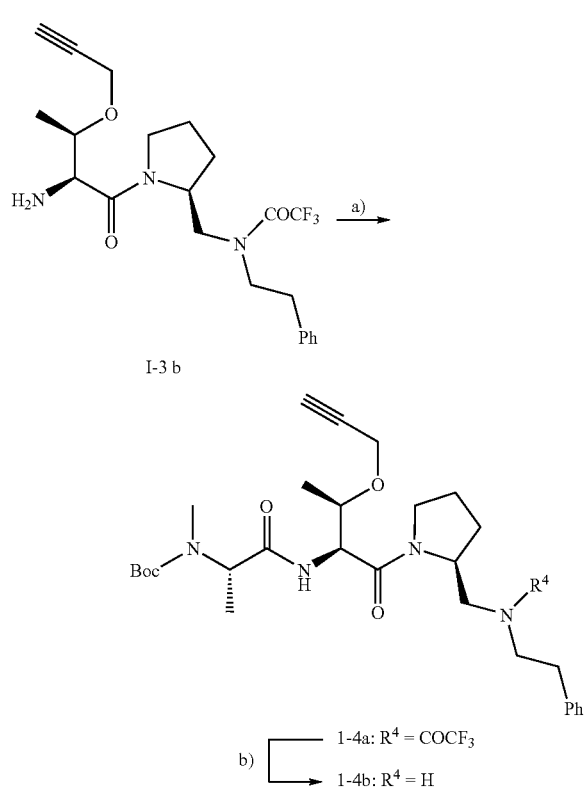

b) ── 1-4a: R⁴ = COCF₃
   → 1-4b: R⁴ = H

Step a)

To a solution of 1-3b (8.9 g, 18.7 mmol) in DMF were sequentially added DIPEA (16.7 mL, 93.6 mmol), HOBt (3.7 g, 24.3 mmol), HBTU (9.2 g, 24.3 mmol). After stirring for 5 min BOC-NMeAlaOH (4.9 g, 24.3 mmol) was added and the reaction mixture was stirred overnight at room temperature. Water and ethyl acetate were added, the organic layer was separated, washed with 10% citric acid, aqueous NaHCO₃ and brine, dried over MgSO₄ and concentrated in vacuo. Purification by flash chromatography provides 1-4a as a white solid.

Step b)

To a solution of 1-4a (8.7 g, 13.4 mmol) in THF cooled to 0° C. was added 2 N LiOH (20 mL) and the reaction was stirred overnight at room temperature. PH was adjusted to 6 with 10% citric acid and ethyl acetate was added, the organic layer was separated, washed with brine dried over MgSO₄ and concentrated in vacuum. Purification by flash chromatography provides 1-4b as a white solid. MS (m/z) M+1=625.

Synthesis of I-2d

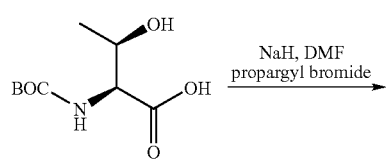   NaH, DMF
                       propargyl bromide →

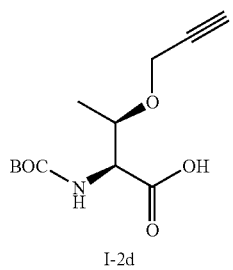

I-2d

To a suspension of NaH (4.56 g, 114.04 mmol) in dry DMF (100 mL) cooled to 0° C. was added portion wise N-Boc-L-threonine (10.00 g, 45.62 mmol). After stirring for 10 min propargyl bromide (10 mL) was slowly added and the reaction was stirred for 1 hr at 0° C.

Water (500 mL) and ethyl acetate (100 mL) were added, the organic layer was separated, the aqueous layer was acidified to pH=5 with 10% citric acid and extracted twice with ethyl acetate. The combined organic extracts were washed with brine, dried over MgSO₄ and concentrated in vacuo. Purification by flash chromatography provides 1-2d as a colorless oil.

2. Synthesis of Compound 4

Step One

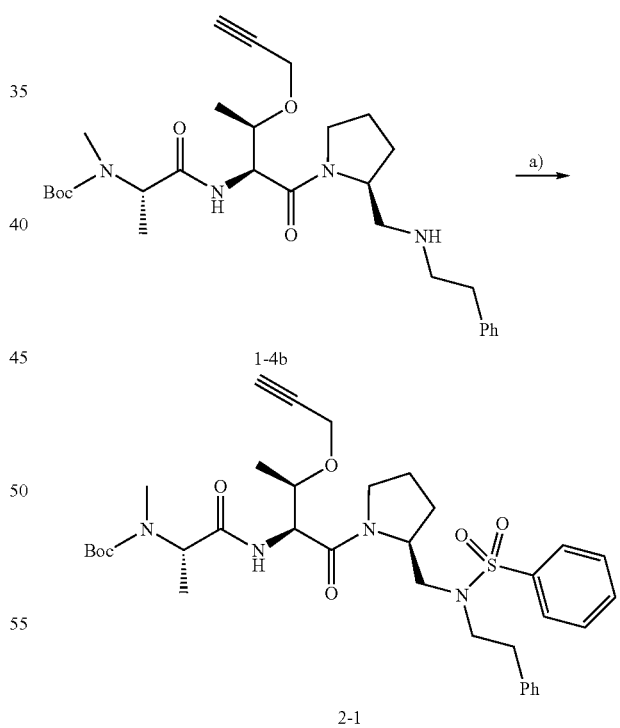

Step a)

To a solution of 1-4b (600 mg, 1.1 mmol) in THF were sequentially added DIPEA (240 uL, 2.3 mmol) and benzenesulfonyl chloride (160 uL, 2.2 mmol). The reaction was stirred for 1 h at room temperature. Water and ethyl acetate were added, the organic layer was separated, washed with 10% citric acid and brine, dried over MgSO₄ and concentrated in vacuum. Purification by flash chromatography provides 2-1 as a white solid.

Step Two

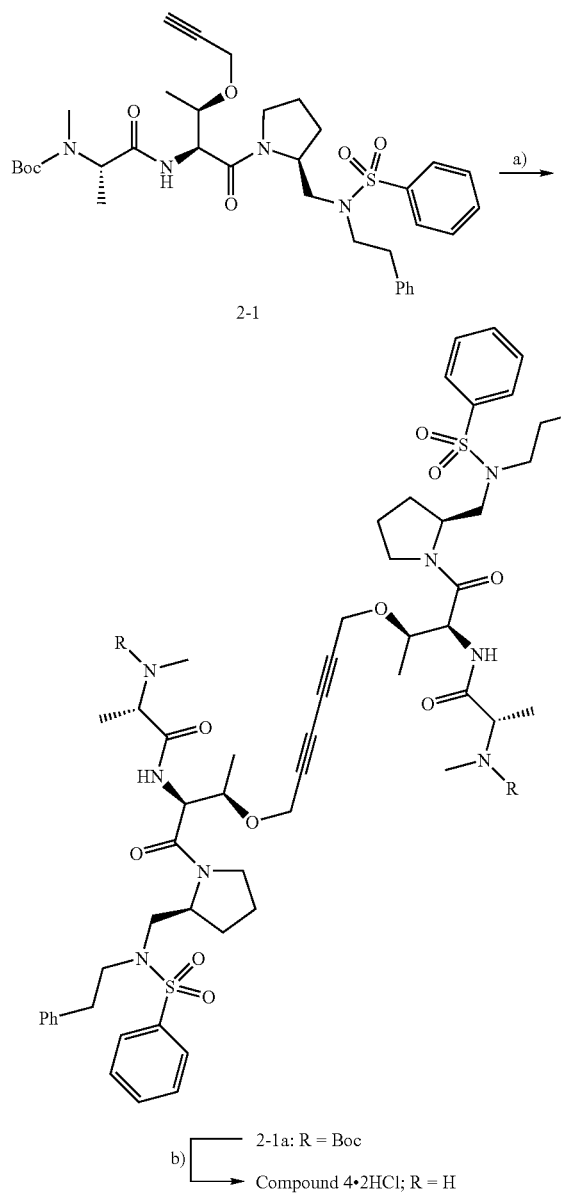

2-1

2-1a: R = Boc
Compound 4·2HCl; R = H

Step a)

To a solution of 2-1 (400 mg, 0.6 mmol) in dry acetone were sequentially added tetramethylethylenediamine (180 uL, 1.2 mmol) and copper (I) chloride (118 mg, 1.2 mmol). The reaction was stirred overnight at room temperature and solvent was removed in vacuo. Water and ethyl acetate were added, the organic layer was separated, washed with 10% citric acid, aqueous NaHCO₃ and brine, dried over MgSO₄ and concentrated in vacuum. Purification by flash chromatography provides 2-1a as a white solid.

Step b)

A 4 N solution of HCl in dioxane (3 mL) was added to 2-1a (542 mg, 0.47 mmol) at 0° C. The solution was stirred for 2 h and then concentrated in vacuo. Crystallization from ether provides compound 4·2HCl as a white solid. MS (m/z) M+1=1136.

3. Synthesis of Compound 2

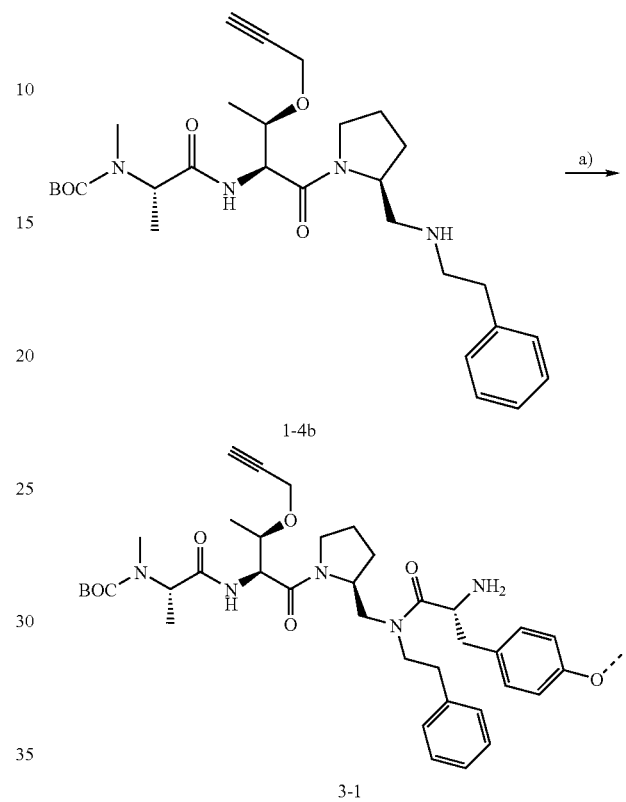

1-4b 3-1

Step One

To a solution of 1-4b (900 mg, 1.7 mmol) in DMF were sequentially added DIPEA (1.5 mL, 8.5 mmol), HBTU (841 mg, 2.2 mmol) and HOBt (340 mg, 2.2 mmol). After stirring for 5 min Boc-D-Tyr(Me)-OH (655 mg, 2.2 mmol) was added and the reaction mixture was stirred overnight at room temperature. Water and ethyl acetate were added, the organic layer was separated, washed with 10% citric acid, aqueous NaHCO₃ and brine, dried over MgSO₄ and concentrated in vacuo. Purification by flash chromatography provides 3-1 as a white solid.

Step Two

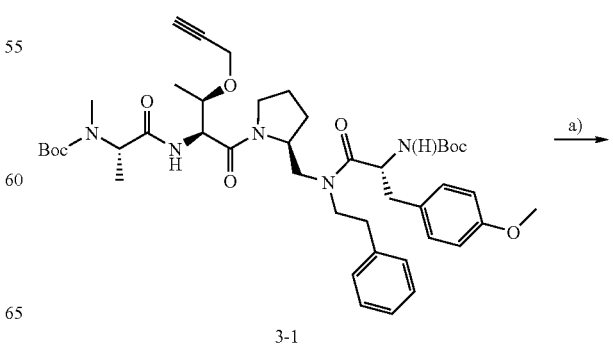

3-1

-continued

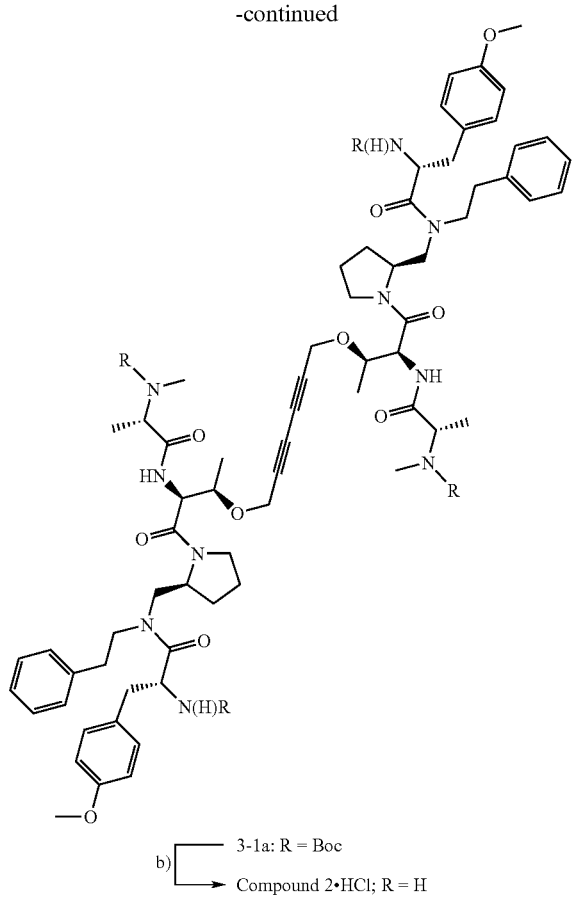

3-1a: R = Boc
b) → Compound 2·HCl; R = H

Step a)

To a solution of 3-1 (225 mg, 0.3 mmol) in dry acetone were sequentially added tetramethylethylenediamine (85 uL, 0.5 mmol) and copper (I) chloride (54 mg, 0.5 mmol) were added and the reaction was stirred overnight at room temperature and solvent was removed in vacuum, Water and ethyl acetate were added, the organic layer was separated, washed with 10% citric acid, aqueous NaHCO$_3$ and brine, dried over MgSO$_4$ and concentrated in vacuo. Purification by flash chromatography provides 3-1a as a white solid.

Step b)

A 4 N solution of HCl in 1,4-dioxane (2 mL) was added to 3-1a (150 mg, 0.1 mmol) at 0° C. and the solution was stirred for 2 h and then concentrated in vacuum. Crystallization from diethyl ether yielded compound 2.2HCl as a white solid. MS (m/z) M+1=1210.

4. Synthesis of Compound 11

Step One

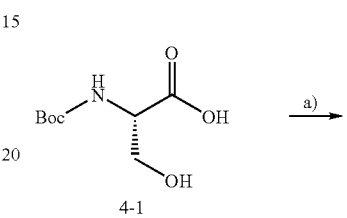

4-1

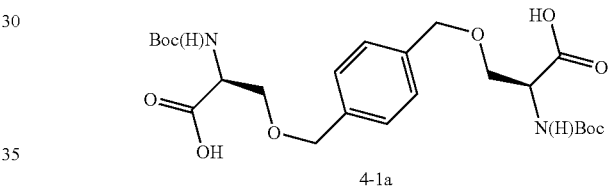

4-1a

To a suspension of NaH (1.46 g, 36.5 mmol) in DMF cooled to 0° C. was added BOC-Ser-OH 4-1 (3.0 g, 14.6 mmol) and after stirring for 15 min α,α'-Dibromo-p-xylene (2.3 g, 8.7 mmol) was added. The reaction was then stirred for 1 h at 0° C. and 15 min at RT. Water was added and PH was acidified to pH 5 with 1N HCl. Ethyl acetate was added, the organic layer was separated, washed with brine, dried over MgSO$_4$ and concentrated in vacuo. Purification by flash chromatography provides 4-1a as a white solid.

Step Two

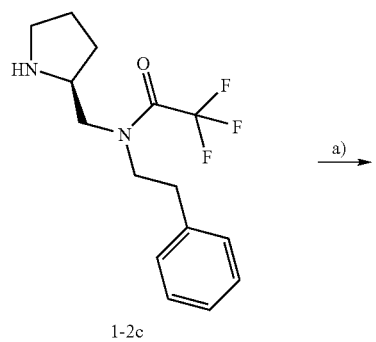

1-2c

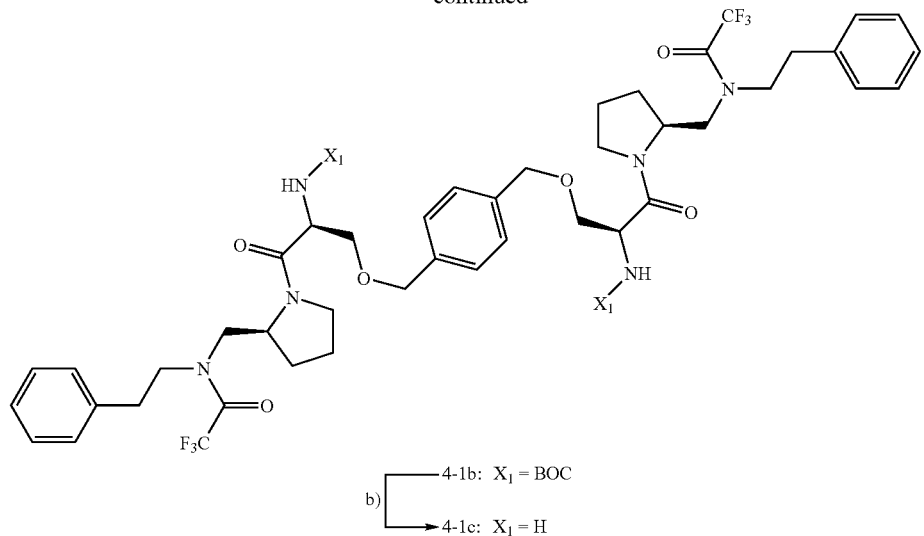

4-1b: $X_1$ = BOC
b)
4-1c: $X_1$ = H

Step a)

To a solution of 4-1a (1.6 g, 3.1 mmol) in DMF were sequentially added DIPEA (1.3 mL, 7.5 mmol), HOBt (1.2 g, 7.8 mmol) and HBTU (2.9 g, 7.8 mmol). After stirring for 5 min 1-2c (1.7 g, 5.7 mmol) was added and the reaction mixture was stirred overnight at room temperature. Water and ethyl acetate were added, the organic layer was separated, washed with 10% citric acid, aqueous NaHCO₃ and brine, dried over MgSO₄ and concentrated in vacuo. Purification by flash chromatography provides 4-1b as a white solid.

Step b)

A 4 N solution of HCl in 1,4-dioxane (5 mL) was added to 4-1b (1.4 g, 1.3 mmol) at room temperature and the solution was stirred for 2 h and then concentrated in vacuo. Crystallization from ether provides 4-1c as a white solid. MS (m/z) M+1=877.

Step Three

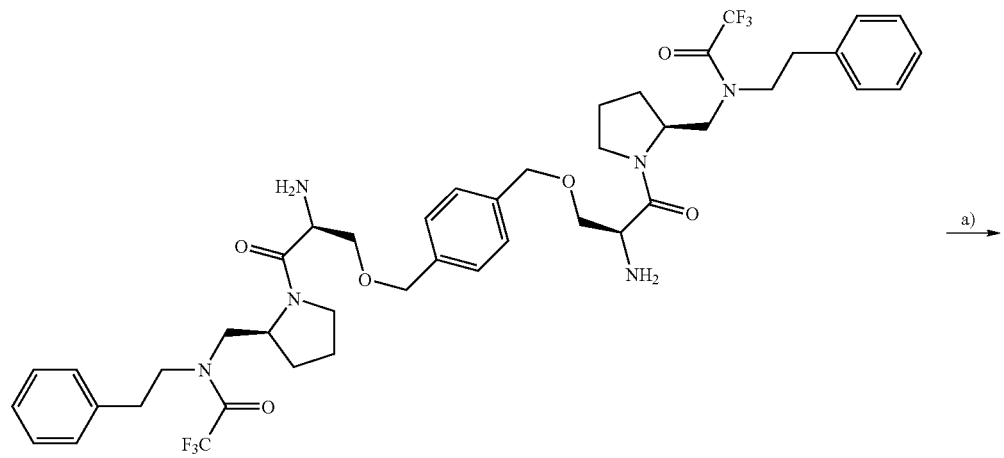

41-c

-continued

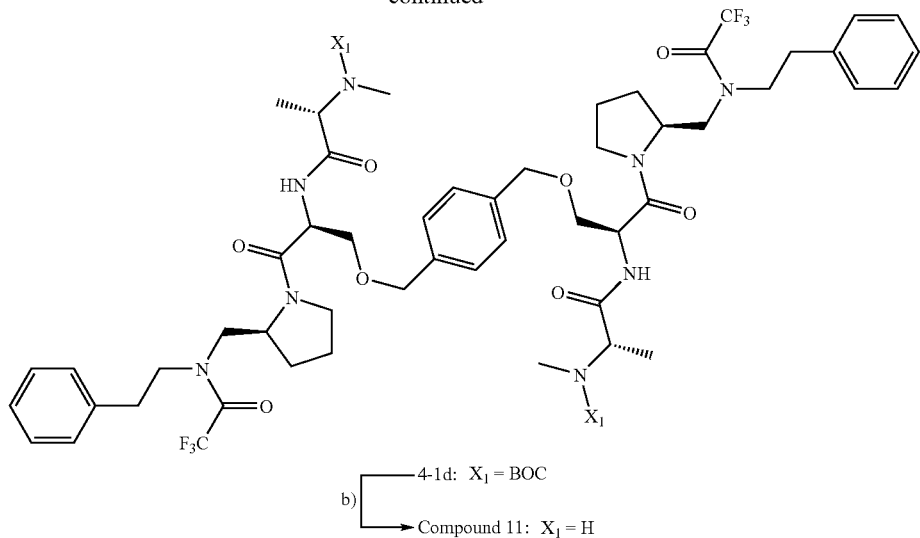

b) ┌── 4-1d: X₁ = BOC
  └── Compound 11: X₁ = H

Step a)

To a solution of 4-1c (550 mg, 0.6 mmol) in DMF were sequentially added DIPEA (550 uL, 3.1 mmol), HBTU (611 mg, 1.6 mmol) and HOBt (246 mg, 1.6 mmol). After stirring for 5 min BOC-NMe-AlaOH (327 mg, 1.6 mmol) was added and the reaction mixture was stirred overnight at room temperature. Water and ethyl acetate were added, the organic layer was separated, washed with 10% citric acid, aqueous NaHCO₃ and brine, dried over MgSO₄ and concentrated in vacuo. Purification by flash chromatography provides 4-1d as a white solid.

Step b)

A 4 N solution of HCl in 1,4-dioxane (5 mL) was added to 4-1d (520 mg, 0.4 mmol) at room temperature and the solution was stirred for 2 h and then concentrated in vacuum. Crystallization from ether provides compound 11.2HCl as a white solid. MS (m/z) M+1=1048.

5. Synthesis of Compound 18

Step One

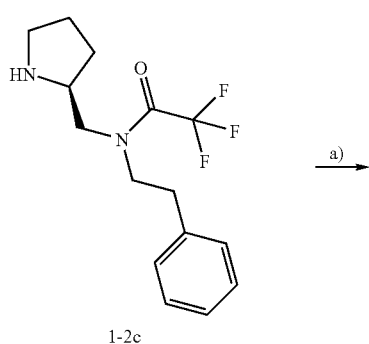

1-2c a) →

-continued

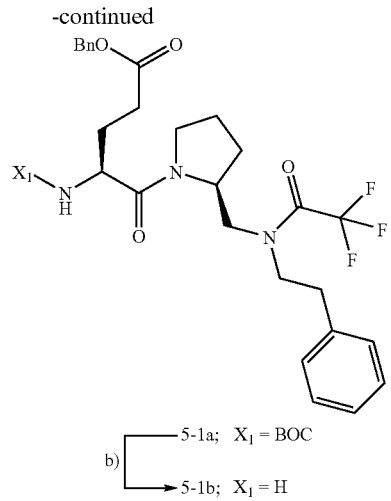

b) ┌── 5-1a; X₁ = BOC
  └── 5-1b; X₁ = H

Step a)

To a solution of Boc-Glu(OBn)—OH (5.55 g, 16.4 mmol) in DMF were sequentially added DIPEA (12.5 mL, 71.8 mmol), HOBt (3.86 g, 28.6 mmol) and HBTU (5.43 g, 14.3 mmol). After stirring for 5 min I-2c (3.04 g, 9.0 mmol) was added and the reaction mixture was stirred overnight at room temperature. Water and ethyl acetate were added, the organic layer was separated, washed with 10% citric acid, aqueous NaHCO₃ and brine, dried over MgSO₄ and concentrated in vacuo. Purification by flash chromatography provides 5-1a as a white solid.

Step b)

A 4 N solution of HCl in 1,4-dioxane (20 mL) was added to 5-1a (5.2 g, 8.4 mmol) at room temperature and the solution was stirred for 2 h and then concentrated in vacuum. Crystallization from ether provides 5-1b as a white solid.

Step Two

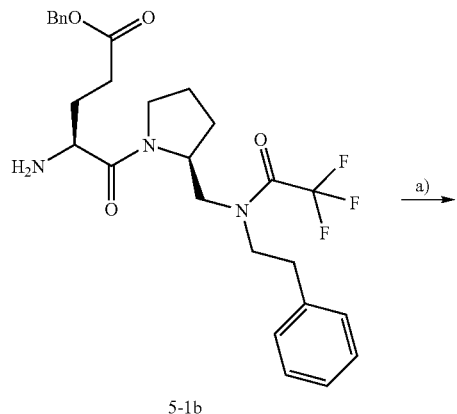

5-1b

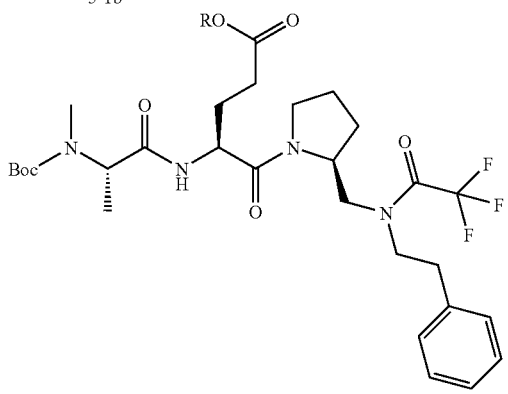

b) ⎡ 5-1c; R = Bn
    ⎣ 5-1d; R = H

Step a)

To a solution of Boc-NMe-Ala-OH (2.1 g, 10.4 mmol) in DMF were sequentially added DIPEA (10.5 mL, 60.3 mmol), HBTU (3.0 g, 9.3 mmol) and HOBt (2.0 g, 15.3 mmol). After stirring for 5 min 5-1b (4.7 g, 8.4 mmol) was added and the reaction mixture was stirred overnight at room temperature. Water and ethyl acetate were added, the organic layer was separated, washed with 10% citric acid, aqueous NaHCO$_3$ and brine, dried over MgSO$_4$ and concentrated in vacuo. Purification by flash chromatography provides 5-1c as a white solid.

Step b)

A suspension of 5-1c (1.9 g, 2.8 mmol) and 10% Pd/C (196 mg) was stirred for 3 hrs under hydrogen atmosphere. The reaction was filtered through celite and filtrate concentrated in vacuo. Purification by flash chromatography provides 5-1d as a white solid.

Step Three

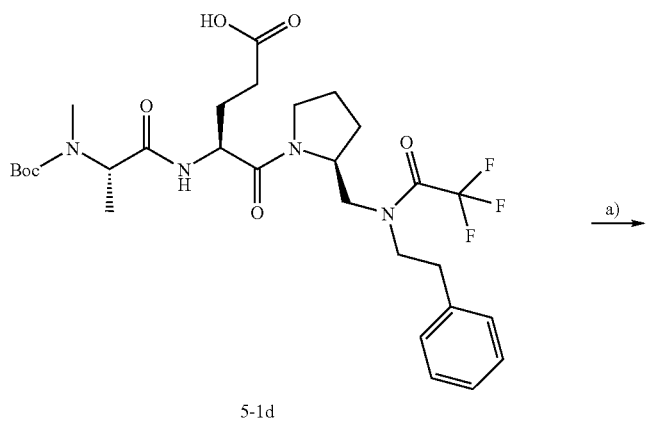

5-1d

-continued

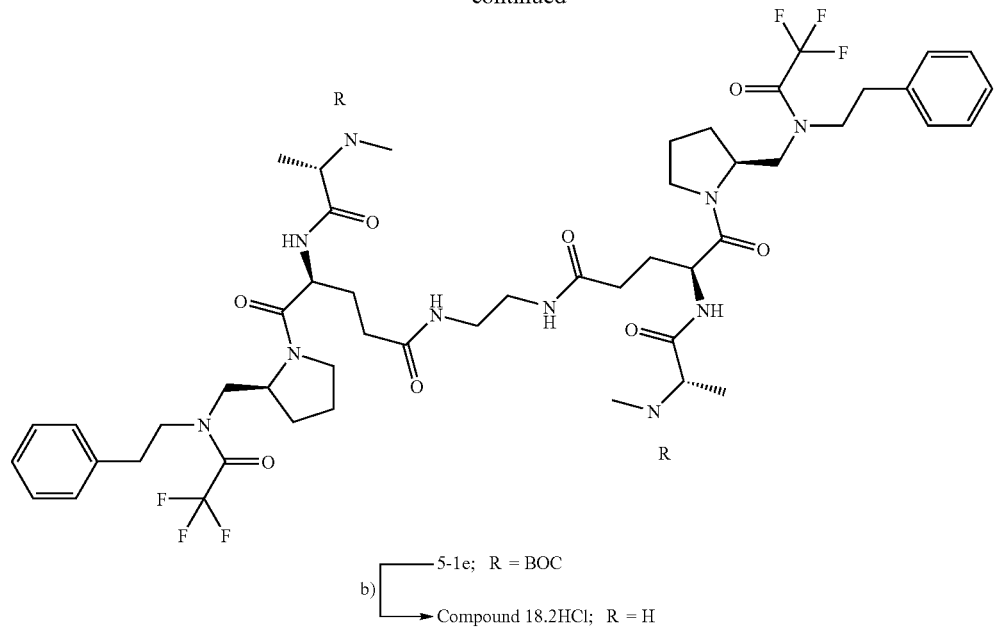

b) ⎡ 5-1e; R = BOC
   ⎣ Compound 18.2HCl; R = H

Step a)

To a solution of 5-1d (101 mg, 0.16 mmol) in DMF were sequentially added DIPEA (200 uL, 1.1 mmol), HBTU (56 mg, 0.14 mmol) and HOBt (24 mg, 0.18 mmol). After stirring for 5 min ethylenediamine (3.7 mg, 0.06 mmol) was added and the reaction mixture was stirred overnight at room temperature. Water and ethyl acetate were added, the organic layer was separated, washed with 10% citric acid, aqueous NaHCO$_3$ and brine, dried over MgSO$_4$ and concentrated in vacu. Purification by flash chromatography provides 5-1e as a white solid.

Step b)

A 4 N solution of HCl in 1,4-dioxane (5 mL) was added to 5-1e (75 mg, 0.06 mmol) at room temperature and the solution was stirred for 2 h and then concentrated in vacuum. Crystallization from ether provided compound 18.2HCl as a white solid. MS (m/z) (M+2)/2=527.3.

6. Synthesis of Compound 15

Step One

Step a)

Boc-L-proline (9.36 g, 43.5 mmol), HOBt (8.0 g, 52.2 mmol), EDC (10 g, 52.2 mmol) and DIPEA (30 mL, 174 mmol) were dissolved in dry dichloromethane (200 mL) under N$_2$ and stirred for 10 min at room temperature. 1,2,3, 4-R-Tetrahydronaphtylamine (6.72 g, 45.6 mmol) was then added and the solution was left to stir for 24 h at RT. The contents were then added to a separatory funnel along with EtOAc and washed with 10% citric acid (2×), saturated NaHCO$_3$ (2×) and brine. The organic layer was collected, dried and concentrated under reduced pressure to provide 6-1a.

Step b)

The product of step a) was treated with 50% CH$_2$Cl$_2$/TFA (50 mL) for 1 hr at room temperature. Volatiles were removed in vacuo. to provide 6-1b as the TFA salt. MS (m/z) M+1=245.

Step Two

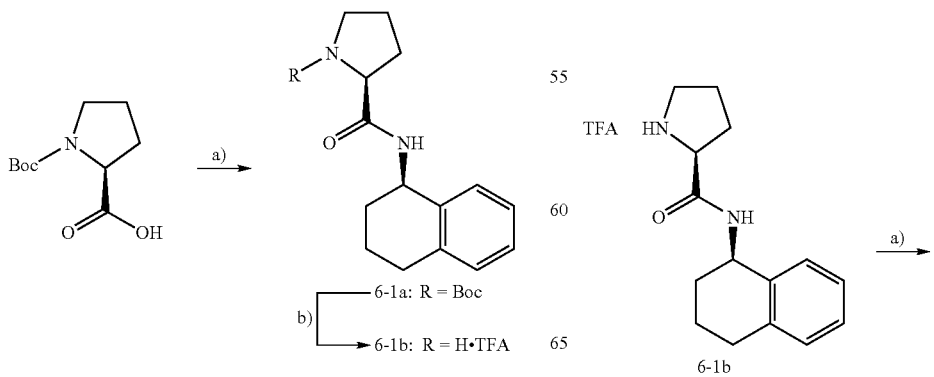

101
-continued

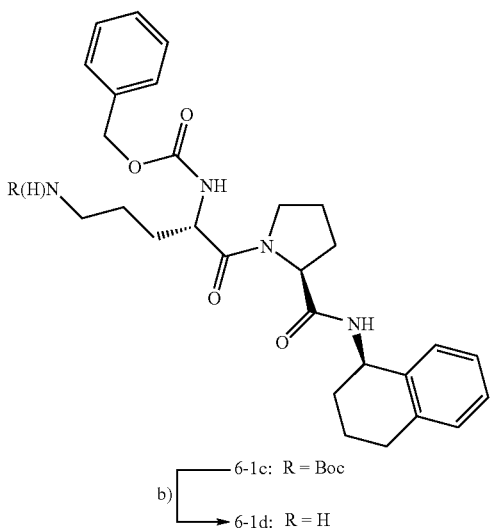

6-1c: R = Boc
b)
6-1d: R = H

102

Step a)

Z-Orn(Boc)OH (2.63 g, 7.2 mmol), HOBt (1.19 g, 7.8 mmol), HBTU (2.96 g, 7.8 mmol) and DIPEA (4.6 mL, 26 mmol) were dissolved in dry DMF (12 ml) under $N_2$ and stirred for 10 min at room temperature. Intermediate 6-1b (3.0 g, 6.5 mmol) was then added and the solution was left to stir for 24 h at room temperature. The contents were then added to a separatory funnel along with EtOAc and washed with 10% citric acid (2×), saturated $NaHCO_3$ (2×) and brine. The organic layer was collected, dried and concentrated under reduced pressure to provide 6-1c.

Step b)
The product from step a) was treated with 10 ml of 50% $CH_2Cl_2$/TFA for 1 hr at room temperature to yield 6-1d as its TFA salt. MS (m/z) M+1=493.

Step Three

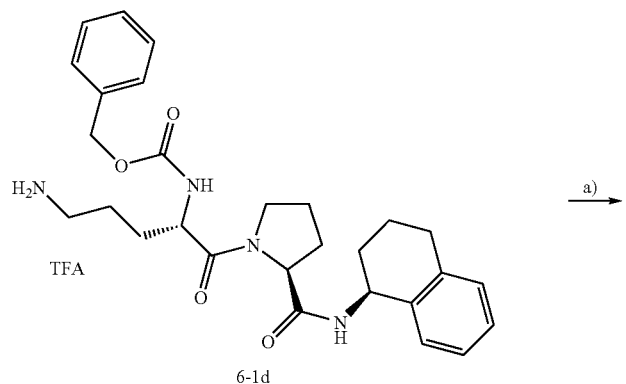

6-1d

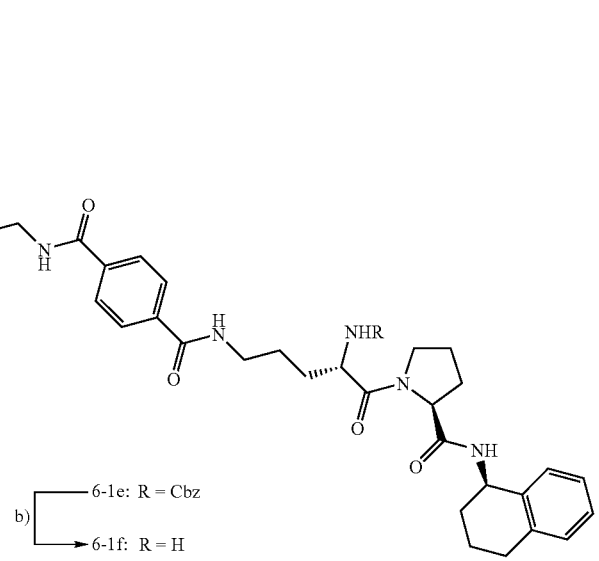

6-1e: R = Cbz
b)
6-1f: R = H

Step a)

Intermediate 6-1d (200 mg, 0.33 mmol), DMAP (5 mg, catalytic) and DIPEA (230 µL, 1.32 mmol) were dissolved in dry dichloromethane (5 mL) under $N_2$ and terephtaloyl chlo- RT. The mixture is filtered on celite, washed with MeOH. The filtrate was collected, dried and concentrated under reduced pressure to yield the product 6-1f. MS (m/z) M+1=847.

Step Four

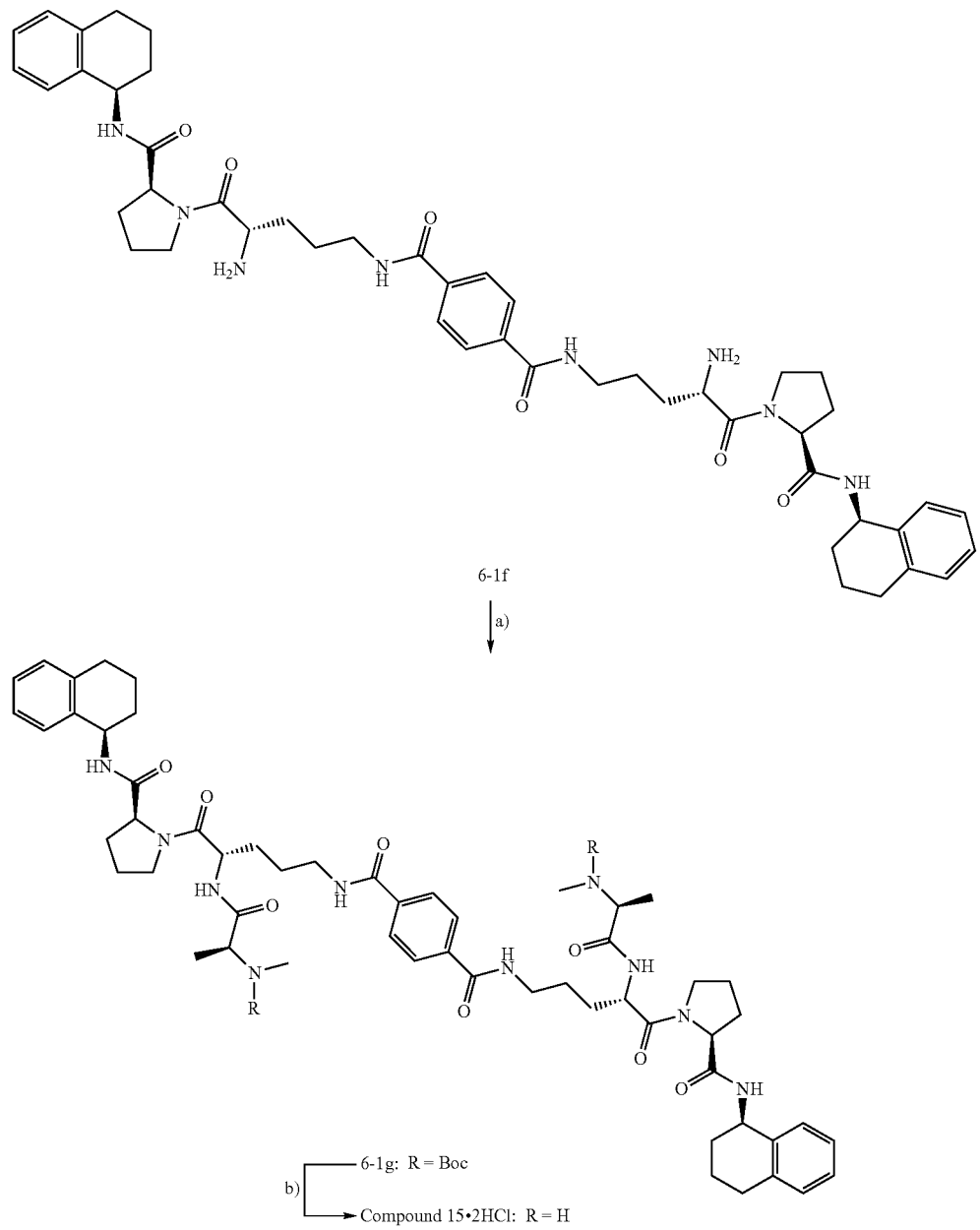

ride (30 mg, 0.15 mmol) was then added and the solution was stirred for 24 h at RT. The contents were then added to a separatory funnel along with EtOAc and washed with 10% citric acid (2×), saturated $NaHCO_3$ (2×) and brine. The organic layer was collected, dried and concentrated under reduced pressure to yield the product 6-1e as a yellow oil.

Step b)

6-1e (160 mg, 0.19 mmol) and 10% Pd/C (50% $H_2O$, 100 mg) were mixed together in MeOH (10 ml) under $N_2$, the $N_2$ is then flushed with $H_2$ and the mixture was stirred for 24 h at Step a)

Boc-N-Me-Ala-OH (74 mg, 0.37 mmol), HOBt (59 mg, 0.38 mmol), HBTU (144 mg, 0.38 mmol) and DIPEA (140 µl, 0.8 mmol) were dissolved in dry DMF (5 ml) under $N_2$ and stirred for 10 min at RT. 6-1f (135 mg, 0.16 mmol) was then added and the solution was left to stir for 24 h at RT. The contents were then added to a separatory funnel along with ETOAc and washed with 10% citric acid (2×), saturated $NaHCO_3$ (2×) and brine. The organic layer was collected, dried and concentrated under reduced pressure to provide 6-1g.

Step b)
Intermediate 6-1g was subsequently treated with 4N HCl in 1,4-dioxane for 1 hr at room temperature. Trituration with diethyl ether provided the bis-HCl salt of compound 15. MS (m/z) M+1=1017.
7. Synthesis of Compound 14
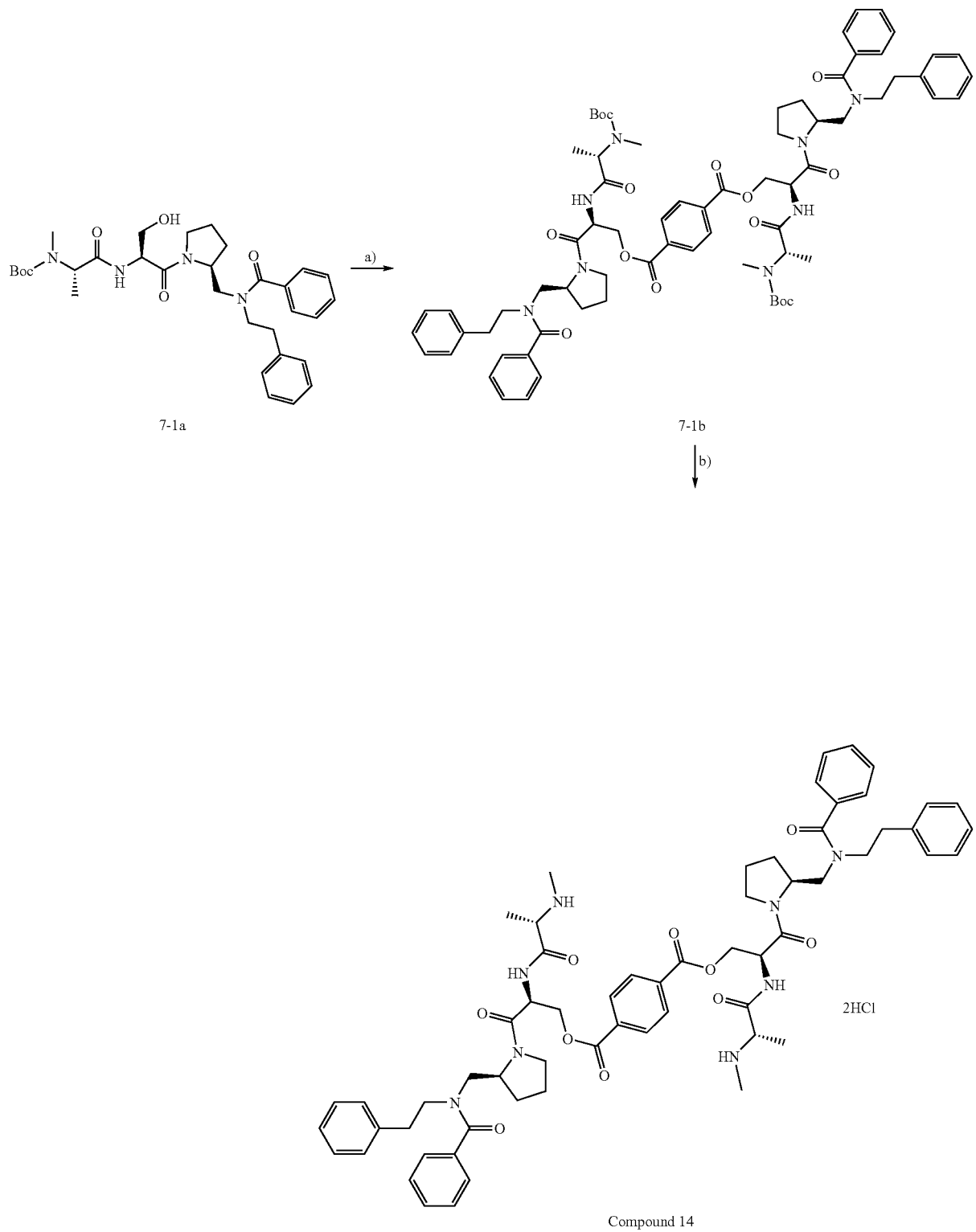
Compound 14

Step a)

To a solution of 7-1a (206 mg, 0.35 mmol) in dichloromethane (5 mL) were sequentially added DIPEA (100 uL, 0.57 mmol) and terephthaloyl chloride (31.3 mg, 0.15 mmol) and the reaction was stirred for 12 hrs at room temperature. Water and ethyl acetate were added, the organic layer was separated, washed with 10% citric acid, aqueous NaHCO$_3$ and brine, dried over MgSO$_4$ and concentrated under reduced pressure. Purification by flash chromatography provided 7-1b as a white solid.

Step b)

A 4 N solution of HCl in 1,4-dioxane (1 mL) was added to 7-1b (16 mg, 0.01 mmol) at room temperature and the solution was stirred for 2 h and then concentrated in vacuum. Trituration with diethyl ether provided compound 14.2HCl as a white solid, MS (m/z) (M+2)/2=546.5.

8. Synthesis of Compound 23

Step a)

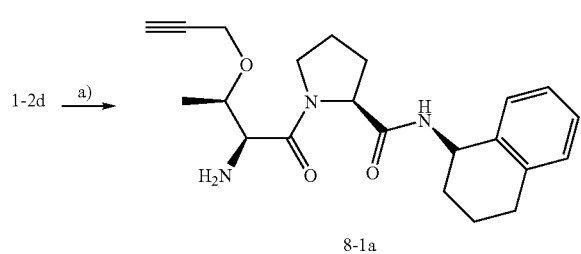

Intermediate 1-2d (250 mg, 0.78 mmol), HOBt (120mg, 0.78 mmol), HBTU (300mg, 0.78 mmol) and DIPEA (525µL, 3 mmol) were dissolved in dry DMF (5 mL) under N$_2$ and stirred for 10 min at room temperature. Intermediate 6-1b (215 mg, 0.6 mmol) was added and the solution was left to stir for 24 h at room temperature. The contents were added to a separatory funnel along with EtOAc and washed with 10% citric acid (2×), brine (2×) and saturated NaHCO$_3$ (2×). The organic layer was collected, dried and concentrated under reduced pressure. The product was purified by flash chromatography (hexanes/EtOAc) and subsequently treated with 4N HCl in 1,4-dioxane, volatiles were removed and trituration with diethyl ether provides 8-1a as the HCl salt. MS (m/z) M+1=384.3.

Step b)

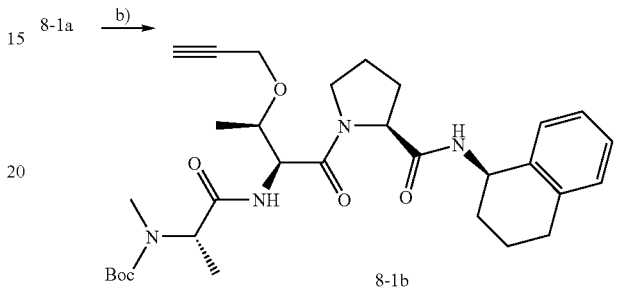

Boc-Me-Ala-OH (130 mg, 0.63 mmol), HOBt (100 mg, 0.63 mmol), HBTU (240mg, 0.63 mmol) and DIPEA (420 µL, 2.4 mmol) were dissolved in dry DMF (5 mL) under N$_2$ and stirred for 10 min at RT. 8-1b (200 mg, 0.48 mmol) was then added and the solution was left to stir for 24 h at RT. The contents were then added to a separatory funnel along with EtOAc and washed with 10% citric acid (2×), brine (2×) and saturated NaHCO$_3$ (2×). The organic layer was collected, dried and concentrated under reduced pressure. The product 8-1b was purified by flash chromatography (hexanes/EtOAc). MS (m/z) M+1=569.4

Step c)

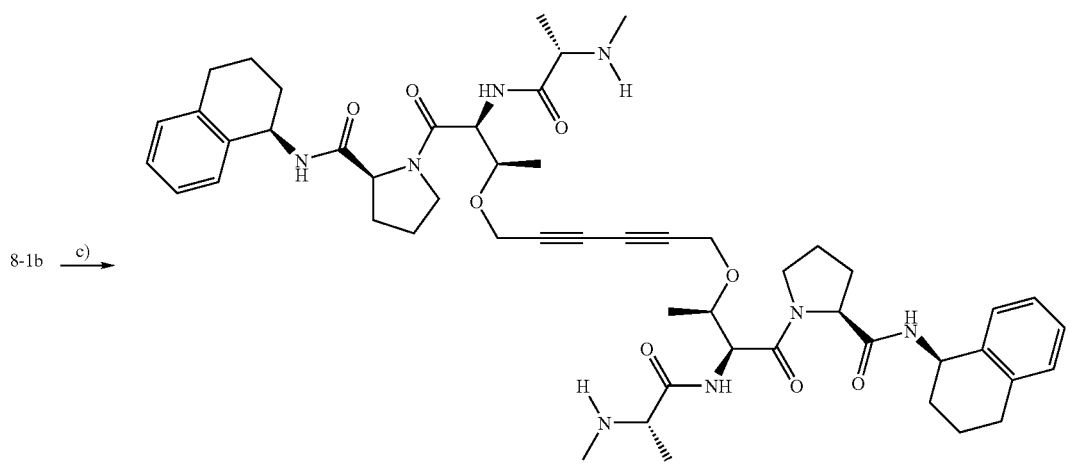

Compound 23·2HCl

Compound 23.2HCl

Intermediate 8-1b (70 mg, 0.123 mmol), CuCl (20 mg, 0.185 mmol) and tetramethylethylenediamine (27 µL, 0.185 mmol) were dissolved in dry acetone (3mL) and stirred at RT under an $O_2$ atmosphere for 72 h. EtOAc was added and the mixture was transferred to a separatory funnel. The mixture was washed with 10% citric acid (2×), brine (2×) and saturated $NaHCO_3$ (2×). The organic layer was collected, dried and concentrated under reduced pressure. The product was purified by flash chromatography (hexanes/THF). The resulting product was stirred with 4N HCl in 1,4-dioxane for 2 hrs. Volatiles were removed under reduced pressure and the residue triturated with diethyl ether to provide compound 23 as its bis-HCl salt. MS (m/z) M+1=935.1.

9. Synthesis of Compound 25

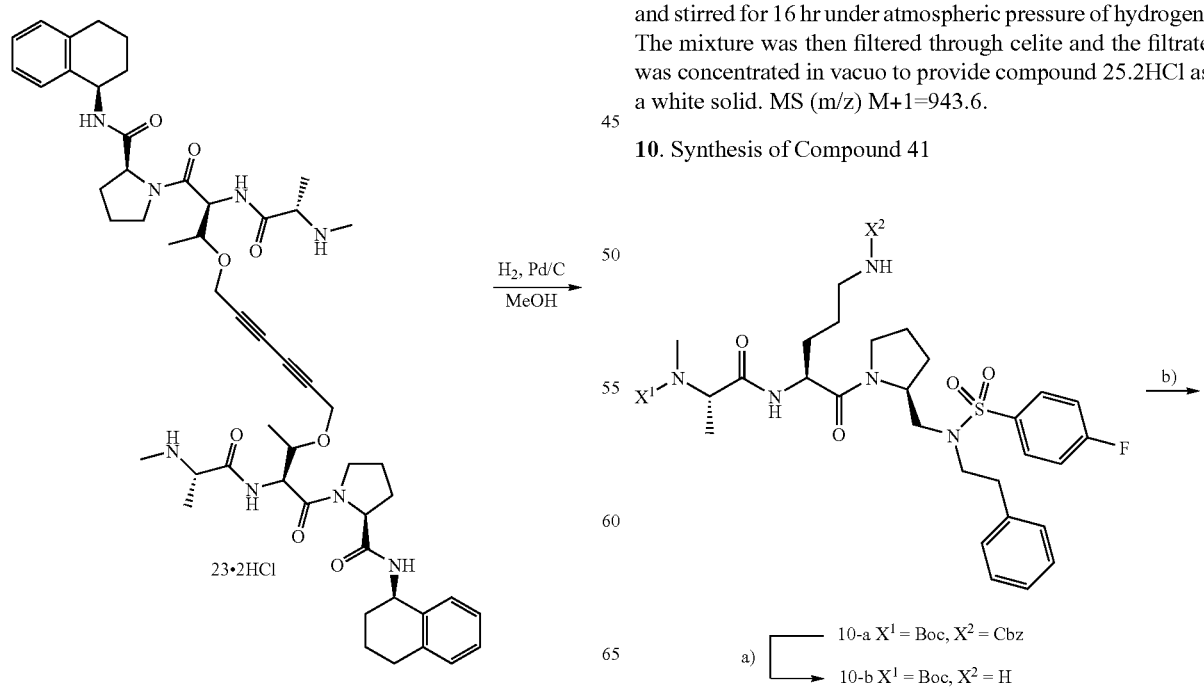

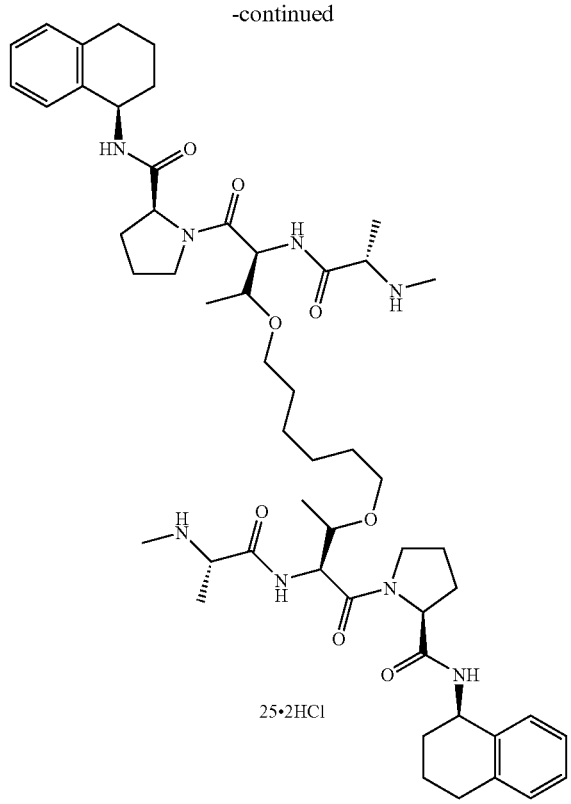

To a solution of 23.2HCL (100 mg, 0.1 mmol) in anhydrous MeOH (10 mL) and stirred under $N_2$ was added 10% Pd/C (500 mg). The reaction mixture was purged with hydrogen and stirred for 16 hr under atmospheric pressure of hydrogen. The mixture was then filtered through celite and the filtrate was concentrated in vacuo to provide compound 25.2HCl as a white solid. MS (m/z) M+1=943.6.

10. Synthesis of Compound 41

-continued

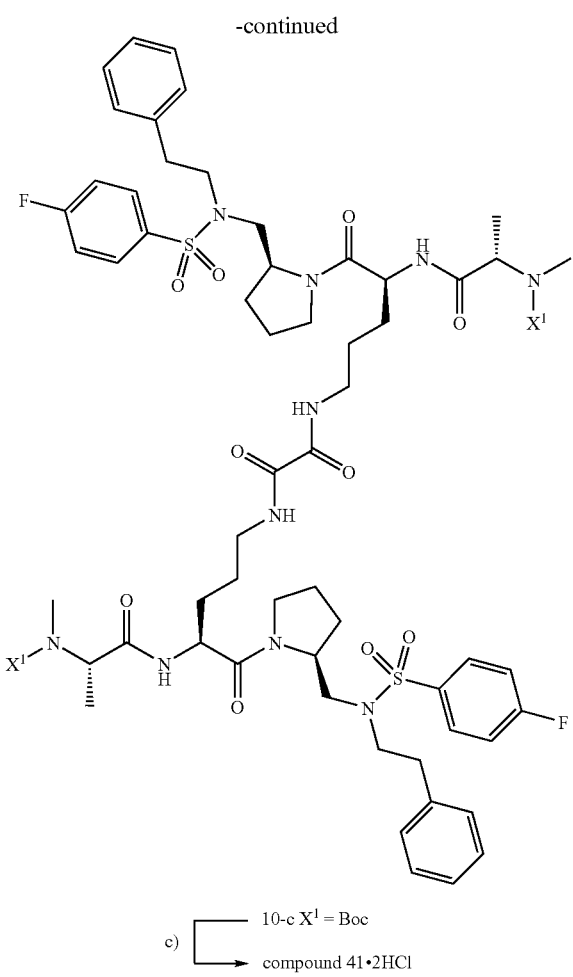

c) {
10-c X¹ = Boc
→ compound 41•2HCl
}

Step a)

To a solution of 10-a (4.90 g, 6.15 mmol) in anhydrous MeOH (120 mL) and stirred under $N_2$ was added 10% Pd/C (500 mg). The reaction mixture was purged with $H_2$ and stirred for 3 hr, then filtered through celite. The filtrate was concentrated in vacuo to provide intermediate 10-b as a white solid. MS (m/z) M+1=662.4.

Step b)

A solution of 10-b (200 mg, 0.30 mmol) in dichloromethane, cooled to 0° C., were sequentially added $Et_3N$ (84 µl, 0.60 mmol) and oxalyl chloride (13 µl, 0.15 mmol). The reaction was then stirred for 4 hrs at room temperature. Aqueous $NaHCO_3$ and ethyl acetate were added, the organic layer was separated, washed with brine, dried over anhydrous $MgSO_4$, filtered and concentrated in vacuo. Purification by silica gel chromatography eluting with a hexane/tetrahydrofuran gradient provided the expected compound 10-c as a white solid.

Step c)

4N HCl in 1,4-dioxane (3 ml) was added to 10-c (95 mg, 0.07 mmol) and the solution was stirred for 2 hrs at room temperature. Volatiles were removed under reduced pressure and the residue was triturated with diethyl ether to provide compound 41 as its bis-HCl salt. MS (m/z) (M+2)/2=589.4.

Representative compounds of the present invention were prepared by simple modification of the above procedures and are illustrated in Table 1:

TABLE 1

| Compound | Structure | (M + 2)/2 |
|---|---|---|
| 1 | 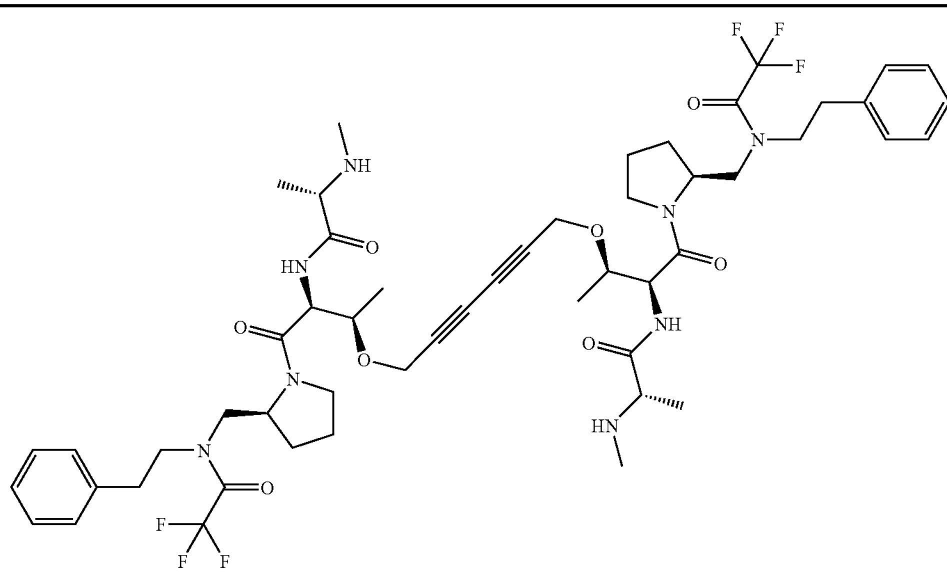 | 524.6 |

TABLE 1-continued

| Compound | Structure | (M + 2)/2 |
|---|---|---|
| 2 | 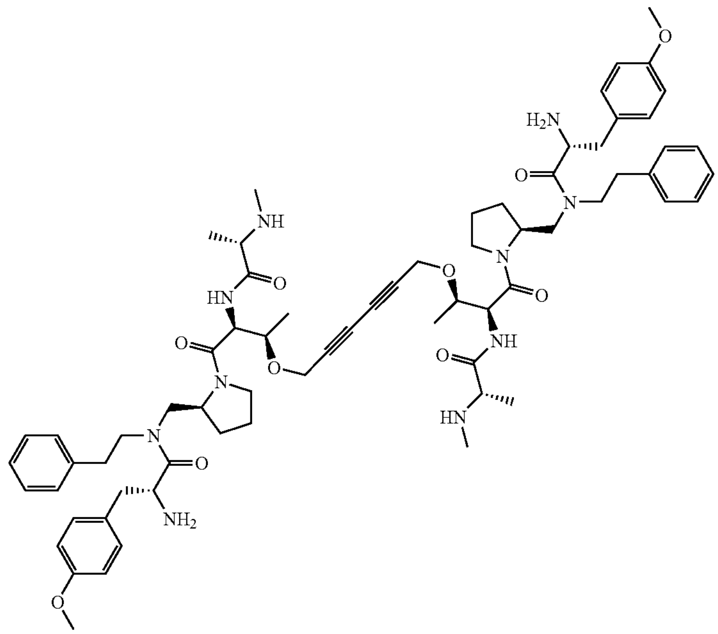 | 605.5 |
| 3 | 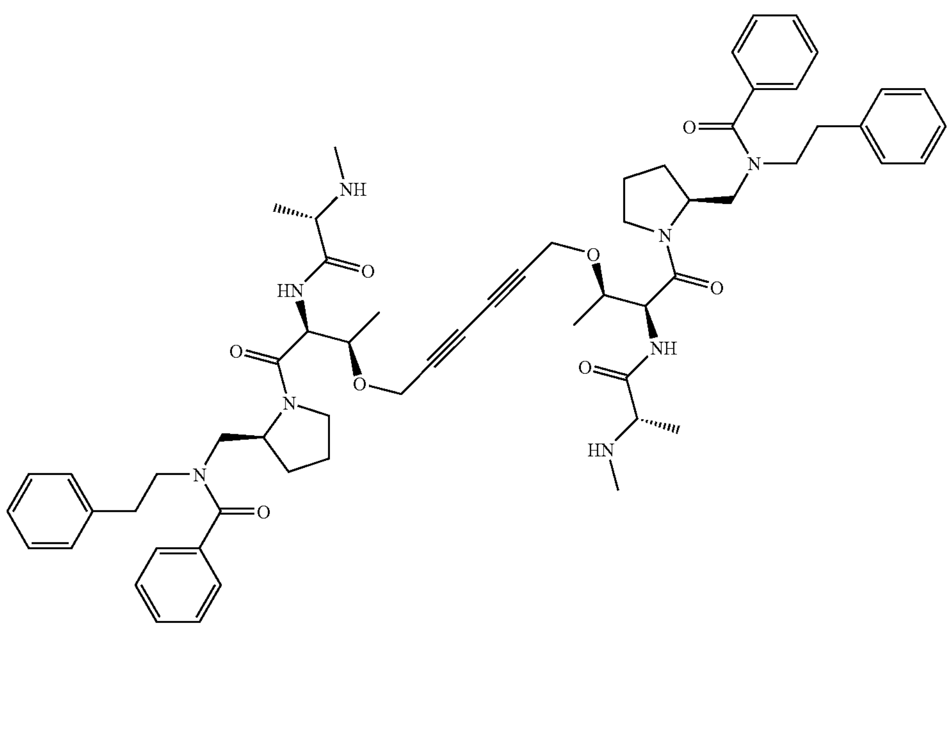 | 532.6 |

TABLE 1-continued

| Compound | Structure | (M + 2)/2 |
|---|---|---|
| 4 | 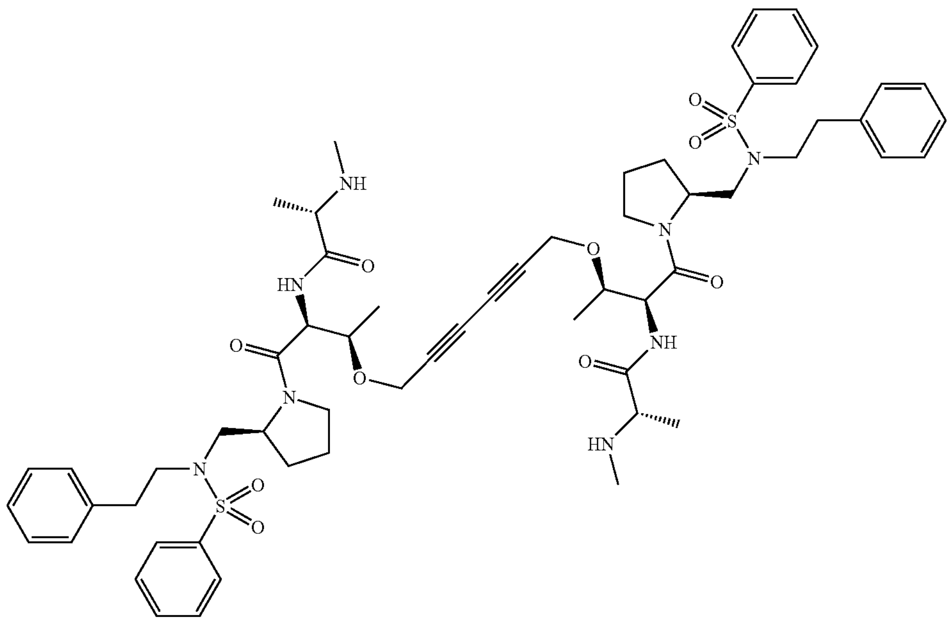 | 568.4 |
| 5 | 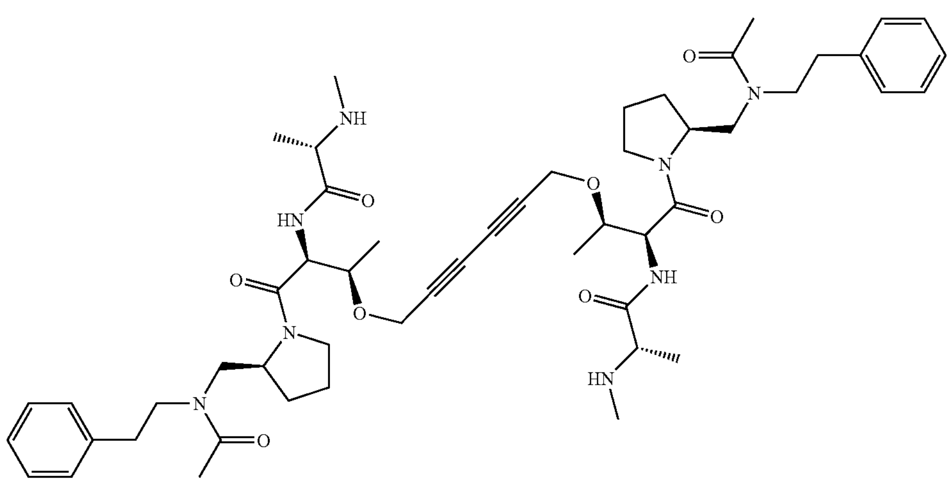 | 470.4 |

TABLE 1-continued
| Compound | Structure | (M + 2)/2 |
|---|---|---|
| 6 | 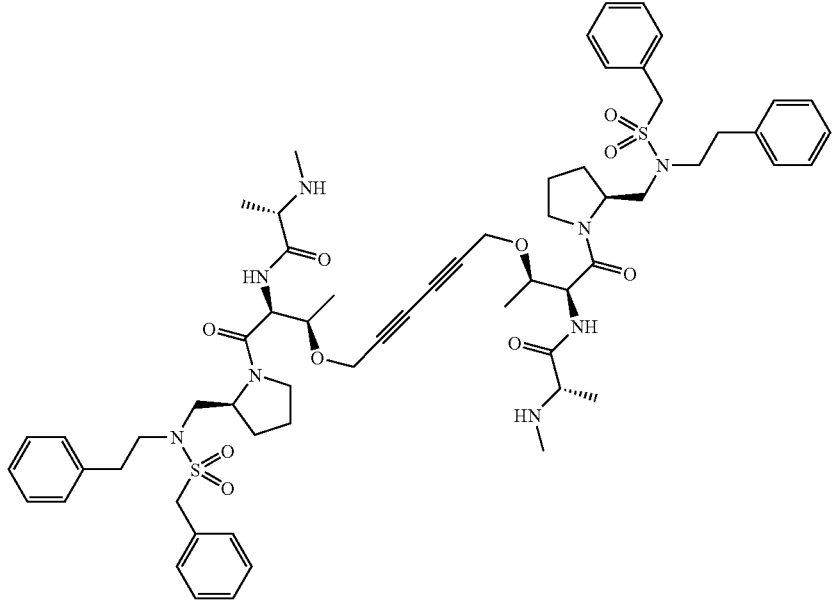 | 582.5 |
| 7 | 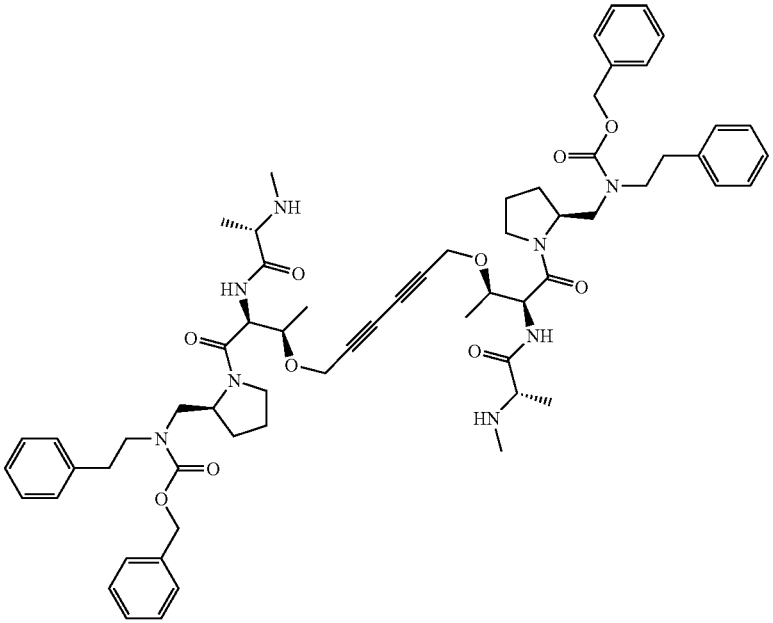 | 562.4 |

TABLE 1-continued
| Compound | Structure | (M + 2)/2 |
| --- | --- | --- |
| 8 | 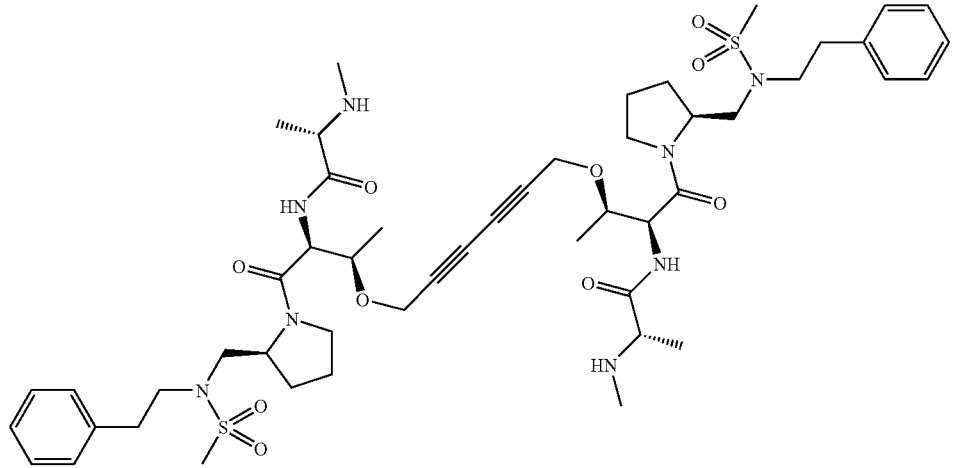 | 506.4 |
| 9 | 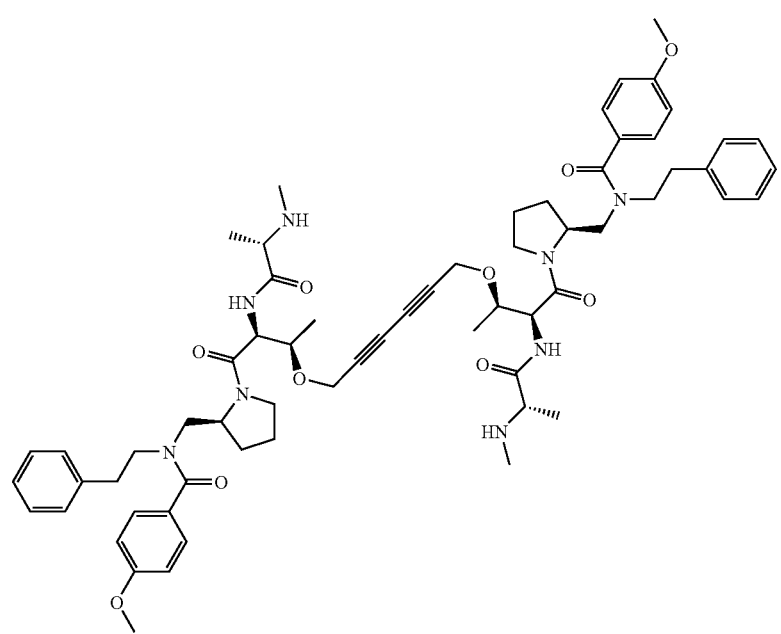 | 562.4 |

TABLE 1-continued

| Compound | Structure | (M + 2)/2 |
|---|---|---|
| 10 | 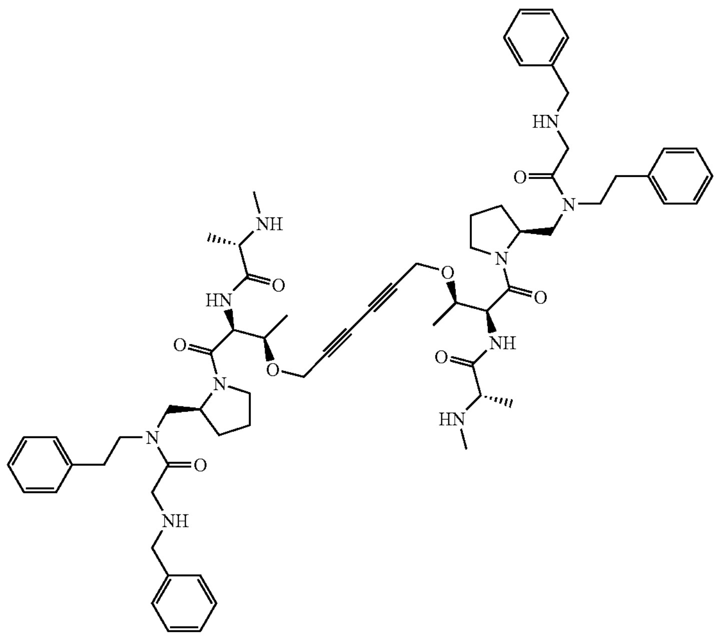 | 575.4 |
| 11 | 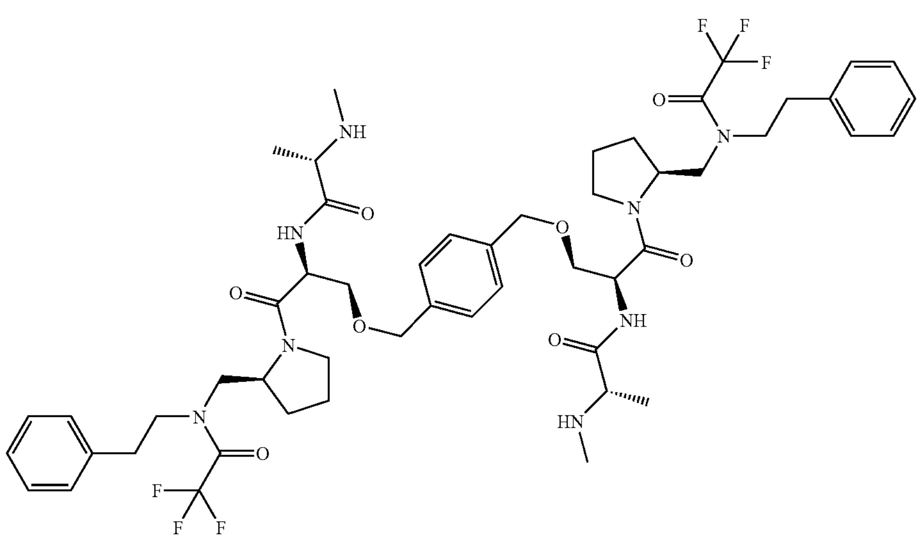 | 526.3 |

TABLE 1-continued

| Compound | Structure | (M + 2)/2 |
|---|---|---|
| 12 | 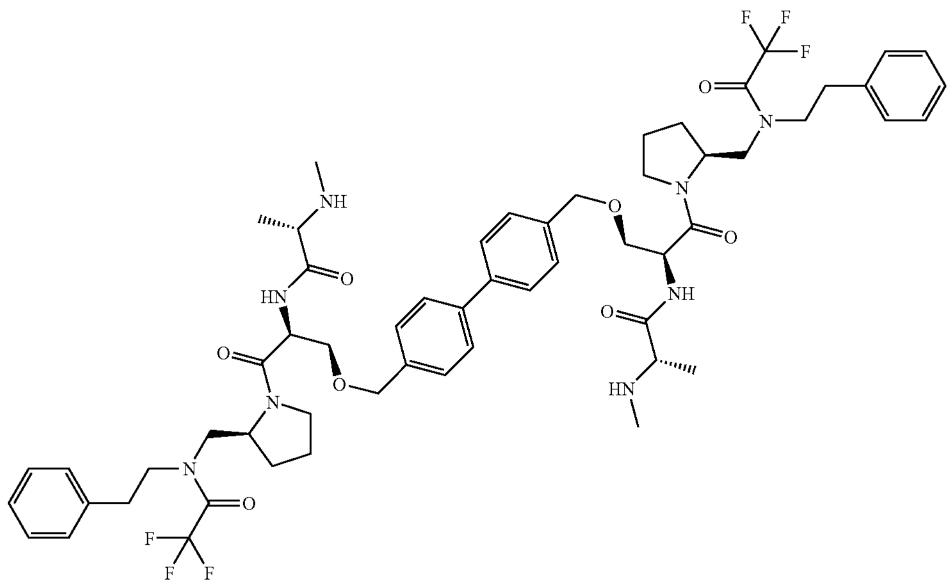 | 562.4 |
| 13 | 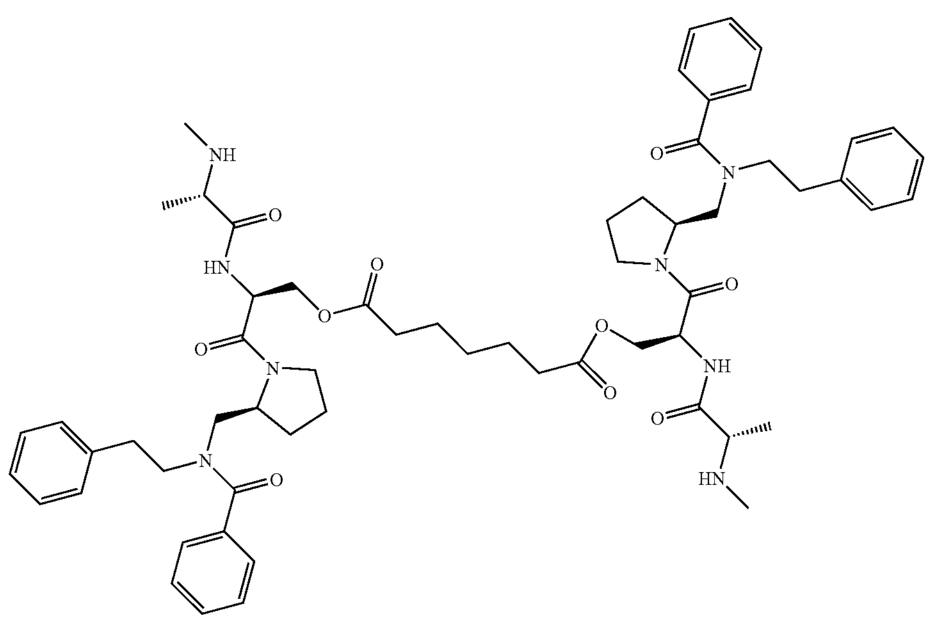 | 543.5 |

TABLE 1-continued

| Compound | Structure | (M + 2)/2 |
|---|---|---|
| 14 | 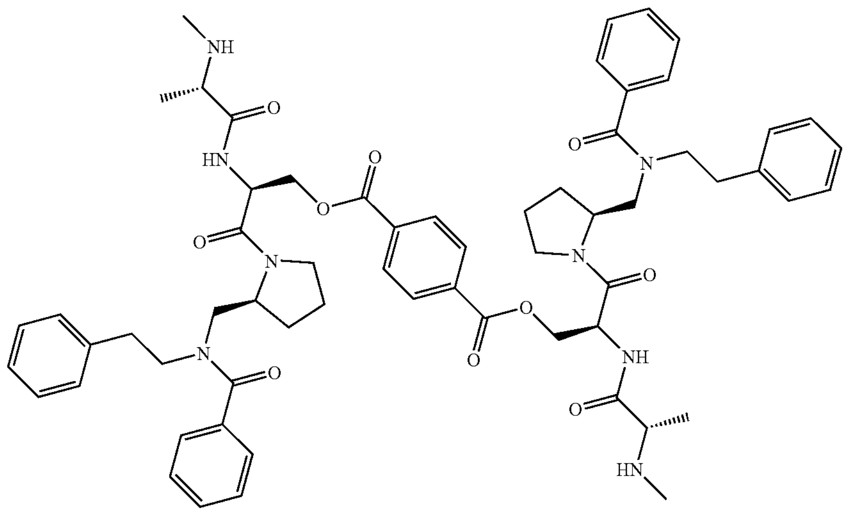 | 546.5 |
| 15 | 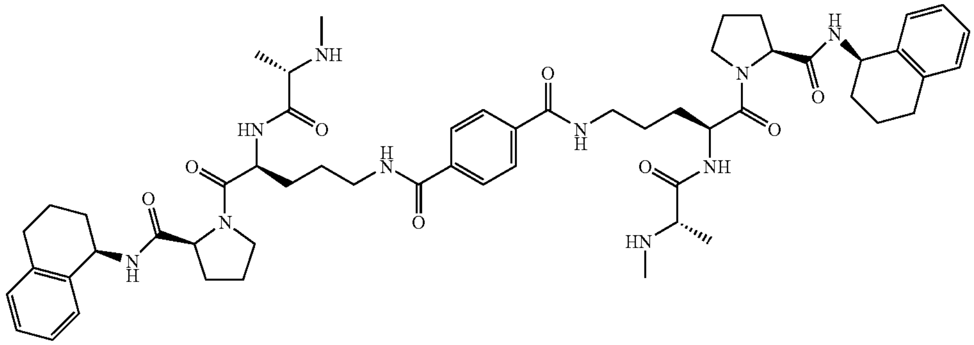 | 509.6 |
| 16 | 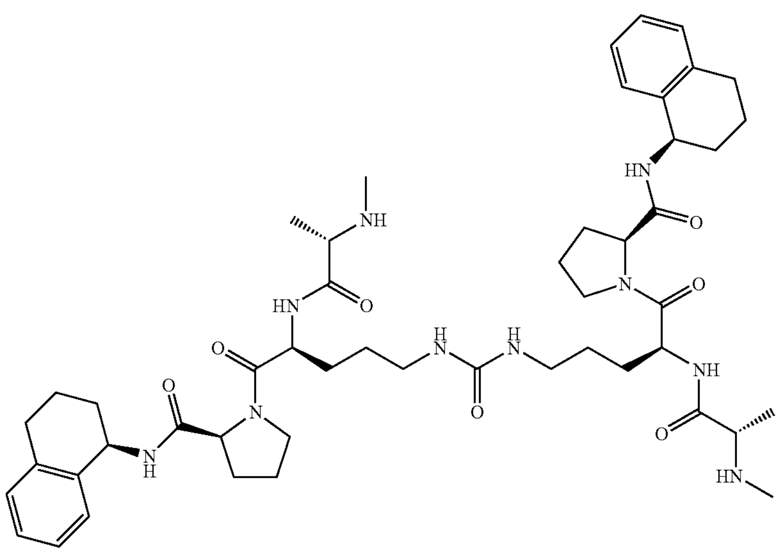 | 457.4 |

TABLE 1-continued

| Compound | Structure | (M + 2)/2 |
|---|---|---|
| 17 | 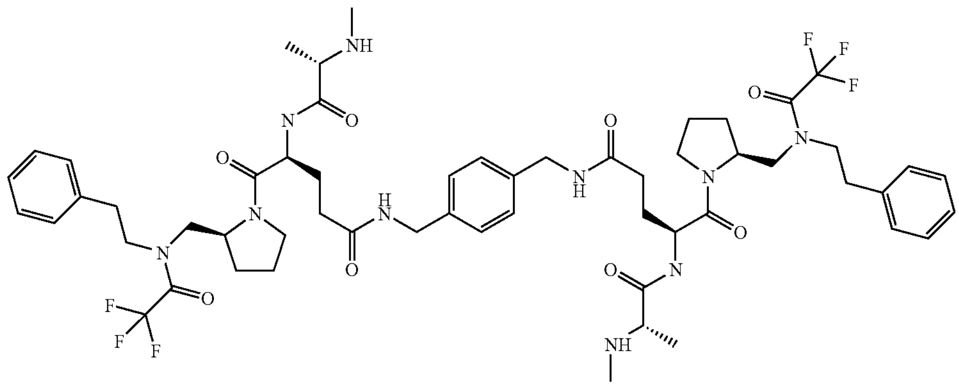 | 565.4 |
| 18 | r = 1 | 527.3 |
| 19 | r = 2 | 534.5 |

TABLE 1-continued
| Compound | Structure | (M + 2)/2 |
|---|---|---|
| 20 | 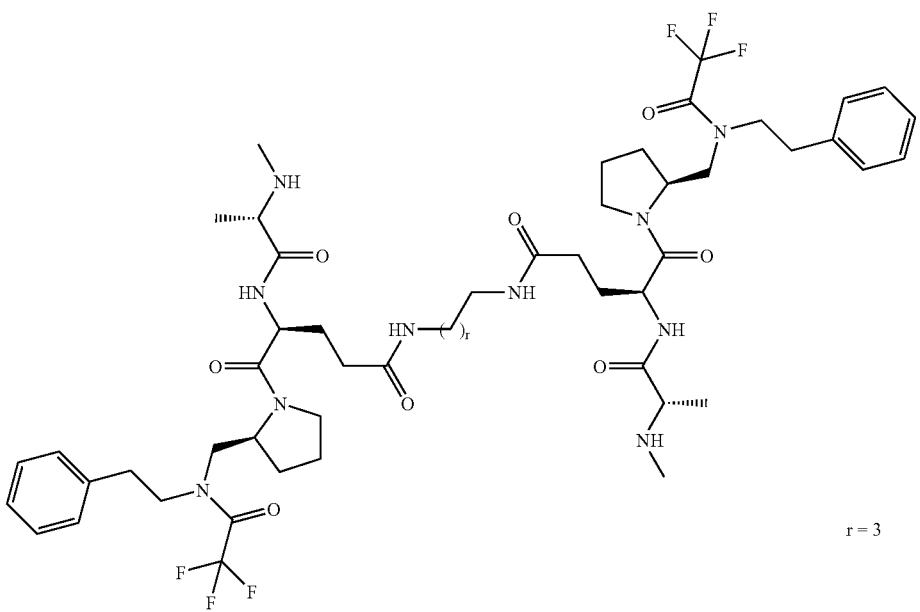 r = 3 | 541.4 |
| 21 | 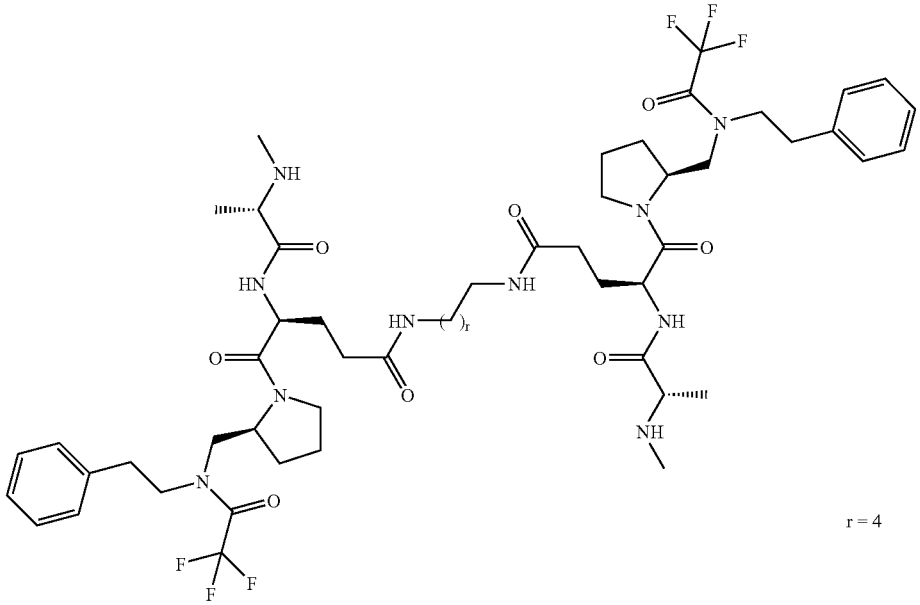 r = 4 | 548.3 |

TABLE 1-continued
| Compound | Structure | (M + 2)/2 |
| --- | --- | --- |
| 22 | 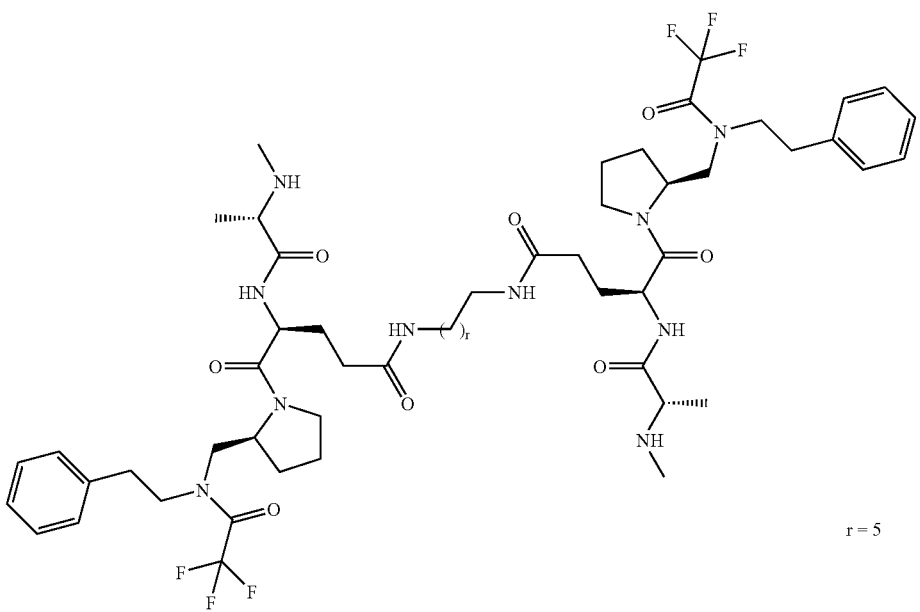 r = 5 | 555.5 |
| 23 | 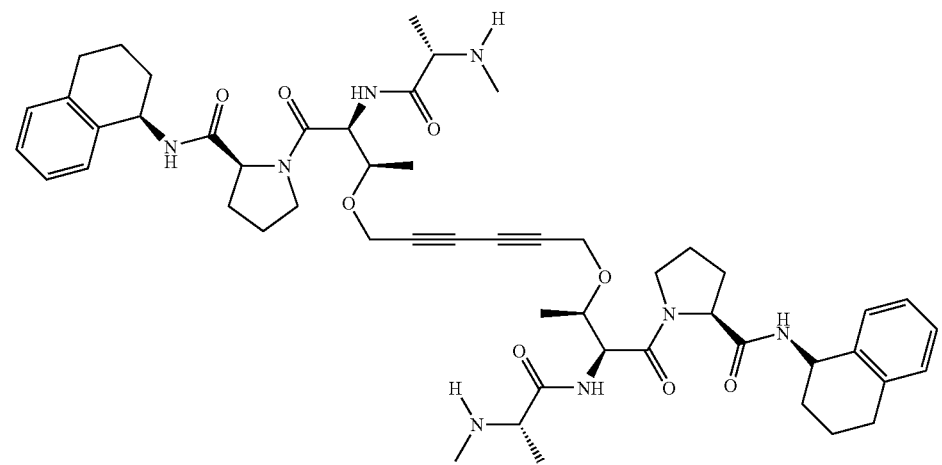 | 935.1 (M + 1) |

TABLE 1-continued

| Compound | Structure | (M + 2)/2 |
|---|---|---|
| 24 | 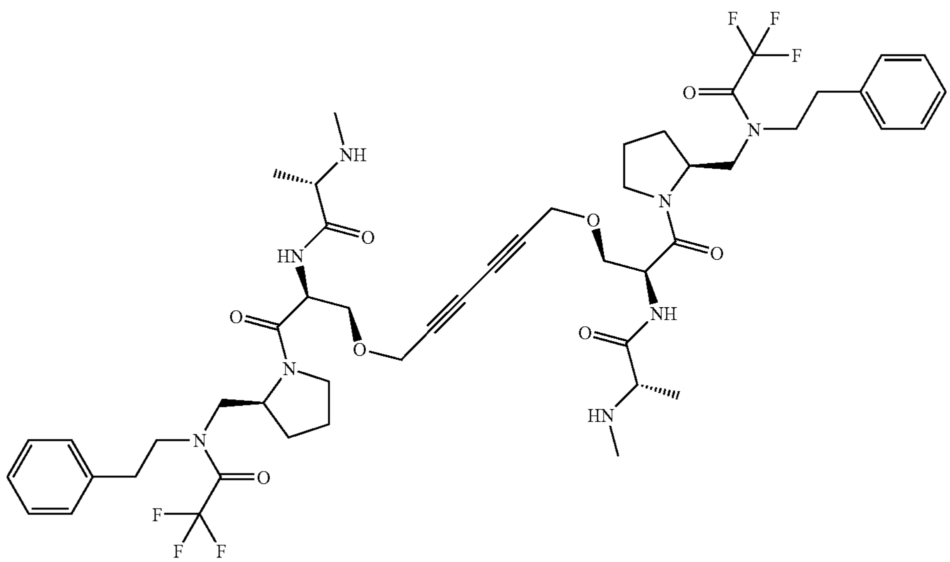 | 510.2 |
| 25 | 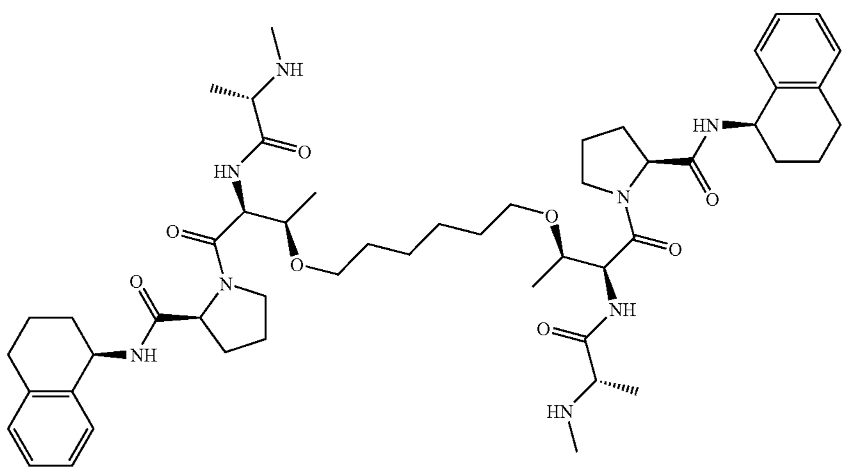 | 942.6 (M + 1) |
| 26 | 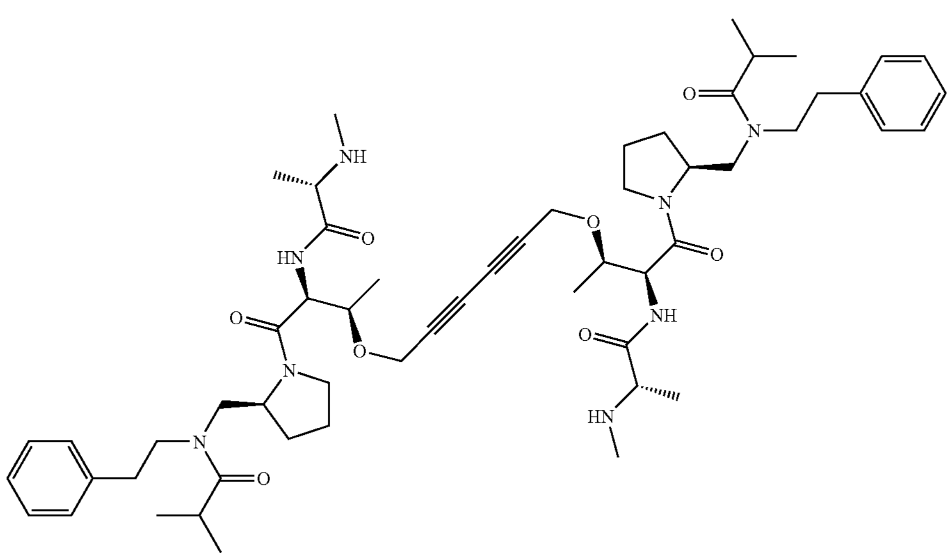 | 498.6 |

TABLE 1-continued
| Compound | Structure | (M + 2)/2 |
|---|---|---|
| 27 | 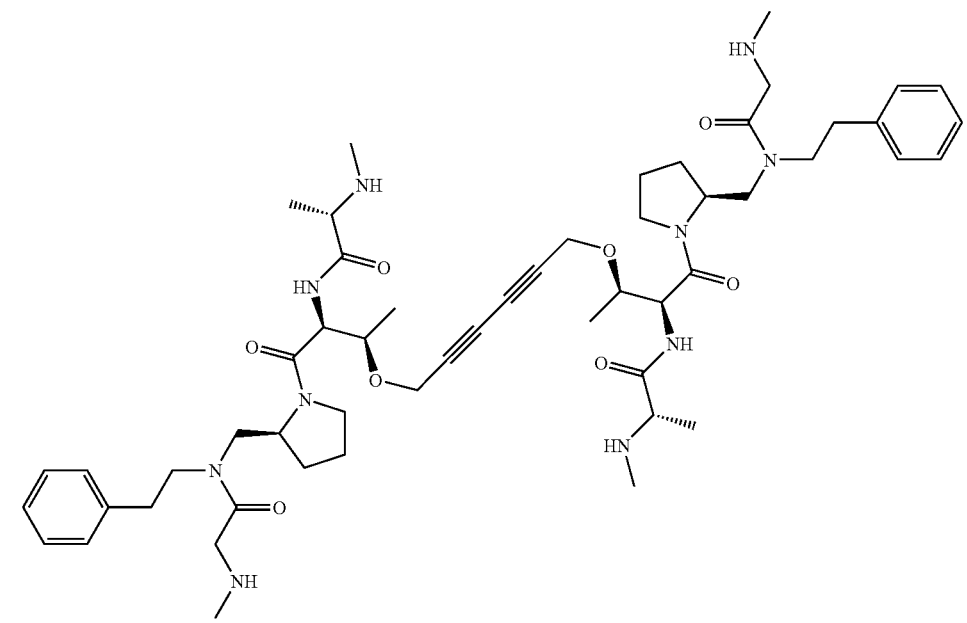 | 499.6 |
| 28 | 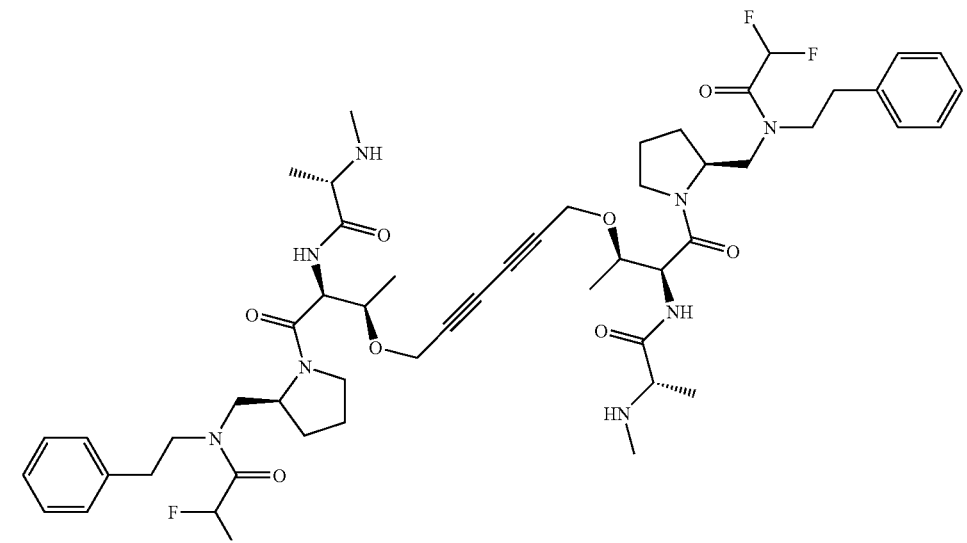 | 506.4 |

US 7,795,298 B2
137                                                                                             138
TABLE 1-continued
| Compound | Structure | (M + 2)/2 |
|---|---|---|
| 29 | 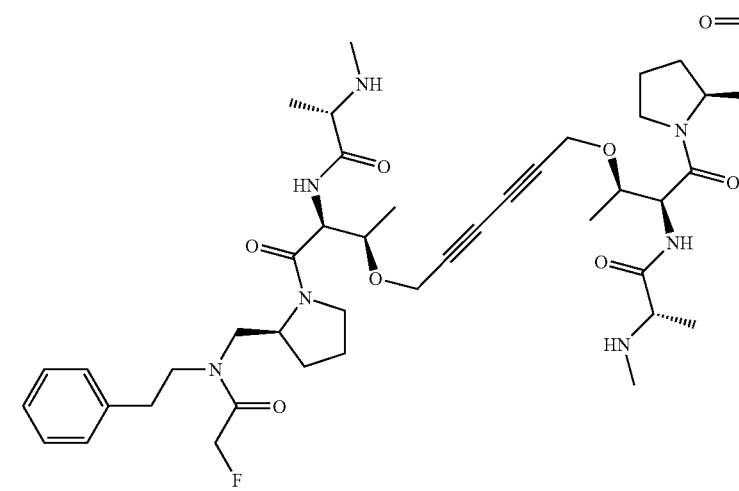 | 488.4 |
| 30 | 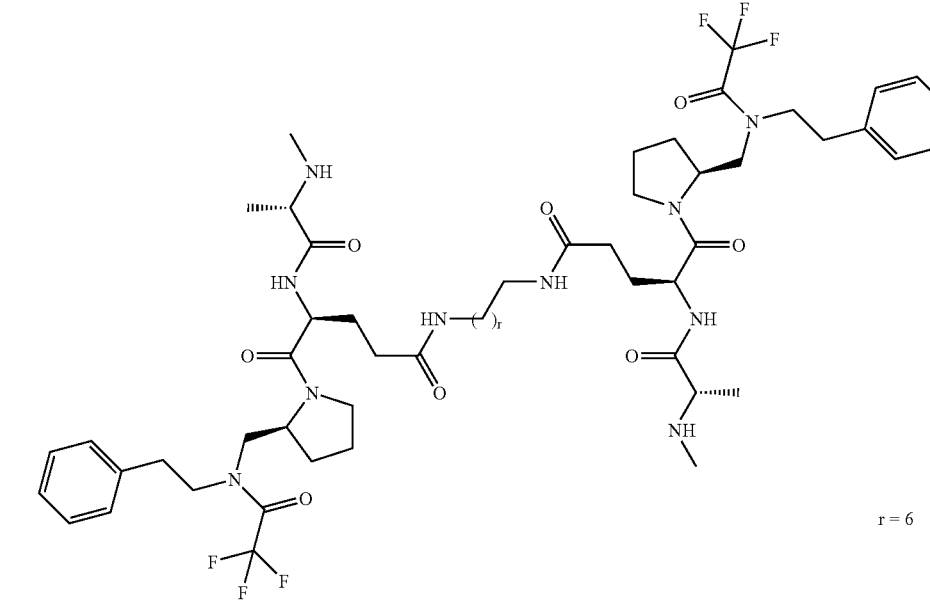<br>r = 6 | 562.7 |

TABLE 1-continued
| Compound | Structure | (M + 2)/2 |
|---|---|---|
| 31 | 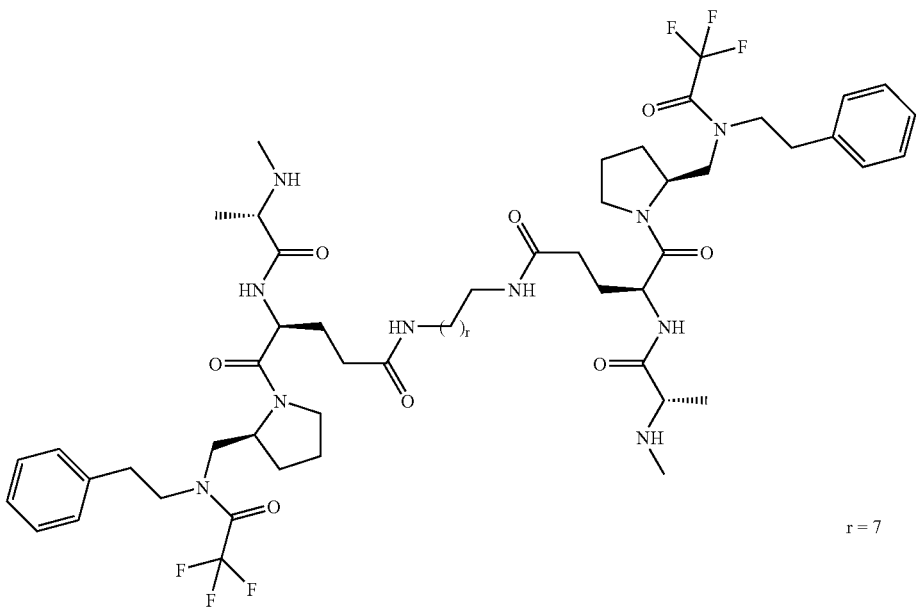 r = 7 | 569.6 |
| 32 | 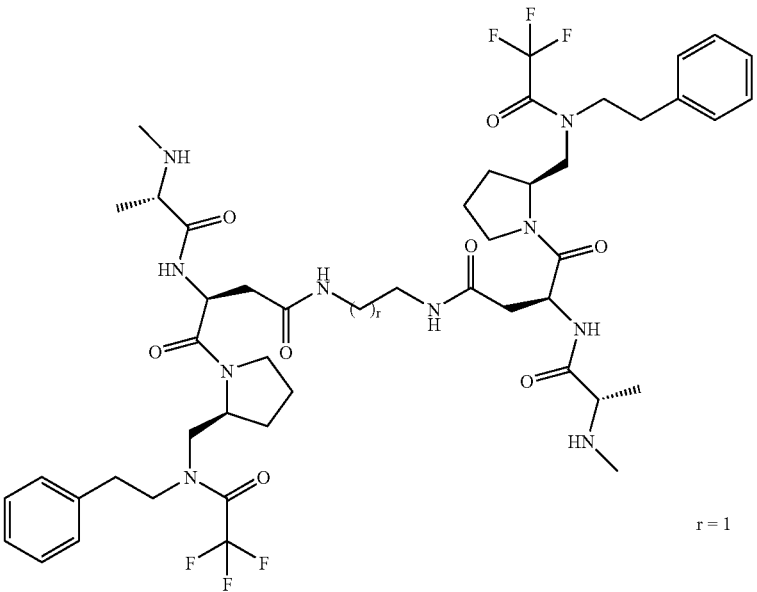 r = 1 | 513.4 |

TABLE 1-continued

| Compound | Structure | (M + 2)/2 |
|---|---|---|
| 33 | r = 3 | 527.4 |
| 34 | r = 5 | 541.4 |

TABLE 1-continued

| Compound | Structure | (M + 2)/2 |
|---|---|---|
| 35 | (structure shown; r = 7) | 555.4 |
| 36 | (structure shown) | 528.4 |
| 37 | (structure shown) | 510.4 |

TABLE 1-continued
| Compound | Structure | (M + 2)/2 |
|---|---|---|
| 38 | 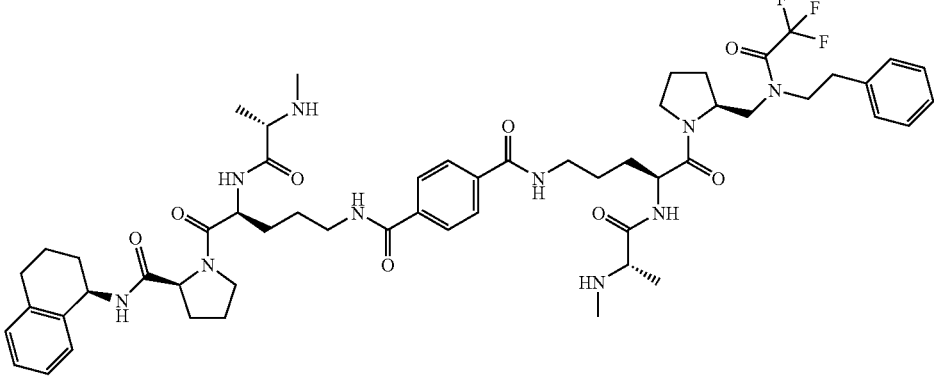 | 537.4 |
| 39 | 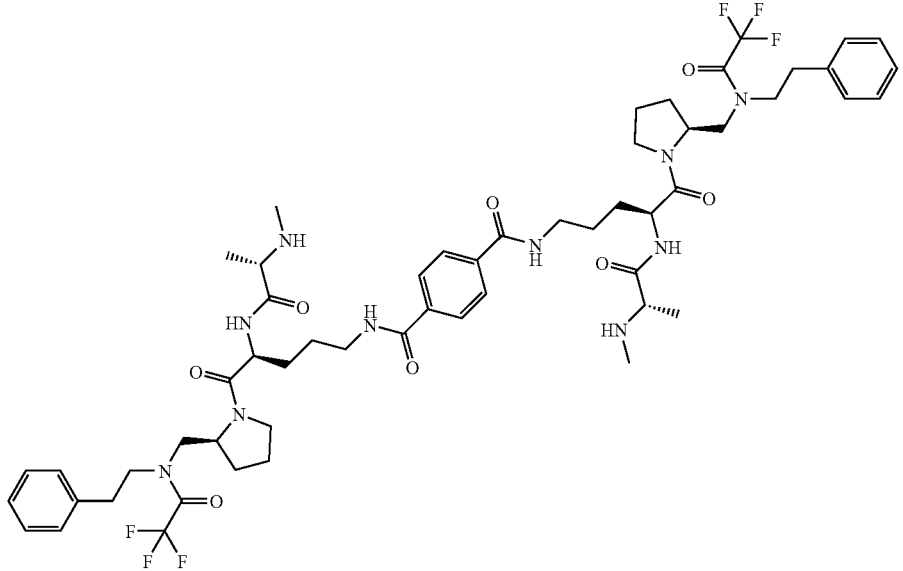 | 524.4 |
| 40 | 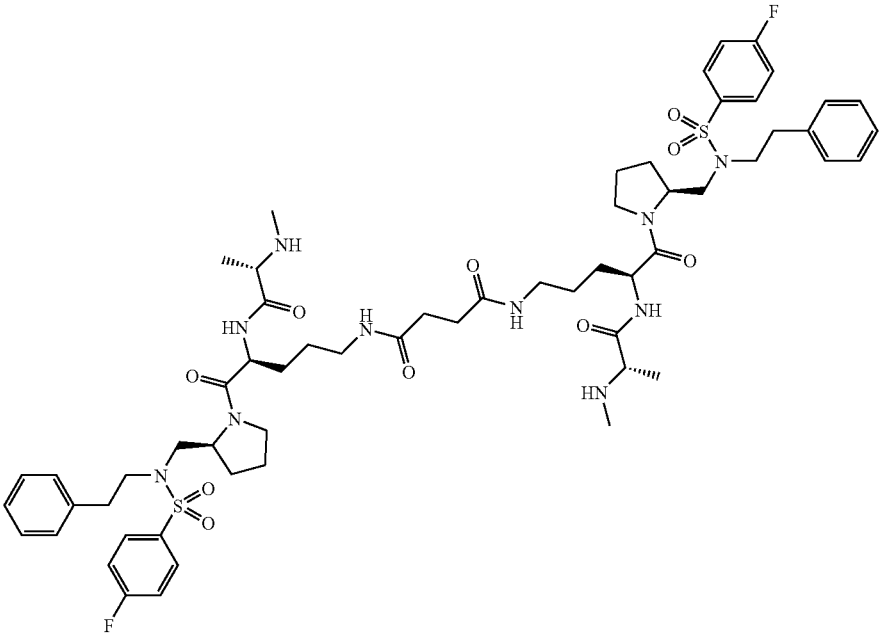 | 603.4 |

TABLE 1-continued

| Compound | Structure | (M + 2)/2 |
|---|---|---|
| 41 | 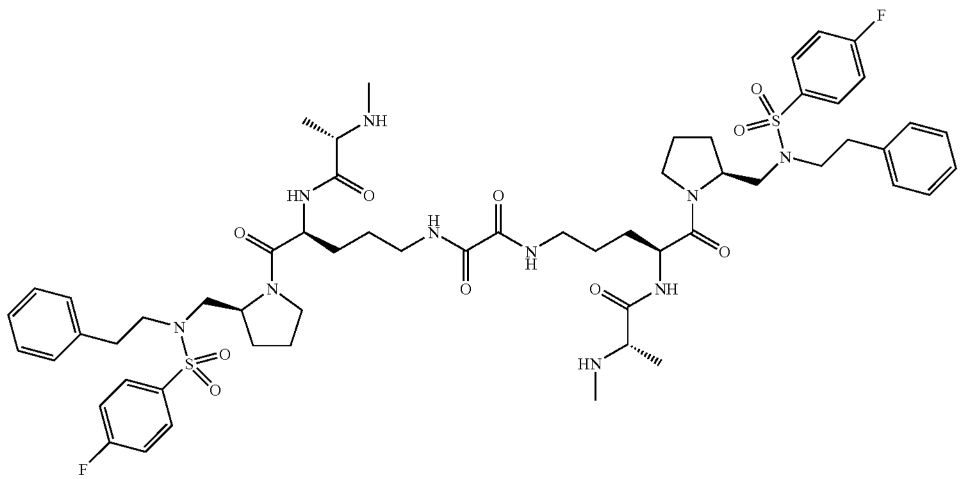 | 589.4 |
| 42 | 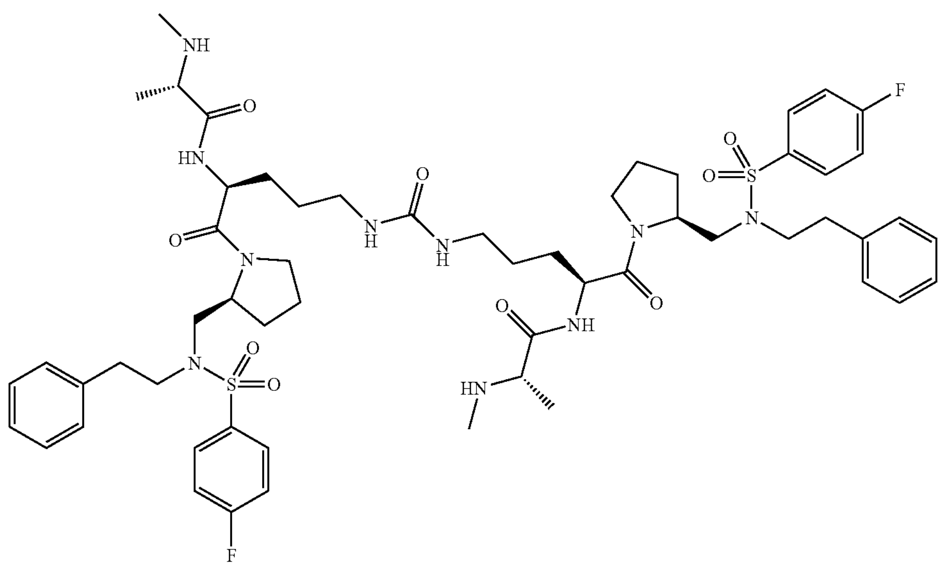 | 575.4 |
| 43 | 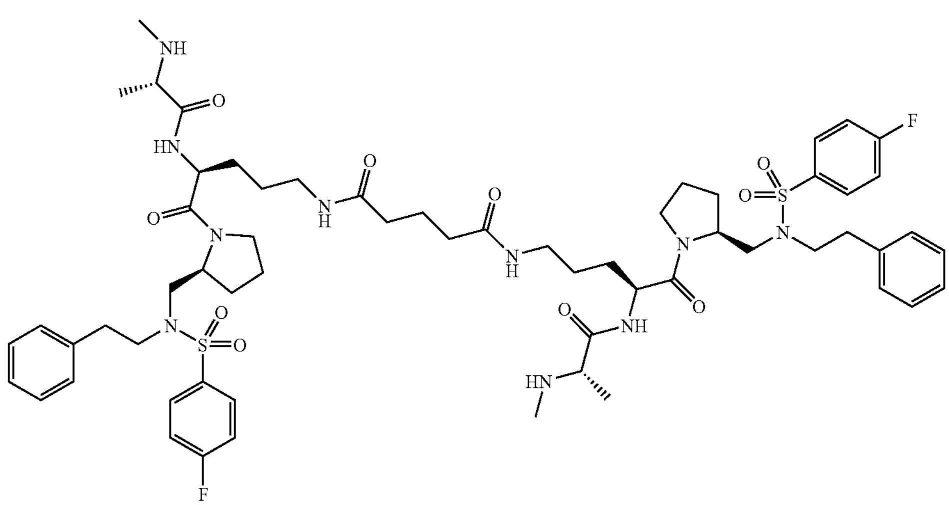 | 610.4 |

TABLE 1-continued

| Compound | Structure | (M + 2)/2 |
|---|---|---|
| 44 | 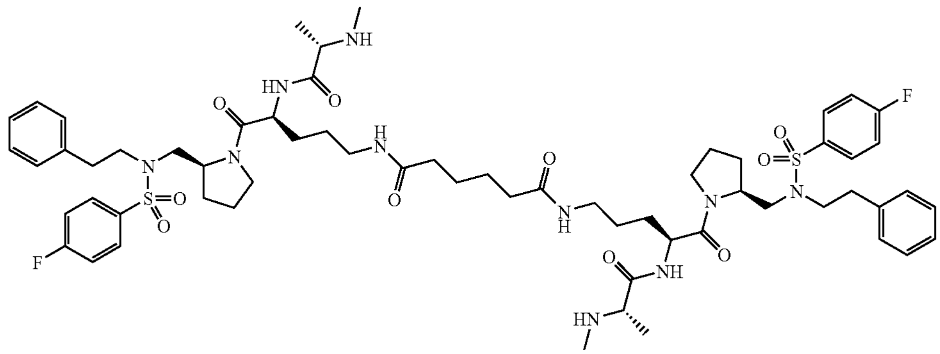 | 617.4 |
| 45 | 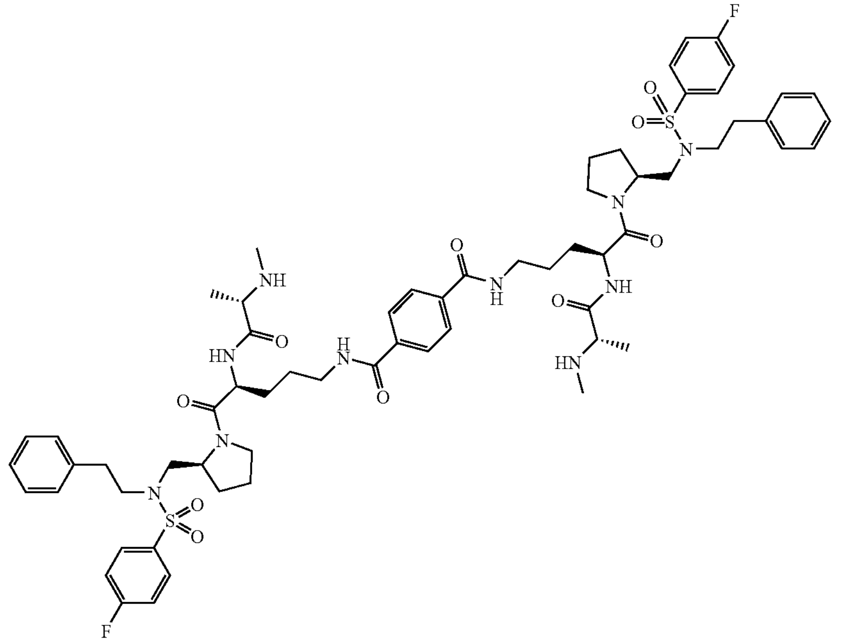 | 627.4 |
| 46 | 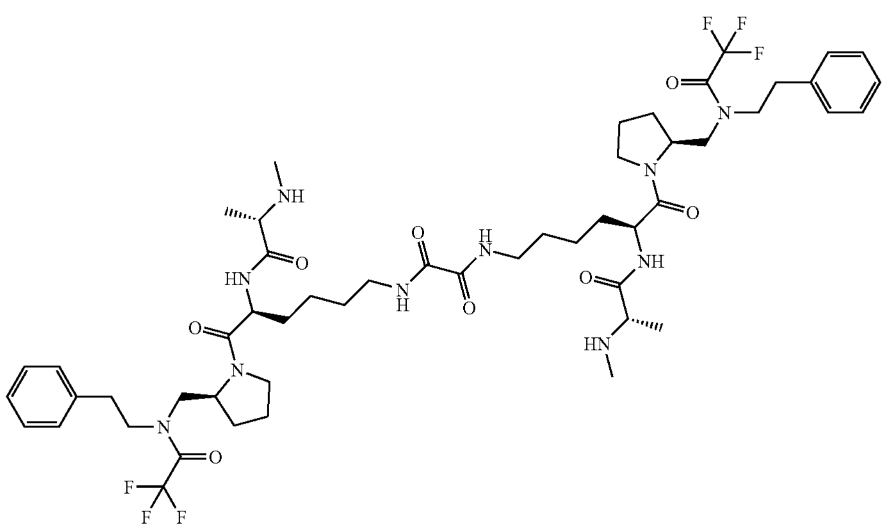 | 541.4 |

TABLE 1-continued
| Compound | Structure | (M + 2)/2 |
|---|---|---|
| 47 | 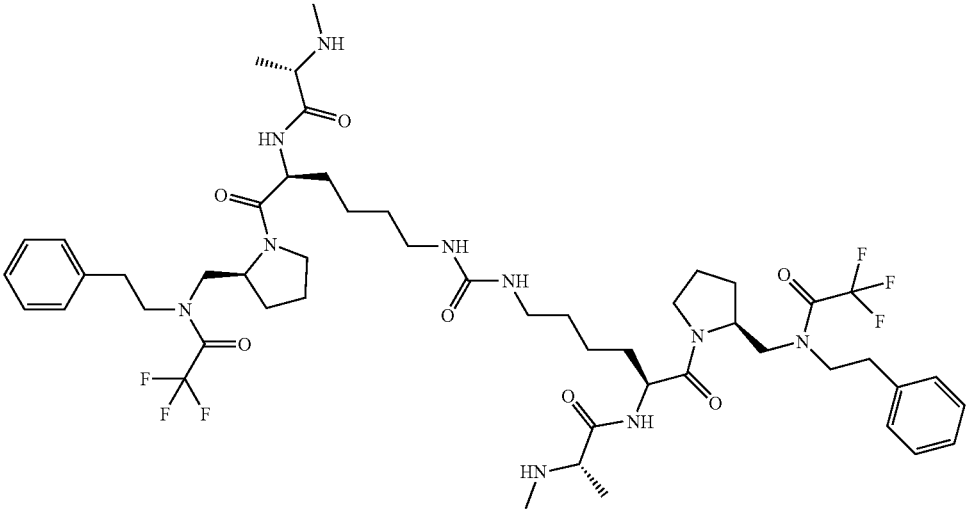 | 527.4 |
Representative compounds of the present invention which can be prepared by simple modification of the above procedures are illustrated in Table 2 through 11:
TABLE 2
M1-BG-M2
Formula IA
BG is 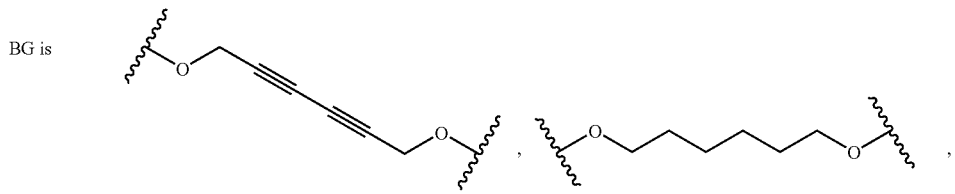
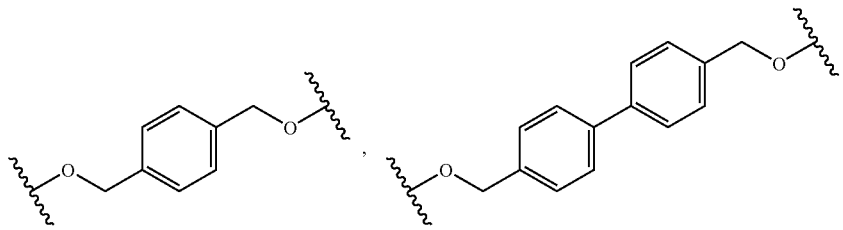
| M1 | M2 |
|---|---|
| 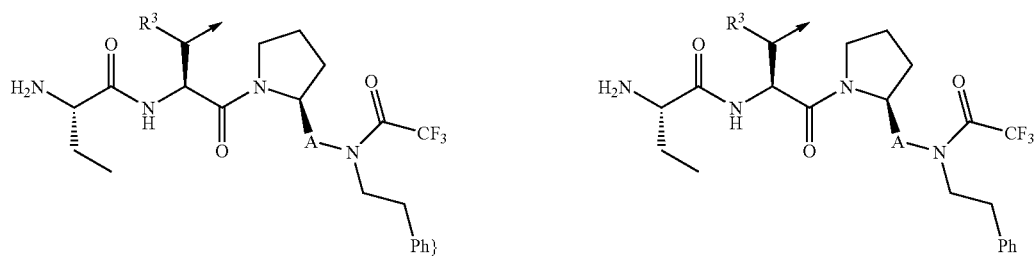 | |
| A = CH$_2$; R$^3$ = H or Me | A = CH$_2$; R$^3$ = H or Me |

TABLE 2-continued
M1-BG-M2
Formula IA
BG is 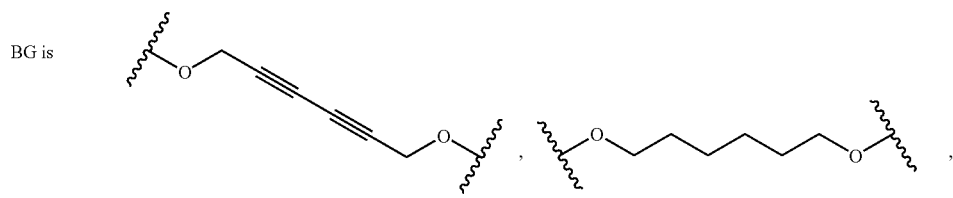
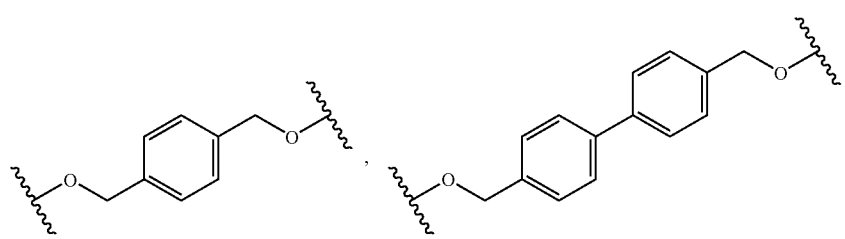
| M1 | M2 |
|---|---|
| 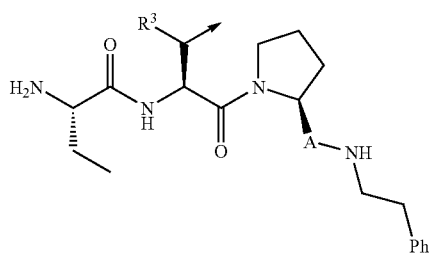<br>A = CH$_2$; R$^3$ = H or Me | 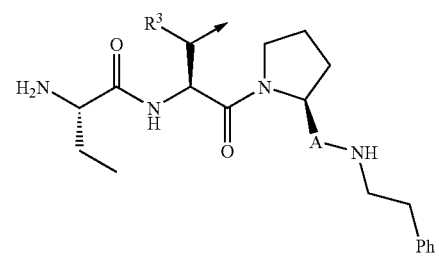<br>A = CH$_2$; R$^3$ = H or Me |
| 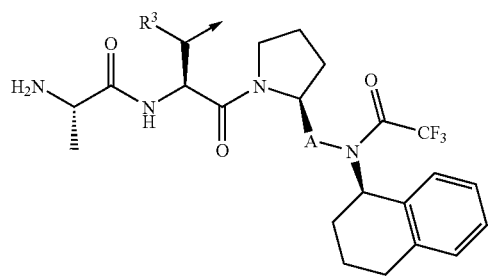<br>A = CH$_2$; R$^3$ = H or Me | 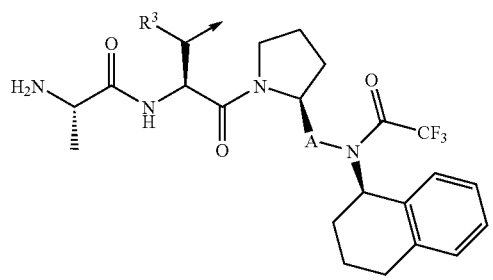<br>A = CH$_2$; R$^3$ = H or Me |
| 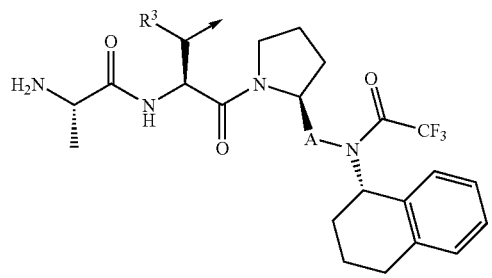<br>A = CH$_2$; R$^3$ = H or Me | 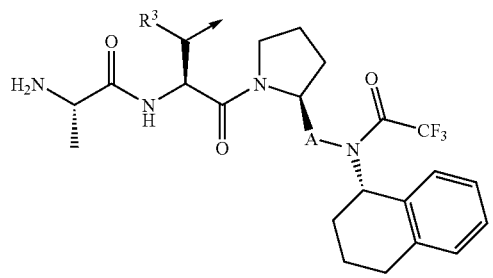<br>A = CH$_2$; R$^3$ = H or Me |

TABLE 2-continued
M1-BG-M2      Formula IA
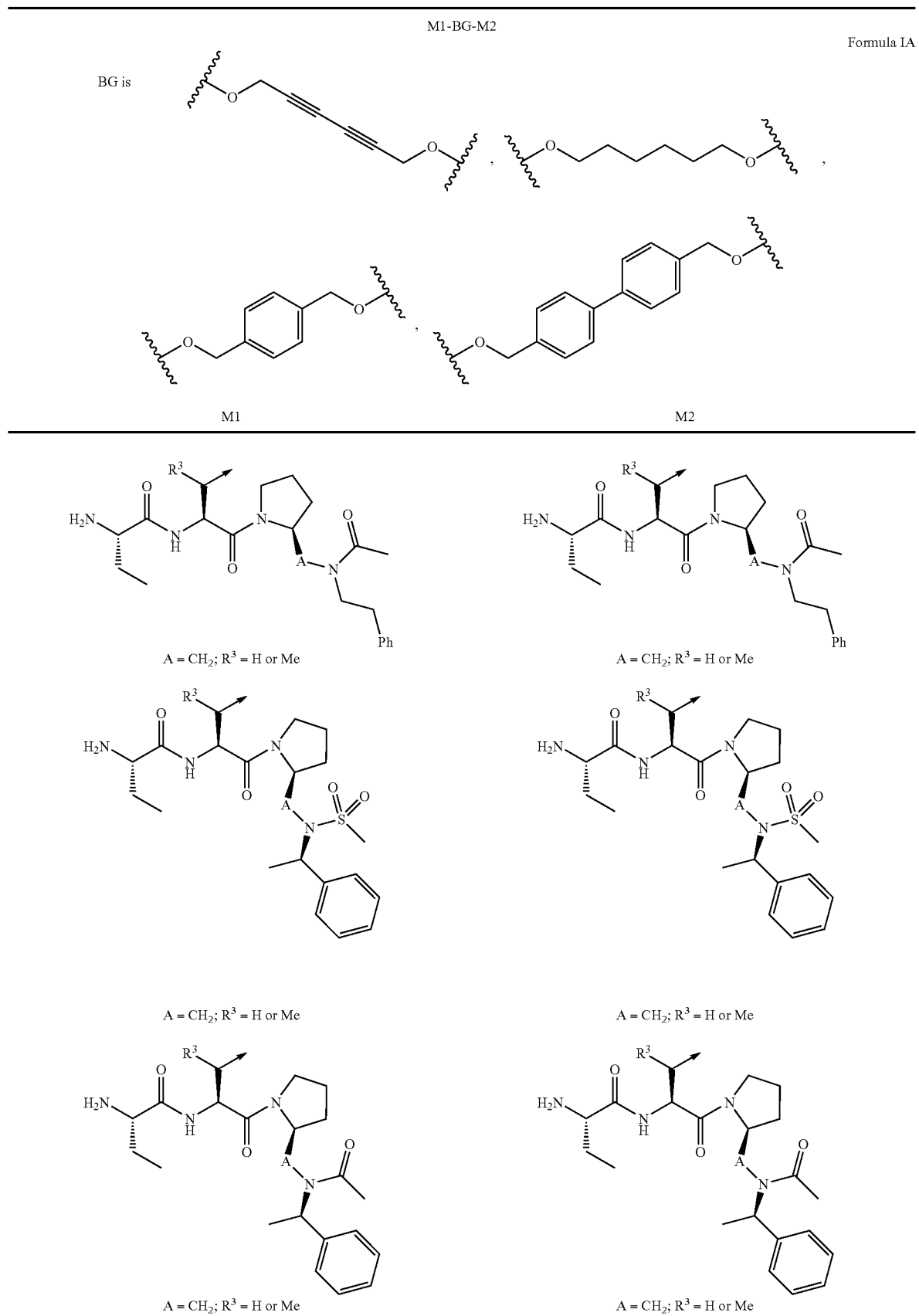

TABLE 2-continued
M1-BG-M2
Formula IA
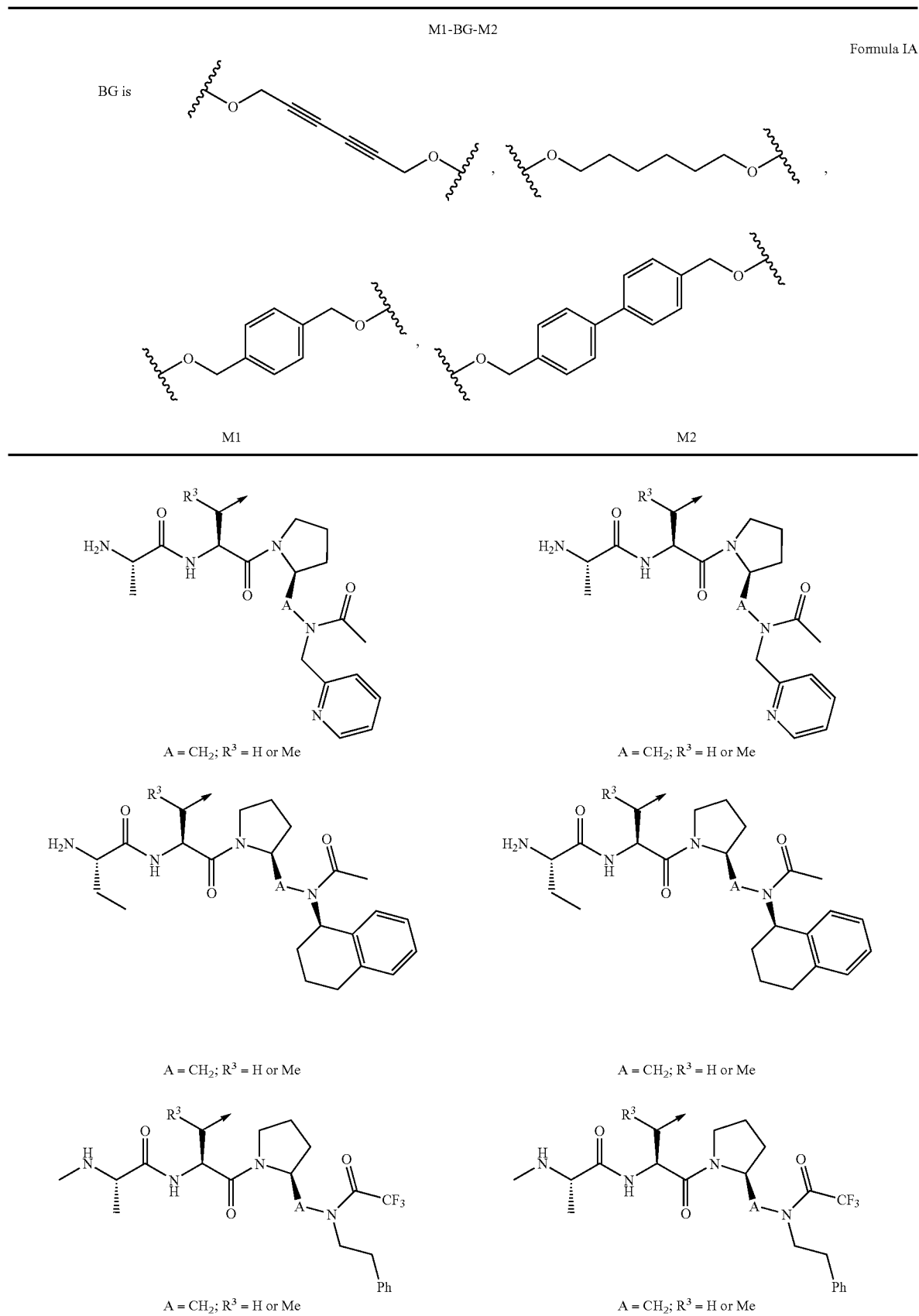

TABLE 2-continued
M1-BG-M2
Formula IA
BG is
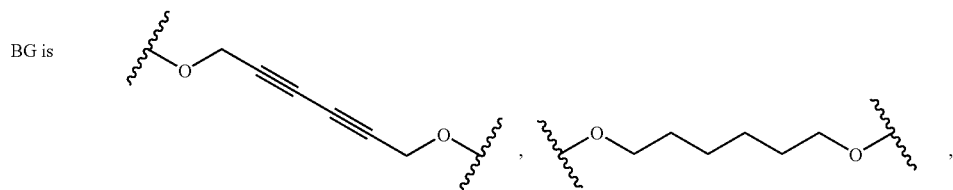
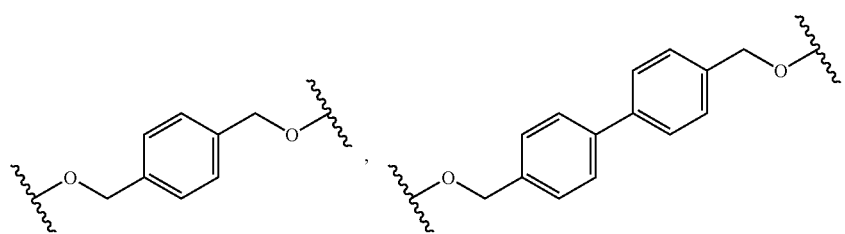
| M1 | M2 |
|---|---|
| 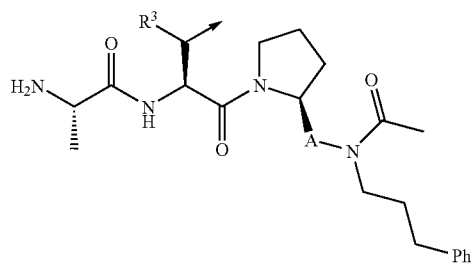<br>A = CH$_2$; R$^3$ = H or Me | 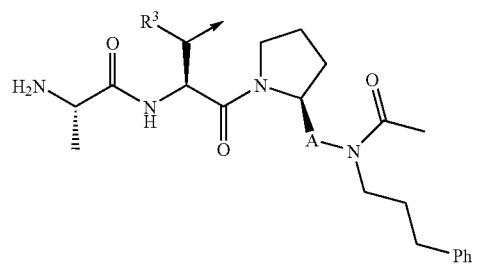<br>A = CH$_2$; R$^3$ = H or Me |
| 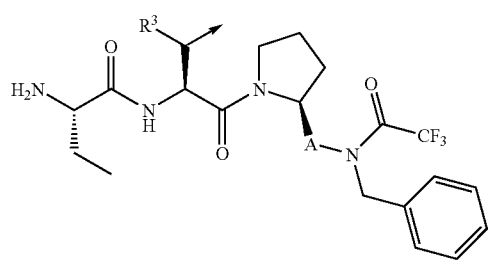<br>A = CH$_2$; R$^3$ = H or Me | 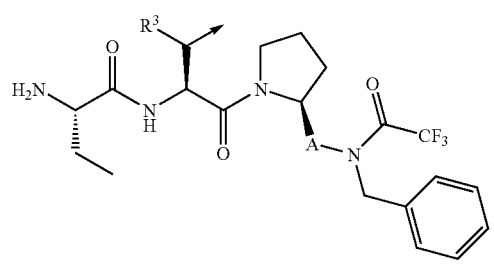<br>A = CH$_2$; R$^3$ = H or Me |
| 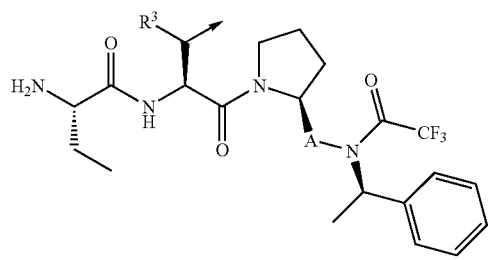<br>A = CH$_2$; R$^3$ = H or Me | 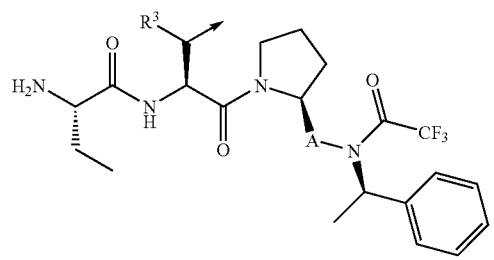<br>A = CH$_2$; R$^3$ = H or Me |

TABLE 2-continued
M1-BG-M2          Formula IA
BG is
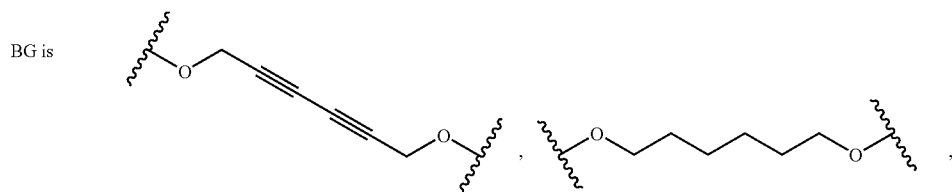
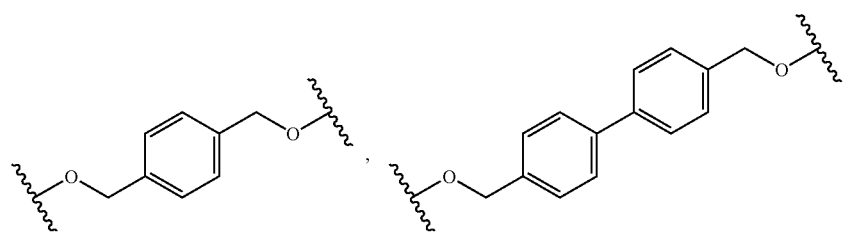
| M1 | M2 |
|---|---|
| 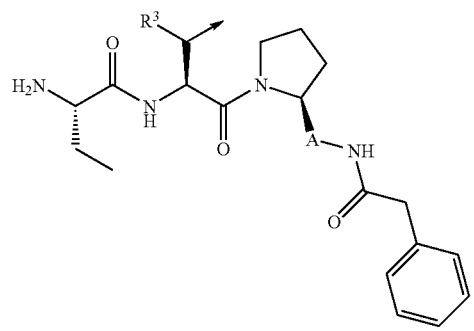<br>A = CH$_2$; R$^3$ = H or Me | 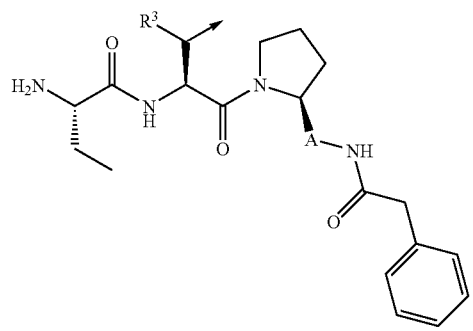<br>A = CH$_2$; R$^3$ = H or Me |
| 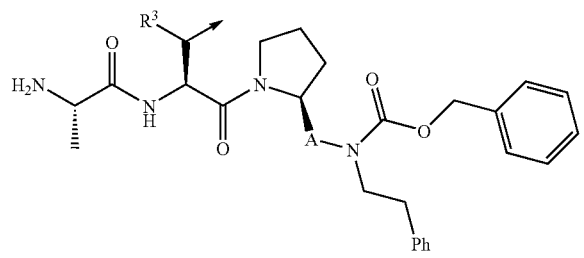<br>A = CH$_2$; R$^3$ = H or Me | 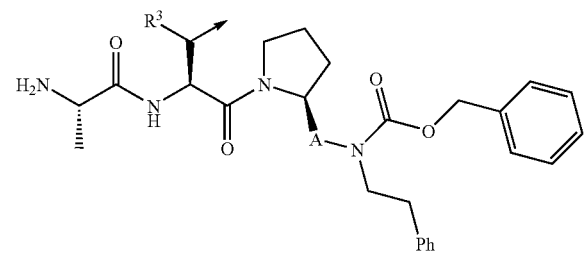<br>A = CH$_2$; R$^3$ = H or Me |
| 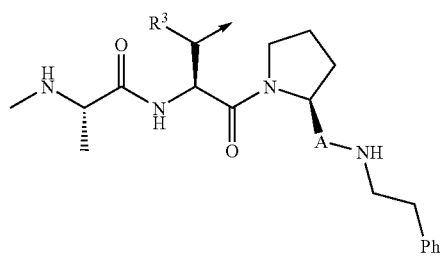<br>A = CH$_2$; R$^3$ = H or Me | 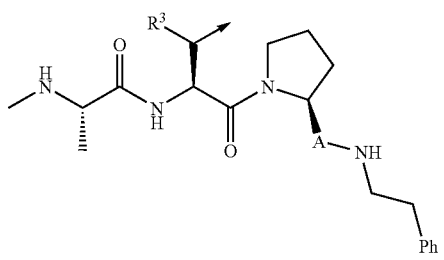<br>A = CH$_2$; R$^3$ = H or Me |

TABLE 2-continued
M1-BG-M2
Formula IA
BG is 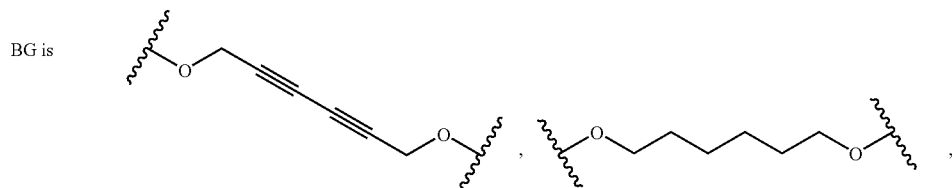
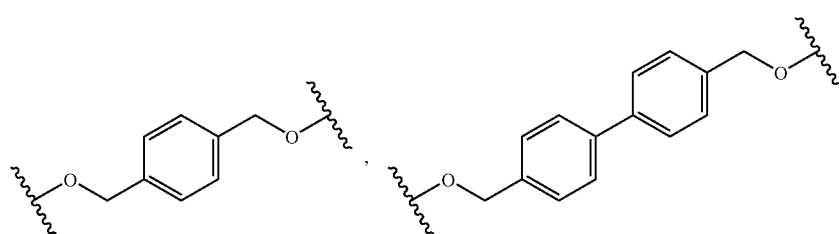
| M1 | M2 |
|---|---|
| 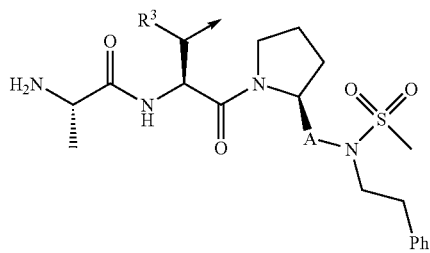 | 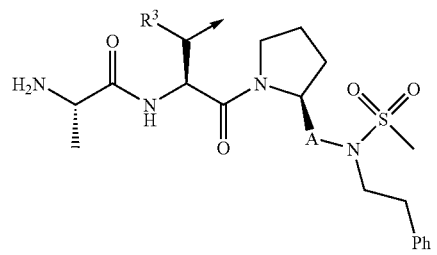 |
| A = CH$_2$; R$^3$ = H or Me | A = CH$_2$; R$^3$ = H or Me |
| 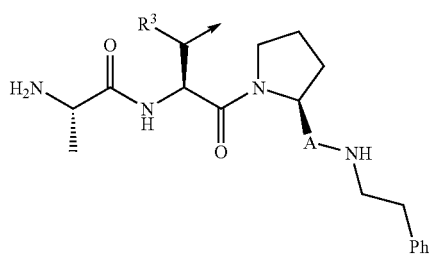 | 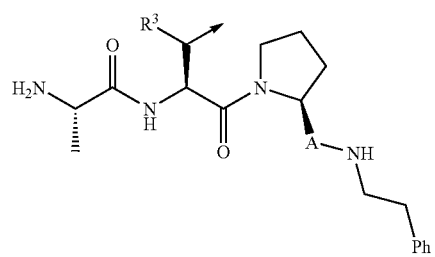 |
| A = CH$_2$; R$^3$ = H or Me | A = CH$_2$; R$^3$ = H or Me |
|  | 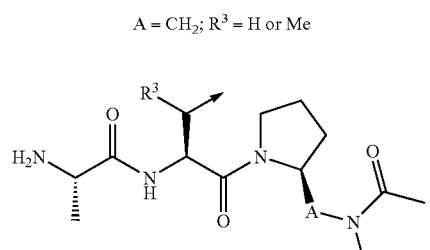 |
| A = CH$_2$; R$^3$ = H or Me | A = CH$_2$; R$^3$ = H or Me |

TABLE 2-continued
M1-BG-M2
Formula IA
BG is
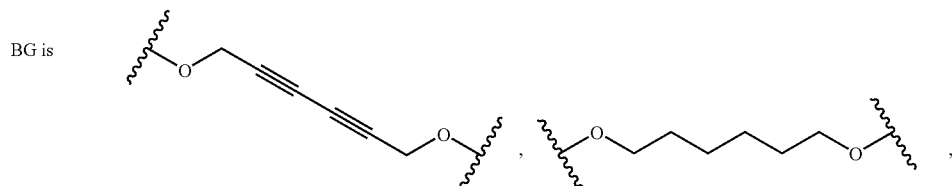
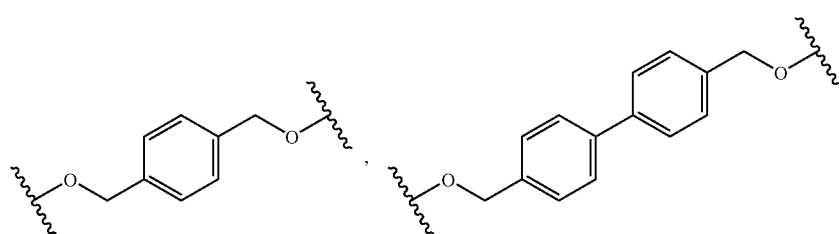
M1
M2
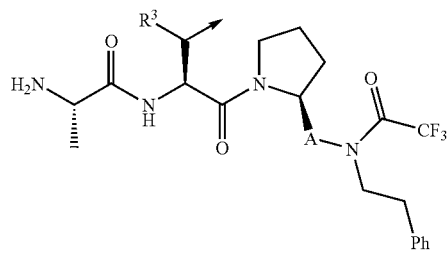
A = CH₂; R³ = H or Me
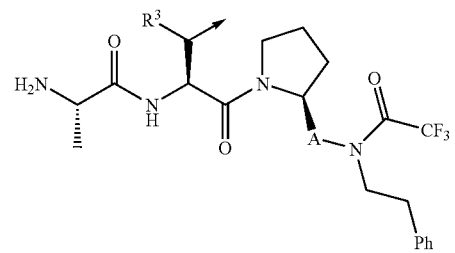
A = CH₂; R³ = H or Me
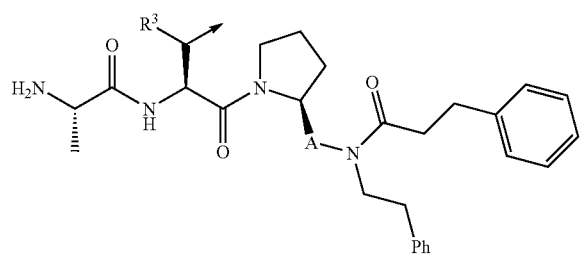
A = CH₂; R³ = H or Me
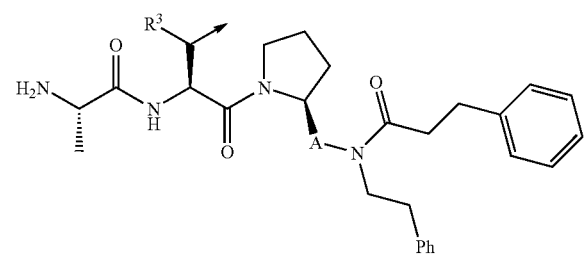
A = CH₂; R³ = H or Me
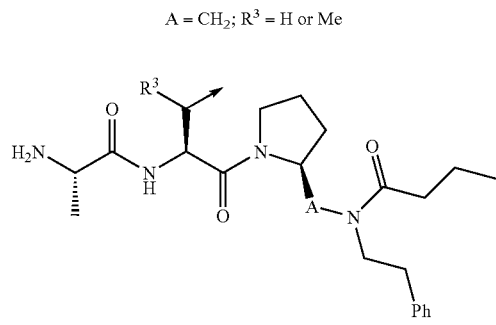
A = CH₂; R³ = H or Me
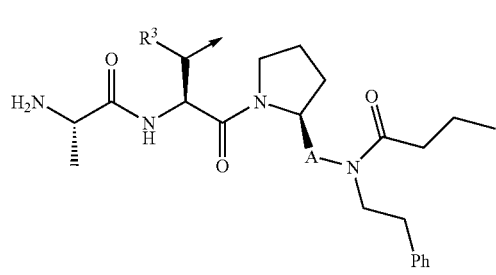
A = CH₂; R³ = H or Me TABLE 2-continued
M1-BG-M2
Formula IA
BG is
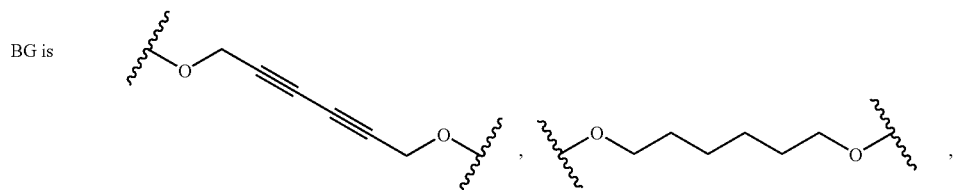,
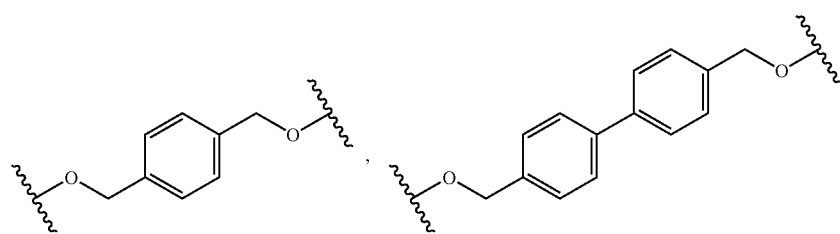
| M1 | M2 |
|---|---|
| 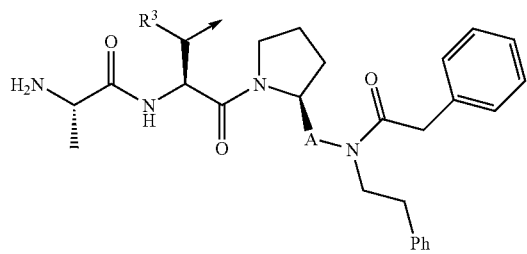<br>A = CH$_2$; R$^3$ = H or Me | 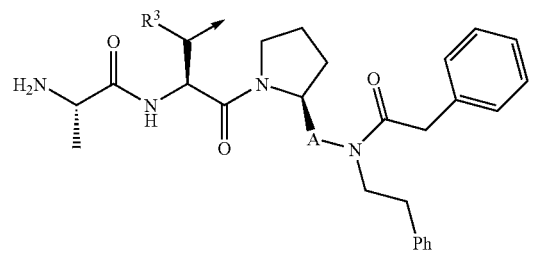<br>A = CH$_2$; R$^3$ = H or Me |
| 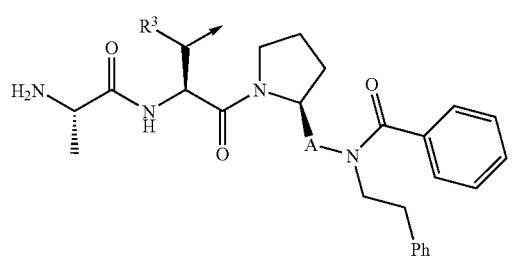<br>A = CH$_2$; R$^3$ = H or Me | 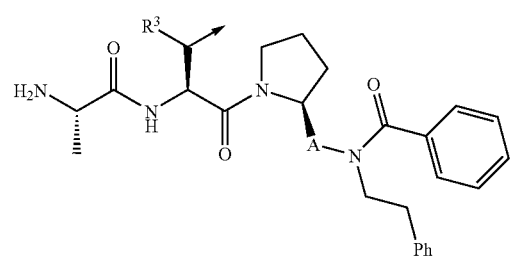<br>A = CH$_2$; R$^3$ = H or Me |
| 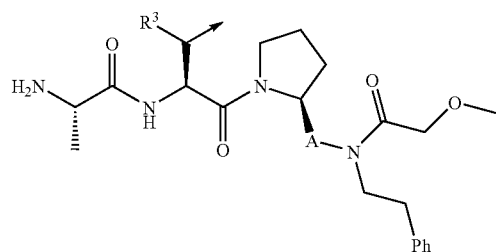<br>A = CH$_2$; R$^3$ = H or Me | 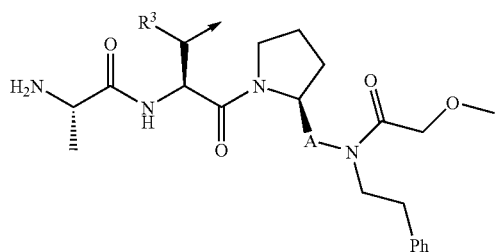<br>A = CH$_2$; R$^3$ = H or Me |

TABLE 2-continued
M1-BG-M2
Formula IA
BG is 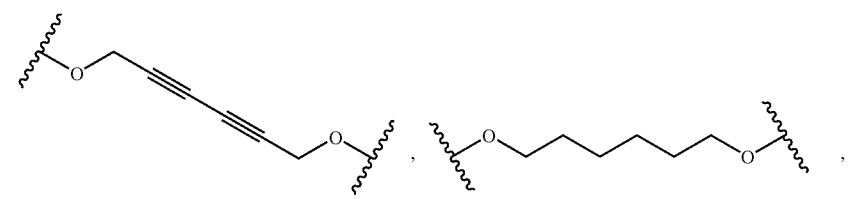
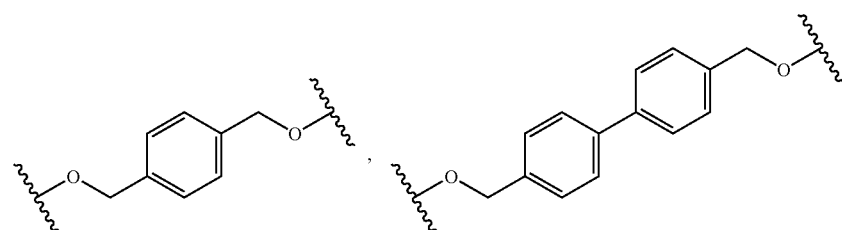
M1     M2
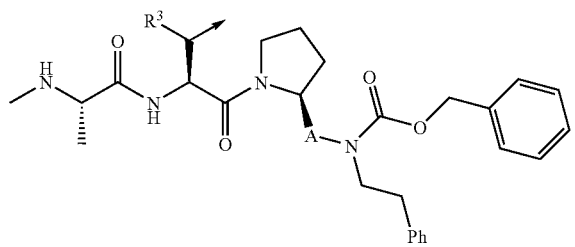
A = CH₂; R³ = H or Me
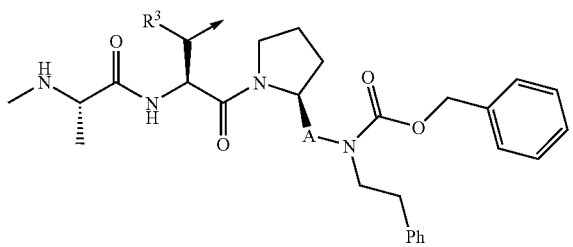
A = CH₂; R³ = H or Me
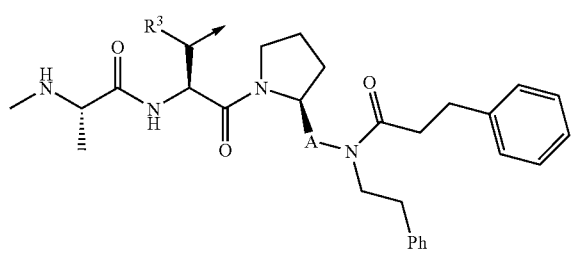
A = CH₂; R³ = H or Me
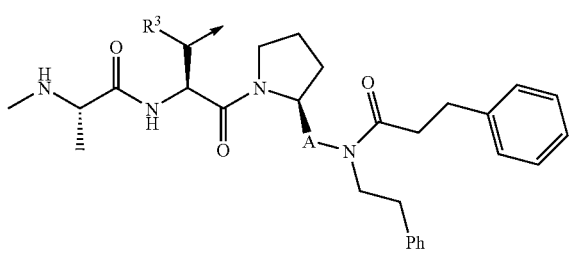
A = CH₂; R³ = H or Me
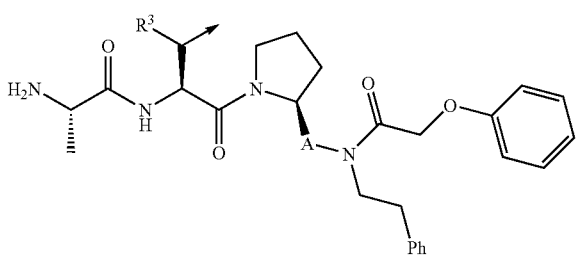
A = CH₂; R³ = H or Me
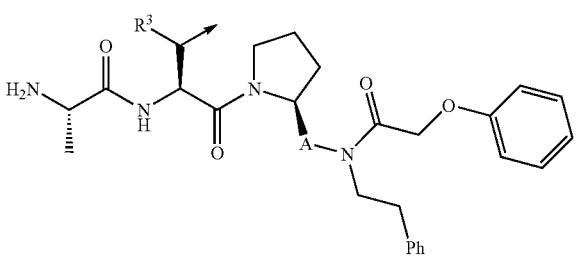
A = CH₂; R³ = H or Me TABLE 2-continued
M1-BG-M2
Formula IA
BG is 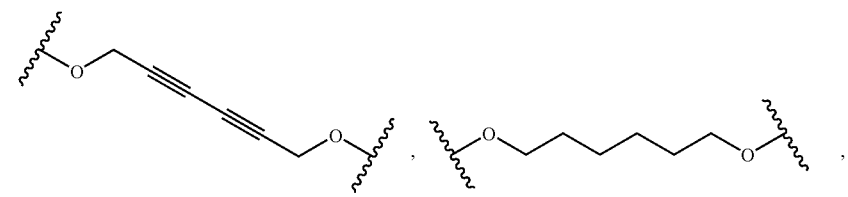
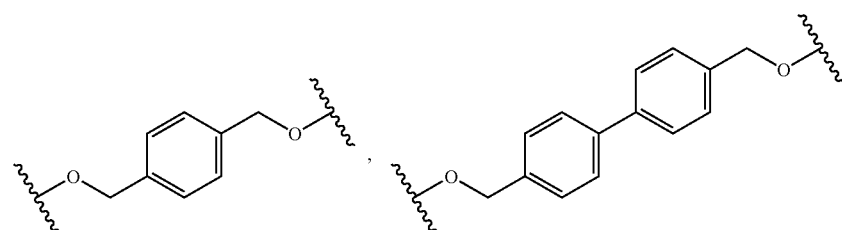
M1 | M2
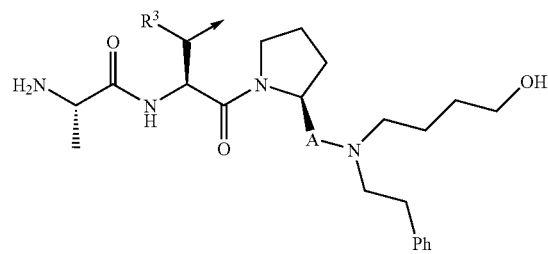 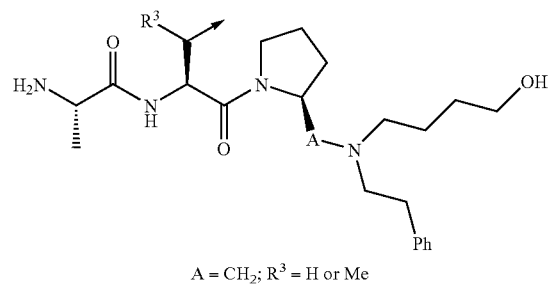
A = CH$_2$; R$^3$ = H or Me | A = CH$_2$; R$^3$ = H or Me
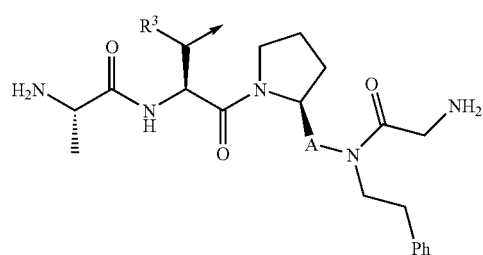 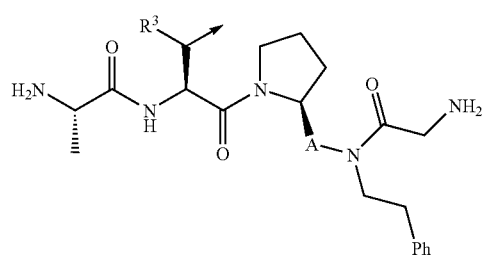
A = CH$_2$; R$^3$ = H or Me | A = CH$_2$; R$^3$ = H or Me
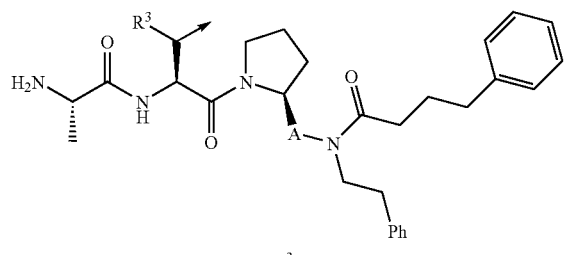 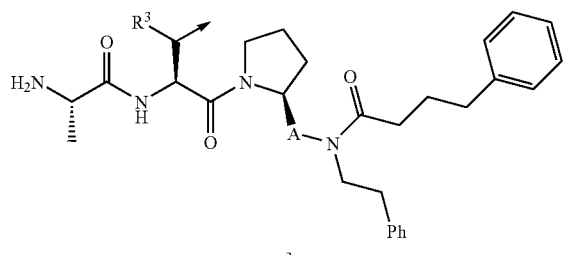
A = CH$_2$; R$^3$ = H or Me | A = CH$_2$; R$^3$ = H or Me TABLE 2-continued
M1-BG-M2
Formula IA
BG is 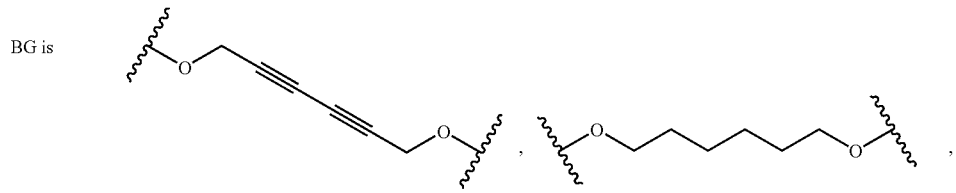
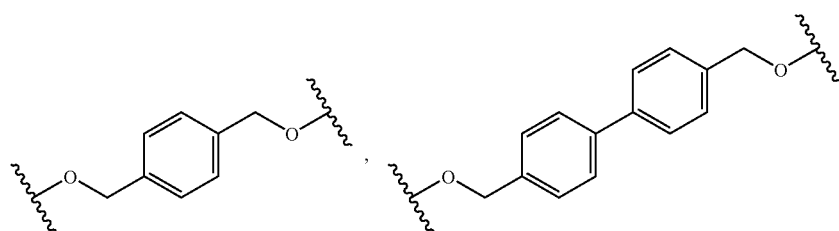
| M1 | M2 |
|---|---|
| 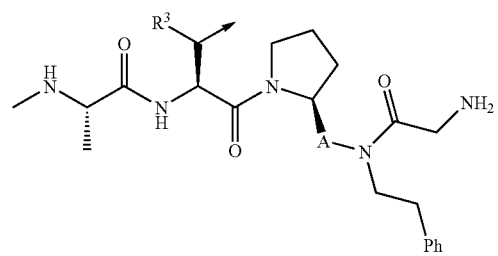 | 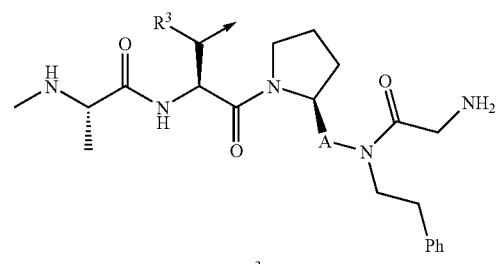 |
| A = CH$_2$; R$^3$ = H or Me | A = CH$_2$; R$^3$ = H or Me |
| 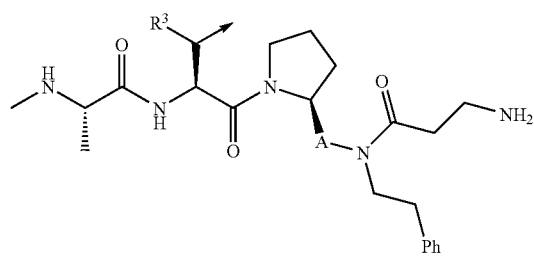 | 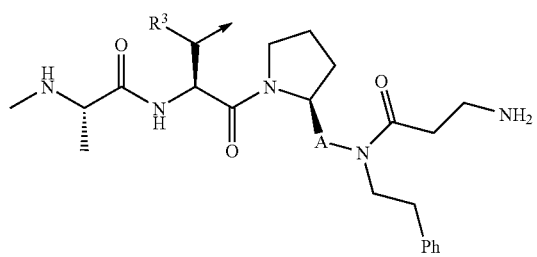 |
| A = CH$_2$; R$^3$ = H or Me | A = CH$_2$; R$^3$ = H or Me |
| 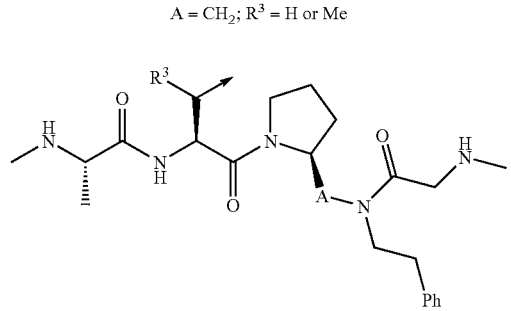 | 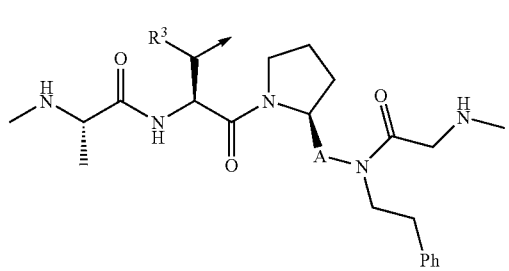 |
| A = CH$_2$; R$^3$ = H or Me | A = CH$_2$; R$^3$ = H or Me |

TABLE 2-continued
M1-BG-M2
Formula IA
BG is 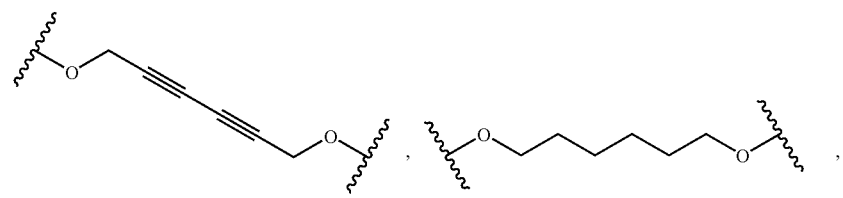
M1 M2
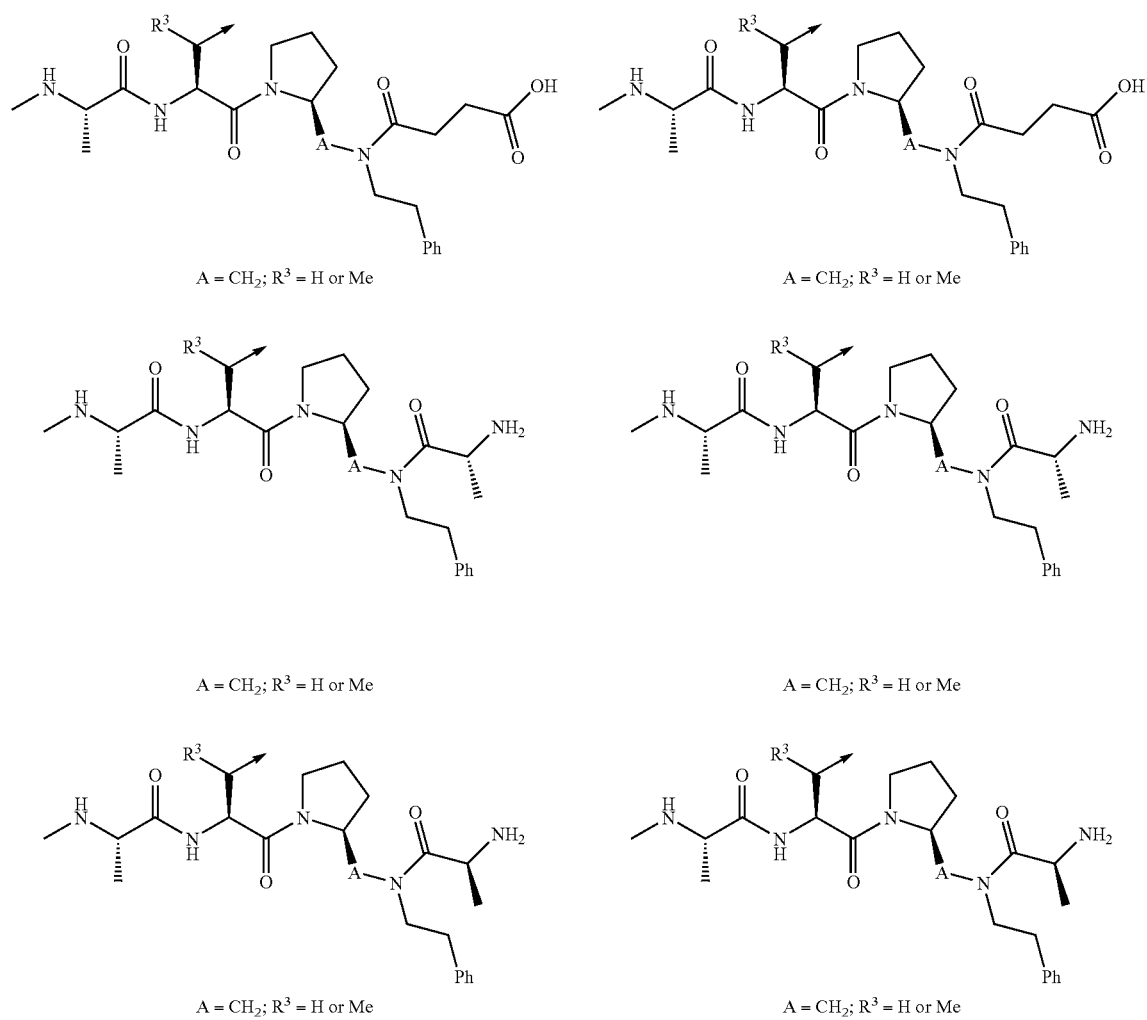
A = CH$_2$; R$^3$ = H or Me TABLE 2-continued
M1-BG-M2
Formula IA
BG is
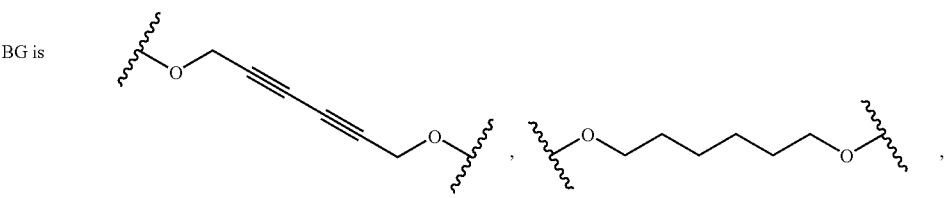
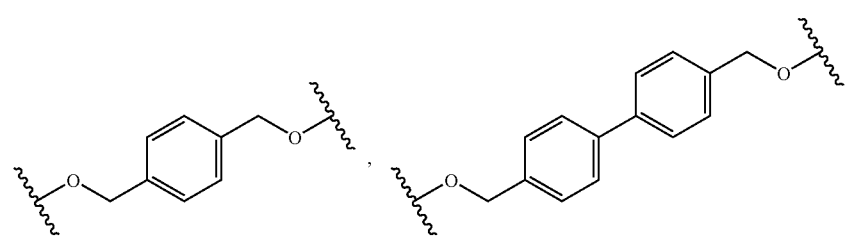
M1   M2
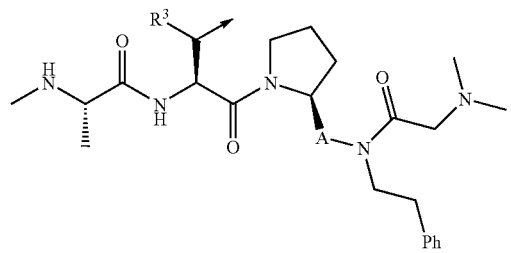 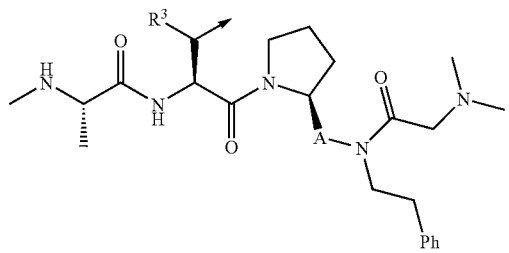
A = CH$_2$; R$^3$ = H or Me   A = CH$_2$; R$^3$ = H or Me
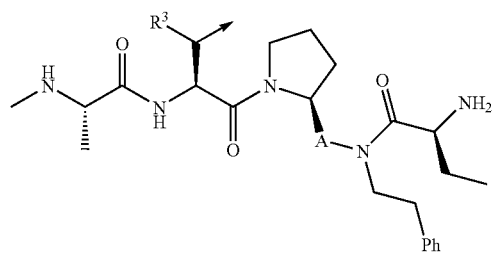 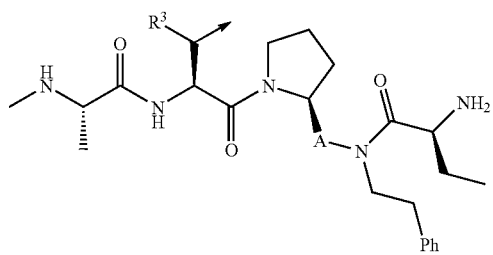
A = CH$_2$; R$^3$ = H or Me   A = CH$_2$; R$^3$ = H or Me
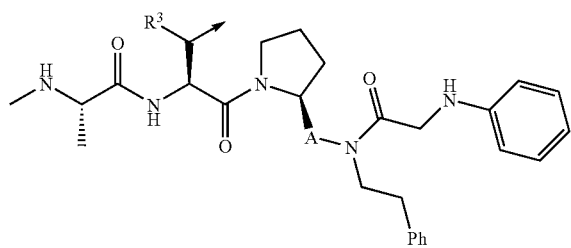 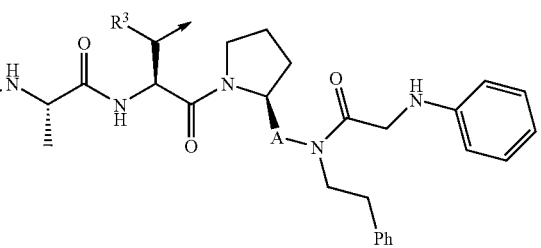
A = CH$_2$; R$^3$ = H or Me   A = CH$_2$; R$^3$ = H or Me TABLE 2-continued
M1-BG-M2
Formula IA
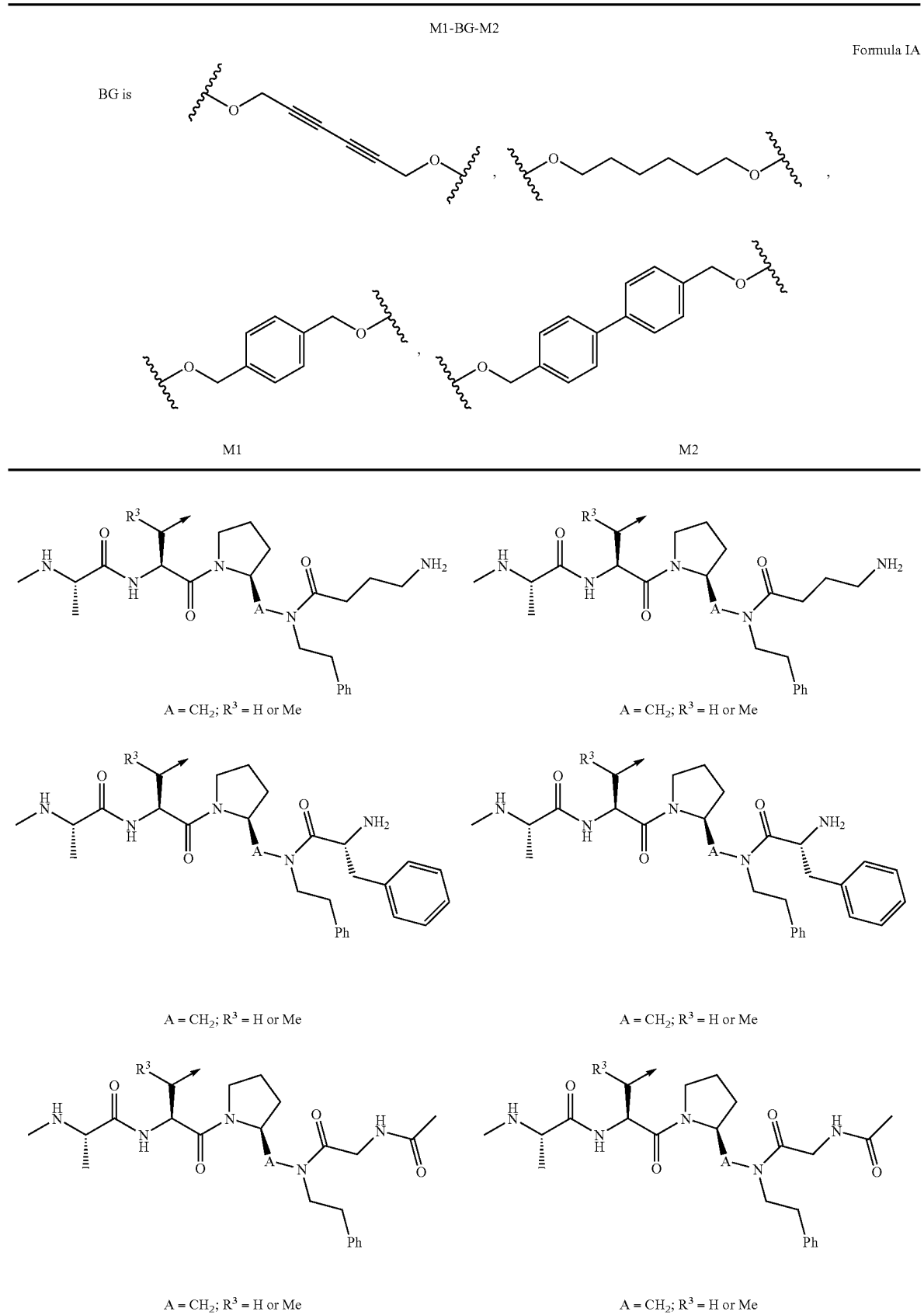

TABLE 2-continued
M1-BG-M2                                        Formula IA
BG is 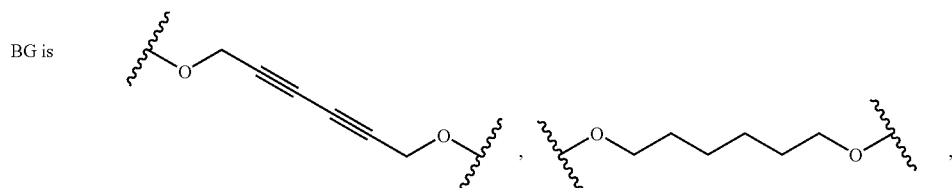
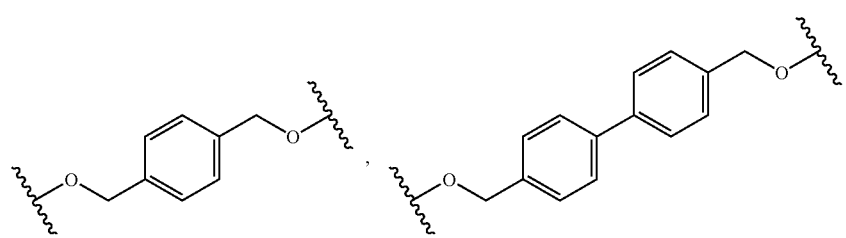
M1                                              M2
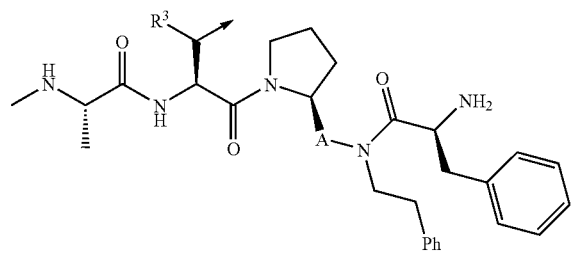
A = CH₂; R³ = H or Me
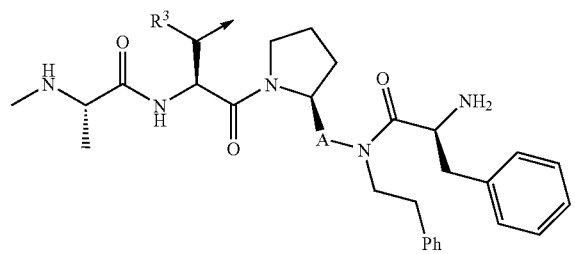
A = CH₂; R³ = H or Me
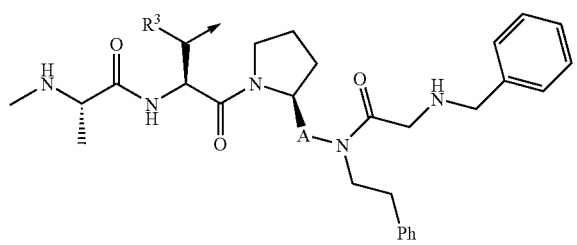
A = CH₂; R³ = H or Me
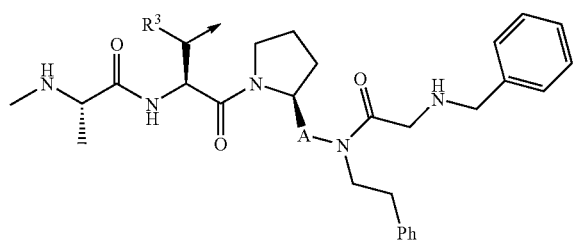
A = CH₂; R³ = H or Me
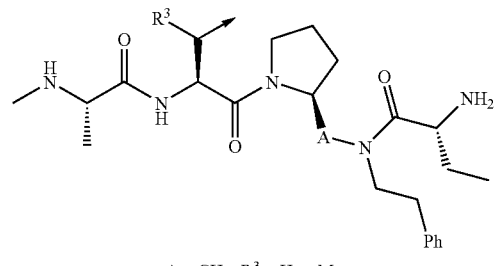
A = CH₂; R³ = H or Me
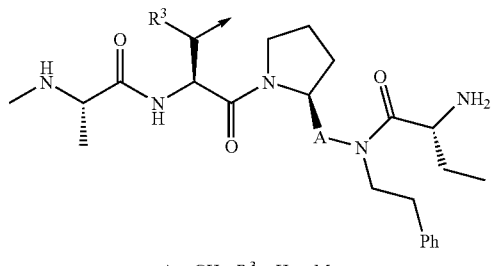
A = CH₂; R³ = H or Me TABLE 2-continued
M1-BG-M2          Formula IA
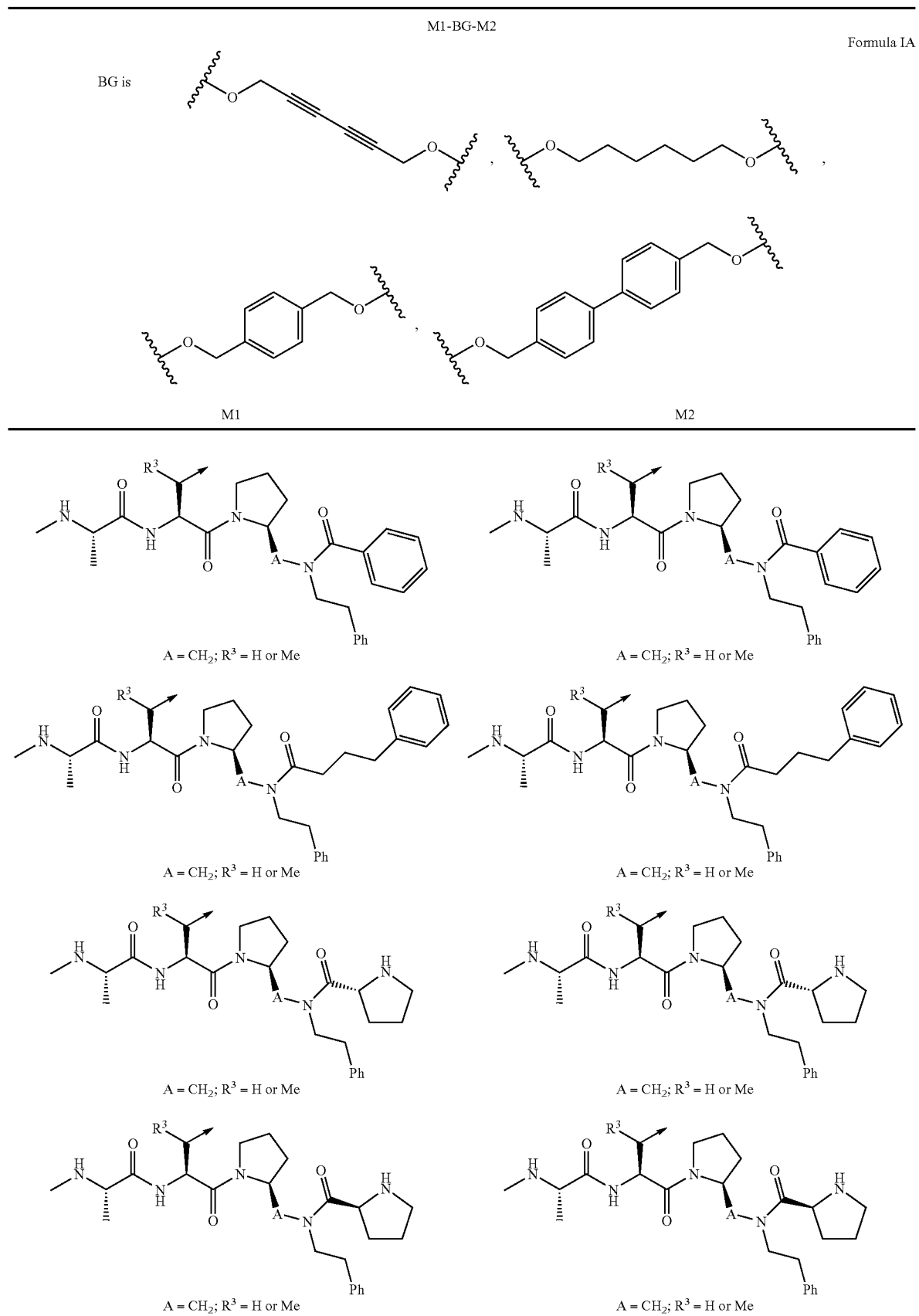

TABLE 2-continued
M1-BG-M2
Formula IA
BG is 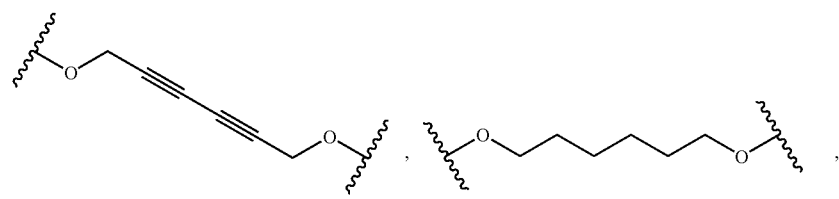
| M1 | M2 |
|---|---|
| 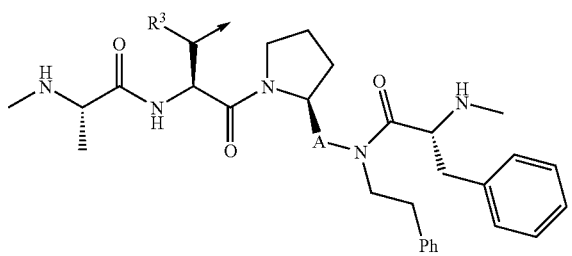<br>A = CH$_2$; R$^3$ = H or Me | 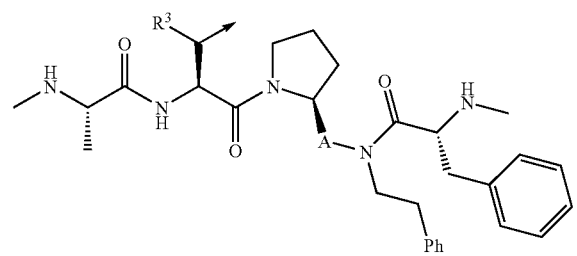<br>A = CH$_2$; R$^3$ = H or Me |
| 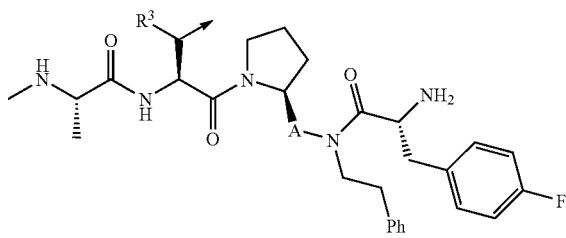<br>A = CH$_2$; R$^3$ = H or Me | 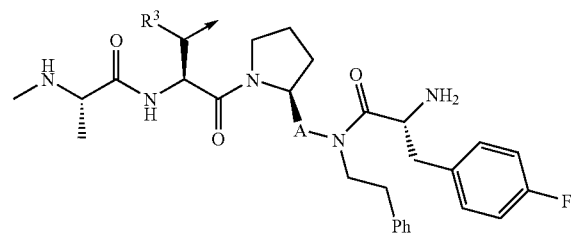<br>A = CH$_2$; R$^3$ = H or Me |
| 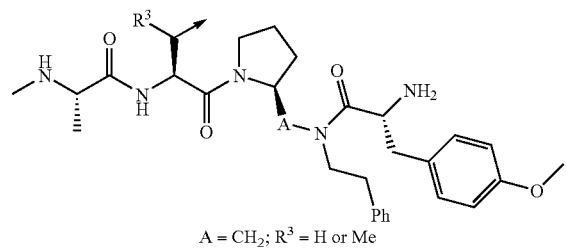<br>A = CH$_2$; R$^3$ = H or Me | 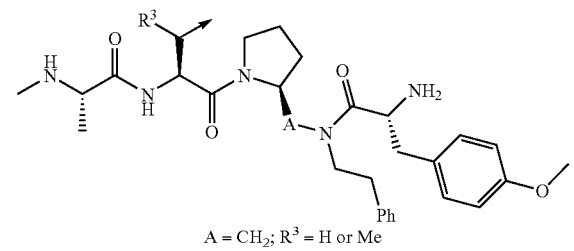<br>A = CH$_2$; R$^3$ = H or Me |
| 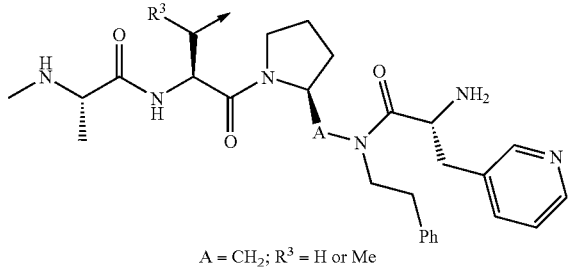<br>A = CH$_2$; R$^3$ = H or Me | 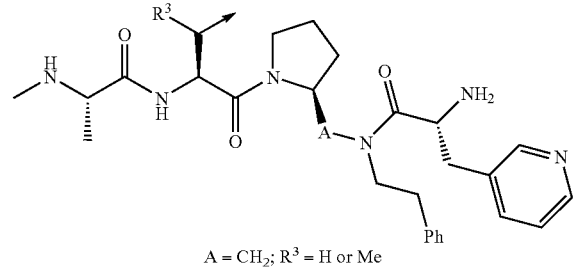<br>A = CH$_2$; R$^3$ = H or Me |

TABLE 2-continued
M1-BG-M2
Formula IA
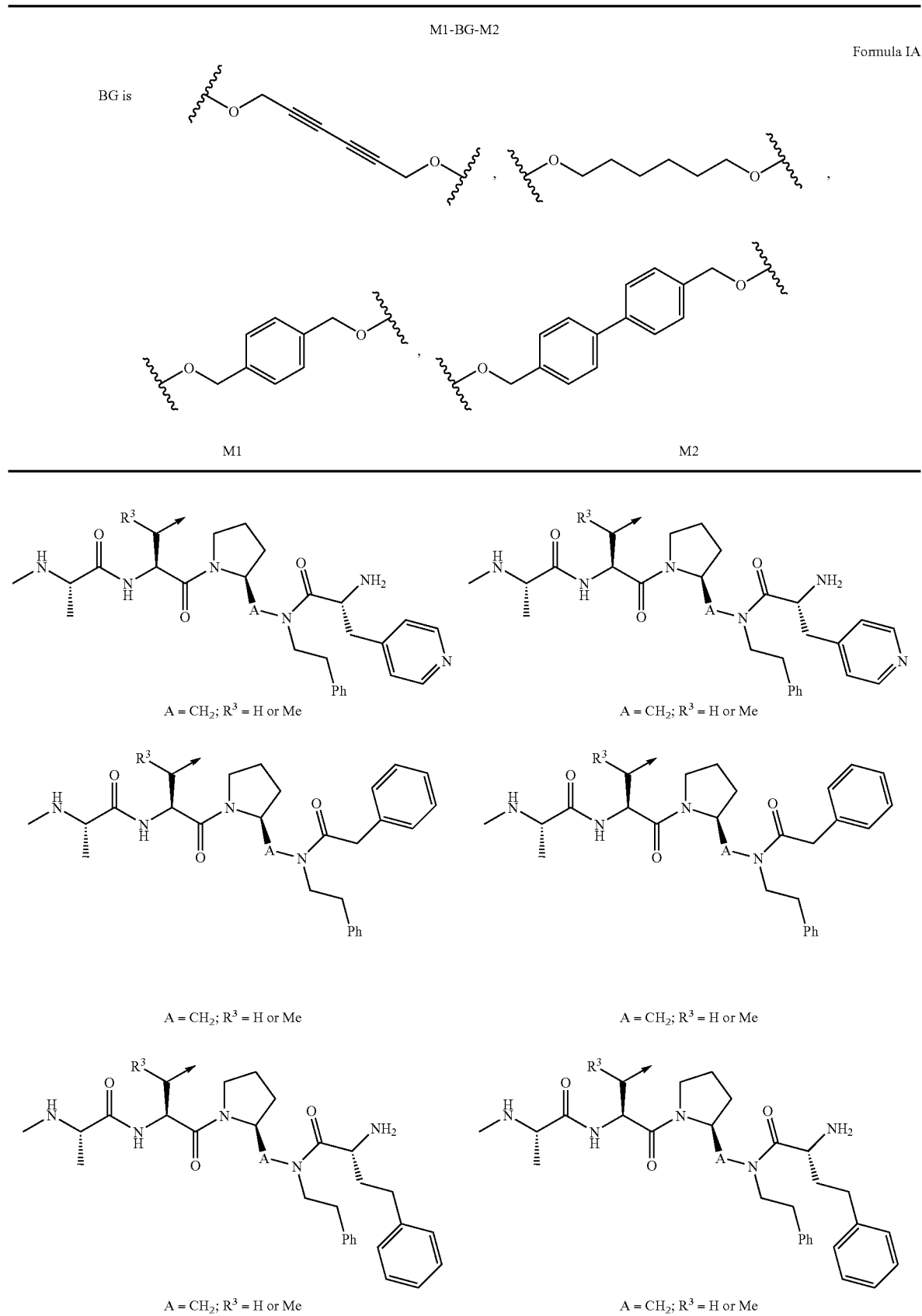

TABLE 2-continued
M1-BG-M2
Formula IA
BG is 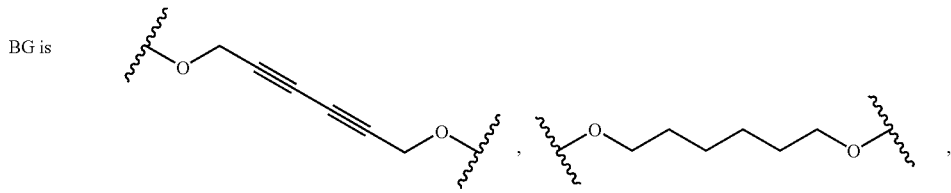
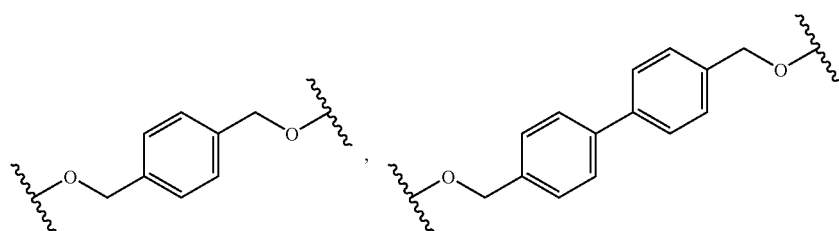
M1 M2
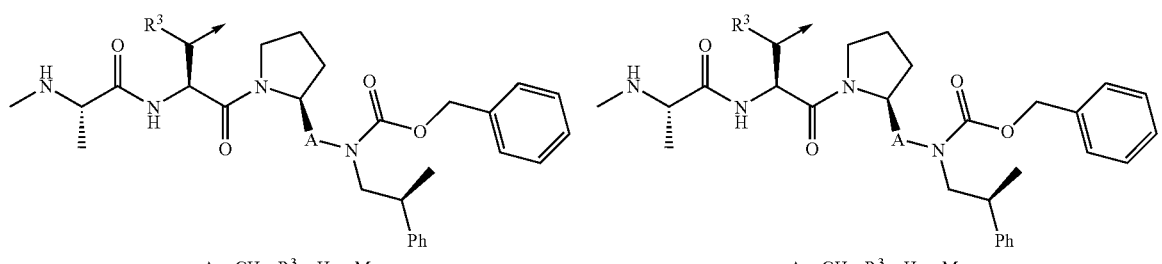
A = CH$_2$; R$^3$ = H or Me        A = CH$_2$; R$^3$ = H or Me
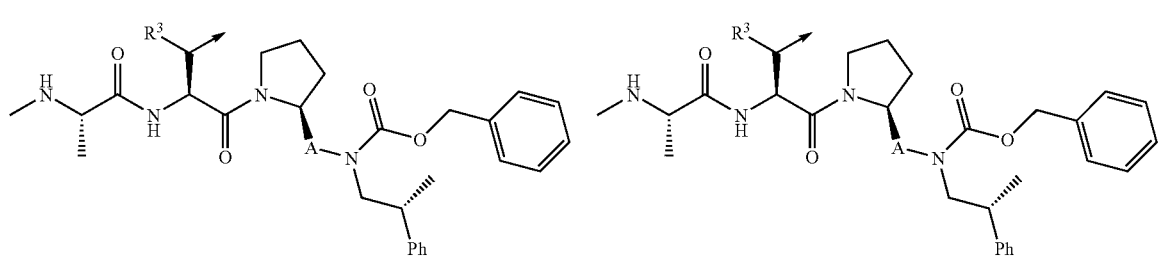
A = CH$_2$; R$^3$ = H or Me        A = CH$_2$; R$^3$ = H or Me
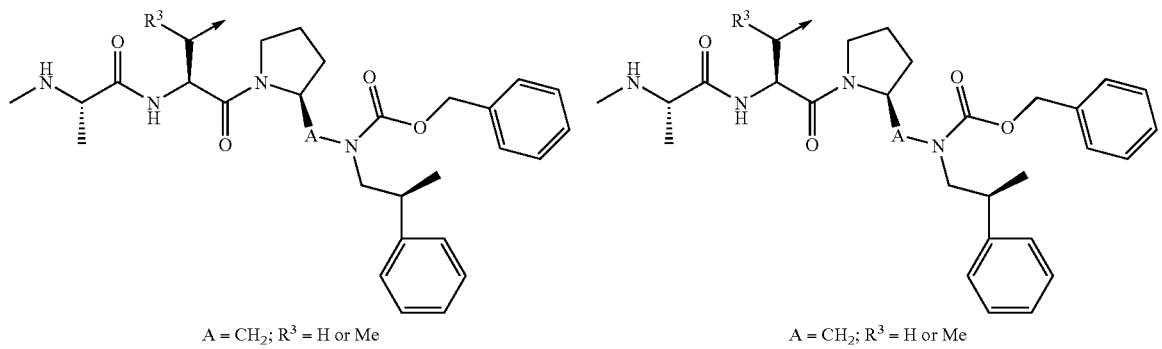
A = CH$_2$; R$^3$ = H or Me        A = CH$_2$; R$^3$ = H or Me TABLE 2-continued
M1-BG-M2
Formula IA
BG is
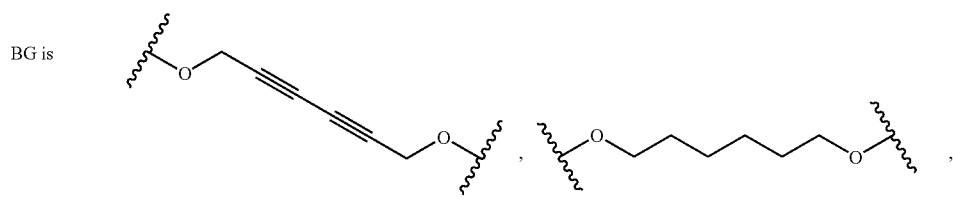
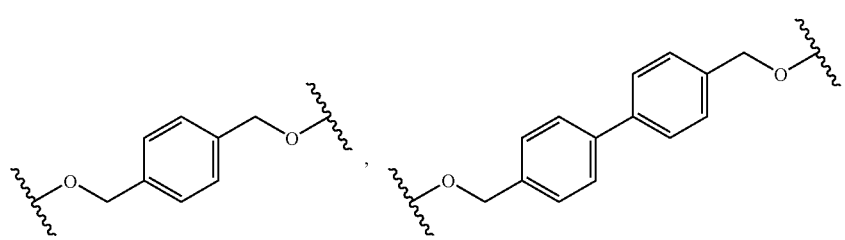
| M1 | M2 |
|---|---|
| 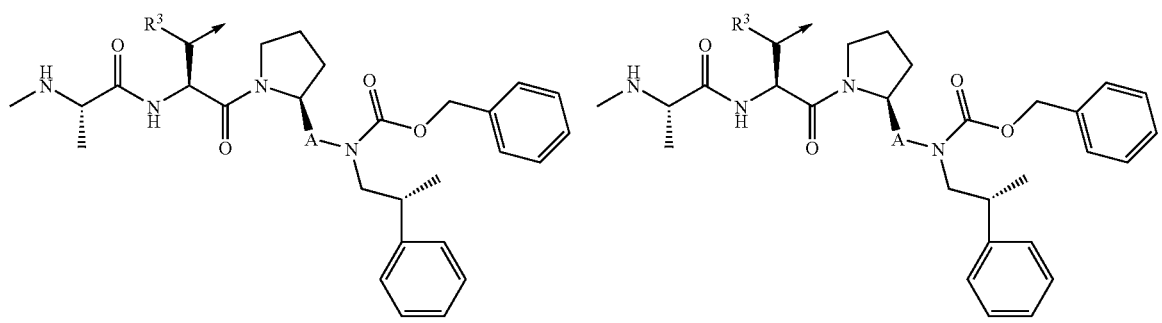 | |
| A = CH₂; R³ = H or Me | A = CH₂; R³ = H or Me |
| 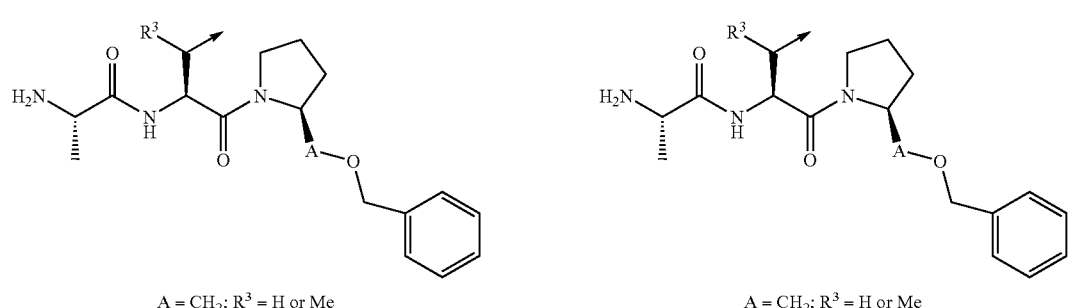 | |
| A = CH₂; R³ = H or Me | A = CH₂; R³ = H or Me |
| 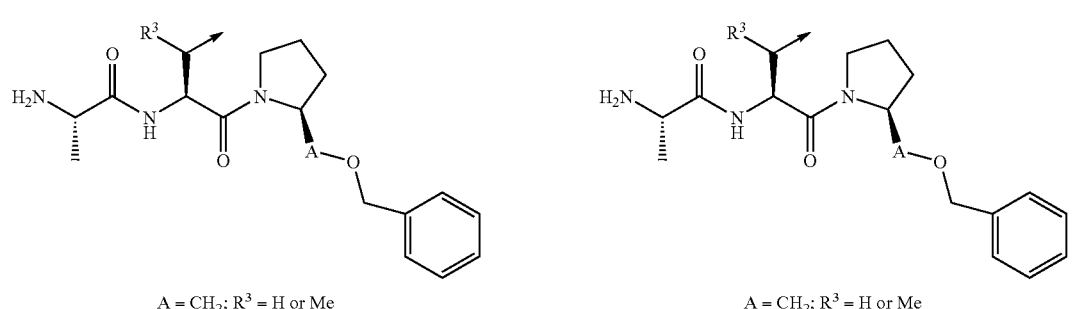 | |
| A = CH₂; R³ = H or Me | A = CH₂; R³ = H or Me |

TABLE 2-continued
M1-BG-M2 Formula IA
BG is
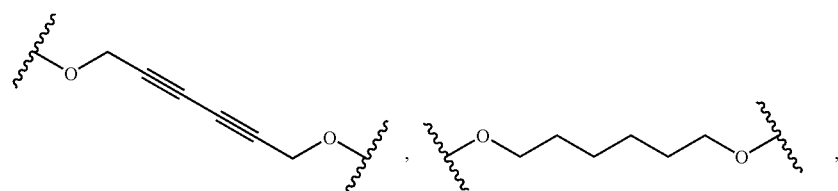
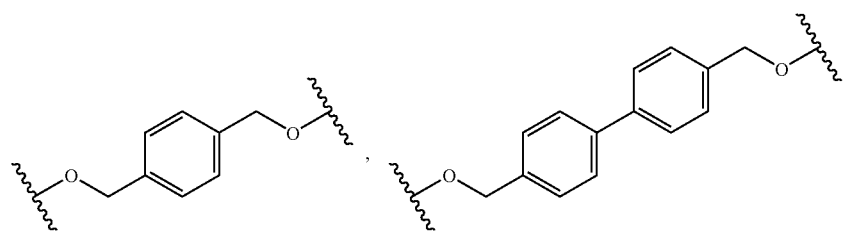
| M1 | M2 |
|---|---|
| 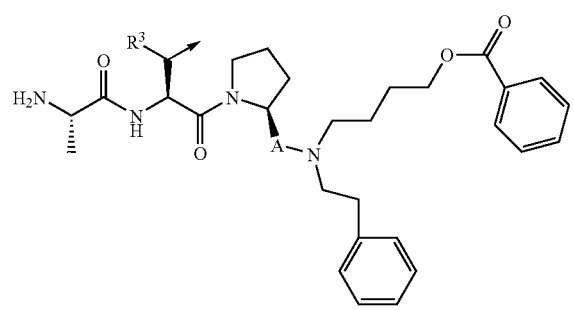 <br> A = $CH_2$; $R^3$ = H or Me | 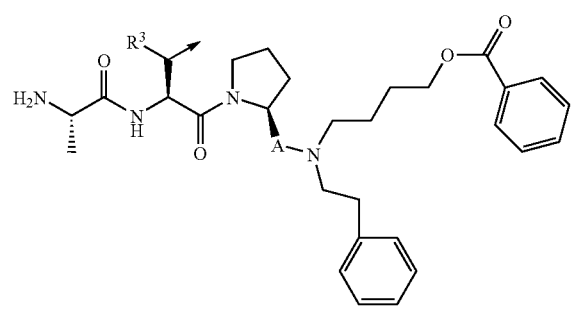 <br> A = $CH_2$; $R^3$ = H or Me |
| 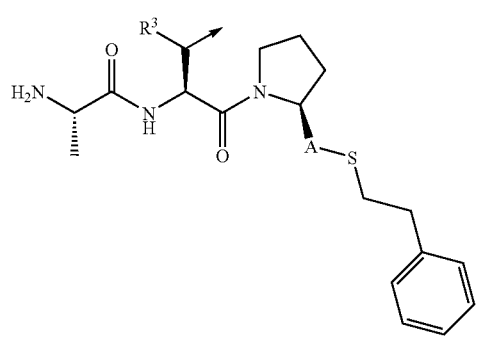 <br> A = $CH_2$; $R^3$ = H or Me | 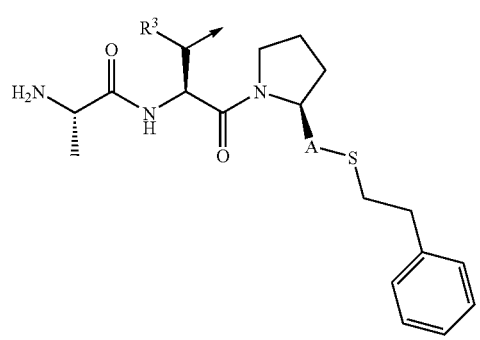 <br> A = $CH_2$; $R^3$ = H or Me |
| 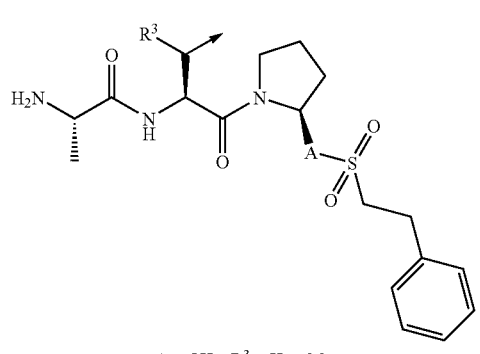 <br> A = $CH_2$; $R^3$ = H or Me | 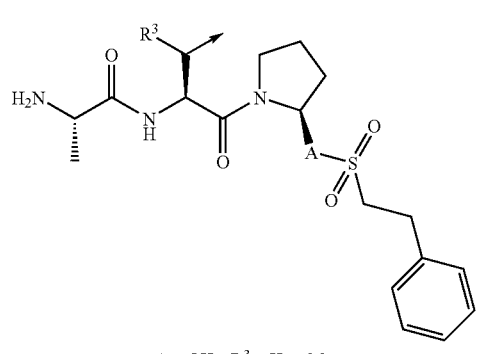 <br> A = $CH_2$; $R^3$ = H or Me |

TABLE 2-continued
M1-BG-M2
Formula IA
BG is
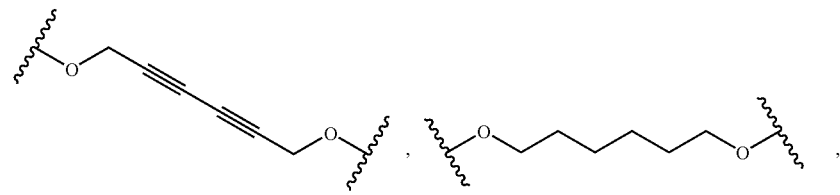
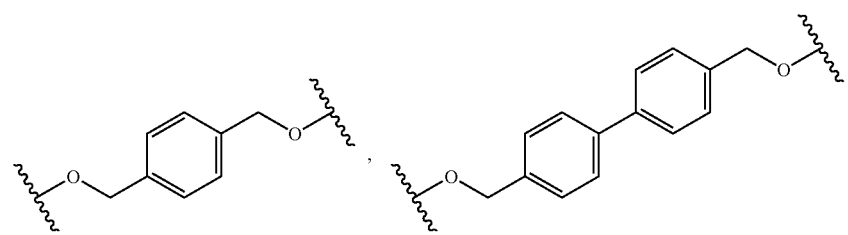
| M1 | M2 |
|---|---|
| 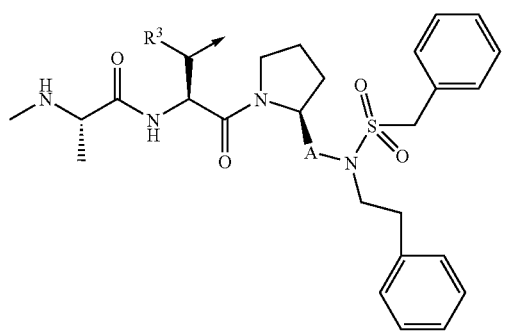<br>A = CH$_2$; R$^3$ = H or Me | 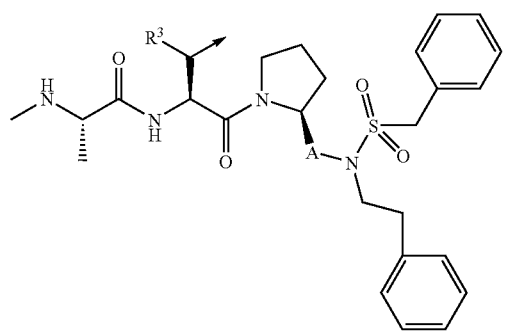<br>A = CH$_2$; R$^3$ = H or Me |
| 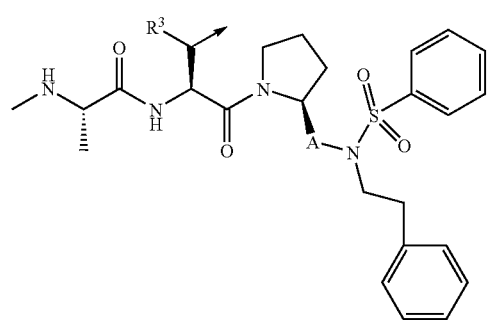<br>A = CH$_2$; R$^3$ = H or Me | 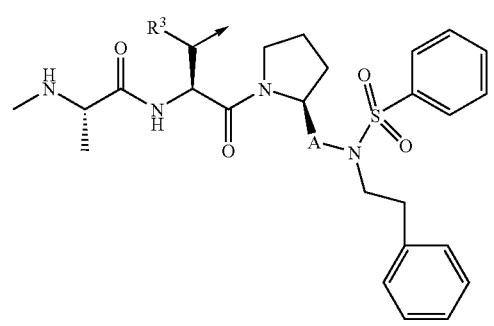<br>A = CH$_2$; R$^3$ = H or Me |
| 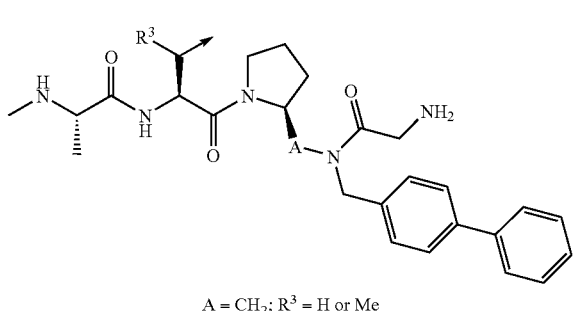<br>A = CH$_2$; R$^3$ = H or Me | 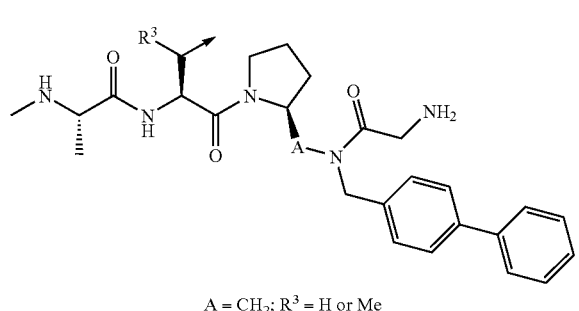<br>A = CH$_2$; R$^3$ = H or Me |

TABLE 2-continued
M1-BG-M2
Formula IA
BG is
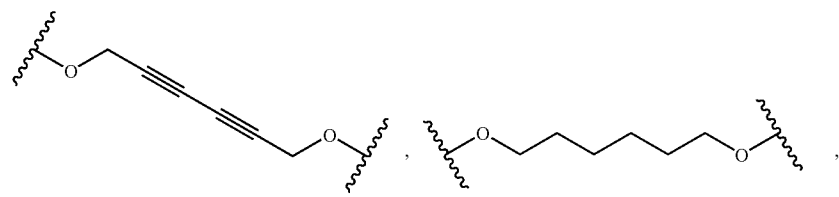
| M1 | M2 |
|---|---|
| 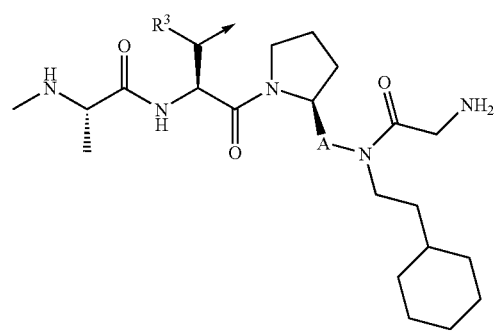<br>A = CH$_2$; R$^3$ = H or Me | 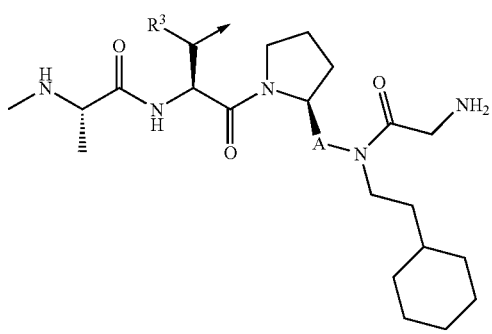<br>A = CH$_2$; R$^3$ = H or Me |
| 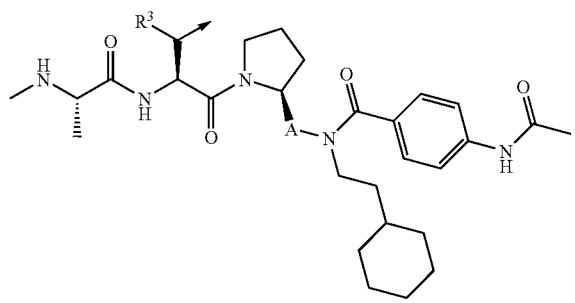<br>A = CH$_2$; R$^3$ = H or Me | 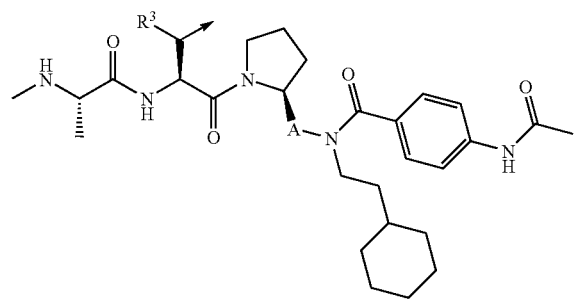<br>A = CH$_2$; R$^3$ = H or Me |
| 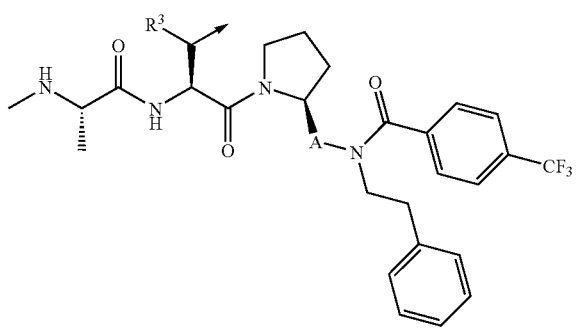<br>A = CH$_2$; R$^3$ = H or Me | 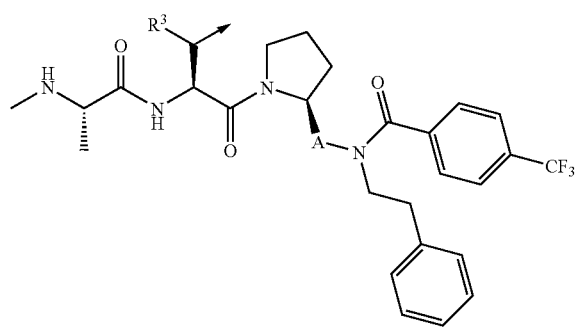<br>A = CH$_2$; R$^3$ = H or Me |

TABLE 2-continued
M1-BG-M2
Formula IA
BG is
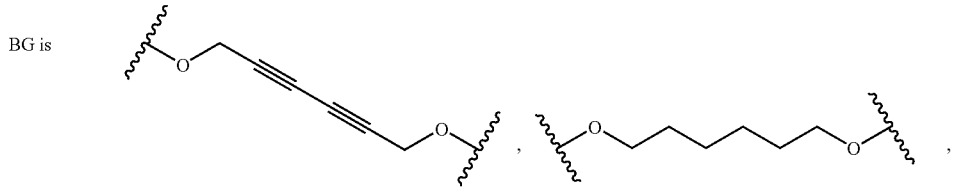
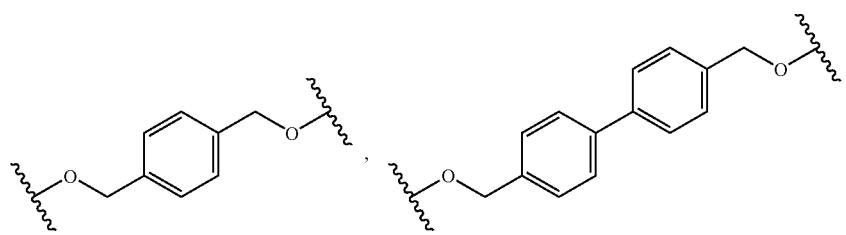
| M1 | M2 |
|---|---|
| 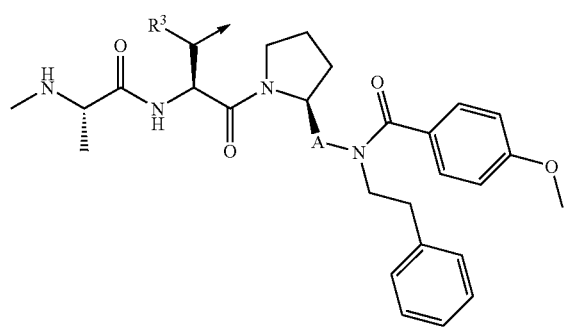<br>A = CH₂; R³ = H or Me | 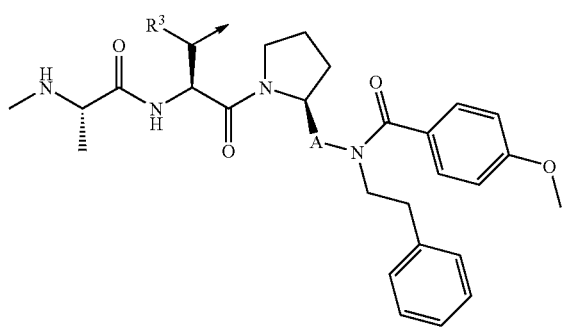<br>A = CH₂; R³ = H or Me |
| 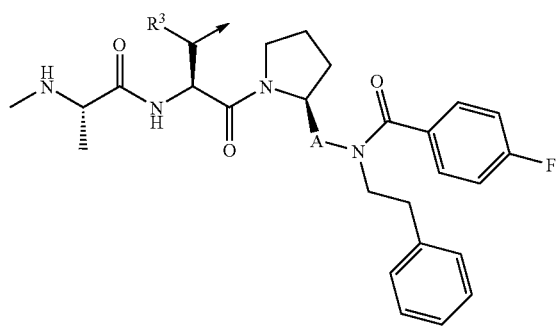<br>A = CH₂; R³ = H or Me | 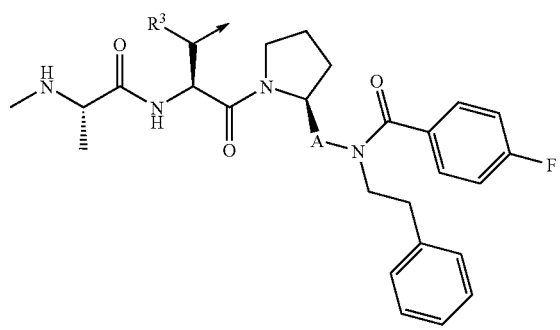<br>A = CH₂; R³ = H or Me |
| 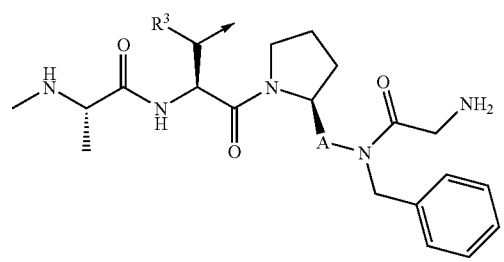<br>A = CH₂; R³ = H or Me | 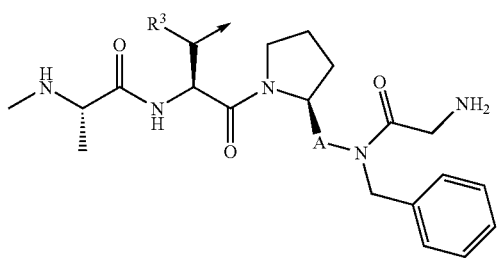<br>A = CH₂; R³ = H or Me |

TABLE 2-continued
M1-BG-M2
Formula IA
BG is 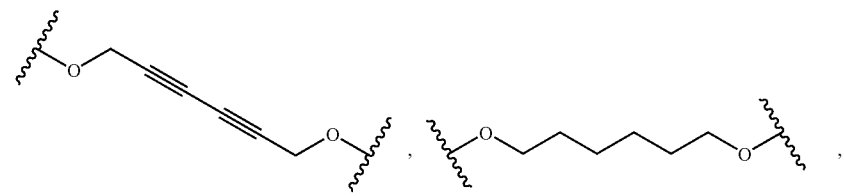
| M1 | M2 |
|---|---|
| 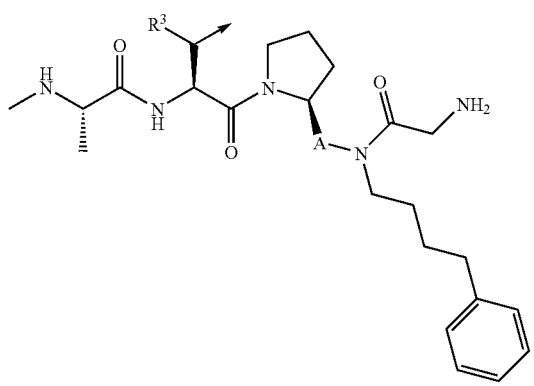<br>A = CH$_2$; R$^3$ = H or Me | 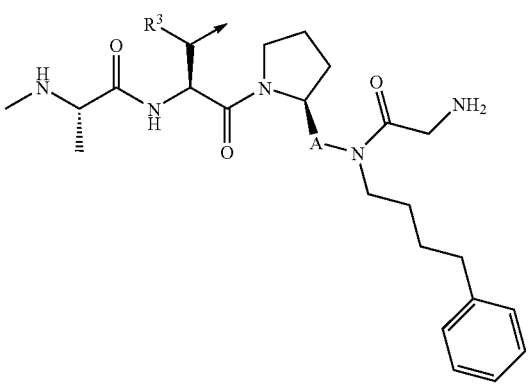<br>A = CH$_2$; R$^3$ = H or Me |
| 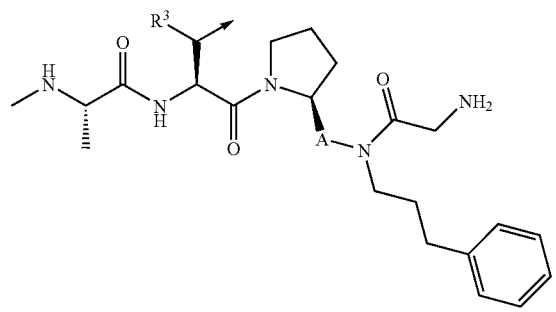<br>A = CH$_2$; R$^3$ = H or Me | 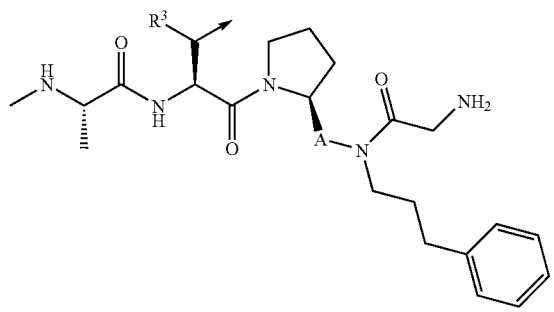<br>A = CH$_2$; R$^3$ = H or Me |
| 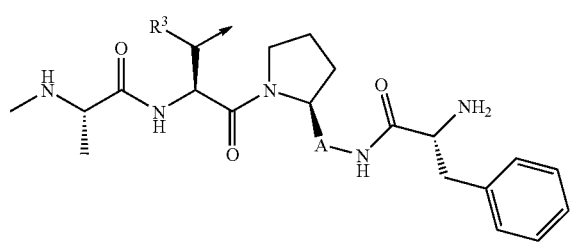<br>A = CH$_2$; R$^3$ = H or Me | 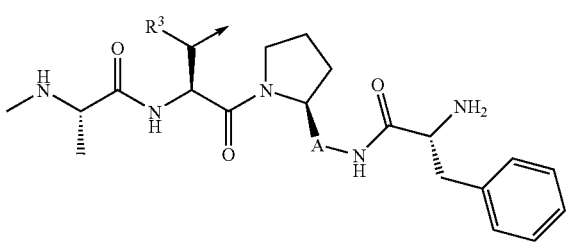<br>A = CH$_2$; R$^3$ = H or Me |

TABLE 2-continued
M1-BG-M2
Formula IA
BG is
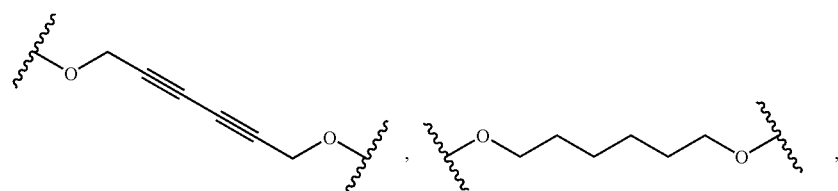
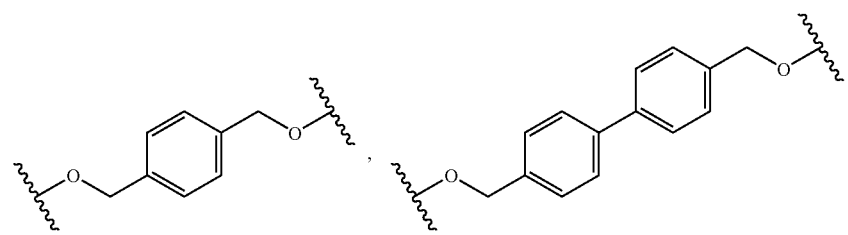
M1 | M2
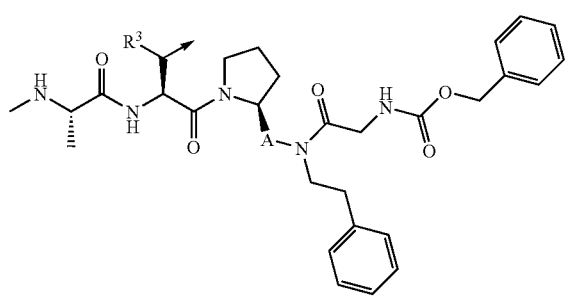
A = CH$_2$; R$^3$ = H or Me
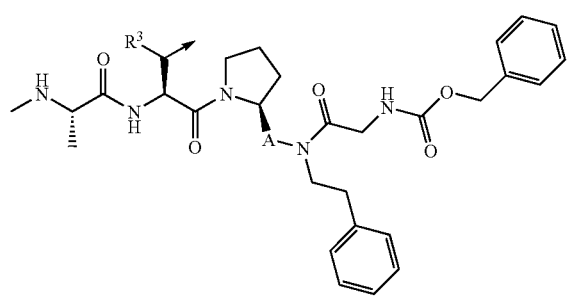
A = CH$_2$; R$^3$ = H or Me
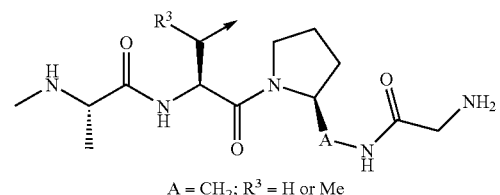
A = CH$_2$; R$^3$ = H or Me
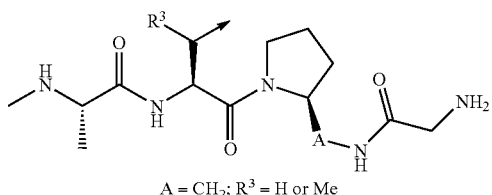
A = CH$_2$; R$^3$ = H or Me
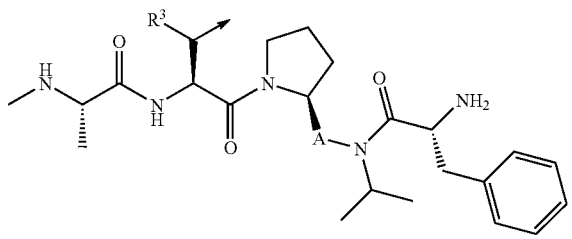
A = CH$_2$; R$^3$ = H or Me
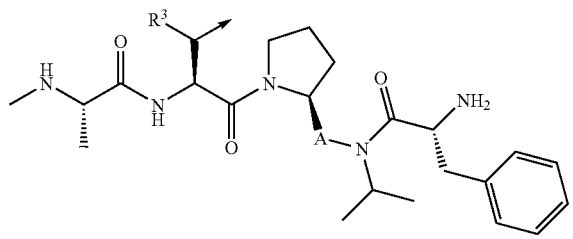
A = CH$_2$; R$^3$ = H or Me
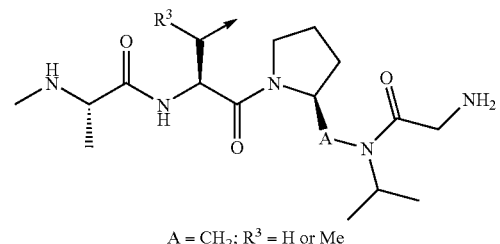
A = CH$_2$; R$^3$ = H or Me
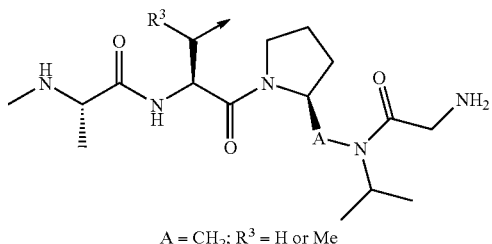
A = CH$_2$; R$^3$ = H or Me TABLE 2-continued
M1-BG-M2
Formula IA
BG is 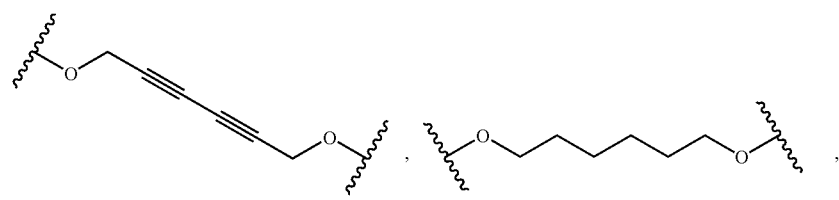
| M1 | M2 |
|---|---|
| 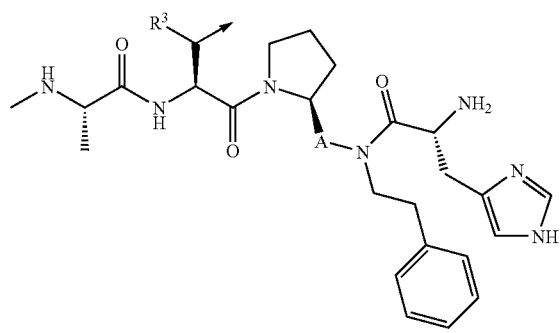<br>A = CH$_2$; R$^3$ = H or Me | 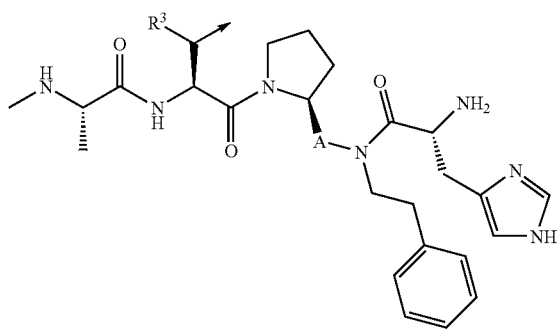<br>A = CH$_2$; R$^3$ = H or Me |
| 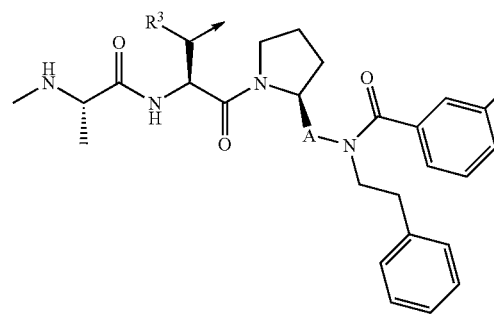<br>A = CH$_2$; R$^3$ = H or Me | 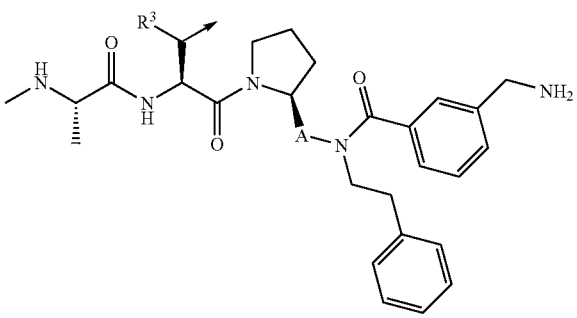<br>A = CH$_2$; R$^3$ = H or Me |
| 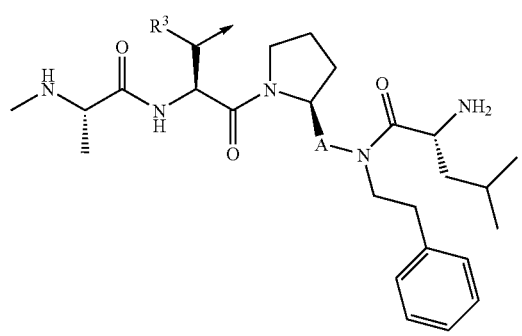<br>A = CH$_2$; R$^3$ = H or Me | 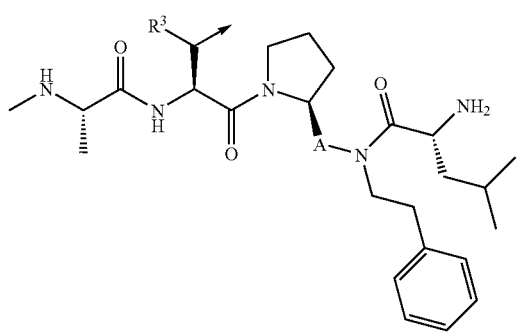<br>A = CH$_2$; R$^3$ = H or Me |

TABLE 2-continued
M1-BG-M2
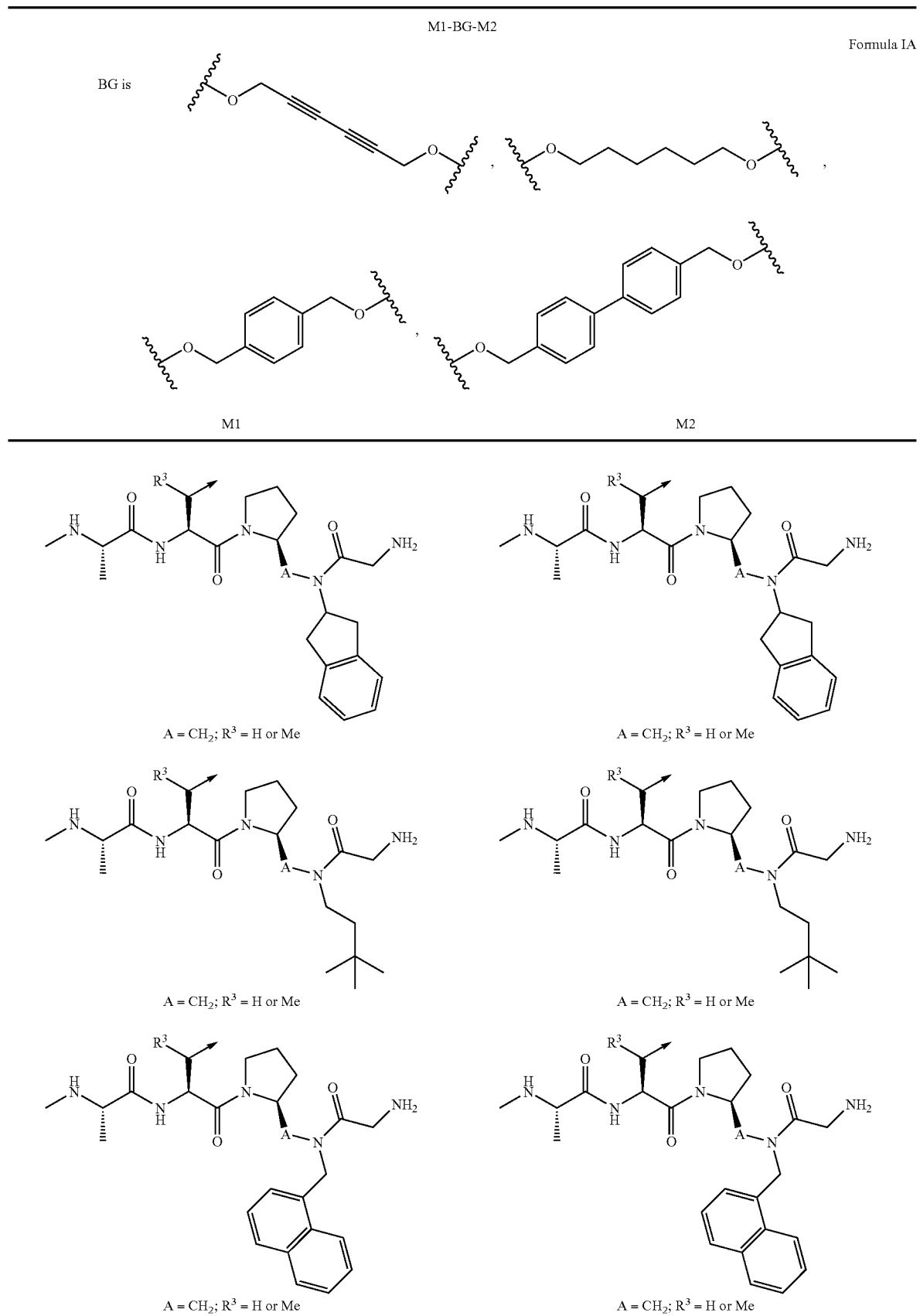

TABLE 2-continued
M1-BG-M2
Formula IA
BG is
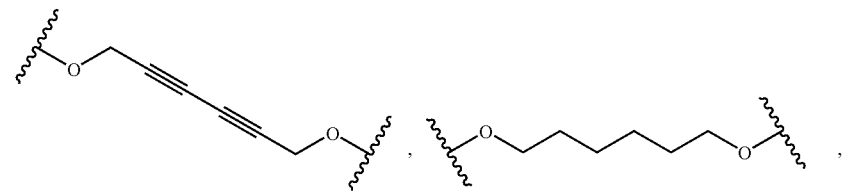
| M1 | M2 |
|---|---|
| 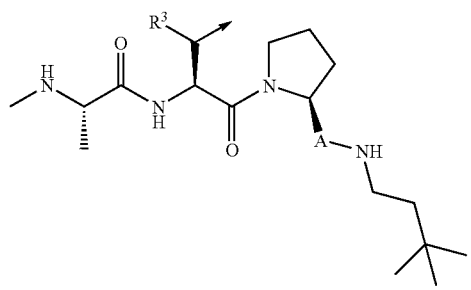<br>A = CH$_2$; R$^3$ = H or Me | 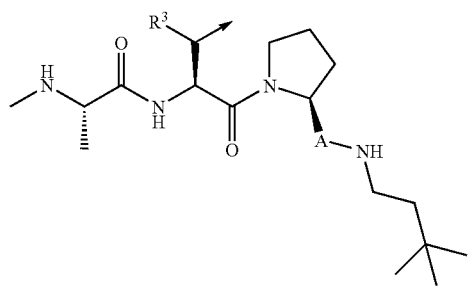<br>A = CH$_2$; R$^3$ = H or Me |
| 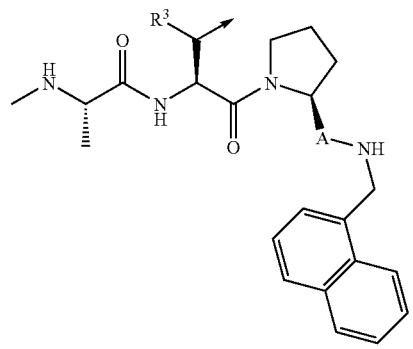<br>A = CH$_2$; R$^3$ = H or Me | 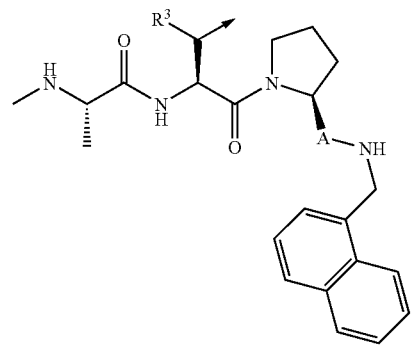<br>A = CH$_2$; R$^3$ = H or Me |
| 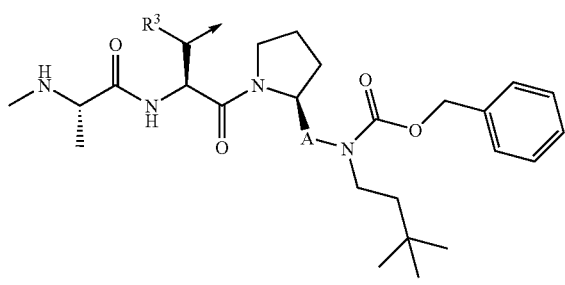<br>A = CH$_2$; R$^3$ = H or Me | 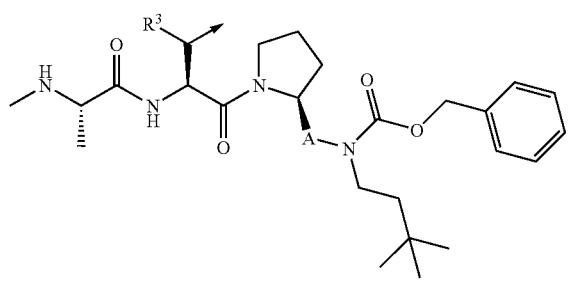<br>A = CH$_2$; R$^3$ = H or Me |

TABLE 2-continued
M1-BG-M2    Formula IA
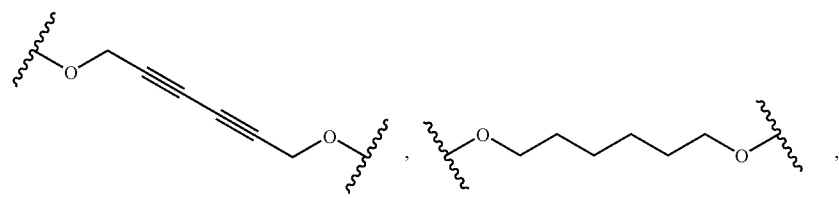
BG is
M1    M2
A = CH₂; R³ = H or Me    A = CH₂; R³ = H or Me
A = CH₂; R³ = H or Me    A = CH₂; R³ = H or Me
A = CH₂; R³ = H or Me    A = CH₂; R³ = H or Me TABLE 2-continued
M1-BG-M2
Formula IA
BG is
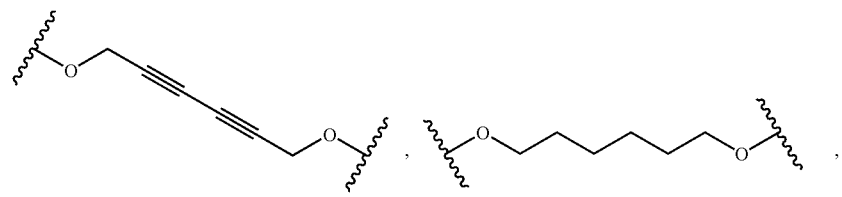
| M1 | M2 |
|---|---|
| 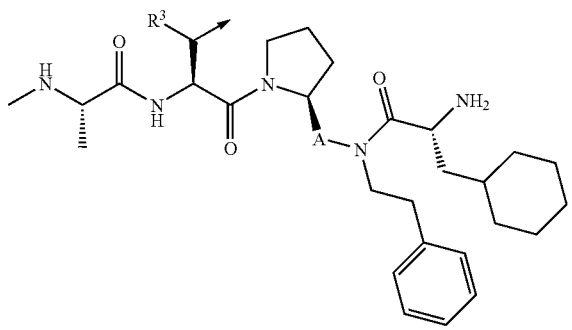<br>A = CH$_2$; R$^3$ = H or Me | 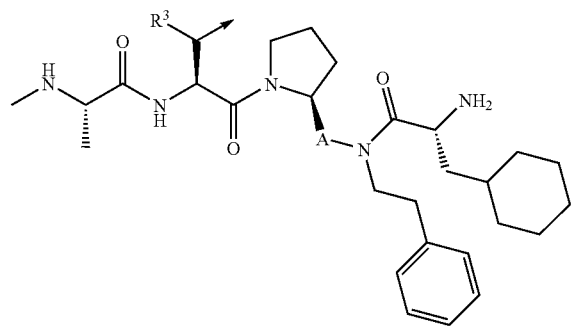<br>A = CH$_2$; R$^3$ = H or Me |
| 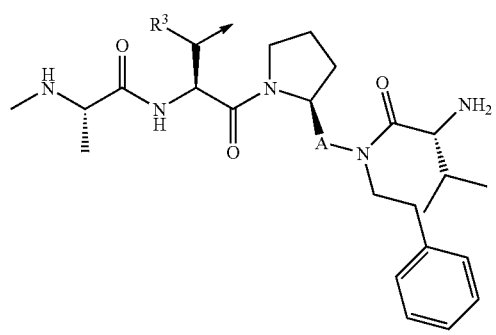<br>A = CH$_2$; R$^3$ = H or Me | 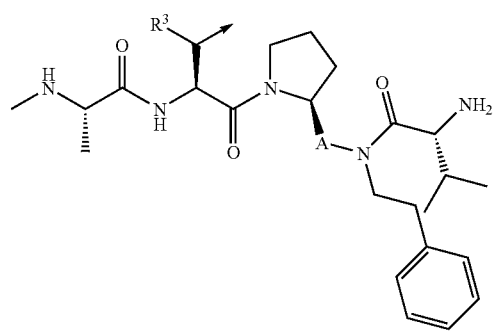<br>A = CH$_2$; R$^3$ = H or Me |
| 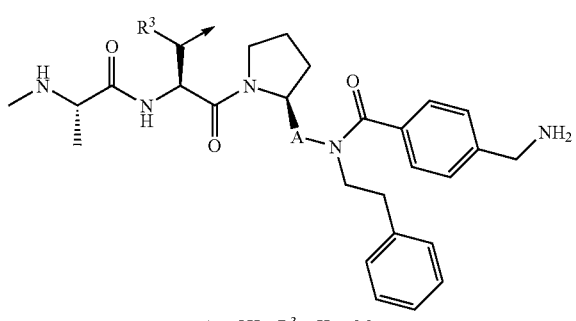<br>A = CH$_2$; R$^3$ = H or Me | 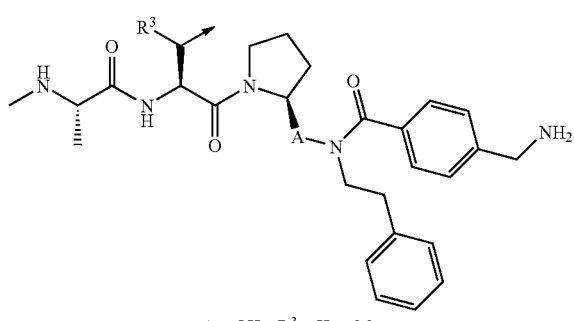<br>A = CH$_2$; R$^3$ = H or Me |

TABLE 2-continued
M1-BG-M2
Formula IA
BG is
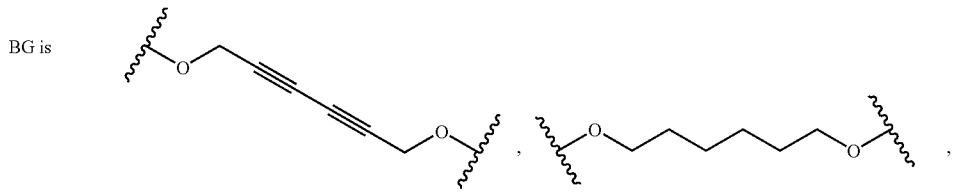
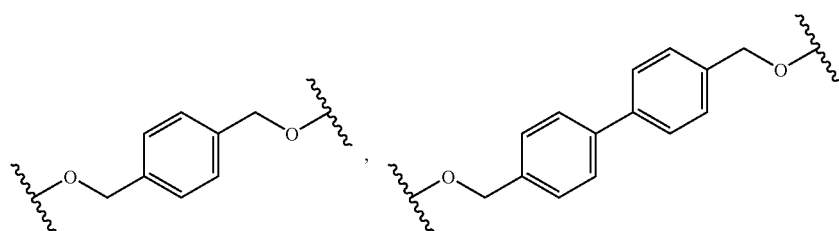
| M1 | M2 |
|---|---|
| 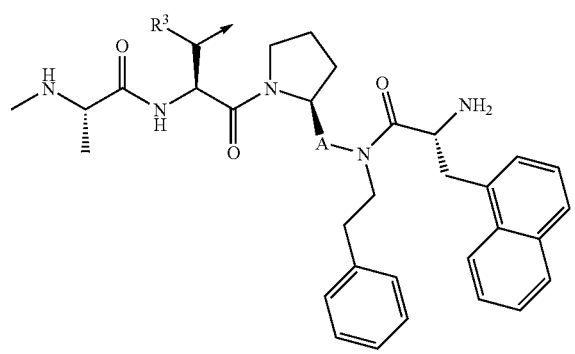<br>A = CH₂; R³ = H or Me | 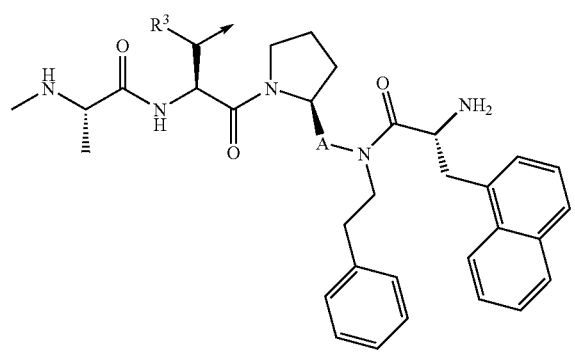<br>A = CH₂; R³ = H or Me |
| 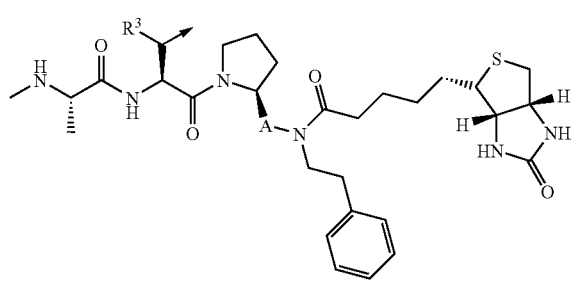<br>A = CH₂; R³ = H or Me | 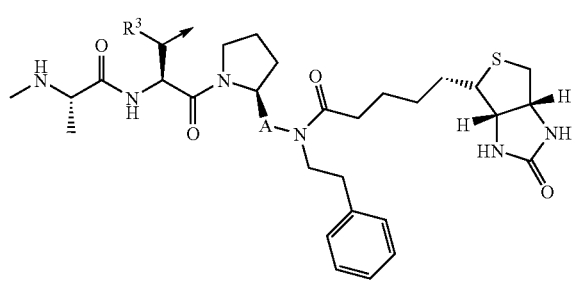<br>A = CH₂; R³ = H or Me |
| 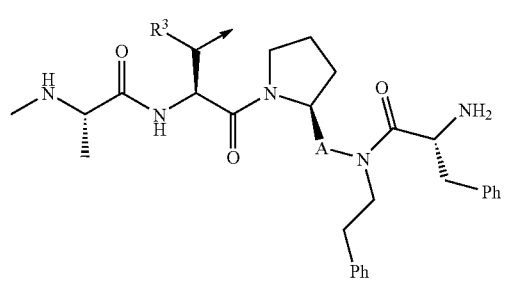<br>A = CH₂; R³ = H or Me | 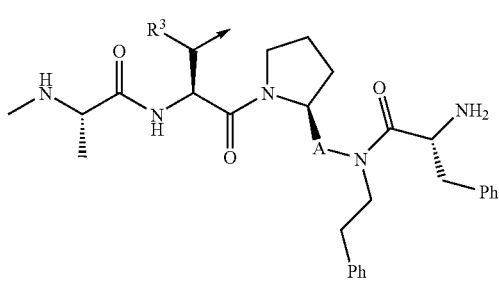<br>A = CH₂; R³ = H or Me |

TABLE 2-continued
M1-BG-M2          Formula IA
BG is 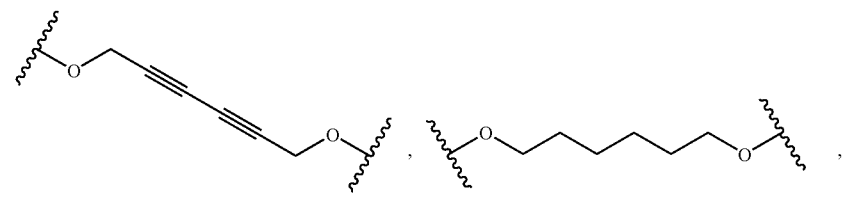
| M1 | M2 |
|---|---|
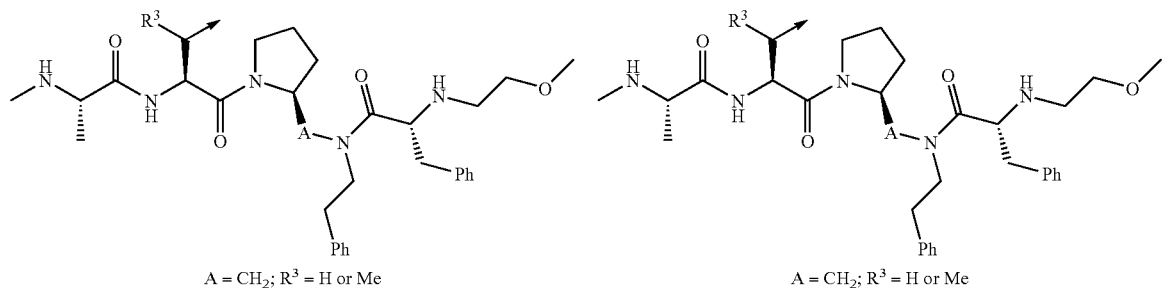
A = CH₂; R³ = H or Me      A = CH₂; R³ = H or Me
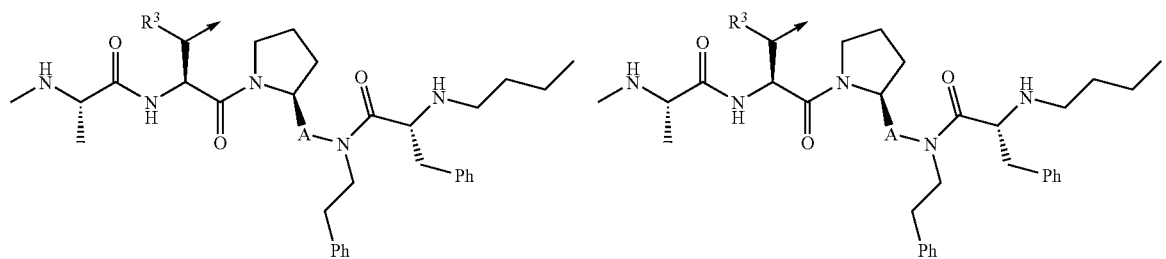
A = CH₂; R³ = H or Me      A = CH₂; R³ = H or Me
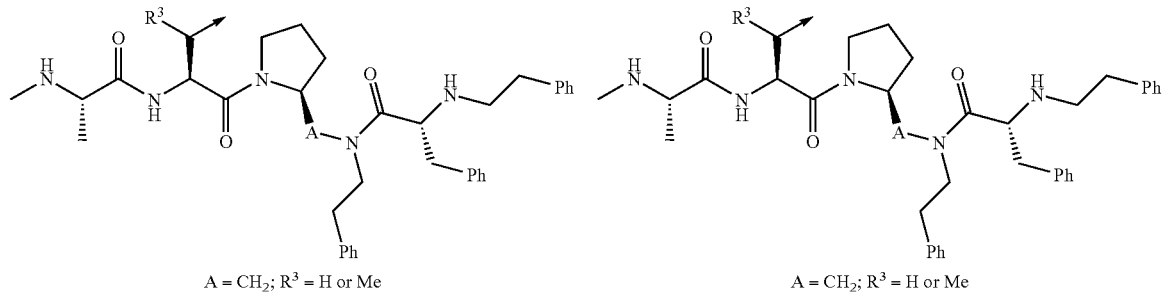
A = CH₂; R³ = H or Me      A = CH₂; R³ = H or Me TABLE 2-continued
M1-BG-M2
Formula IA
BG is
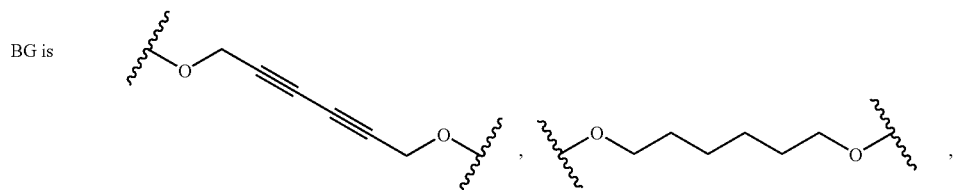
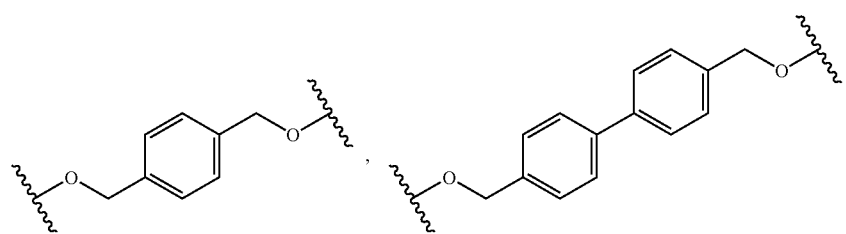
| M1 | M2 |
|---|---|
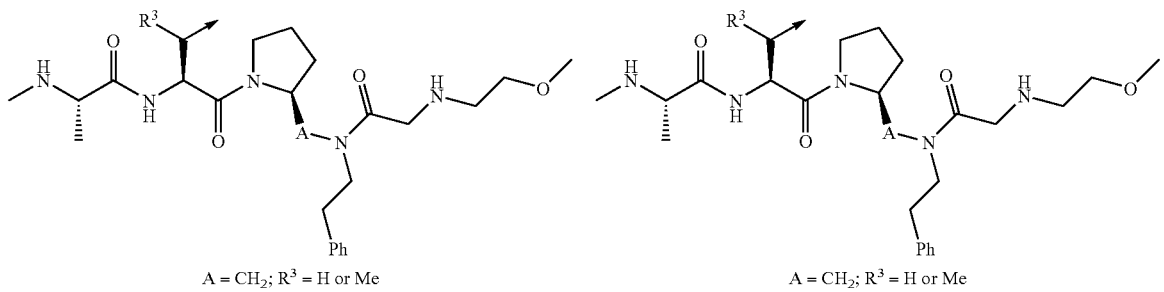
A = CH$_2$; R$^3$ = H or Me              A = CH$_2$; R$^3$ = H or Me
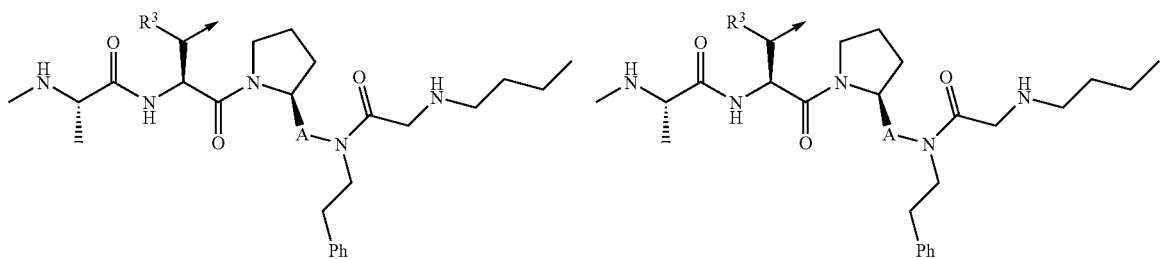
A = CH$_2$; R$^3$ = H or Me              A = CH$_2$; R$^3$ = H or Me
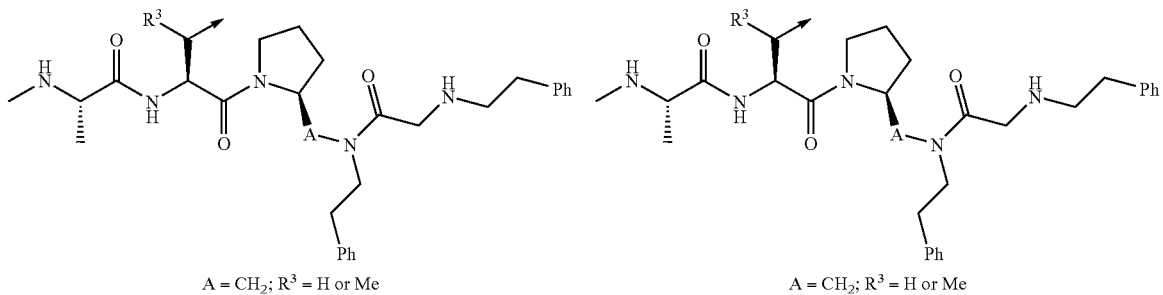
A = CH$_2$; R$^3$ = H or Me              A = CH$_2$; R$^3$ = H or Me TABLE 2-continued
M1-BG-M2 Formula IA
BG is
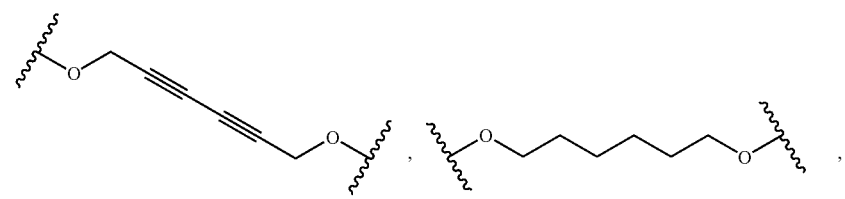
| M1 | M2 |
|---|---|
| 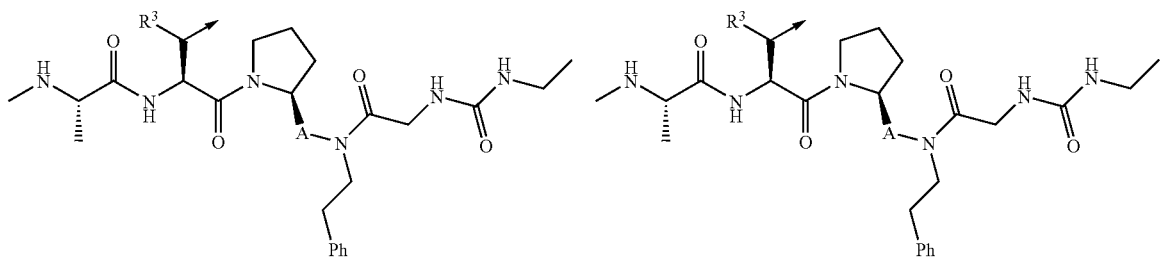 | |
| A = CH₂; R³ = H or Me | A = CH₂; R³ = H or Me |
| 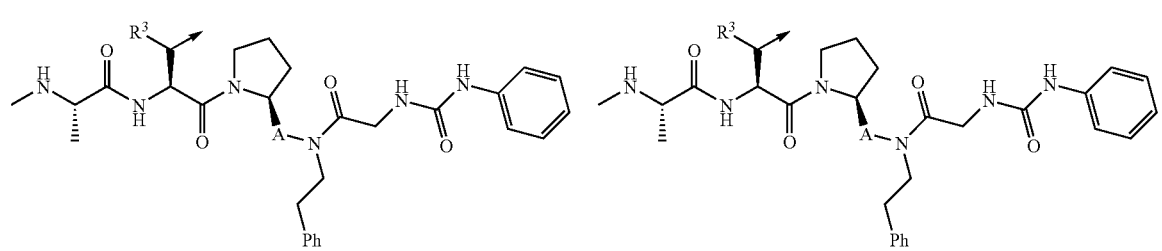 | |
| A = CH₂; R³ = H or Me | A = CH₂; R³ = H or Me |
| 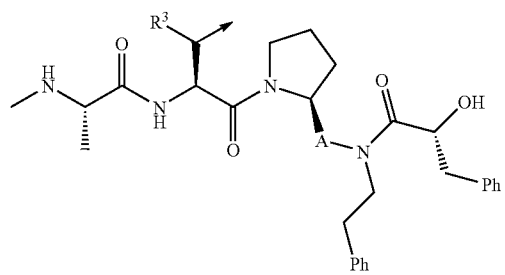 | 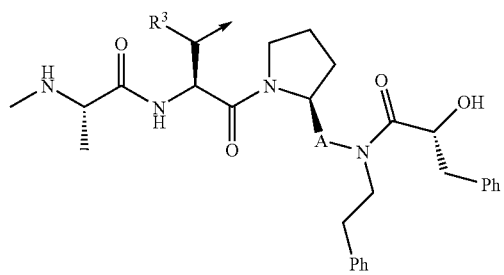 |
| A = CH₂; R³ = H or Me | A = CH₂; R³ = H or Me |

TABLE 2-continued
M1-BG-M2
Formula IA
BG is
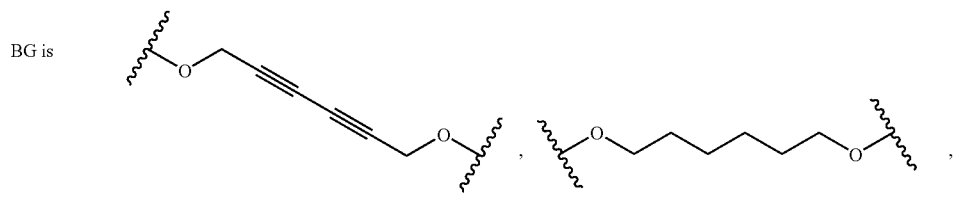
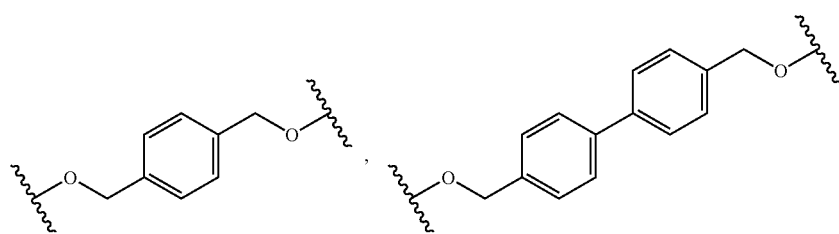
| M1 | M2 |
|---|---|
| 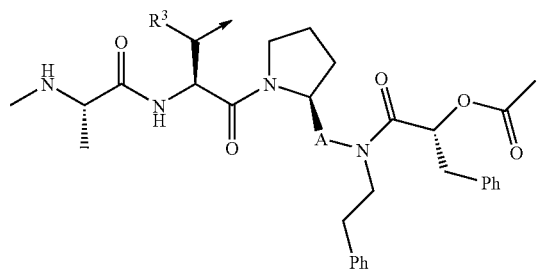<br>A = CH$_2$; R$^3$ = H or Me | 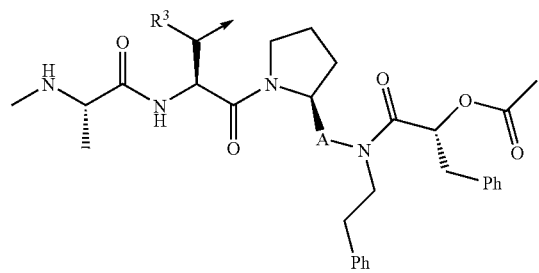<br>A = CH$_2$; R$^3$ = H or Me |
| 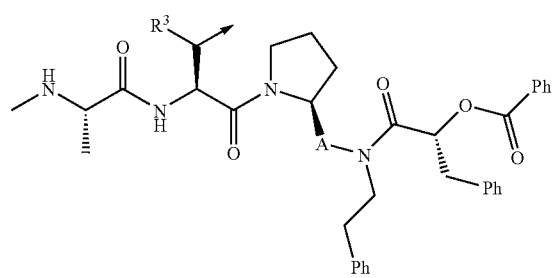<br>A = CH$_2$; R$^3$ = H or Me | 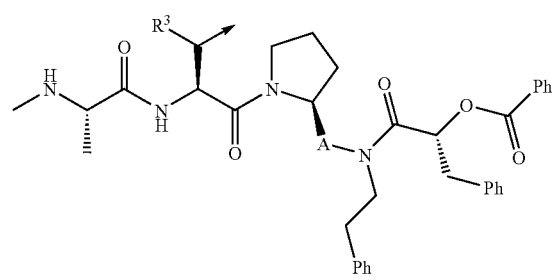<br>A = CH$_2$; R$^3$ = H or Me |
| 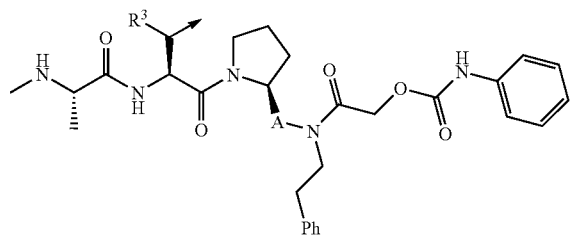<br>A = CH$_2$; R$^3$ = H or Me | 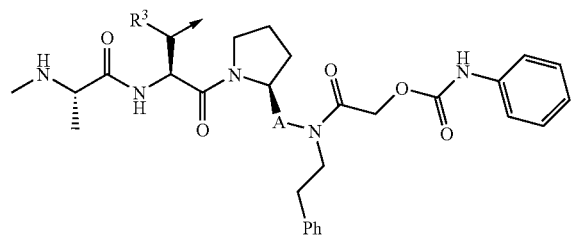<br>A = CH$_2$; R$^3$ = H or Me |

TABLE 2-continued
M1-BG-M2
Formula IA
BG is
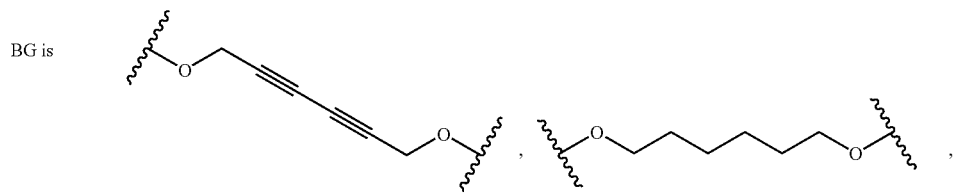
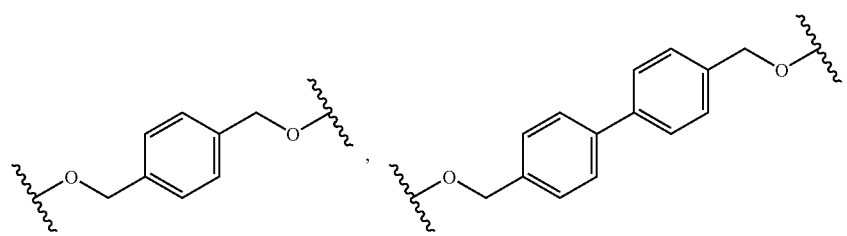
| M1 | M2 |
|---|---|
| 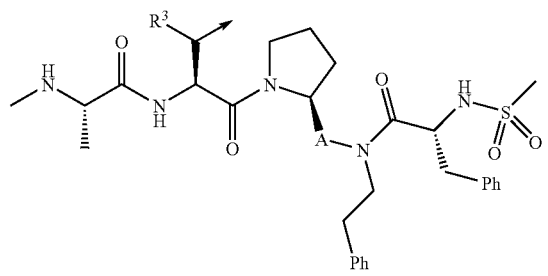<br>A = CH$_2$; R$^3$ = H or Me | 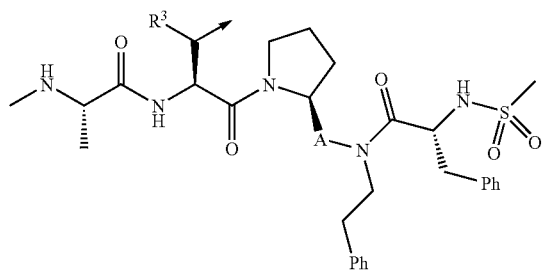<br>A = CH$_2$; R$^3$ = H or Me |
| 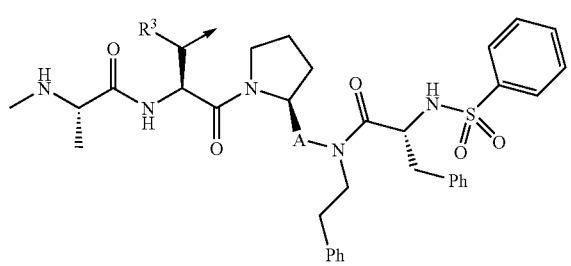<br>A = CH$_2$; R$^3$ = H or Me | 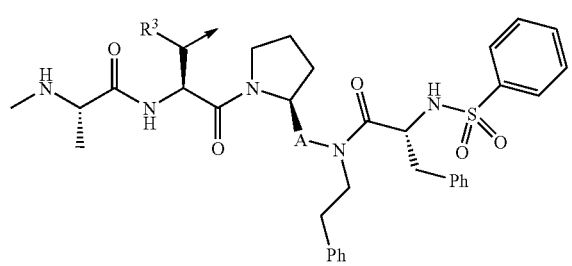<br>A = CH$_2$; R$^3$ = H or Me |
| 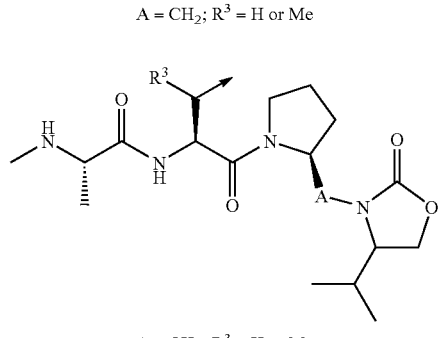<br>A = CH$_2$; R$^3$ = H or Me | 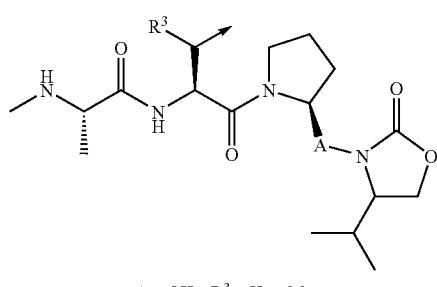<br>A = CH$_2$; R$^3$ = H or Me |

TABLE 2-continued
M1-BG-M2
Formula IA
BG is
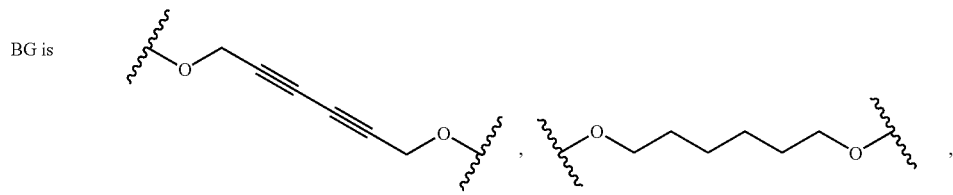
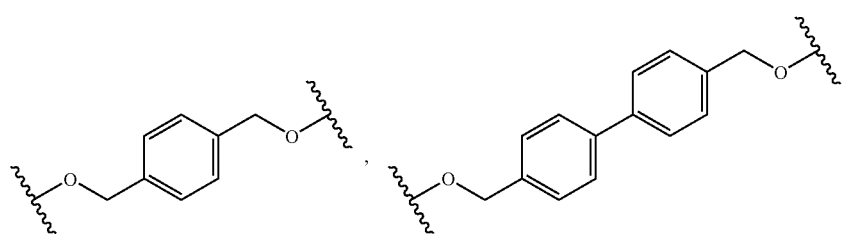
| M1 | M2 |
|---|---|
| 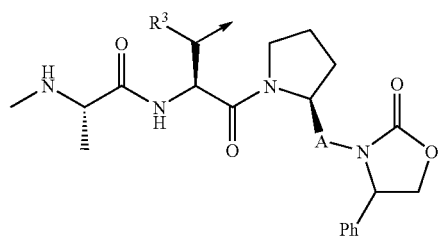<br>A = CH$_2$; R$^3$ = H or Me | 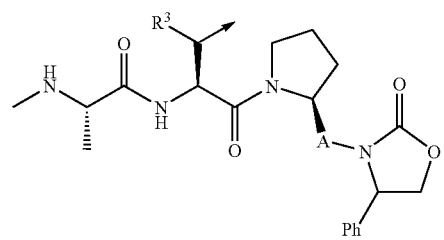<br>A = CH$_2$; R$^3$ = H or Me |
| 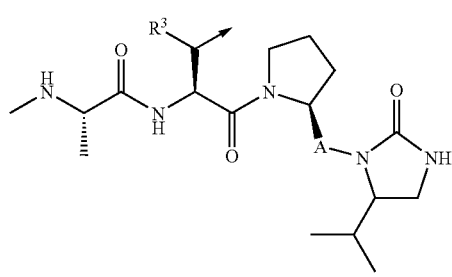<br>A = CH$_2$; R$^3$ = H or Me | 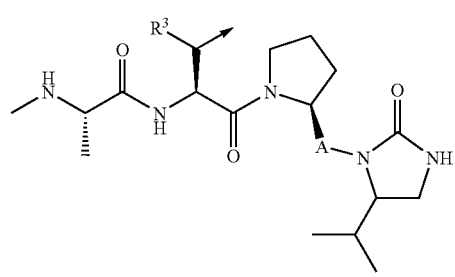<br>A = CH$_2$; R$^3$ = H or Me |
| 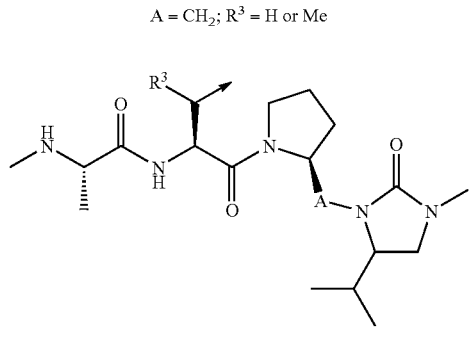<br>A = CH$_2$; R$^3$ = H or Me | 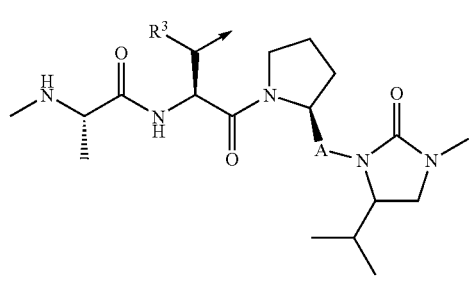<br>A = CH$_2$; R$^3$ = H or Me |

TABLE 2-continued
M1-BG-M2
Formula IA
BG is 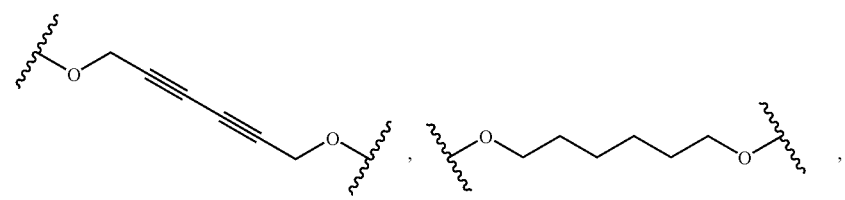
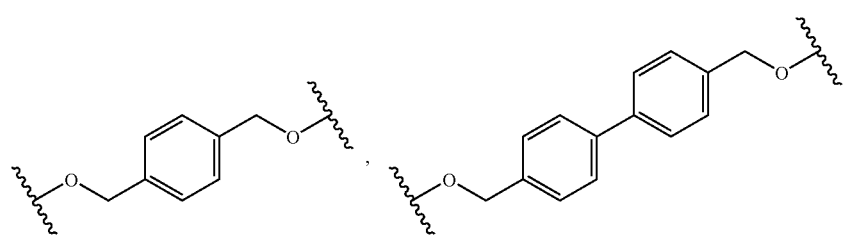
| M1 | M2 |
|---|---|
| 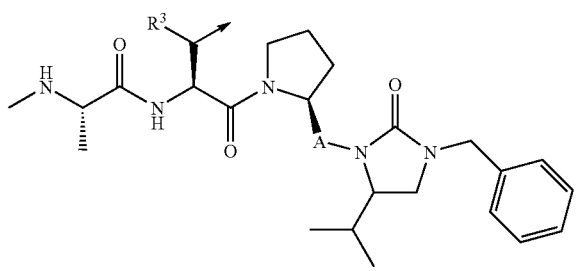 A = CH$_2$; R$^3$ = H or Me | 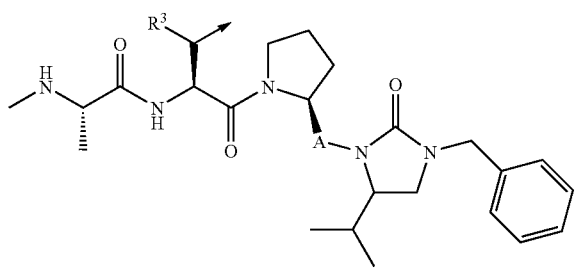 A = CH$_2$; R$^3$ = H or Me |
| 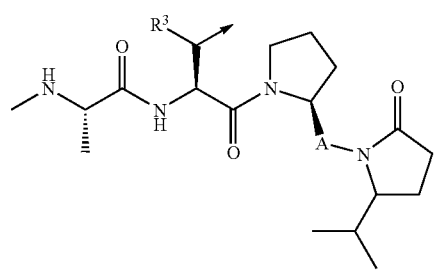 A = CH$_2$; R$^3$ = H or Me | 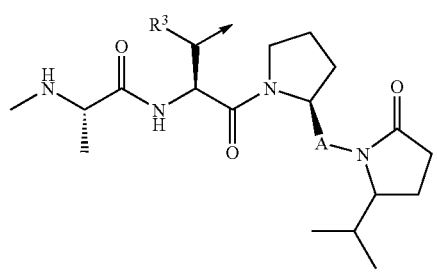 A = CH$_2$; R$^3$ = H or Me |
| 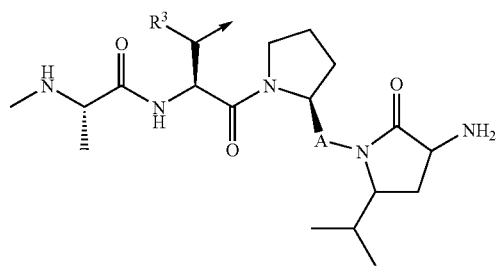 A = CH$_2$; R$^3$ = H or Me | 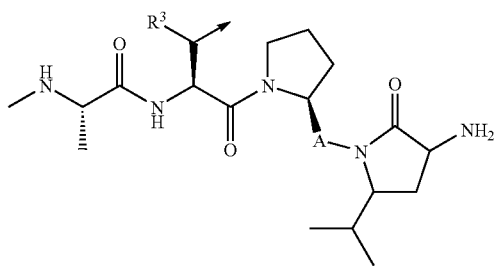 A = CH$_2$; R$^3$ = H or Me |

TABLE 3
$$M1-B-BG-B^1-M2 \quad \text{Formula 1B}$$
BG is:
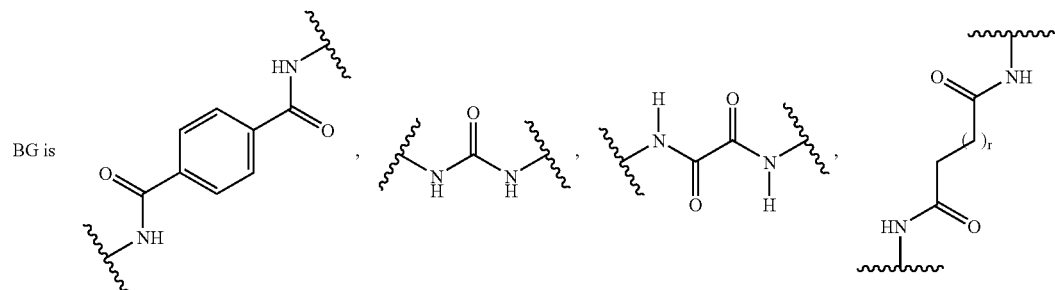
| M1 | M2 |
|---|---|
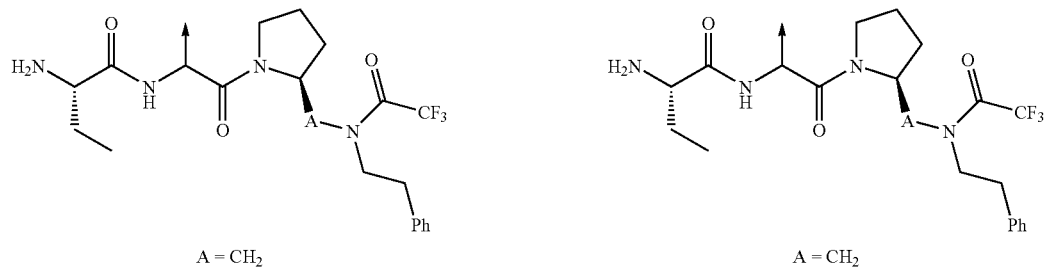
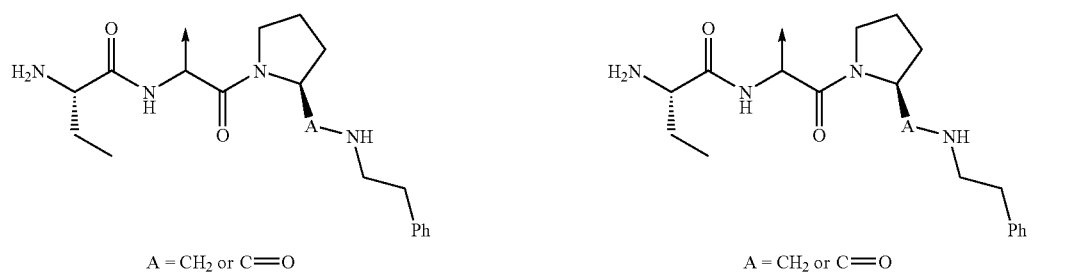
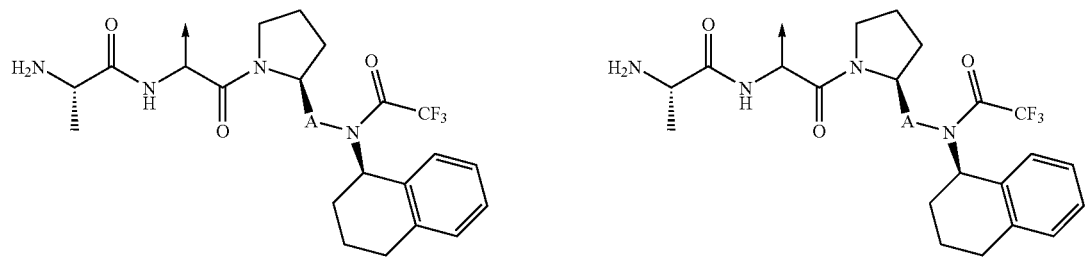
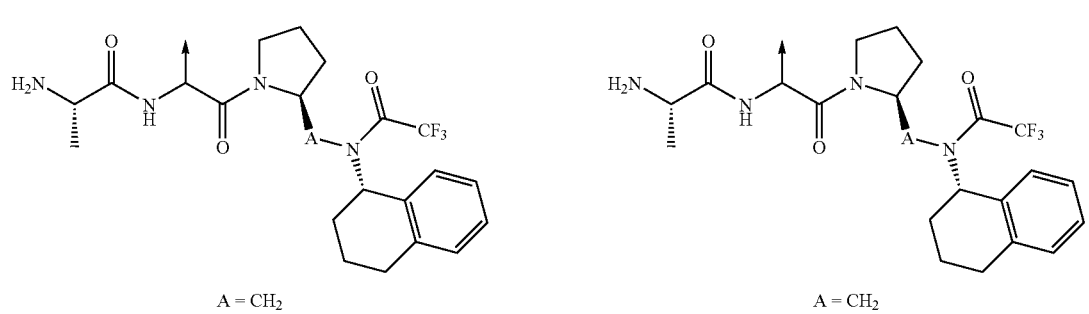

TABLE 3-continued
Formula 1B
M1—B—BG—B¹—M2
BG is
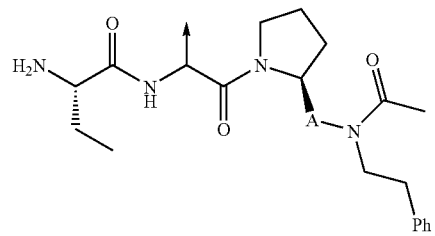
| M1 | M2 |
|---|---|
| 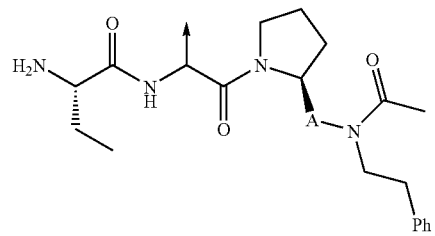 A = CH$_2$ | 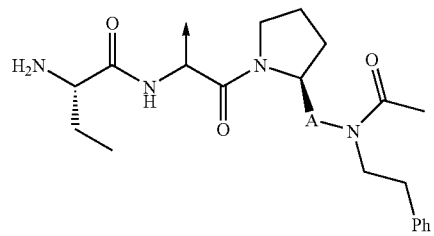 A = CH$_2$ |
| A = CH$_2$ | A = CH$_2$ |
| 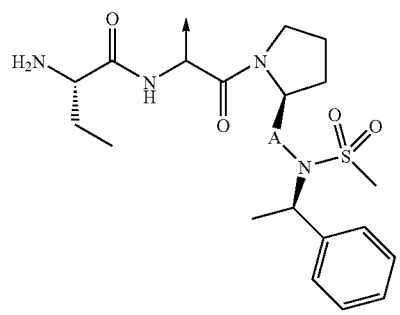 A = CH$_2$ | A = CH$_2$ |
| 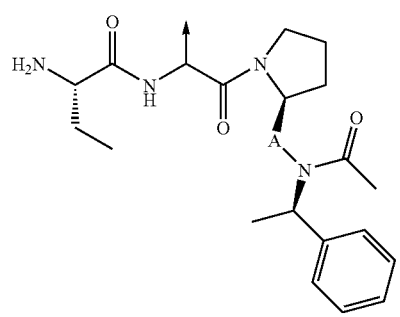 A = CH$_2$ | A = CH$_2$ |

TABLE 3-continued
Formula 1B
M1—B—BG—B¹—M2
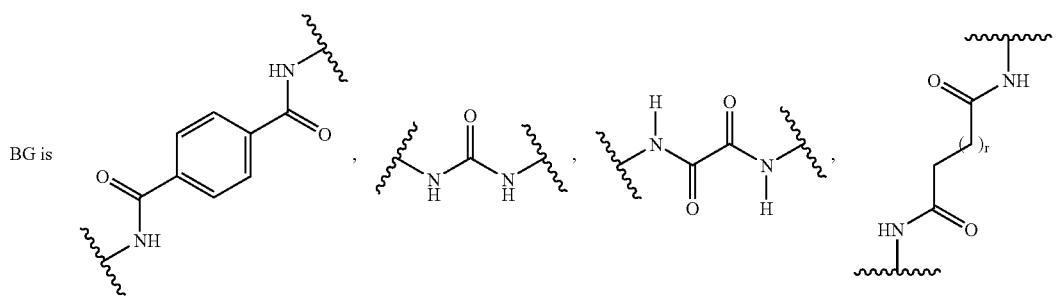
| M1 | M2 |
|---|---|
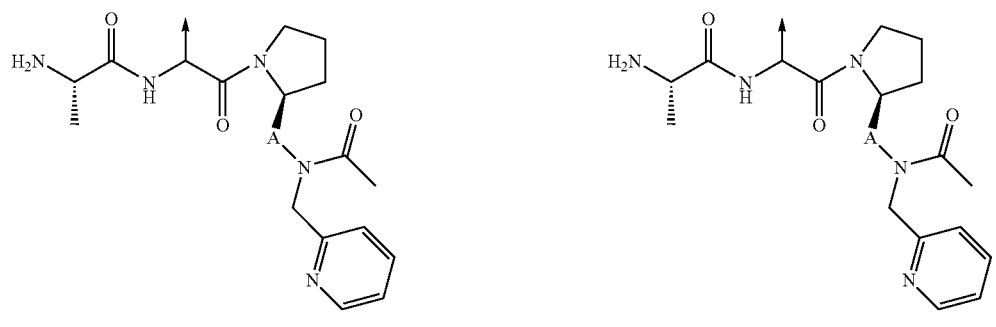
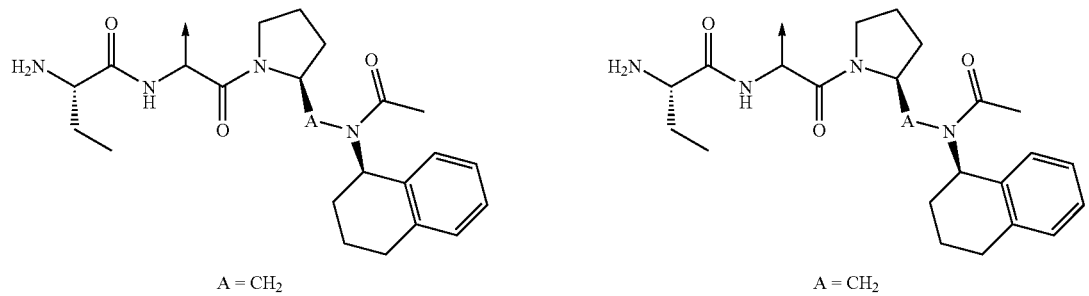
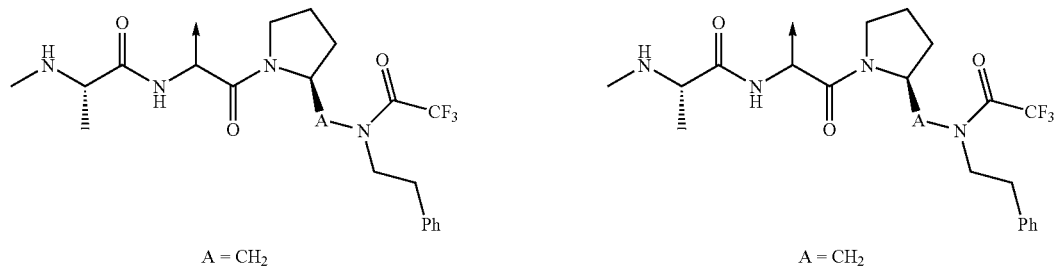

TABLE 3-continued

Formula 1B

M1—B—BG—B¹—M2

BG is: [structures shown]

| M1 | M2 |
|---|---|
| [structure] A = CH₂ | [structure] A = CH₂ |
| [structure] A = CH₂ | [structure] A = CH₂ |
| [structure] A = CH₂ | [structure] A = CH₂ |

TABLE 3-continued
$$M1-B-BG-B^1-M2 \quad \text{Formula 1B}$$
BG is
, , , 
| M1 | M2 |
|---|---|
| 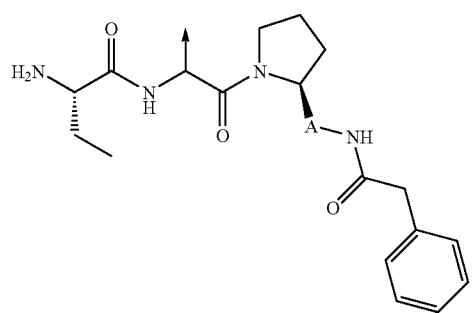<br>A = CH$_2$ | 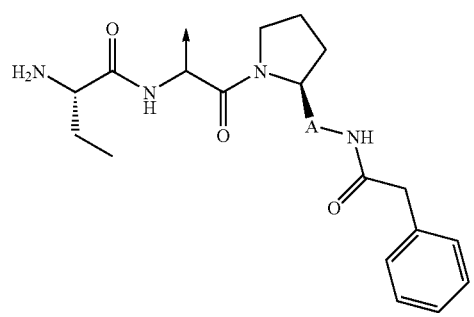<br>A = CH$_2$ |
| 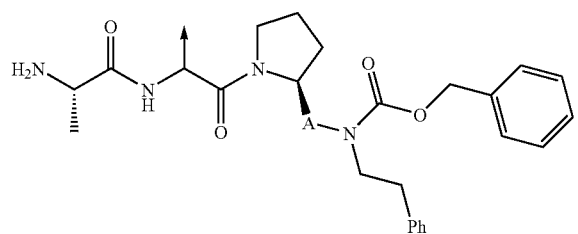<br>A = CH$_2$ | 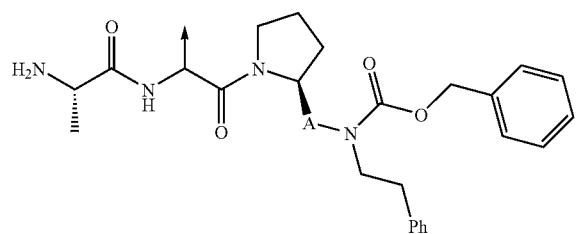<br>A = CH$_2$ |
| 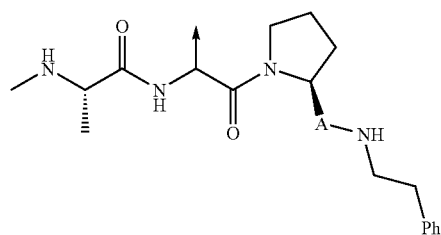<br>A = CH$_2$ or C=O | 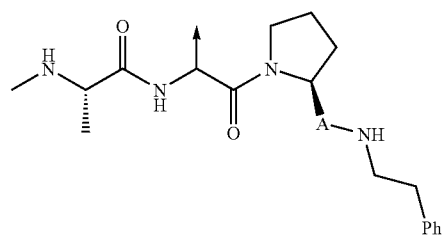<br>A = CH$_2$ or C=O |
| 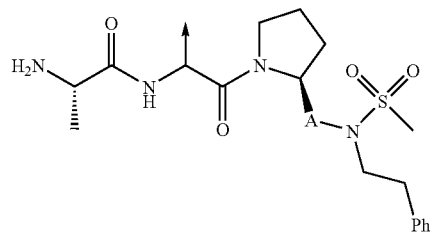<br>A = CH$_2$ | 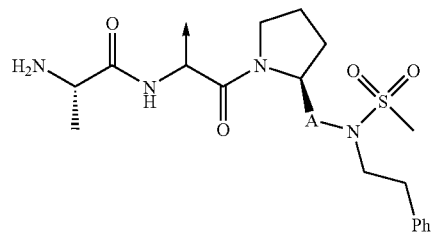<br>A = CH$_2$ |

TABLE 3-continued
Formula 1B
M1—B—BG—B¹—M2
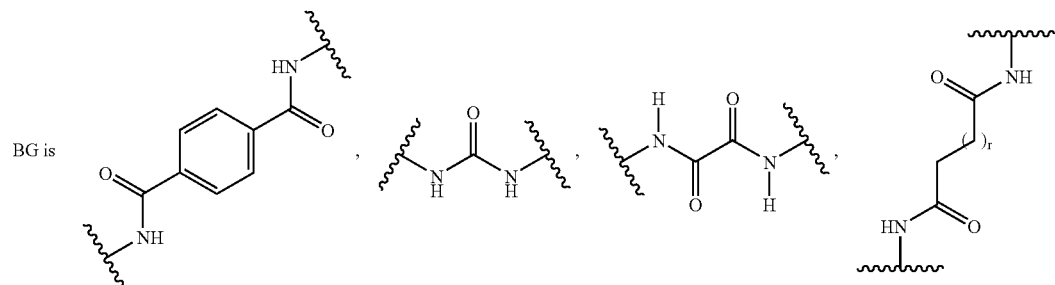
BG is
| M1 | M2 |
| --- | --- |
| 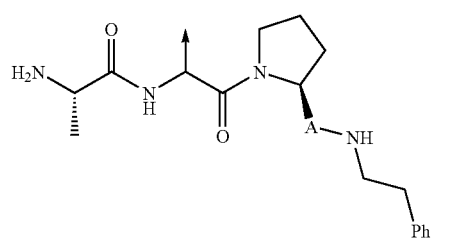<br>A = CH₂ or C=O | 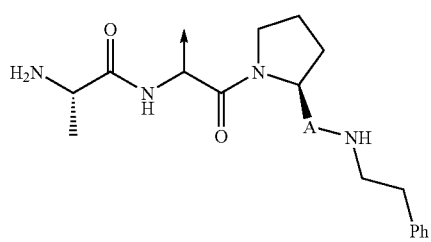<br>A = CH₂ or C=O |
| 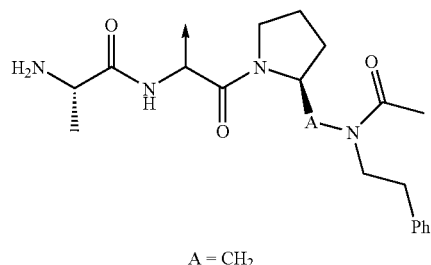<br>A = CH₂ | 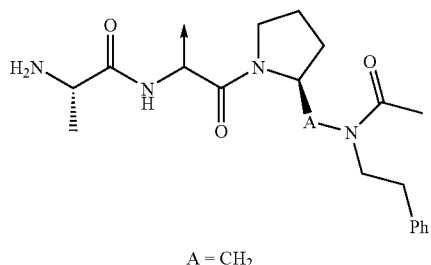<br>A = CH₂ |
| 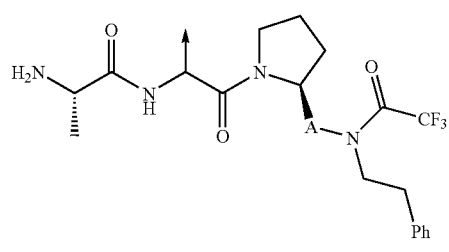<br>A = CH₂ | 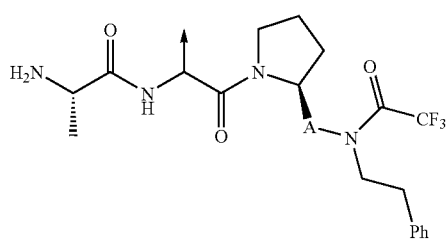<br>A = CH₂ |
| 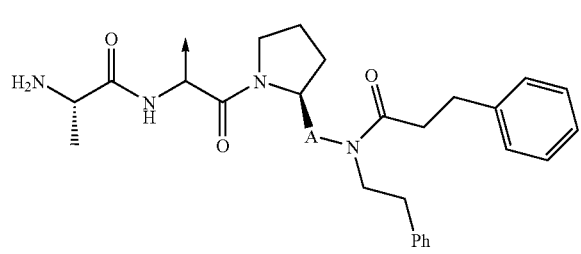<br>A = CH₂ | 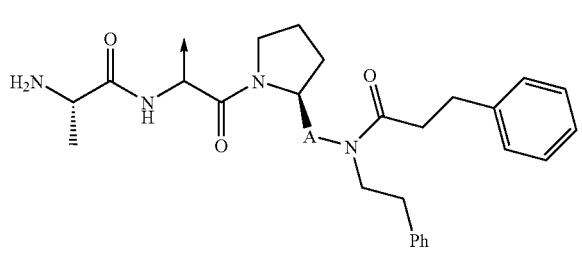<br>A = CH₂ |

TABLE 3-continued
Formula 1B
M1—B—BG—B¹—M2
BG is 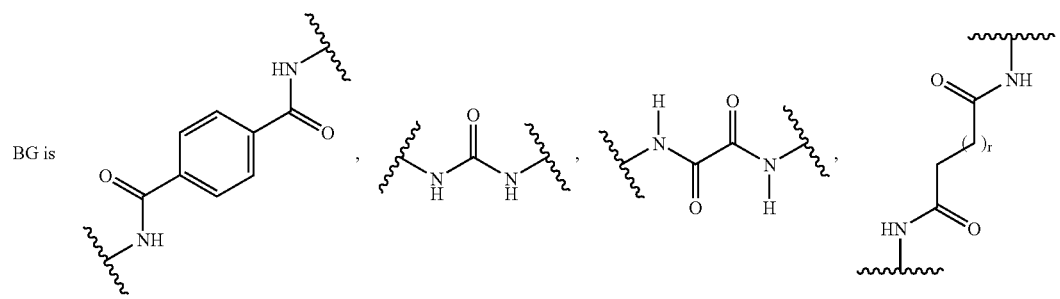
| M1 | M2 |
|---|---|
| 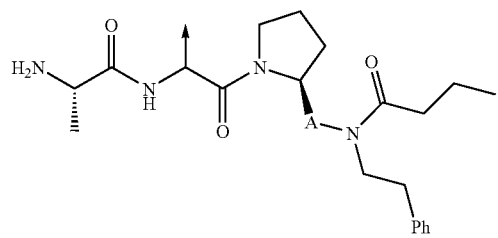<br>A = CH₂ | 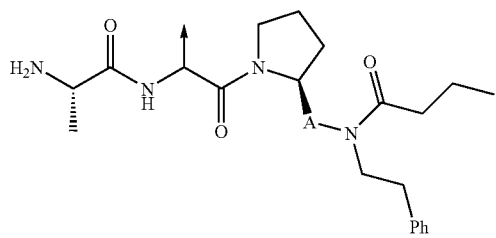<br>A = CH₂ |
| 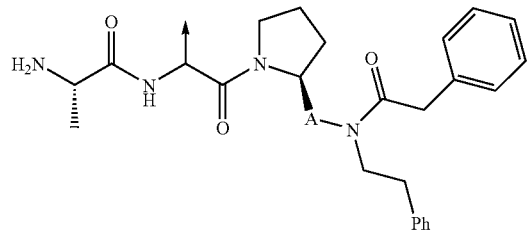<br>A = CH₂ | 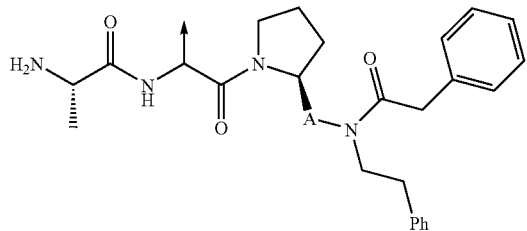<br>A = CH₂ |
| 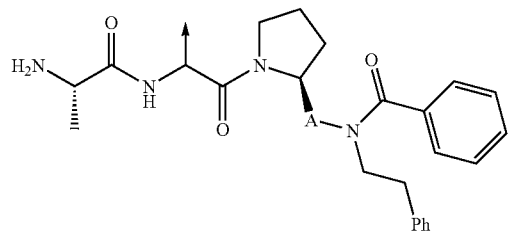<br>A = CH₂ | 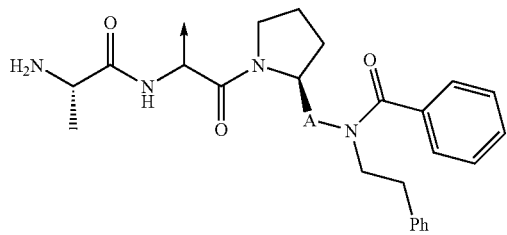<br>A = CH₂ |

TABLE 3-continued
Formula 1B
$$M1-B-BG-B^1-M2$$
BG is 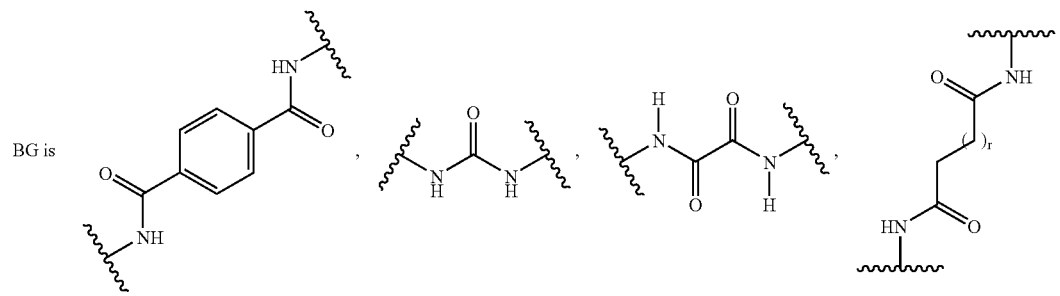
| M1 | M2 |
|---|---|
| 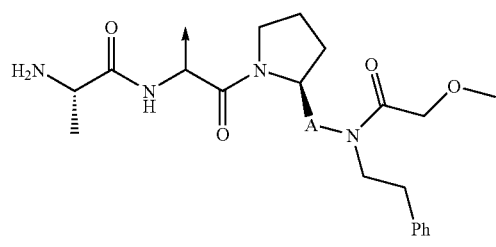<br>A = CH$_2$ | 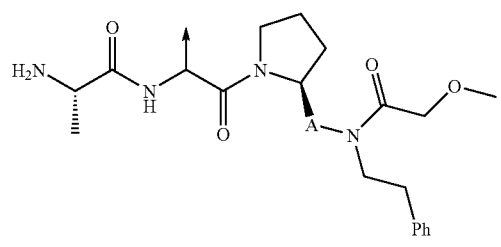<br>A = CH$_2$ |
| 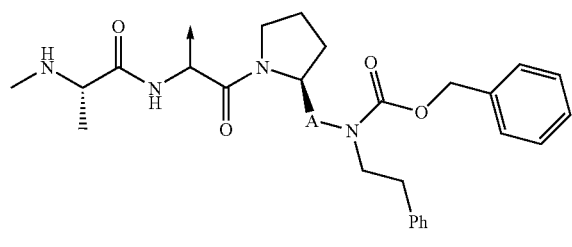<br>A = CH$_2$ | 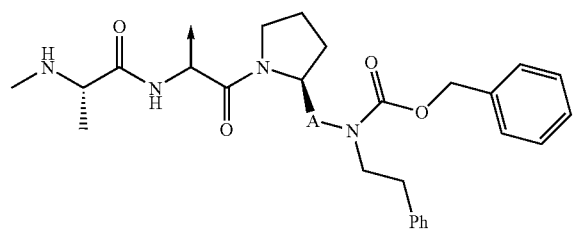<br>A = CH$_2$ |
| 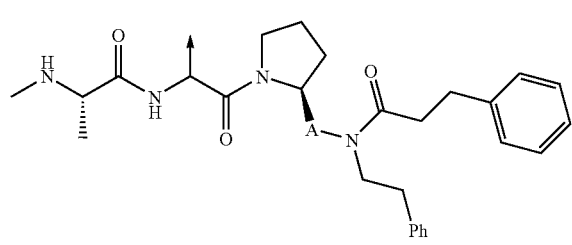<br>A = CH$_2$ | 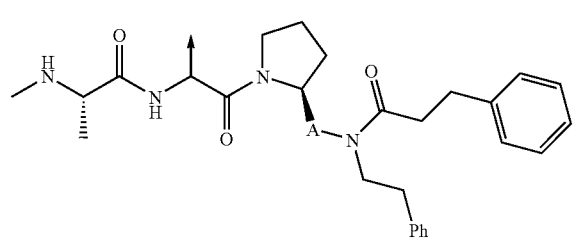<br>A = CH$_2$ |
| 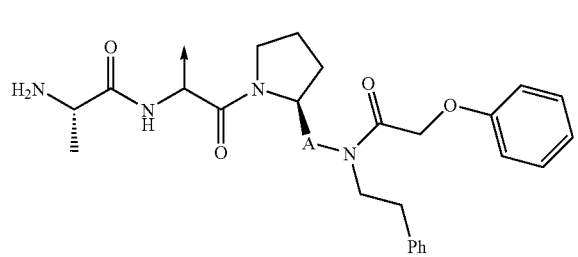<br>A = CH$_2$ | 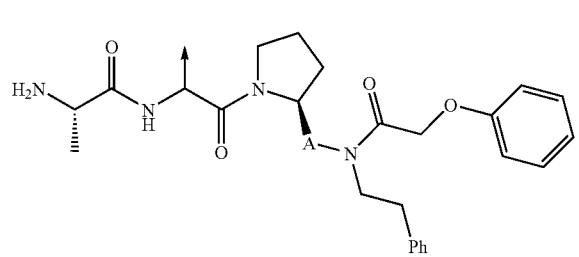<br>A = CH$_2$ |

TABLE 3-continued
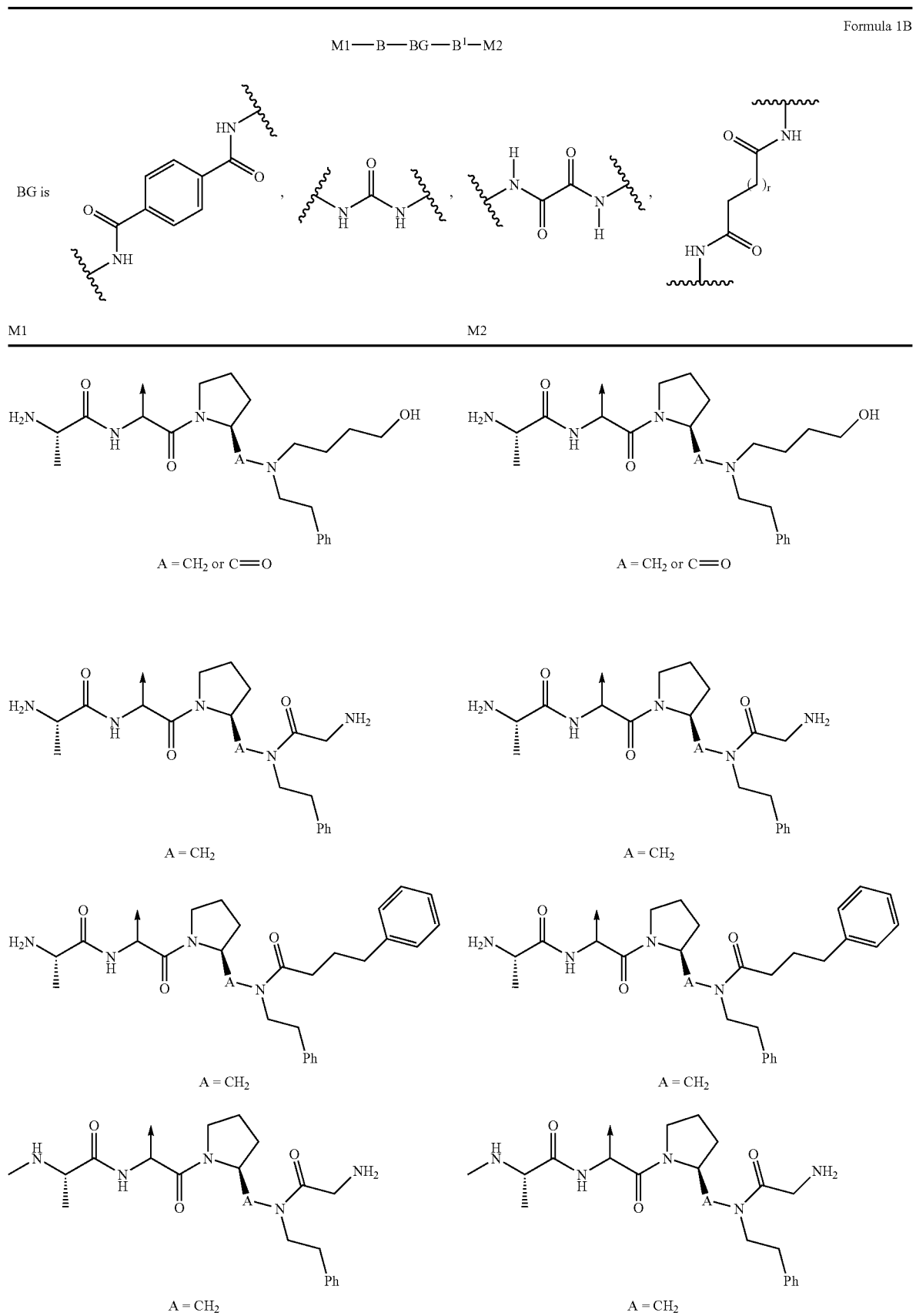

TABLE 3-continued
Formula 1B
M1—B—BG—B¹—M2
BG is 
| M1 | M2 |
|---|---|
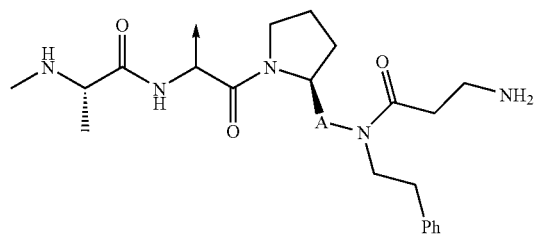
A = CH₂
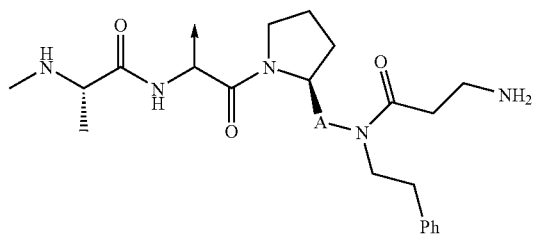
A = CH₂
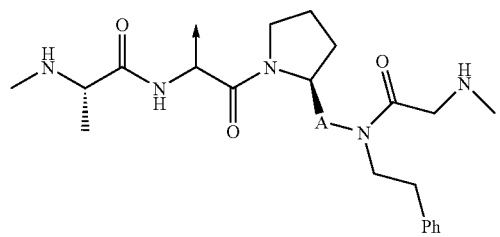
A = CH₂
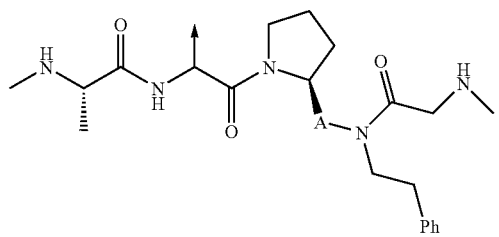
A = CH₂
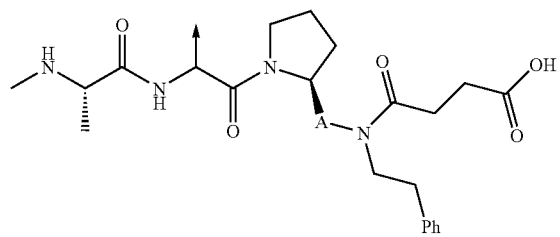
A = CH₂
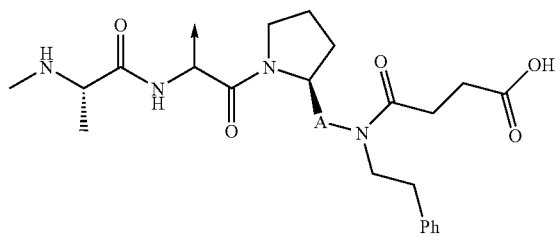
A = CH₂
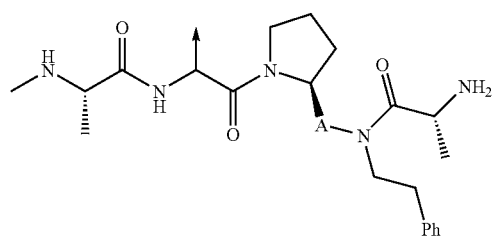
A = CH₂
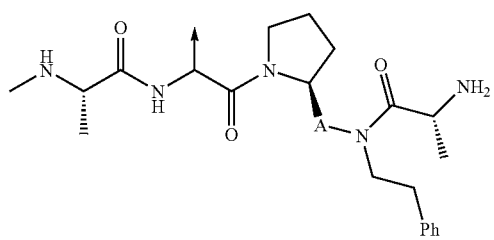
A = CH₂

TABLE 3-continued
Formula 1B
M1—B—BG—B¹—M2
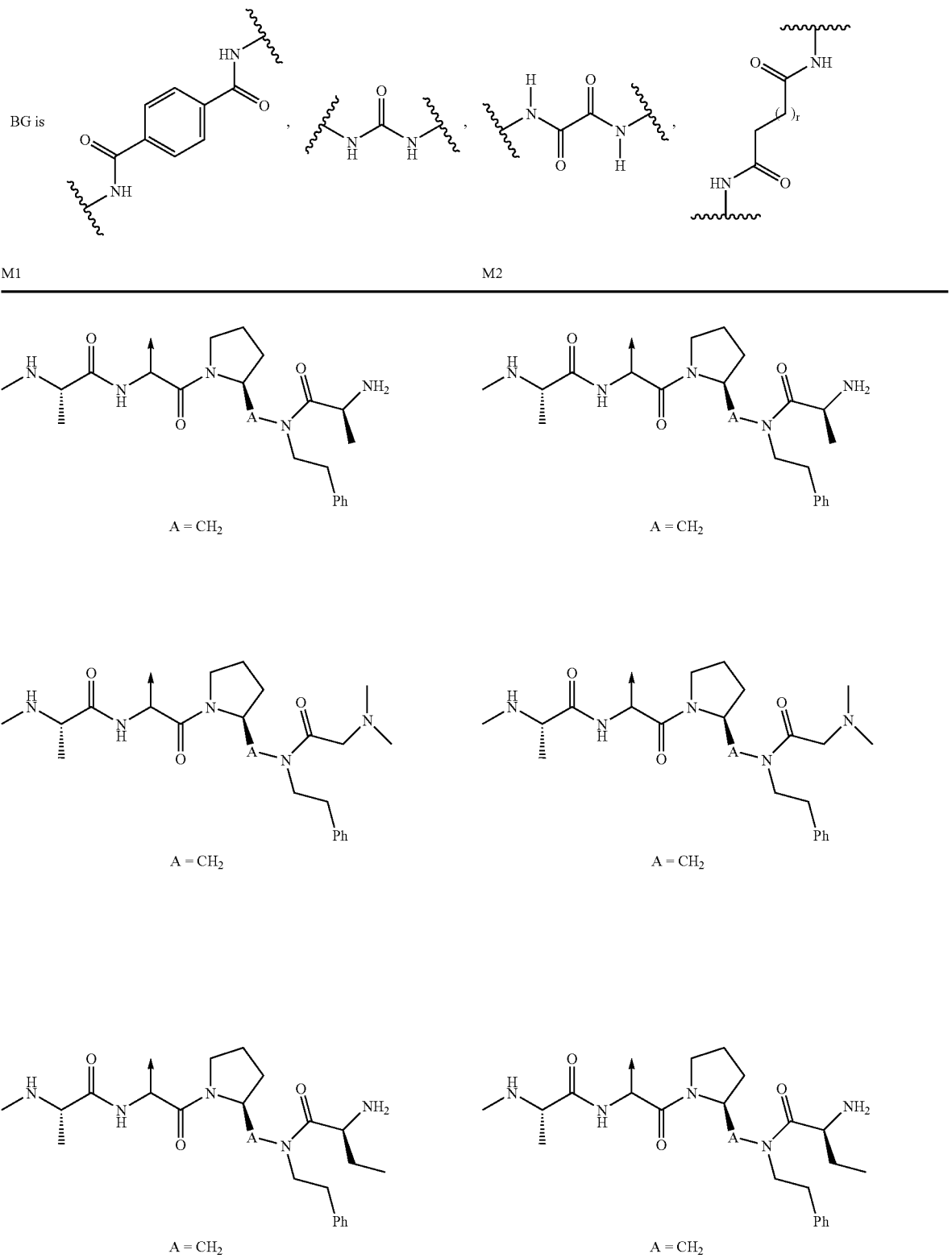

TABLE 3-continued
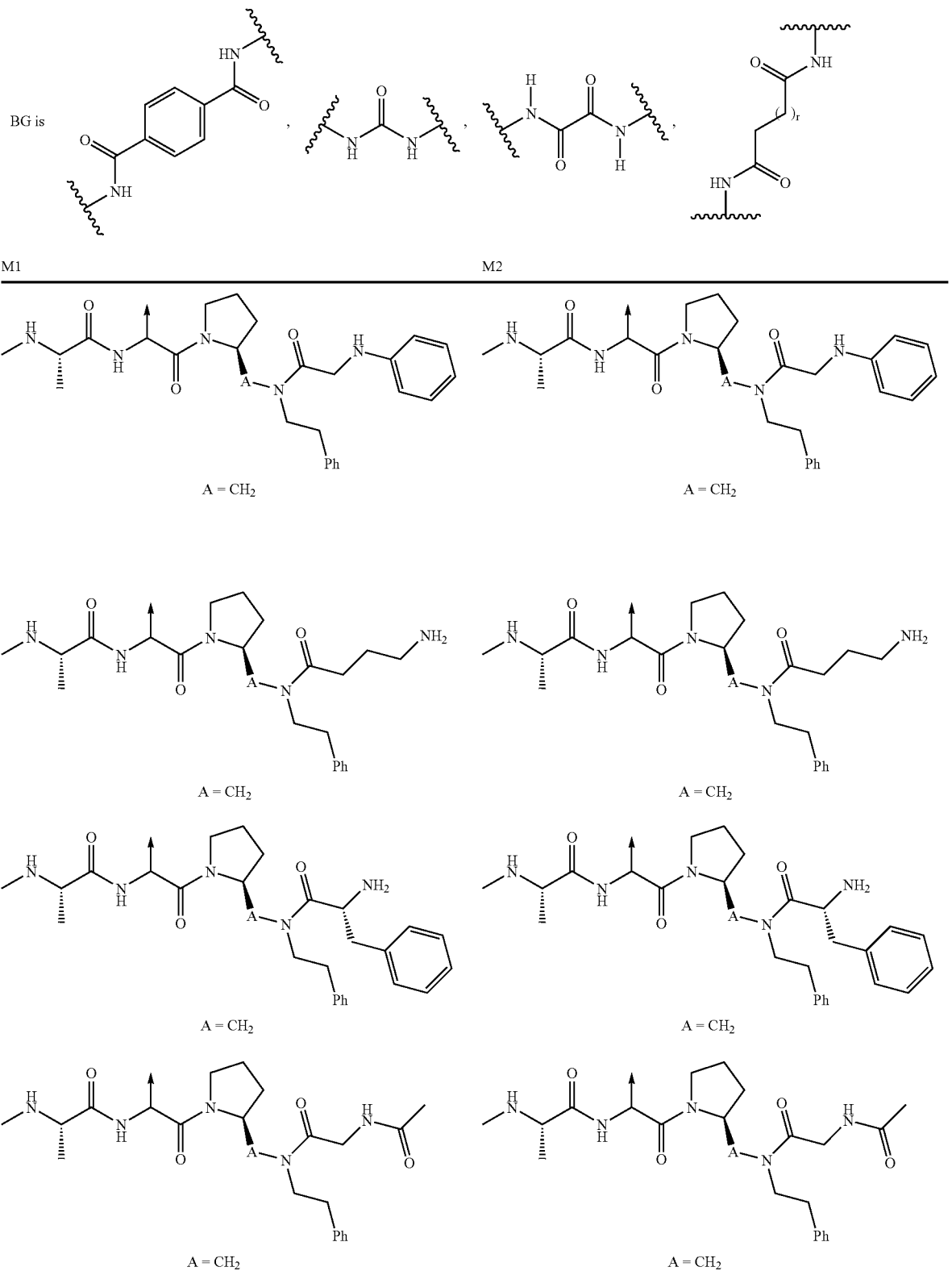

TABLE 3-continued
Formula 1B
M1—B—BG—B¹—M2
BG is 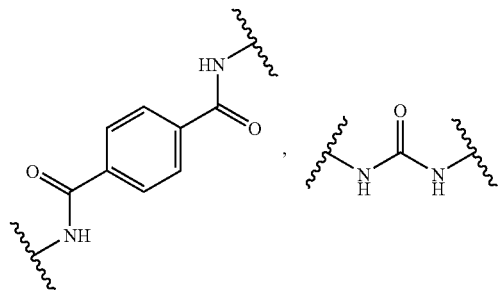 , 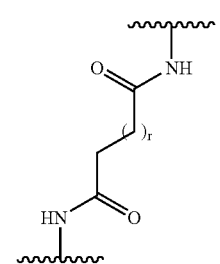
| M1 | M2 |
|---|---|
| 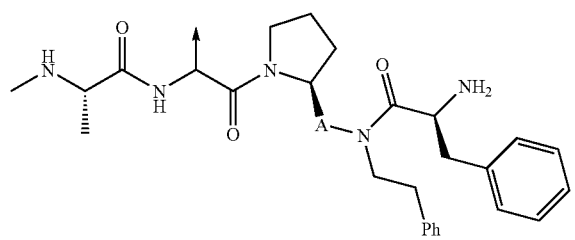<br>A = CH₂ | 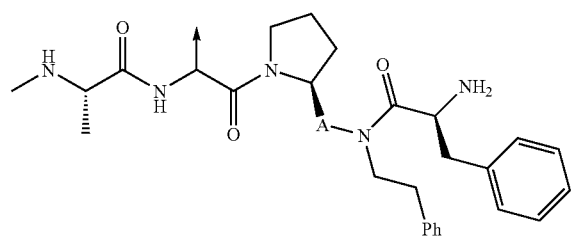<br>A = CH₂ |
| | 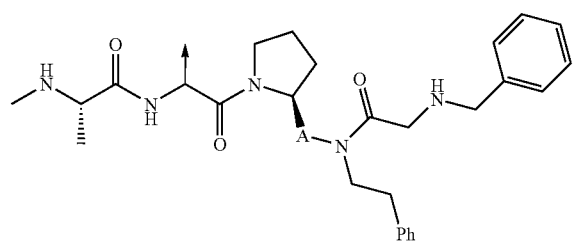<br>A = CH₂ |
| 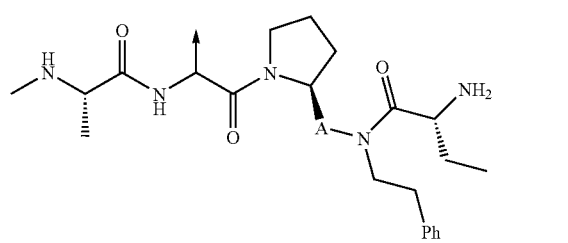<br>A = CH₂ | 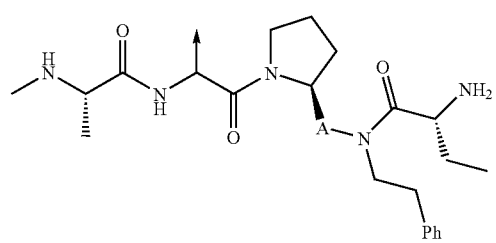<br>A = CH₂ |
| 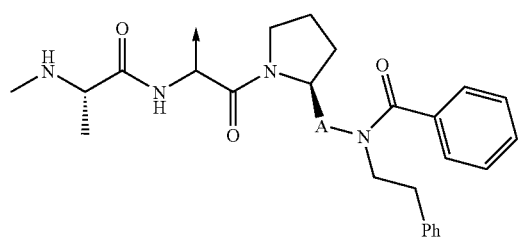<br>A = CH₂ | 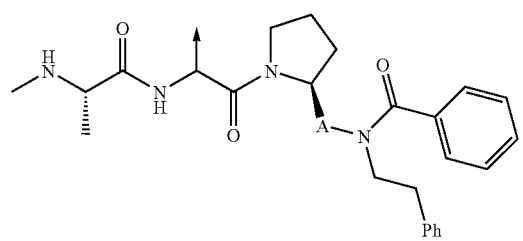<br>A = CH₂ |

TABLE 3-continued
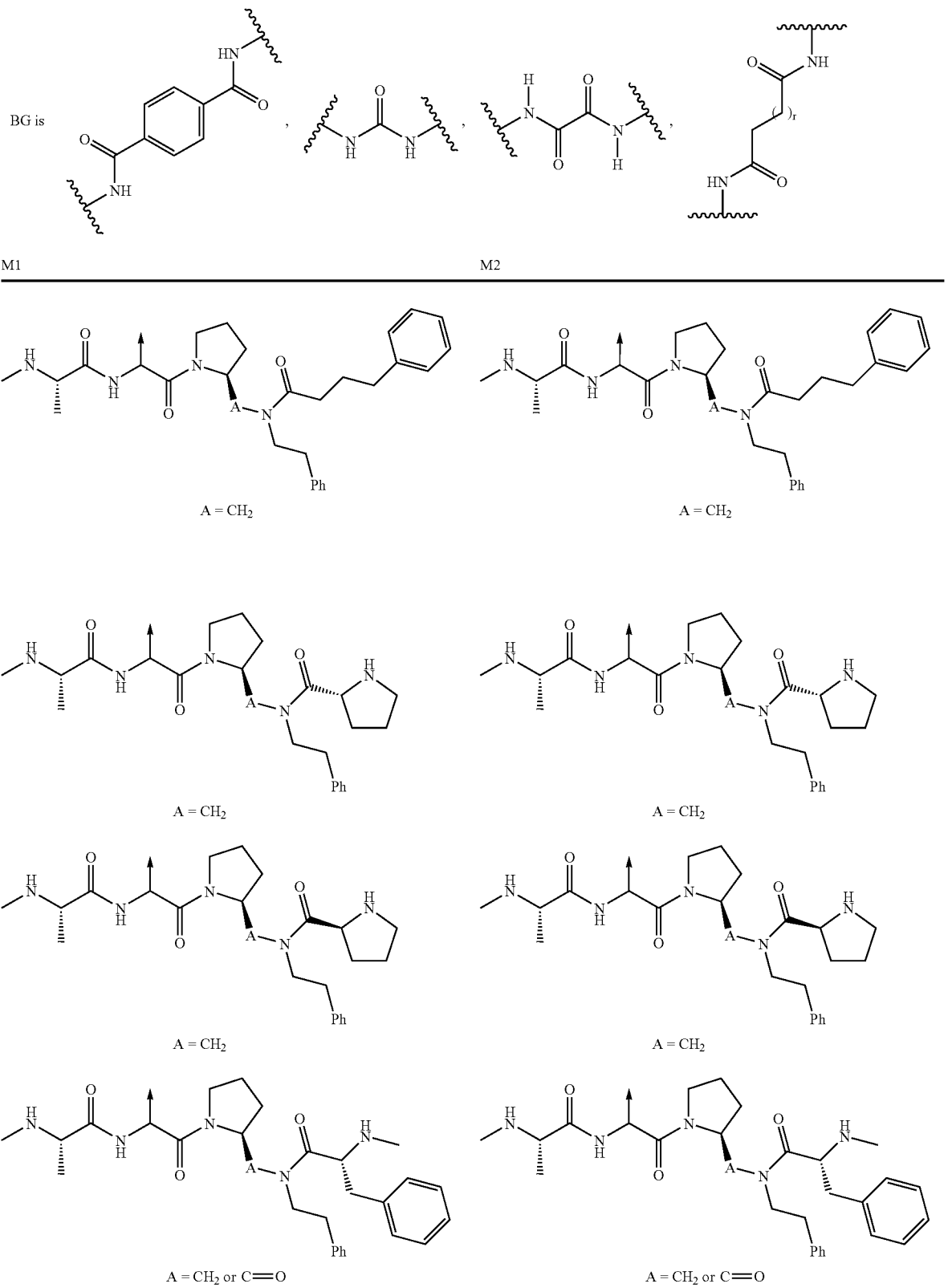

TABLE 3-continued
$$M1-B-BG-B^1-M2 \quad \text{Formula 1B}$$
BG is 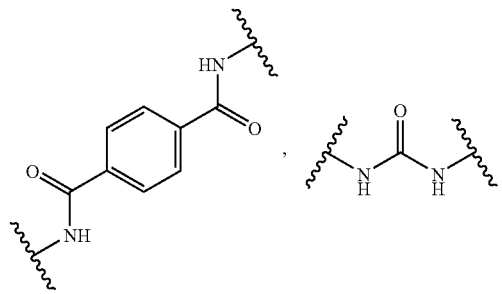 , 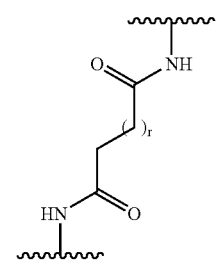
| M1 | M2 |
|---|---|
| 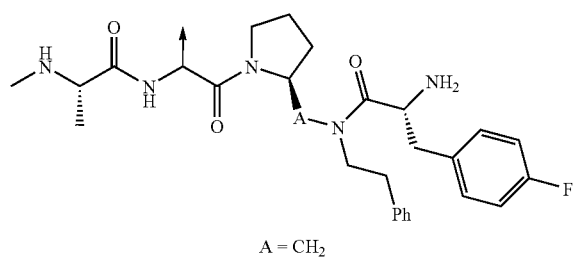<br>A = CH₂ | 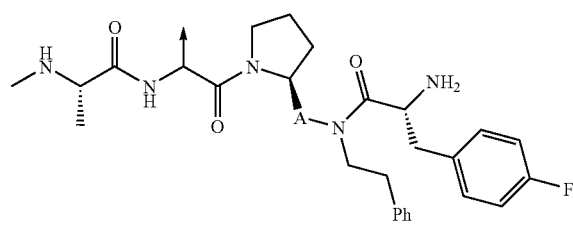<br>A = CH₂ |
| 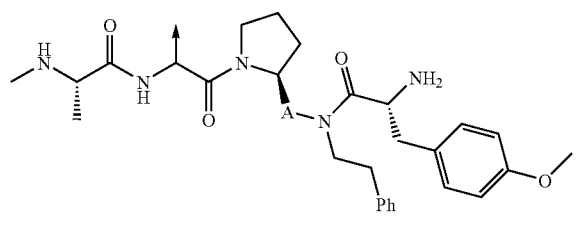<br>A = CH₂ | 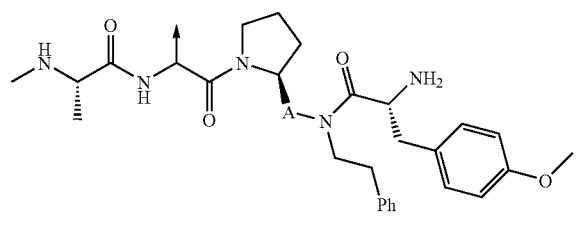<br>A = CH₂ |
| 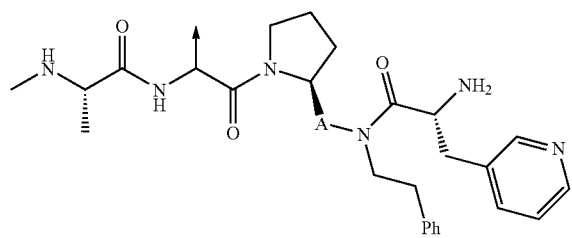<br>A = CH₂ | 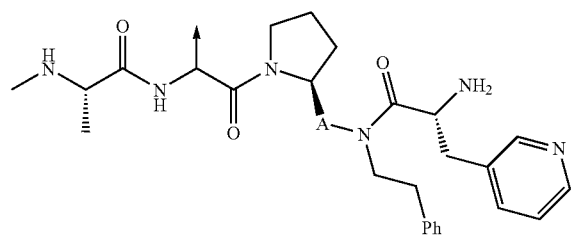<br>A = CH₂ |
| 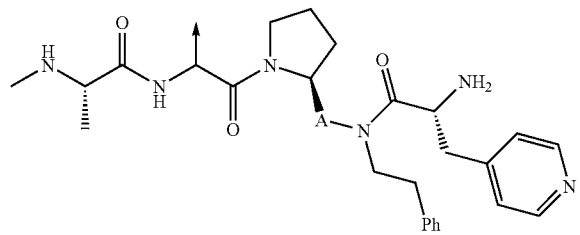<br>A = CH₂ | 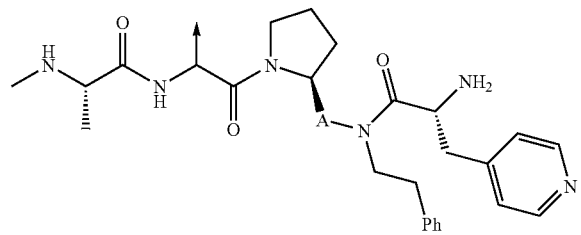<br>A = CH₂ |

TABLE 3-continued
Formula 1B
$$M1-B-BG-B^1-M2$$
BG is 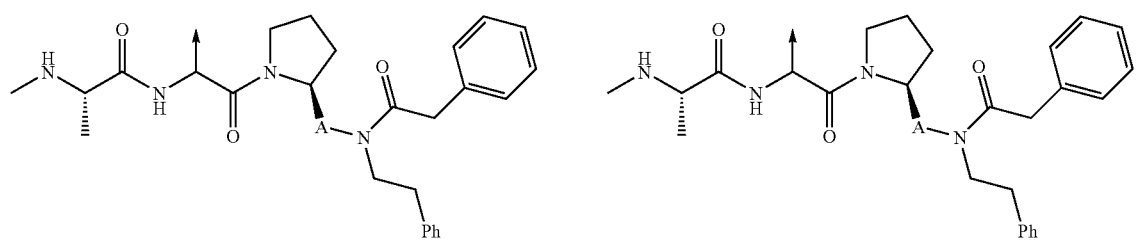
| M1 | M2 |
|---|---|
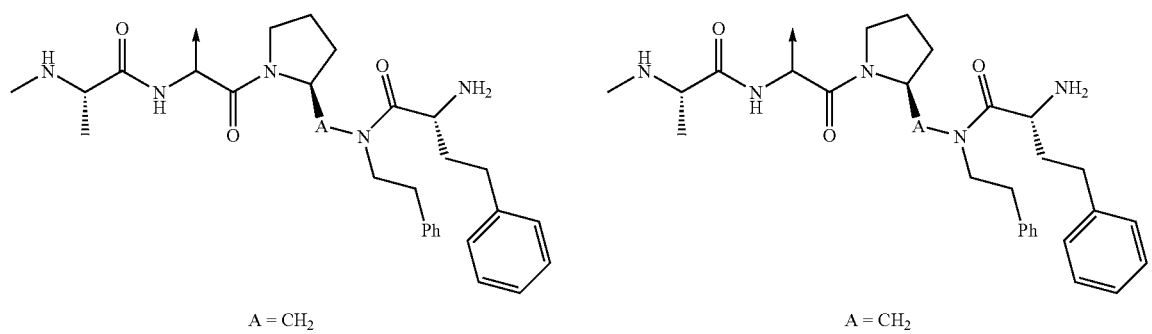
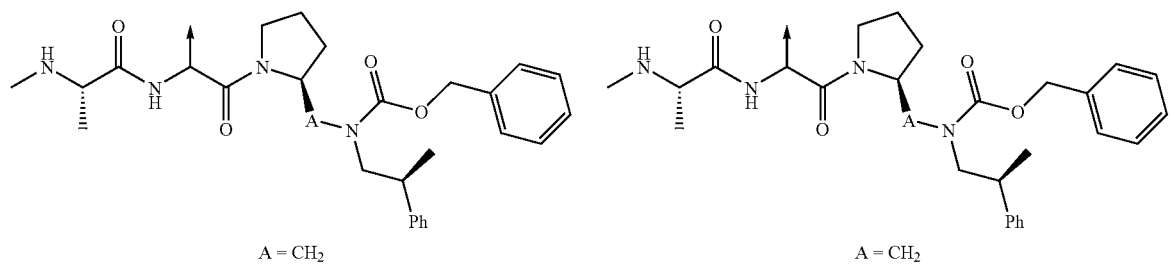
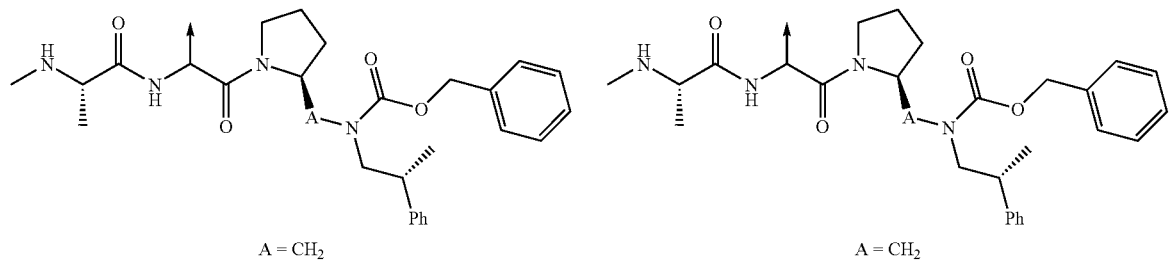

TABLE 3-continued
Formula 1B
M1—B—BG—B¹—M2
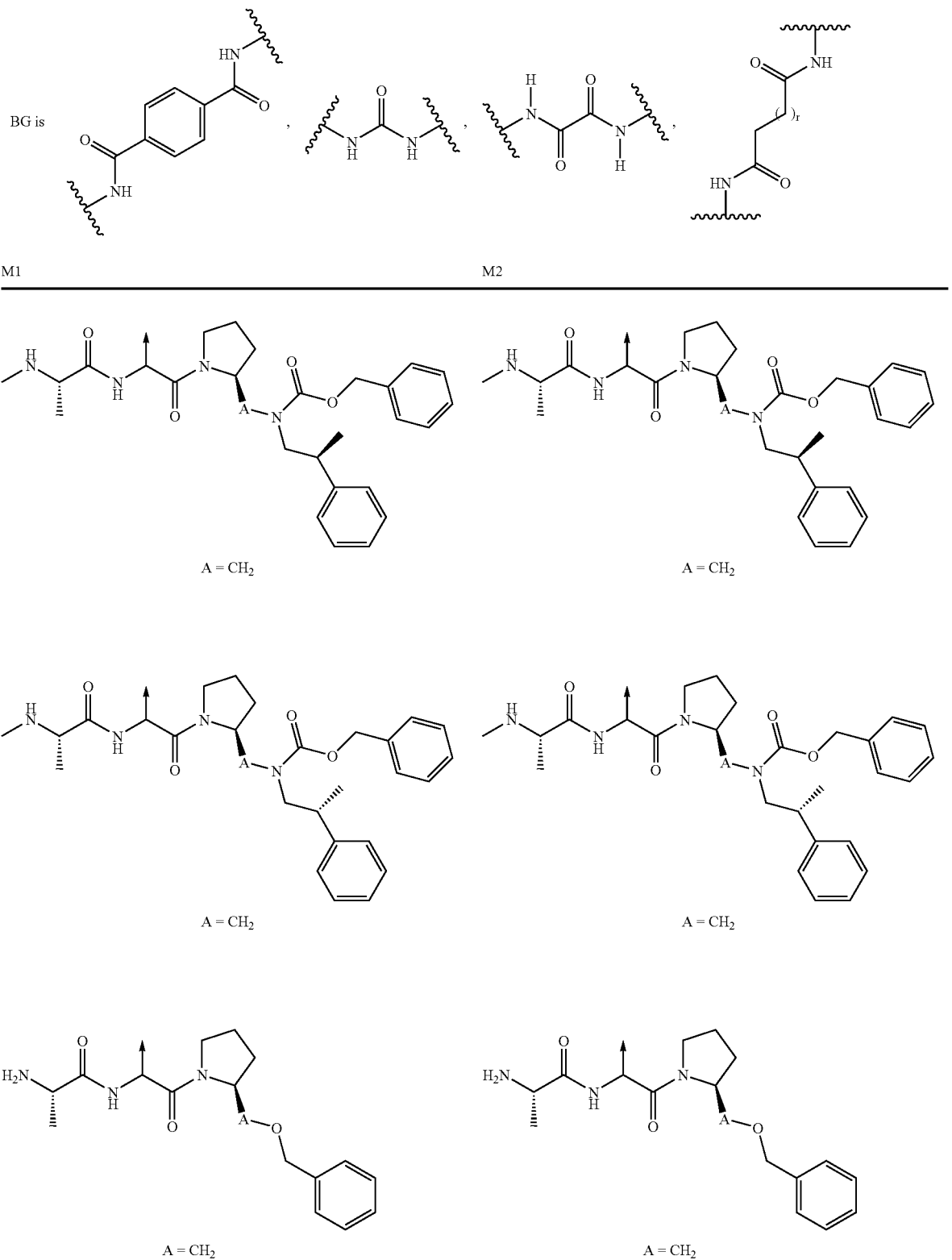

TABLE 3-continued
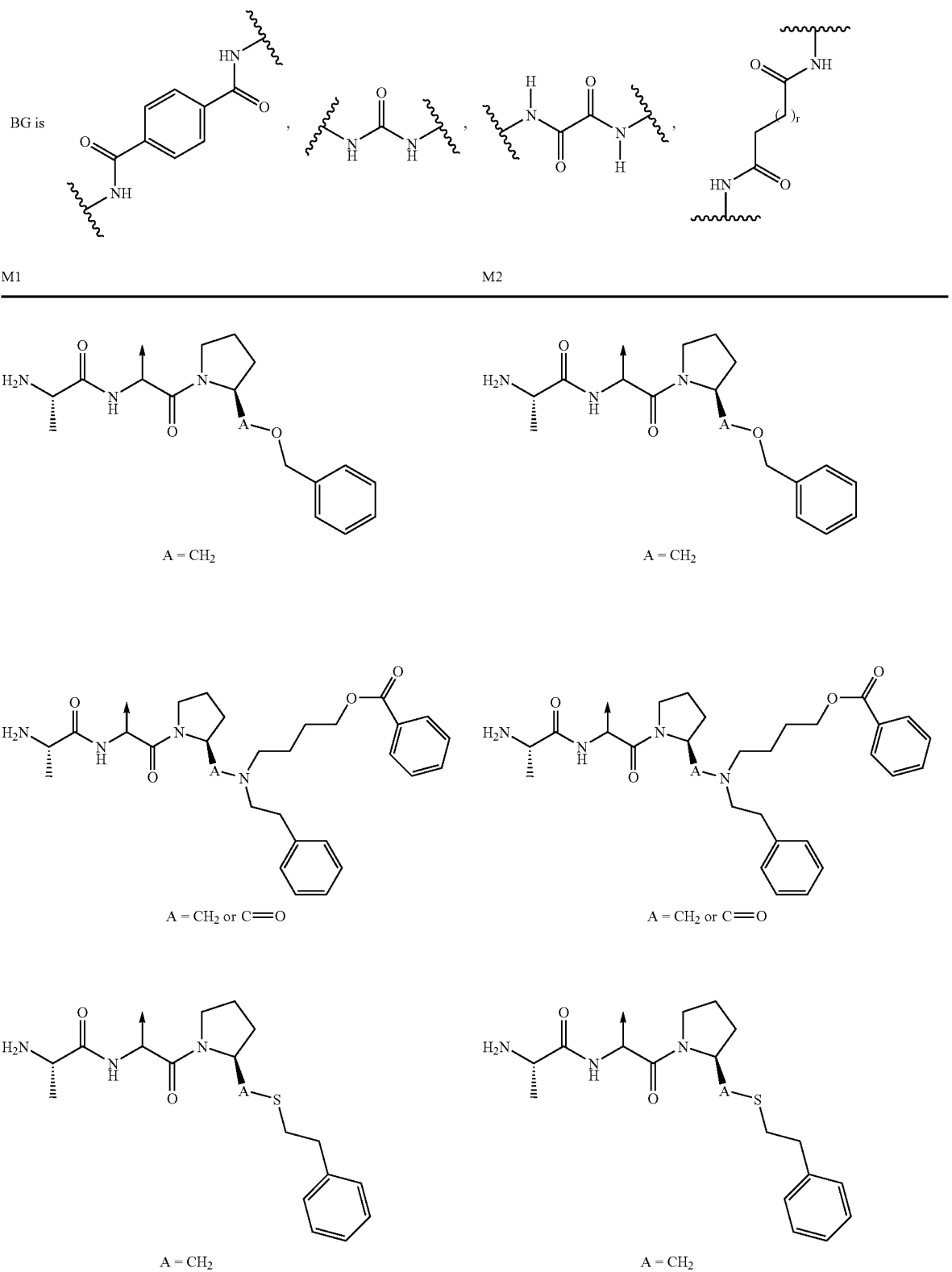

TABLE 3-continued
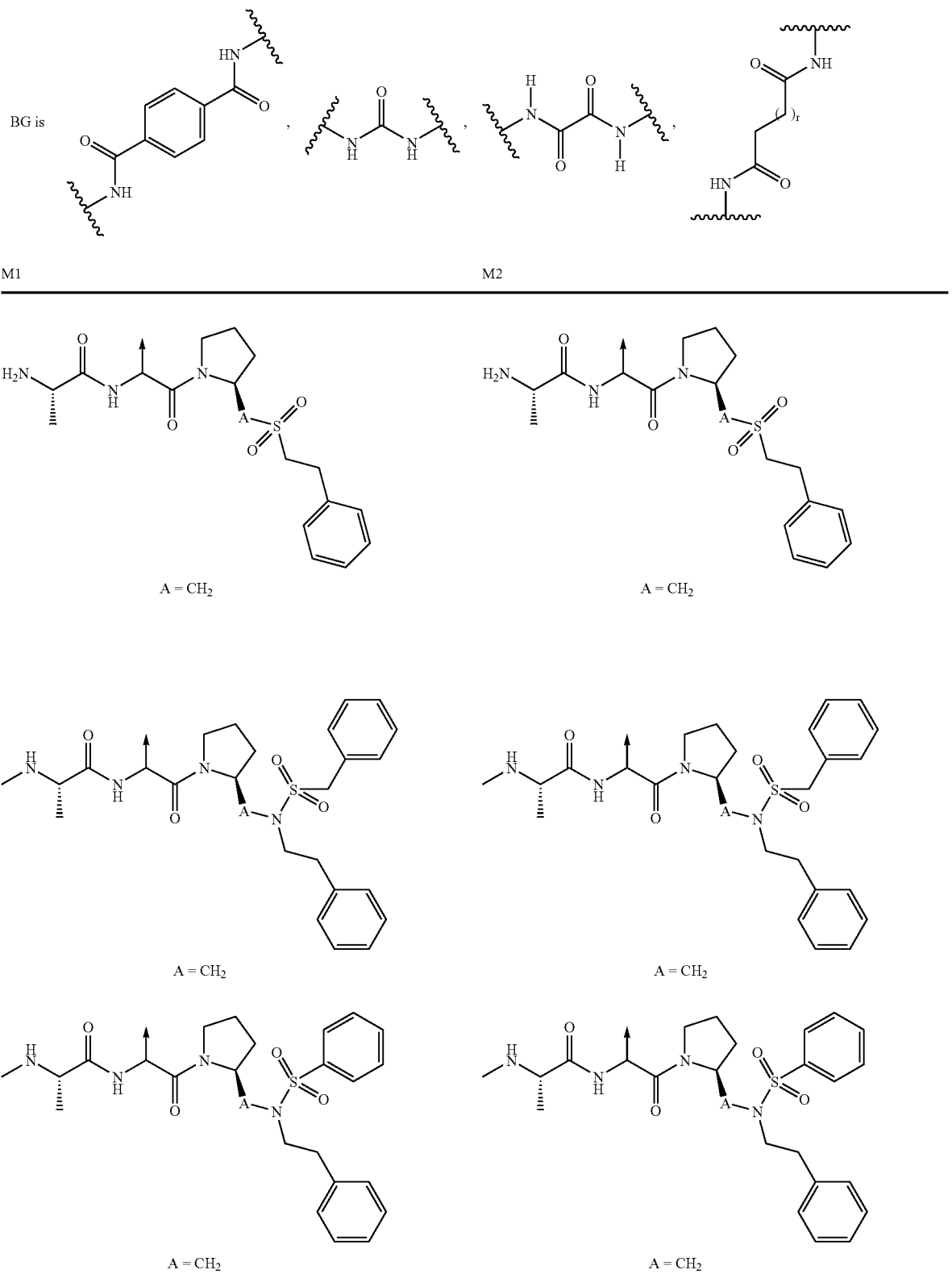

TABLE 3-continued
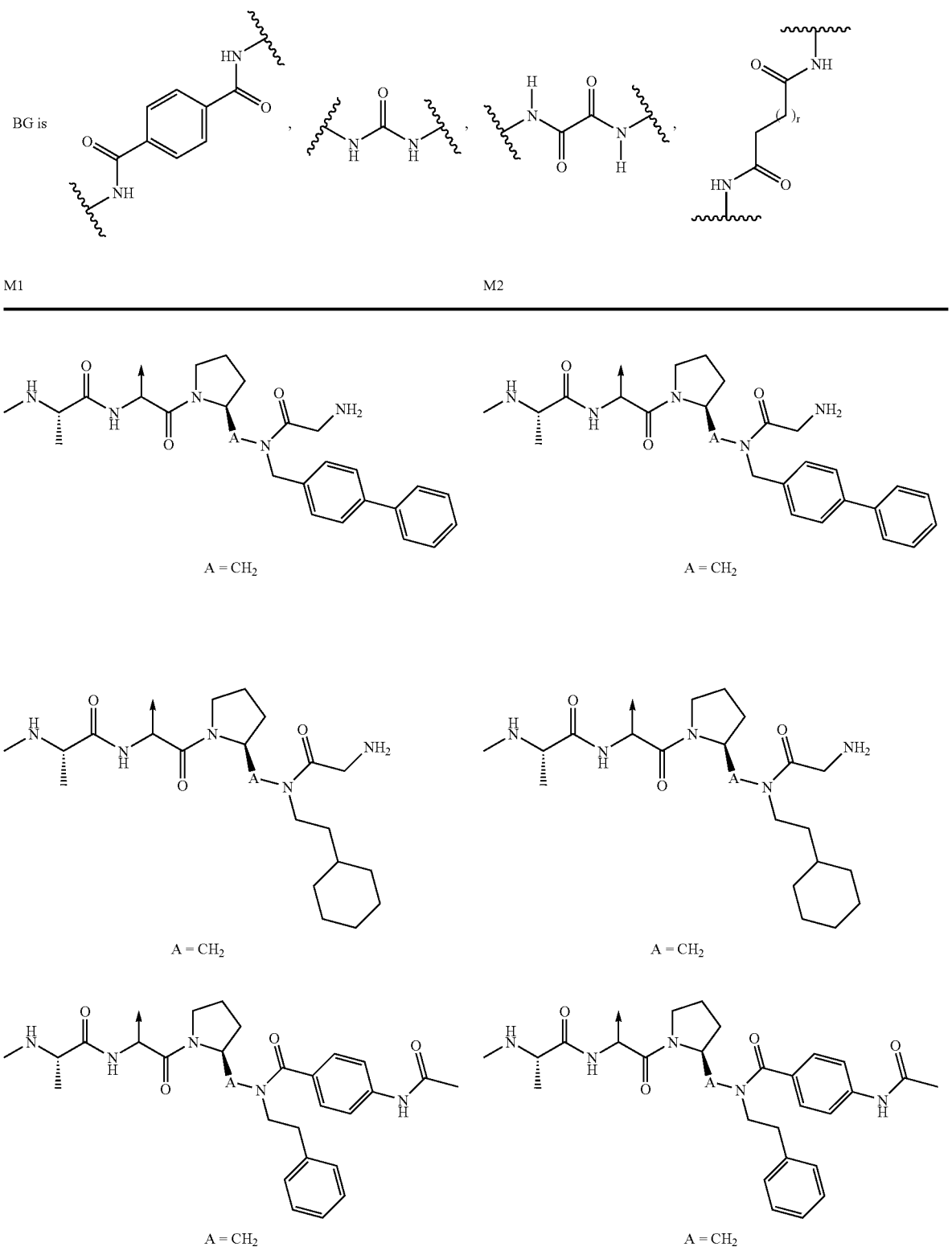

TABLE 3-continued
Formula 1B
M1—B—BG—B¹—M2
BG is 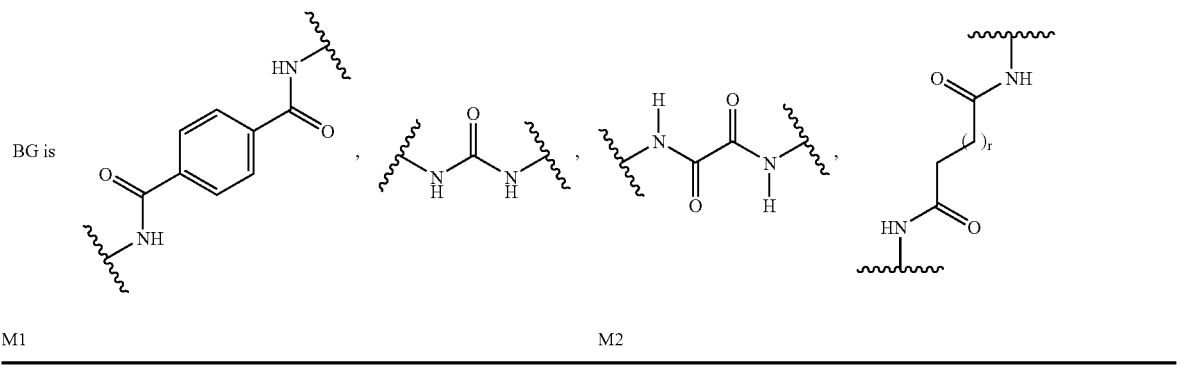
| M1 | M2 |
|---|---|
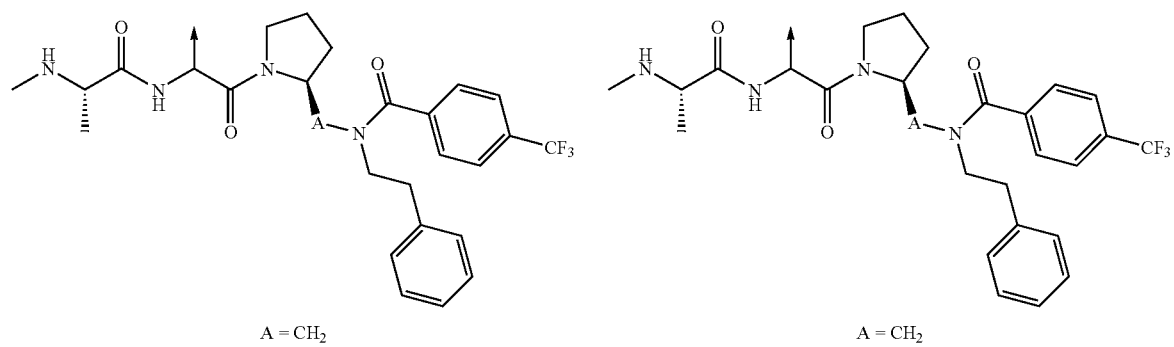
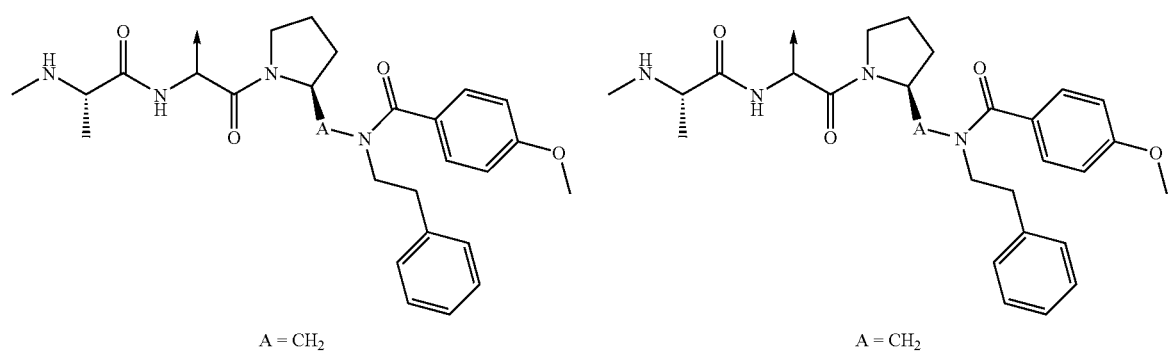
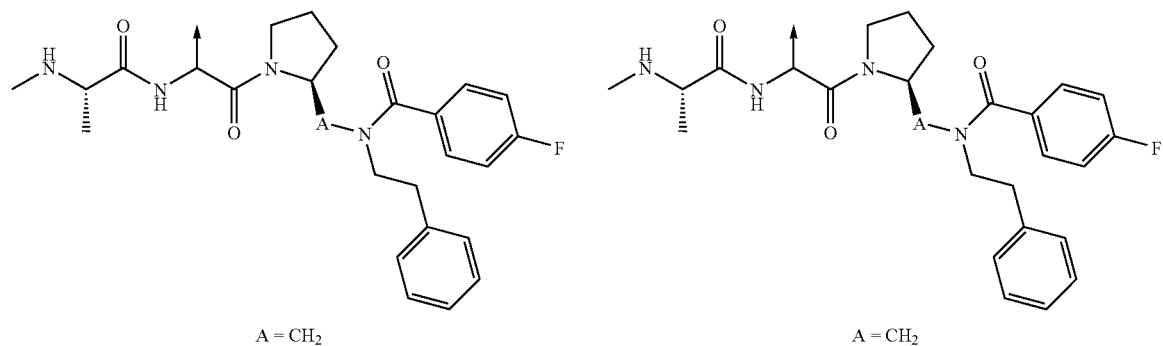

TABLE 3-continued
Formula 1B
M1—B—BG—B¹—M2
BG is
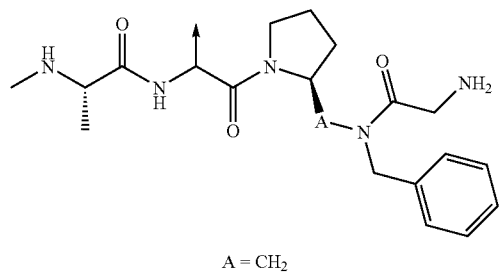
| M1 | M2 |
| --- | --- |
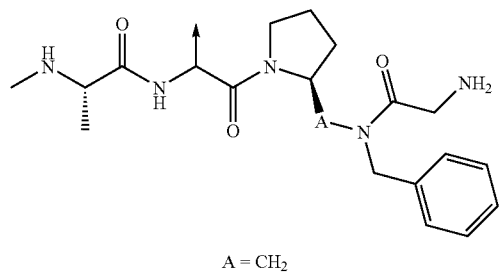
A = CH₂
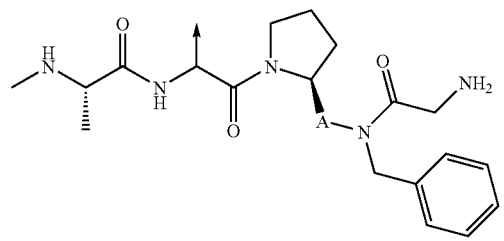
A = CH₂
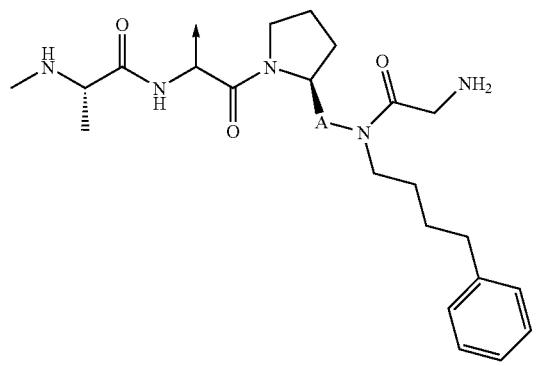
A = CH₂
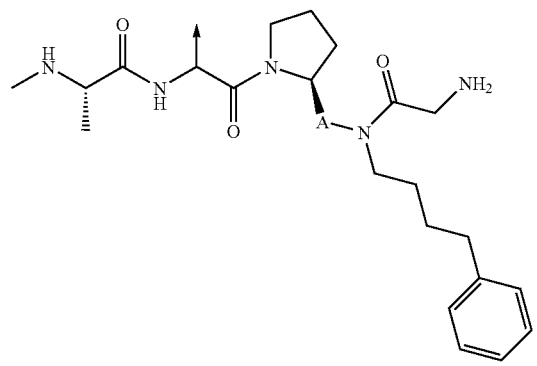
A = CH₂
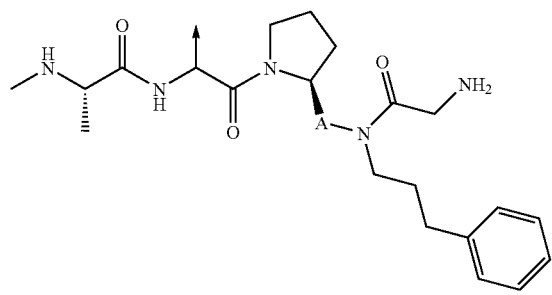
A = CH₂
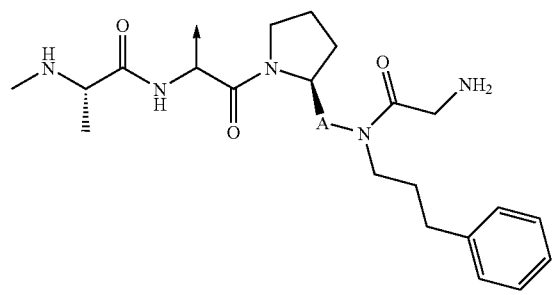
A = CH₂

TABLE 3-continued
$$M1-B-BG-B^1-M2$$
Formula 1B
BG is 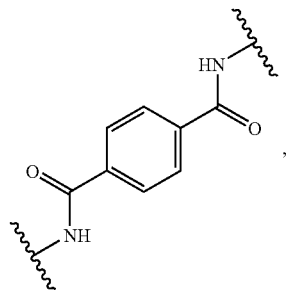
| M1 | M2 |
|---|---|
| 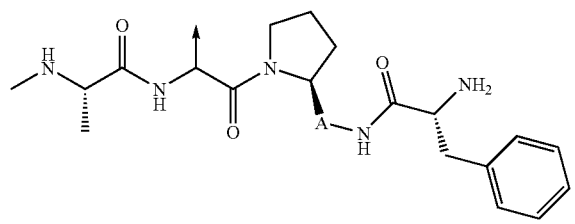<br>A = CH$_2$ | 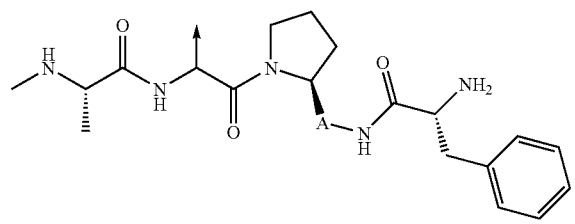<br>A = CH$_2$ |
| 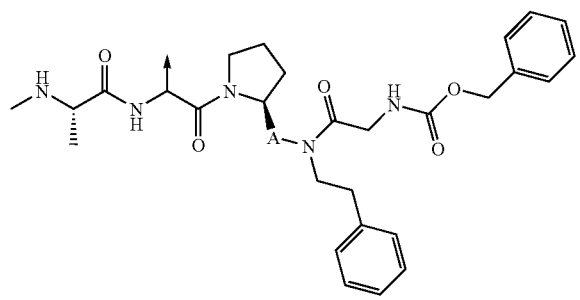<br>A = CH$_2$ | 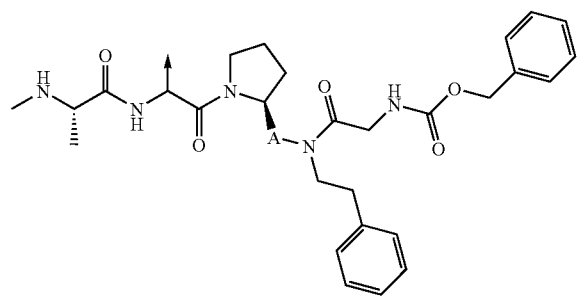<br>A = CH$_2$ |
| 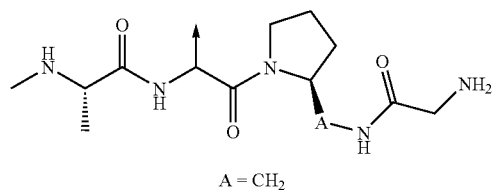<br>A = CH$_2$ | 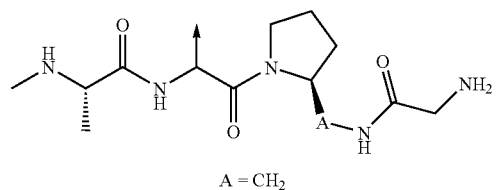<br>A = CH$_2$ |
| 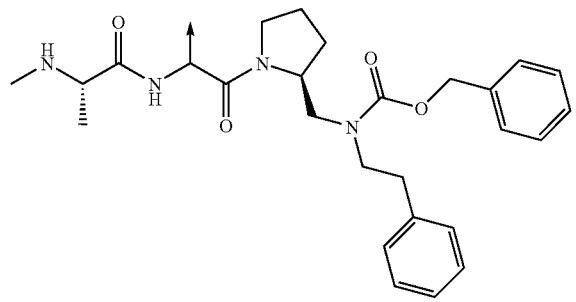<br>A = CH$_2$ | 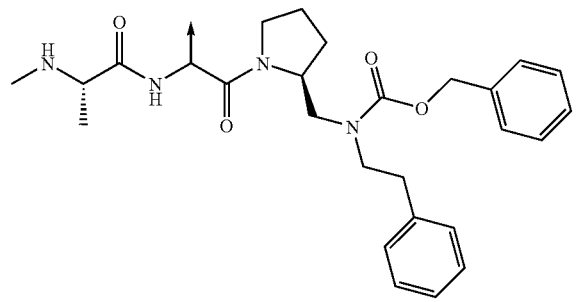<br>A = CH$_2$ |

TABLE 3-continued
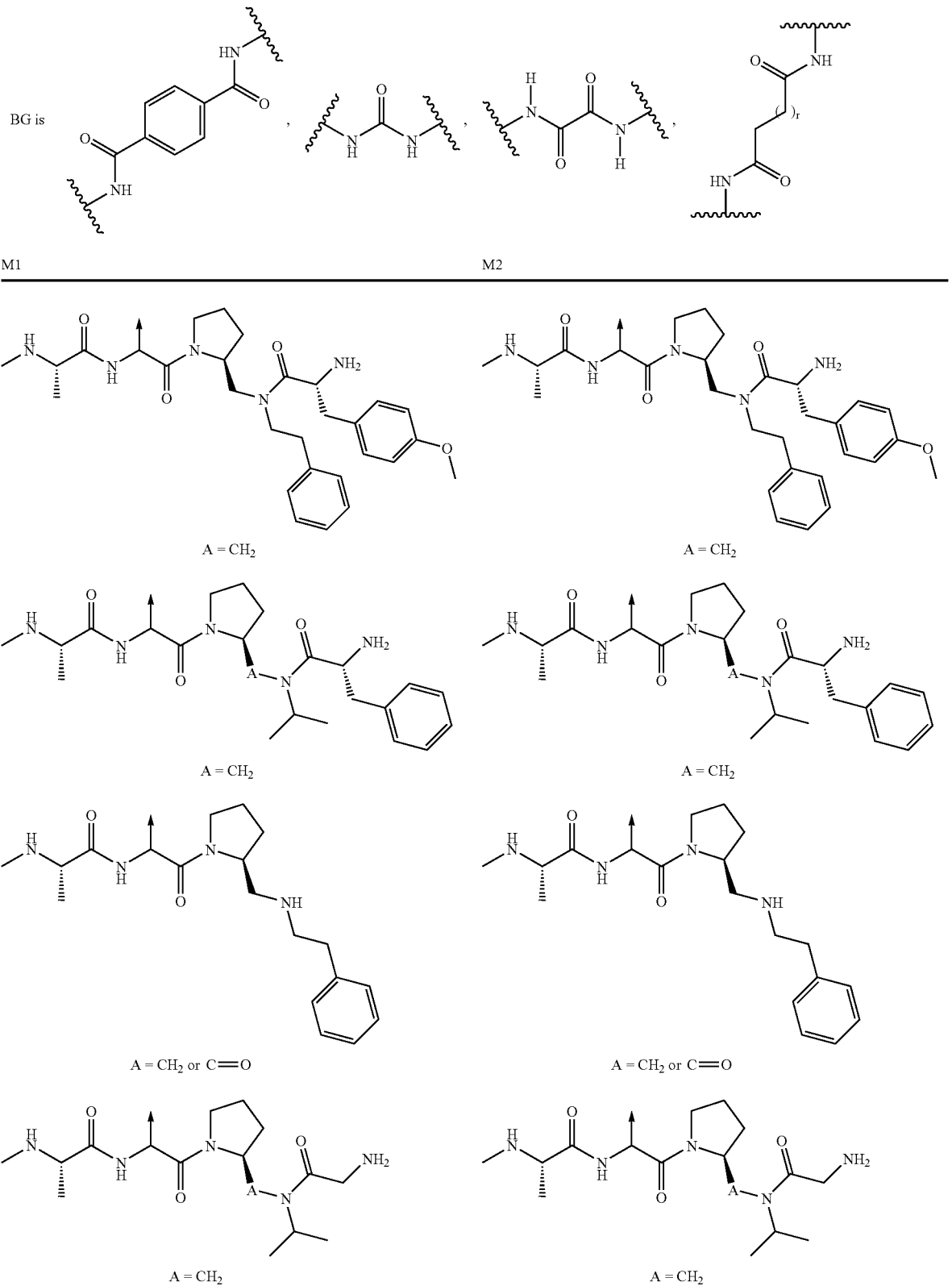

TABLE 3-continued
Formula 1B
M1—B—BG—B¹—M2
BG is
| M1 | M2 |
|---|---|
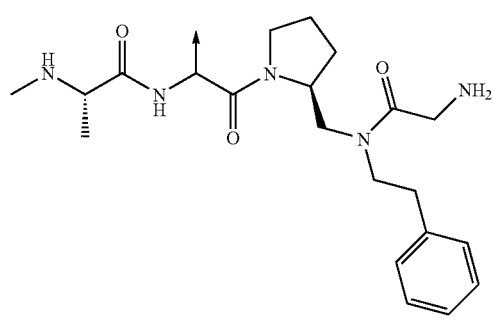
A = CH₂
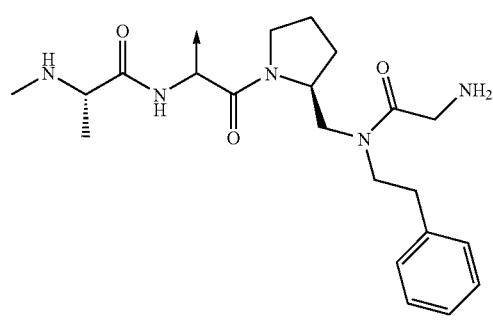
A = CH₂
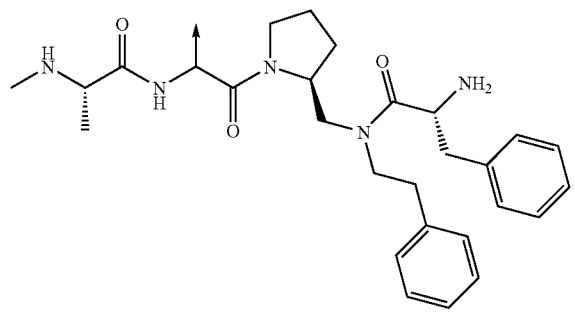
A = CH₂
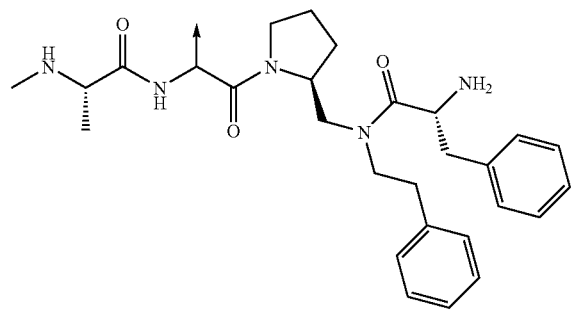
A = CH₂
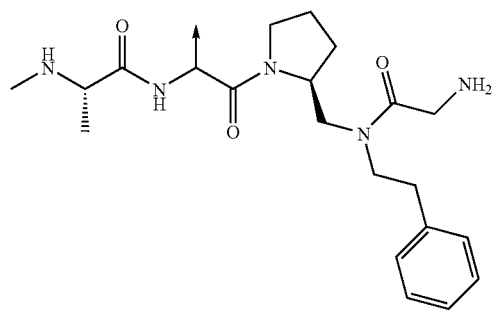
A = CH₂
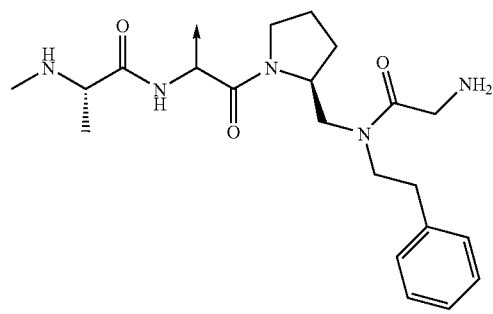
A = CH₂

TABLE 3-continued
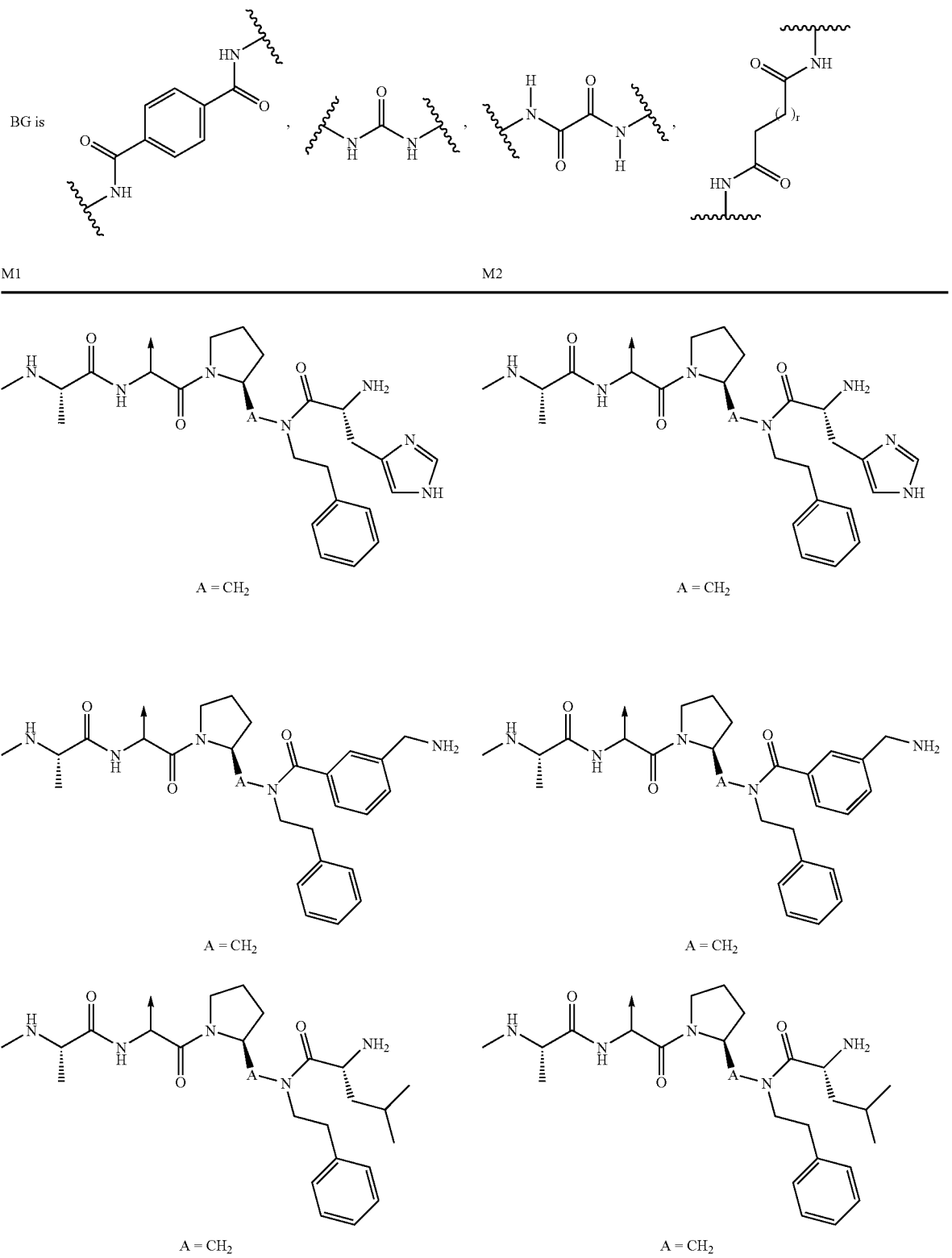

TABLE 3-continued
Formula 1B
M1—B—BG—B¹—M2
BG is 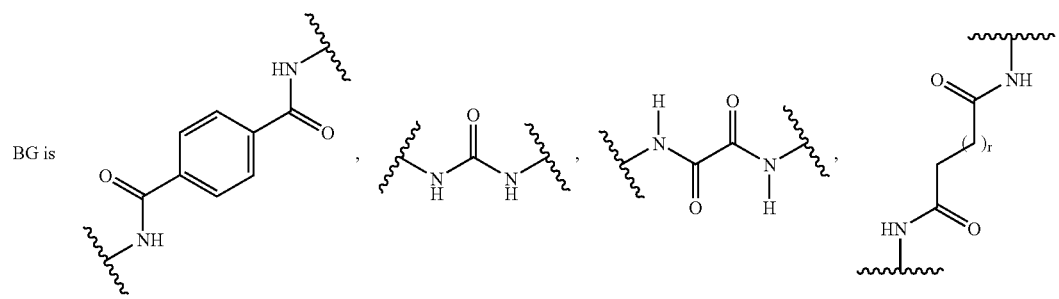
| M1 | M2 |
|---|---|
| 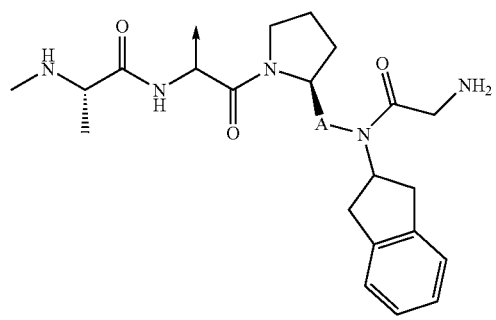<br>A = CH₂ | 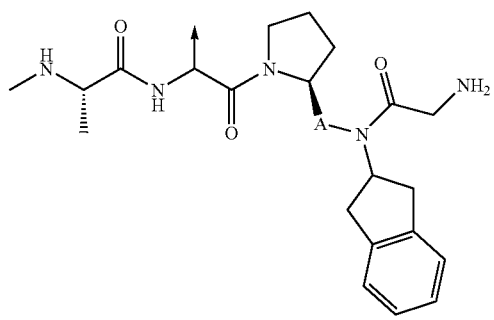<br>A = CH₂ |
| 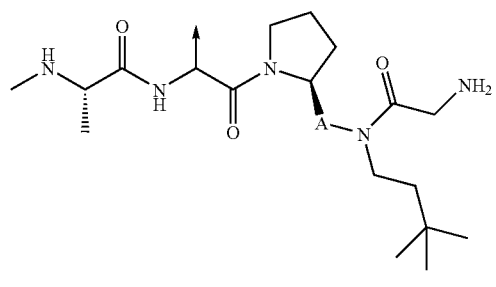<br>A = CH₂ | 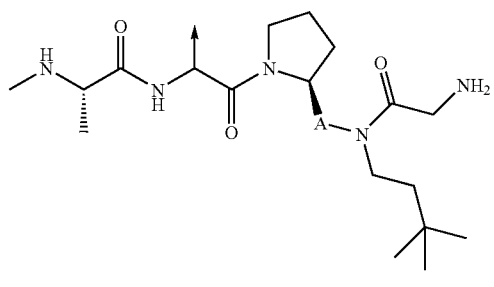<br>A = CH₂ |
| 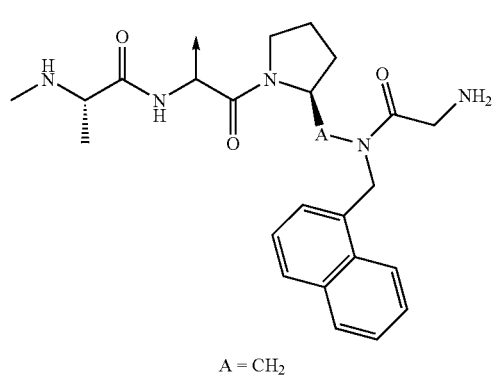<br>A = CH₂ | 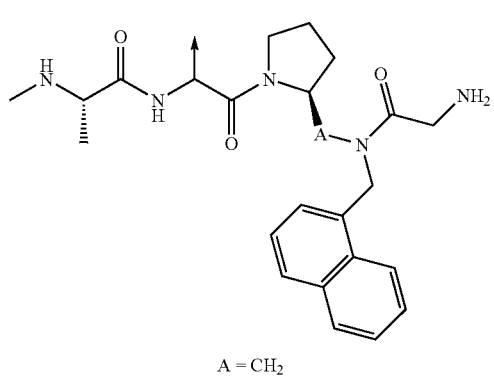<br>A = CH₂ |

TABLE 3-continued
Formula 1B
M1—B—BG—B¹—M2
BG is 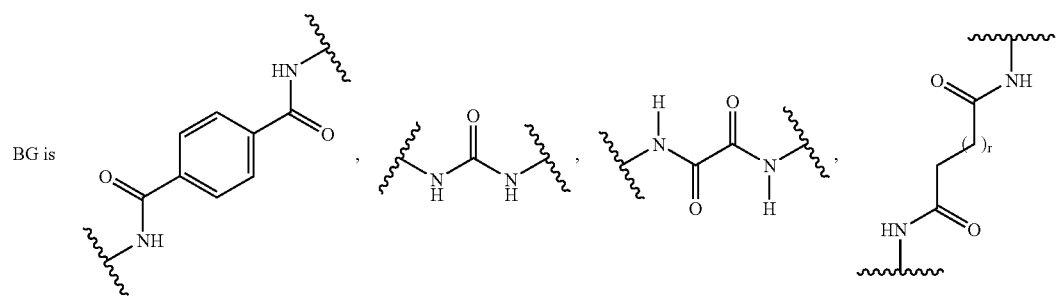
| M1 | M2 |
|---|---|
| 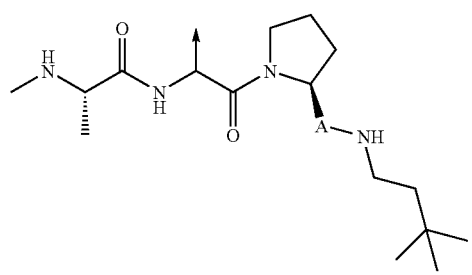<br>A = CH₂ or C=O | 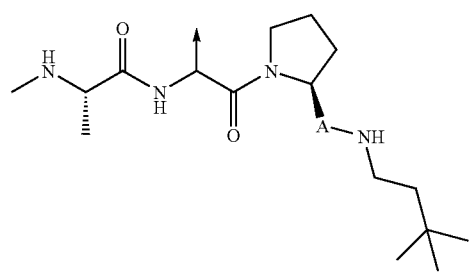<br>A = CH₂ or C=O |
| 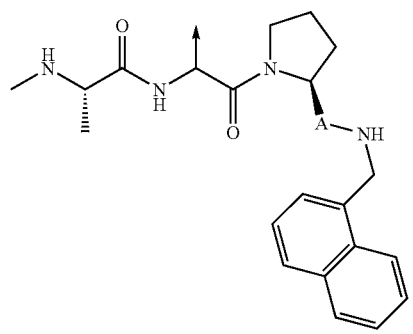<br>A = CH₂ or C=O | 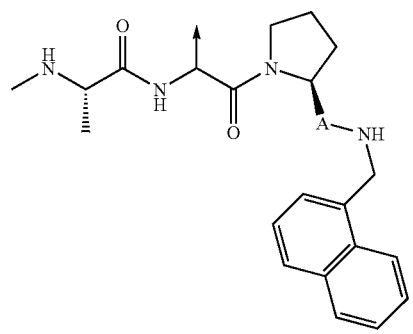<br>A = CH₂ or C=O |
| 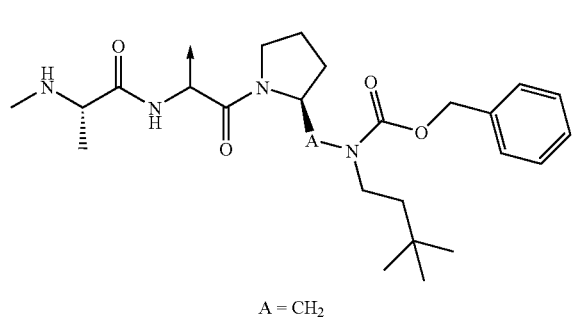<br>A = CH₂ | 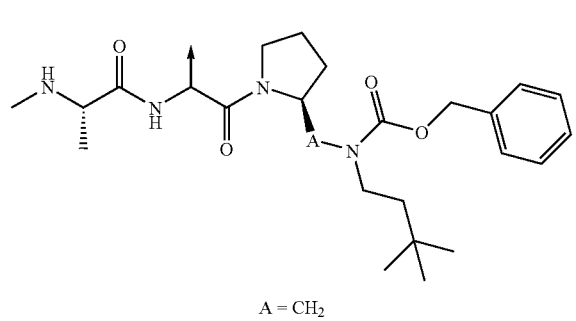<br>A = CH₂ |

TABLE 3-continued
Formula 1B
M1—B—BG—B¹—M2
BG is 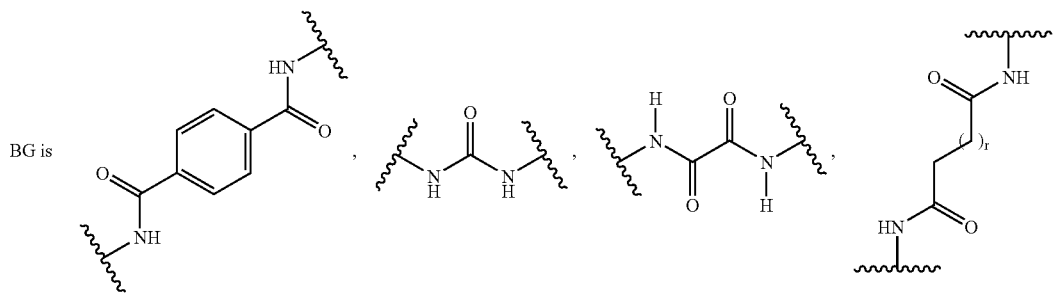
| M1 | M2 |
|---|---|
| 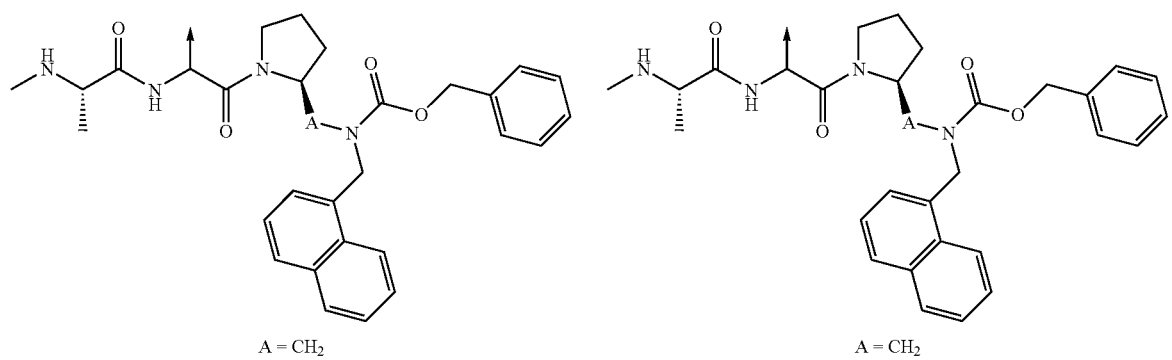 | |
| A = CH₂ | A = CH₂ |
| 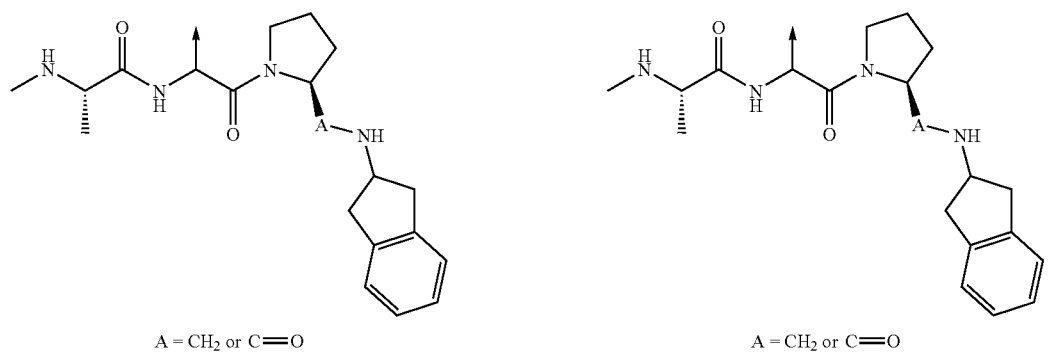 | |
| A = CH₂ or C=O | A = CH₂ or C=O |
| 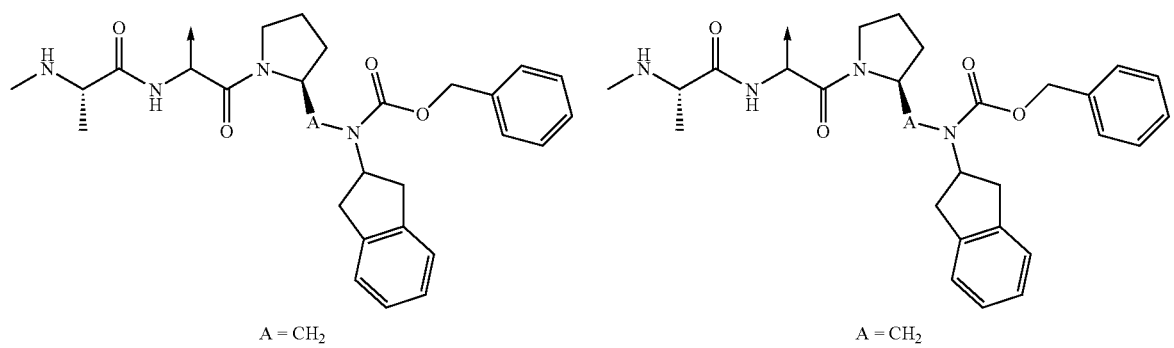 | |
| A = CH₂ | A = CH₂ |

TABLE 3-continued
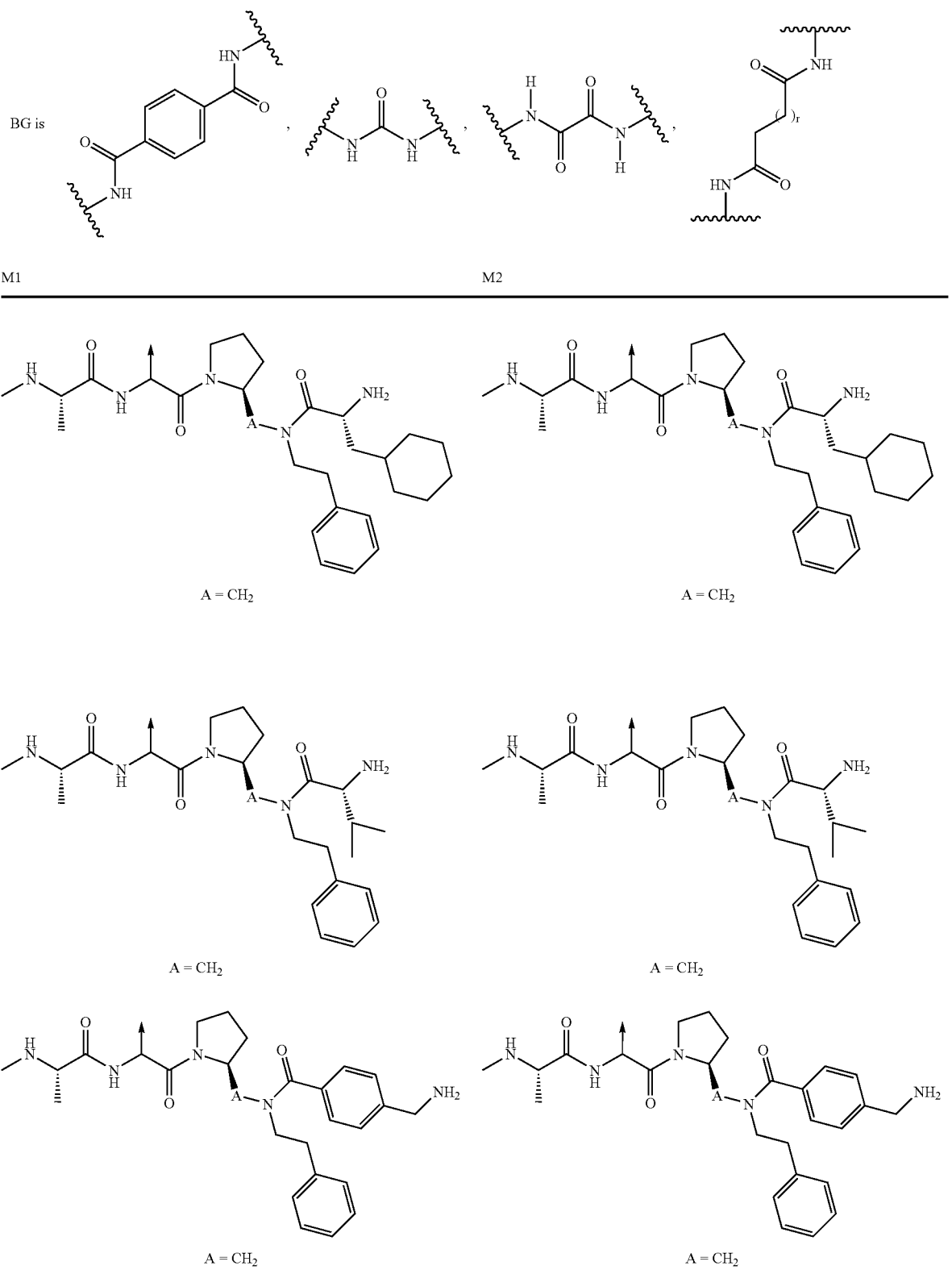

TABLE 3-continued
Formula 1B
M1—B—BG—B¹—M2
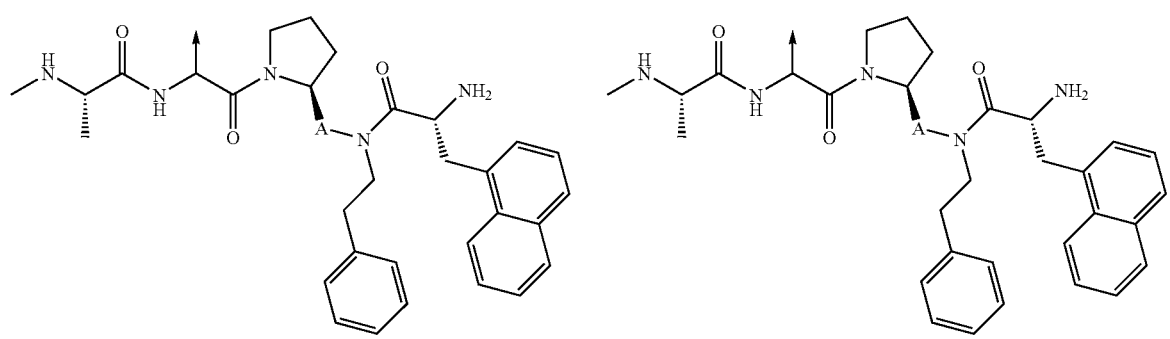
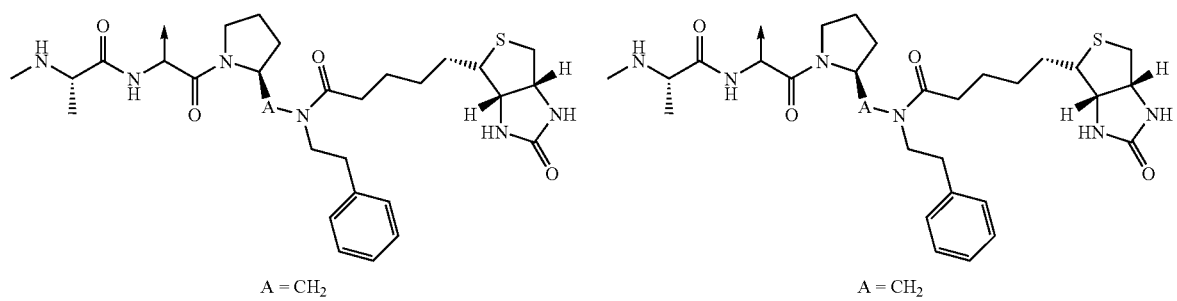
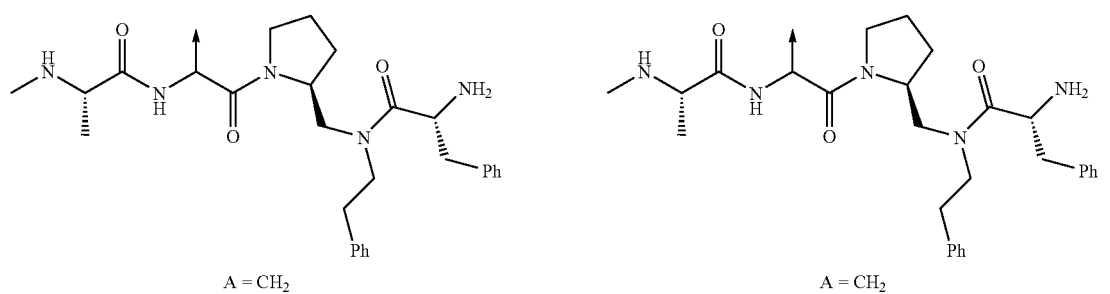

TABLE 3-continued
$$M1-B-BG-B^1-M2 \quad \text{Formula 1B}$$
BG is 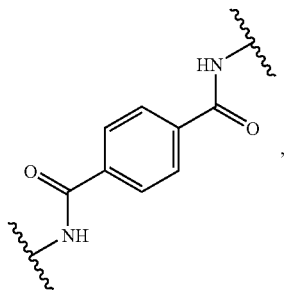
| M1 | M2 |
|---|---|
| 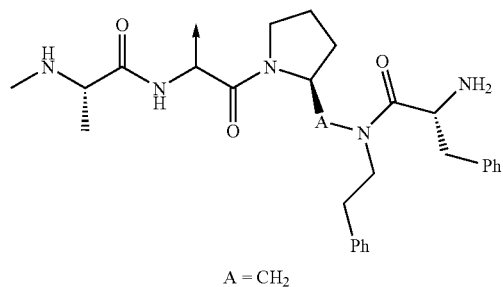<br>A = CH$_2$ | 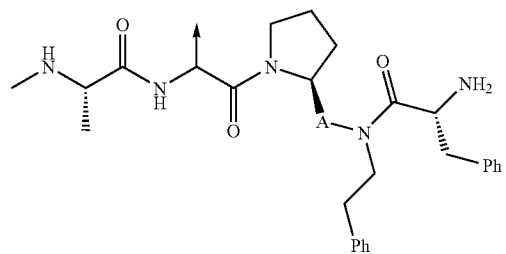<br>A = CH$_2$ |
| 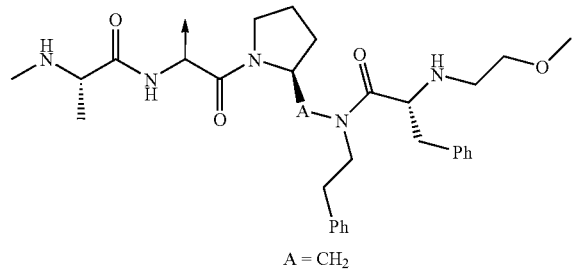<br>A = CH$_2$ | 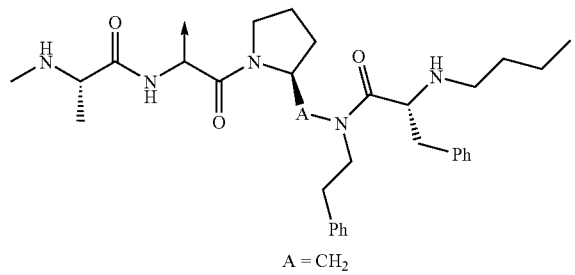<br>A = CH$_2$ |
| 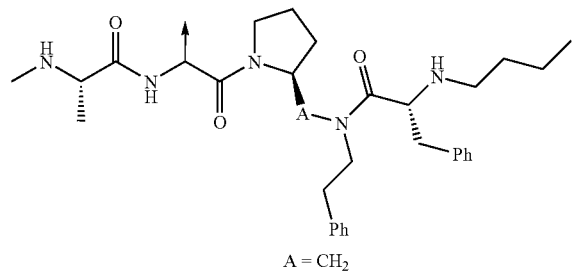<br>A = CH$_2$ | 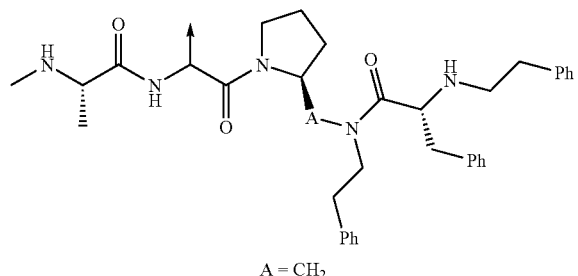<br>A = CH$_2$ |
| 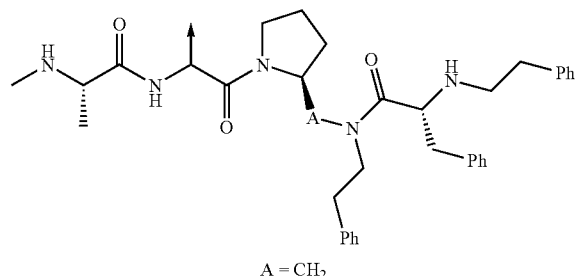<br>A = CH$_2$ | |

TABLE 3-continued
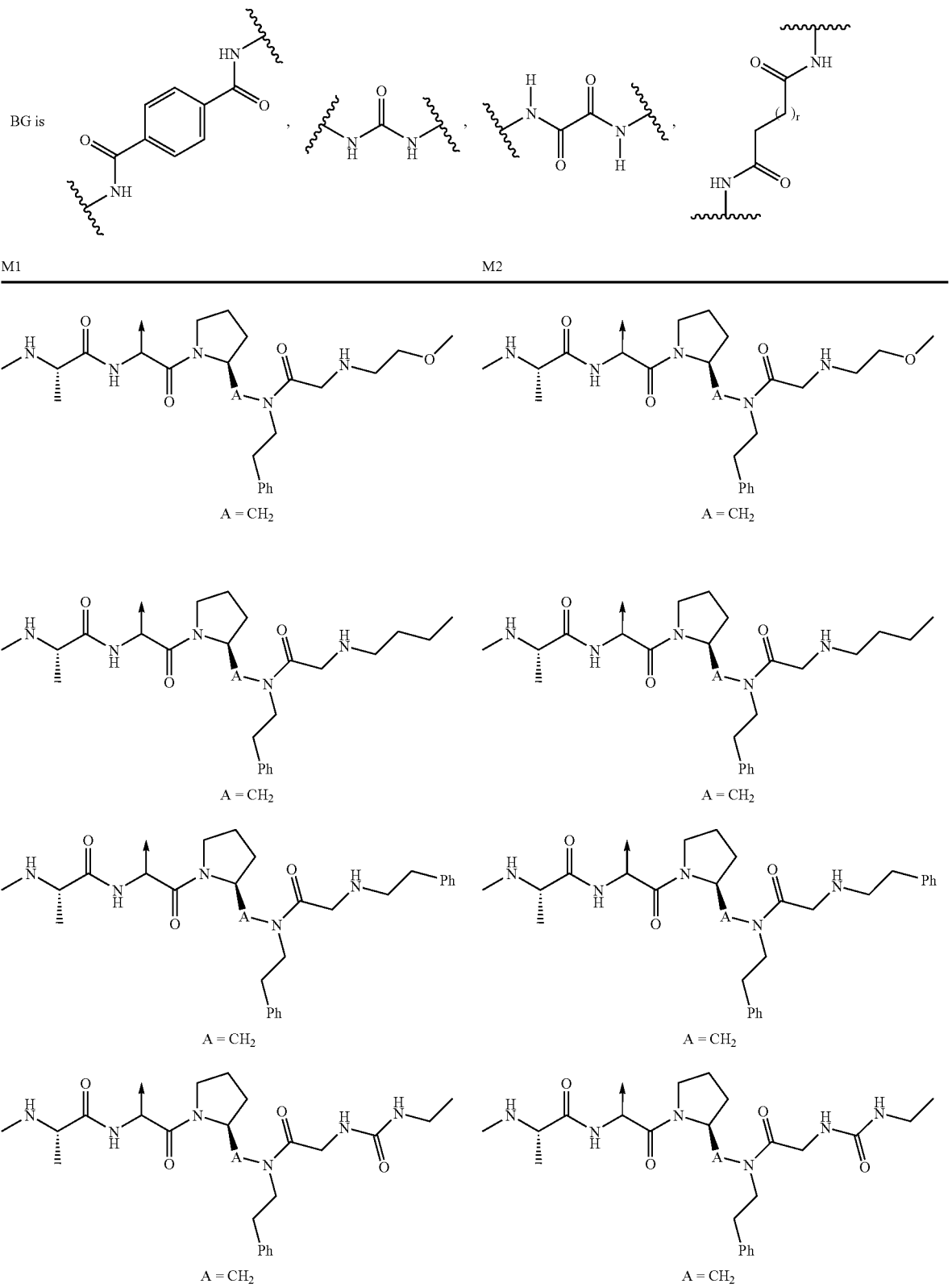

TABLE 3-continued
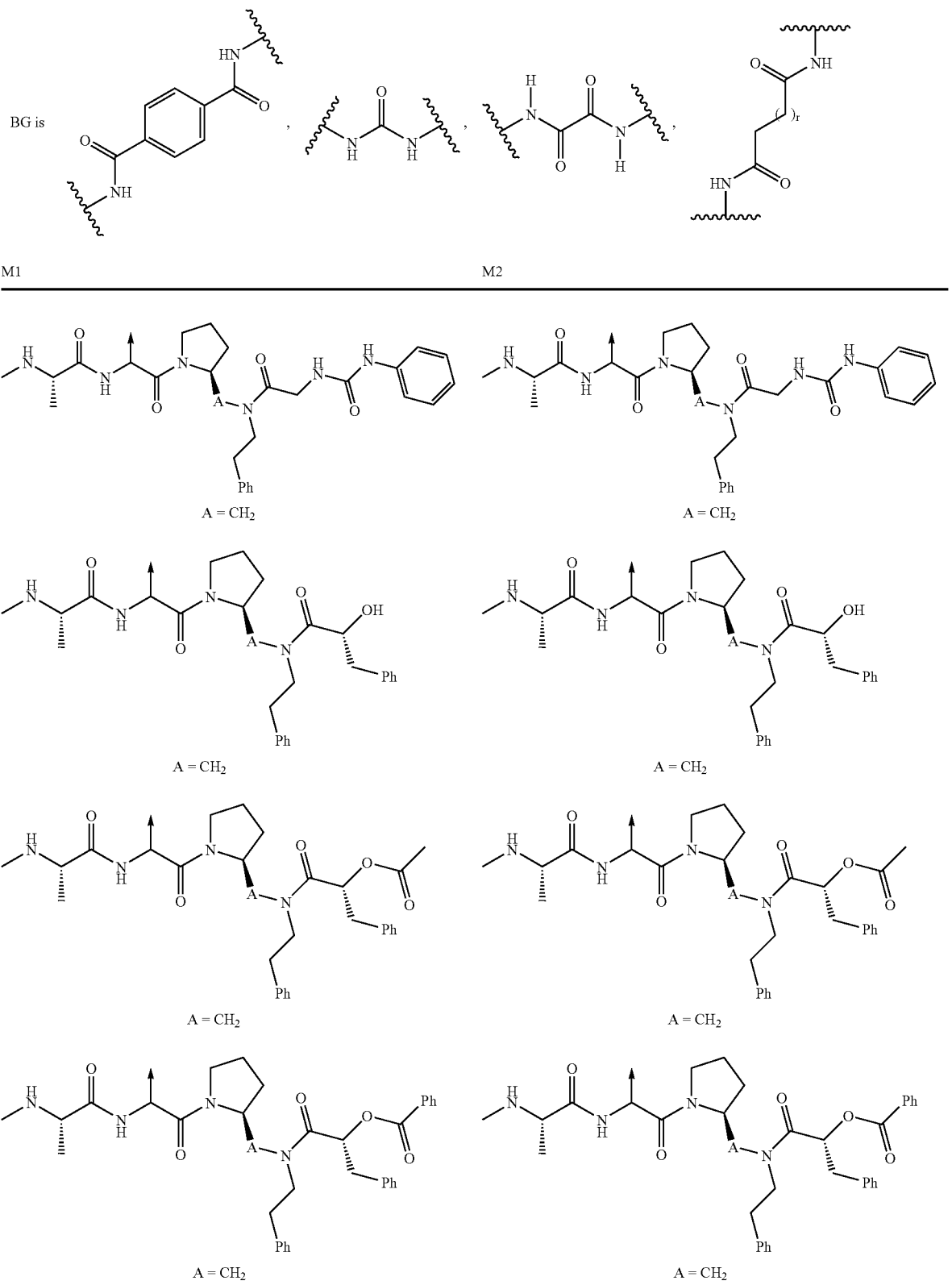

TABLE 3-continued
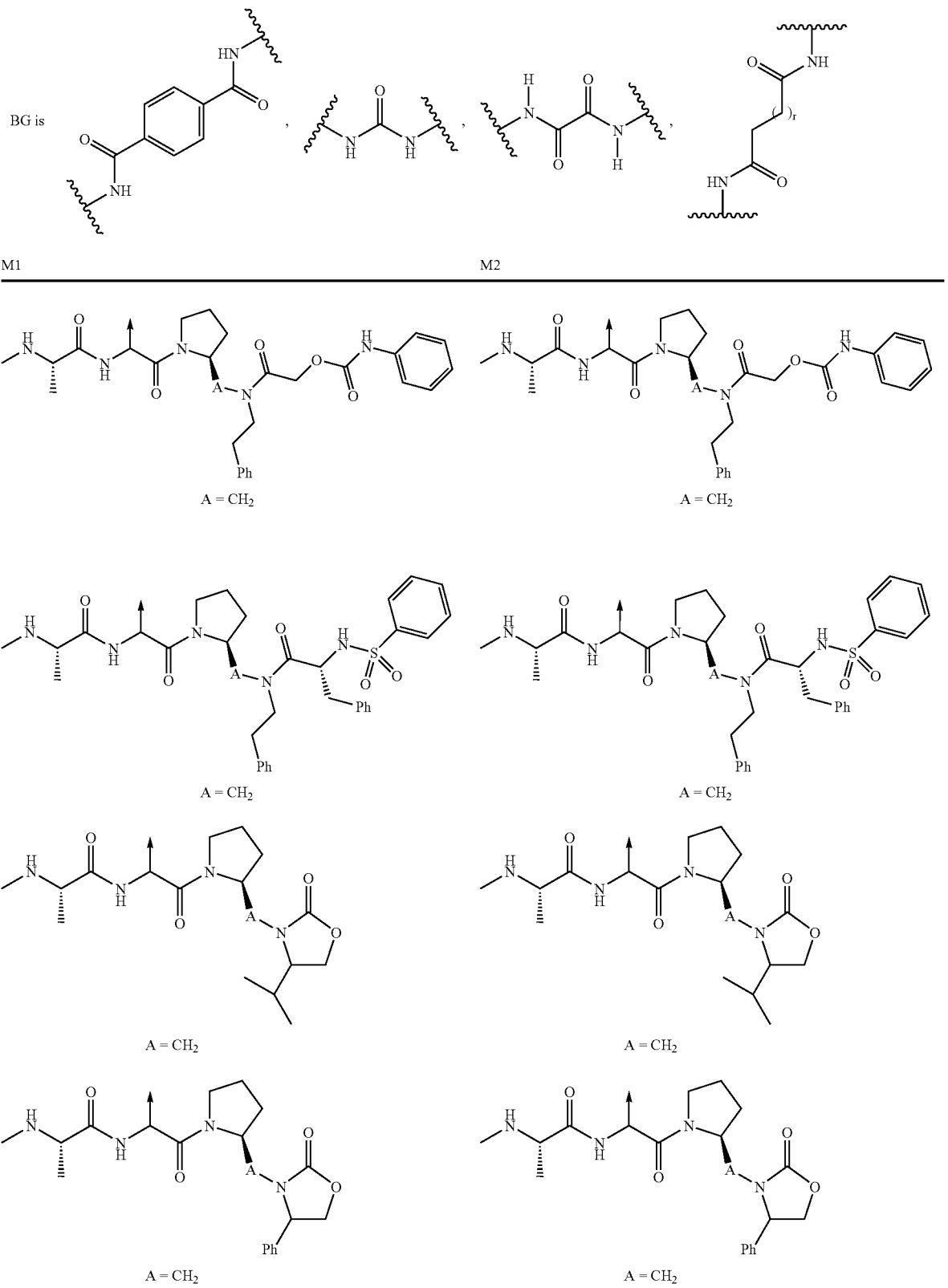

TABLE 3-continued
Formula 1B
$$M1-B-BG-B^1-M2$$
BG is 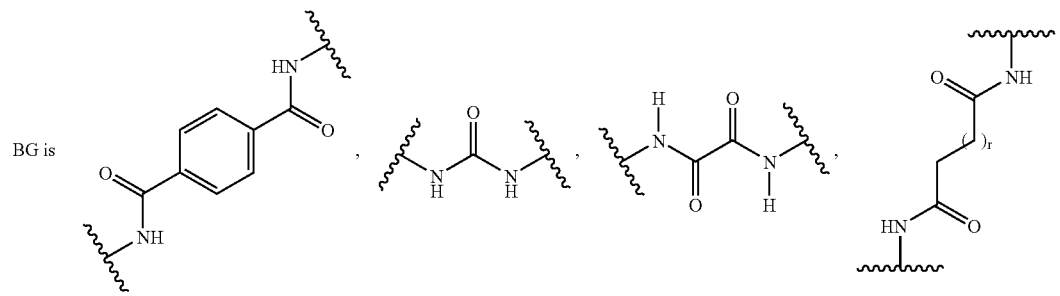
| M1 | M2 |
|---|---|
| 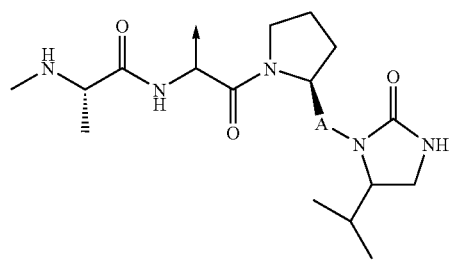<br>A = CH$_2$ | 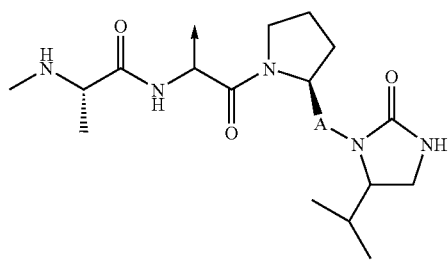<br>A = CH$_2$ |
| 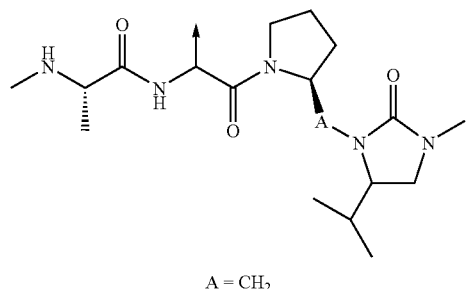<br>A = CH$_2$ | 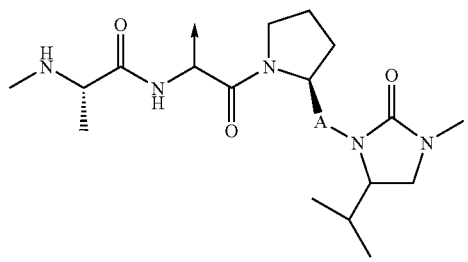<br>A = CH$_2$ |
| 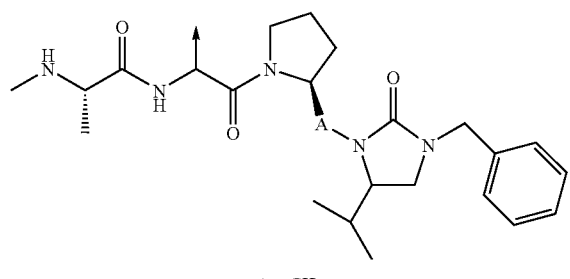<br>A = CH$_2$ | 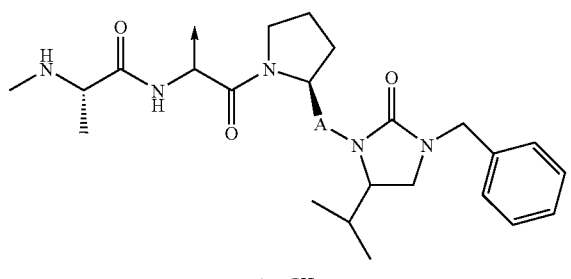<br>A = CH$_2$ |

TABLE 3-continued
Formula 1B
$$M1—B—BG—B^1—M2$$
BG is 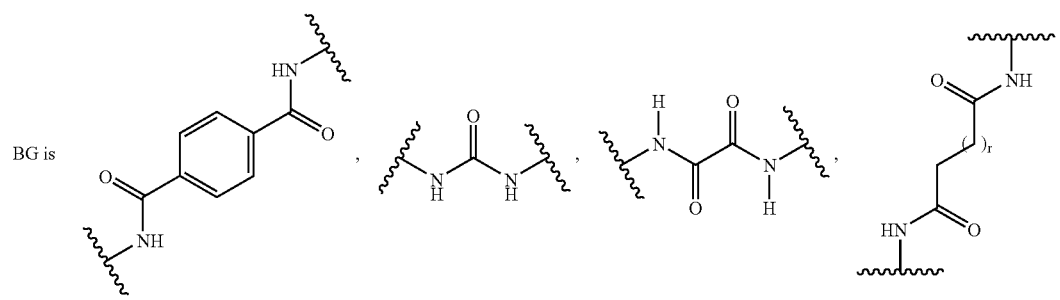
M1 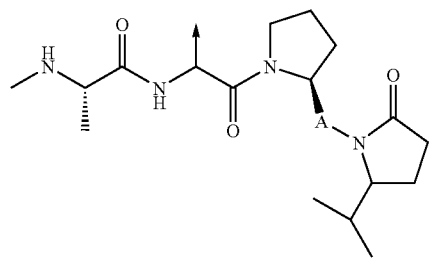
A = CH$_2$
M2 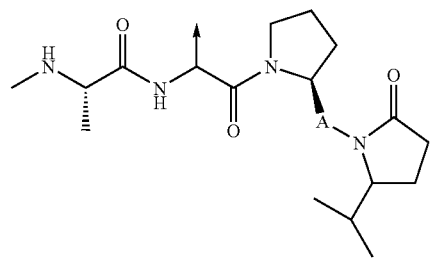
A = CH$_2$
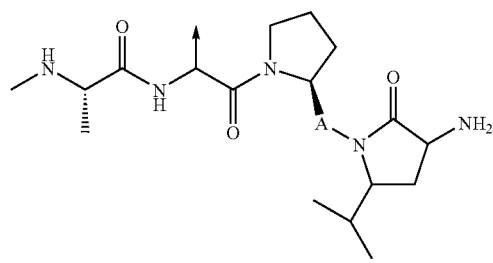
A = CH$_2$
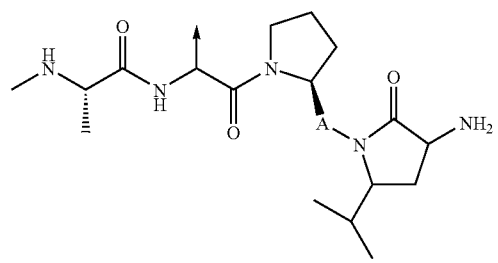
A = CH$_2$
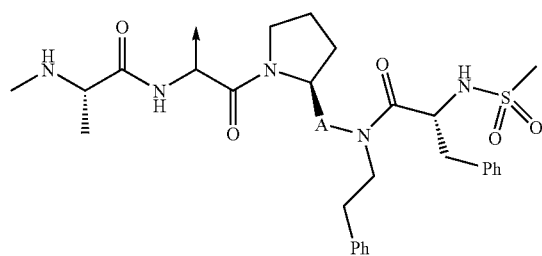
A = CH$_2$
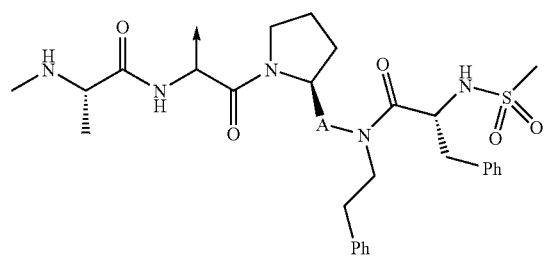
A = CH$_2$
B and B are C$_1$–C$_6$ alkyl
Note:
In M1 and M2, the stereochemistry at the connecting carbon is (S)

TABLE 4
$$M1-B-BG-B^1-M2 \quad \text{Formula 1B}$$
BG is 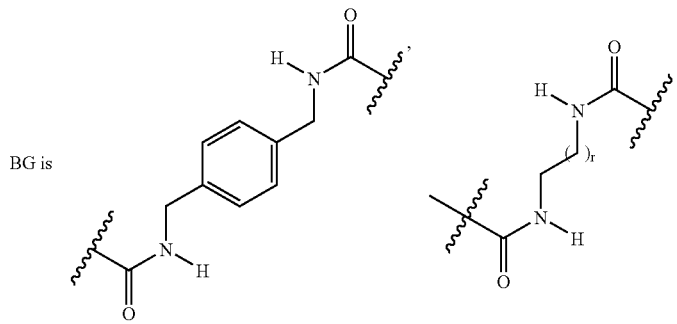
| M1 | M2 |
|---|---|
| 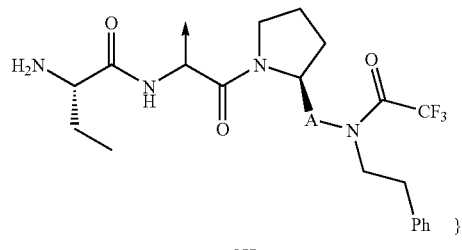<br>A = CH$_2$ | 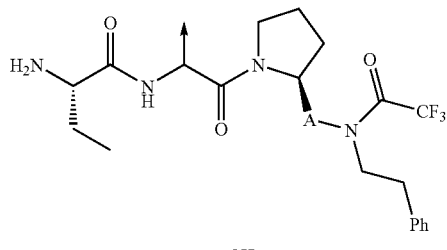<br>A = CH$_2$ |
| 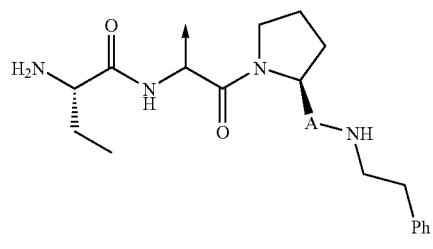<br>A = CH$_2$ or C=O | 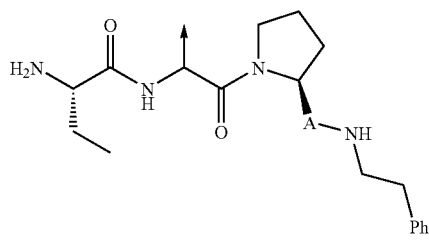<br>A = CH$_2$ or C=O |
| 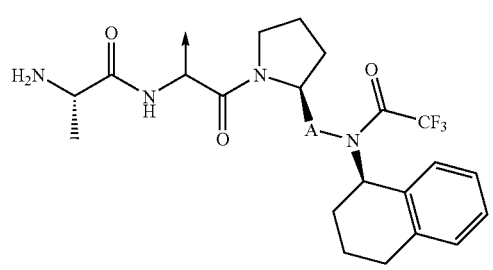<br>A = CH$_2$ | 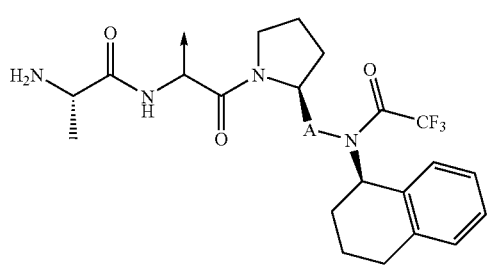<br>A = CH$_2$ |
| 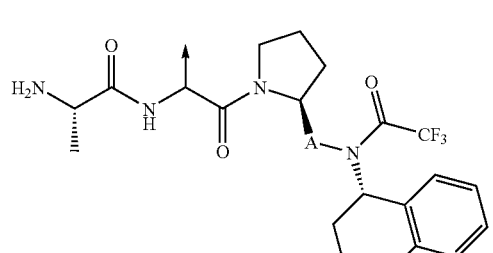<br>A = CH$_2$ | 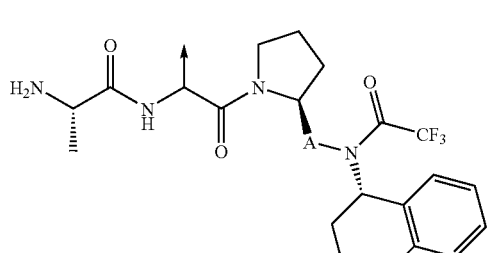<br>A = CH$_2$ |

TABLE 4-continued
Formula 1B
$$M1—B—BG—B^1—M2$$
BG is
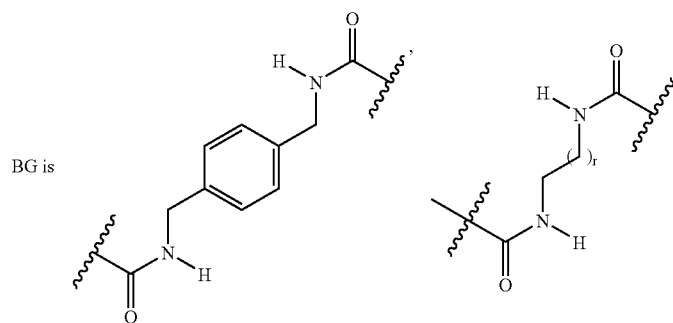
| M1 | M2 |
|---|---|
| 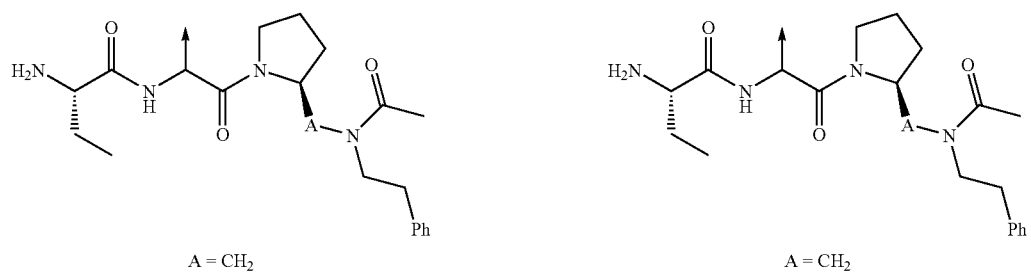 | |
| A = CH₂ | A = CH₂ |
| 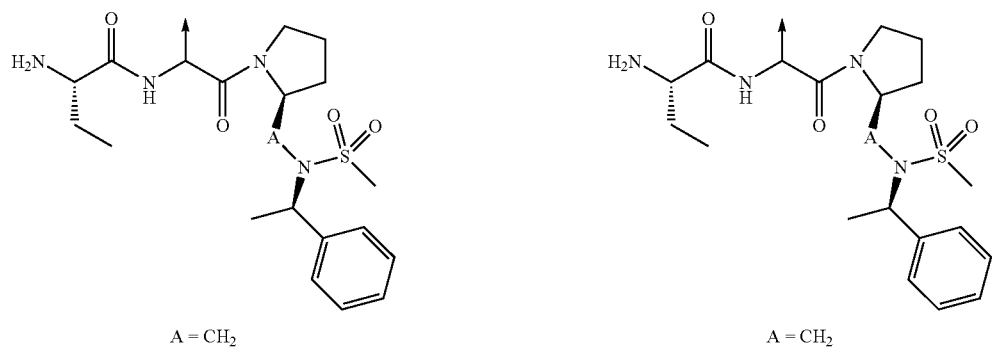 | |
| A = CH₂ | A = CH₂ |
| 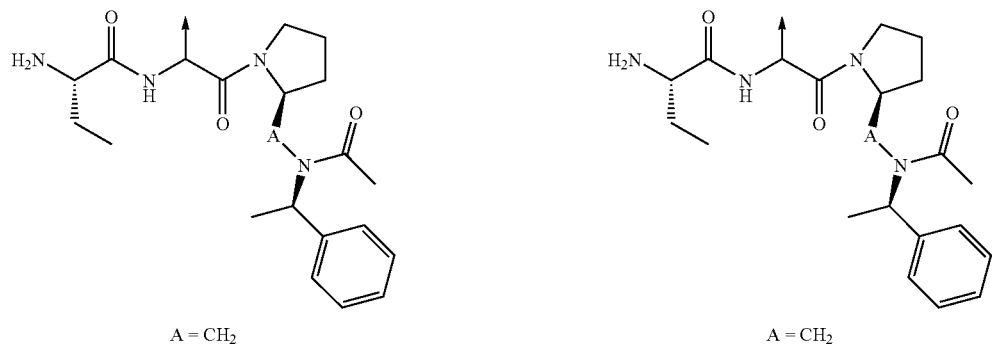 | |
| A = CH₂ | A = CH₂ |

TABLE 4-continued
Formula 1B
$$M1-B-BG-B^1-M2$$
BG is 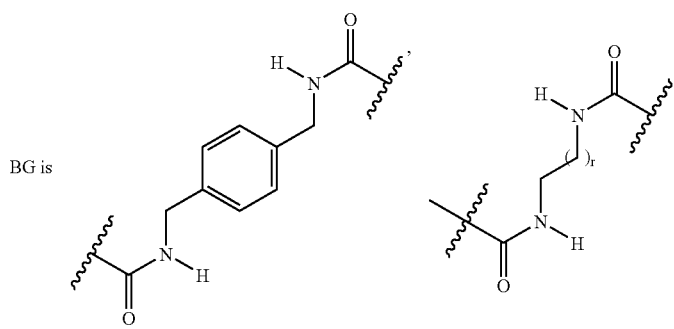
| M1 | M2 |
|---|---|
| 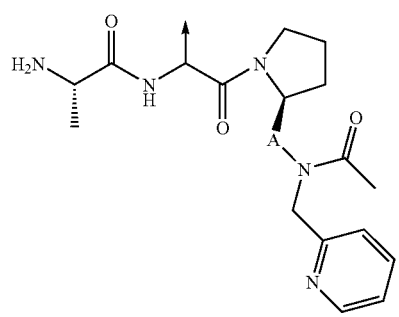<br>A = CH$_2$ | 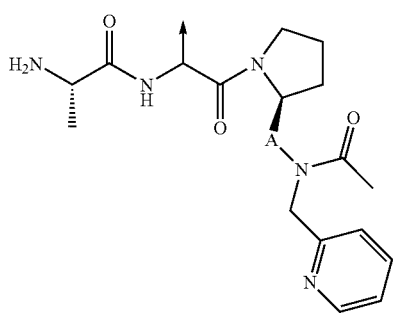<br>A = CH$_2$ |
| 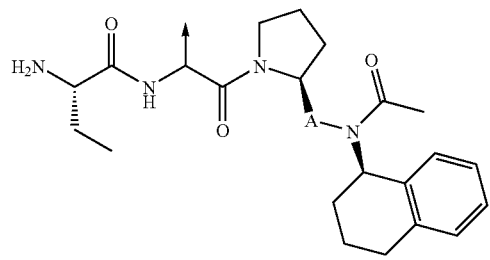<br>A = CH$_2$ | 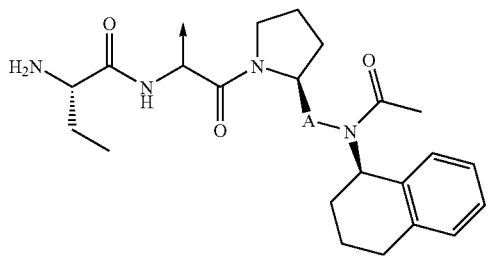<br>A = CH$_2$ |
| 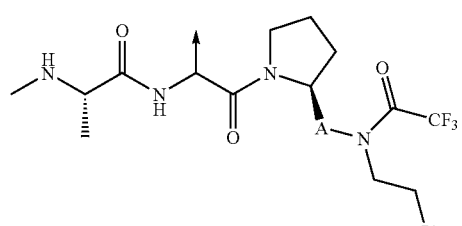<br>A = CH$_2$ | 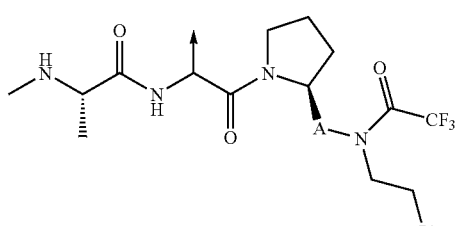<br>A = CH$_2$ |

TABLE 4-continued
Formula 1B
$$M1-B-BG-B^1-M2$$
BG is 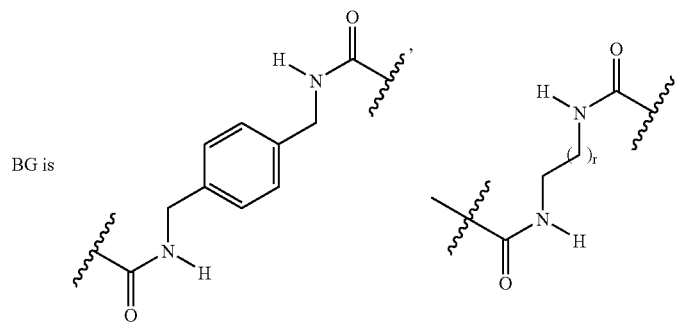
| M1 | M2 |
|---|---|
| 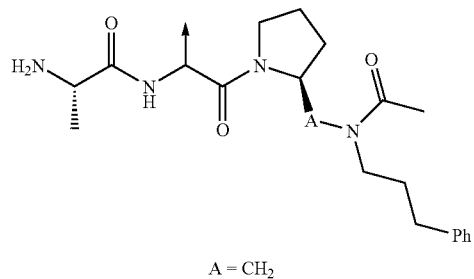<br>A = CH₂ | 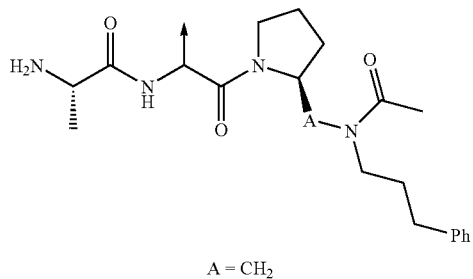<br>A = CH₂ |
| 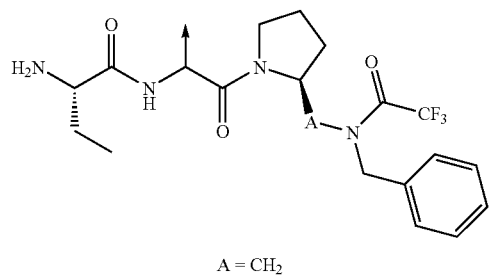<br>A = CH₂ | 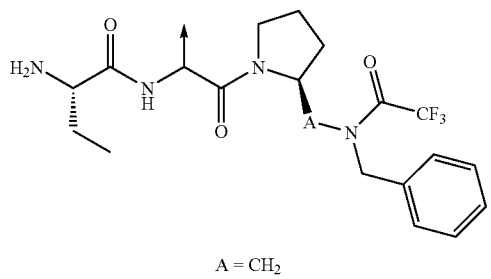<br>A = CH₂ |
| 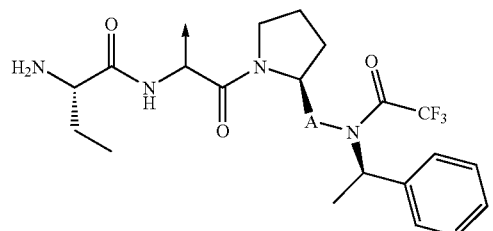<br>A = CH₂ | 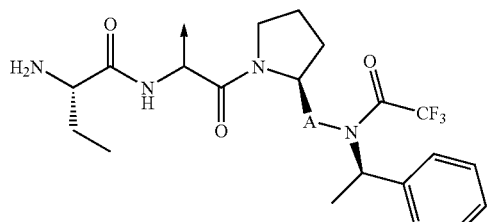<br>A = CH₂ |

TABLE 4-continued
Formula 1B
M1—B—BG—B¹—M2
BG is 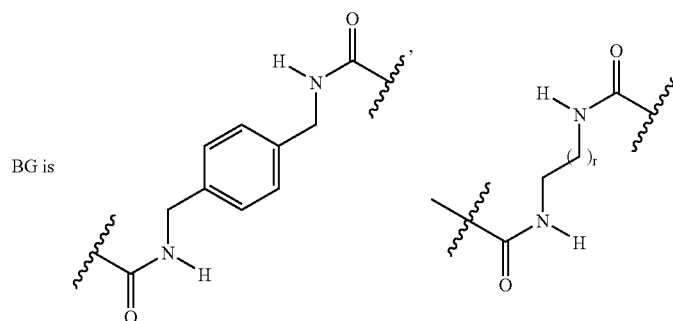
| M1 | M2 |
|---|---|
| 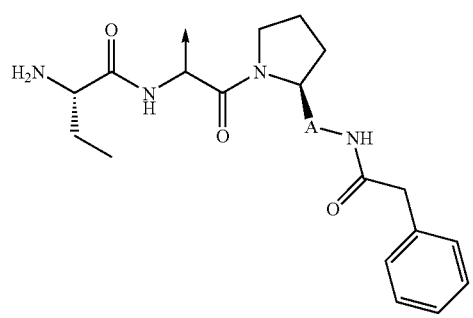<br>A = CH₂ | 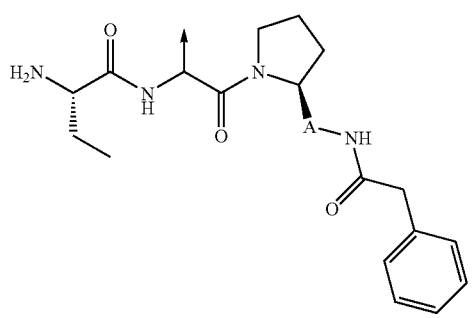<br>A = CH₂ |
| 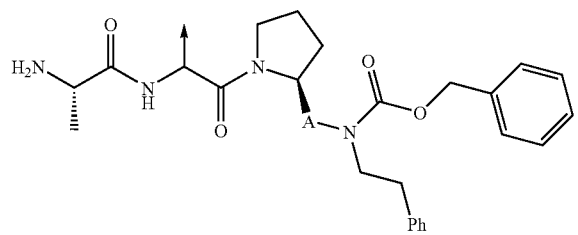<br>A = CH₂ | 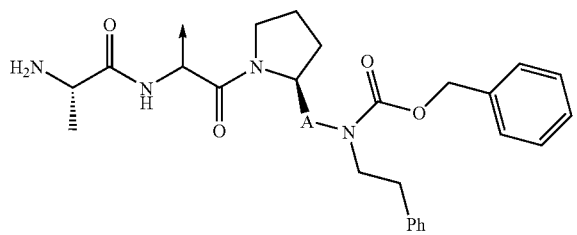<br>A = CH₂ |
| 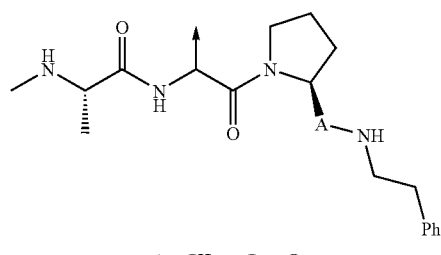<br>A = CH₂ or C═O | 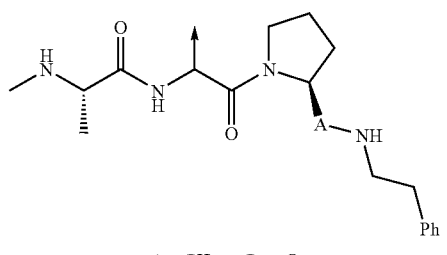<br>A = CH₂ or C═O |

TABLE 4-continued
$$M1—B—BG—B^1—M2$$
Formula 1B
BG is 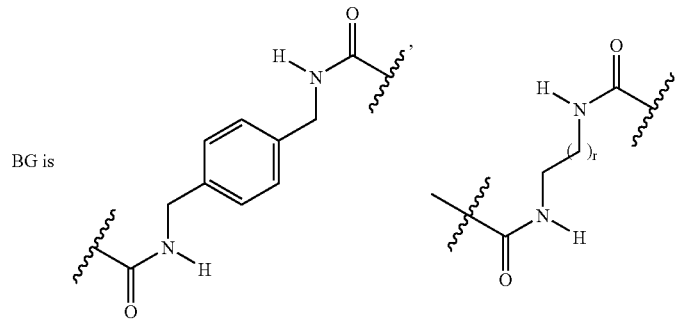
| M1 | M2 |
|---|---|
| 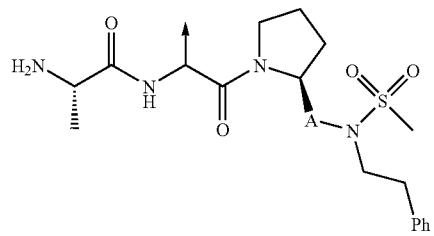<br>A = CH$_2$ | 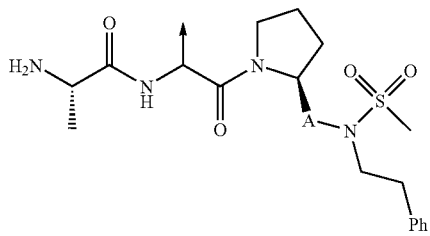<br>A = CH$_2$ |
| 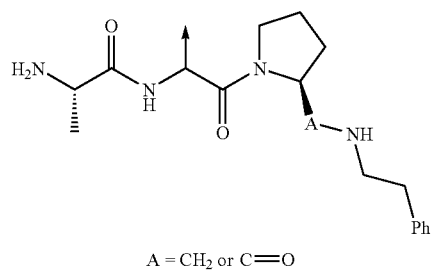<br>A = CH$_2$ or C═O | 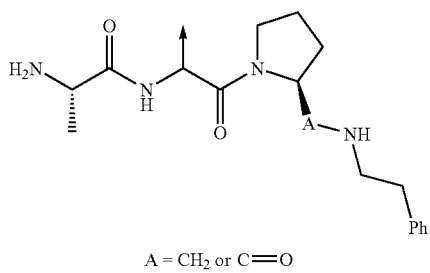<br>A = CH$_2$ or C═O |
| 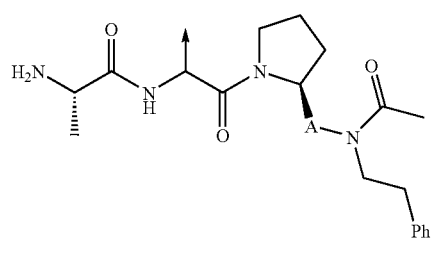<br>A = CH$_2$ | 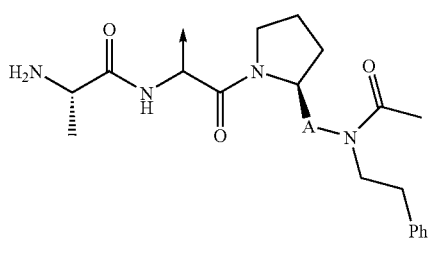<br>A = CH$_2$ |
| 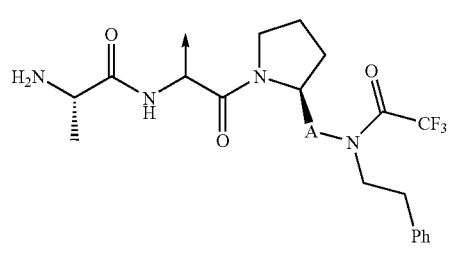<br>A = CH$_2$ | 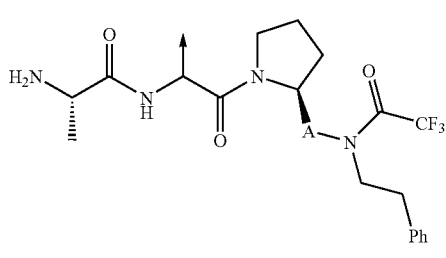<br>A = CH$_2$ |

TABLE 4-continued
Formula 1B
M1—B—BG—B¹—M2
BG is 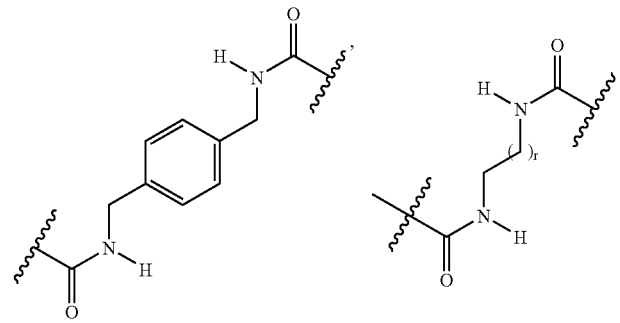
| M1 | M2 |
|---|---|
| 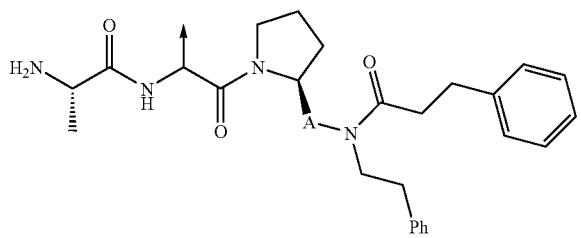<br>A = CH₂ | 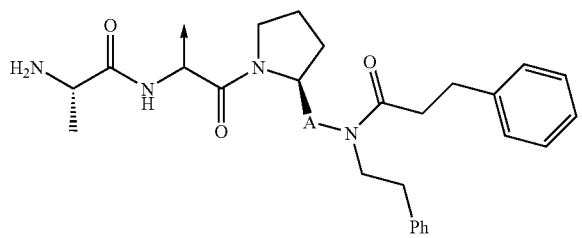<br>A = CH₂ |
| 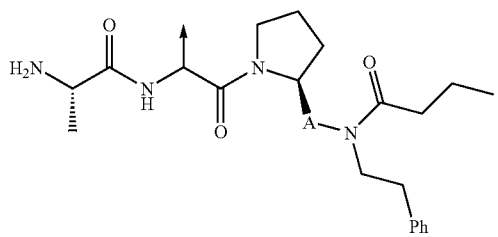<br>A = CH₂ | 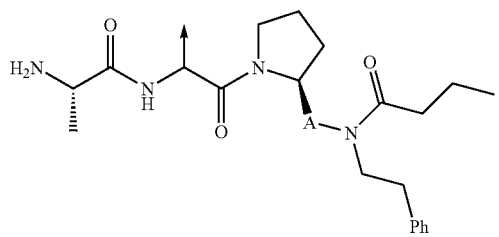<br>A = CH₂ |
| 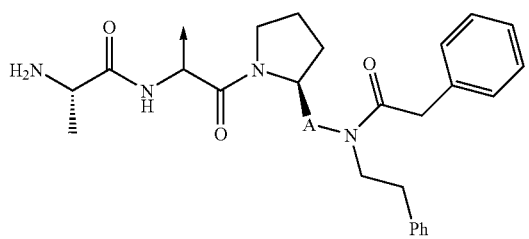<br>A = CH₂ | 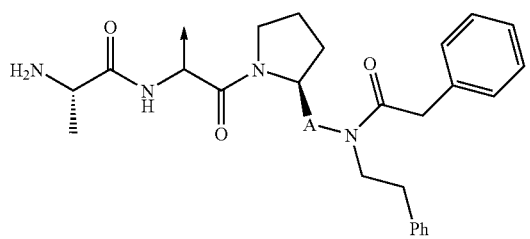<br>A = CH₂ |
| 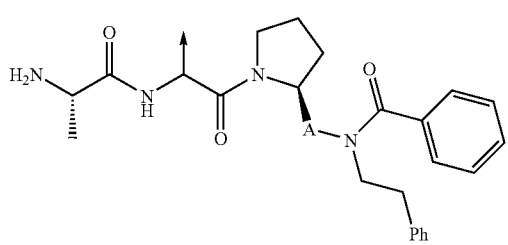<br>A = CH₂ | 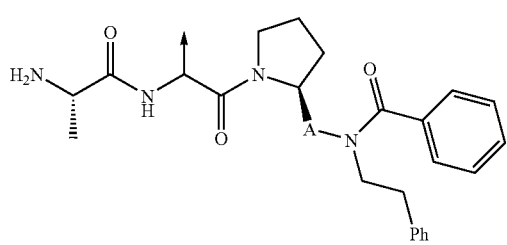<br>A = CH₂ |

TABLE 4-continued
Formula 1B
M1—B—BG—B¹—M2
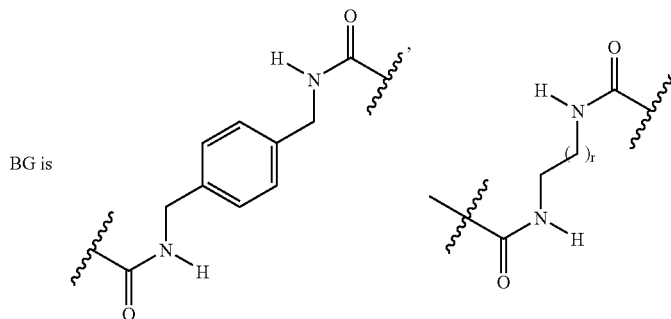
BG is
| M1 | M2 |
|---|---|
| 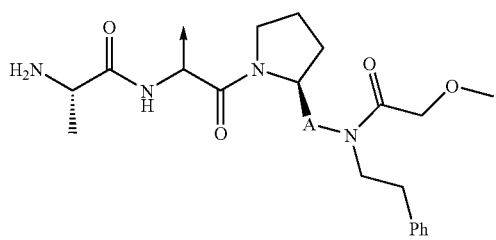<br>A = CH₂ | 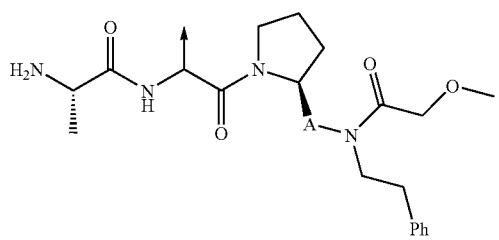<br>A = CH₂ |
| 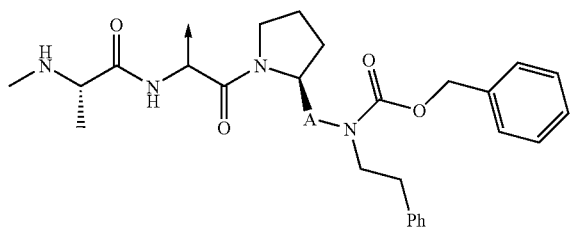<br>A = CH₂ | 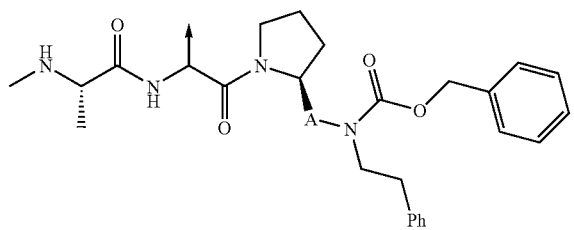<br>A = CH₂ |
| 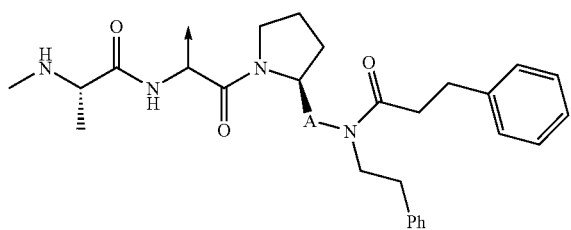<br>A = CH₂ | 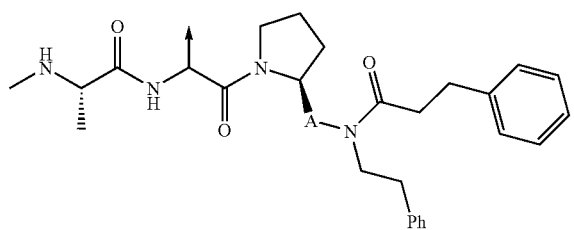<br>A = CH₂ |
| 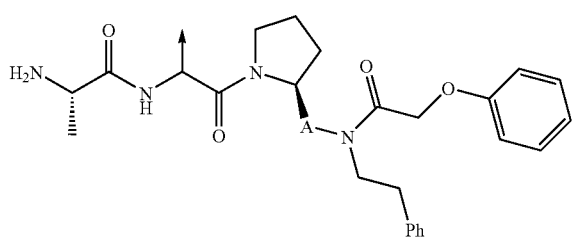<br>A = CH₂ | 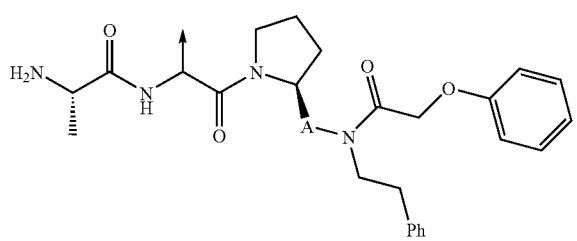<br>A = CH₂ |

TABLE 4-continued
Formula 1B
M1—B—BG—B¹—M2
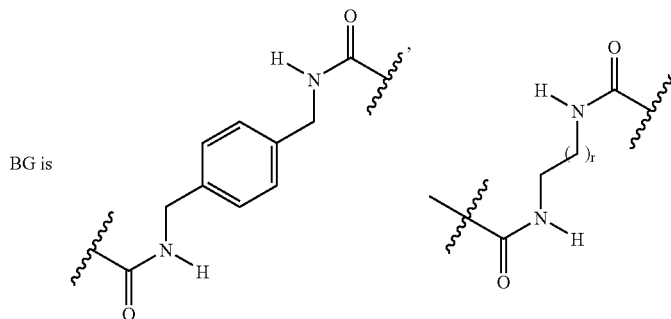
BG is
| M1 | M2 |
|---|---|
| 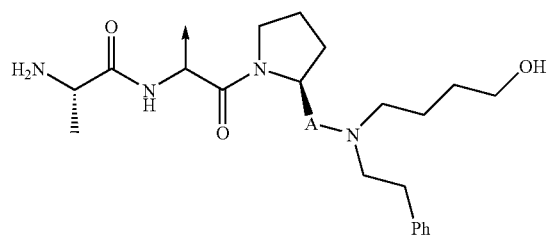<br>A = CH₂ or C=O | 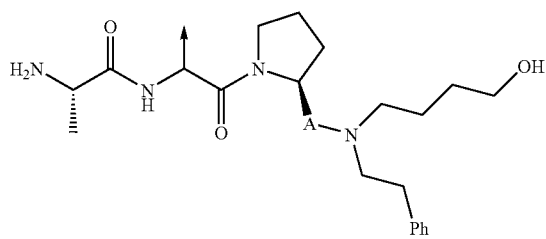<br>A = CH₂ or C=O |
| 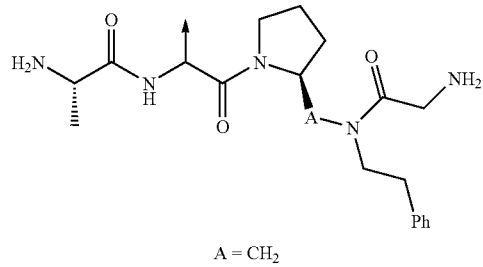<br>A = CH₂ | 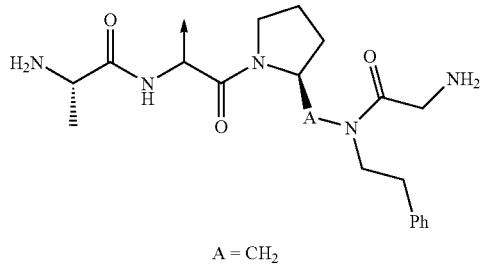<br>A = CH₂ |
| 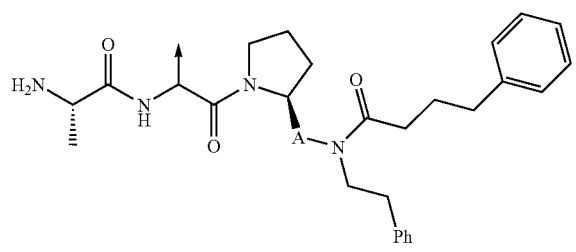<br>A = CH₂ | 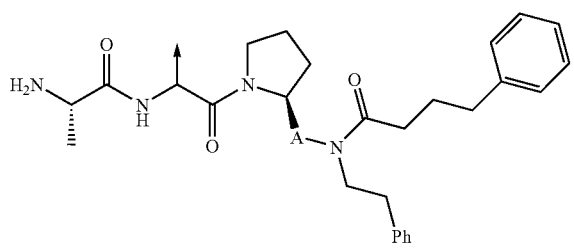<br>A = CH₂ |
| 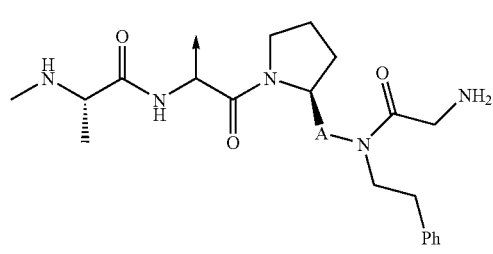<br>A = CH₂ | 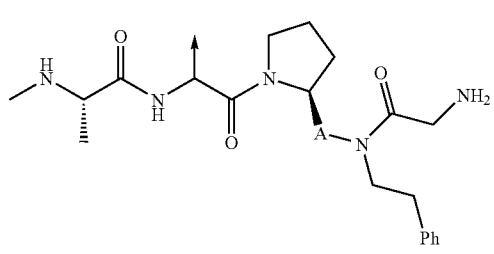<br>A = CH₂ |

TABLE 4-continued
Formula 1B
M1—B—BG—B¹—M2
BG is 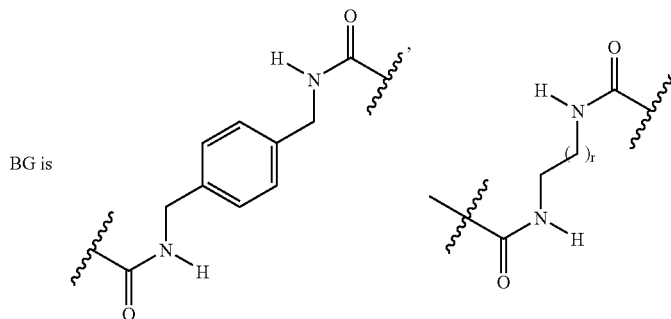
| M1 | M2 |
|---|---|
| 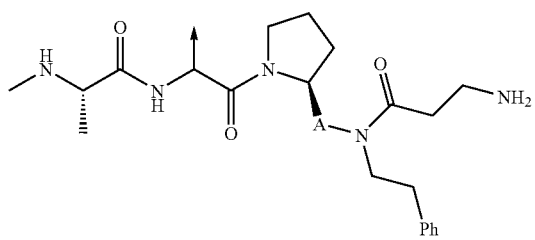<br>A = CH₂ | 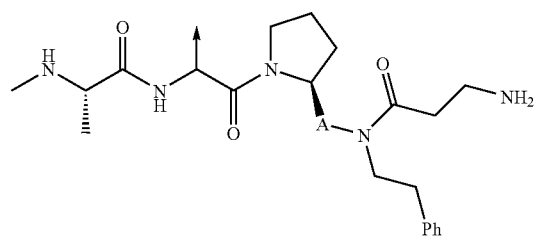<br>A = CH₂ |
| 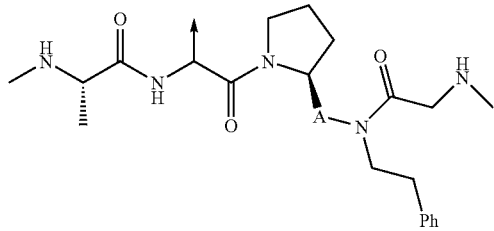<br>A = CH₂ | 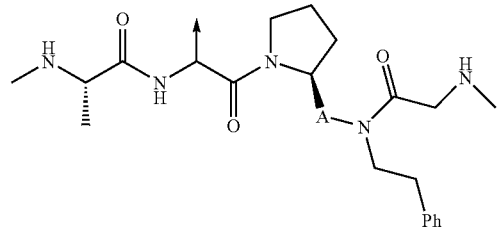<br>A = CH₂ |
| 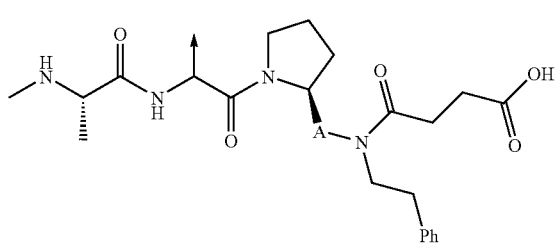<br>A = CH₂ | 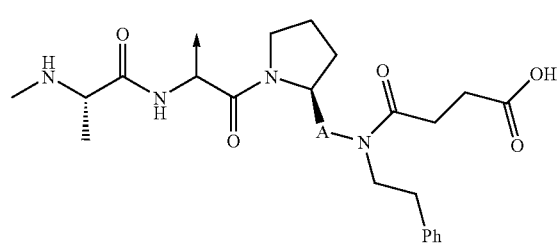<br>A = CH₂ |
| 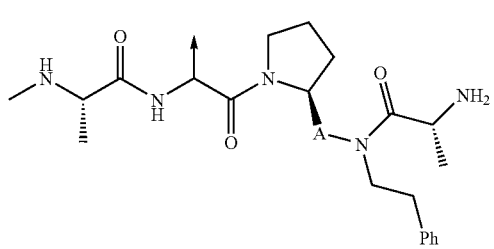<br>A = CH₂ | 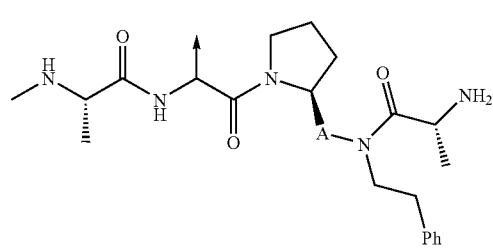<br>A = CH₂ |

TABLE 4-continued
Formula 1B
M1—B—BG—B¹—M2
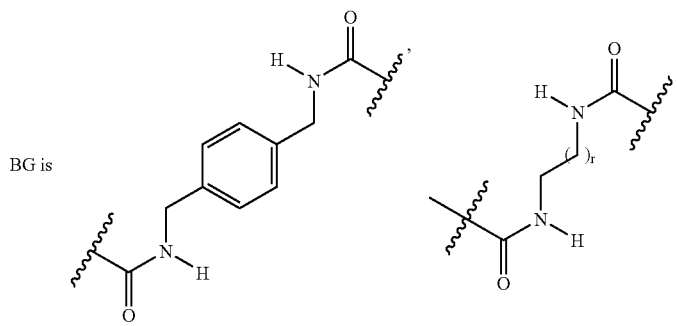
BG is
| M1 | M2 |
|---|---|
| 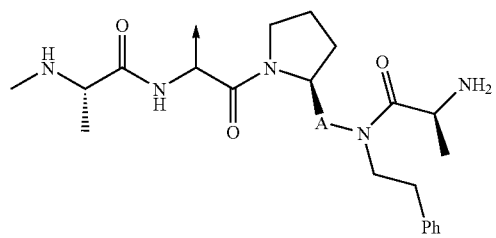<br>A = CH₂ | 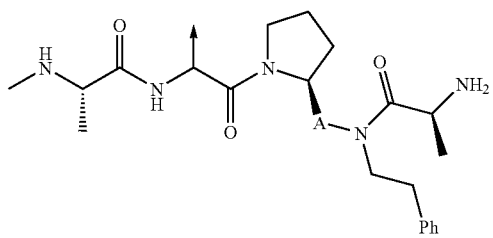<br>A = CH₂ |
| 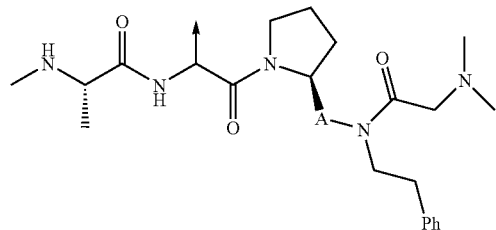<br>A = CH₂ | 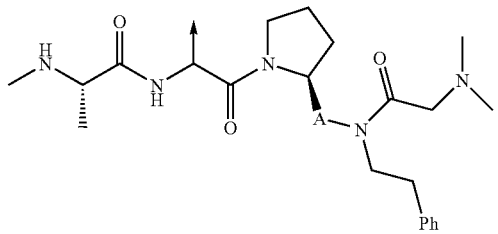<br>A = CH₂ |
| 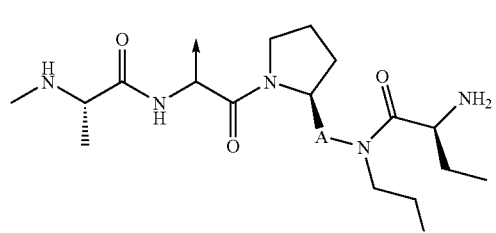<br>A = CH₂ | 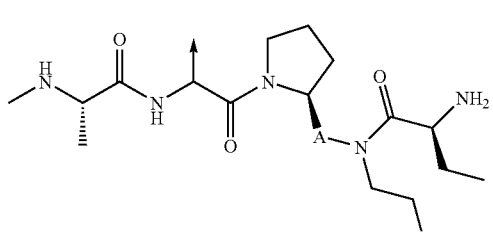<br>A = CH₂ |
| 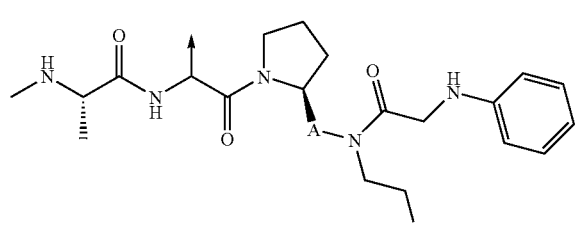<br>A = CH₂ | 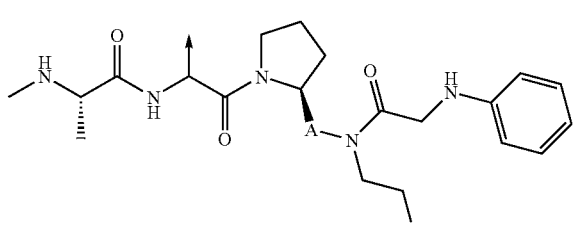<br>A = CH₂ |

TABLE 4-continued
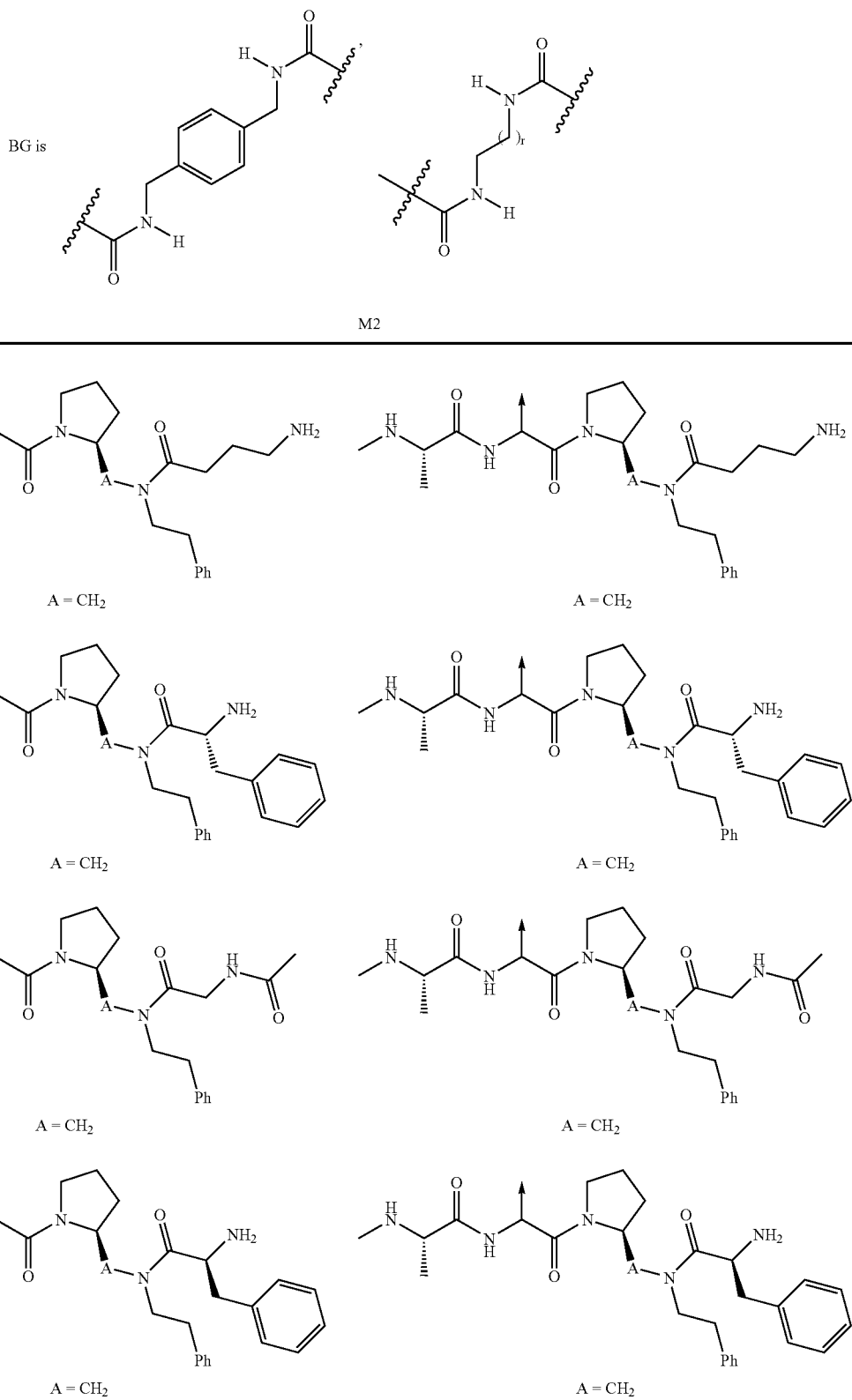

TABLE 4-continued
Formula 1B
$$M1-B-BG-B^1-M2$$
BG is 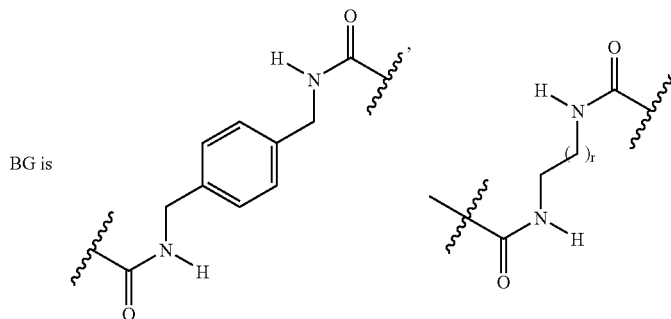
| M1 | M2 |
|---|---|
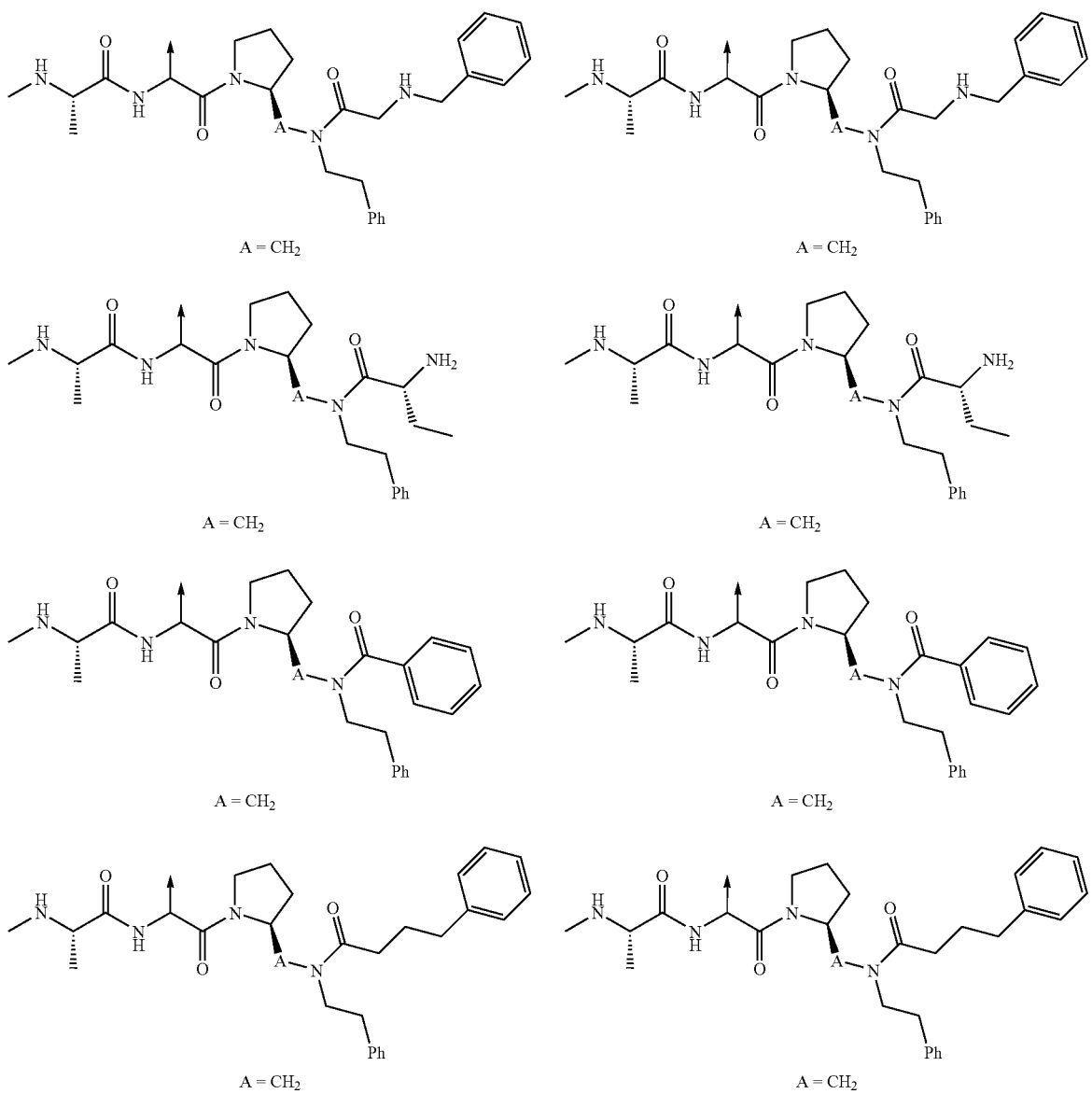

TABLE 4-continued
Formula 1B
M1—B—BG—B¹—M2
BG is 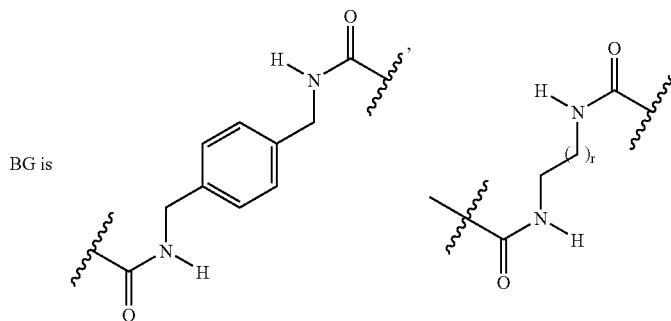
| M1 | M2 |
|---|---|
| 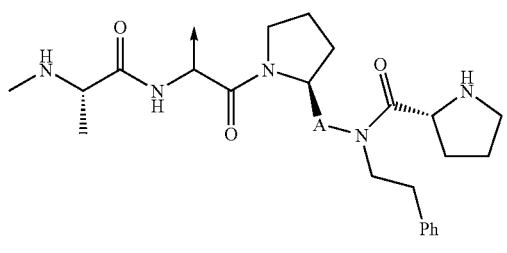  A = CH₂ | 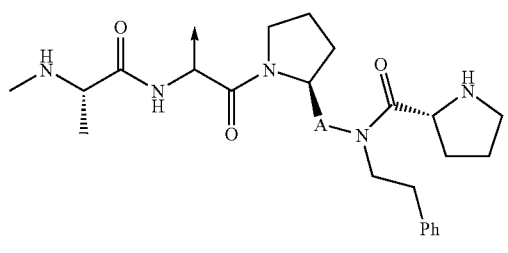  A = CH₂ |
| 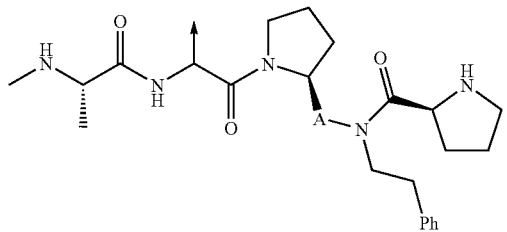  A = CH₂ | 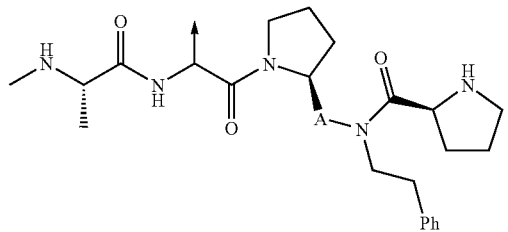  A = CH₂ |
| 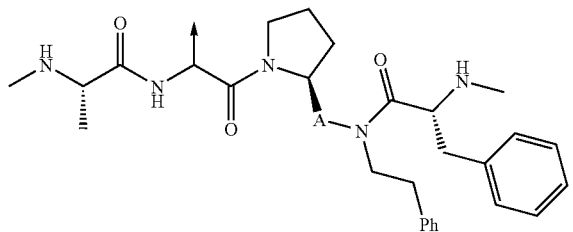  A = CH₂ or C=O | 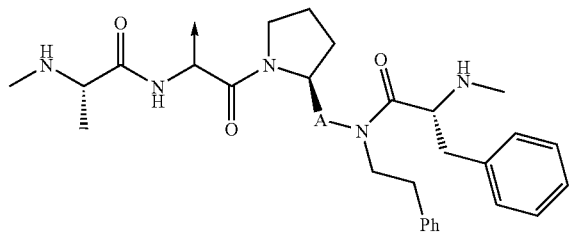  A = CH₂ or C=O |
| 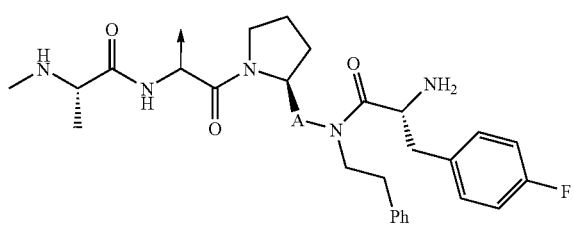  A = CH₂ | 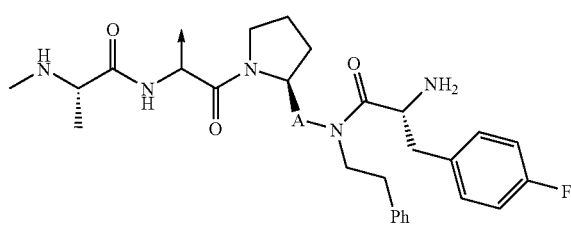  A = CH₂ |

TABLE 4-continued
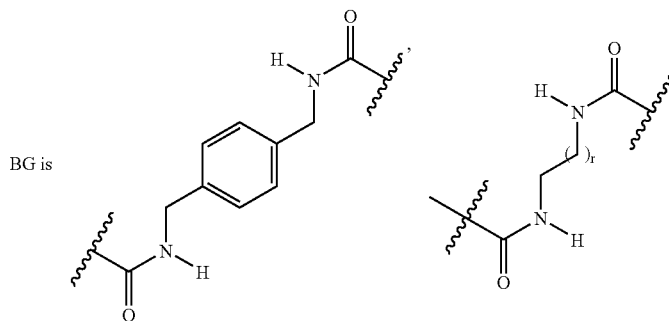
| M1 | M2 |
|---|---|
| 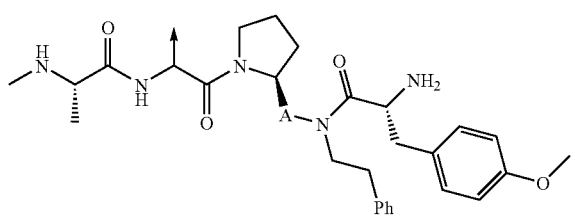<br>A = CH$_2$ | 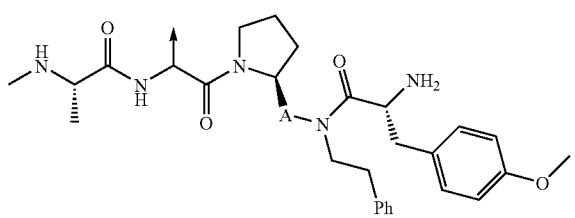<br>A = CH$_2$ |
| 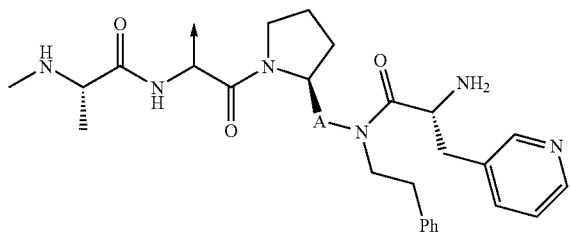<br>A = CH$_2$ | 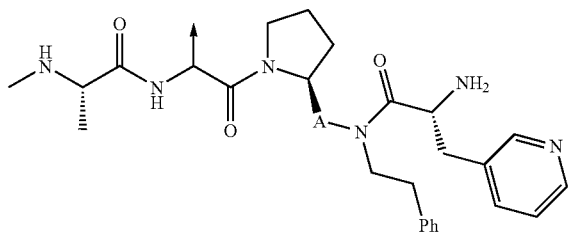<br>A = CH$_2$ |
| 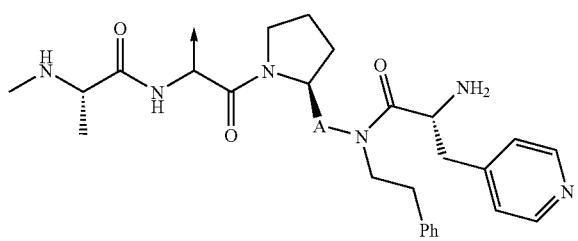<br>A = CH$_2$ | 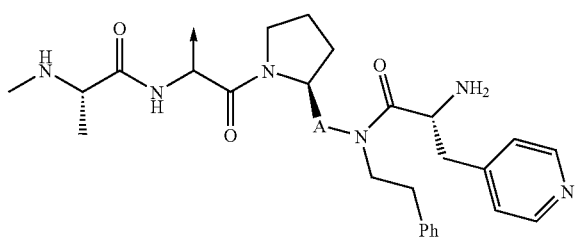<br>A = CH$_2$ |
| 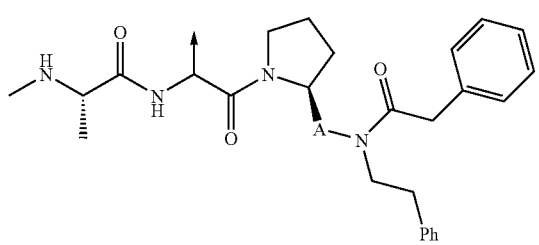<br>A = CH$_2$ | 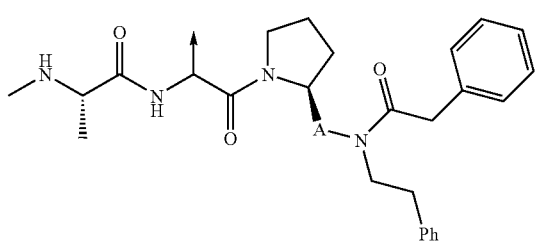<br>A = CH$_2$ |

TABLE 4-continued
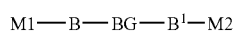
Formula 1B
BG is 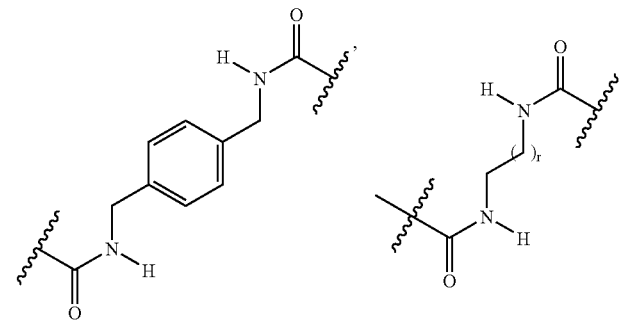
| M1 | M2 |
|---|---|
| 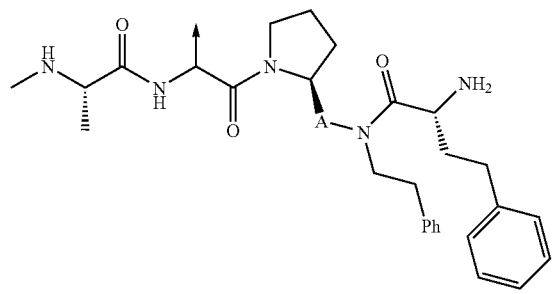  A = CH$_2$ | 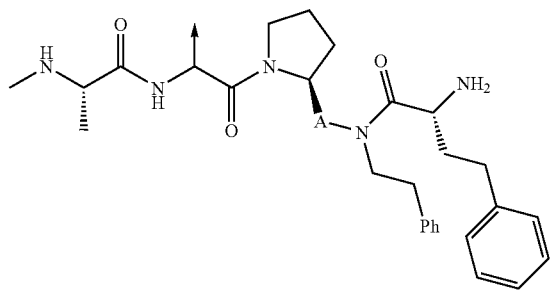  A = CH$_2$ |
| 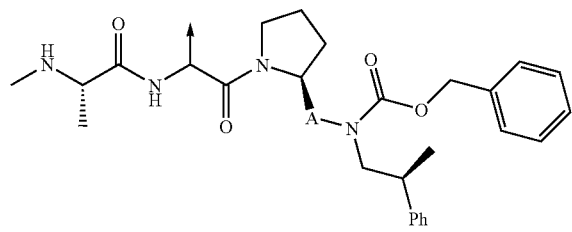  A = CH$_2$ | 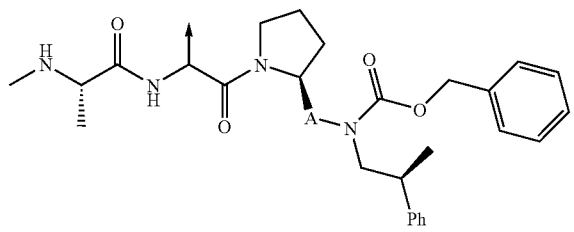  A = CH$_2$ |
| 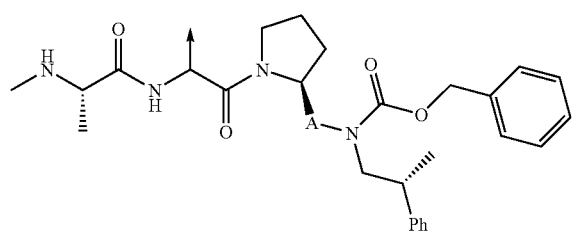  A = CH$_2$ | 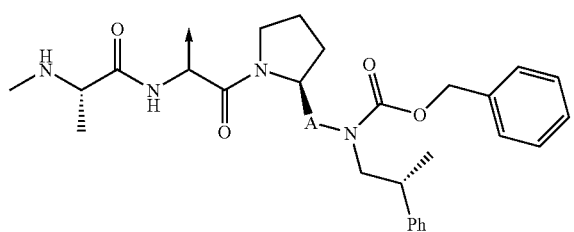  A = CH$_2$ |

TABLE 4-continued
Formula 1B
M1—B—BG—B¹—M2
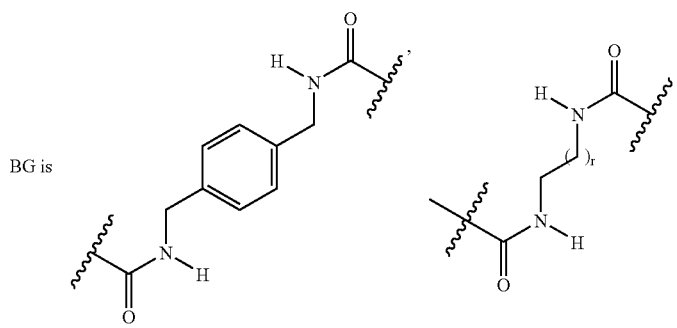
| M1 | M2 |
|---|---|
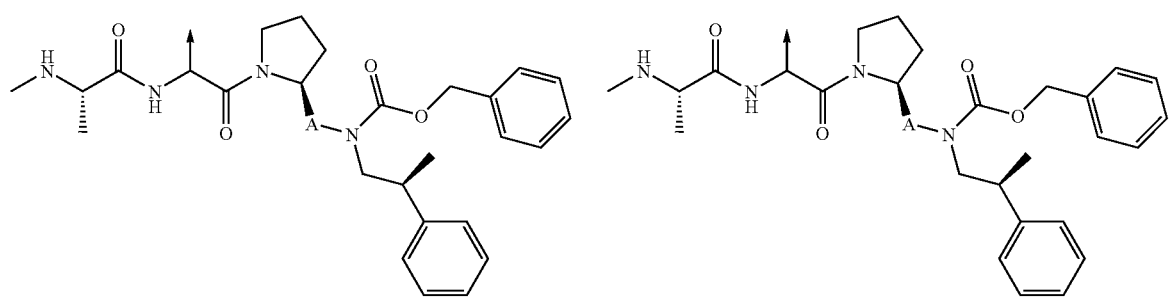
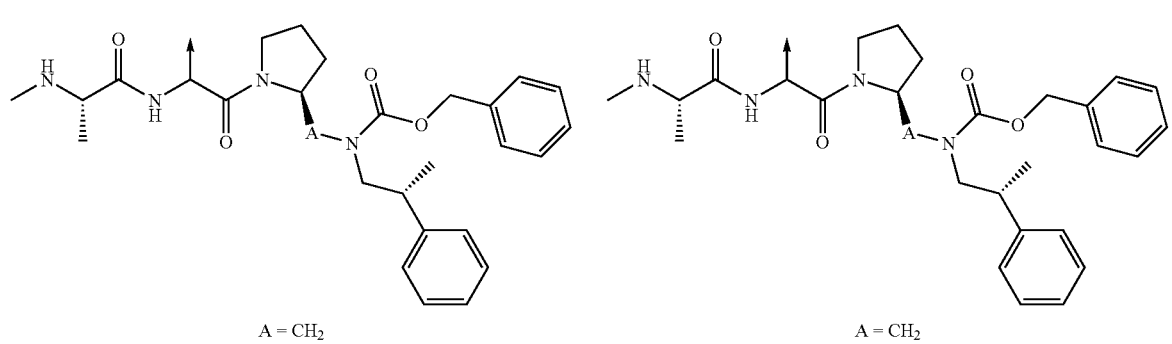
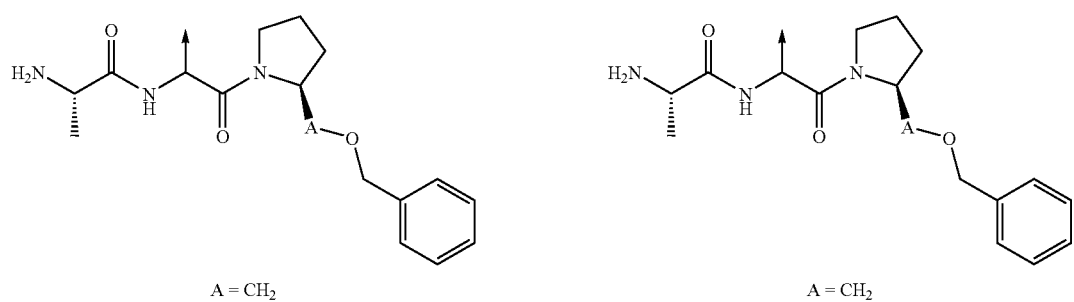

TABLE 4-continued
Formula 1B
$$M1 - B - BG - B^1 - M2$$
BG is 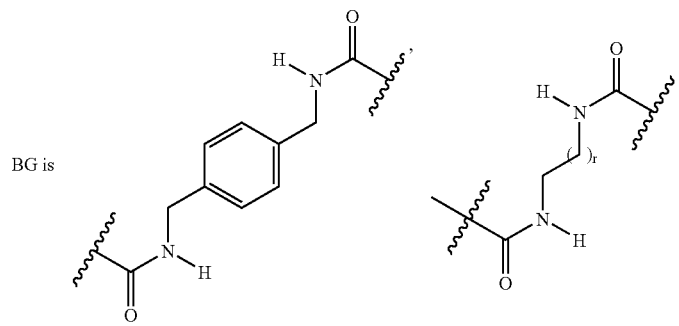
| M1 | M2 |
|---|---|
| 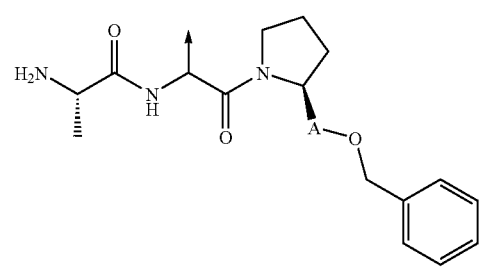 <br> A = CH₂ | 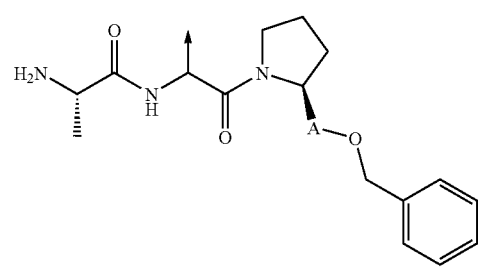 <br> A = CH₂ |
| 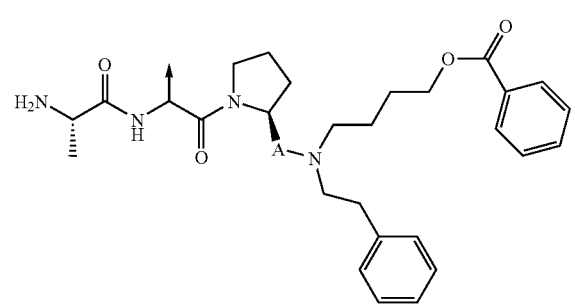 <br> A = CH₂ or C=O | 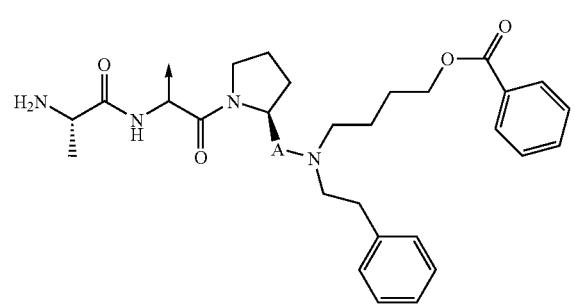 <br> A = CH₂ or C=O |
| 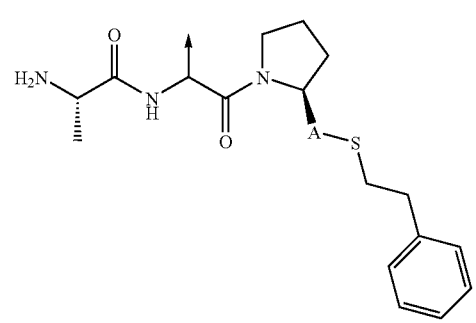 <br> A = CH₂ | 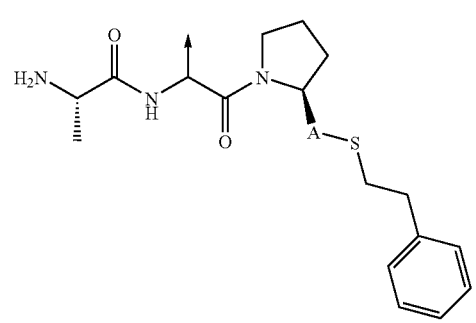 <br> A = CH₂ |

TABLE 4-continued
Formula 1B
M1—B—BG—B¹—M2
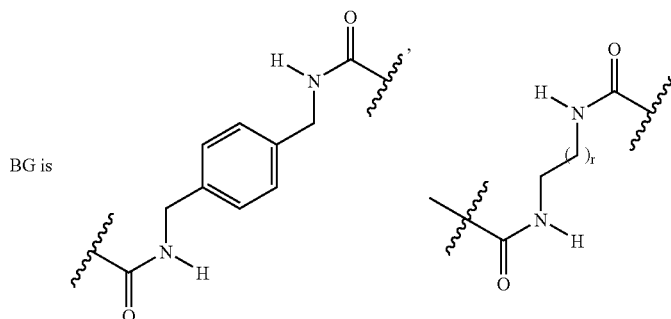
BG is
| M1 | M2 |
| --- | --- |
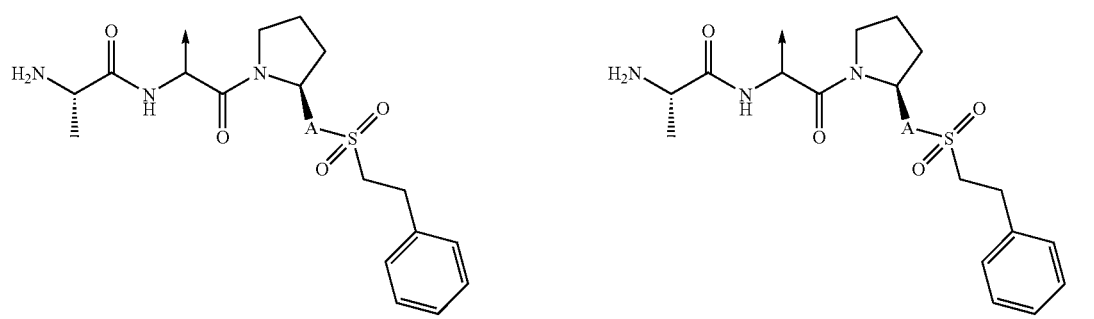
A = CH₂        A = CH₂
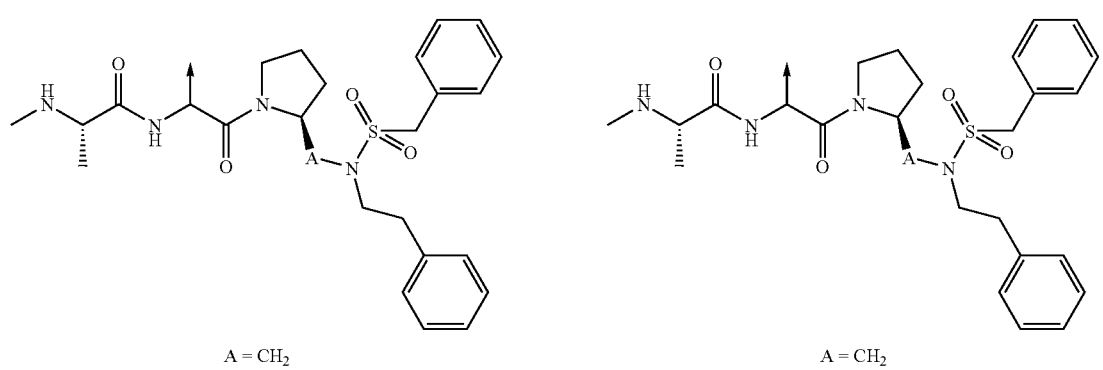
A = CH₂        A = CH₂
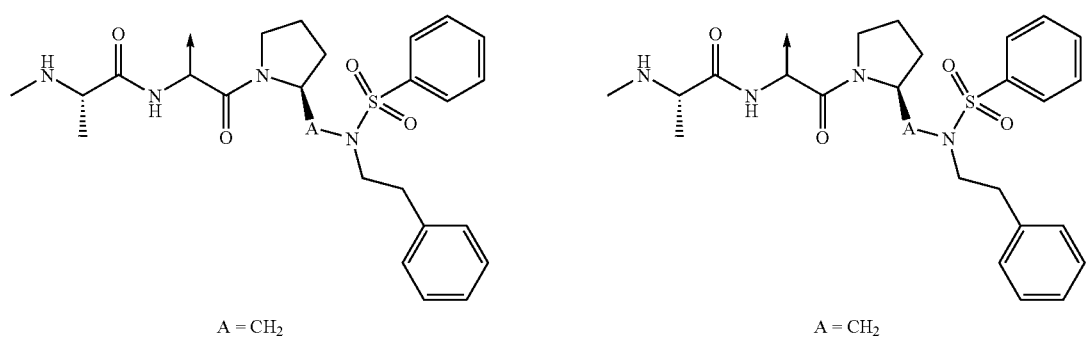
A = CH₂        A = CH₂

TABLE 4-continued
Formula 1B
M1—B—BG—B¹—M2
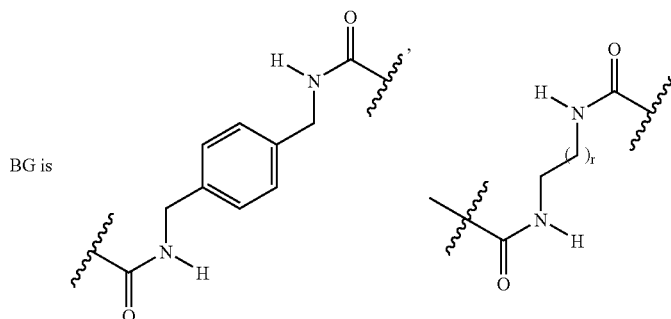
BG is
| M1 | M2 |
|---|---|
| 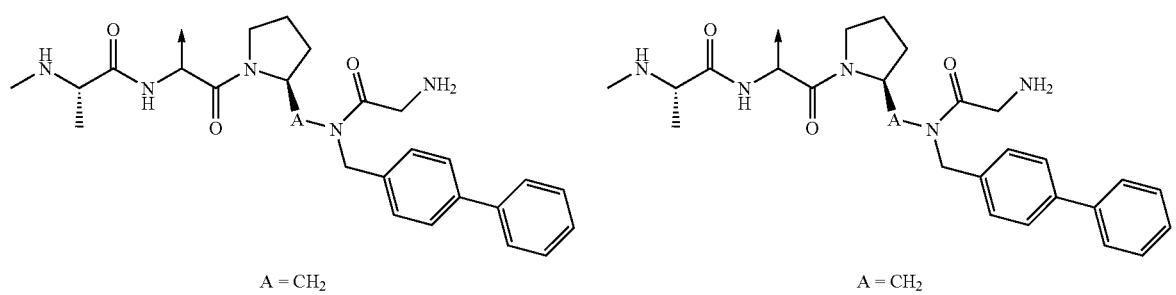 | |
| A = CH₂ | A = CH₂ |
| 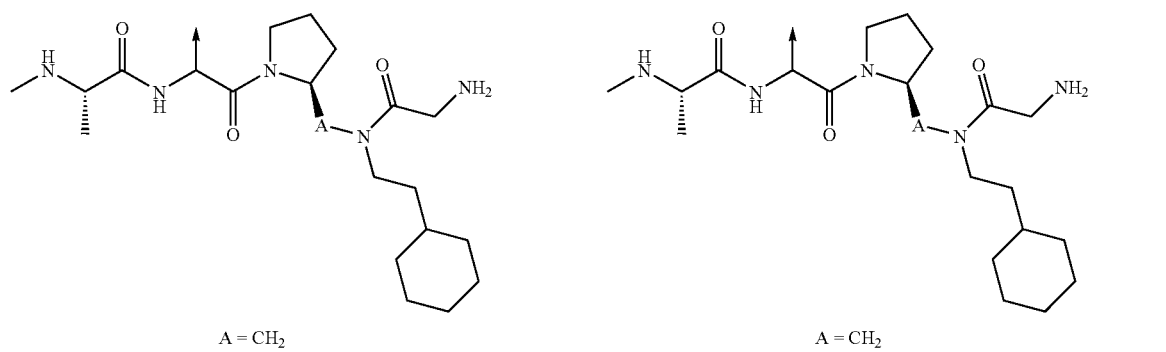 | |
| A = CH₂ | A = CH₂ |
| 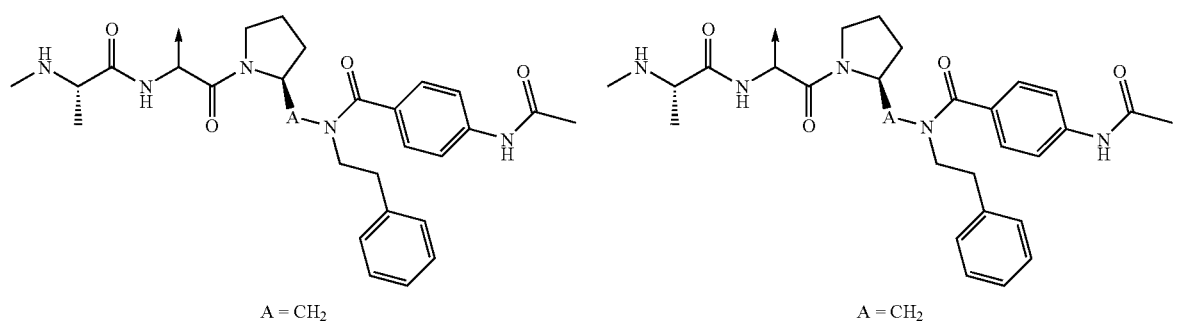 | |
| A = CH₂ | A = CH₂ |

TABLE 4-continued
Formula 1B
M1—B—BG—B¹—M2
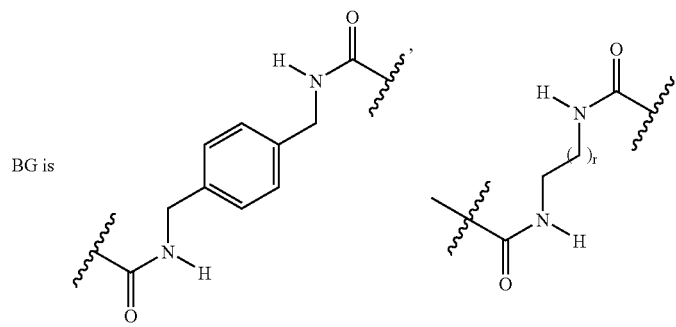
BG is
| M1 | M2 |
|---|---|
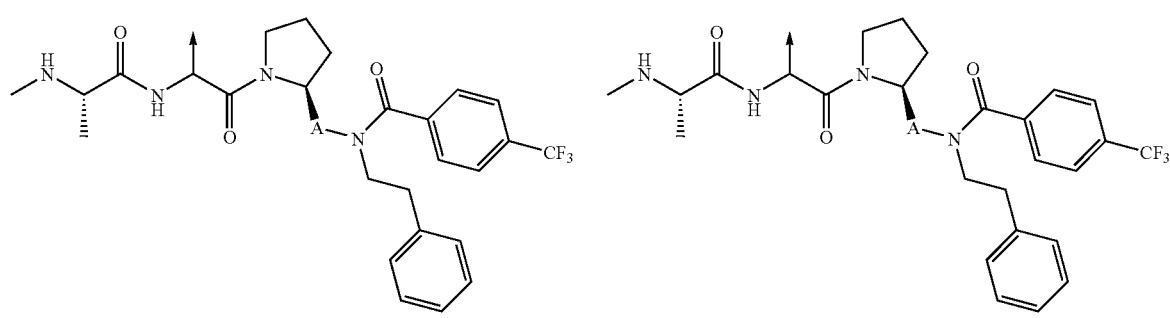
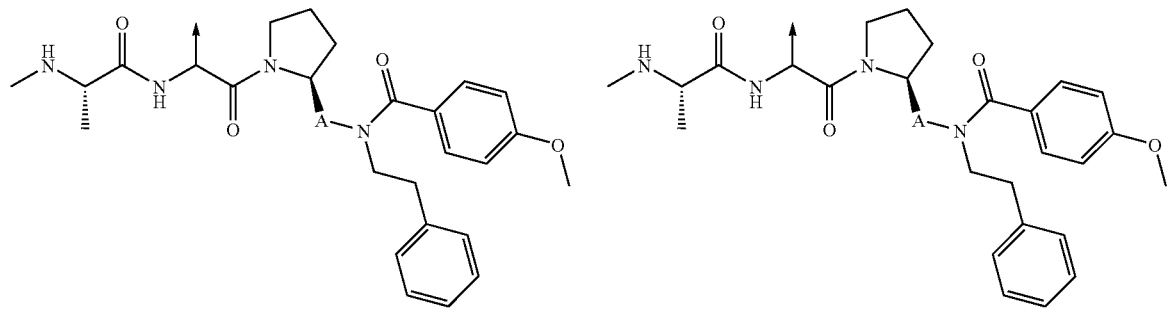
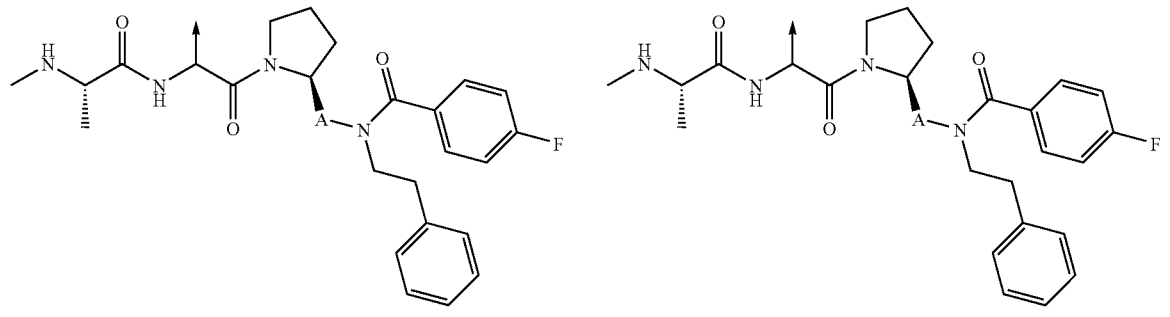

TABLE 4-continued
Formula 1B
M1—B—BG—B¹—M2
BG is 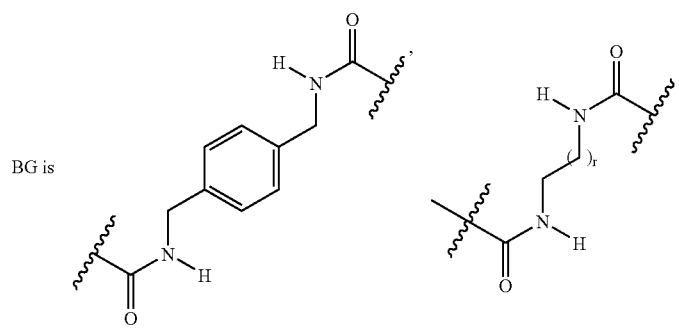
| M1 | M2 |
|---|---|
| 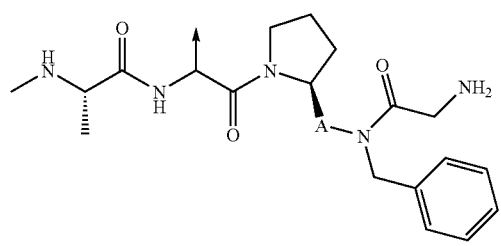<br>A = CH₂ | 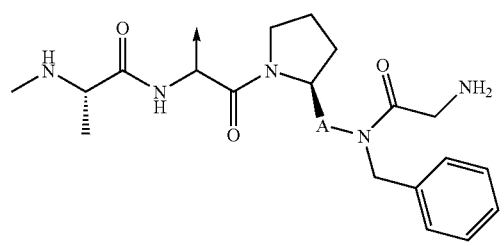<br>A = CH₂ |
| 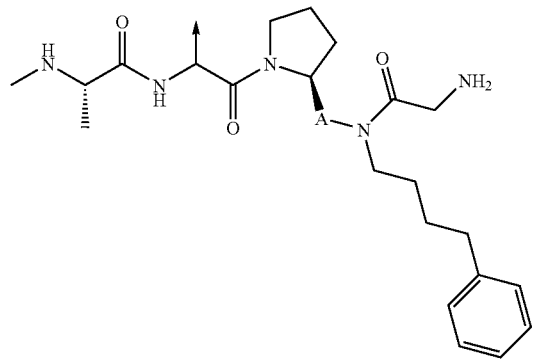<br>A = CH₂ | 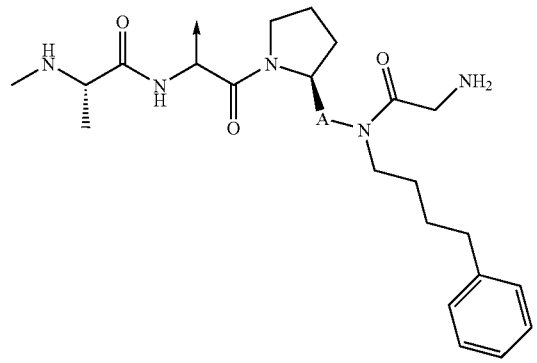<br>A = CH₂ |
| 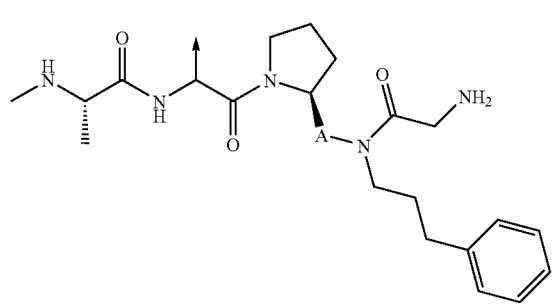<br>A = CH₂ | 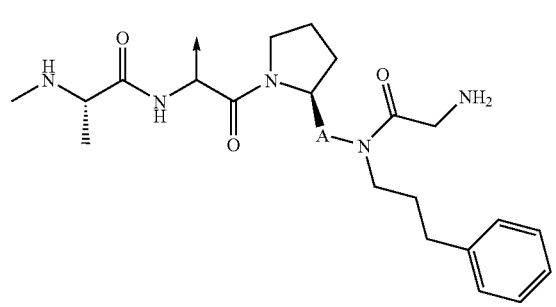<br>A = CH₂ |

TABLE 4-continued
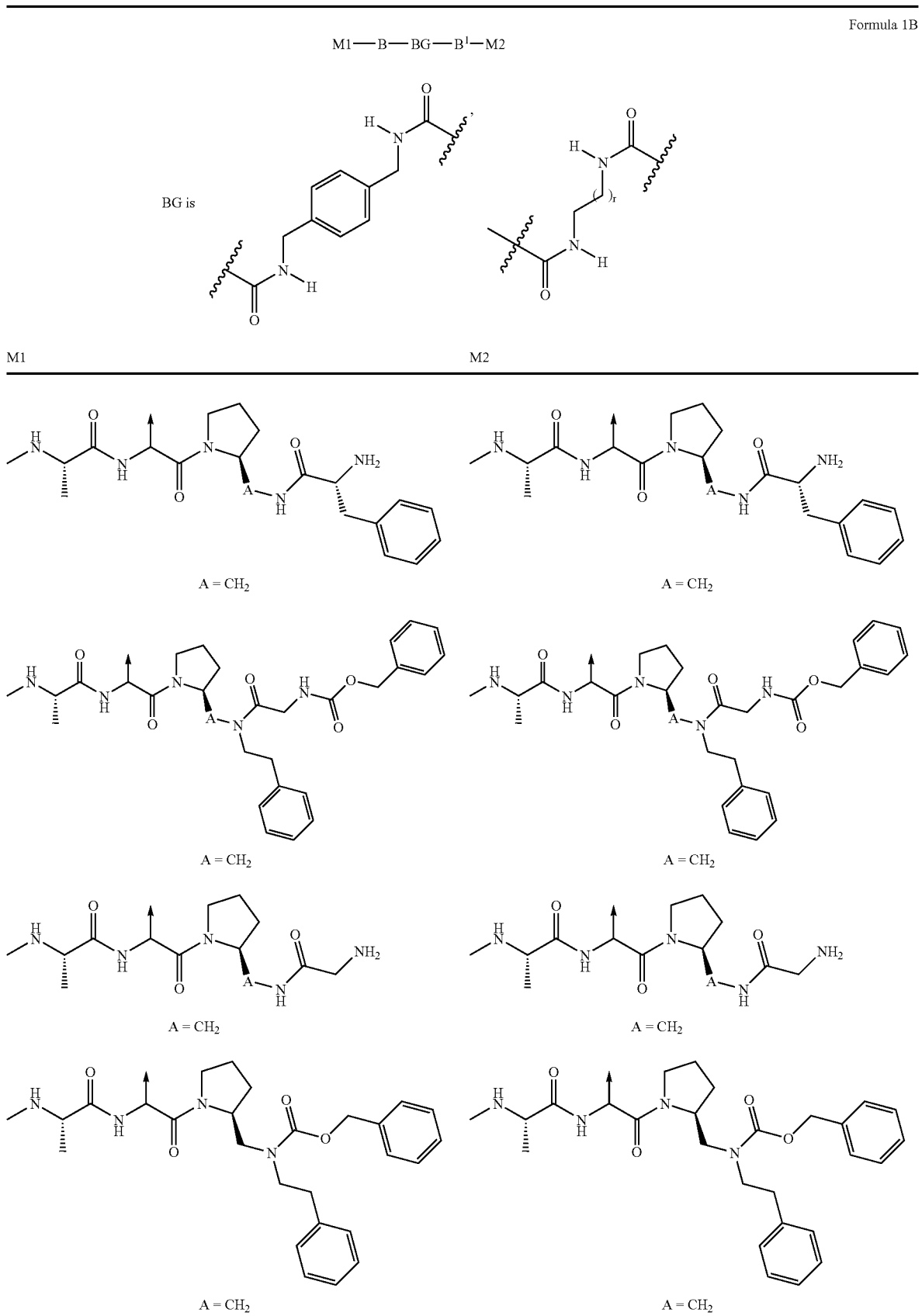

TABLE 4-continued
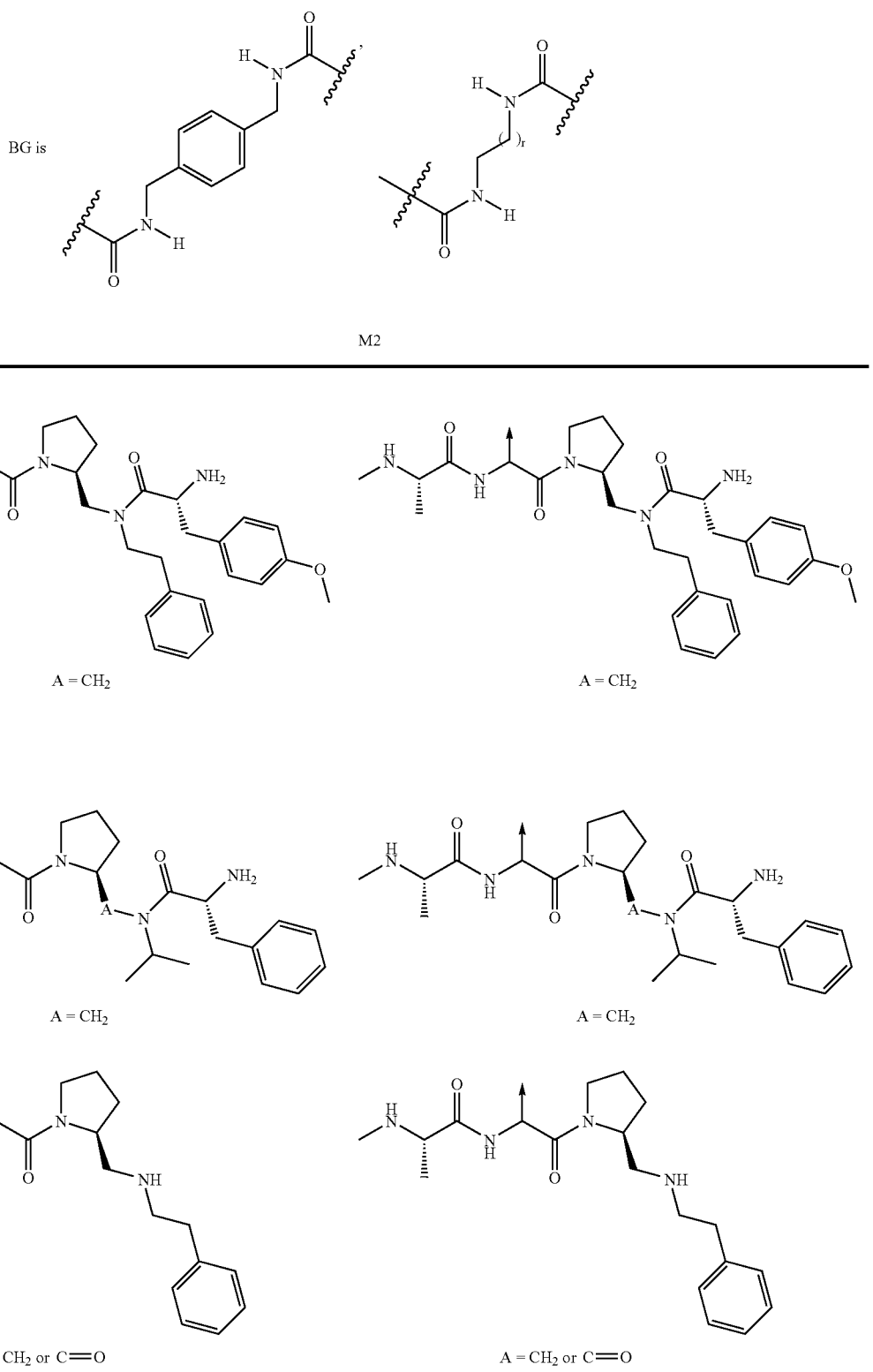

TABLE 4-continued
Formula 1B
M1—B—BG—B¹—M2
BG is 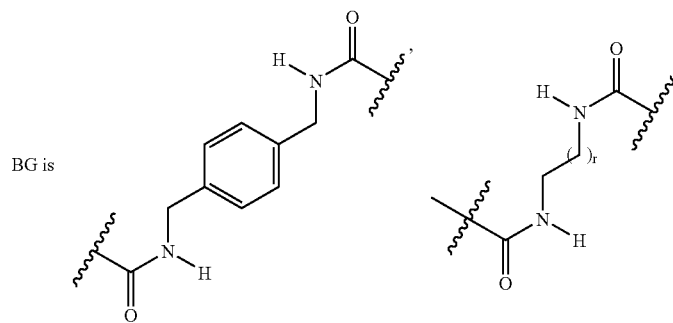
| M1 | M2 |
|---|---|
| 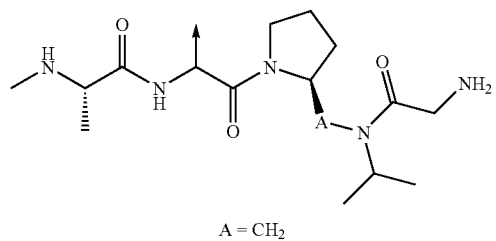<br>A = CH₂ | 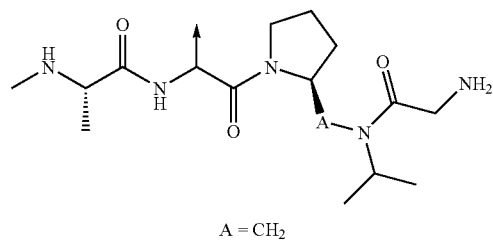<br>A = CH₂ |
| 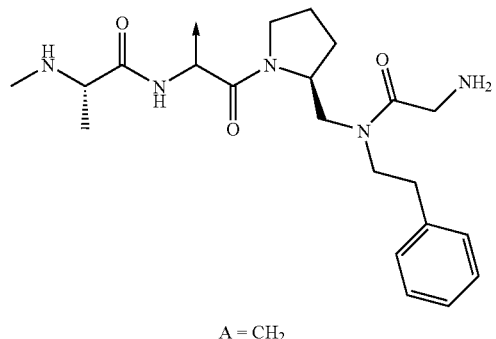<br>A = CH₂ | 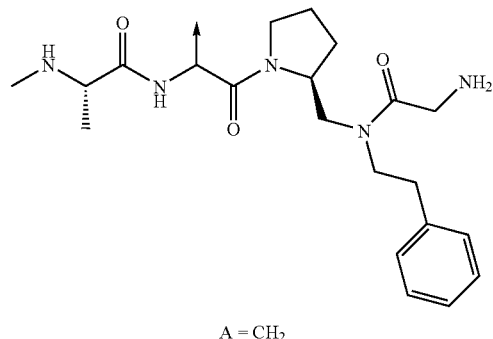<br>A = CH₂ |
| 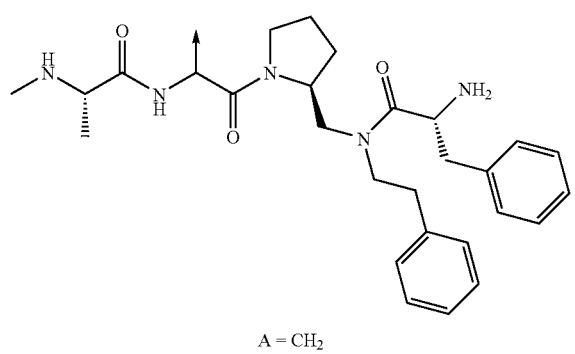<br>A = CH₂ | 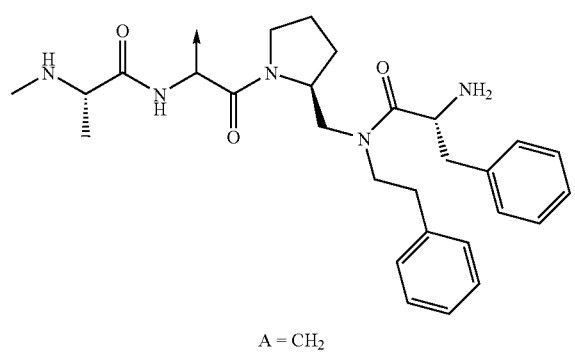<br>A = CH₂ |

TABLE 4-continued
Formula 1B
M1—B—BG—B¹—M2
BG is 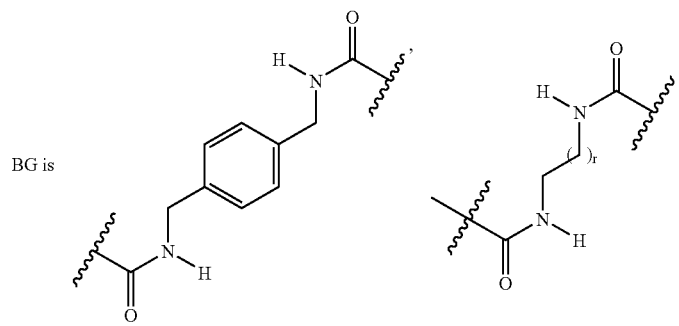
| M1 | M2 |
|---|---|
| 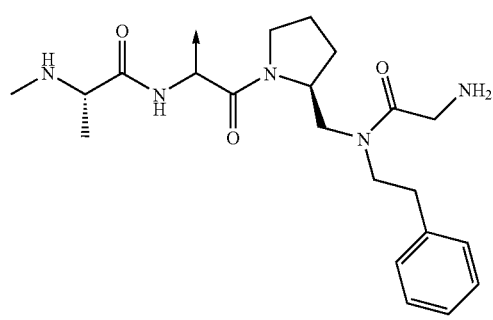<br>A = CH$_2$ | 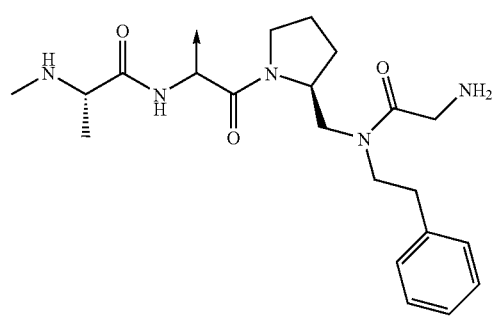<br>A = CH$_2$ |
| 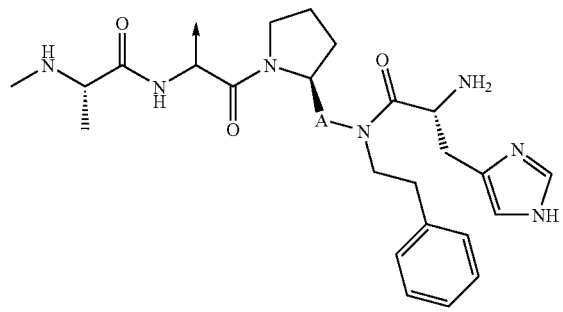<br>A = CH$_2$ | 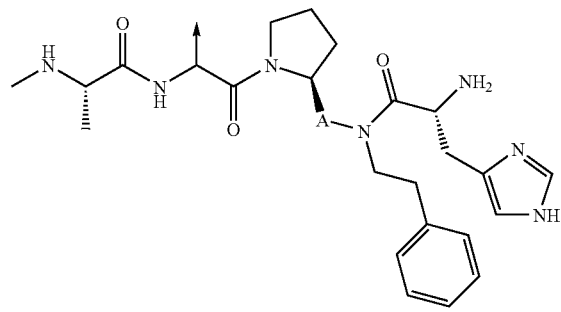<br>A = CH$_2$ |
| 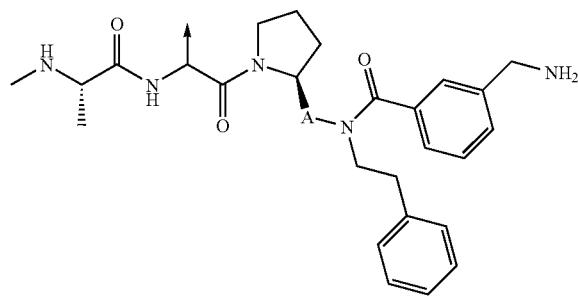<br>A = CH$_2$ | 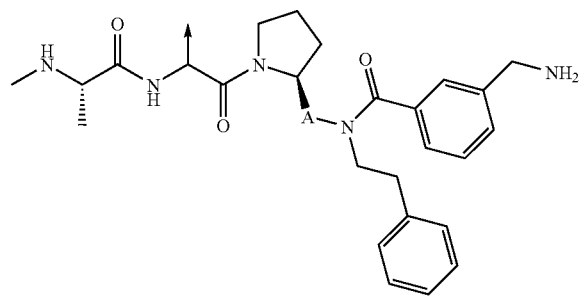<br>A = CH$_2$ |

TABLE 4-continued
Formula 1B
M1—B—BG—B¹—M2
BG is 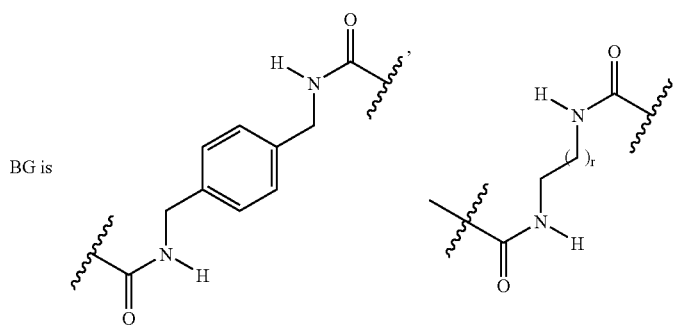
| M1 | M2 |
| --- | --- |
| 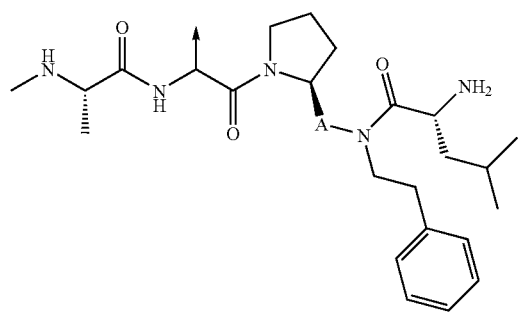<br>A = CH₂ | 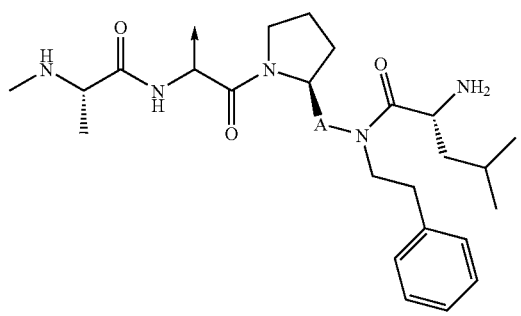<br>A = CH₂ |
| 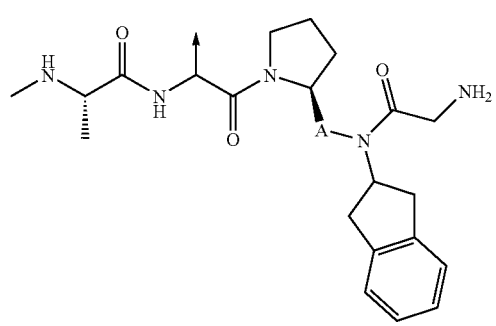<br>A = CH₂ | 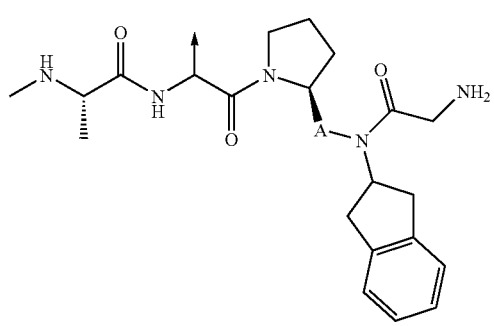<br>A = CH₂ |
| 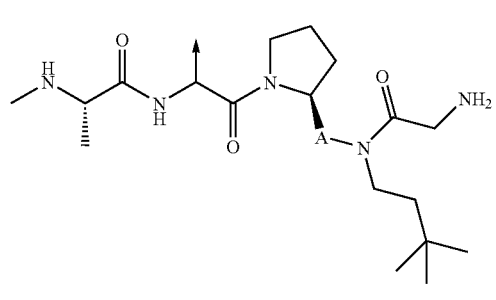<br>A = CH₂ | 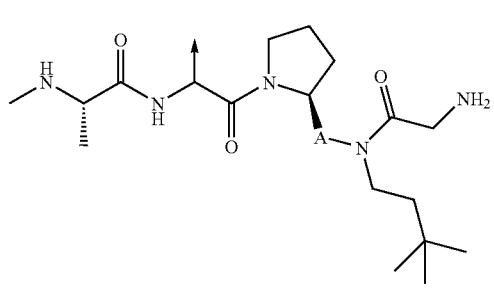<br>A = CH₂ |

TABLE 4-continued
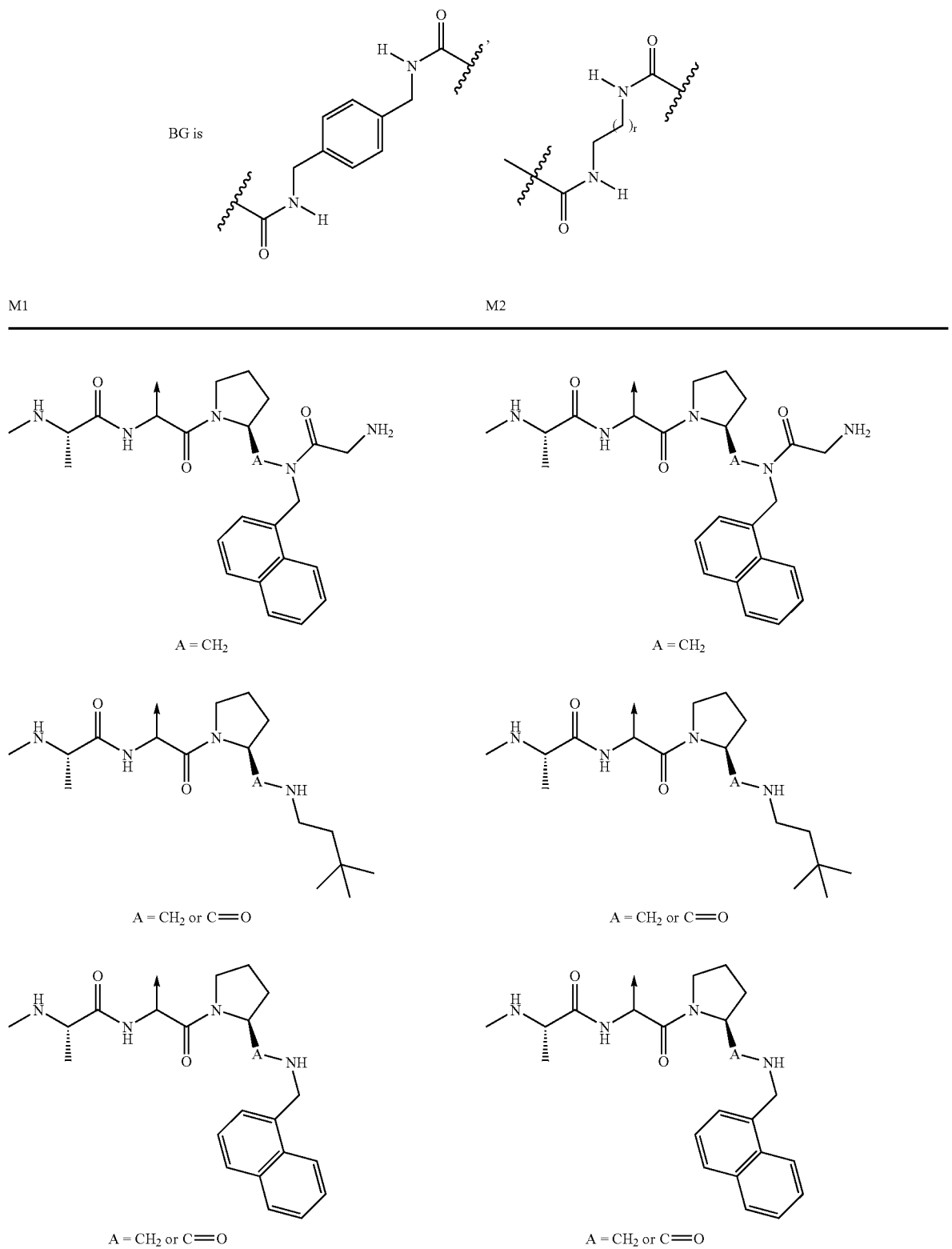

TABLE 4-continued
Formula 1B
M1—B—BG—B¹—M2
BG is 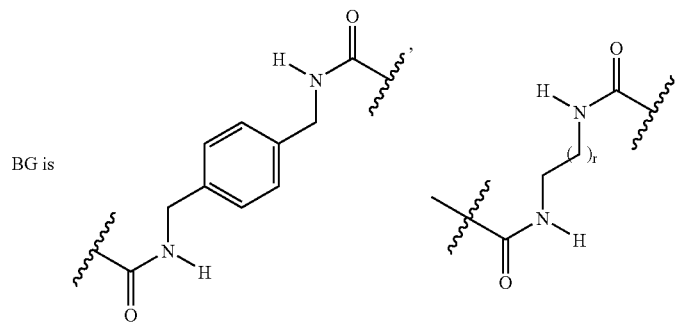
| M1 | M2 |
|---|---|
| 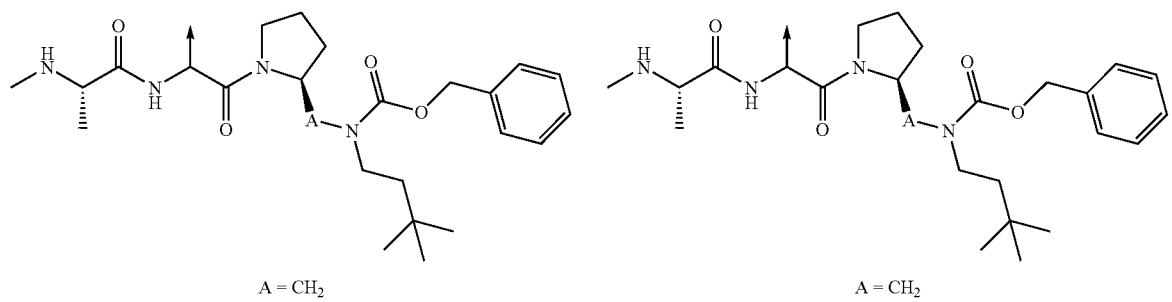 | |
| A = CH₂ | A = CH₂ |
| 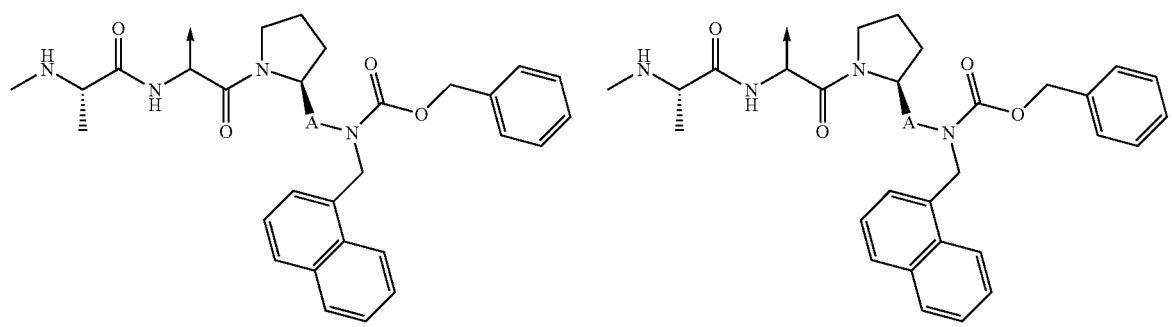 | |
| A = CH₂ | A = CH₂ |
| 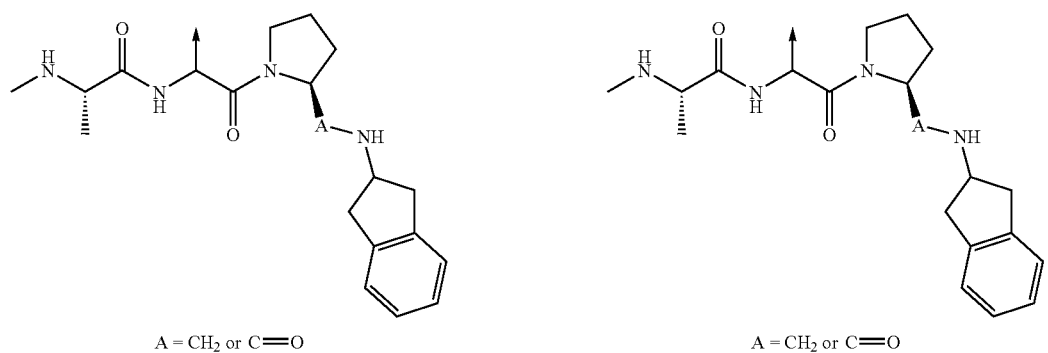 | |
| A = CH₂ or C=O | A = CH₂ or C=O |

TABLE 4-continued
Formula 1B
$$M1-B-BG-B^1-M2$$
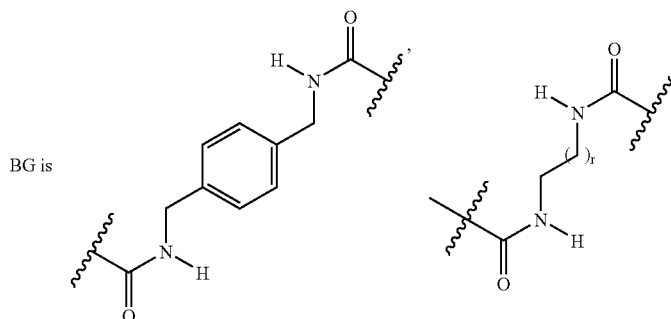
BG is
| M1 | M2 |
|---|---|
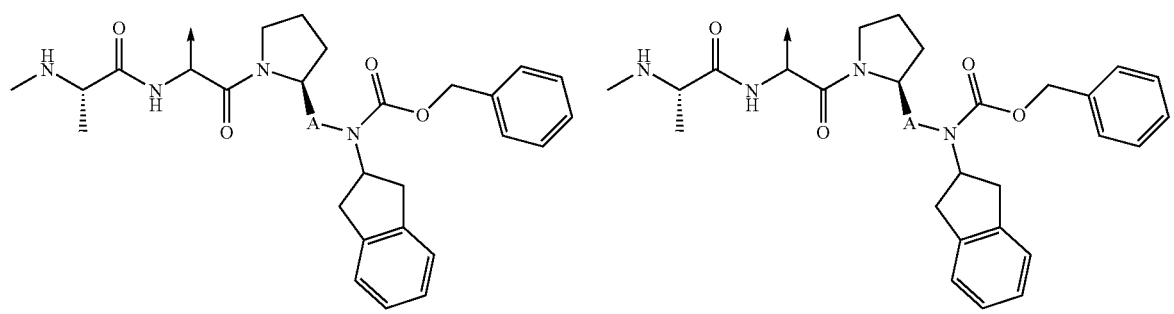
A = CH₂          A = CH₂
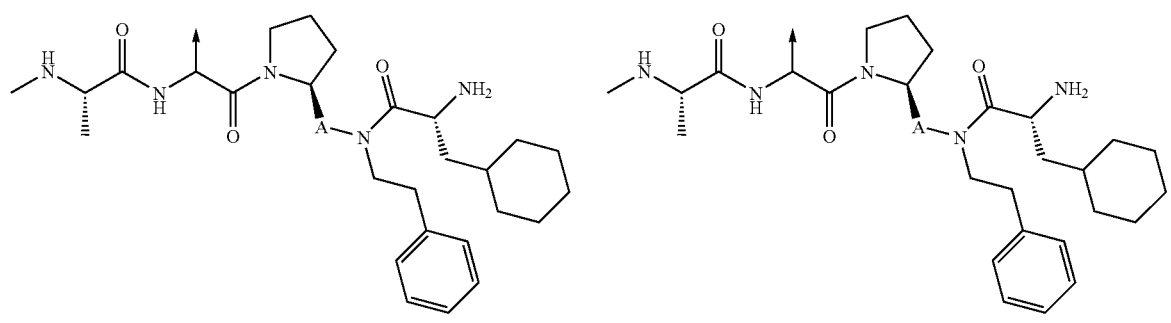
A = CH₂          A = CH₂
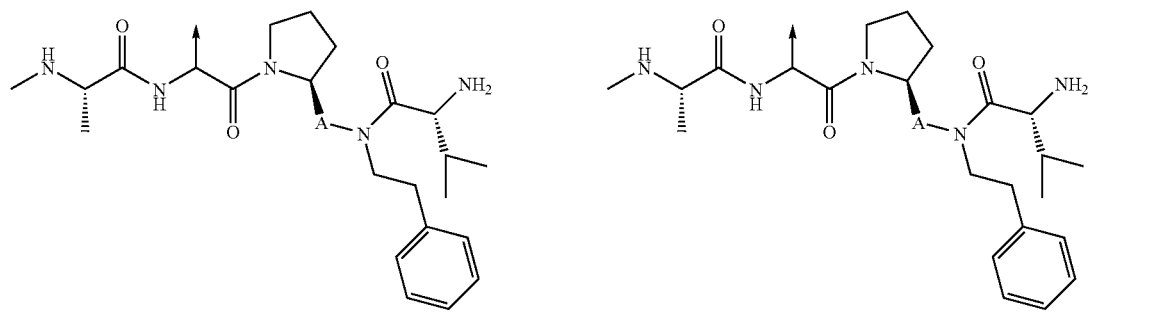
A = CH₂          A = CH₂

TABLE 4-continued
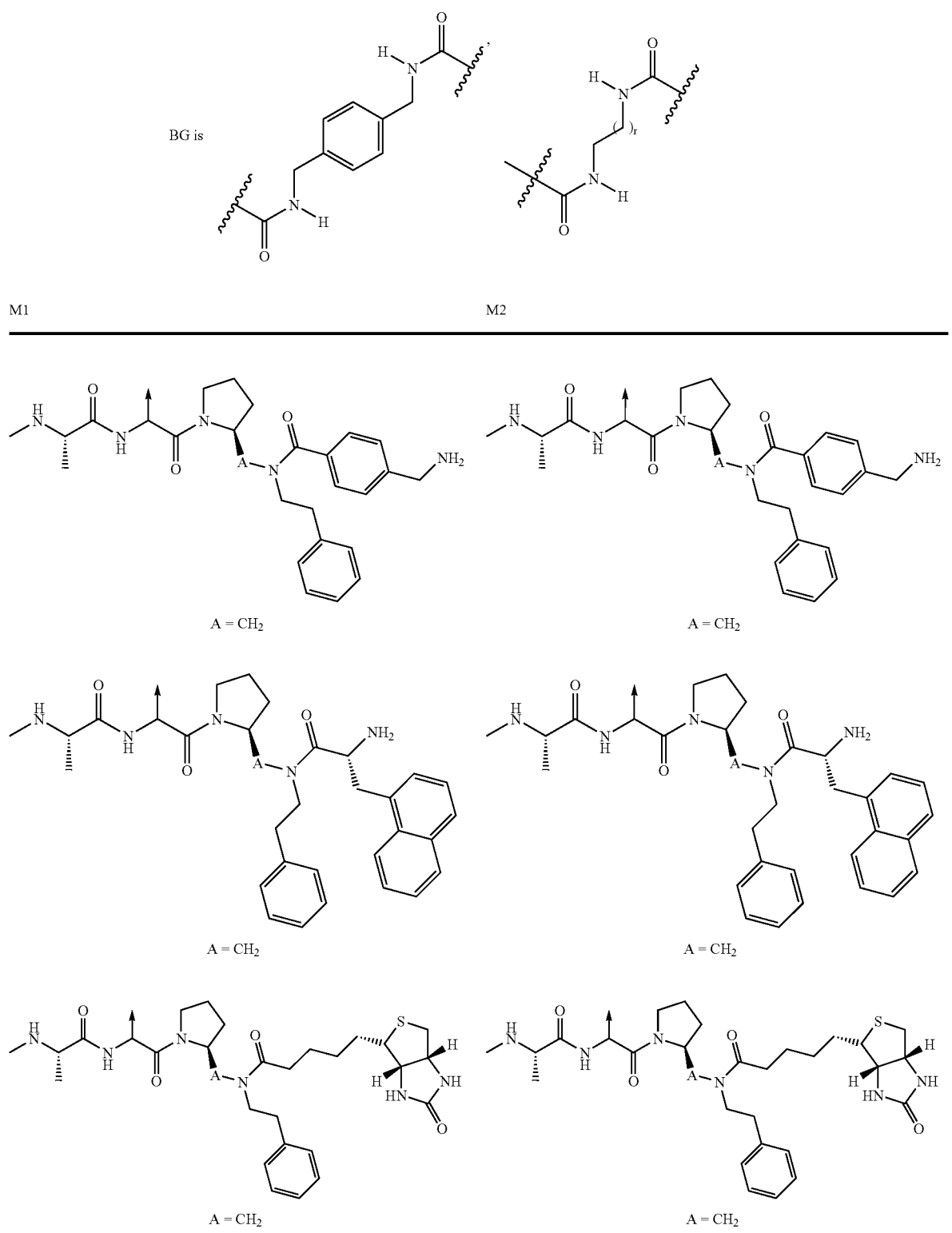

TABLE 4-continued
Formula 1B
M1—B—BG—B¹—M2
BG is 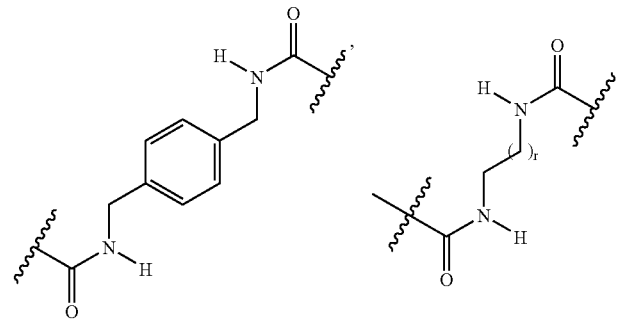
| M1 | M2 |
|---|---|
| 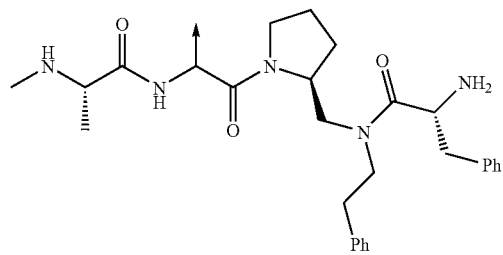<br>A = CH₂ | 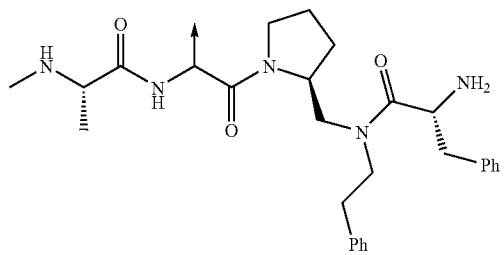<br>A = CH₂ |
| 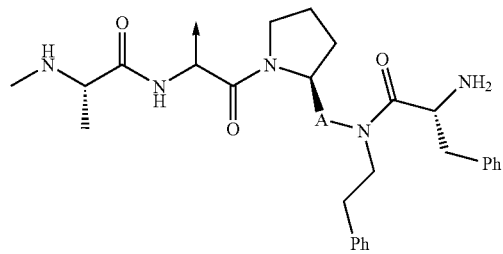<br>A = CH₂ | 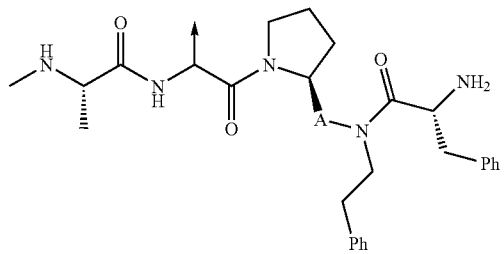<br>A = CH₂ |
| 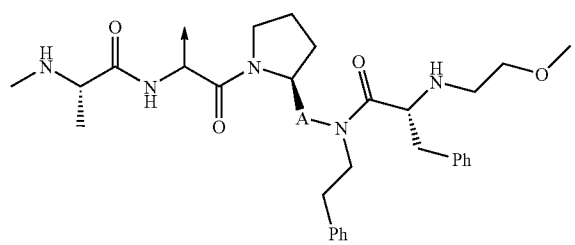<br>A = CH₂ | 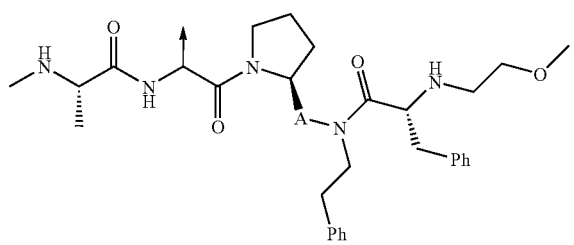<br>A = CH₂ |
| 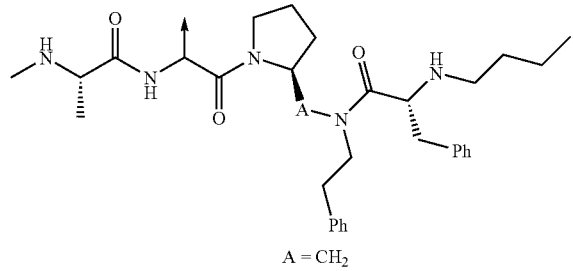<br>A = CH₂ | 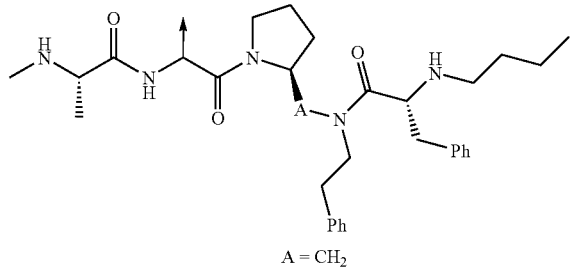<br>A = CH₂ |

TABLE 4-continued
Formula 1B
M1—B—BG—B¹—M2
BG is
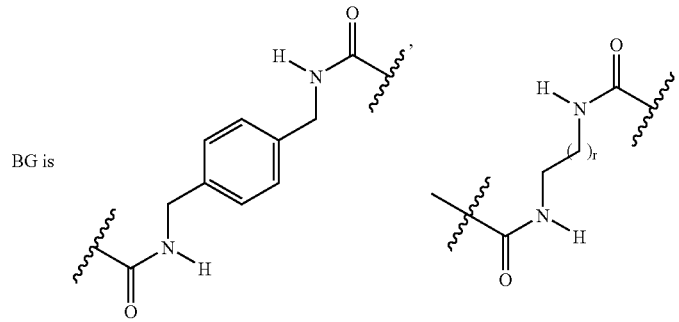
| M1 | M2 |
|---|---|
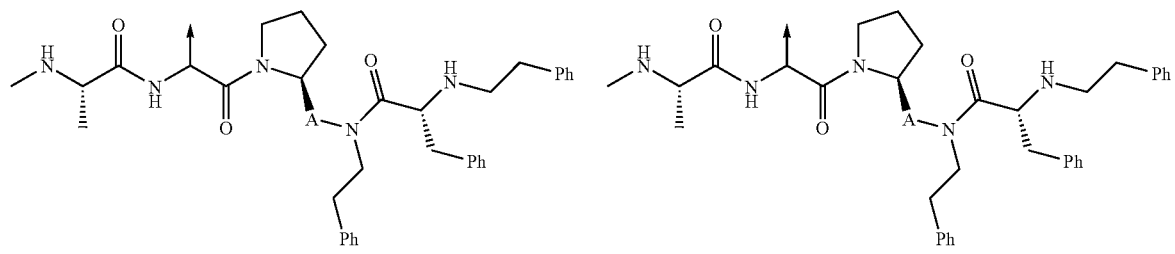
A = CH₂        A = CH₂
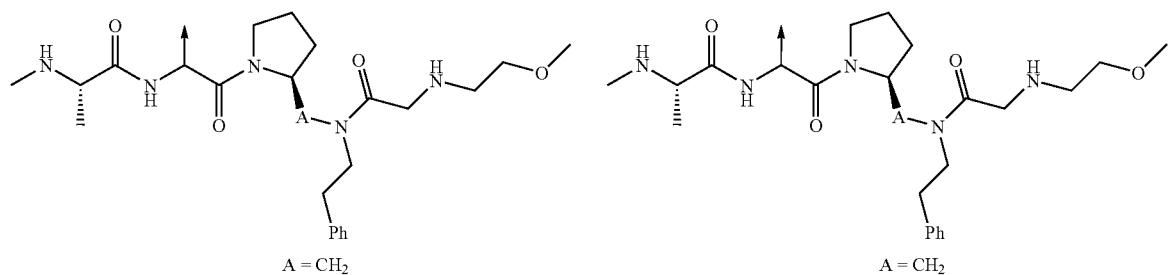
A = CH₂        A = CH₂
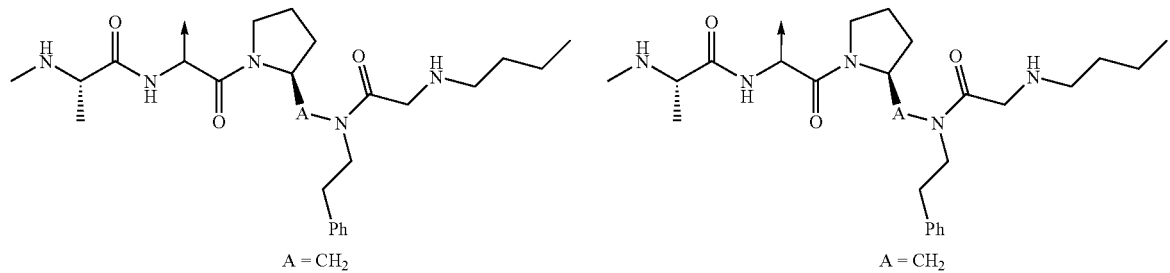
A = CH₂        A = CH₂
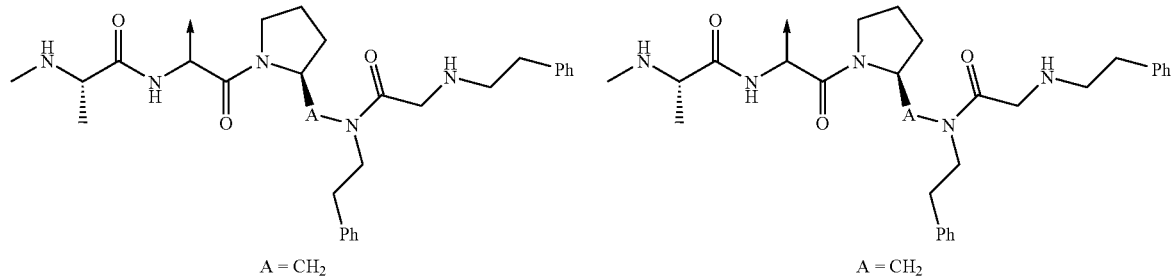
A = CH₂        A = CH₂

TABLE 4-continued
Formula 1B
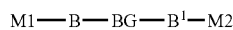
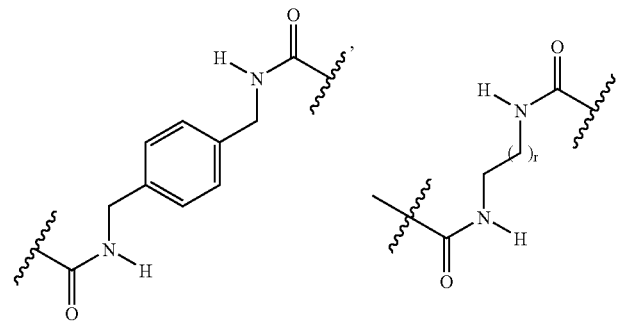
BG is
M1            M2
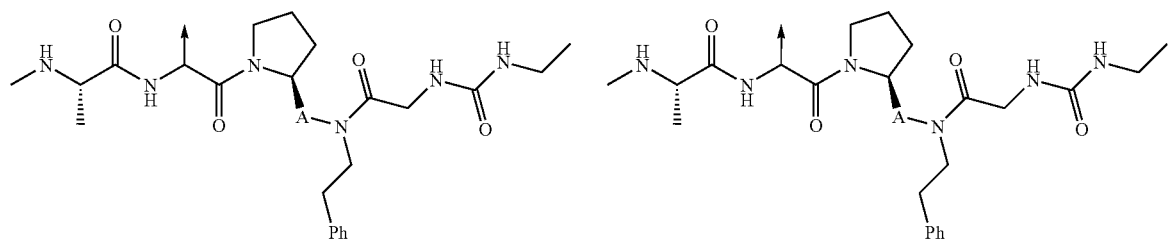
A = CH₂        A = CH₂
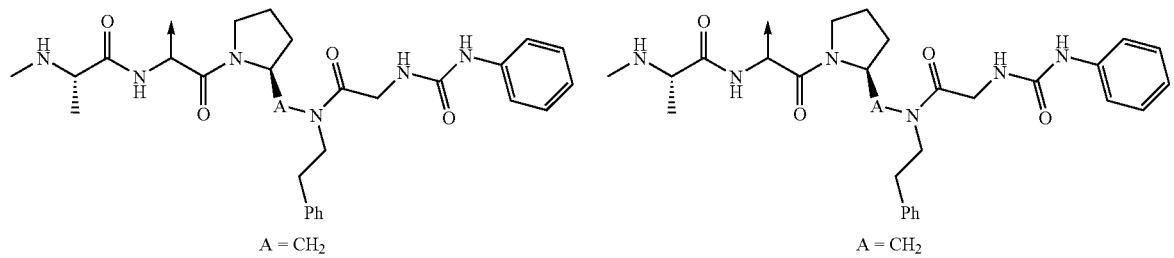
A = CH₂        A = CH₂
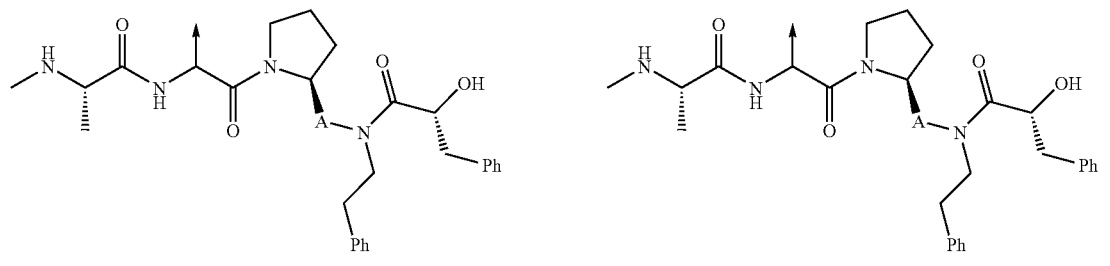
A = CH₂        A = CH₂
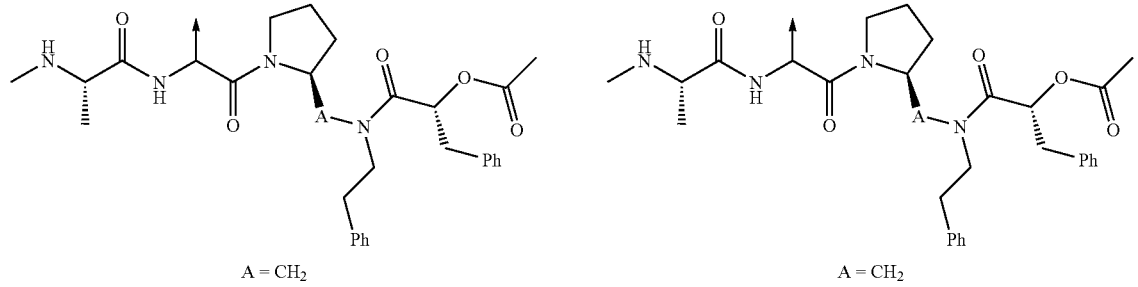
A = CH₂        A = CH₂

TABLE 4-continued
$$M1-B-BG-B^1-M2 \quad \text{Formula 1B}$$
BG is 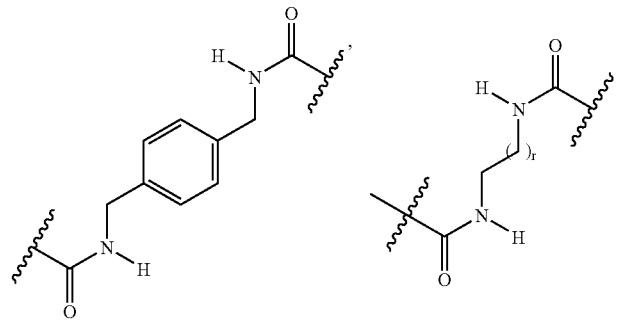
| M1 | M2 |
|---|---|
| 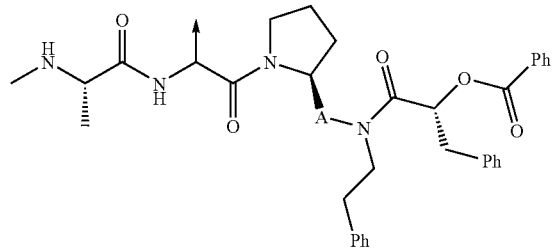 A = CH$_2$ | 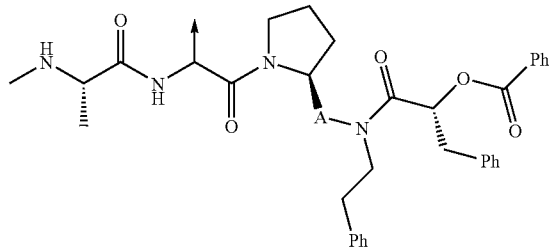 A = CH$_2$ |
| 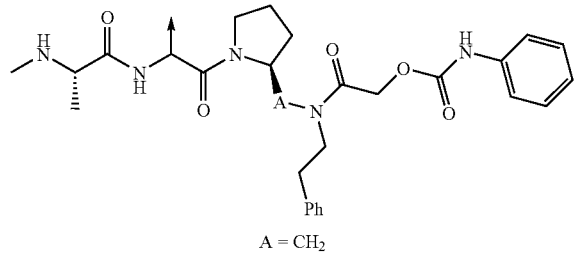 A = CH$_2$ | 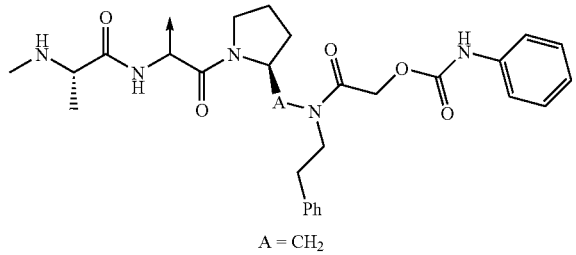 A = CH$_2$ |
| 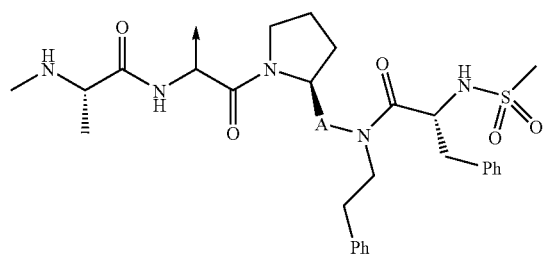 A = CH$_2$ | 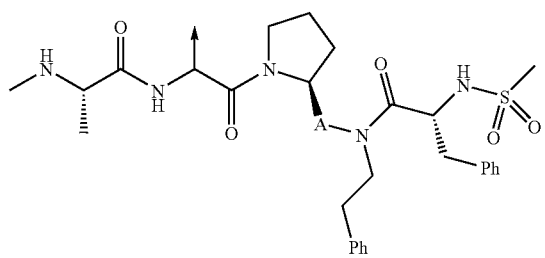 A = CH$_2$ |
| 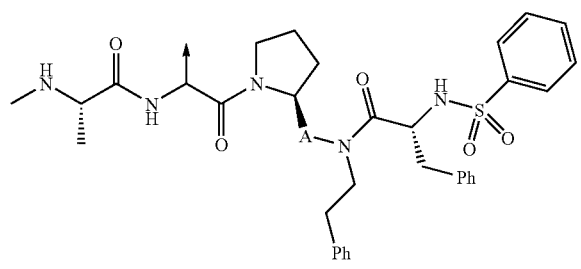 A = CH$_2$ | 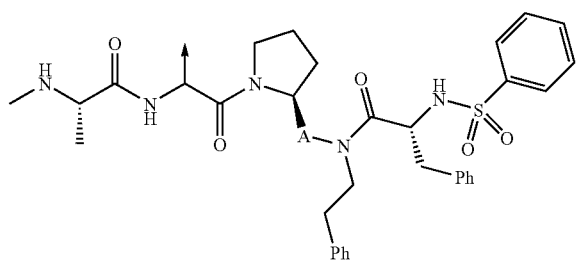 A = CH$_2$ |

TABLE 4-continued
Formula 1B
M1—B—BG—B¹—M2
BG is 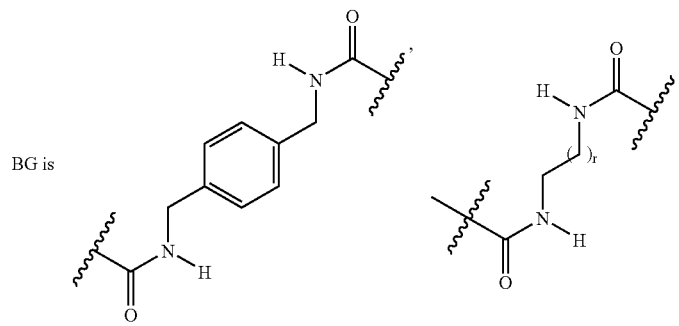
| M1 | M2 |
|---|---|
| 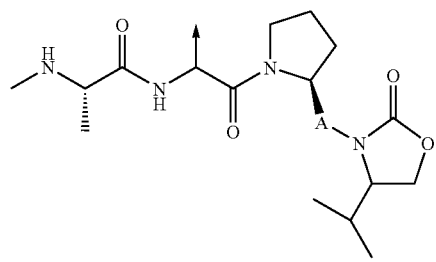<br>A = CH₂ | 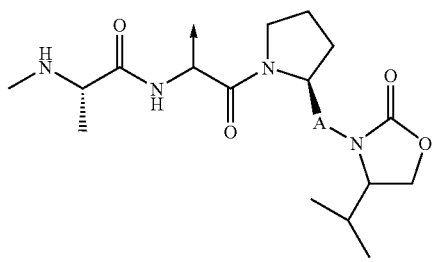<br>A = CH₂ |
| 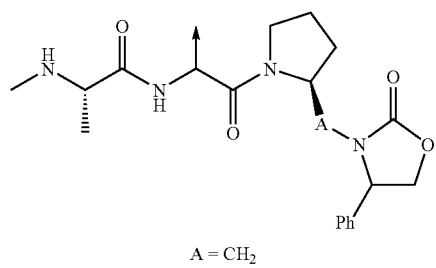<br>A = CH₂ | 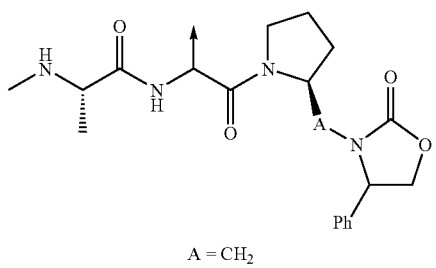<br>A = CH₂ |
| 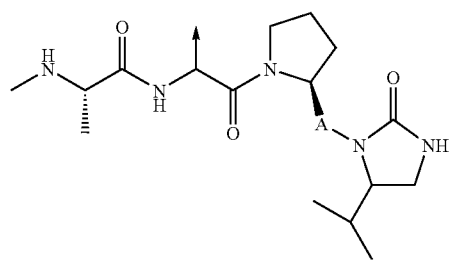<br>A = CH₂ | 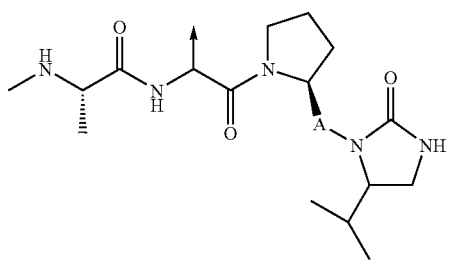<br>A = CH₂ |

TABLE 4-continued
Formula 1B
M1—B—BG—B¹—M2
BG is 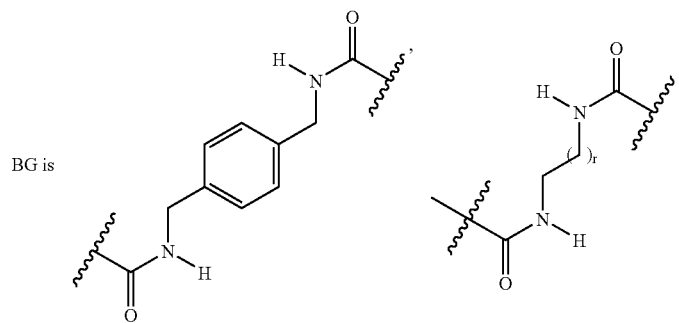
| M1 | M2 |
|---|---|
| 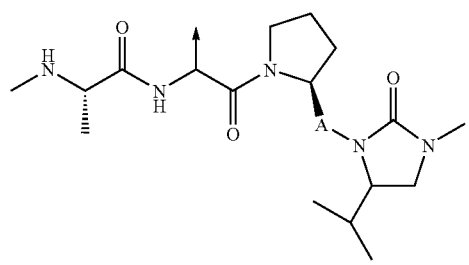 A = CH$_2$ | 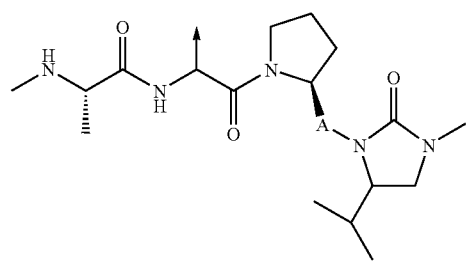 A = CH$_2$ |
| 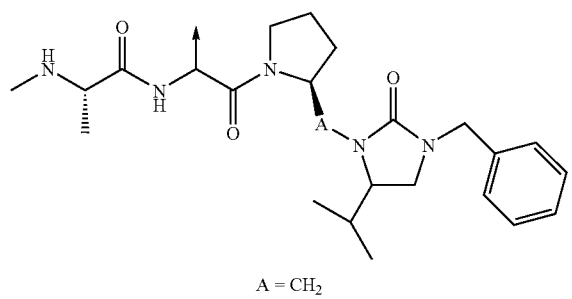 A = CH$_2$ | 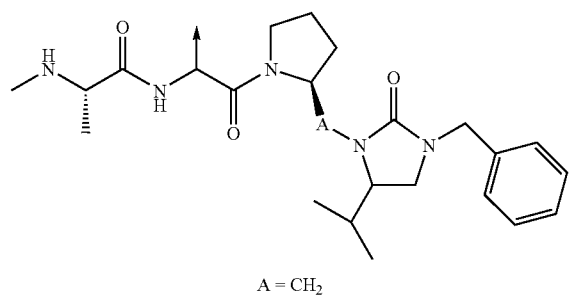 A = CH$_2$ |

TABLE 4-continued
$$M1-B-BG-B^1-M2 \quad \text{Formula 1B}$$
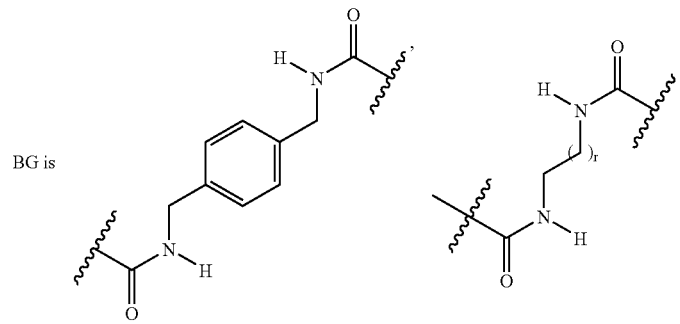
BG is
| M1 | M2 |
|---|---|
| 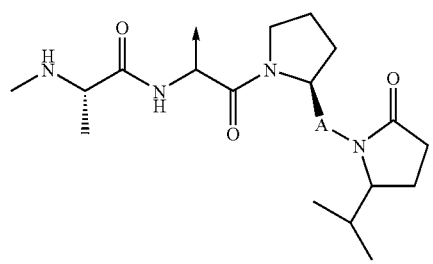<br>A = CH$_2$ | 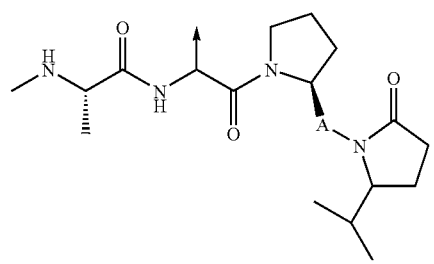<br>A = CH$_2$ |
| 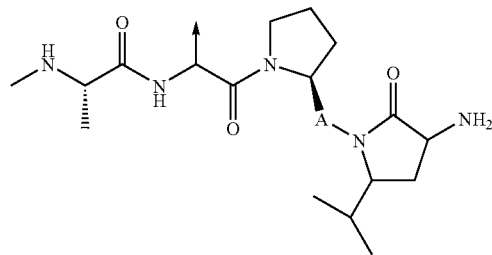<br>A = CH$_2$ | 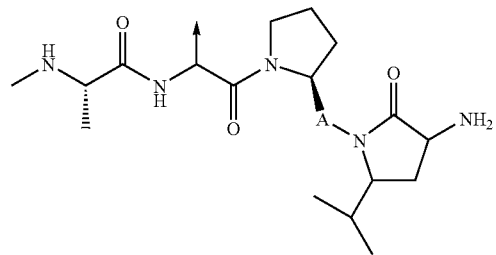<br>A = CH$_2$ |
B and B$^1$ are C$_1$–C$_6$ alkyl
Note:
In M1 and M2, the stereochemistry at the connecting carbon is (S)

TABLE 5
M1—BG—M2                                                                  Formula 1A
BG is  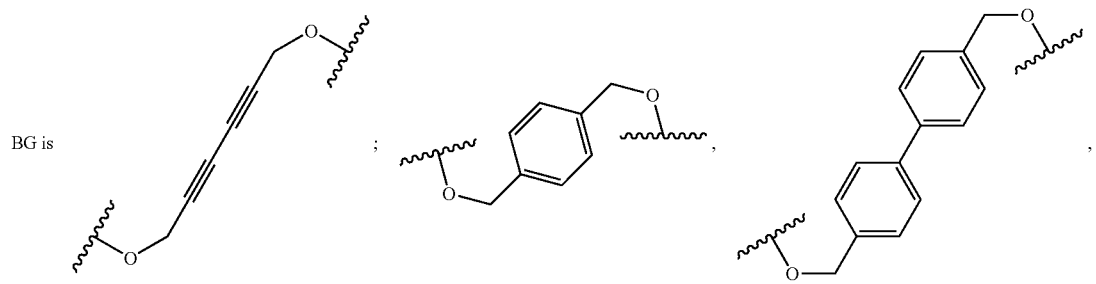
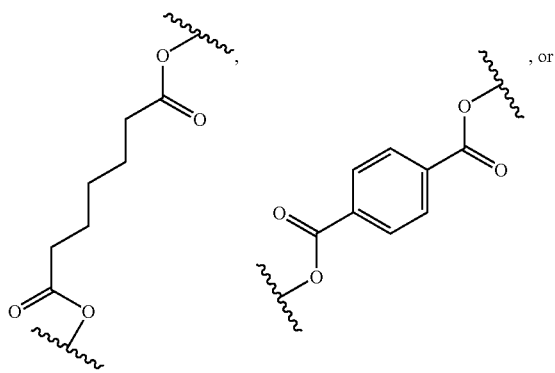
| M1 | M2 |
|---|---|
| 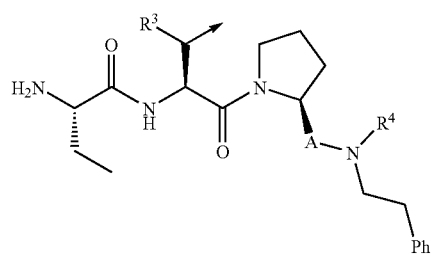<br>A is C═O; R³ = H or Me | 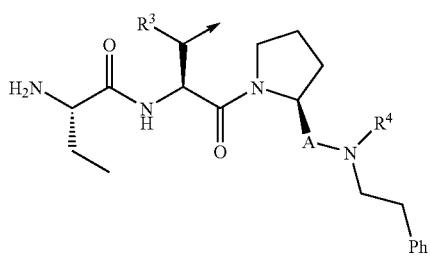<br>A is C═O; R³ = H or Me |
| 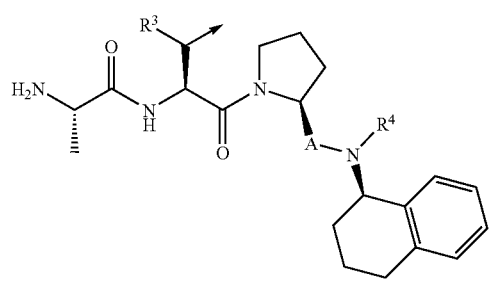<br>A is C═O; R³ = H or Me | 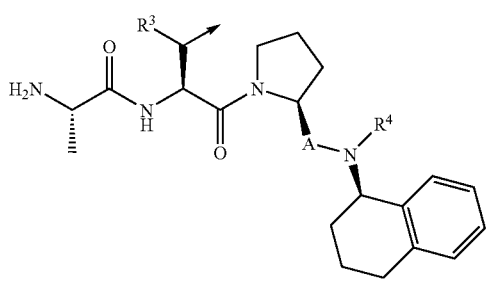<br>A is C═O; R³ = H or Me |

TABLE 5-continued
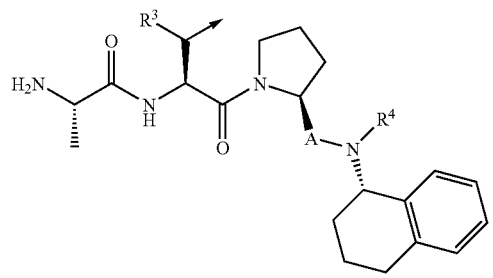
A is C═O; R³ = H or Me
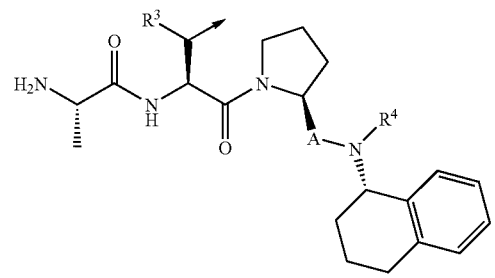
A is C═O; R³ = H or Me
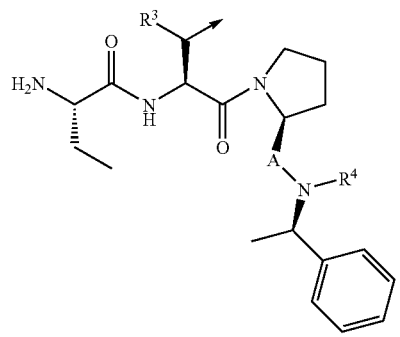
A is C═O; R³ = H or Me
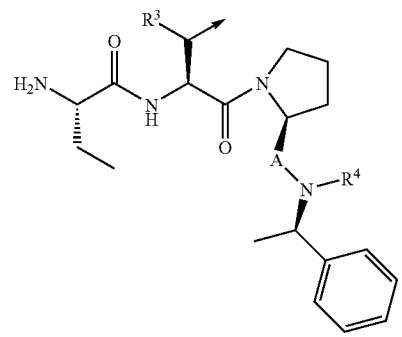
A is C═O; R³ = H or Me
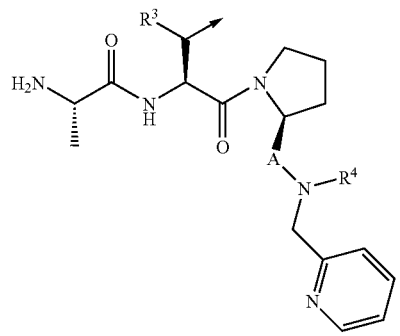
A is C═O; R³ = H or Me
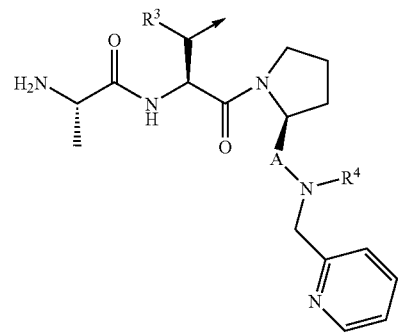
A is C═O; R³ = H or Me
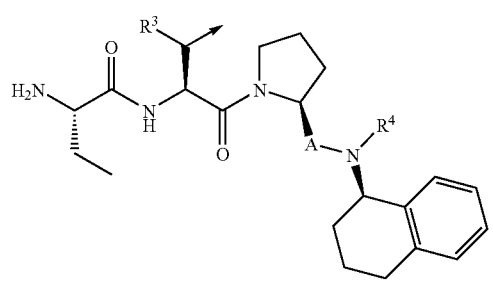
A is C═O; R³ = H or Me
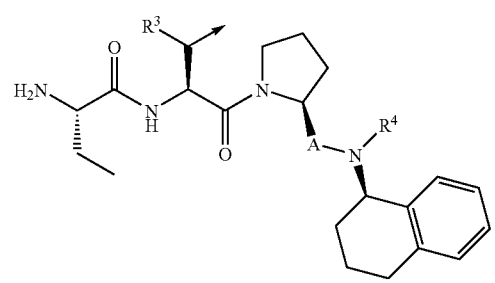
A is C═O; R³ = H or Me TABLE 5-continued
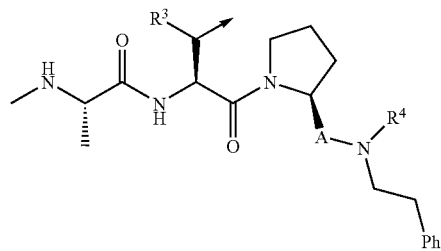
A is C═O; R³ = H or Me
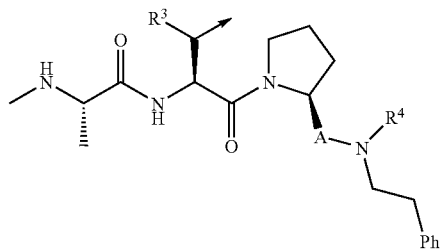
A is C═O; R³ = H or Me
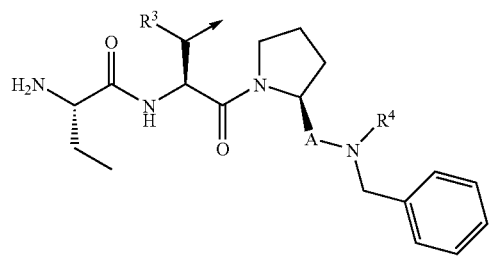
A is C═O; R³ = H or Me
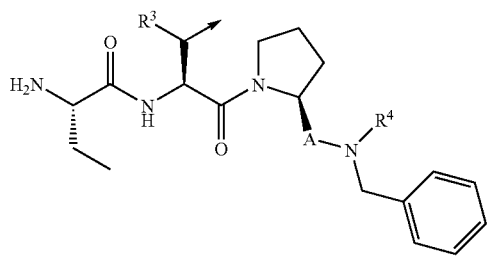
A is C═O; R³ = H or Me
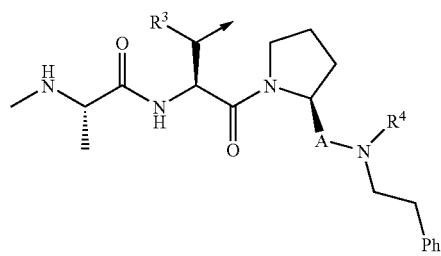
A is C═O; R³ = H or Me
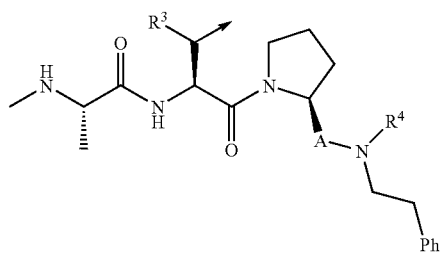
A is C═O; R³ = H or Me
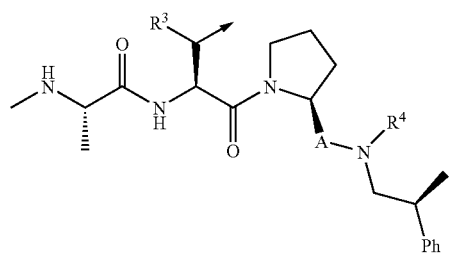
A is C═O; R³ = H or Me
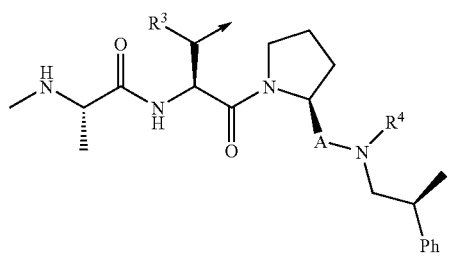
A is C═O; R³ = H or Me
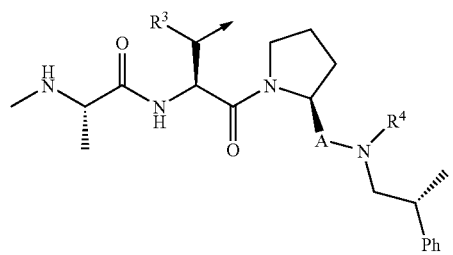
A is C═O; R³ = H or Me
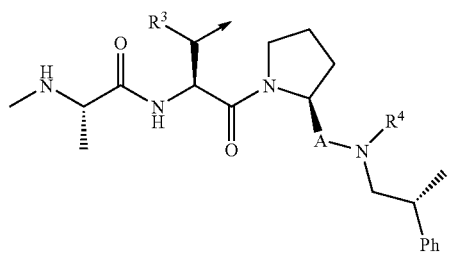
A is C═O; R³ = H or Me TABLE 5-continued
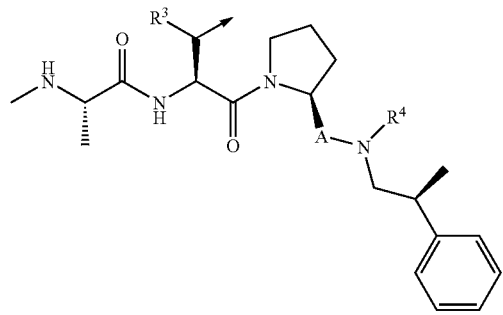
A is C═O; R³ = H or Me
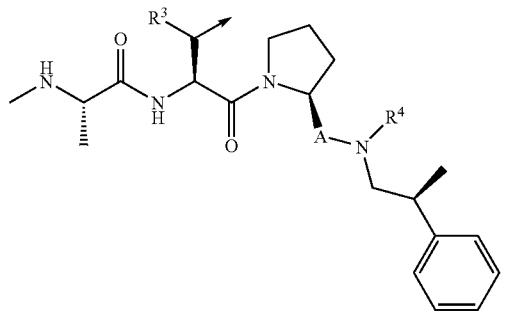
A is C═O; R³ = H or Me
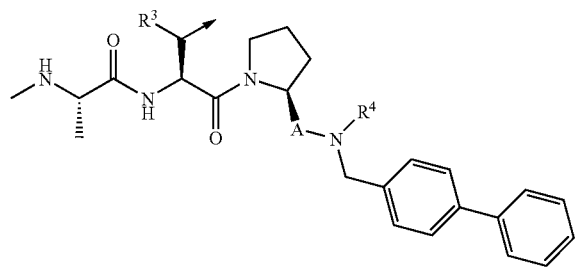
A is C═O; R³ = H or Me
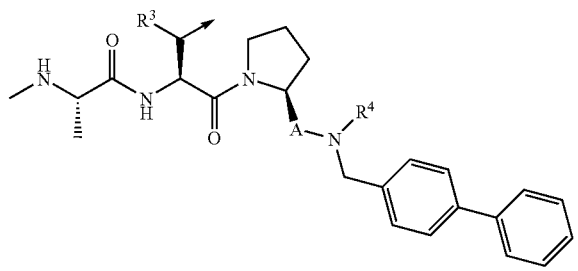
A is C═O; R³ = H or Me
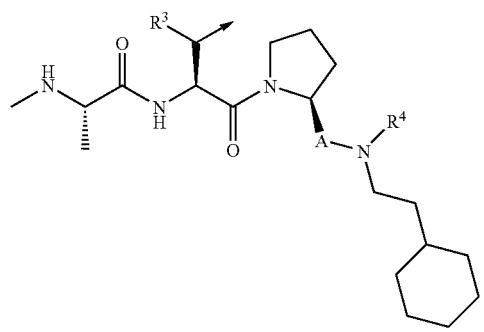
A is C═O; R³ = H or Me
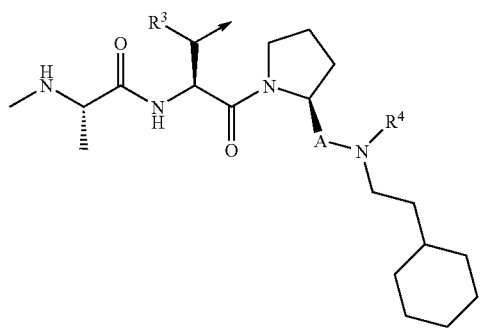
A is C═O; R³ = H or Me
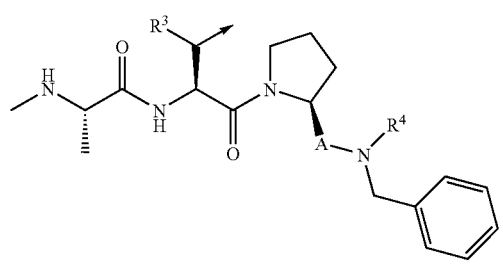
A is C═O; R³ = H or Me
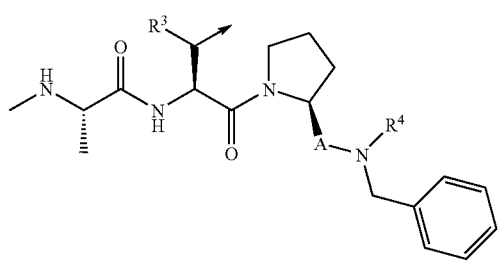
A is C═O; R³ = H or Me TABLE 5-continued
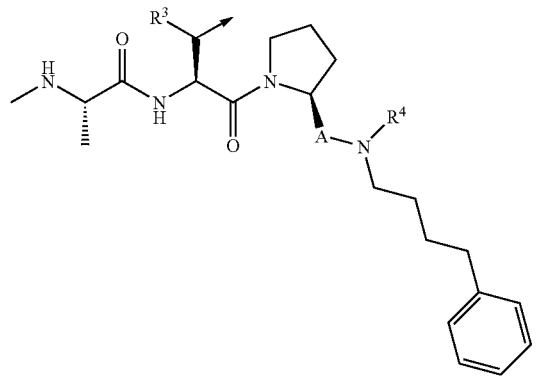
A is C═O; R³ = H or Me
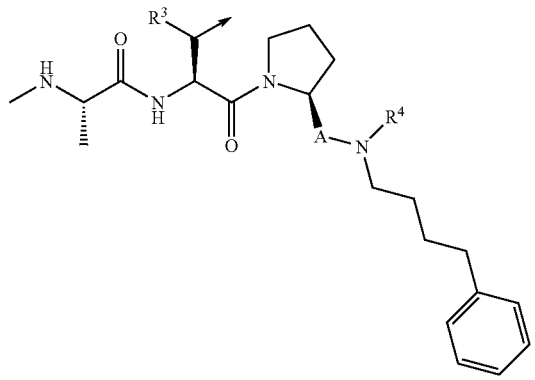
A is C═O; R³ = H or Me
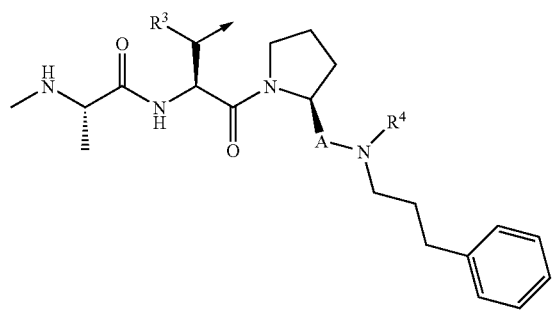
A is C═O; R³ = H or Me
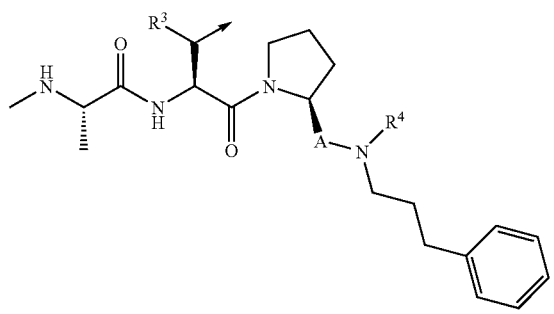
A is C═O; R³ = H or Me
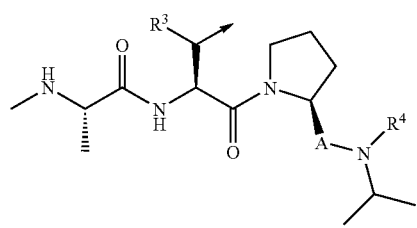
A is C═O; R³ = H or Me
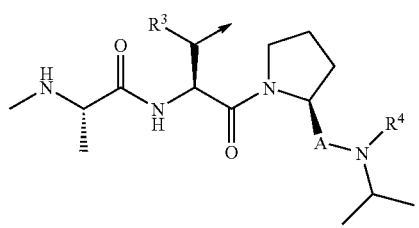
A is C═O; R³ = H or Me
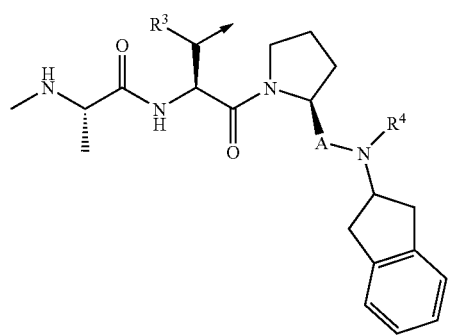
A is C═O; R³ = H or Me
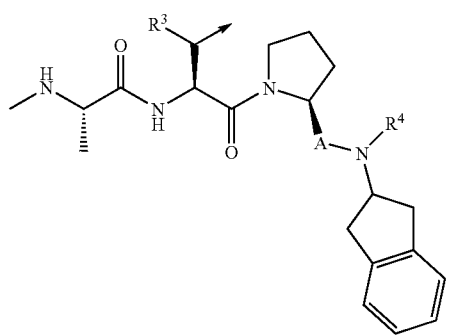
A is C═O; R³ = H or Me TABLE 5-continued
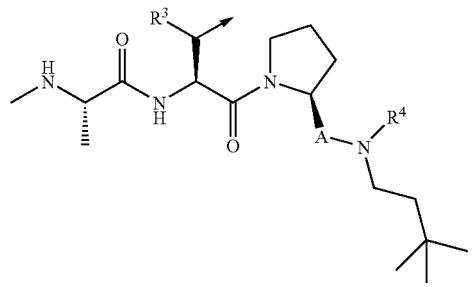
A is C═O; R³ = H or Me
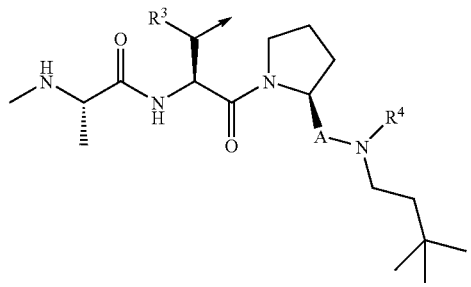
A is C═O; R³ = H or Me
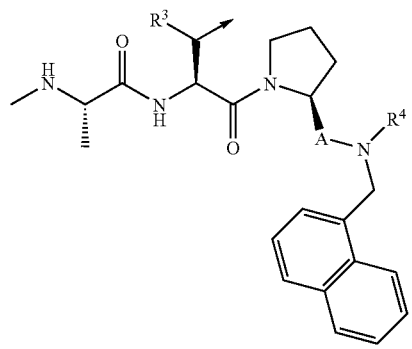
A is C═O; R³ = H or Me
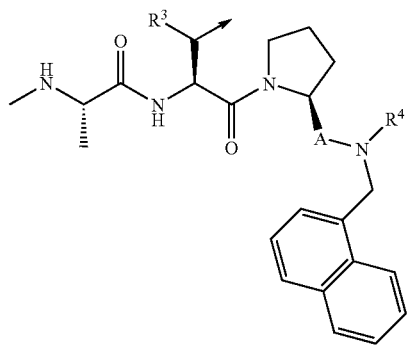
A is C═O; R³ = H or Me
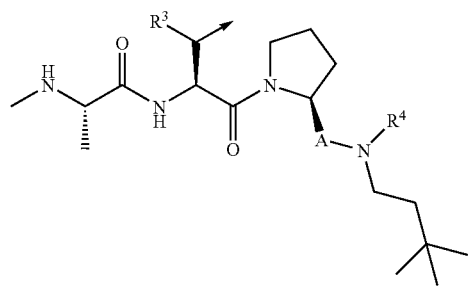
A is C═O; R³ = H or Me
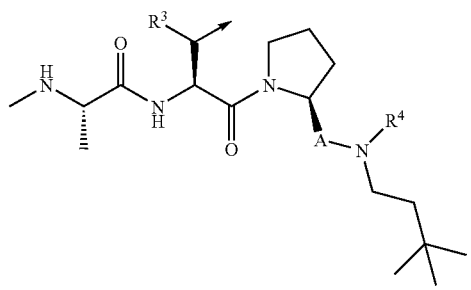
A is C═O; R³ = H or Me
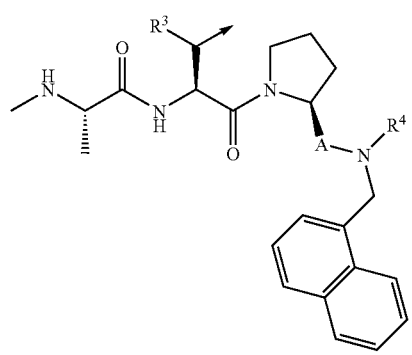
A is C═O; R³ = H or Me
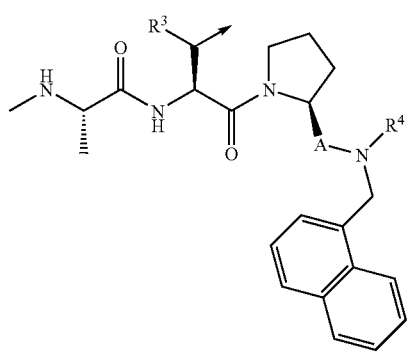
A is C═O; R³ = H or Me
Note:
In the following Table, R⁴ is H or any non-acyl substituent TABLE 6
Formula 1B
M1—B—BG—B¹—M2
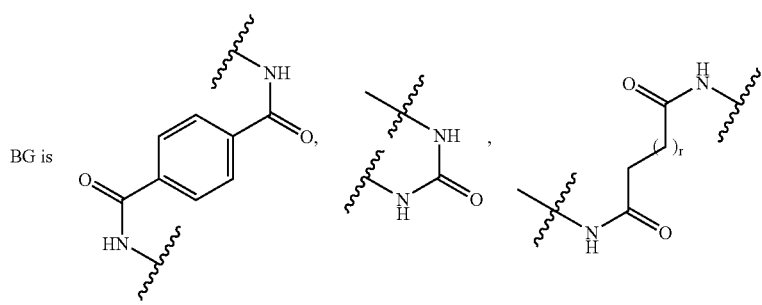
| M1 | M2 |
|---|---|
| 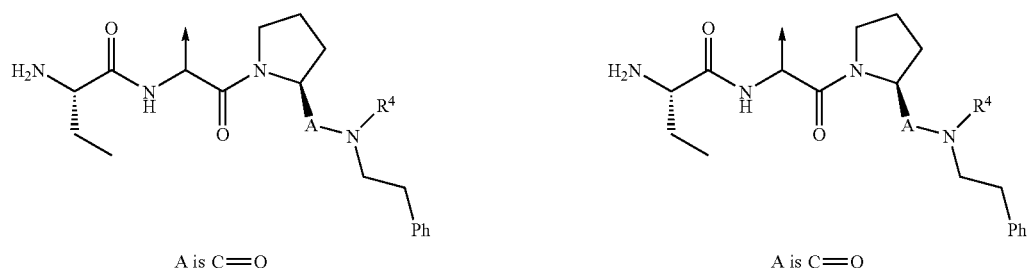 | |
| A is C=O | A is C=O |
| 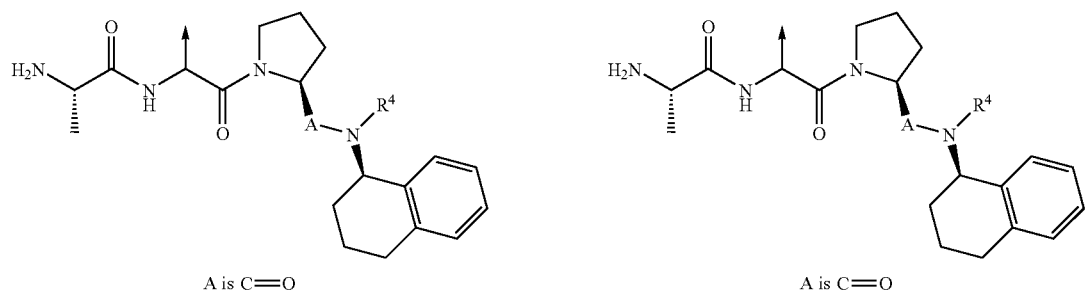 | |
| A is C=O | A is C=O |
| 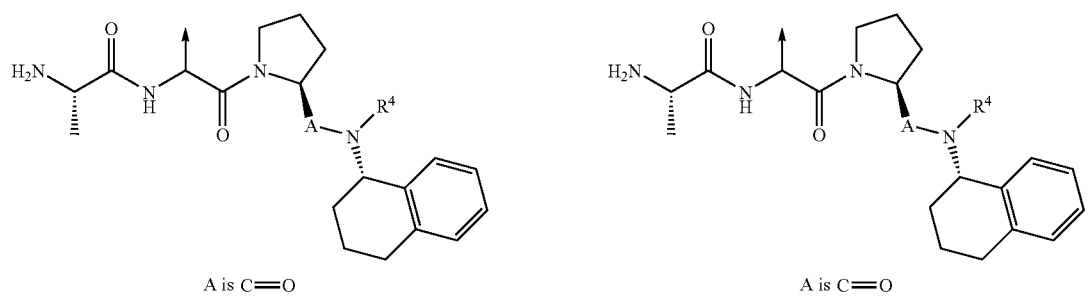 | |
| A is C=O | A is C=O |

TABLE 6-continued
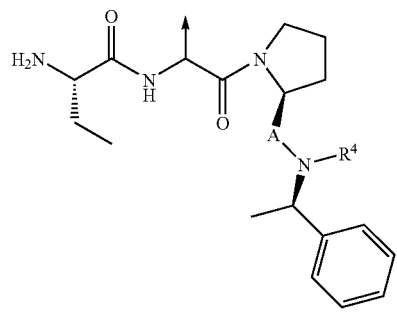
A is C=O
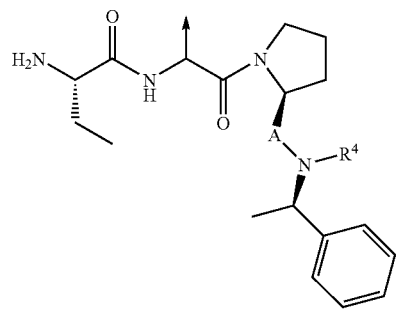
A is C=O
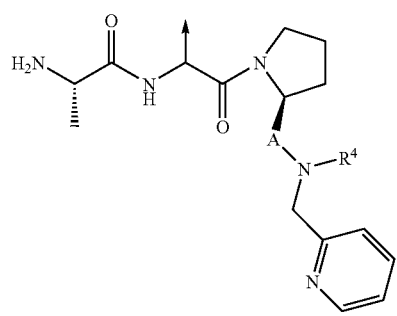
A is C=O
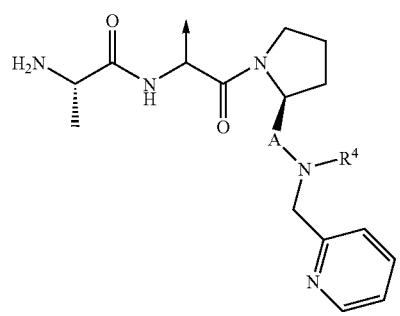
A is C=O
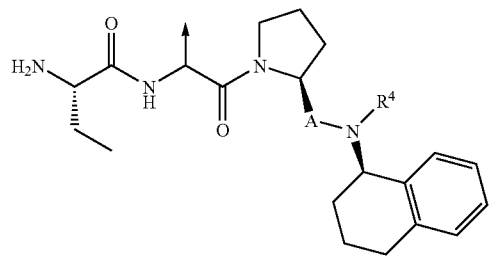
A is C=O
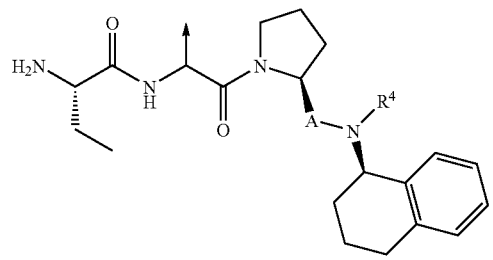
A is C=O
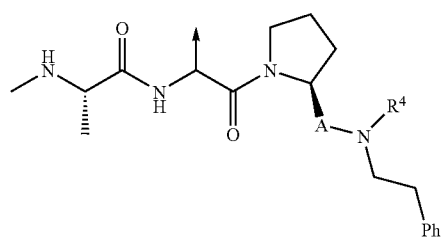
A is C=O
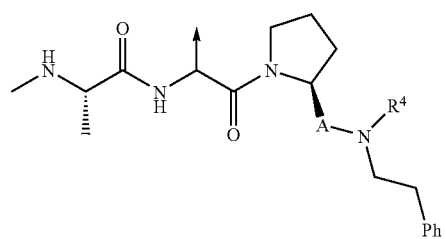
A is C=O
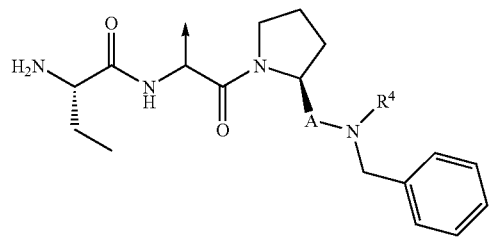
A is C=O
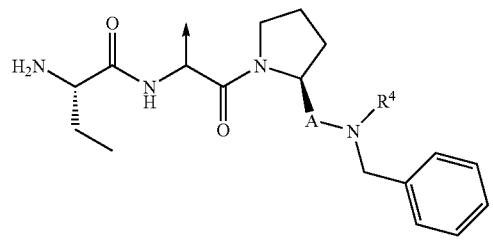
A is C=O TABLE 6-continued
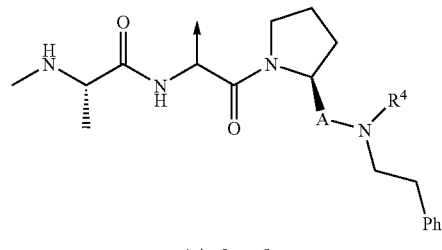
A is C=O
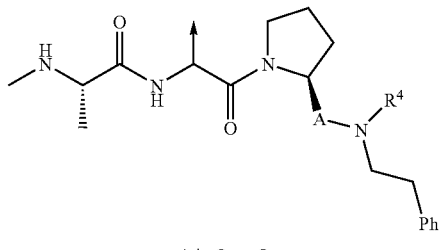
A is C=O
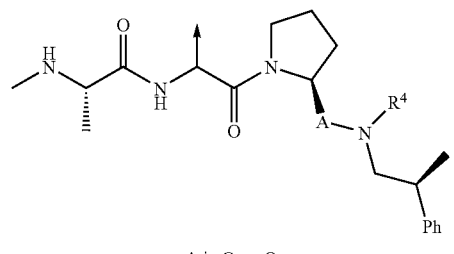
A is C=O
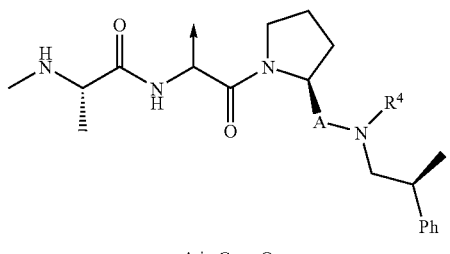
A is C=O
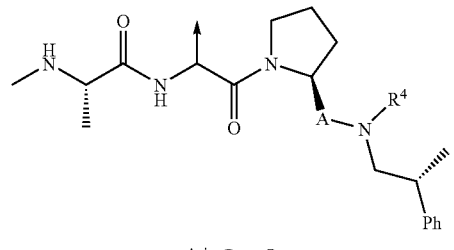
A is C=O
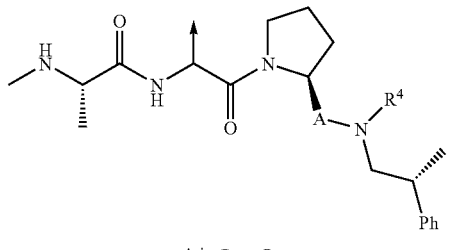
A is C=O
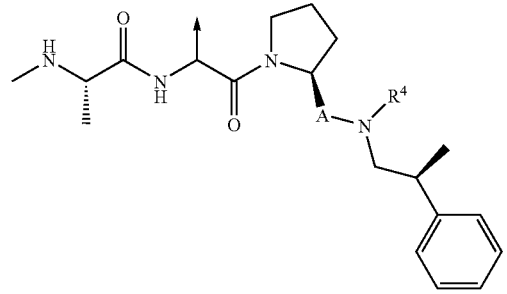
A is C=O
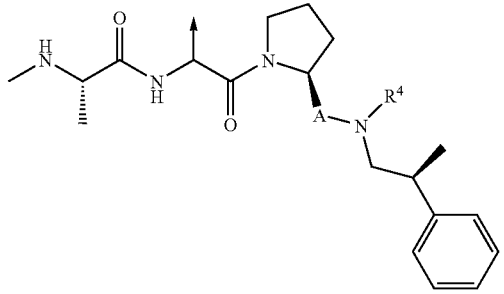
A is C=O
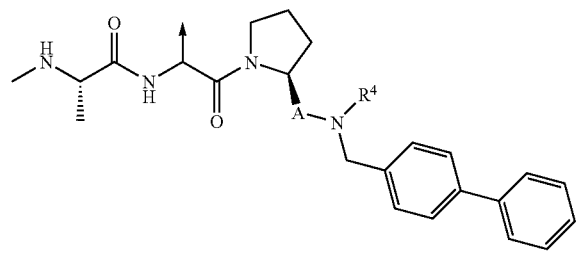
A is C=O
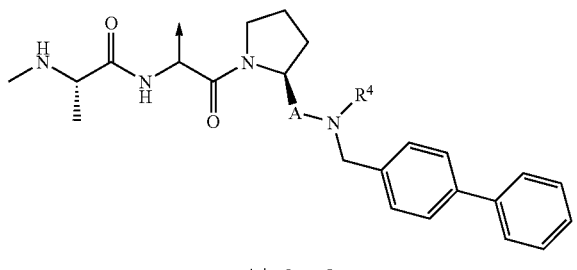
A is C=O TABLE 6-continued
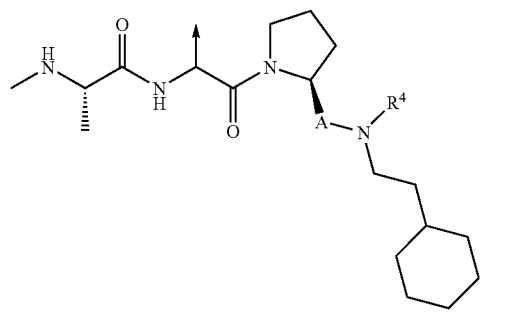
A is C=O
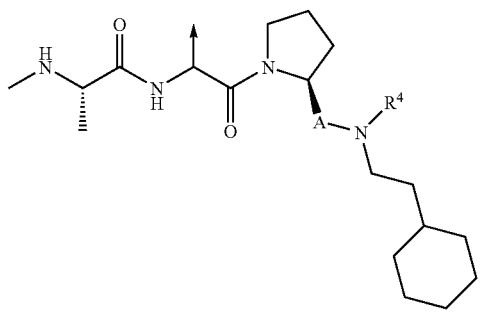
A is C=O
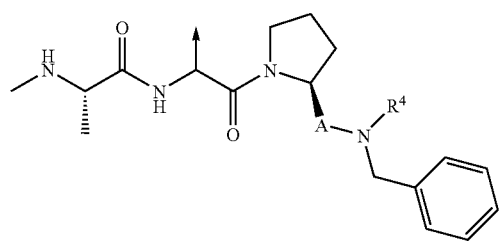
A is C=O
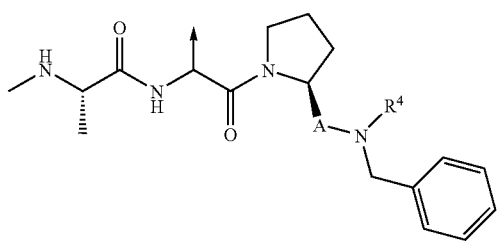
A is C=O
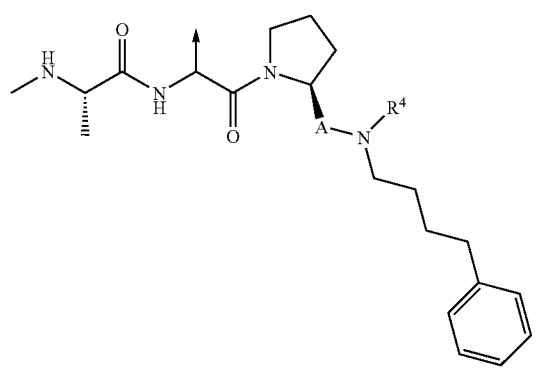
A is C=O
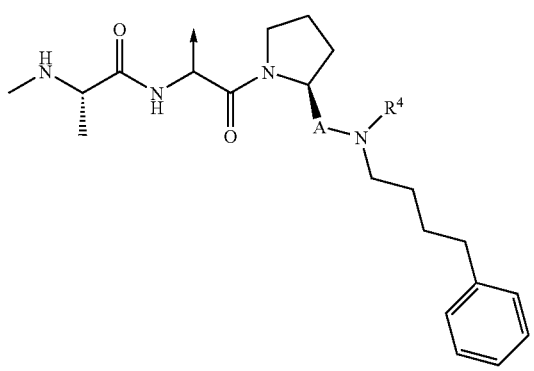
A is C=O
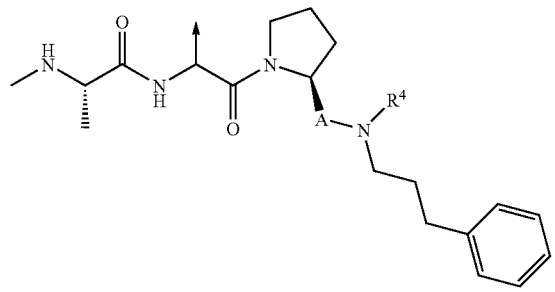
A is C=O
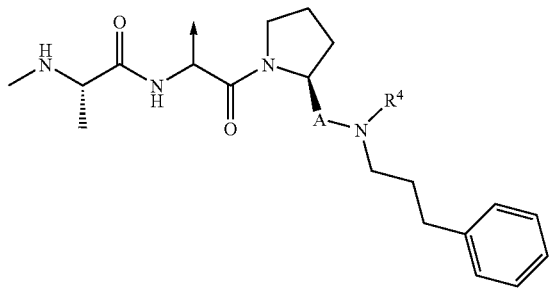
A is C=O
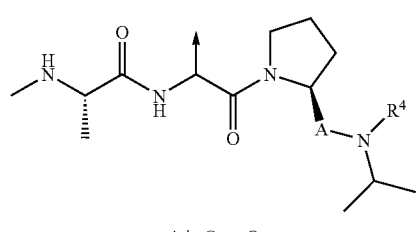
A is C=O
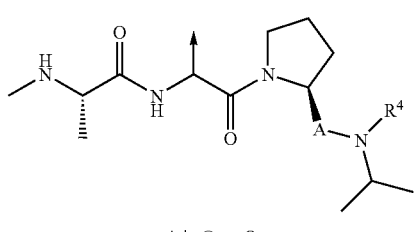
A is C=O TABLE 6-continued
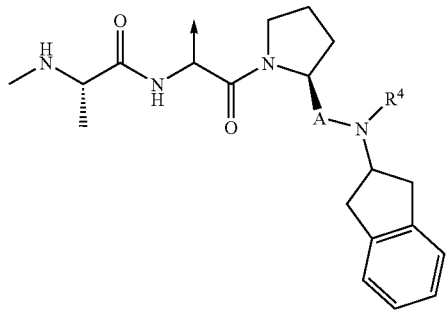
A is C═O
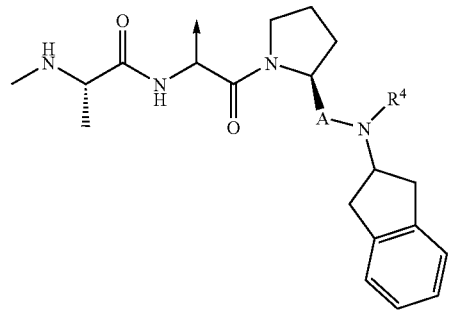
A is C═O
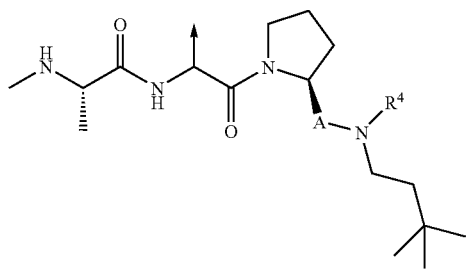
A is C═O
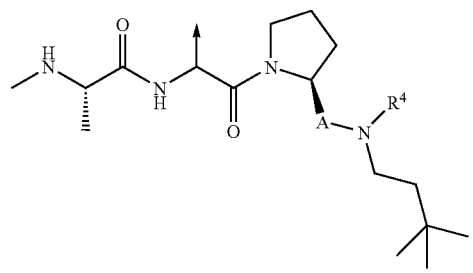
A is C═O
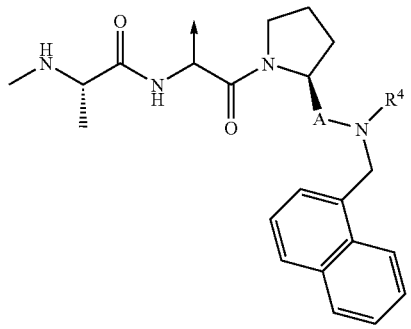
A is C═O
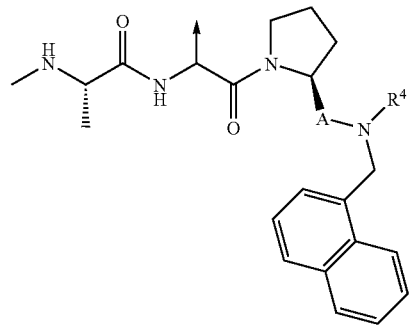
A is C═O
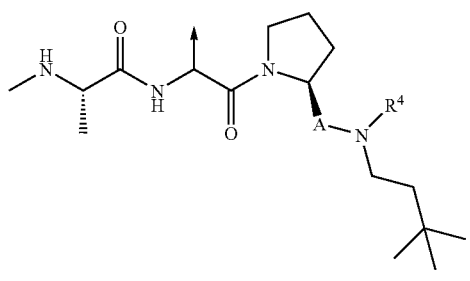
A is C═O
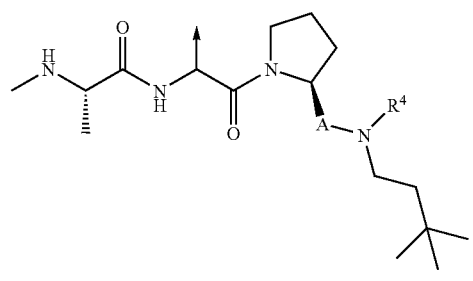
A is C═O TABLE 6-continued
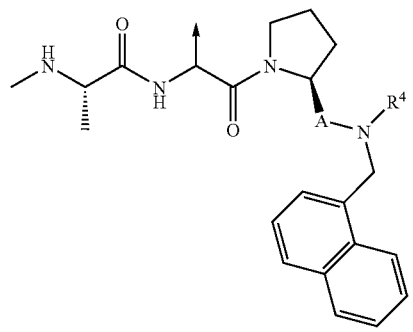
A is C=O
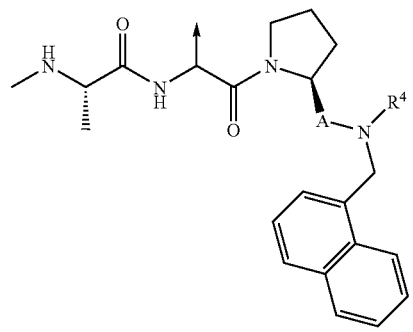
A is C=O
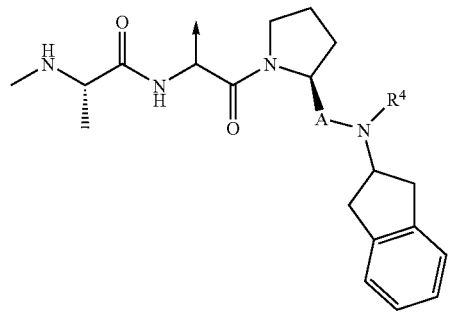
A is C=O
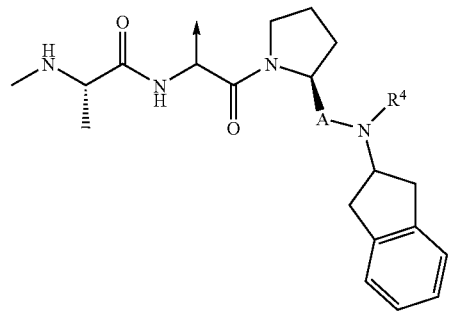
A is C=O
B and $B^1$ are $C_1$–$C_6$ alkyl
Note:
In M1 and M2, the stereochemistry at the connecting carbon is (S)
Note:
In the following Table $R^4$ is H or any non-acyl substituent TABLE 7
Formula 1B
$$M1-B-BG-B^1-M2$$
BG is 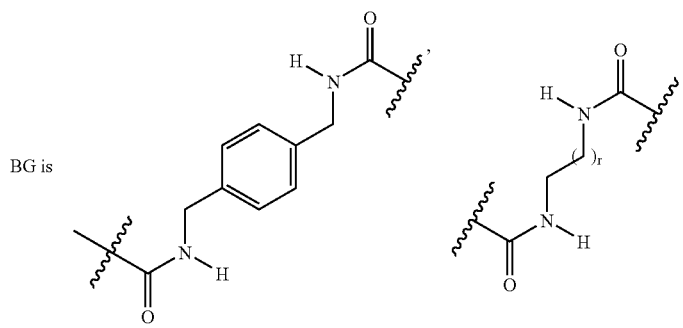
| M1 | M2 |
|---|---|
| 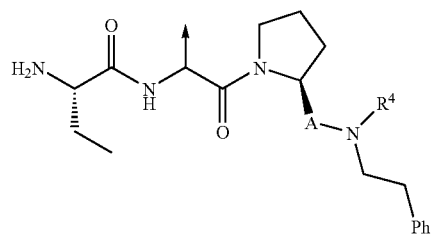<br>A is C=O | 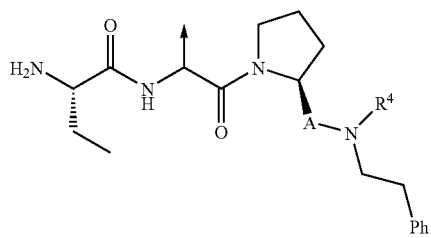<br>A is C=O |
| 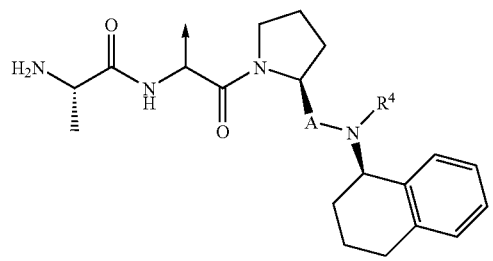<br>A is C=O | 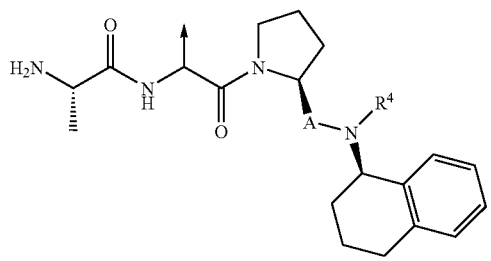<br>A is C=O |
| 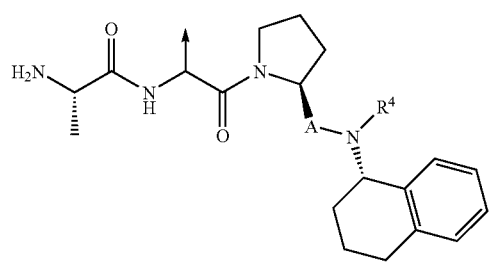<br>A is C=O | 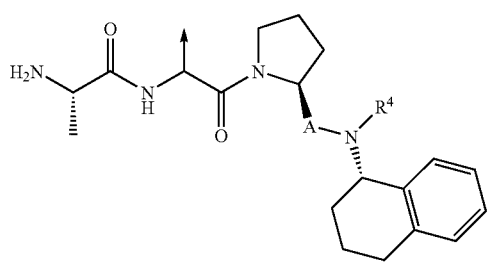<br>A is C=O |

TABLE 7-continued
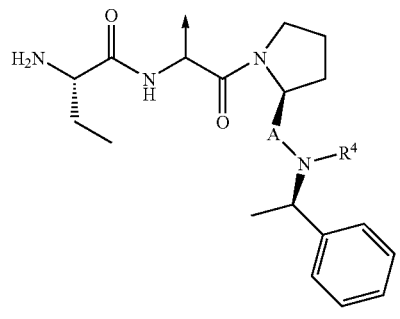
A is C=O
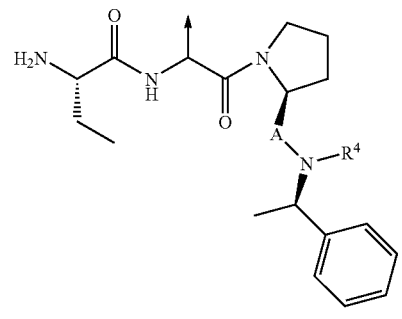
A is C=O
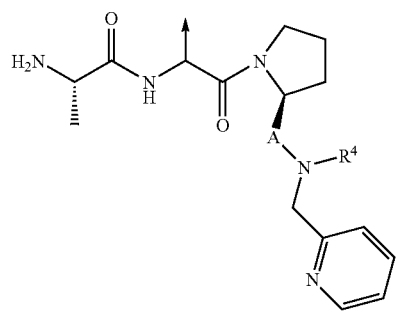
A is C=O
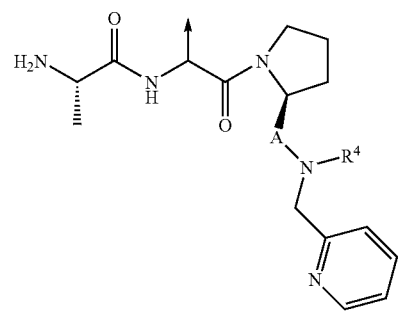
A is C=O
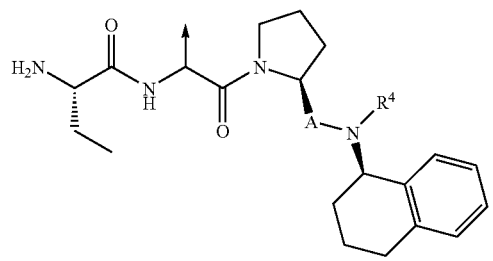
A is C=O
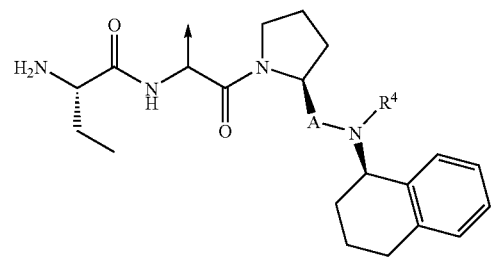
A is C=O
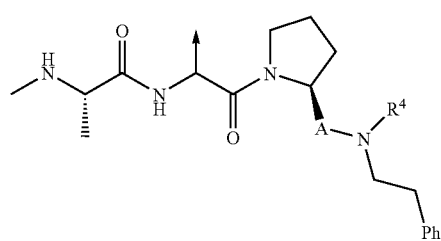
A is C=O
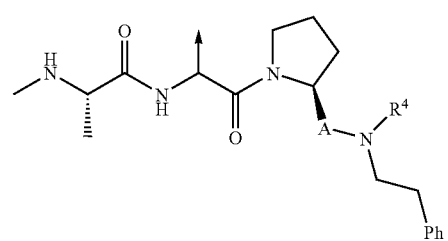
A is C=O
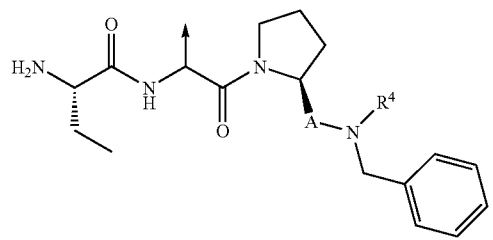
A is C=O
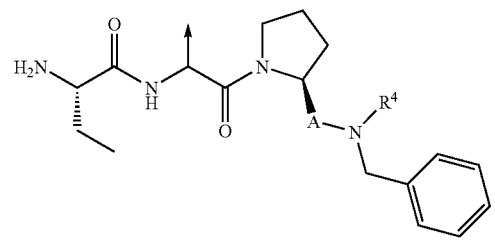
A is C=O TABLE 7-continued
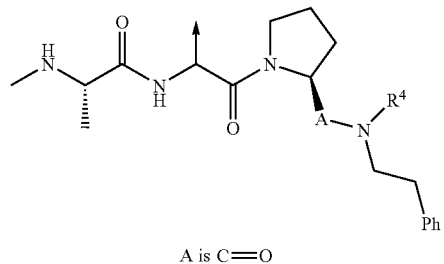
A is C=O
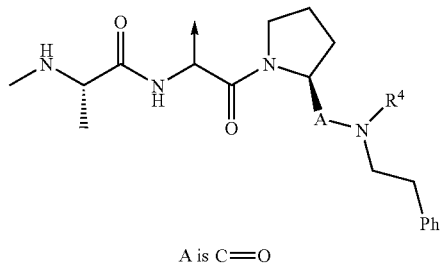
A is C=O
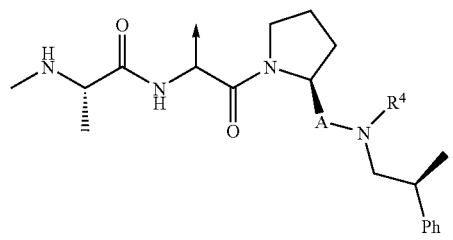
A is C=O
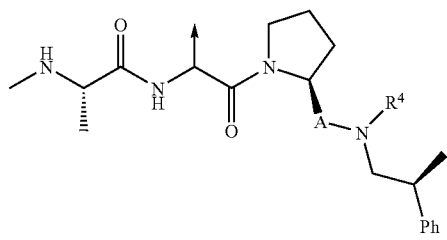
A is C=O
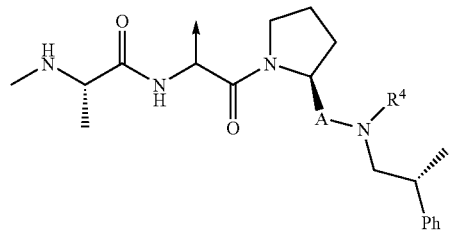
A is C=O
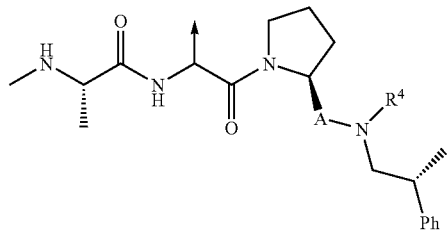
A is C=O
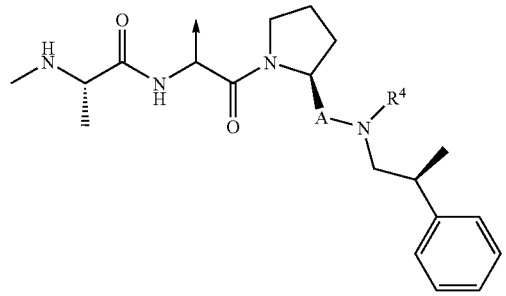
A is C=O
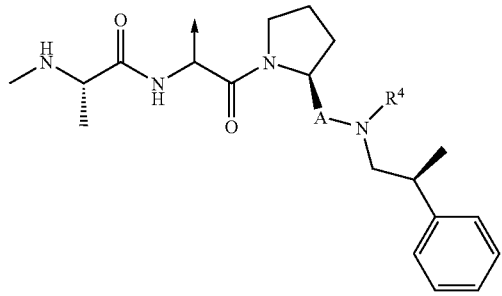
A is C=O
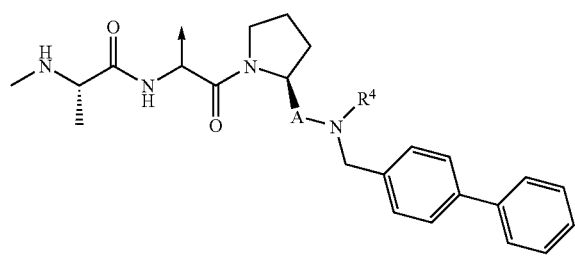
A is C=O
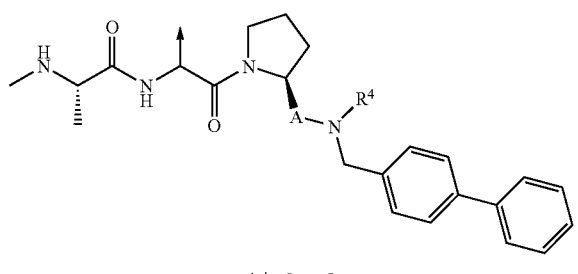
A is C=O TABLE 7-continued
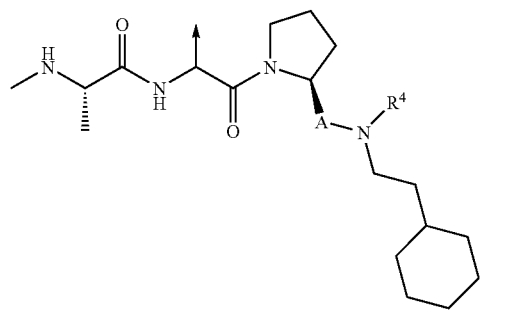
A is C=O
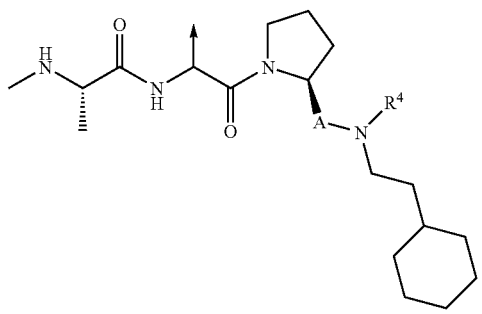
A is C=O
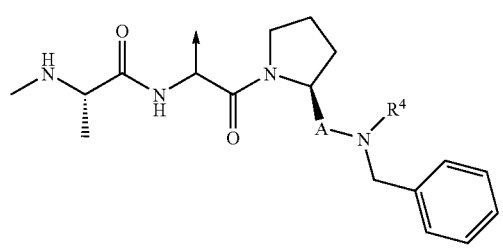
A is C=O
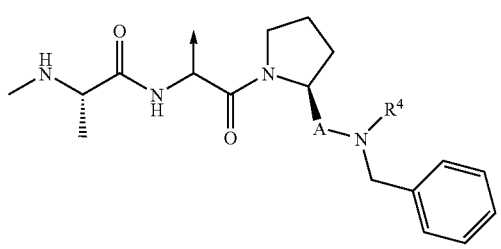
A is C=O
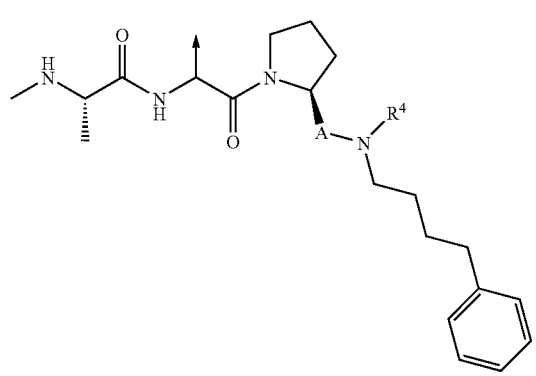
A is C=O
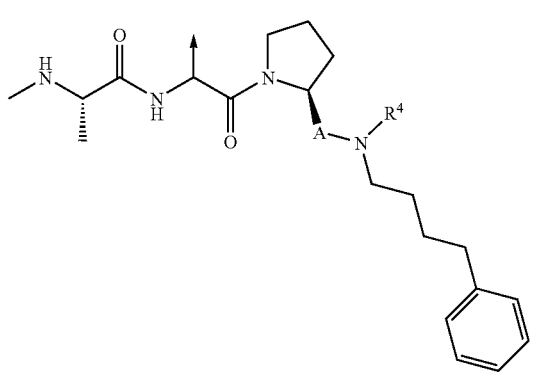
A is C=O
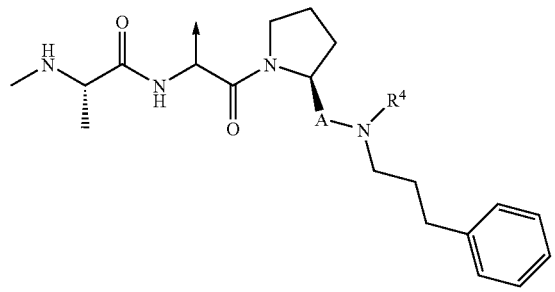
A is C=O
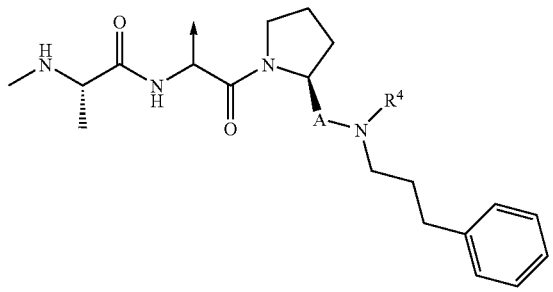
A is C=O
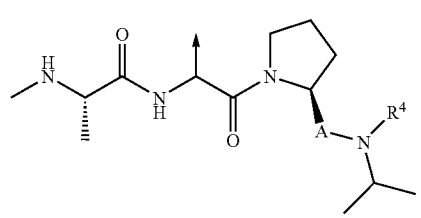
A is C=O
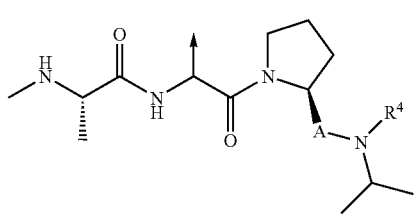
A is C=O TABLE 7-continued
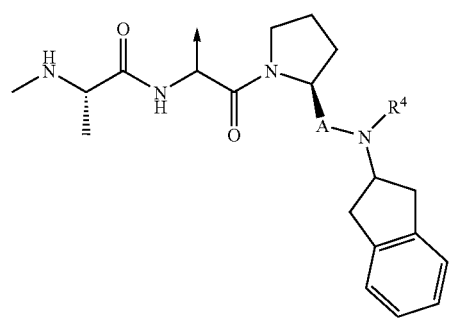
A is C=O
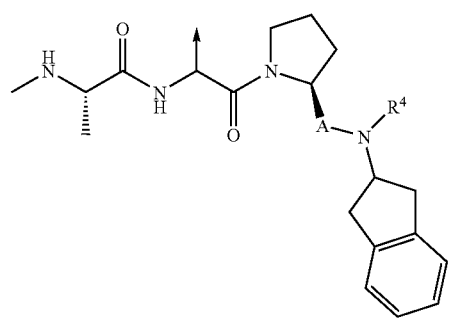
A is C=O
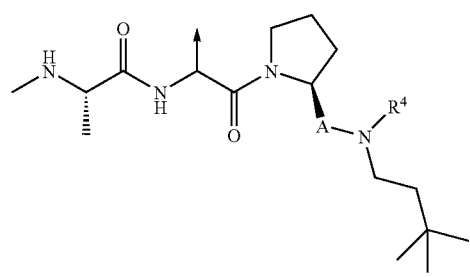
A is C=O
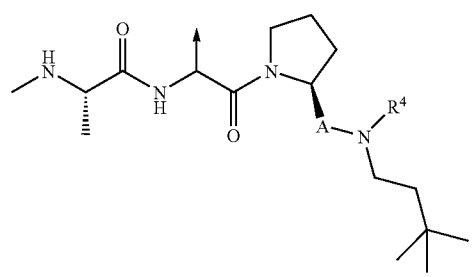
A is C=O
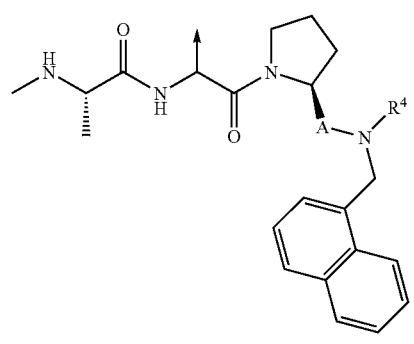
A is C=O
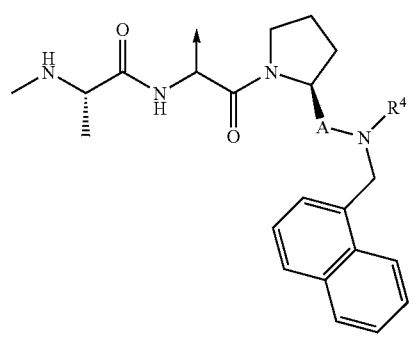
A is C=O
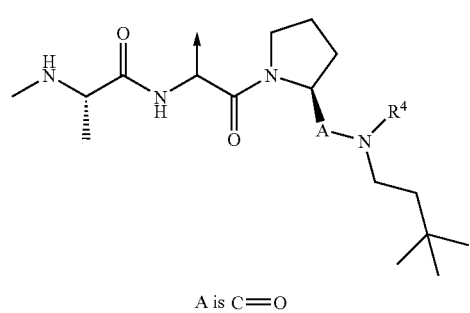
A is C=O
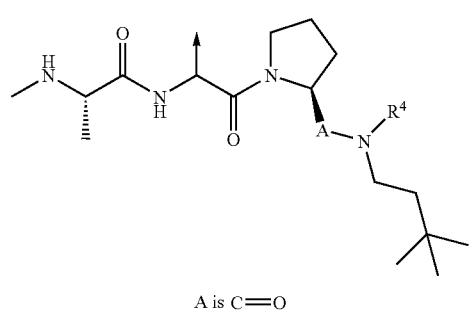
A is C=O TABLE 7-continued
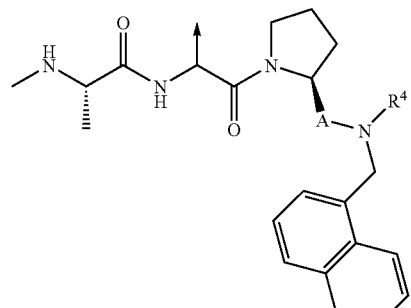
A is C=O
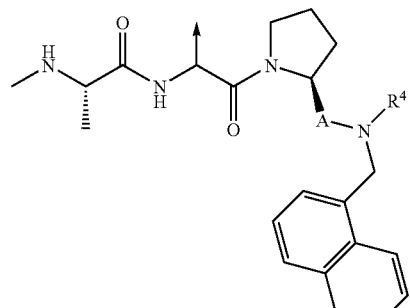
A is C=O
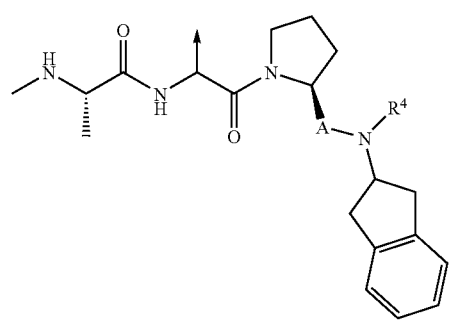
A is C=O
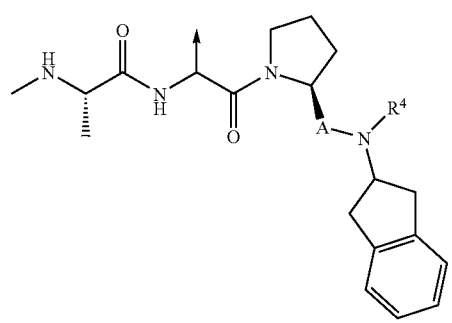
A is C=O
B and $B^1$ are $C_1$–$C_6$ alkyl
Note:
In M1 and M2, the stereochemistry at the connecting carbon is (S)
Note:
In the following Table $R^4$ is H or any non-acyl substituent TABLE 8
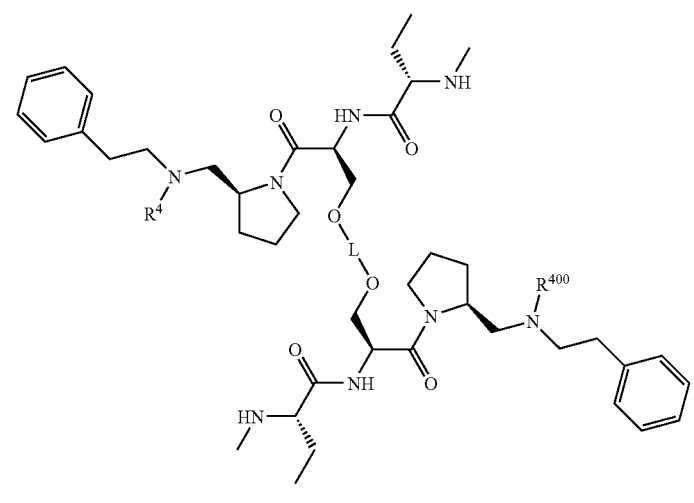
| R⁴ | R⁴⁰⁰ |
|---|---|
| 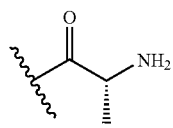 | 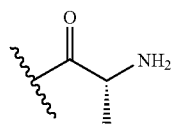 |
| 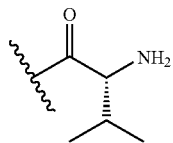 | 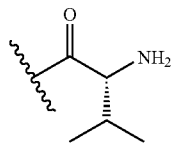 |
| 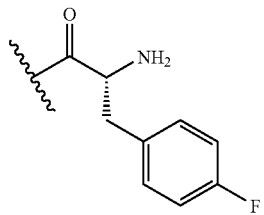 | 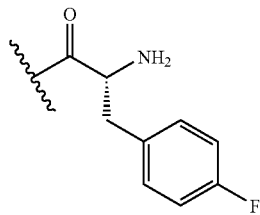 |
| 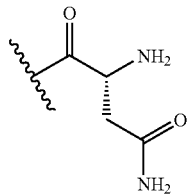 | 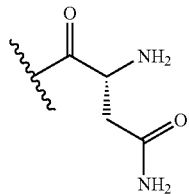 |
| 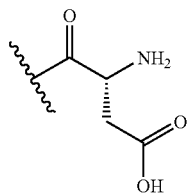 | 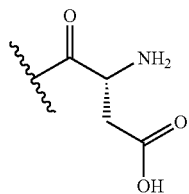 |

TABLE 8-continued
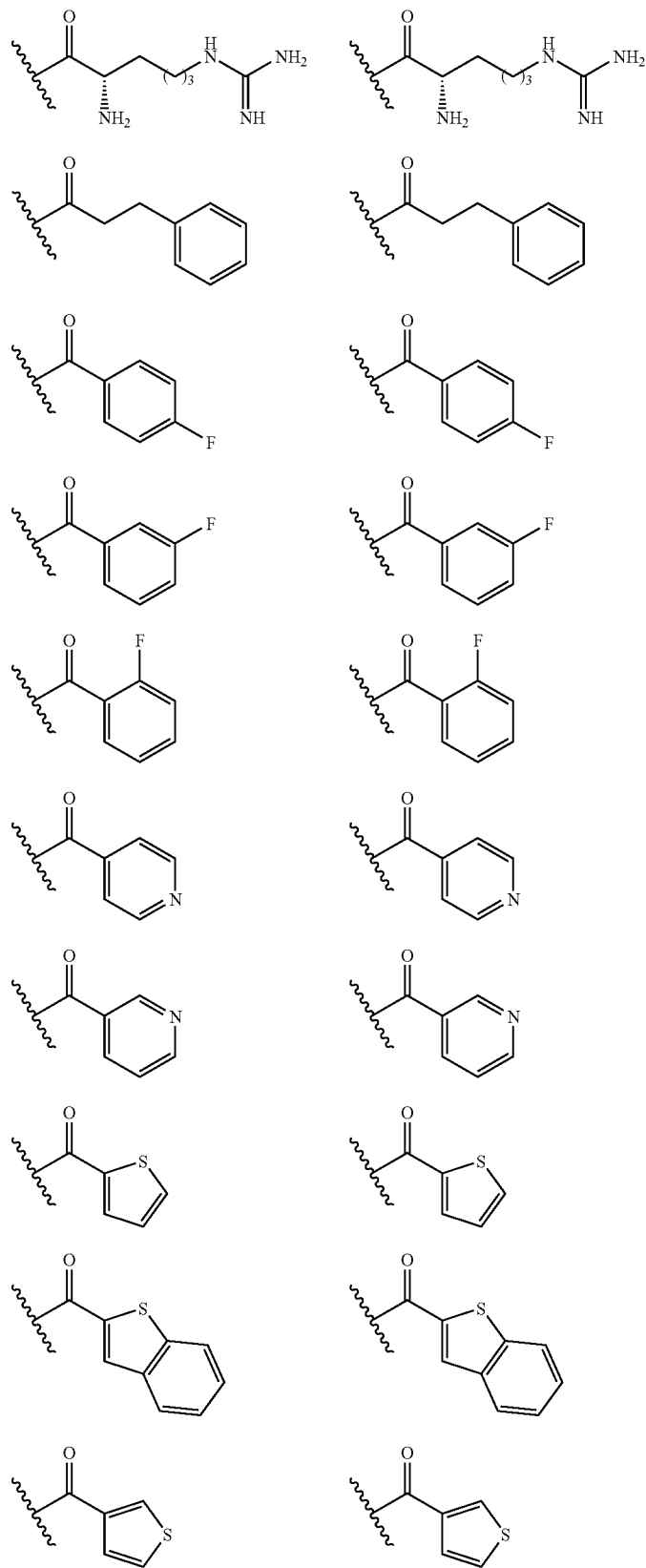

TABLE 8-continued
| | |
|---|---|
| 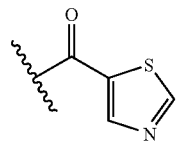 | 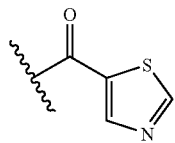 |
| 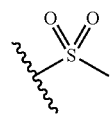 | 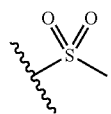 |
| 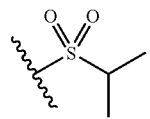 | 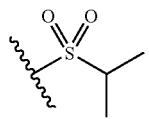 |
| 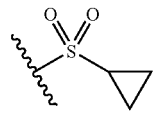 | 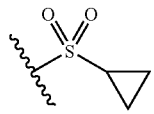 |
| 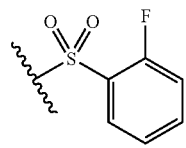 | 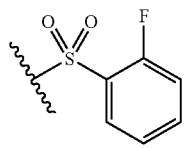 |
| 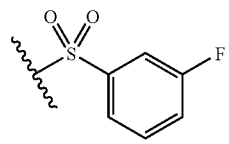 | 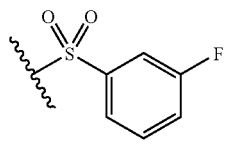 |
| 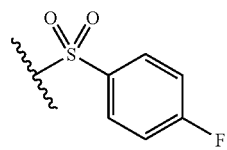 | 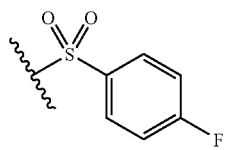 |
| 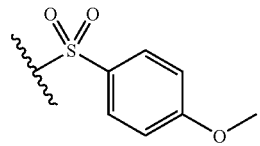 | 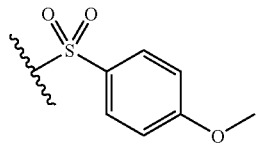 |

TABLE 9
Q and Q¹ are independently defined as NR⁴R⁵, wherein R⁵ is defined as herein and R⁴ is chosen from the following:
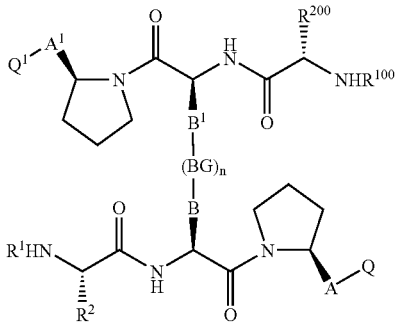
wherein R¹, R¹⁰⁰, R², R²⁰⁰, B, B¹, n, BG, A, A¹ are defined herein;
R⁴
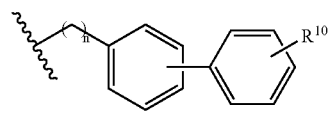
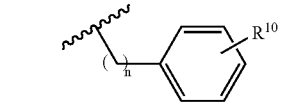
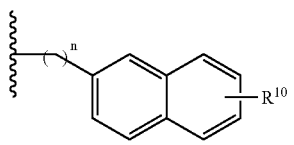
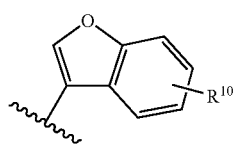
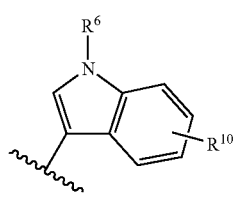
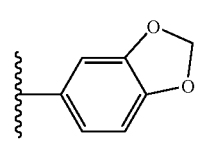
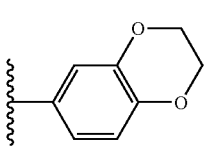
TABLE 9-continued
Q and Q¹ are independently defined as NR⁴R⁵, wherein R⁵ is defined as herein and R⁴ is chosen from the following:
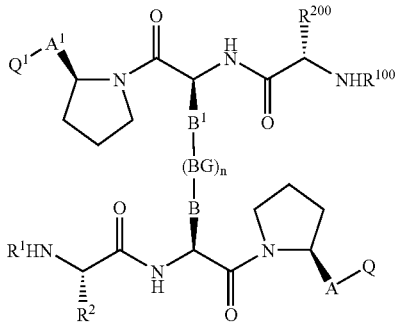
wherein R¹, R¹⁰⁰, R², R²⁰⁰, B, B¹, n, BG, A, A¹ are defined herein;
R⁴
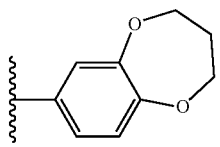
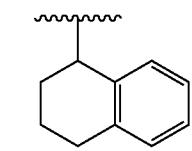
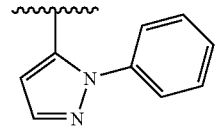
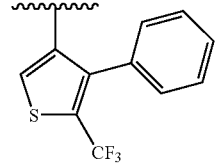
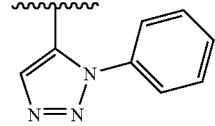
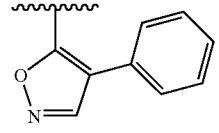
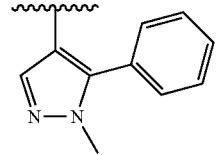

TABLE 9-continued

Q and Q$^1$ are independently defined as NR$^4$R$^5$, wherein R$^5$ is defined as herein and R$^4$ is chosen from the following:

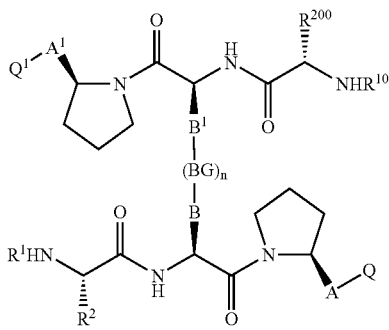

wherein R$^1$, R$^{100}$, R$^2$, R$^{200}$, B, B$^1$, n, BG, A, A$^1$ are defined herein;

R$^4$

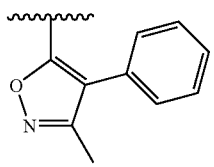

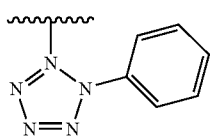

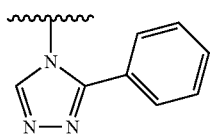

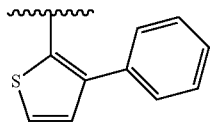

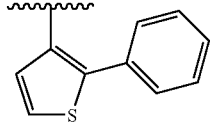

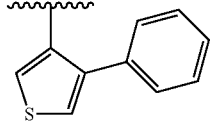

TABLE 10

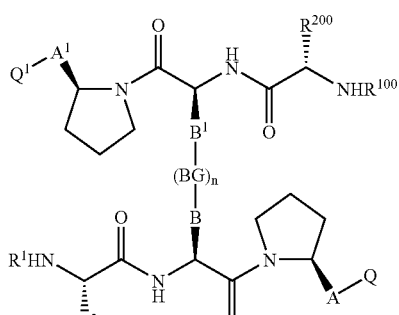

wherein R$^1$, R$^{100}$, R$^2$, R$^{200}$, B, B$^1$, n, BG, A, A$^1$ are as defined herein; Q and Q$^1$ are independently defined as OR$^{11}$, and R$^{11}$ is chosen from the following:

R$^{11}$

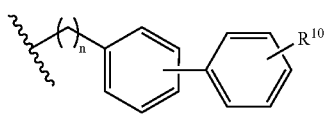

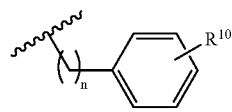

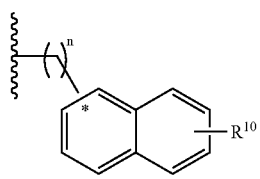

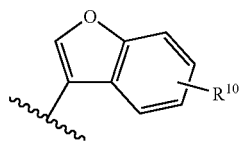

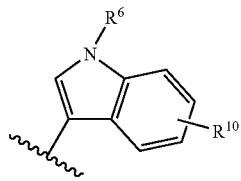

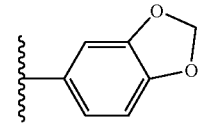

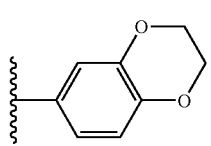

TABLE 10-continued
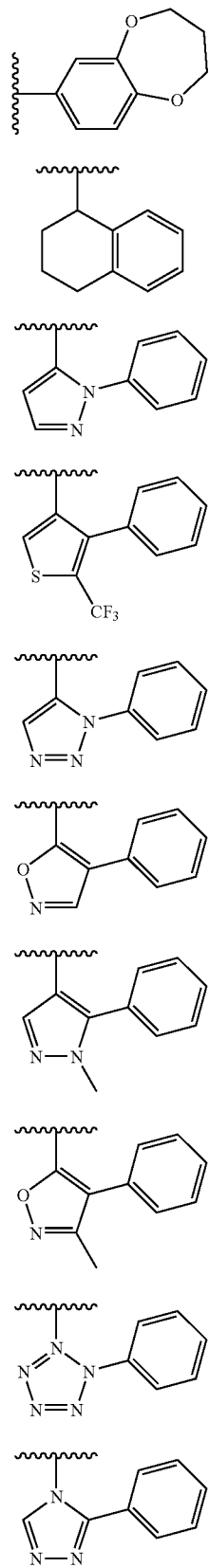
TABLE 10-continued
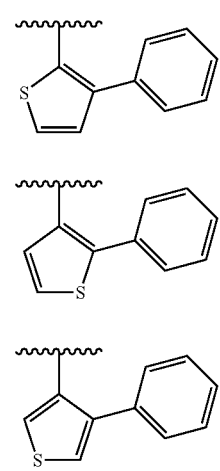
TABLE 11
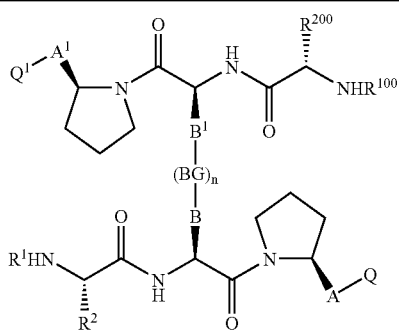
wherein $R^1$, $R^{100}$, $R^2$, $R^{200}$, B, $B^1$, n, m, BG, A, $A^1$ are as defined herein; Q and $Q^1$ are independently defined as $S(O)_m R^{11}$, and $R^{11}$ is chosen from the following:
$R^{11}$
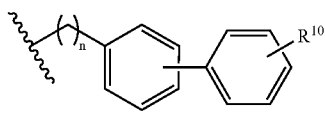
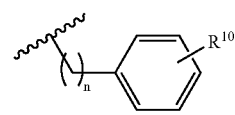
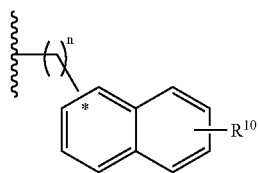
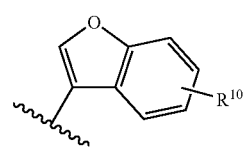

TABLE 11-continued

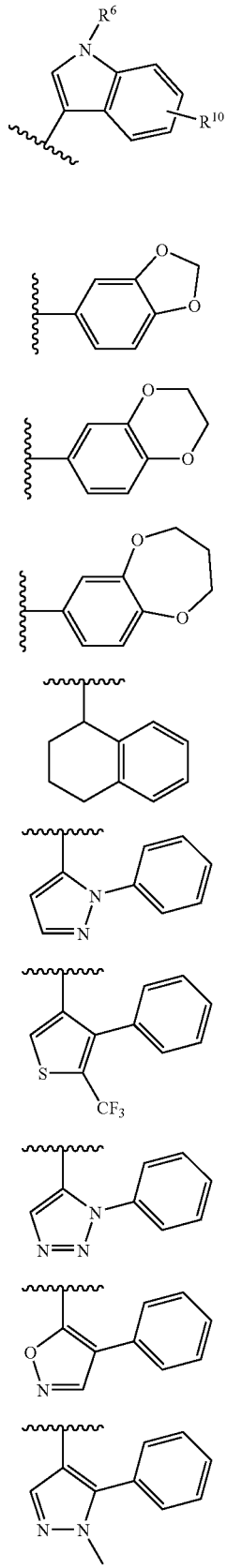

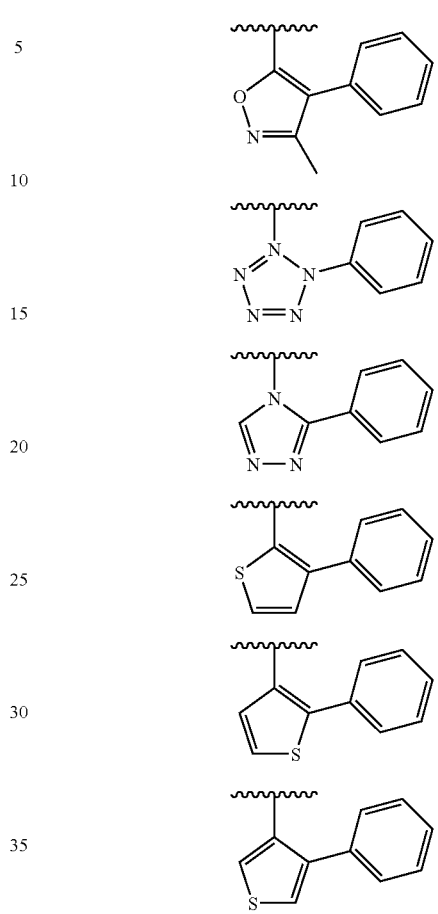

Assays

11. Molecular Constructs for Expression

GST-XIAP BIR3RING: XIAP coding sequence amino acids 246-497 cloned into PGEX2T1 via BamH1 and AVA I. The plasmid was transformed into *E. coli* DH5α for use in protein expression and purification.

GST-HIAP2 (cIAP-1) BIR 3: HIAP2 coding sequence from amino acids 251-363 cloned into PGex4T3 via BamH1 and XhoI. The plasmid was transformed into *E. coli* DH5α for use in protein expression and purification.

GST-HIAP1(cIAP-2) BIR 3: HIAP1 coding sequence from amino acids 236-349, cloned into PGex4T3 via BamH1 and XhoI. The plasmid was transformed into *E. coli* DH5α for use in protein expression and purification.

GST-linker BIR 2 BIR3Ring: XIAP coding sequence from amino acids 93-497 cloned into PGex4T1 via BamH1 and XhoI. Amino acids 93-497 were amplified from full length XIAP in pGex4t3, using the primers: TTAATAGGATCCAT-CAACGGCTTTTATC and GCTGCATGTGTGTCAGAGG, using standard PCR conditions. The PCR fragment was TA cloned into pCR-2.1 (invitrogen). Linker BIR 2 BIR 3Ring was subcloned into pGex4T1 by BamHI/XhoI digestion. The plasmid was transformed into *E. coli* DH5α for use in protein expression and purification.

Full-length human XIAP, Aegera plasmid number 23. XIAP coding sequence amino acids 1-497 cloned into GST fusion vector, PGEX4T1 via BamH1 and Xho I restriction sites. (a gift from Bob Korneluk and Peter Liston). The plasmid was transformed into *E. coli* DH5α for use in protein purification.

GST-XIAP linker BIR 2: XIAP linker BIR 2 coding sequence from amino acids 93-497 cloned into pGex4T3 via BamHI and XhoI. The plasmid was transformed into *E. coli* DH5α for use in protein expression and purification.

12. Synthesis of Fluorescent Probe for FP Assay

A fluorescent peptide probe, Fmoc-Ala-Val-Pro-Phe-Tyr(t-Bu)-Leu-Pro-Gly(t-Bu)-Gly-OH was prepared using standard Fmoc chemistry on 2-chlorotrityl chloride resin (Int. J. Pept. Prot. Res. 38:555-561, 1991). Cleavage from the resin was performed using 20% acetic acid in dichloromehane (DCM), which left the side chain still blocked. The C-terminal protected carboxylic acid was coupled to 4'-(aminomethy)fluorescein (Molecular Probes, A-1351; Eugene, Oreg.) using excess diisopropylcarbodiimide (DIC) in dimethylformamide (DMF) at room temperature and was purified by silica gel chromatography (10% methanol in DCM). The N-terminal Fmoc protecting group was removed using piperidine (20%) in DMF, and purified by silica gel chromatography (20% methanol in DCM, 0.5% HOAc). Finally, the t-butyl side chain protective groups were removed using 95% trifluoroacetic acid containing 2.5% water and 2.5% triisopropyl silane. The peptide obtained displayed a single peak by HPLC (>95% pure).

13. Expression and Purification of Recombinant Proteins

A. Recombinant Proteins Expression

Glutathione S-transferase (GST) tagged proteins were expressed in *Escherichia coli* strains DH5-alpha. For expression full length XIAP, individual or combinations of XIAP-BIR domains, cIAP-1, cIAP-2 and Livin transformed bacteria were cultured overnight at 37° C. in Luria Broth (LB) medium supplemented with 50 ug/ml of ampicillin. The overnight culture was then diluted 25 fold into fresh LB ampicillin supplemented media and bacteria were grown up to $A_{600}$=0.6 then induced with 1 mM isopropyl-D-1-thiogalactopyranoside for 3 hours. Upon induction, cells were centrifuged at 5000 RPM for 10 minutes and the media was removed. Each pellet obtained from a 1 liter culture received 10 ml of lysis buffer (50 mM Tris-HCl, 200 mM NaCl, 1 mM DTT, 1 mM PMSF, 2 mg/ml of lysosyme, 100 µg/ml)), was incubated at 4° C. with gentle shaking. After 20 minutes of incubation, the cell suspension was placed at −80° C. overnight or until needed.

B. Purification of Recombinant Proteins

For purification of recombinant proteins, the IPTG-induced cell lysate was thawed vortexed and then disrupted by flash freezing in liquid nitrogen two times with vortexing after each thaw. The cells were disrupted further by passing the extract four times through a Bio-Neb Cell disruptor device (Glas-col) set at 100 psi with Nitrogen gas. The extract was clarified by centrifugation at 4 C at 15000 RPM in a SS-34 Beckman rotor for 30 minutes. The resulting supernatant was then mixed with 2 ml of glutathione-Sepharose beads (Pharmacia) per 500 ml cell culture (per 1000 ml culture for full length XIAP) for 1 hour at 4 C. Afterwards, the beads were washed 3 times with 1× Tris-Buffered Saline (TBS) to remove unbound proteins. The retained proteins were eluted with 2 washes of 2 ml of 50 mM TRIS pH 8.0 containing 10 mM reduced glutathione. The eluted proteins were pooled and precipitated with 604 g/liter of ammonium sulfate and the resulting pellet re-suspended into an appropriate buffer. As judged by SDS-PAGE the purified proteins were >90% pure. The protein concentration of purified proteins was determined from the Bradford method.

His-tag proteins were expressed in the *E. Coli* strain in *E. coli* AD494 cells using a pet28ACPP32 construct. The soluble protein fraction was prepared as described above. For protein purification, the supernatant was purified by affinity chromatography using chelating-Sepharose (Pharmacia) charged with $NiSO_4$ according to the manufacturer's instructions. Purity of the eluted protein was >90% pure as determined by SDS-PAGE. The protein concentration of purified proteins was determined from the Bradford assay.

Binding Assay

14. Fluorescence Polarization-Based Competition Assay

For all assays, the fluorescence and fluorescence-polarization was evaluated using a Tecan Polarion instrument with the excitation filter set at 485 nm and the emission filter set at 535 nm. For each assay, the concentration of the target protein was first establish by titration of the selected protein in order to produce a linear dose-response signal when incubated alone in the presence of the fluorescent probe. Upon establishing these conditions, the compounds potency ($IC_{50}$) and selectivity, was assessed in the presence of a fix defined- amount of target protein and fluorescent probe and a 10 point serial dilution of the selected compounds. For each $IC_{50}$ curve, the assays were run as followed: 25 ul/well of diluted compound in 50 mM MES buffer pH 6.5 were added into a black 96 well plate then 25 ul/well of bovine serum albumin (BSA) at 0.5 mg/ml in 50 mM MES pH 6.5. Auto-fluorescence for each compound was first assessed by performing a reading of the compound/BSA solution alone. Then 25 ul of the fluorescein probe diluted into 50 mM MES containing 0.05 mg/ml BSA were added and a reading to detect quenching of fluorescein signal done. Finally 25 ul/well of the target or control protein (GST-BIRs) diluted at the appropriate concentration in 50 mM MES containing 0.05 mg/ml BSA were added and the fluorescence polarization evaluated.

15. Determination of $IC_{50}$ and Inhibitory Constants

For each assay the relative polarization-fluorescence units were plotted against the final concentrations of compound and the $IC_{50}$ calculated using the Grad pad prism software and/or Cambridge soft. The ki value were derived from the calculated $IC_{50}$ value as described above and according to the equation described in Nikolovska-Coleska, Z. (2004) Anal Biochem 332, 261-273.

16. Caspase-3 Full Length XIAP, Linker BIR2 or Linker-BIR2-BIR3-RING Derepression Assay In order to determine the relative activity of the selected compound against XIAP-Bir2, we setup an in vitro assay where caspase-3 was inhibited by GST fusion proteins of XIAP linker-bir2, XIAP Linker Bir2-Bir3-RING or full-length XIAP. Caspase 3 (0.125 ul) and 12.25-34.25 nM (final concentration) of GST-XIAP fusion protein (GST-Bir2, GST-Bir2Bir3RING or full-length XIAP) were co-incubated with serial dilutions of compound (200 uM-5 pM). Caspase 3 activity was measured by overlaying 25 ul of a 0.4 mM DEVD-AMC solution. Final reaction volume was 1100 ul. All dilutions were performed in caspase buffer (50 mM Hepes pH 7.4, 100 mM NaCl, 10% sucrose, 1 mM EDTA, 10 mM DTT, 0.1% CHAPS (Stennicke, H. R., and Salvesen, G. S. (1997). Biochemical characteristics of caspase-3, -6, -7, and -8. J. Biol. Chem. 272, 25719-25723)

The fluorescent AMC released from the caspase-3 hydrolysis of the substrate was measured in a TECAN spectrophotometer at 360 nm excitation and 444 nm emission, after 15 minutes of incubation at room temperature. IC50 values were calculated on a one or two-site competition model using GraphPad v4.0, using the fluorescence values after 15 minutes of incubation plotted against the log 10 concentration of compound.

The compounds which were tested in the apoptosome assay and the linker-BIR2-Bir3/caspase-3 inhibition assay were found to have $IC_{50}$s as illustrated in Table 12.

TABLE 12

In vitro activitity of selected compounds against IAP's.

| Cpd# Number | Apoptosome L-Bir2-Bir3 XIAP µM | Fluorescent polarization (FP) assay | | |
|---|---|---|---|---|
| | | Xiap nM | cIAP-1 nM | cIAP-2 nM |
| 1 | A | B | C | C |
| 2 | A | B | B | C |
| 3 | B | B | B | A |
| 4 | B | A | nd | nd |
| 6 | B | A | nd | nd |
| 7 | B | B | nd | nd |
| 8 | B | A | nd | nd |
| 11 | C | nd | nd | C |
| 12 | C | C | B | A |
| 13 | nd | B | nd | nd |
| 14 | nd | B | nd | nd |
| 15 | nd | nd | nd | nd |
| 23 | B | B | A | B | nd = Not determined;
Legend:
FP assay: A $\leq$5 nM; B $\leq$100 nM; C $\geq$100 nM;
Legend:
Apoptosome assay: A $\leq$0.1 µM; B $\leq$0.5 µM; C $\geq$1 µM Results demonstrate that the selected compounds can inhibit the caspase-blocking activity of XIAP in an apoptosome assay (express in effective concentration to achieve 50% of activation and report the Ki to bind to various IAP's. This Ki was calculated from the displacement a fluorescent probe capable to bind to the bir3 domain of various IAP's using a fluorescent polarization assay.

Cell-Free Assay

17. Caspase De-Repression Assay Using Cellular Extracts (Apoptosome)

100 ug of 293 cell S100 extract and 0.25 uM-2 uM of GST-XIAP fusion protein (XIAP-Bir3RING, XIAP-Linker Bir2Bir3RING, or full-length XIAP) were co-incubated with serial dilutions of compound (40 uM-5 pM). Caspases present in the extracts were activated by adding 1 mM dATP, 0.1 mM ALLN, 133 ug Cytochrome C (final concentrations), and incubating at 37° C. for 25 minutes. All reactions and dilutions used S100 buffer (50 mM Pipes pH 7.0, 50 mM KCl, 0.5 mM EGTA pH 8.0, 2 mM MgCl2 supplemented with 1/1000 dilutions of 2 mg/ml Cytochalisin B, 2 mg/ml Chymotstatin, Leupeptin, Pepstatin, Antipain, 0.1M PMSF, 1M DTT). Final reaction volume was 30 ul. Caspase-3 activity was measured by overlaying 30 ul of a 0.4 mM DEVD-AMC solution. released AMC cleavage was measured in a TECAN spectrophotometer at 360 nm excitation and 444 nm emission, on a kinetic cycle of 1 hour with readings taken every 5 minutes. Caspase activity was calculated as $V_o$ of AMC fluorescence/sec. Caspase de-repression by our compounds was compared to fully activated extract and activated extract repressed by the presence of XIAP fusion protein.

18. Cell Culture and Cell Death Assays

A. Cell Culture

MDA-MD-231 (breast) and SKOV-3 (ovarian) cancer cells were cultured in RPMI1640 media supplemented with 10% FBS and 100 units/mL of Penicillin and Steptomycin.

B. Assays

Viability assays were done on a number of cells including MDA-MB-231, SKOV-3, H460, PC3, HCT-116, and SW480 cells. Cells were seeded in 96 well plates at a respective density of 5000 and 2000 cells per well and incubated at 37° C. in presence of 5% $CO_2$ for 24 hours. selected compounds were diluted into the media at various concentration ranging from 0.01 uM up to 100 uM. Diluted compounds were added onto the MDA-MB-231 cells. For the MDA-MB-231 SKOV3, H460, PC3, HCT-116, and SW480 cells, the compounds were added either alone or in presence of 1-3 ng/ml of TRAIL. After 72 hours cellular viability was evaluated by MTT based assays. $IC_{50}$s of select compounds against MDA and SKOV3 cell lines are presented in Table 13:

TABLE 13

$IC_{50}$s of select compounds against MDA and SKOV3 cell lines

| Compound | MDA $EC_{50}$ (nM) | SKOV3 $EC_{50}$ (nM) |
|---|---|---|
| 1 | A | A |
| 2 | A | |
| 3 | A | |
| 4 | A | |
| 5 | A | |
| 6 | A | |
| 7 | A | |
| 8 | A | |
| 9 | A | |
| 10 | A | |
| 11 | A | |
| 12 | A | |
| 13 | B | |
| 14 | B | |
| 15 | A | |
| 16 | A | |
| 17 | B | |
| 18 | B | |
| 19 | B | |
| 20 | B | |
| 21 | B | |
| 22 | A | |
| 23 | A | A |
| 24 | A | |
| 25 | A | |
| 26 | A | |
| 27 | B | |
| 28 | A | |
| 29 | A | |
| 30 | A | |

| Compound | MDA $EC_{50}$ (nM) | SKOV3 $EC_{50}$ (nM) |
|---|---|---|
| 31 | A | |
| 32 | | C |
| 33 | | C |
| 34 | | C |
| 35 | B | B |
| 36 | | A |
| 37 | | A |
| 38 | | A |
| 39 | | B |
| 40 | | B |

-continued

| Compound | MDA EC$_{50}$ (nM) | SKOV3 EC$_{50}$ (nM) |
|---|---|---|
| 41 |  | B |
| 42 |  | C |
| 43 |  | B |
| 44 |  | B |
| 45 |  | B |
| 46 |  | A |
| 47 |  | B |

The compounds exemplified in Table 1 were tested and found to have IC$_{50}$s in the following ranges: A<1000 nM; B<1000 nM; C>1000 nM.

19. Apoptosis Assay: Measurement of Caspase-3 Activity from Cultured Cells.

One day, prior to the treatment, 10 000 cells per well were plated in a white tissue culture treated 96 well plate with 100 ul of media. On the day of compound treatment, compounds were diluted with cell culture media to a working stock concentration of 2× and 100 ul of diluted compound were added to each well and the plate was incubated for 5 h at 37° C. in presence of 5% CO$_2$. Upon incubation, the plate was washed twice with 200 ul of cold TRIS Buffered Saline (TBS) buffer. Cells were lysed with 50 ul of Caspase assay buffer (20 mM Tris-HCl pH 7.4, 0.1% NP-40, 0.1% Chaps, 1 mM DTT, 0.1 mM EDTA, 0.1 mM PMSF, 2 mg/ml Chymotstatin, Leupptin, Pepstatin, Antipain) then incubated at 4° C. with shaking for 30 minutes. 45 ul of Caspase assay buffer and 5 ul of Ac-DEVD-AMC at 1 mg/ml were added to each well, the plate shaken and incubated for 16 h at 37° C. The amount of release AMC was measured in a TECAN spectrophotometer at with the excitation and emission filter set at 360 nm and 444 nm. The percentage of Caspase-3 activity was expressed in comparison of the signal obtained with the non-treated cells.

20. Cellular Biochemistry:

A. Detection of XIAP and PARP/Caspase-3/Caspase-9

Detection of cell expressed XIAP and PARP were done by western blotting. Cells were plated at 300 000 cells/well in a 60 mm wells (6 wells plate dish). The next day the cells were treated with selected compound at the indicated concentration. 24 hours later cells the trypsinized cells, pelleted by centrifugation at 1800 rpm at 4° C. The resulting pellet was rinsed twice with cold TBS. The final washed pellet of cells was the lysed with 250 ul Lysis buffer (NP-40, glycerol, 1% of a protease inhibitor cocktail (Sigma)), placed at 4° C. for 25 min with gentle shaking. The cells extract was centrifuged at 4° C. for 10 min at 10 000 rpm. Both the supernatant and the pellet were kept for western blotting analysis as described below. From the supernatant, the protein content was evaluated and about 50 ug of protein was fractionated onto a 10% SDS-PAGE. Pellets were washed with the lysis buffer and re-suspend into 50 ul of Lamelli buffer 1×, boiled and fractionated on SDS-PAGE. Upon electrophoresis each gel was electro-transferred onto a nitrocellulose membrane at 0.6 A for 2 hours. Membrane non-specific sites were blocked for 1 hours with 5% Skim milk in TBST (TBS containing 0.1% (v/v) Tween-20) at RT. For protein immuno-detection, membranes were incubated overnight with primary antibodies raised against XIAP clone 48 obtained from Becton-Dickinson) or PARP: obtained from Cell signal or caspase-3 or caspase-9 primary antibodies were incubated at 4° C. with shaking at dilutions as follows:

| | |
|---|---|
| XIAP clone 80 (Becton-Dickinson) | 1/2500 |
| PARP (Cell Signal) | 1/2500 |
| Caspase 3 (Sigma) | 1/1500 |
| Caspase 9 (Upstate) | 1/1000 |

Upon overnight incubation, the membranes received three washes of 15 min in TBST then were incubated for 1 hour at room temperature in the presence of a secondary antibody coupled with HRP-enzyme (Chemicon) and diluted at 1/5 000. Upon incubation each membrane were washed three times with TBST and the immunoreactive bands were detected by addition of a luminescent substrate (ECL kit Amersham) and capture of signal on a X-RAY film for various time of exposure. Active compounds were shown to induce the cleavage of PARP and XIAP as well as to translocate XIAP into an insoluble compartment.

21. Hollow Fiber Model

Hollow fiber in vivo model were used to demonstrate in vivo efficacy of selected compounds against selected cell lines as single agent therapy or in combination with selected cytotoxic agents. At day 1, selected cell lines were cultured and the fiber filled at a cell density of about 40,000 cells/fiber. At the day of operation (day 4), three fibers are implanted sub-cutaneous into 28-35 g Nu/Nu CD-1 male mice. On day 5, mice start to receive daily injection via intravenous or sub-cutaneous route of control vehicle or vehicle containing the selected compound at the appropriate concentration and/or injection of cytotoxic agent via intra-peritoneal route. Upon 7 days of non-consecutive treatments, the animals are sacrificed, each fiber is removed and the metabolic viability of the remaining cells determined by MTT assay. Efficacy of the compound is define as the difference between the MTT values obtained from the cell containing fiber taken from the vehicle-treated animal and the from the animal treated with the compound alone or the compound given in combination of the cytotoxic agent 22. Combination Anti-Cancer Therapy In Vivo Female nude mice received 2×10 HCT-116 subdermally on the right flank. On day 26, when tumors were ~90 mm, animals were assigned to groups using a balanced design based on tumor size. At that time mitomycin-C and Compound 23 treatment was initated. Mitomycin-C was administered ip at 1 mg/kg, Monday through Friday for two weeks. Compound 23 was given iv at 1 or 5 mg/kg five times per week for the duration of the experiment. Tumor measurements were taken twice weekly. As illustrated in FIG. 1, compound 23 showed an increasing anti-tumor effect in combination with mitomycin-C with increasing dose, with 5 mg/kg showing superior anti-tumor effects compared to the 1 mg/kg dose.

23. Pharmacokinetic Studies

Selected compounds were dissolved into normal saline or appropriate vehicle and given at various doses using different route of administration, including intravenous bolus, intravenous infusion, oral and subcutaneous injection.

All literature, patents, published patent applications cited herein are hereby incorporated by reference.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for the treatment of cancer in a subject, the method comprising administering to the subject a therapeutically effective amount of a compound represented by Formula I:

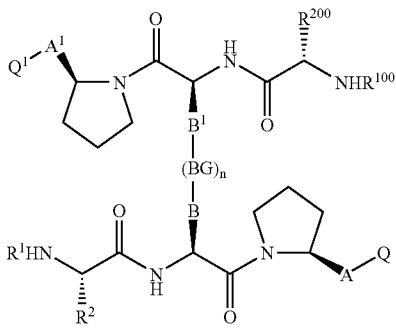

or a pharmaceutically acceptable salt thereof,
wherein:
n is 0 or 1;
m is 0, 1, or 2;
p is 1 or 2;
Y is NH, O, or S;
A and $A^1$ are independently selected from
    1) —$CH_2$—,
    2) —$CH_2CH_2$—,
    3) —$C(CH_3)_2$—,
    4) —$CH(C_1$-$C_6$ alkyl)-,
    5) —$CH(C_3$-$C_7$ cycloalkyl)-,
    6) —$C_3$-$C_7$ cycloalkyl-,
    7) —$CH(C_1$-$C_6$ alkyl-$C_3$-$C_7$ cycloalkyl)-, or
    8) —C(O)—;
B and $B^1$ are independently $C_1$-$C_6$ alkyl;
BG is
    1) -X-L-$X^1$-, 2) 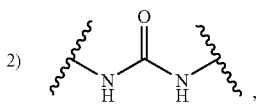

3) 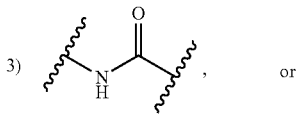, or

4) 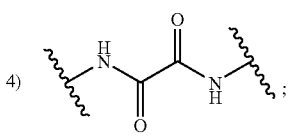;

X and $X^1$ are independently selected from

1) O,
2) $NR^{13}$,
3) S,

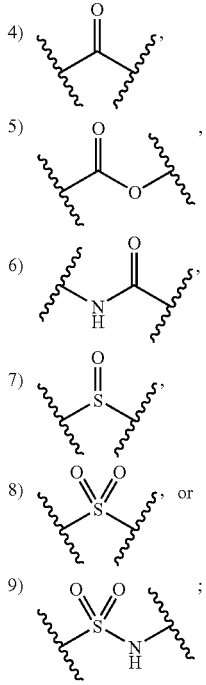

L is selected from:
    1) —$C_1$-$C_{10}$ alkyl-,
    2) —$C_2$-$C_6$ alkenyl-,
    3) —$C_2$-$C_4$ alkynyl-,
    4) —$C_3$-$C_7$ cycloalkyl-,
    5) -phenyl-,
    6) -biphenyl-,
    7) -heteroaryl-,
    8) -heterocycyl-,
    9) —$C_1$-$C_6$ alkyl-($C_2$-$C_6$ alkenyl)-$C_1$-$C_6$ alkyl-,
    10) —$C_1$-$C_6$ alkyl-($C_2$-$C_4$ alkynyl)-$C_1$-$C_6$ alkyl-,
    11) —$C_1$-$C_6$ alkyl-($C_3$-$C_7$ cycloalkyl)-$C_1$-$C_6$ alkyl-,
    12) —$C_1$-$C_6$ alkyl-phenyl-$C_1$-$C_6$ alkyl-,
    13) —$C_1$-$C_6$ alkyl-biphenyl-$C_1$-$C_6$ alkyl-,
    14) —$C_1$-$C_6$ alkyl-heteroaryl-$C_1$-$C_6$ alkyl-,
    15) —$C_1$-$C_6$ alkyl-heterocycyl-$C_1$-$C_6$ alkyl-, or
    16) —$C_1$-$C_6$ alkyl-O—$C_1$-$C_6$ alkyl-;
$R^1$, $R^{100}$, $R^2$ and $R^{200}$ are independently selected from:
    1) H, or
    2) $C_1$-$C_6$ alkyl optionally substituted with one or more $R^6$ substituents;
Q and $Q^1$ are each independently
    1) $NR^4R^5$,
    2) $OR^{11}$, or
    3) $S(O)_mR^{11}$; or Q and $Q^1$ are each independently

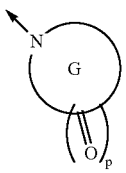

wherein G is a 5, 6, or 7 membered ring which optionally incorporates one or more heteroatoms chosen from S, N, or O, the ring being optionally substituted with one or more $R^{12}$ substituents;

$R^4$ and $R^5$ are each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)$—$R^{11}$,
13) $C(O)O$—$R^{11}$,
14) $C(=Y)NR^8R^9$, or
15) $S(O)_2$—$R^{11}$,
wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

$R^6$ is
1) halogen,
2) $NO_2$,
3) CN,
4) haloalkyl,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) aryl,
11) heteroaryl,
12) heterocyclyl,
13) heterobicyclyl,
14) $OR^7$,
15) $S(O)_mR^7$,
16) $NR^8R^9$,
17) $NR^8S(O)_2R^{11}$,
18) $COR^7$,
19) $C(O) OR^7$,
20) $CONR^8R^9$,
21) $S(O)_2NR^8R^9$
22) $OC(O)R^7$,
23) $OC(O)Y$—$R^{11}$,
24) $SC(O)R^7$, or
25) $NC(Y)NR^8R^9$,
wherein the aryl, heteroaryl, heterocyclyl, and heterobicyclyl are optionally substituted with one or more $R^{10}$ substituents;

$R^7$ is
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $R^8R^9NC(=Y)$, or
13) $C_1$-$C_6$ alkyl-$C_2$-$C_4$ alkenyl, or
14) $C_1$-$C_6$ alkyl-$C_2$-$C_4$ alkynyl,
wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

$R^8$ and $R^9$ each independently
1) H,
2) haloalkyl,
3) $C_1$-$C_6$ alkyl,
4) $C_2$-$C_6$ alkenyl,
5) $C_2$-$C_4$ alkynyl,
6) $C_3$-$C_7$ cycloalkyl,
7) $C_3$-$C_7$ cycloalkenyl,
8) aryl,
9) heteroaryl,
10) heterocyclyl,
11) heterobicyclyl,
12) $C(O)R^{11}$,
13) $C(O)Y$—$R^{11}$, or
14) $S(O)_2$—$R^{11}$,
wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;
or $R^8$ and $R^9$ together with the nitrogen atom to which they are bonded form a five, six or seven membered heterocyclic ring optionally substituted with one or more $R^6$ substituents;

$R^{10}$ is
1) halogen,
2) $NO_2$,
3) CN,
4) $R(OR^{13})(OR^{14})$,
5) $C_1$-$C_6$ alkyl,
6) $C_2$-$C_6$ alkenyl,
7) $C_2$-$C_4$ alkynyl,
8) $C_3$-$C_7$ cycloalkyl,
9) $C_3$-$C_7$ cycloalkenyl,
10) haloalkyl,
11) $OR^7$,
12) $NR^8R^9$,
13) $SR^7$,
14) $COR^7$,
15) $C(O) OR^7$,
16) $S(O)_mR^7$,
17) $CONR^8R^9$,
18) $S(O)_2NR^8R^9$,
19) aryl,
20) heteroaryl,
21) heterocyclyl, or
22) heterobicyclyl, wherein the alkyl, alkenyl, alkynyl, cycloalkyl, and cycloalkenyl are optionally substituted with one or more $R^6$ substituents;

$R^{11}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl, or
10) heterobicyclyl, wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

$R^{12}$ is
1) haloalkyl,
2) $C_1$-$C_6$ alkyl,
3) $C_2$-$C_6$ alkenyl,
4) $C_2$-$C_4$ alkynyl,
5) $C_3$-$C_7$ cycloalkyl,
6) $C_3$-$C_7$ cycloalkenyl,
7) aryl,
8) heteroaryl,
9) heterocyclyl,
10) heterobicyclyl,
11) C(O)—$R^{11}$,
12) C(O)O—$R^{11}$,
13) C(O)N$R^8R^9$,
14) S(O)$_m$—$R^{11}$, or
15) C(=Y)N$R^8R^9$, wherein the alkyl, alkenyl, alkynyl, cycloalkyl, and cycloalkenyl are optionally substituted with one or more $R^6$ substituents; and wherein the aryl, heteroaryl, heterocyclyl, and heterobicyclyl are optionally substituted with one or more $R^{10}$ substituents;

$R^{13}$ and $R^{14}$ are each independently
1) H, or
2) $C_1$-$C_6$ alkyl; or $R^{13}$ and $R^{14}$ are combined to form a heterocyclic ring or a heterobicyclic ring;

so as to treat the cancer, wherein the cancer is adrenal gland cancer, bone cancer, cardiac cancer, gastrointestinal cancer, genitourinary cancer, gynecological cancer, hematologic cancer, lung cancer, nervous system cancer, skin cancer, or breast cancer.

2. The method, according to claim 1, in which the compound is a pharmaceutically acceptable salt.

3. The method, according to claim 1, further comprising administering to the subject a therapeutically effective amount of a chemotherapeutic agent prior to, simultaneously with, or after administration of the compound.

4. The method, according to claim 1, further comprising administering to the subject a therapeutically effective amount of a death receptor agonist prior to, simultaneously with, or after administration of the compound.

5. The method, according to claim 4, in which the death receptor agonist is TRAIL.

6. The method, according to claim 4, in which the death receptor agonist is a TRAIL receptor antibody.

7. The method, according to claim 4, in which the death receptor agonist is administered in an amount that produces a synergistic effect.

8. The method, according to claim 1, in which the cancer is adrenal gland cancer.

9. The method, according to claim 1, in which the cancer is bone cancer.

10. The method, according to claim 1, in which the cancer is cardiac cancer.

11. The method, according to claim 1, in which the cancer is gastrointestinal cancer.

12. The method, according to claim 1, in which the cancer is genitourinary cancer.

13. The method, according to claim 1, in which the cancer is gynecological cancer.

14. The method, according to claim 1, in which the cancer is hematological cancer.

15. The method, according to claim 1, in which the cancer is lung cancer.

16. The method, according to claim 1, in which the cancer is nervous system cancer.

17. The method, according to claim 1, in which the cancer is skin cancer.

18. The method, according to claim 1, in which the cancer is a solid tumor.

19. The method, according to claim 1, in which the cancer is leukemia, lymphoma, or multiple myeloma.

20. The method, according to claim 1, in which the cancer is breast cancer, ovarian cancer, prostate cancer, or large or small bowel cancer.

21. The method, according to claim 1, in which the cancer is acute myeloid leukemia, non-Hodgkin's lymphoma, or myelodysplastic syndrome.

22. The method, according to claim 1, in which the cancer is gastrointestinal carcinoma, breast carcinoma, or lung carcinoma.

23. The method, according to claim 1, in which the cancer is large bowel or small bowel adenocarcinoma, prostate adenocarcinoma, or ovarian cystadenocarcinoma.

24. The method, according to claim 1, in which the cancer is squamous cell lung carcinoma, large cell lung carcinoma, or lung adenocarinoma.

25. The method, according to claim 1, wherein n is 1; L is

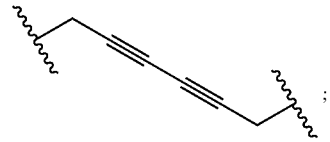

and

X and $X^1$ are independently selected from

1) O,
2) N$R^{13}$,
3) S,
4) 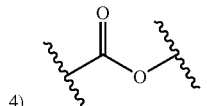
5) 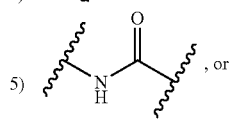, or

-continued

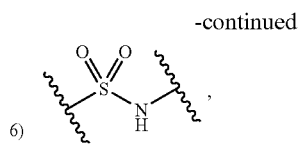
6)

26. The method, according to claim 25, in which A and A¹ are both C=O.

27. The method, according to claim 25, in which A and A¹ are both CH$_2$.

28. The method, according to claim 25, wherein Q and Q¹ are NR⁴R⁵.

29. The method, according to claim 28, wherein R⁴ is
1) H
2) C(O)—R¹¹,
3) C(O)O—R¹¹, or
4) S(O)$_2$—R¹¹.

30. The method of claim 28, wherein R⁵ is
1) haloalkyl,
2) C$_1$-C$_6$ alkyl,
3) C$_2$-C$_6$ alkenyl,
4) C$_2$-C$_4$ alkynyl,
5) C$_3$-C$_7$ cycloalkyl,
6) C$_3$-C$_7$ cycloalkenyl,
7) aryl,
8) heteroaryl,
9) heterocyclyl, or
10) heterobicyclyl;
wherein the alkyl, alkenyl, alkynyl, cycloalkyl, and cycloalkenyl are optionally substituted with one or more R⁶ substituents; and wherein the aryl, heteroaryl, heterocyclyl, and heterobicyclyl are optionally substituted with one or more R¹⁰ substituents.

31. The method, according to claim 30, wherein R⁵ is a C$_1$-C$_6$ alkyl substituted with a phenyl.

32. The method, according to claim 1, in which the compound is:

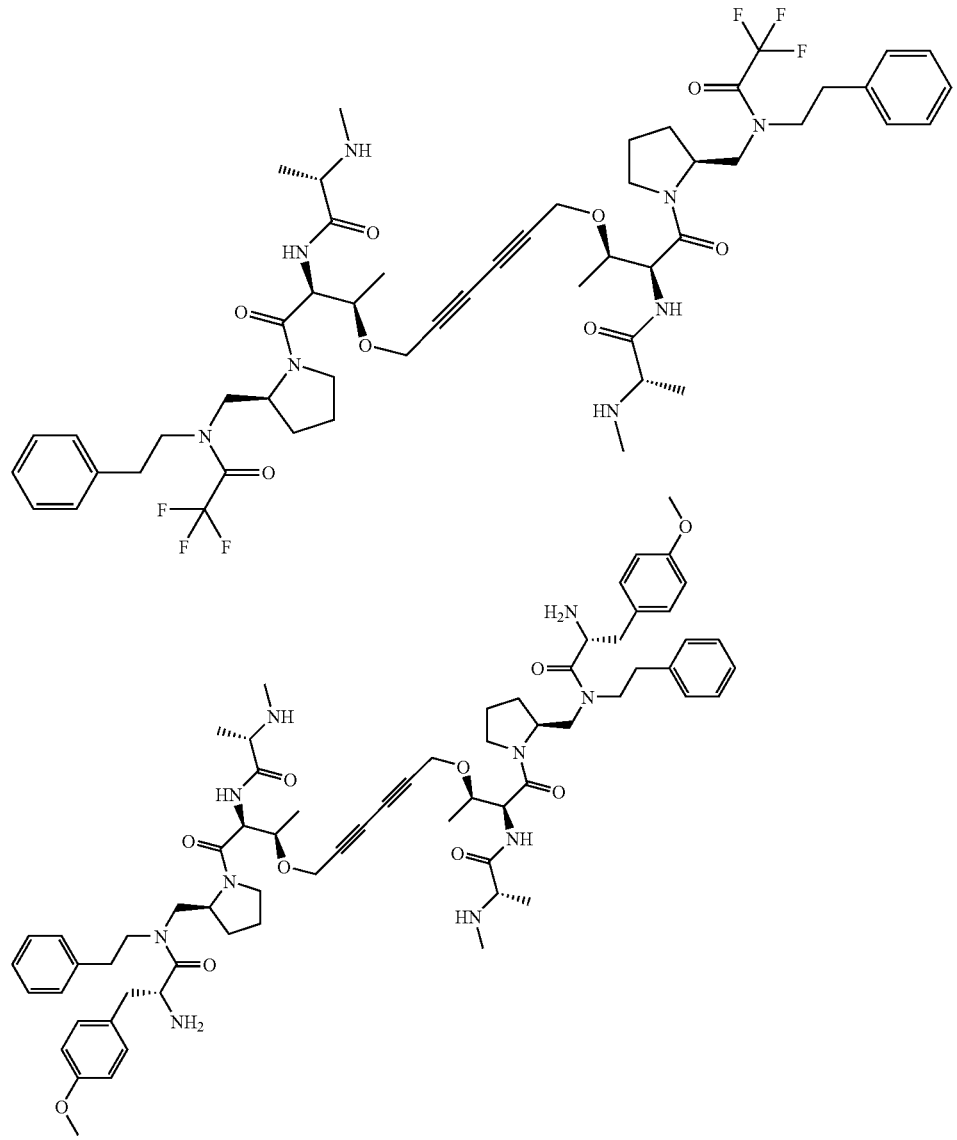

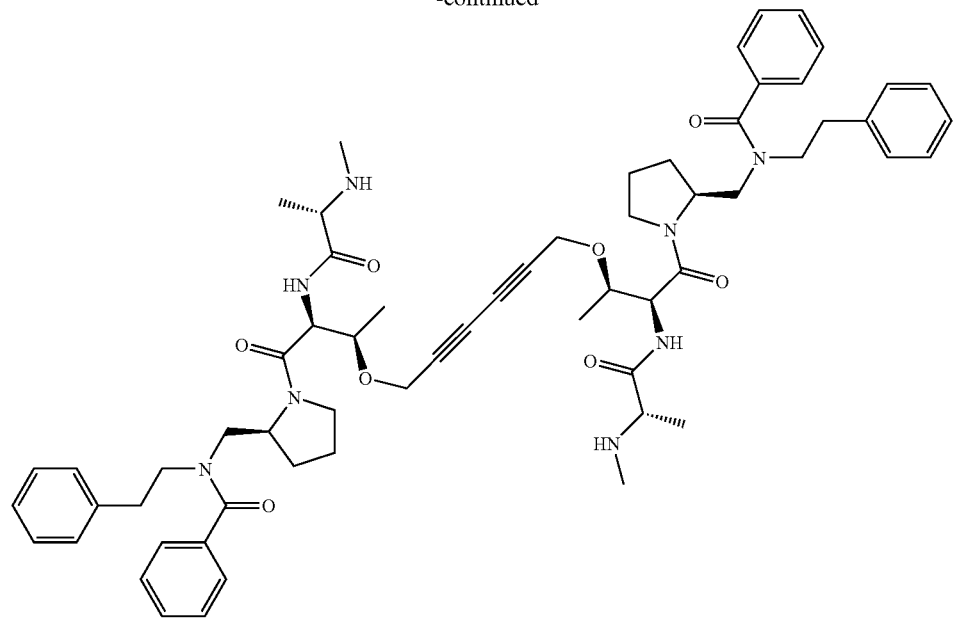
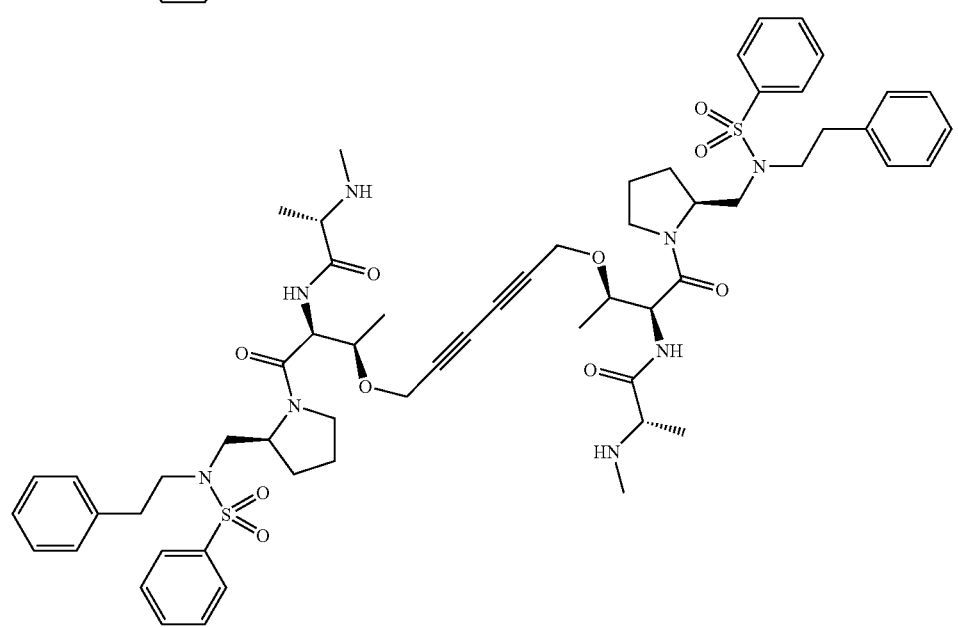
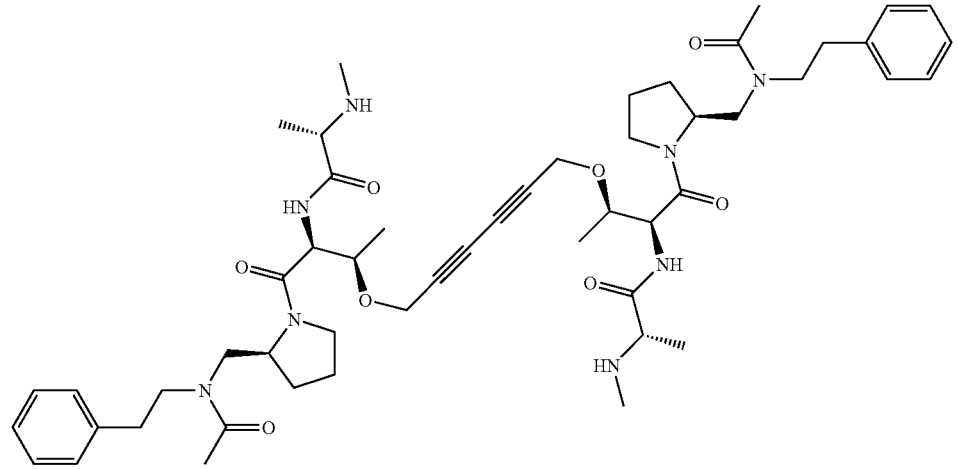

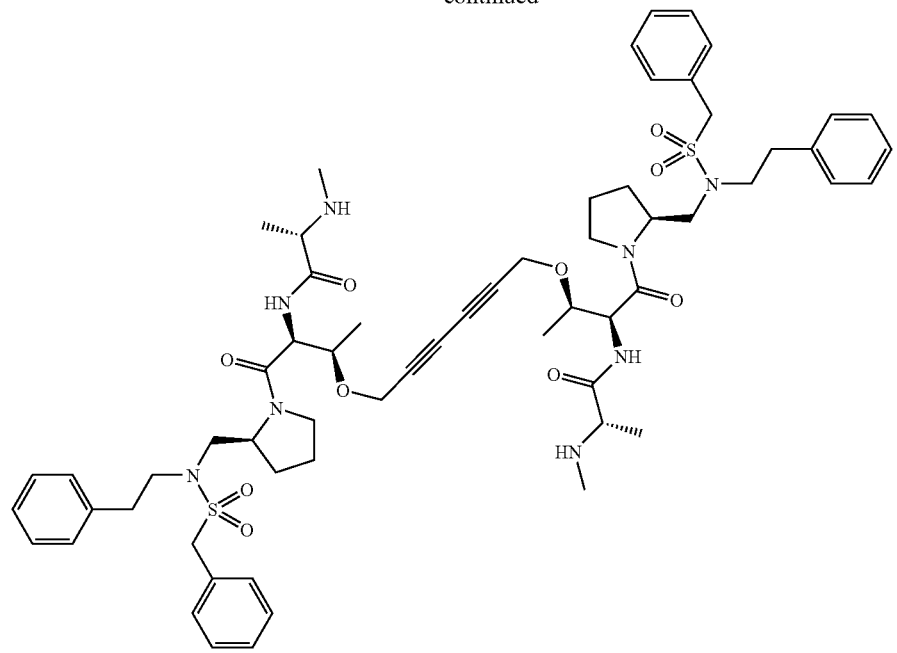
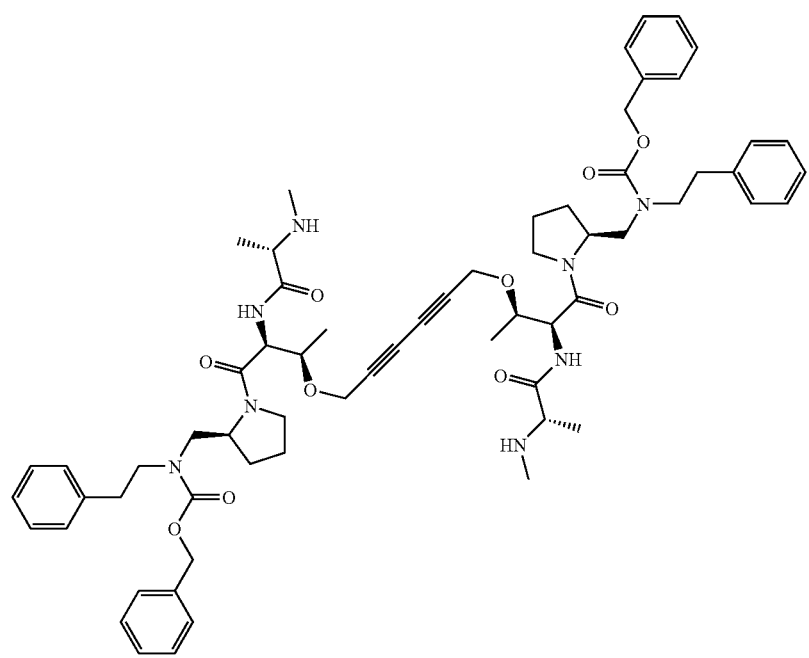

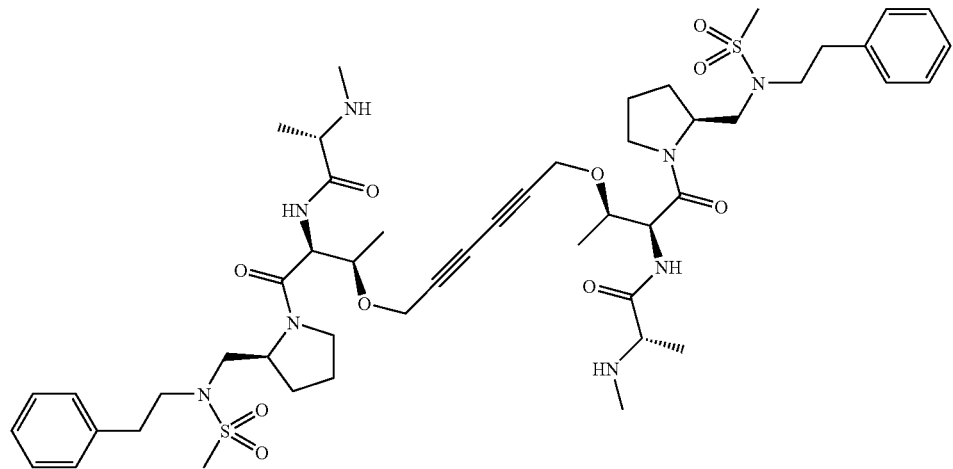
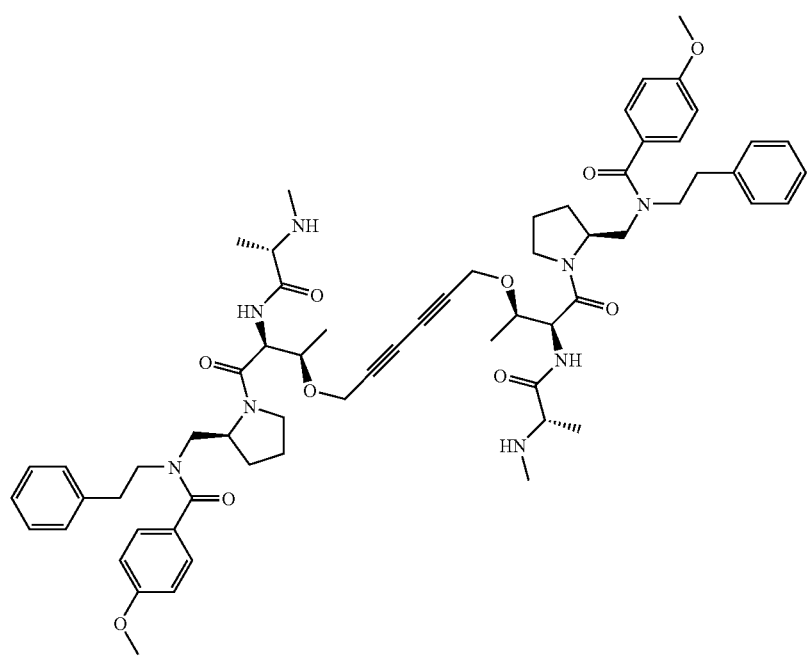

-continued
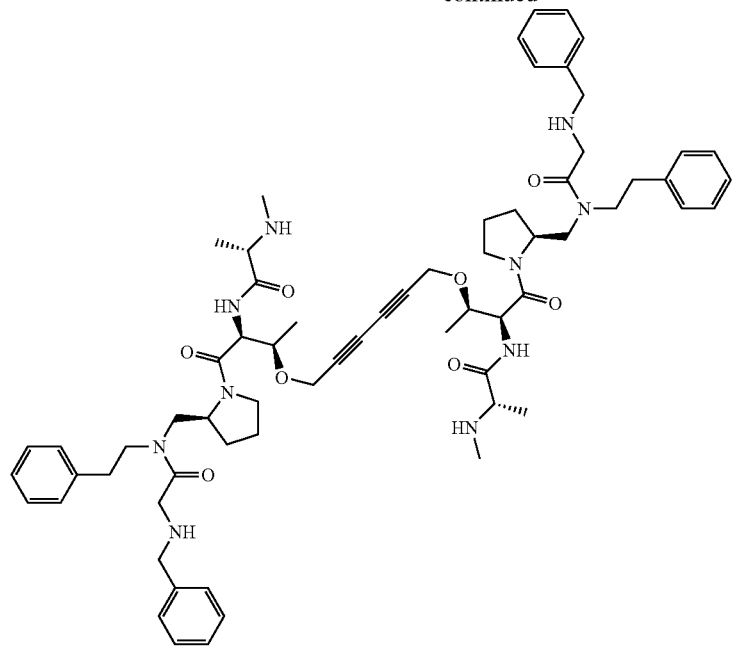
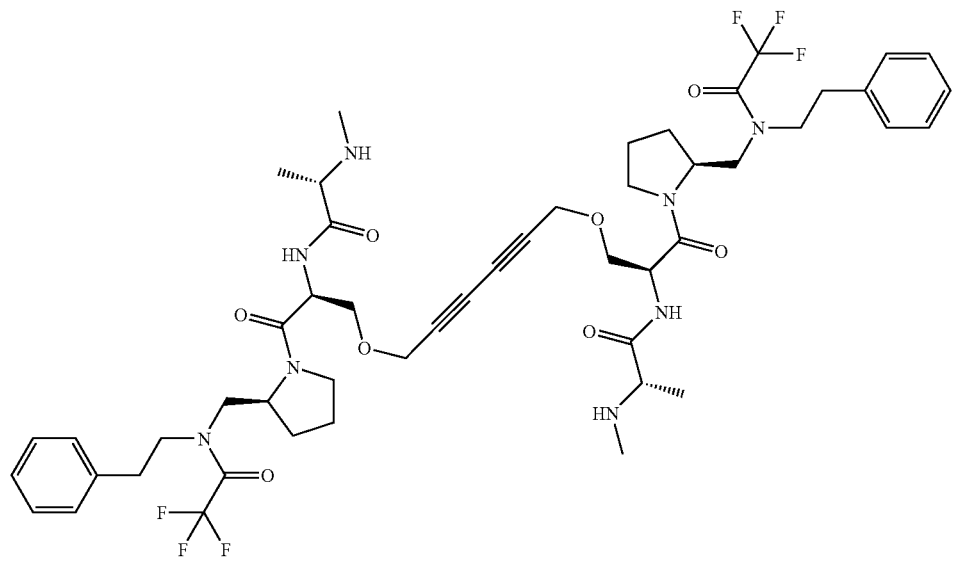

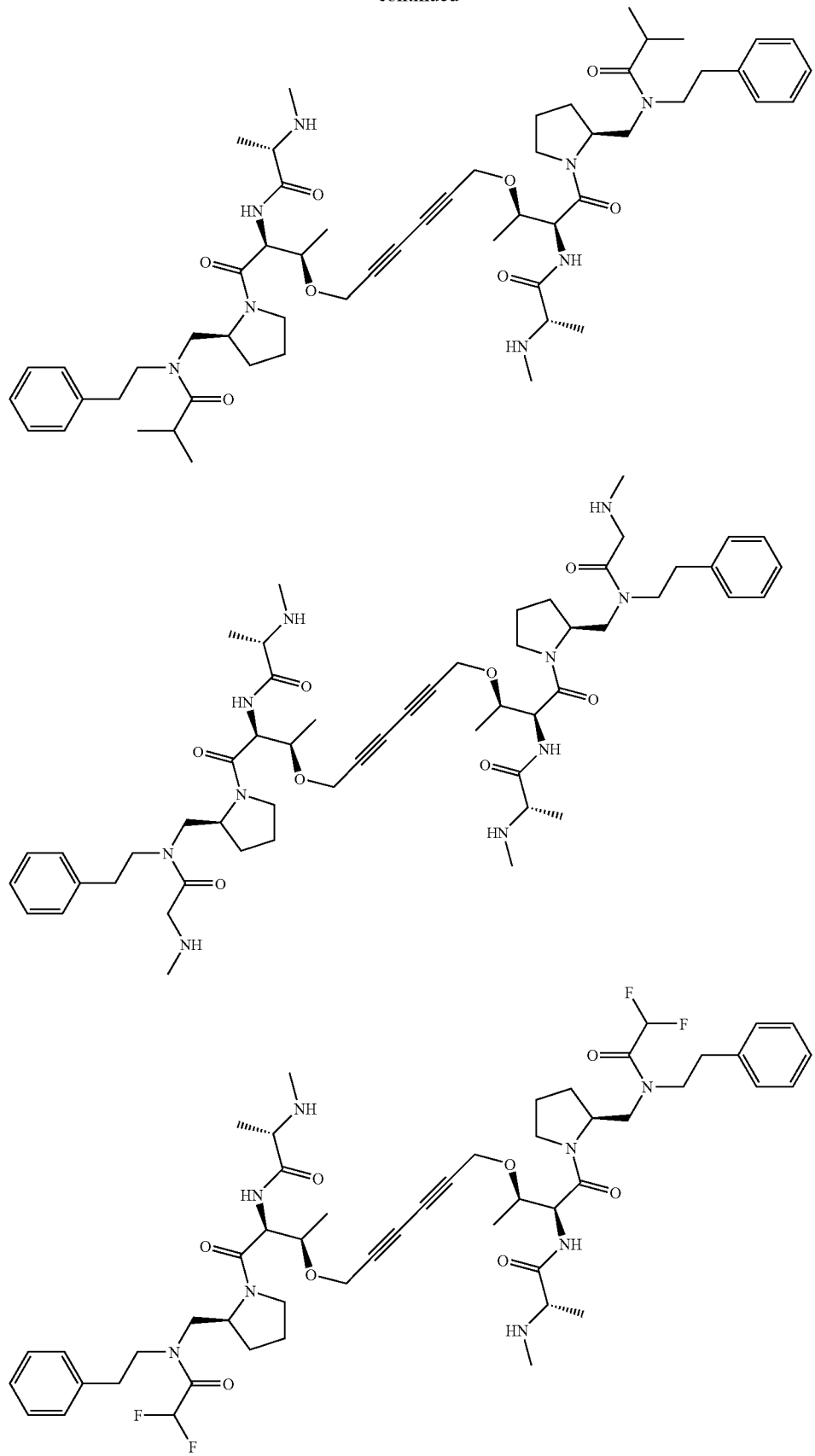

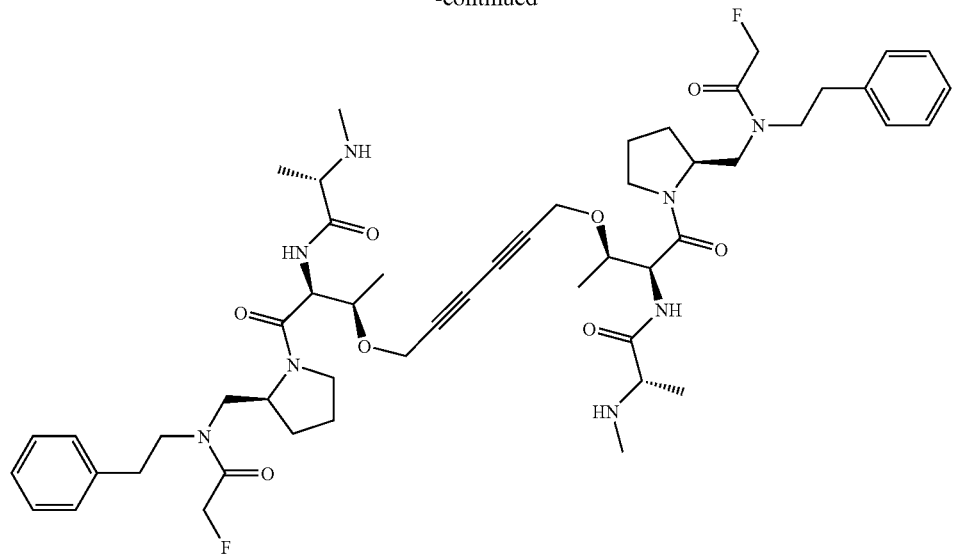
33. The method, according to claim 1, wherein the compound is
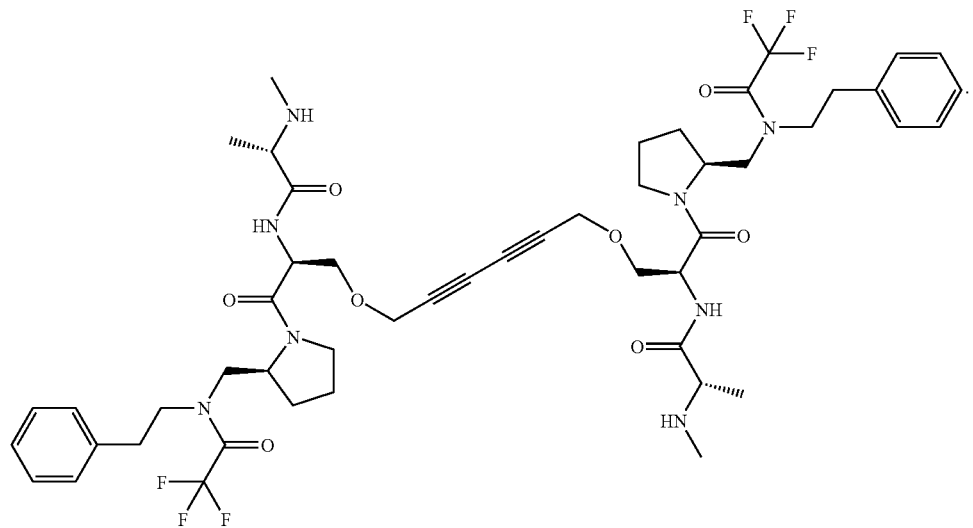
* * * * *